(12) United States Patent
McCall et al.

(10) Patent No.: US 8,912,188 B2
(45) Date of Patent: Dec. 16, 2014

(54) SUBSTITUTED QUINOXALINE CARBOXYLIC ACIDS FOR THE INHIBITION OF PASK

(75) Inventors: John M. McCall, Boca Grande, FL (US); Donna L. Romero, Chesterfield, MO (US); Robert C. Kelly, Augusta, MI (US)

(73) Assignee: BioEnergenix, LLC, San Francisco, CA (US)

( * ) Notice: Subject to any disclaimer, the term of this patent is extended or adjusted under 35 U.S.C. 154(b) by 0 days.

(21) Appl. No.: 13/410,650

(22) Filed: Mar. 2, 2012

(65) Prior Publication Data
US 2012/0232056 A1 Sep. 13, 2012

Related U.S. Application Data

(60) Provisional application No. 61/448,527, filed on Mar. 2, 2011, provisional application No. 61/449,009, filed on Mar. 3, 2011, provisional application No. 61/448,533, filed on Mar. 2, 2011.

(51) Int. Cl.

| | | |
|---|---|---|
| *A61K 31/498* | (2006.01) | |
| *C07D 241/44* | (2006.01) | |
| *C07D 413/04* | (2006.01) | |
| *C07D 403/04* | (2006.01) | |
| *C07D 409/14* | (2006.01) | |
| *C07D 401/12* | (2006.01) | |
| *C07D 417/14* | (2006.01) | |
| *C07D 405/04* | (2006.01) | |
| *C07D 413/14* | (2006.01) | |
| *C07D 417/04* | (2006.01) | |
| *C07D 403/14* | (2006.01) | |
| *C07D 405/14* | (2006.01) | |
| *C07D 401/14* | (2006.01) | |
| *C07D 409/04* | (2006.01) | |
| *C07D 401/04* | (2006.01) | |

(52) U.S. Cl.
CPC .......... *C07D 405/04* (2013.01); *C07D 413/04* (2013.01); *C07D 403/04* (2013.01); *C07D 409/14* (2013.01); *C07D 401/12* (2013.01); *C07D 417/14* (2013.01); *C07D 413/14* (2013.01); *C07D 417/04* (2013.01); *C07D 403/14* (2013.01); *C07D 405/14* (2013.01); *C07D 241/44* (2013.01); *C07D 401/14* (2013.01); *C07D 409/04* (2013.01); *C07D 401/04* (2013.01)
USPC .......... 514/249; 540/599; 544/116; 544/353; 544/359; 546/152; 546/199; 546/268.1; 548/159; 548/217; 548/257; 548/305.1; 548/361.1; 548/373.1; 548/469; 548/518; 548/560; 548/950; 549/49; 549/355; 549/356; 549/398; 549/429; 549/434

(58) Field of Classification Search
CPC .......................... A61K 31/498; C07D 241/44
USPC .......... 514/249; 540/599; 544/116, 353, 359; 546/152, 199, 268.1; 548/159, 217, 548/257, 305.1, 361.1, 373.1, 469, 518, 548/560, 950; 549/49, 355, 356, 398, 429, 549/434
See application file for complete search history.

(56) References Cited

U.S. PATENT DOCUMENTS

| | | | |
|---|---|---|---|
| 6,331,555 | B1 | 12/2001 | Hirth |
| 7,189,724 | B2 | 3/2007 | An |
| 2003/0059917 | A1 | 3/2003 | McKnight |
| 2003/0207886 | A1 | 11/2003 | Plucker |
| 2004/0034028 | A1 | 2/2004 | Guevel |
| 2008/0194803 | A1 | 8/2008 | Sinclair |
| 2012/0225863 | A1* | 9/2012 | McCall et al. ........... 514/217.05 |

FOREIGN PATENT DOCUMENTS

| | | |
|---|---|---|
| CH | 419399 | 3/1967 |
| WO | 2005007099 | 1/2005 |
| WO | 2006076681 A2 | 7/2006 |
| WO | 2006079021 A2 | 7/2006 |
| WO | 2006091395 | 8/2006 |
| WO | 2007146747 A2 | 12/2007 |
| WO | 2010093808 A1 | 8/2010 |
| WO | 2010143168 A2 | 12/2010 |
| WO | 2010143169 A2 | 12/2010 |
| WO | 2010143170 A2 | 12/2010 |
| WO | 2011028947 A3 | 3/2011 |

OTHER PUBLICATIONS

Hackam, et al. JAMA, 296(14), 2006, 1731-1732.*
Jordan, V. C. Nature Reviews: Drug Discovery, 2, 2003, 205.*

* cited by examiner

*Primary Examiner* — Douglas M Willis
(74) *Attorney, Agent, or Firm* — Dennis A. Bennett; Brock Levin

(57) ABSTRACT

Disclosed herein are substituted quinoxaline carboxylic acids of Formula (I):

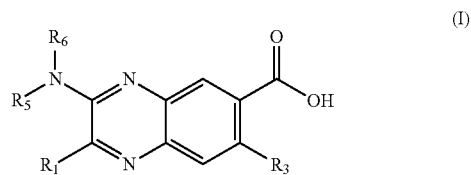

and compositions thereof, which may be useful as inhibitors of PAS Kinase (PASK) activity in a human or animal for the treatment of diseases such as diabetes mellitus.

8 Claims, No Drawings

SUBSTITUTED QUINOXALINE CARBOXYLIC ACIDS FOR THE INHIBITION OF PASK

CROSS REFERENCE TO RELATED APPLICATIONS

This application claims the benefit of priority of U.S. Provisional Applications No. 61/448,527, filed Mar. 2, 2011, No. 61/449,009, filed Mar. 3, 2011, and No. 61/448,533, filed Mar. 2, 2011, the disclosures of which are hereby incorporated by reference as if written herein in their entireties.

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

The regulation of glycogen metabolism is critical for the maintenance of glucose and energy homeostasis in mammals. Glycogen, a large branched polymer of glucose, acts as a reserve of carbon and energy in a variety of organisms. In mammals, the most important stores are found in the liver and skeletal muscle (1). Liver glycogen is required to efficiently buffer blood glucose levels during fasting, whereas muscle glycogen is primarily used locally as a fuel for muscle contraction (2). Dysregulation of glycogen metabolism has been implicated in the development of many diseases, including Type 2 diabetes mellitus (3, 4).

The synthesis of glycogen is primarily controlled through regulation of the enzyme glycogen synthase (GYS, various isoforms), which catalyzes bulk glycogen synthesis (5, 6, 7). The muscle isoform of glycogen synthase (GYS1) is inactivated by reversible phosphorylation that occurs at nine distinct sites within the enzyme (8, 9, 10). In the best characterized form of glycogen synthase, the phosphorylation sites are clustered at the N and C termini (14). Glycogen synthase kinase-3 (GSK-3), an insulin-dependent kinase which has long been implicated in the stepwise phosphorylation of four key sites in the C terminus of glycogen synthase including Ser-640 (one of the most important endogenous regulatory phosphorylation sites in mammalian glycogen synthase (15, 32) and Ser-644 (10, 11-13, 24, 25). GSK-3, however, is not the sole kinase that phosphorylates C-terminal regulatory sites; GSK-3-independent mechanisms also exist, since serine-to-alanine substitutions at Ser-7 and Ser-10 block GSK-3-mediated phosphorylation of the important regulatory sites Ser-640 and Ser-644, and phosphorylation at these sites still occurs.

PASK (purine-analog sensitive kinase, PAS kinase) is a PAS domain-containing serine/threonine kinase, and genetic experiments in *S. cerevisiae* yeast have implicated PASK as a physiological regulator of glycogen synthase and glycogen accumulation (16, 17). As with the entire glycogen synthase regulatory system, PASK is highly conserved from yeast to man. Human PASK (hPASK) phosphorylates glycogen synthase primarily at Ser-640, causing near complete inactivation. It is interesting to note that the exact site of PASK-dependent phosphorylation is similar but not identical in yeast and mammalian glycogen synthase (18, 19); yeast PASK phosphorylates glycogen synthase at the site analogous to Ser-644, four residues C-terminal (18). It appears that the hPASK mid region (residues 444-955) is required for efficient phosphorylation of glycogen synthase in vitro and for interaction with glycogen synthase in cells: an hPASK mutant (4955) lacking the noncatalytic N terminus was unable to efficiently phosphorylate glycogen synthase. Since this region is not required for the phosphorylation of generic, nonphysiological substrates, such as histones and synthetic peptides, it has been proposed that the mid region of hPASK is essential for substrate-targeting. A similar substrate region has been discovered in many protein kinases (26-29). Unlike GSK-3, the activity of hPASK has been shown to be independent of insulin and probably regulated instead by a more direct metabolic signal (23).

Genetic and proteomic screens using yeast PASK identified a number of substrates and implicated this kinase in the regulation of carbohydrate metabolism and translation (18). It has previously been shown that yeast PASK phosphorylates glycogen synthase in vitro and that strains lacking the PASK genes (PSK1 and PSK2) had elevated glycogen synthase activity and an approximately 5- to 10-fold accumulation of glycogen relative to wild-type strains, consistent with impaired ability to phosphorylate glycogen synthase in vivo (18). Because glycogen synthesis and translation are two processes tightly regulated in response to nutrient availability and because PAS domains are frequently involved in metabolic sensing, a role for PASK in the cellular response to metabolic status has been proposed. Indeed, it was recently demonstrated that mammalian PASK plays a role in the cellular response to nutrients. The catalytic activity of PASK in pancreatic islet β-cells is rapidly increased in response to glucose addition, and PASK is required for the glucose-responsive expression of some β-cell genes, including preproinsulin (23).

PASK catalytic activity is not responsive to glucose alone, however. The interaction between the hPASK midregion and glycogen synthase is regulated by at least two factors. First, the PAS domain of PAS kinase plays a negative role in regulating this interaction. If the PAS domain is deleted or disrupted, hPASK associates more stably with glycogen synthase. PAS domain function is usually controlled by the metabolic status of the host cell, as has been suggested for the PASK PAS domain (23). This observation raises the intriguing possibility that the hPASK-glycogen synthase interaction is regulated by the metabolic status of the cell, thereby enabling an additional layer of metabolic regulation of glycogen synthesis. Second, glycogen negatively regulates the hPASK-glycogen synthase interaction, which would initially seem counterintuitive, since glycogen would thereby stimulate its own continued synthesis. It is possible, however, that this mechanism exists to spatially coordinate the synthesis of glycogen. It is becoming increasingly apparent that glycogen is synthesized in cells in a highly organized spatial pattern (30). Perhaps one function of hPASK is to maintain free, unlocalized glycogen synthase in a phosphorylated, inactive form until it is properly localized to an existing, properly organized glycogen particle. These data strongly suggest that the hPASK midregion plays an important role in targeting hPASK catalytic activity to specific substrates within the cell.

Since hPASK has been recently implicated in glucose-sensing and glucose-responsive transcription, it appears likely that glucose signaling by means of hPASK affects glycogen metabolism in vivo. It is well established that derangement in glycogen metabolism is one of the hallmarks of both Type 1 and Type 2 diabetes (20) and related conditions (21), including a panoply of life-threatening cardiovascular conditions (22). Using PASK1 mice, it has further been demonstrated that PASK is indeed required for normal insulin secretion by pancreatic β cells, and that PASK deletion results in nearly complete resistance to the phenotypes caused by a high-fat diet, including obesity, insulin resistance and hepatic fat accumulation. Therefore, PASK inhibition would comprise a system for the metabolic control of glucose utilization and storage in mammalian cells, and offer a new method to treat metabolic diseases including but not limited to diabetes and its complications, the metabolic syndrome, insulin resistance, and various cardiovascular conditions.

The hallmarks of cancer, cellular overgrowth and hyperproliferation, require the rapid synthesis of all cellular materials, including protein and lipids. Both of these synthetic processes are controlled, to some extent, by PASK. As a result of these observations, it is possible that inhibition of PASK could be a viable therapeutic strategy for many cancers. By preventing the rapid synthesis of proteins and lipids, such an inhibitor should prevent the rapid and uncontrolled growth and division of cells that characterizes many cancers.

DETAILED DESCRIPTION OF THE INVENTION

Novel compounds and pharmaceutical compositions, certain of which have been found to inhibit PASK have been discovered, together with methods of synthesizing and using the compounds including methods for the treatment of PASK-mediated diseases in a patient by administering the compounds.

In certain embodiments of the present invention, a compound has structural Formula I:

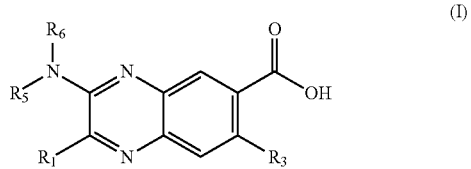

or a salt, stereoisomer, ester or prodrug thereof, wherein:
$R_1$ is chosen from aryl and heteroaryl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NO_2$, oxo, amino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and haloalkoxy;
$R_3$ is chosen from hydrogen, hydroxyl, halo, $C_1$-$C_5$ alkyl, and $C_1$-$C_5$ alkoxy, any of which may be optionally substituted;
$R_5$ and $R_6$ are independently chosen from hydrogen, $C_1$-$C_6$ alkyl, $C_1$-$C_7$ cycloalkyl, $C_1$-$C_7$ heterocycloalkyl, $C_1$-$C_6$ alkenyl, $C_1$-$C_6$ alkynyl, aryl, heteroaryl, aralkyl, haloalkyl, and heteroaralkyl, or taken together, $R_5$ and $R_6$ may form a heterocycloalkyl or heteroaryl, any of which may be optionally substituted; and
$R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

Certain compounds disclosed herein may possess useful PASK modulating activity, and may be used in the treatment or prophylaxis of a disease or condition in which PASK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating PASK. Other embodiments provide methods for treating a PASK-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PASK.

In further embodiments, compounds of Formula I are provided wherein
$R_1$ is phenyl and has one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy and $OCF_3$; and
$R_{12}$, $R_{12a}$ and $R_{12b}$ are independently chosen from hydrogen, $C_1$-$C_6$ alkyl, aryl, heteroaryl, aralkyl and heteroaralkyl, any of which may be optionally substituted.

In certain embodiments compounds of Formula I are provided wherein $R_5$ and $R_6$ are independently $C_1$-$C_6$ alkyl, cycloalkyl, heterocycloalkyl, and aryl, or taken together, $R_5$ and $R_6$ may form a heterocycloalkyl, any of which may be optionally substituted.

In certain embodiments compounds of Formula I are provided wherein $R_3$ is hydrogen.

In certain embodiments compounds of Formula I are provided wherein $R_5$ and $R_6$ are independently $C_1$-$C_6$ alkyl, or taken together, $R_5$ and $R_6$ may form a heterocycloalkyl which may be optionally substituted.

In certain embodiments of the present invention, a compound has structural Formula II:

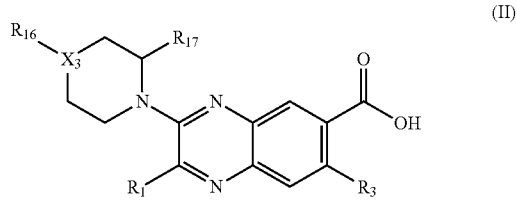

or a salt, stereoisomer, ester or prodrug thereof, wherein:
$R_1$ is chosen from aryl which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$;
$R_3$ is chosen from hydrogen, hydroxyl, halo, $C_1$-$C_5$ alkyl, and $C_1$-$C_5$ alkoxy, any of which may be optionally substituted;
$R_{12}$, $R_{12a}$ and $R_{12b}$ are independently chosen from hydrogen, $C_1$-$C_6$ alkyl, aryl, heteroaryl, aralkyl and heteroaralkyl, any of which may be optionally substituted;
$R_{16}$ is chosen from null, hydrogen, alkyl, $COR_{18}$, $SO_2R_{18}$, cycloalkyl, heterocycloalkyl, aryl, and heteroaryl any of which may be optionally substituted;
$R_{17}$ is chosen from hydrogen, $C_1$-$C_6$ alkyl and $C_1$-$C_6$ haloalkyl, any of which may be optionally substituted;
$R_{18}$ is chosen from hydrogen, $C_1$-$C_6$ alkyl, $C_1$-$C_6$ cycloalkyl, $C_1$-$C_6$ heterocycloalkyl, aryl, and heteroaryl, any of which may be optionally substituted; and
$X_3$ is chosen from CH, N, O, and a bond.

In further embodiments, compounds of Formula II are provided wherein $R_1$ is phenyl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$.

In further embodiments, compounds of Formula II are provided wherein $R_1$ is phenyl optionally substituted with one or more halo substituents.

In further embodiments, compounds of Formula II are provided wherein $X_3$ is chosen from CH and N.

In further embodiments, compounds of Formula II are provided wherein $R_{16}$ is hydrogen.

In further embodiments, compounds of Formula II are provided wherein $X_3$ is O and $R_{16}$ is null.

In certain embodiments of the present invention, a compound has structural Formula III:

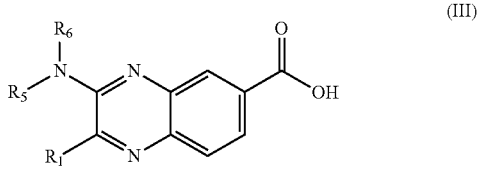

or a salt, stereoisomer, ester or prodrug thereof, wherein:

$R_1$ is chosen from aryl which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and $OCF_3$;

$R_5$ and $R_6$ are independently chosen from hydrogen, $C_1$-$C_6$ alkyl, $C_1$-$C_7$ cycloalkyl, $C_1$-$C_7$ heterocycloalkyl, aryl, heteroaryl, aralkyl, and heteroaralkyl, any of which may be optionally substituted; and $R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

In another embodiment, compounds of Formula III are provided wherein $R_1$ is phenyl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$.

In another embodiment, compounds of Formula III are provided wherein $R_1$ is phenyl optionally substituted with one or more halo substituents.

In another embodiment, compounds of Formula III are provided wherein $R_5$ and $R_6$ are independently chosen from hydrogen, $C_1$-$C_6$ alkyl, $C_1$-$C_7$ cycloalkyl, $C_1$-$C_7$ heterocycloalkyl, and aryl, any of which may be optionally substituted.

In another embodiment, compounds have structural Formula IV:

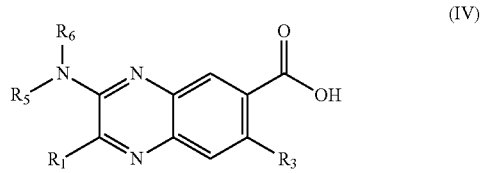

or a salt, ester, enantiomer or prodrug thereof, wherein:

$R_1$ is heteroaryl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, haloalkoxy, oxo, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, and $SO_2NHR_{12}$, any of which may be optionally substituted;

$R_3$ is hydrogen;

$R_5$ and $R_6$ are independently chosen from $C_1$-$C_6$ alkyl, $C_1$-$C_6$ branched alkyl, $C_1$-$C_7$ cycloalkyl, $C_1$-$C_7$ heterocycloalkyl, or taken together, $R_5$ and $R_6$ may form a heterocycloalkyl, any of which may be optionally substituted with one or more of $C_1$-$C_6$ alkyl, alkoxyalkyl, and $C_1$-$C_6$ haloalkyl; and $R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

Further provided is a compound having structural Formula IV, wherein $R_5$ and $R_6$ are independently chosen from $C_1$-$C_6$ alkyl, $C_1$-$C_6$ branched alkyl, and $C_1$-$C_7$ cycloalkyl.

Further provided is a compound as disclosed above for use as a medicament.

Further provided is a compound as disclosed above for use in the manufacture of a medicament for the prevention or treatment of a disease or condition ameliorated by the inhibition of PASK.

Further provided is a compound as disclosed above for use in the manufacture of a medicament for the prevention or treatment of a disease or condition ameliorated by the inhibition of PASK.

Further provided is a pharmaceutical composition comprising a compound as recited above together with a pharmaceutically acceptable carrier.

Further provided is a method of inhibiting PASK comprising contacting PASK with a compound as disclosed above.

Further provided is a method of treatment of a disease comprising the administration of a therapeutically effective amount of a compound as disclosed above to a patient in need thereof.

Further provided is the method as recited above wherein said disease is chosen from cancer and a metabolic disease.

Further provided is the method as recited above wherein said disease is a metabolic disease.

Further provided is the method as recited above wherein said metabolic disease is chosen from metabolic syndrome, diabetes, dyslipidemia, fatty liver disease, non-alcoholic steatohepatitis, obesity, and insulin resistance.

Further provided is the method disclosed above wherein said diabetes is Type II diabetes.

Further provided is the method as disclosed above wherein said dyslipidemia is hyperlipidemia.

Further provided is a method for achieving an effect in a patient comprising the administration of a therapeutically effective amount of a compound as disclosed above to a patient, wherein the effect is selected from the group consisting of reduction of triglycerides, reduction of cholesterol, and reduction of hemoglobin A1c.

Further provided is the method as disclosed above wherein said cholesterol is chosen from LDL and VLDL cholesterol.

Further provided is the method as disclosed above wherein said triglycerides are chosen from plasma triglycerides and liver triglycerides.

Further provided is a method of treatment of a PASK-mediated disease comprising the administration of:
 a. a therapeutically effective amount of a compound as disclosed above; and
 b. another therapeutic agent.

Not to be bound by any theory or mechanism, the compounds disclosed herein can be used to treat or modulate metabolic disease (including but not limited to diabetes, metabolic disorder, dyslipidemia, fatty liver disease, non-alcoholic steatohepatitis, obesity, and insulin resistance, as well as to reduce triglycerides, cholesterol, and hemoglobin A1c) and cancer.

As used herein, the terms below have the meanings indicated.

When ranges of values are disclosed, and the notation "from $n_1$ . . . to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be substituted or quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, 3,4-methylenedioxyphenyl and the like. The heterocycle groups may be optionally substituted unless specifically prohibited.

The term "hydrazinyl" as used herein, alone or in combination, refers to two amino groups joined by a single bond, i.e., —N—N— and not embodied in a ring.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aralkyl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PASK inhibitor" as used herein refers to a compound that exhibits an ($IC_{50}/EC_{50}$) with respect to PASK activity of no more than about 100 µM and more typically not more than about 50 µM, as measured in the PASK assay described generally hereinbelow. $IC_{50}$ is that concentration of inhibitors which reduces the activity of PASK to half-maximal level. Certain compounds disclosed herein have been discovered to exhibit inhibition against PASK.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound as disclosed herein, and at least one other agent selected from the group comprising:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPARδ agonist e.g. GI-262570;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor), PXR (pregnane X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; (3-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) an HDL increasing compound;

f) cholesterol absorption modulator such as etizimibe and KT6-971;

g) Apo-A1 analogues and mimetics;

h) thrombin inhibitors such as Ximelagatran;

i) aldosterone inhibitors such as anastrazole, fadrazole, and eplerenone;

j) inhibitors of platelet aggregation such as aspirin, and clopidogrel bisulfate;

k) estrogen, testosterone, a selective estrogen receptor modulator, and a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, and compounds decreasing the protein kinase activity such as a PDGF receptor tyrosine kinase inhibitor such as miatinib; and m) an agent interacting with a 5-HT3 receptor and/or an agent interacting with 5-HT4 receptor such as tegaserod described in the U.S. Pat. No. 5,510,353 as example 13, tegaserod hydrogen maleate, cisapride, and cilansetron.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PASK-mediated disorders in a human or animal subject in need of such treatment comprising administering to said subject an amount of a compound disclosed herein effective to reduce or prevent said disorder in the subject, optionally in combination with at least one additional agent that is known in the art. In a related aspect, certain embodiments provide therapeutic compositions comprising at least one compound disclosed herein in combination with one or more additional agents for the treatment of PASK-mediated disorders.

Recent studies have found that elevated medium glucose concentrations caused post-translational activation of PASK. It has also been demonstrated that PASK activity is required for glucose-stimulated insulin expression, as shown by studies in PASK1 mice. It has also been demonstrated that PASK deletion results in nearly complete resistance to the phenotypes caused by a high-fat diet, including obesity, insulin resistance and hepatic fat accumulation. It appears that PASK inhibition can provide an effective therapeutic strategy for the treatment of diseases, for example Type 2 diabetes, insulin resistance in general, and the metabolic syndrome.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing Type 2 diabetes, as well as PCOS (polycystic ovarian syndrome) in women and prostate cancer in men.

As described above, insulin resistance can be manifested in several ways, including Type 2 diabetes. Type 2 diabetes is the condition most obviously linked to insulin resistance. Compensatory hyperinsulinemia helps maintain normal glucose levels—often for decades, before overt diabetes develops. Eventually the beta cells of the pancreas are unable to overcome insulin resistance through hypersecretion. Glucose levels rise, and a diagnosis of diabetes can be made. Patients with Type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with Type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Increased insulin levels in insulin resistance have also been directly correlated with high very-low-density lipoprotein synthesis and increased plasma triglyceride levels.

Accordingly, also disclosed are methods of treating insulin resistance in a subject comprising selecting a subject in need of treatment for insulin resistance; and administering to the subject an effective amount of a compound that inhibits PASK.

Specific diseases to be treated by the compounds, compositions, and methods disclosed herein are those mediated at least in part, directly or indirectly, by PASK. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; for reducing hemoglobin A1c in a subject; or for treating disease; all comprising the administration of a therapeutic amount of a compound as described herein, to a patient in need thereof. In further embodiments, the disease to be treated may be a metabolic disease. In further embodiments, the metabolic disease may be chosen from: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be chosen from: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

In further embodiments, the metabolic disease may be a neurological disease known to be associated with metabolic disease and/or insulin resistance, such as Alzheimer's disease.

Additionally, the PASK modulators disclosed herein may be used to treat proliferative disorders such as cancers. Hematological and non-hematological cancers which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CLL), lymphomas, including Hodgkin's lymphoma and non-Hodgkin's lymphoma (low, intermediate, and high grade), malignancies of the brain, head and neck, breast, lung, reproductive tract, upper digestive tract, pancreas, liver, renal, bladder, prostate and colon/rectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

REFERENCES CITED

This application incorporates by reference United States Non-Provisional application Ser. No. 12/874,967, filed Sep. 2, 2010, the disclosure of which is hereby incorporated by reference as if written herein in its entirety. The following is a list of references cited herein which, while not necessarily comprehensive, is provided for the convenience of the reader. All references, patents, and patent applications cited herein are hereby incorporated by reference as if written herein in their entireties. When the teachings of these references contradict the teachings presented expressly herein, the present disclosure controls.

1. Roach, P. J. et al. (2001) in The Endocrine Pancreas and Regulation of Metabolism, eds. Chemington, A. D. & Jefferson, L. S. (Oxford Univ. Press, New York), pp. 609-647.
2. Bergstrom, J. et al. (1967) Acta Physiol. Scand. 71: 140-150.
3. Cline, G. W. et al. (1994) J. Clin. Invest. 94: 2369-2376.
4. Shulman, G. I. et al. G. (1990) N. Engl. J. Med. 322: 223-228.
5. Cohen, P. (1982) Nature 296: 613-620.
6. Roach, P. J. (1986) in The Enzymes, eds. Boyer, P. D. & Krebs, E. G. (Academic, Orlando, Fla.), Vol. 17: pp. 499-539.
7. Cohen, P. (1986) in The Enzymes, eds. Boyer, P. D. & Krebs, E. G. (Academic, Orlando, Fla.), Vol. 17: pp. 461-497.
8. Friedman, D. L. & Lamer, J. (1963) Biochemistry 128: 669-675.
9. Lamer, J. (1990) Adv. Enzymol. Relat. Areas Mol. Biol. 63: 173-231.
10. Roach, P. J. (1990) FASEB J. 4: 2961-2968.
11. Skurat, A. V., et al. (1994) J. Biol. Chem. 269: 25534-25542.
12. Flotow, H. & Roach, P. J. (1989) J. Biol. Chem. 264: 9126-9128.
13. Nakielny, S., Campbell, D. G. & Cohen, P. (1991) Eur. J. Biochem. 199: 713-722.
14. Wilson W A et al., *Proc Natl Acad Sci USA*. 2005 Nov. 15; 102(46):16596-601, FIG. 6
15. Skurat, A. V. & Roach, P. J. (1995) J. Biol. Chem. 270: 12491-12497.
16. Hardy, T. A. & Roach, P. J. (1993) J. Biol. Chem. 268: 23799-23805
17. Francois, J. & Parrou, J. L. (2001) FEMS Microbiol. Rev. 25: 125-145.
18. Rutter, J., Probst, B. L. & McKnight, S. L. (2002) Cell 111: 17-28.
19. Rutter, J et al. (2001) Proc. Natl. Acad. Sci. USA 98: 8991-8996.
20. Roden M, Bernroider E: *Best Pract Res Clin Endocrinol Metab*. 2003 September; 17(3):365-83
21. Van Steenbergen W, Lanckmans S: *Int J Obes Relat Metab Disord*. 1995 September; 19 Suppl 3:S27-36.

22. Arad M et al., *Circ Res.* 2007 Mar. 2; 100(4):474-88
23. da Silva Xavier, G. et al. (2004) Proc. Natl. Acad. Sci. USA 101: 8319-8324.
24. Picton, C. et al. (1982) FEBS Lett. 150: 191-196.
25. DePaoli-Roach, A. A. et al., (1983) J. Biol. Chem. 258: 10702-10709.
26. Elia, A. E. et al. (2003) Science 299: 1228-1231.
27. Gao, T. et al. (1997) Neuron 19: 185-196.
28. Wilson, W. A. et al. (1999) Mol. Cell. Biol. 19: 7020-7030.
29. Yedovitzky, M. et al. (1997) J. Biol. Chem. 272: 1417-1420.
30. Fernandez-Novell, J. M., et al. (2002) FEBS Lett. 531: 222-228.
31. Hao H-X. et al., "PAS kinase is required for normal cellular energy balance," *Proc. Natl. Acad. Sci.* (USA) v 104, pp 15466-15471, 2007.
32. Horton J D. et al., "Regulation of sterol regulatory element binding proteins in livers of fasted and refed mice," *Proc. Natl. Acad. Sci.* (USA) v 95, pp 5987-5992, 1998.
33. Evans M J et al., "A synthetic farnesoid X receptor (FXR) agonist promotes cholesterol lowering in models of dyslipidemia," *Am. J. Physiol. Gastrointest. Liver Physiol.* V296, G543-G552, 2009.
34. Hartman, H B. Et al., "Activation of farnesoid X receptor prevents atherosclerotic lesion formation in LDLR$^{-/-}$ and apoE$^{-/-}$ mice," *J. Lipid Res.*, v 50, 1090-1100, 2009.
35. Zhang, S. et al., "Farnesoid X receptor agonist WAY-362450 attenuates liver inflammation and fibrosis in murine model of non-alcoholic steatohepatitis," *J. of Hepatology*, v 51, 380-388, 2009.
36. Flatt, B. et al., "Discovery of XL335 (WAY-362450), a Highly Potent, Selective, and Orally Active Agonist of the Farnesoid X Receptor," *J. Med. Chem.*, v 52, 904-907, 2009.

General Synthetic Methods for Preparing Compounds

The following schemes can generally be used to practice the present invention.

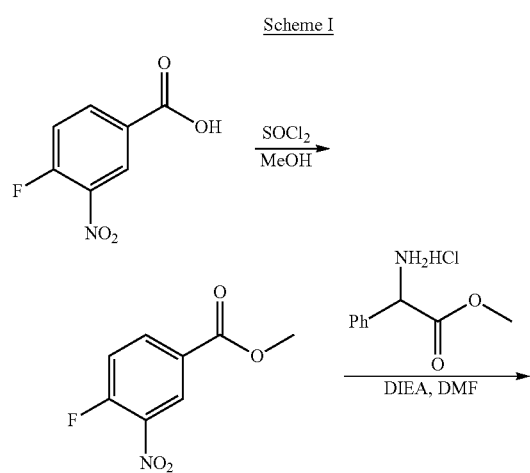

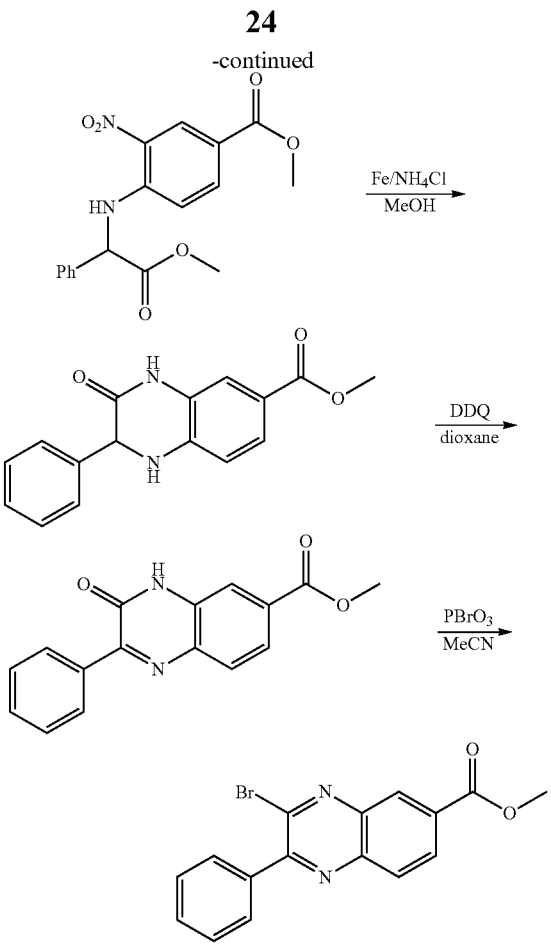

Step 1. Synthesis of methyl 4-fluoro-3-nitrobenzoate

Thionyl chloride (6.5 g, 54.62 mmol, 1.01 equiv) was added dropwise, with stirring at 0° C., to a methanolic solution (60 mL) of 4-fluoro-3-nitrobenzoic acid (10 g, 54.05 mmol, 1.00 equiv) in a 250-mL round-bottom flask, then stirred for 3 hr at reflux in an oil bath. The resulting mixture was concentrated under vacuum, diluted with 100 mL of EtOAc, and the pH of the solution adjusted to 7-8 with aqueous NaHCO$_3$ (saturated). The solution was then extracted with 6×50 mL of ethyl acetate, the organic layers combined and dried over anhydrous sodium sulfate, and concentrated under vacuum, affording 12.42 g (crude) of methyl 4-fluoro-3-nitrobenzoate as a white solid.

Step 2. Synthesis of methyl 4-(2-methoxy-2-oxo-1-phenylethylamino)-3-nitrobenzoate A solution of methyl 2-amino-2-phenylacetate hydrochloride (2.5 g, 12.38 mmol, 1.00 equiv) in DMF (30 mL), methyl 4-fluoro-3-nitrobenzoate (5 g, 25.13 mmol, 2.00 equiv), and DIEA (5 g, 38.76 mmol, 3.13 equiv) was reacted overnight at 30° C. in a 100-mL round-bottom flask. The reaction was then quenched by the addition of 200 mL of water, and the solids were collected by filtration. Purification via silica gel column (petroleum ether/EtOAc (50:1)) yielded 3.82 g (90%) of methyl 4-(2-methoxy-2-oxo-1-phenylethylamino)-3-nitrobenzoate as a yellow solid. LC-MS (ES, m/z): 345 [M+H]$^+$.

Step 3. Synthesis of methyl 3-oxo-2-phenyl-1,2,3,4-tetrahydroquinoxaline-6-carboxylate Iron (34.89 g, 623.04 mmol, 5.00 equiv) was added portionwise to a stirred solution of methyl 4-(2-methoxy-2-oxo-1-phenylethylamino)-3-nitrobenzoate (42.87 g, 124.62 mmol, 1.00 equiv) and aqueous NH₄Cl (32.1 g, 600.00 mmol, 5.00 equiv, 80 mL) in methanol (300 mL). The resulting solution was heated under reflux for 5 h. Upon cooling, the solids were filtered out. The resulting filtrate was concentrated under vacuum, affording 19.81 g (56%) of methyl 3-oxo-2-phenyl-1,2,3,4-tetrahydroquinoxaline-6-carboxylate as a yellow solid. LC-MS (ES, m/z): 283 [M+H]⁺.

Step 4. Synthesis of methyl 3-oxo-2-phenyl-3,4-dihydroquinoxaline-6-carboxylate DDQ (21.25 g, 93.6 mmol, 2.62 equiv) was added to a stirred solution of methyl 3-oxo-2-phenyl-1,2,3,4-tetrahydroquinoxaline-6-carboxylate (10.07 g, 35.7 mmol, 1.00 equiv) in dioxane (750 mL) and allowed to react, with stirring, overnight at room temperature. The solids were collected by filtration. The filter cake was washed with 2×500 mL of aqueous K₂CO₃ (saturated). This resulted in 7.29 g (crude) of methyl 3-oxo-2-phenyl-3,4-dihydroquinoxaline-6-carboxylate as an off-white solid. LC-MS (ES, m/z): 281 [M+H]⁺.

Step 5. Synthesis of methyl 3-bromo-2-phenylquinoxaline-6-carboxylate

A solution of methyl 3-oxo-2-phenyl-3,4-dihydroquinoxaline-6-carboxylate (2.1 g, 7.50 mmol, 1.00 equiv) and POBr₃ (21.5 g, 74.91 mmol, 10.00 equiv) in CH₃CN (120 mL) in a 1000-mL round-bottom flask was heated under reflux overnight in an oil bath. The resulting mixture was concentrated under vacuum; the pH value was adjusted to 7-8 with aqueous sodium bicarbonate (saturated), and the solution extracted with 4×100 mL of dichloromethane. The organic layers were combined, dried over anhydrous sodium sulfate and concentrated under vacuum, giving 2 g (78%) of methyl 3-bromo-2-phenylquinoxaline-6-carboxylate as a white solid. LC-MS (ES, m/z): 343 [M+H]⁺. ¹H-NMR (300 MHz, DMSO-d₆) 8.620-8.615 (d, J=1.5 Hz, 1H), 8.38-8.35 (q, J=3.3 Hz, 1H), 8.28-8.25 (d, J=8.7 Hz, 1H), 7.85-7.82 (q, J=6 Hz, 2H), 7.60-7.58 (t, J=2.4 Hz, 3H), 3.99 (s, 3H).

Scheme II

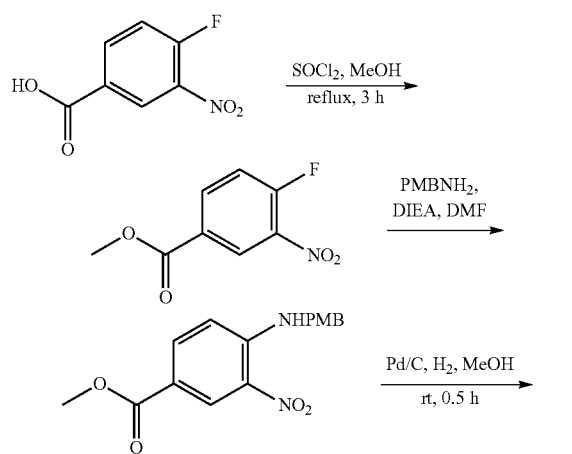

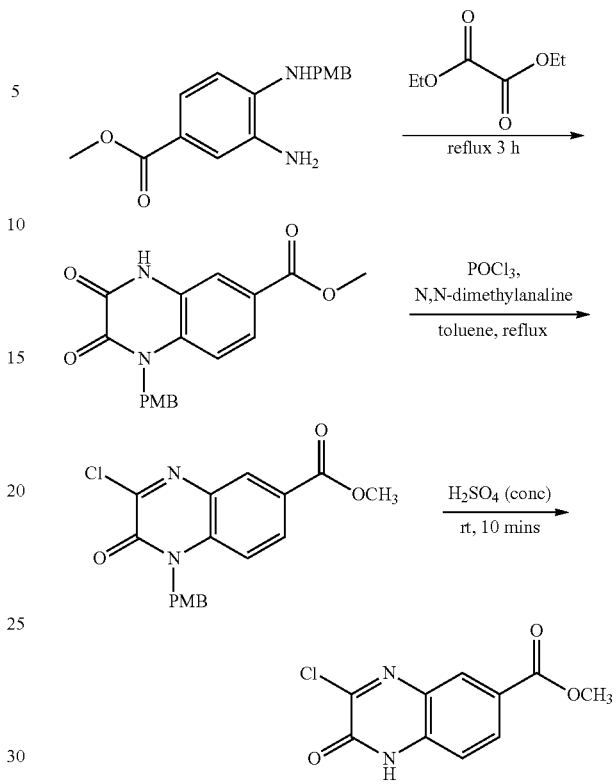

Scheme III

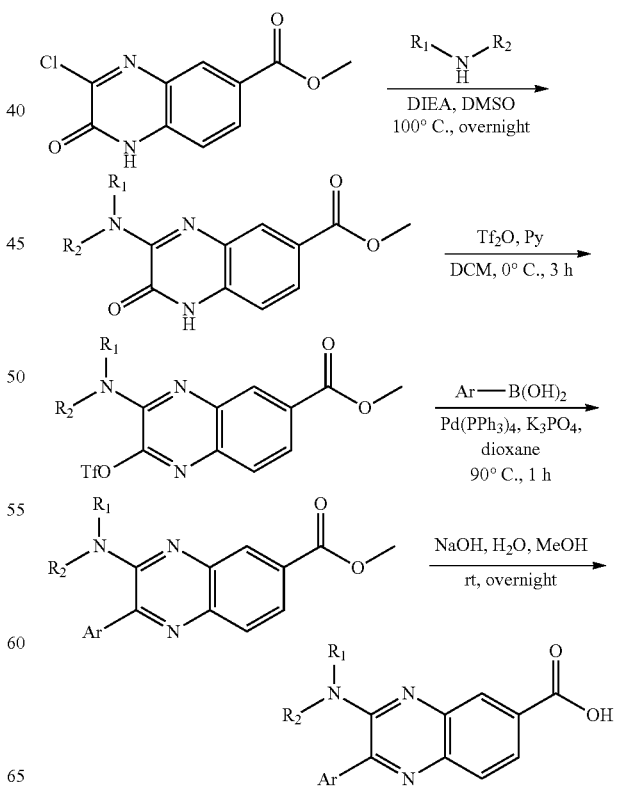

Scheme IV
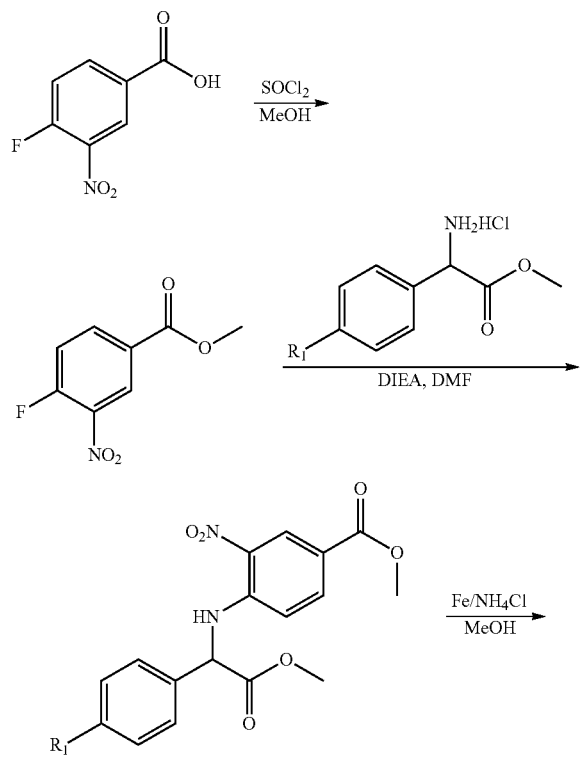
Scheme V
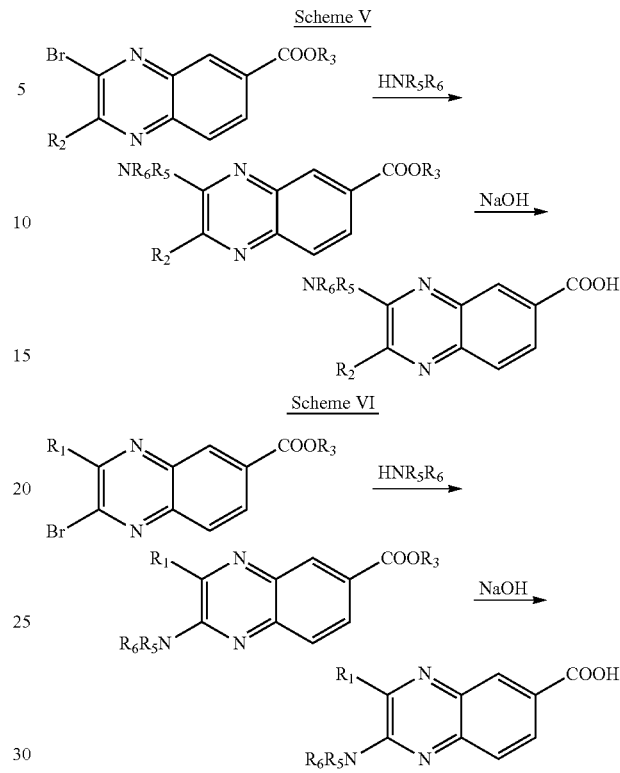
wherein $R_1$ and $R_2$ are each independently chosen from alkyl, cycloalkyl, heterocycloalkyl, aryl, heteroaryl, and amino any of which may be optionally substituted; and $R_3$ is chosen from hydrogen and optionally substituted alkyl.
Scheme VII
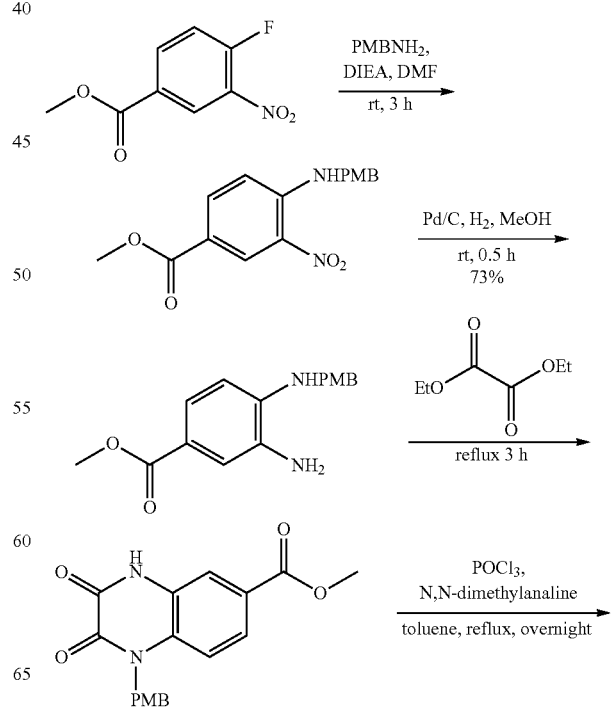
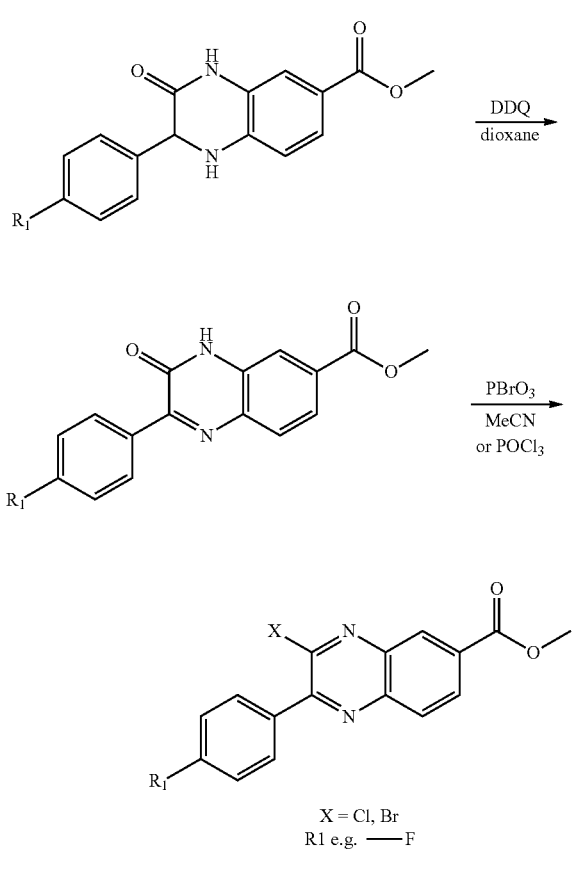

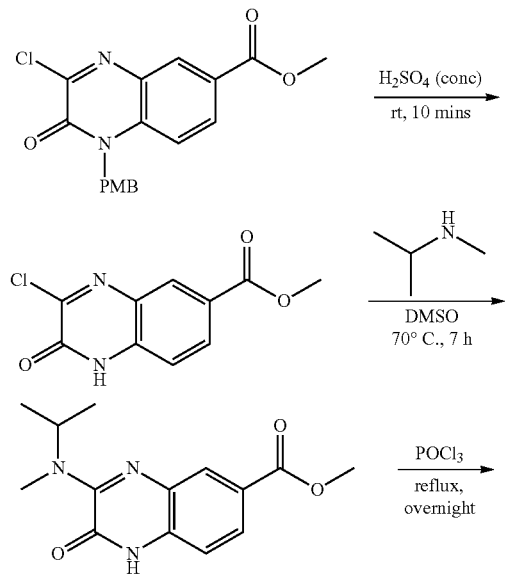

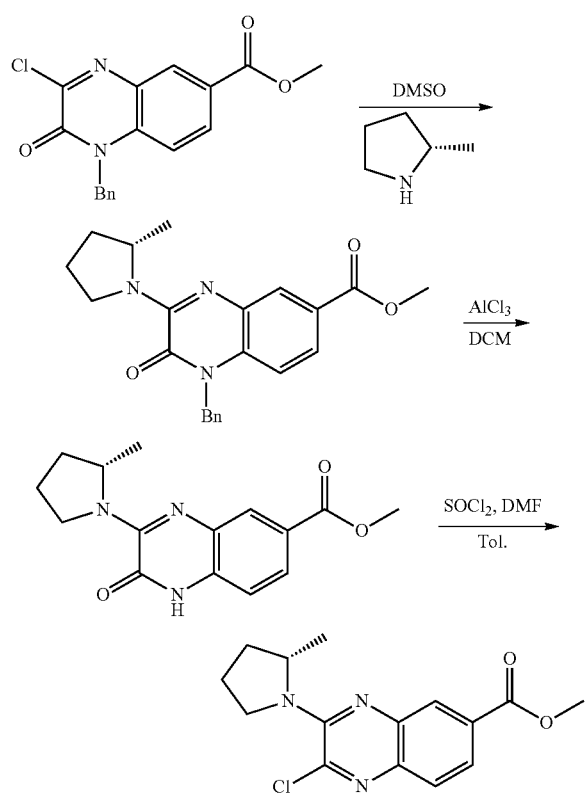

Scheme VIII

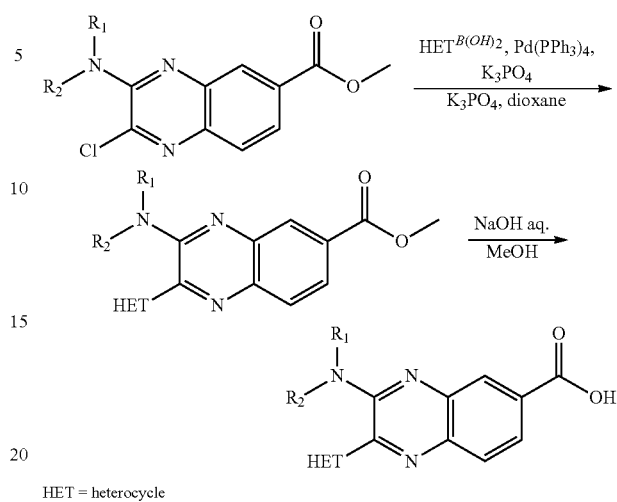

Scheme IX

HET = heterocycle

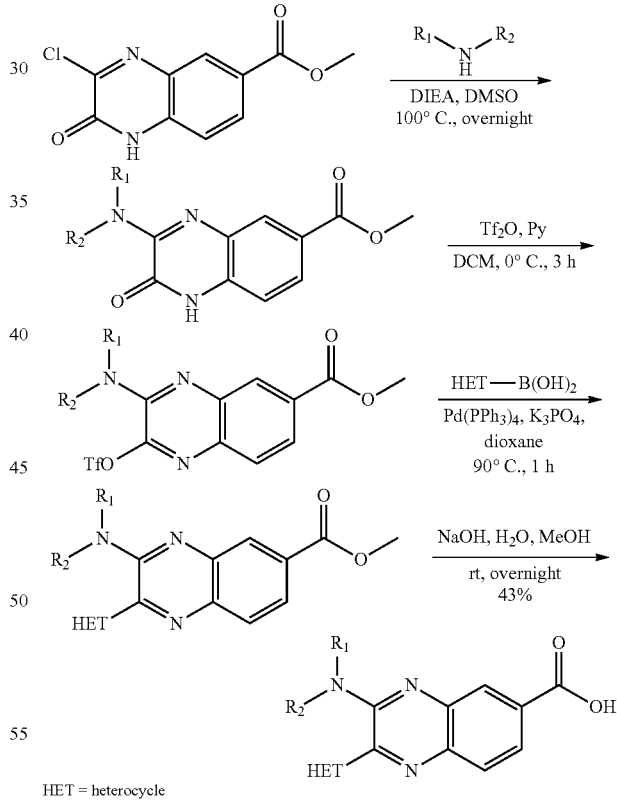

Scheme X

HET = heterocycle

The invention is further illustrated by the following examples, which can be made by the methods described herein or by one skilled in the art without undue experimentation, or can be purchased from commercial sources. Throughout the experimental protocols, the following abbreviations may be used. The list below is provided for convenience and is not intended to be inclusive.

| Abbreviation/Acronym | Meaning |
| --- | --- |
| Ar | Aryl |
| $Pd_2(dba)_3$ | Tris(dibenzylideneacetone)dipalladium(0) |
| BINAP | 2,2'-bis(diphenylphosphino)-1,1'-binaphthyl |
| NaOt-Bu | Sodium t-Butoxide |
| PE | Petroleum Ether |
| EA | Ethyl Acetate |
| DCM | Dichloromethane |
| TFA | Trifluoroacetic Acid |
| AcOH | Acetic Acid |
| DMF | N,N-Dimethylformamide |
| DIEA | N,N-Diisopropylethylamine |
| MeOH | Methanol |
| THF | Tetrahydrofuran |
| BOC | N-t-butoxycarbonyl |
| Tol | Toluene |
| DMSO | Dimethyl Sulfoxide |
| PCy3 | Tricyclohexylphosphine |
| TLC | Thin Layer Chromatography |
| X-Phos | 2-Dicyclohexylphosphino-2',4',6'-triisopropylbiphenyl |
| DDQ | 2,3-dichloro-5,6-dicyanobenzoquinone |

Example 1

2-(Benzofuran-3-yl)-3-(isopropyl(methyl)amino)quinoxaline-6-carboxylic acid

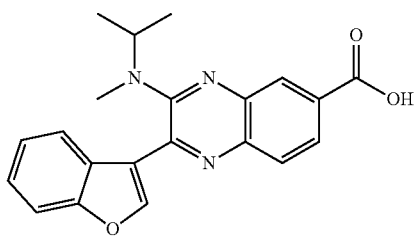 [SMILES: CC(C)N(C)c1nc2cc(C(=O)O)ccc2nc1-c1coc2ccccc12]

Step 1. Methyl 2-(benzofuran-3-yl)-3-(isopropyl(methyl)amino)quinoxaline-6-carboxylate

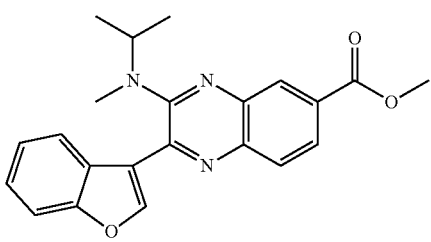 [SMILES: COC(=O)c1ccc2nc(-c3coc4ccccc34)c(N(C)C(C)C)nc2c1]

To a solution of methyl 2-chloro-3-(isopropyl(methyl)amino)quinoxaline-6-carboxylate (Scheme I, 150 mg, 0.51 mmol) in 1,4-dioxane (3 mL) was added 2-(benzofuran-3-yl)-4,4,5,5-tetramethyl-1,3,2-dioxaborolane (312 mg, 1.28 mmol), $K_3PO_4$ (326 mg, 1.53 mmol), $Pd(PPh_3)_4$ (30 mg, 0.03 mmol) and water (3 drops). After stirring 40 min at 95° C. under nitrogen atmosphere, the reaction mixture was dissolved in water (10 mL), extracted with dichloromethane (3×30 mL), dried over anhydrous magnesium sulfate and concentrated under reduced pressure to afford a residue, which was purified by a silica gel column with 1% ethyl acetate in petroleum ether to afford methyl 2-(benzofuran-3-yl)-3-(isopropyl(methyl)amino)quinoxaline-6-carboxylate as a light yellow solid (110 mg, 57%).

LC/MS: (ES, m/z): [M+H]$^+$ 376.0

$^1$H-NMR (300 MHz, DMSO) δ 8.75 (s, 1H), 8.25-8.31 (m, 2H), 7.98-8.06 (m, 2H), 7.72-7.75 (m, 1H), 7.41-7.46 (m, 2H), 4.24-4.28 (t, J=6.6 Hz, 1H), 3.93 (s, 3H), 2.76 (s, 3H), 1.09 (d, J=6.6 Hz, 6H)

Step 2. 2-(Benzofuran-3-yl)-3-(isopropyl(methyl)amino)quinoxaline-6-carboxylic acid

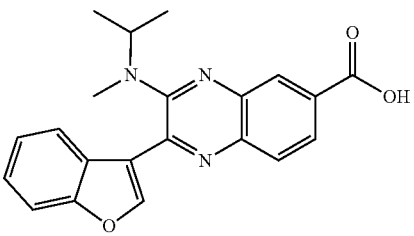 [SMILES: CC(C)N(C)c1nc2cc(C(=O)O)ccc2nc1-c1coc2ccccc12]

To a solution of methyl 2-(benzofuran-3-yl)-3-(isopropyl(methyl)amino)quinoxaline-6-carboxylate (100 mg, 0.27 mmol) in tetrahydrofuran (20 mL) and water (1 mL) was added sodium hydroxide (105 mg, 2.62 mmol). After stirring overnight at room temperature, the reaction mixture was concentrated under reduced pressure to afford a residue, which was dissolved in water (10 mL), the pH was adjusted to 6 with HCl (3N) and filtered to give 2-(benzofuran-3-yl)-3-(isopropyl(methyl)amino)quinoxaline-6-carboxylic acid as a light yellow solid (35.7 mg, 37%).

LC/MS (ES, m/z): [M+H]$^+$ 362.0

$^1$H-NMR (300 MHz, DMSO) δ 8.75 (s, 1H), 8.25-8.28 (t, J=4.2 Hz, 2H), 8.00 (d, J=7.2 Hz, 2H), 7.72-7.75 (t, J=4.5 Hz, 1H), 7.41-7.46 (m, 2H), 4.17-4.23 (t, J=6.6 Hz, 1H), 2.76 (s, 3H), 1.08 (d, J=6.6 Hz, 6H)

Example 2

3-(Isopropyl(methyl)amino)-2-(1H-pyrazol-4-yl)quinoxaline-6-carboxylic acid

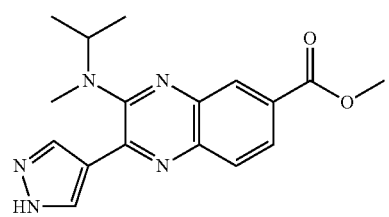 [SMILES: COC(=O)c1ccc2nc(-c3cn[nH]c3)c(N(C)C(C)C)nc2c1]

Step 1. Methyl 3-(isopropyl(methyl)amino)-2-(1H-pyrazol-4-yl)quinoxaline-6-carboxylate

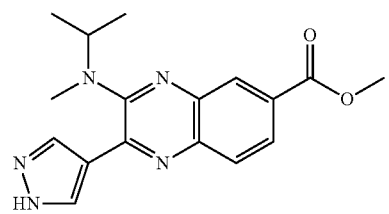 [SMILES: COC(=O)c1ccc2nc(-c3cn[nH]c3)c(N(C)C(C)C)nc2c1]

To a solution of methyl 2-chloro-3-(isopropyl(methyl)amino)quinoxaline-6-carboxylate (Scheme I, 200.0 mg, 0.68 mmol) in dioxane (3 mL) was added 1H-pyrazol-4-ylboronic acid (172.0 mg, 1.54 mmol), K$_3$PO$_4$ (326.0 mg, 1.54 mmol), Pd(PPh$_3$)$_4$ (29.6 mg, 0.03 mmol) and 3 drops water. The resulting solution was stirred for 20 min at 90° C. with an inert atmosphere of nitrogen and then diluted with water (20 mL), extracted with dichloromethane (4×20 mL), dried over anhydrous magnesium sulfate and concentrated under vacuum. The residue was purified by a silica gel column with 2%-10% ethyl acetate in petroleum ether to afford methyl 3-(isopropyl(methyl)amino)-2-(1H-pyrazol-4-yl)quinoxaline-6-carboxylate as a yellow solid (130 mg, 58.6%).

LC/MS (ES, m/z): [M+H]$^+$ 326.0

$^1$H-NMR (300 MHz, DMSO), δ 13.2 (s, 1H), 8.26 (d, J=1.5 Hz, 3H), 7.69-7.99 (m, 2H), 4.14-4.23 (m, 1H), 3.92 (s, 3H), 2.76 (s, 3H), 1.12 (d, J=6.6 Hz, 2H)

Step 2. 3-(Isopropyl(methyl)amino)-2-(1H-pyrazol-4-yl)quinoxaline-6-carboxylic acid

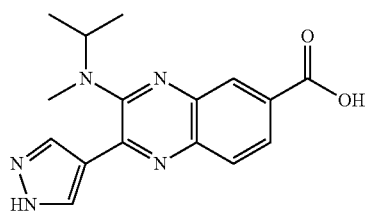 [SMILES: CC(C)N(C)c1nc2cc(C(=O)O)ccc2nc1-c1cn[nH]c1]

To a solution of methyl 3-(isopropyl(methyl)amino)-2-(1H-pyrazol-4-yl)quinoxaline-6-carboxylate (130.0 mg, 0.40 mmol,) in methanol (20 mL) and water (1 mL) was added lithium hydroxide hydrate (50.0 mg, 1.12 mmol). The resulting solution was stirred overnight at room temperature and then concentrated under vacuum. The residue was diluted with water (10 mL) and adjusted to pH 5 with citric acid (1N). The product were collected by filtration to afford 3-(isopropyl(methyl)amino)-2-(1H-pyrazol-4-yl)quinoxaline-6-carboxylic acid as yellow solid (64.7 mg, 52%).

LC/MS (ES, m/z): [M+H]$^+$ 312.0

$^1$H-NMR (300 MHz, DMSO), 13.2 (s, 1H), 8.25-8.28 (t, J=1.8 Hz, 3H), 7.96-7.99 (m, 1H), 7.87 (d, J=8.7 Hz, 1H), 4.11-4.20 (m, 1H), 2.76 (s, 3H), 1.11 (d, J=6.6 Hz, 2H).

Example 3

3-(Isopropyl(methyl)amino)-2-(6-methoxypyridin-3-yl)quinoxaline-6-carboxylic acid

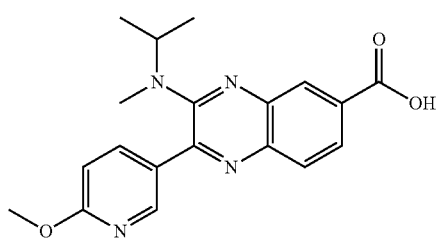 [SMILES: COc1ccc(-c2nc3ccc(C(=O)O)cc3nc2N(C)C(C)C)cn1]

Step 1. Methyl 3-(isopropyl(methyl)amino)-2-(6-methoxypyridin-3-yl)quinoxaline-6-carboxylate

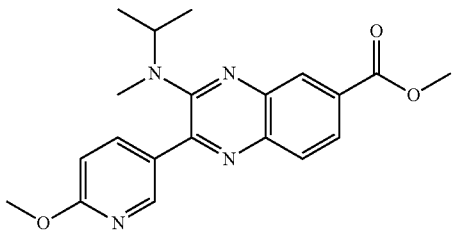

To a solution of methyl 2-chloro-3-(isopropyl(methyl)amino)quinoxaline-6-carboxylate (Scheme I, 120 mg, 0.41 mmol) in dioxane (3 mL) was added K$_3$PO$_4$ (257 mg, 1.22 mmol), 6-methoxypyridin-3-ylboronic acid (187 mg, 1.22 mmol) and Pd(PPh$_3$)$_4$ (23.54 mg, 0.02 mmol) with stirring for 1 h at 90° C. in an oil bath with an inert atmosphere of nitrogen. The reaction mixture was concentrated under vacuum to get a residue, which was purified by a silica gel column with 1%-2% ethyl acetate in petroleum ether to afford methyl 3-(isopropyl(methyl)amino)-2-(6-methoxypyridin-3-yl)quinoxaline-6-carboxylate as a light yellow solid (120 mg, 80%).

$^1$H NMR (300 MHz, DMSO) δ 13.01 (m, 1H), 8.27 (t, J=1.2 Hz, 1H), 8.18-8.21 (m, 1H), 7.96 (m, 2H), 6.97-7.01 (m, 2H), 4.17-4.26 (m, 1H), 3.92 (t, 6H), 2.68 (s, 3H), 1.08 (d, J=6.60 Hz, 6H)

Step 2. 3-(Isopropyl(methyl)amino)-2-(6-methoxypyridin-3-yl)quinoxaline-6-carboxylic acid

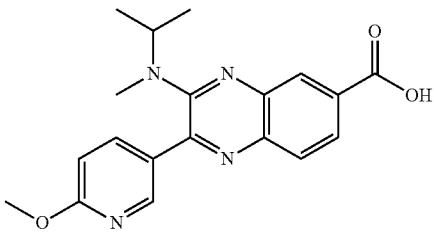 [SMILES: COc1ccc(-c2nc3ccc(C(=O)O)cc3nc2N(C)C(C)C)cn1]

To a solution of methyl 3-(isopropyl(methyl)amino)-2-(6-methoxypyridin-3-yl)quinoxaline-6-carboxylate (140 mg, 0.38 mmol) in methanol (25 mL) was added sodium hydroxide (45.9 mg, 1.15 mmol) with stirring overnight at room temperature. The reaction mixture was concentrated under vacuum, dissolved in water (30 mL) and adjusted to pH 6 with HCl (3N). The product were collected by filtration to afford 3-(isopropyl(methyl)amino)-2-(6-methoxypyridin-3-yl)quinoxaline-6-carboxylic acid as a light yellow solid (105 mg, 78%). LC/MS (ES, m/z): [M+H]$^+$ 352.0

$^1$H-NMR (300 MHz, DMSO) δ 13.15 (s, 1H), 8.70 (d, J=1.8 Hz, 1H), 8.18-8.27 (m, 2H), 7.95 (d, J=1.20 Hz, 2H), 6.97-7.00 (m, 1H), 4.19 (m, 1H), 3.94 (s, 3H), 2.69 (s, 3H), 1.08 (d, J=6.60 Hz, 6H)

Example 4

2-(1H-Indazol-6-yl)-3-(isopropyl(methyl)amino)quinoxaline-6-carboxylic acid

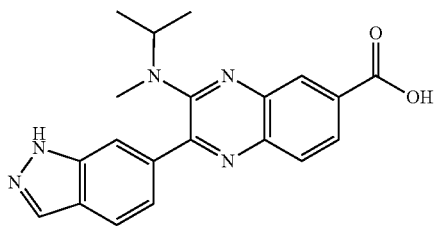 [SMILES: CC(C)N(C)c1nc2cc(C(=O)O)ccc2nc1-c1ccc2cn[nH]c2c1]

Step 1. Methyl 2-(1H-indazol-6-yl)-3-(isopropyl(methyl)amino)quinoxaline-6-carboxylate

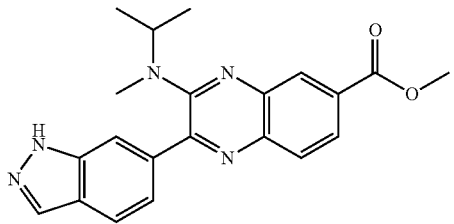 [SMILES: COC(=O)c1ccc2nc(-c3ccc4cn[nH]c4c3)c(N(C)C(C)C)nc2c1]

To a solution of methyl 2-chloro-3-(isopropyl(methyl)amino)quinoxaline-6-carboxylate (Scheme I, 200.0 mg, 0.68 mmol) in 1,4-dioxane (1 mL) was added 1H-indazol-6-ylboronic acid (386.0 mg, 2.38 mmol), K₃PO₄ (434.0 mg, 2.05 mmol), Pd(PPh₃)₄ (39.0 mg, 0.03 mmol) under nitrogen atmosphere. After stirring 20 min at 90° C., the reaction mixture was dissolved in dichloromethane (30 mL), washed with water (3×20 mL), dried over anhydrous magnesium sulfate and concentrated under reduced pressure to afford a residue, which was purified by a silica gel column with 1%-10% ethyl acetate in petroleum ether to afford methyl 2-(1H-indazol-6-yl)-3-(isopropyl(methyl)amino)quinoxaline-6-carboxylate as a light yellow solid (200 mg, 78%).

LC/MS (ES, m/z): [M+H]$^+$ 376.0

$^1$H-NMR (300 MHz, CDCl$_3$) δ 8.55 (s, 1H), 8.17 (s, 1H), 8.05-8.10 (m, 2H), 7.99 (d, J=8.4 Hz, 1H), 7.87 (d, J=8.4 Hz, 1H), 7.70 (d, J=8.4 Hz, 1H), 7.48-7.65 (m, 1H), 4.27-4.31 (t, J=6.6 Hz, 1H), 4.01 (s, 3H), 2.77 (s, 3H), 1.08 (d, J=6.6 Hz, 6H).

Step 2. 2-(1H-Indazol-6-yl)-3-(isopropyl(methyl)amino)quinoxaline-6-carboxylic acid

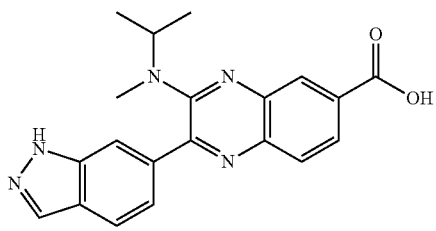 [SMILES: CC(C)N(C)c1nc2cc(C(=O)O)ccc2nc1-c1ccc2cn[nH]c2c1]

To a solution of methyl 2-(1H-indazol-6-yl)-3-(isopropyl(methyl)amino)quinoxaline-6-carboxylate (195.0 mg, 0.52 mmol) in tetrahydrofuran (20 mL) was added LiOH.H₂O (25.0 mg, 1.04 mmol) and water (1 mL). After stirring overnight at room temperature, the reaction mixture was concentrated under reduced pressure to afford a residue, which was dissolved in water (30 mL) and adjusted to pH 6 with hydrochloric acid (3N) and filtered to give 2-(1H-indazol-6-yl)-3-(isopropyl(methyl)amino)quinoxaline-6-carboxylic acid as a light yellow solid (121.5 mg, 65%).

LC/MS (ES, m/z): [M+H]$^+$ 362.0

$^1$H-NMR (300 MHz, DMSO) δ 13.23 (s, 1H), 8.28 (s, 1H), 8.16 (d, J=0.6 Hz, 1H), 8.05 (d, J=0.6 Hz, 1H), 7.89-7.99 (m, 3H), 7.57-7.62 (m, 1H), 4.17-4.22 (t, J=6.8 Hz, 1H), 2.69 (s, 3H), 1.01 (d, J=6.6 Hz, 6H).

Example 5

3-(Isopropyl(methyl)amino)-2-(1-methyl-1H-indazol-6-yl)quinoxaline-6-carboxylic acid

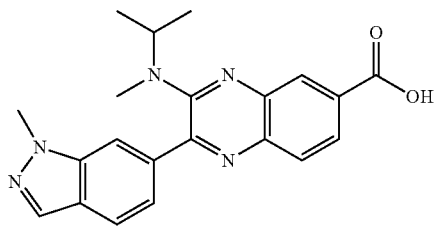 [SMILES: CC(C)N(C)c1nc2cc(C(=O)O)ccc2nc1-c1ccc2cnn(C)c2c1]

Step 1. Methyl 3-(isopropyl(methyl)amino)-2-(1-methyl-1H-indazol-6-yl)quinoxaline-6-carboxylate

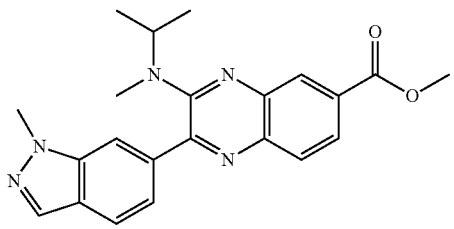 [SMILES: COC(=O)c1ccc2nc(-c3ccc4cnn(C)c4c3)c(N(C)C(C)C)nc2c1]

To a solution of methyl 2-chloro-3-(isopropyl(methyl)amino)quinoxaline-6-carboxylate (Scheme I, 180.0 mg, 0.61 mmol) in dioxane (1 mL) was added 1-methyl-1H-indazol-6-ylboronic acid (276.0 mg, 1.57 mmol), K₃PO₄ (391.2 mg, 1.85 mmol), and Pd(PPh₃)₄ (35.0 mg, 0.03 mmol) under nitrogen atmosphere. After stirring 20 min at 90° C., the reaction mixture was dissolved in dichloromethane (30 mL), washed with water (3×20 mL), dried over anhydrous magnesium sulfate and concentrated under reduced pressure to afford a residue, which was purified by a silica gel column with 0.05%-0.2% ethyl acetate in petroleum ether to afford methyl 3-(isopropyl(methyl)amino)-2-(1-methyl-1H-indazol-6-yl)quinoxaline-6-carboxylate as a light yellow solid (70 mg, 29%).

LC/MS (ES, m/z): [M+H]$^+$ 390.0

$^1$H-NMR (300 MHz, CDCl$_3$) δ 8.55 (d, J=2.4 Hz, 1H), 7.99-8.09 (m, 4H), 7.82-7.85 (m, 1H), 7.65-7.68 (m, 1H), 4.25-4.32 (m, 1H), 4.18 (s, 3H), 4.01 (s, 3H), 2.77 (s, 3H), 1.08 (d, J=6.6 Hz, 6H).

Step 2. 3-(Isopropyl(methyl)amino)-2-(1-methyl-1H-indazol-6-yl)quinoxaline-6-carboxylic acid

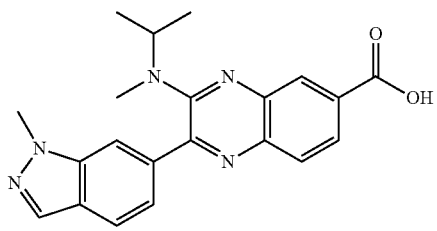 [SMILES: CC(C)N(C)c1nc2cc(C(=O)O)ccc2nc1-c1ccc2cnn(C)c2c1]

To a solution of methyl 3-(isopropyl(methyl)amino)-2-(1-methyl-1H-indazol-6-yl)quinoxaline-6-carboxylate (70 mg, 0.18 mmol) in tetrahydrofuran (20 mL) was added LiOH.H$_2$O (9.0 mg, 0.36 mmol) and water (1 mL). After stirring overnight at room temperature, the reaction mixture was concentrated under reduced pressure to afford a residue, which was dissolved in water (30 mL), adjusted the pH to 6 with hydrochloric acid (3N), and filtered to give 3-(isopropyl(methyl)amino)-2-(1-methyl-1H-indazol-6-yl)quinoxaline-6-carboxylic acid as a light yellow solid (20.5 mg, 30%).

LC/MS (ES, m/z): [M+H]$^+$ 376.0

$^1$H-NMR (300 MHz, DMSO) δ 13.20 (s, 1H), 8.28 (s, 1H), 8.20 (d, J=2.1 Hz, 2H), 7.88-7.99 (m, 2H), 7.59 (d, J=9.6 Hz, 1H), 4.18-4.27 (m, 1H), 4.12 (s, 3H), 2.68 (s, 3H), 1.01 (d, J=6.6 Hz, 6H)

Example 6

3-(Isopropyl(methyl)amino)-2-(5-methoxy-1H-indol-2-yl)quinoxaline-6-carboxylic acid

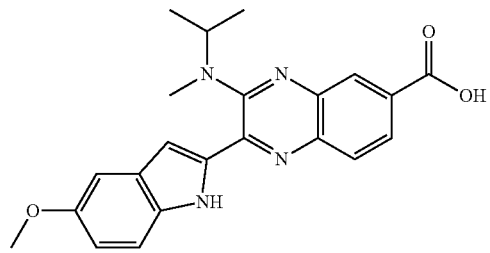 [SMILES: COc1ccc2[nH]c(-c3nc4ccc(C(=O)O)cc4nc3N(C)C(C)C)cc2c1]

Step 1. Methyl 2-(1-(tert-butoxycarbonyl)-5-methoxy-1H-indol-2-yl)-3-(isopropyl(methyl)amino)quinoxaline-6-carboxylate

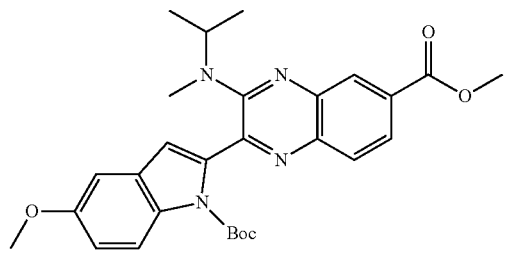

To a solution of methyl 2-chloro-3-(isopropyl(methyl)amino)quinoxaline-6-carboxylate (200.0 mg, 0.68 mmol) in 1,4-dioxane (1 mL) was added 1-(tert-butoxycarbonyl)-5-methoxy-1H-indol-2-ylboronic acid (320.0 mg, 1.40 mmol), K$_3$PO$_4$ (440.0 mg, 2.08 mmol), Pd(PPh$_3$)$_4$ (40.0 mg, 0.03 mmol) under nitrogen atmosphere. After stirring 1 h at 90° C., the reaction mixture was dissolved in dichloromethane (50 mL), washed with water (3×20 mL), dried over anhydrous magnesium sulfate and concentrated under reduced pressure to afford a residue, which was purified by a silica gel column with 0.1%-1% ethyl acetate in petroleum ether to afford methyl 2-(1-(tert-butoxycarbonyl)-5-methoxy-1H-indol-2-yl)-3-(isopropyl(methyl)amino)quinoxaline-6-carboxylate as a light yellow solid (280.0 mg, 81%).

LC/MS (ES, m/z): [M+H]$^+$ 505.1

$^1$H-NMR (300 MHz, CDCl$_3$) δ 8.61 (d, J=1.5 Hz, 1H), 8.05-8.13 (m, 2H), 7.95 (d, J=8.4 Hz, 1H), 7.01-7.10 (m, 2H), 6.94 (s, 1H), 4.21-4.25 (t, J=6.6 Hz, 1H), 4.01 (s, 3H), 3.90 (s, 3H), 2.82 (s, 3H), 1.28 (d, J=7.5 Hz, 9H), 1.07 (d, J=6.6 Hz, 6H)

Step 2. Methyl 3-(isopropyl(methyl)amino)-2-(5-methoxy-1H-indol-2-yl)quinoxaline-6-carboxylate

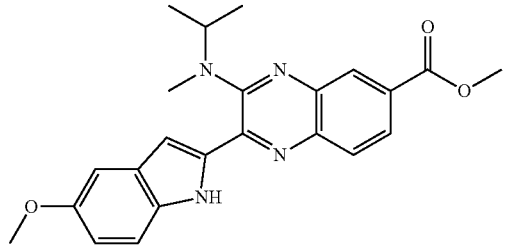

A solution of methyl 2-(1-(tert-butoxycarbonyl)-5-methoxy-1H-indol-2-yl)-3-(isopropyl(methyl)amino)quinoxaline-6-carboxylate (180.0 mg, 0.36 mmol) in 20% TFA/DCM (30 mL) was stirred overnight at room temperature and then quenched by the addition of water (100 ml). The reaction mixture was adjusted to pH 7 with aq. sodium bicarbonate, extracted with chloroform, dried over anhydrous magnesium sulfate and concentrated under reduced pressure. The residue was purified by a silica gel column with 0.1%-1% methanol in dichloromethane to afford methyl 3-(isopropyl(methyl)amino)-2-(5-methoxy-1H-indol-2-yl)quinoxaline-6-carboxylate as a light yellow solid (100.0 mg, 69%).

LC/MS (ES, m/z): [M+H]$^+$ 405.0

$^1$H-NMR (300 MHz, DMSO) δ 11.64 (s, 1H), 8.29 (d, J=1.2 Hz, 1H), 7.96-8.03 (m, 2H), 7.41 (d, J=8.7 Hz, 1H), 7.24 (d, J=8.7 Hz, 1H), 7.14 (d, J=8.7 Hz, 1H), 6.85-6.88 (m, 1H), 4.28-4.33 (t, J=6.8 Hz, 1H), 3.93 (s, 3H), 3.78 (s, 3H), 2.85 (s, 3H), 1.16 (d, J=6.6 Hz, 6H)

Step 3. 3-(Isopropyl(methyl)amino)-2-(5-methoxy-1H-indol-2-yl)quinoxaline-6-carboxylic acid

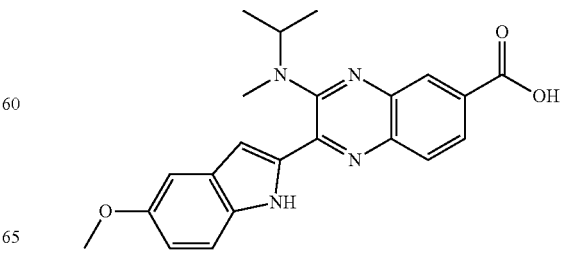

To a solution of methyl 3-(isopropyl(methyl)amino)-2-(5-methoxy-1H-indol-2-yl)quinoxaline-6-carboxylate (100.0 mg, 0.25 mmol) in methanol (30 mL) was added sodium hydroxide (20.0 mg, 0.50 mmol) in water (1 mL) and stirred overnight at room temperature. The reaction mixture was concentrated under vacuum and dissolved in water (10 mL), adjusted to pH 6 with hydrochloric acid (3N). The solid was precipitated and filtered to afford 3-(isopropyl(methyl)amino)-2-(5-methoxy-1H-indol-2-yl)quinoxaline-6-carboxylic acid as a light yellow solid as a light yellow solid (23.5 mg, 24%).

LC/MS (ES, m/z): [M+H]$^+$ 391.0

$^1$H-NMR (300 MHz, DMSO) δ 11.55 (s, 1H), 8.25 (s 1H), 8.04 (d, J=8.7 Hz, 1H), 7.84 (d, J=7.5 Hz, 1H), 7.41 (d, J=8.7 Hz, 1H), 7.23 (s, 1H), 7.13 (d, J=1.8 Hz, 1H), 6.82-6.86 (m, 1H), 4.16-4.23 (m, 1H), 3.77 (s, 3H), 2.83 (s, 3H), 1.14 (d, J=6.6 Hz, 6H)

Example 7

2-(5-Bromopyridin-3-yl)-3-(isopropyl(methyl)amino)quinoxaline-6-carboxylic acid

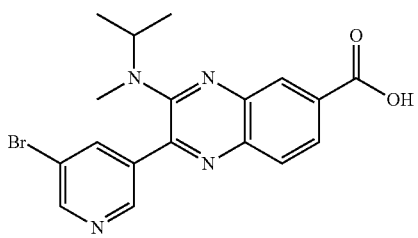 [SMILES: CC(C)N(C)c1nc2cc(C(=O)O)ccc2nc1-c1cncc(Br)c1]

Step 1. Methyl 2-(5-bromopyridin-3-yl)-3-(isopropyl(methyl)amino)quinoxaline-6-carboxylate

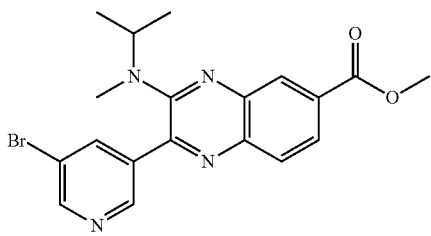 [SMILES: COC(=O)c1ccc2nc(-c3cncc(Br)c3)c(N(C)C(C)C)nc2c1]

To a solution of 5-bromopyridin-3-ylboronic acid (288.0 mg, 1.43 mmol) in dioxane (5 mL) was added methyl 2-chloro-3-(isopropyl(methyl)amino)quinoxaline-6-carboxylate (Scheme I, 140.0 mg, 0.48 mmol), K$_3$PO$_4$ (302.0 mg, 1.43 mmol), Pd(PPh$_3$)$_4$ (27.6 mg, 0.02 mmol) and three drops water. The reaction mixture was stirred for 1 h at 90° C. with an inert atmosphere of nitrogen and then concentrated under vacuum to give a residue, which was purified by a silica gel column with 1% ethyl acetate in petroleum ether to afford methyl 2-(5-bromopyridin-3-yl)-3-(isopropyl(methyl)amino)quinoxaline-6-carboxylate (150.0 mg, 72%) as a light yellow solid.

LC/MS (ES, m/z): [M+H]$^+$ 414.9

$^1$H-NMR (300 MHz, DMSO) δ 9.02 (d, J=1.8 Hz, 1H), 8.85 (d, J=2.1 Hz, 1H), 8.50-8.51 (t, J=2.1 Hz, 1H), 8.31 (d, J=1.50 Hz, 1H), 7.96-8.05 (m, 2H), 4.07-4.06 (m, 1H), 3.94 (s, 3H), 2.69 (s, 3H), 1.04 (d, J=6.60 Hz, 6H)

Step 2. 2-(5-Bromopyridin-3-yl)-3-(isopropyl(methyl)amino)quinoxaline-6-carboxylic acid

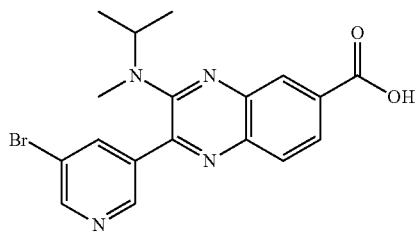

To a solution of methyl 2-(5-bromopyridin-3-yl)-3-(isopropyl(methyl)amino)quinoxaline-6-carboxylate (150.0 mg, 0.36 mmol) in methanol (30 mL) was added sodium hydroxide (43 mg, 1.08 mmol) and water (1 mL) The reaction mixture was stirred overnight at room temperature and concentrated under vacuum. The residue was dissolved in water (30 mL) and adjusted to PH 5 with HCl (3 N). The product were collected by filtration to afford 2-(5-bromopyridin-3-yl)-3-(isopropyl(methyl)amino)quinoxaline-6-carboxylic acid as a light yellow solid (120.0 mg, 80%).

LC/MS (ES, m/z): [M+H]$^+$ 400.9

$^1$H-NMR (300 MHz, DMSO) δ 13.24 (s, 1H), 9.02 (d, J=1.8 Hz, 1H), 8.84 (d, J=2.1 Hz, 1H), 8.51-8.52 (t, J=2.1 Hz, 1H), 8.28 (d, J=0.50 Hz, 1H), 7.96-8.03 (m, 2H), 4.02-4.11 (m, 1H), 2.70 (s, 3H), 1.20 (d, J=6.6 Hz, 6H)

Example 8

2-(1H-Indazol-5-yl)-3-(isopropyl(methyl)amino)quinoxaline-6-carboxylic acid

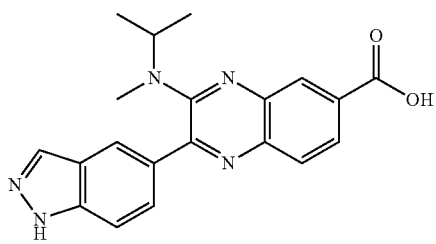 [SMILES: CC(C)N(C)c1nc2cc(C(=O)O)ccc2nc1-c1ccc2[nH]ncc2c1]

Step 1. Methyl 2-(1H-indazol-5-yl)-3-(isopropyl(methyl)amino)quinoxaline-6-carboxylate

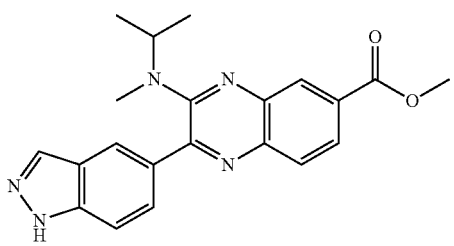 [SMILES: COC(=O)c1ccc2nc(-c3ccc4[nH]ncc4c3)c(N(C)C(C)C)nc2c1]

To a solution of methyl 2-chloro-3-(isopropyl(methyl)amino)quinoxaline-6-carboxylate (Scheme I, 200.0 mg, 0.68 mmol) in 1,4-dioxane (1 mL), was added 1H-indazol-5-ylboronic acid (386.0 mg, 2.38 mmol), $K_3PO_4$ (434.0 mg, 2.05 mmol), $Pd(PPh_3)_4$ (39.0 mg, 0.03 mmol) under nitrogen atmosphere and water (3 drops). After stirring for 20 min at 90° C., the reaction mixture was dissolved in water (30 mL), extracted with dichloromethane (3×20 mL), dried over anhydrous magnesium sulfate and concentrated under reduced pressure to afford a residue, which was purified by a silica gel column with 2%-10% ethyl acetate in petroleum ether to afford methyl 2-(1H-indazol-5-yl)-3-(isopropyl(methyl)amino)quinoxaline-6-carboxylate as a light yellow solid (110.0 mg, 45%).

LC/MS (ES, m/z): $[M+H]^+$ 376.0

$^1$H-NMR (300 MHz, DMSO) δ 13.27 (s, 1H), 8.29 (d, J=9.6 Hz, 2H), 8.22 (s, 1H), 7.86-7.99 (m, 3H), 7.67 (d, J=8.7 Hz, 1H), 4.19-4.23 (t, J=6.6 Hz, 1H), 3.93 (s, 3H), 2.70 (s, 3H), 1.01 (d, J=6.6 Hz, 6H)

Step 2. 2-(1H-Indazol-5-yl)-3-(isopropyl(methyl)amino)quinoxaline-6-carboxylic acid

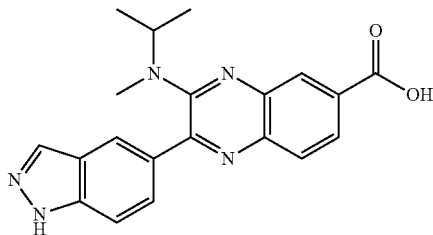 [SMILES: CC(C)N(C)c1nc2cc(C(=O)O)ccc2nc1-c1ccc2[nH]ncc2c1]

To a solution of methyl 2-(1H-indazol-5-yl)-3-(isopropyl(methyl)amino)quinoxaline-6-carboxylate (110.0 mg, 0.29 mmol) in methanol (20 mL) and water (1 mL), was added $LiOH \cdot H_2O$ (50 mg, 2.08 mmol,). After stirring for 2 days at room temperature, the reaction mixture was concentrated under reduced pressure to afford a residue, which was dissolved in water (10 mL), adjusted to pH 6 with hydrochloric acid (1N) and filtered to give 2-(1H-indazol-5-yl)-3-(isopropyl(methyl)amino)quinoxaline-6-carboxylic acid as a light yellow solid (47.4 mg, 45%).

LCMS (ES, m/z): $[M+H]^+$ 362.0

$^1$H-NMR (300 MHz, DMSO) δ 13.27 (s, 1H), 8.21-8.32 (t, J=16.2 Hz, 3H), 7.95-7.98 (t, J=8.7 Hz, 1H), 7.87 (d, J=9.0 Hz, 2H), 7.66 (d, J=8.7 Hz, 1H), 4.12-4.16 (t, J=6.6 Hz, 1H), 2.70 (s, 3H), 0.99 (d, J=6.6 Hz, 6H)

Example 9

3-(Isopropyl(methyl)amino)-2-(3-(trifluoromethyl)-1H-pyrazol-4-yl)quinoxaline-6-carboxylic acid

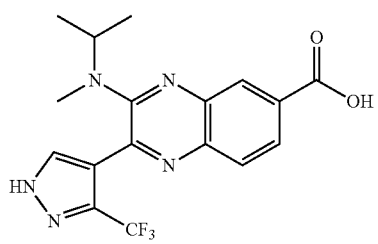 [SMILES: CC(C)N(C)c1nc2cc(C(=O)O)ccc2nc1-c1c[nH]nc1C(F)(F)F]

Step 1. Methyl 3-(isopropyl(methyl)amino)-2-(3-(trifluoromethyl)-1H-pyrazol-4-yl)quinoxaline-6-carboxylate

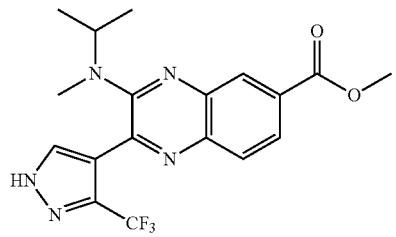 [SMILES: COC(=O)c1ccc2nc(-c3c[nH]nc3C(F)(F)F)c(N(C)C(C)C)nc2c1]

To a solution of 4-(4,4,5,5-tetramethyl-1,3,2-dioxaborolan-2-yl)-3-(trifluoromethyl)-1H-pyrazole (536.0 mg, 2.05 mmol) in DME (5 mL) and water (0.5 mL) was added methyl 2-chloro-3-(isopropyl(methyl)amino)quinoxaline-6-carboxylate (200.0 mg, 0.68 mmol), sodium carbonate (217.0 mg, 2.05 mmol) and $Pd(PPh_3)_4$ (39 mg, 0.03 mmol) with stirring for 0.5 h at 90° C. in an oil bath with an inert atmosphere of nitrogen. The reaction mixture was concentrated under vacuum to get a residue, which was purified by a silica gel column with 2%-10% ethyl acetate in petroleum to afford methyl 3-(isopropyl(methyl)amino)-2-(3-(trifluoromethyl)-1H-pyrazol-4-yl)quinoxaline-6-carboxylate as a light yellow solid (80 mg, 30%).

LC/MS (ES, m/z): $[M+H]^+$ 394.0

$^1$H-NMR (300 MHz, $CDCl_3$): δ 8.54 (d, J=1.8 Hz, 1H), 8.08-8.14 (m, 2H), 7.98 (d, J=8.7 Hz, 1H), 4.13-4.24 (m, 1H), 4.01 (s, 3H), 2.76 (s, 3H), 1.13 (d, J=6.6 Hz, 6H)

Step 2. 3-(isopropyl(methyl)amino)-2-(3-(trifluoromethyl)-1H-pyrazol-4-yl)quinoxaline-6-carboxylic acid

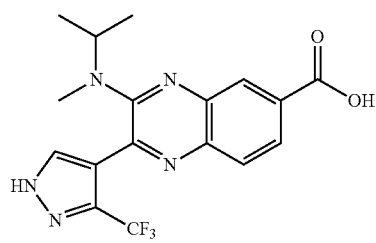 [SMILES: CC(C)N(C)c1nc2cc(C(=O)O)ccc2nc1-c1c[nH]nc1C(F)(F)F]

To solution of methyl 3-(isopropyl(methyl)amino)-2-(3-(trifluoromethyl)-1H-pyrazol-4-yl)quinoxaline-6-carboxylate (80.0 mg, 0.20 mmol) in methanol (30 mL) was added sodium hydroxide (24 mg, 0.60 mmol) and water (1 mL) with stirring overnight at room temperature. The reaction mixture was concentrated under vacuum, dissolved in water (30 mL) and then adjusted to pH 5 with hydrochloric acid (3N). The solids were collected by filtration, dried in an oven under reduced pressure to afford 3-(isopropyl(methyl)amino)-2-(3-(trifluoromethyl)-1H-pyrazol-4-yl)quinoxaline-6-carboxylic acid as a light yellow solid (64.0 mg, 79%).

LC/MS (ES, m/z): $[M+H]^+$ 380.0

$^1$H-NMR (300 MHz, DMSO) δ 8.42 (s, 1H), 8.26 (d, J=1.5 Hz, 1H), 7.94-7.98 (m, 1H), 7.86 (d, J=8.7 Hz, 1H), 4.11-4.20 (m, 1H), 2.66 (s, 3H), 1.04 (d, J=6.6 Hz, 6H)

Example 10

2-(6-(tert-Butoxycarbonylamino)pyridin-3-yl)-3-(isopropyl(methyl)amino)quinoxaline-6-carboxylic acid

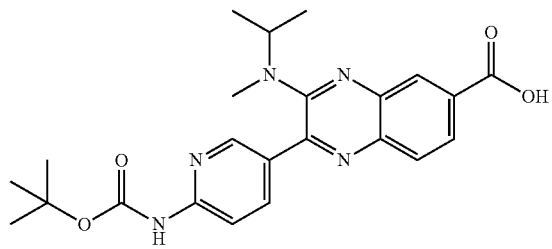 [SMILES: CC(C)N(C)c1nc2cc(C(=O)O)ccc2nc1-c1ccc(NC(=O)OC(C)(C)C)nc1]

Step 1. Methyl 2-(6-(tert-butoxycarbonylamino)pyridin-3-yl)-3-(isopropyl(methyl)amino)quinoxaline-6-carboxylate

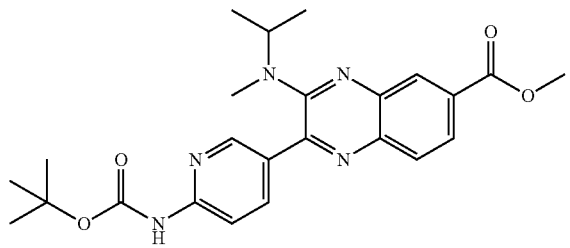 [SMILES: COC(=O)c1ccc2nc(-c3ccc(NC(=O)OC(C)(C)C)nc3)c(N(C)C(C)C)nc2c1]

To a solution of 6-(tert-butoxycarbonylamino)pyridin-3-ylboronic acid (316.0 mg, 1.33 mmol) in dioxane (5 mL) was added methyl 2-chloro-3-(isopropyl(methyl)amino)quinoxaline-6-carboxylate (130.0 mg, 0.44 mmol), $K_3PO_4$ (280.0 mg, 1.33 mmol) and Pd(PPh$_3$)$_4$ (25.6 mg, 0.02 mmol) and three drops water. The reaction mixture was stirred for 1 h at 90° C. in an oil bath with an inert atmosphere of nitrogen and concentrated under vacuum to give a residue, which was purified by a silica gel column with 1% ethyl acetate in petroleum ether to afford methyl 2-(6-(tert-butoxycarbonylamino)pyridin-3-yl)-3-(isopropyl(methyl)amino)quinoxaline-6-carboxylate as a light yellow solid (160 mg, 80%).

$^1$H-NMR (300 MHz, CDCl$_3$) δ 8.95 (d, J=2.4 Hz, 1H), 8.52-8.60 (m, 2H), 8.29-8.45 (m, 1H), 8.06-8.17 (m, 2H), 7.53-7.74 (m, 1H), 4.21-4.28 (m, 1H), 4.00 (s, 3H), 1.58 (s, 9H), 1.14 (d, J=6.6 Hz, 6H)

Step 2. 2-(6-(tert-Butoxycarbonylamino)pyridin-3-yl)-3-(isopropyl(methyl)amino)quinoxaline-6-carboxylic acid

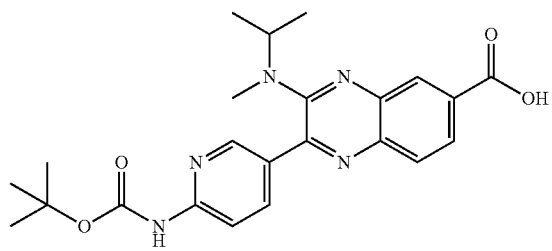 [SMILES: CC(C)N(C)c1nc2cc(C(=O)O)ccc2nc1-c1ccc(NC(=O)OC(C)(C)C)nc1]

To a solution of methyl 2-(6-(tert-butoxycarbonylamino)pyridin-3-yl)-3-(isopropyl(methyl)amino)quinoxaline-6-carboxylate (160.0 mg, 0.35 mmol) in methanol (30 mL) was added sodium hydroxide (43.0 mg, 1.06 mmol) and water (1 mL). The reaction mixture was stirred overnight at room temperature and concentrated under vacuum. The residue was dissolved in water (30 mL) and adjusted to pH 6 with HCl (3N). The solids were collected, dried in an oven under reduced pressure to afford 2-(6-(tert-butoxycarbonylamino)pyridin-3-yl)-3-(isopropyl(methyl)amino)quinoxaline-6-carboxylic acid as a light yellow solid (53.5 mg, 33%).

LC/MS (ES, m/z): [M+H]$^+$ 438.0

$^1$H-NMR (300 MHz, DMSO) δ 13.11 (s, 1H), 10.08 (s, 1H), 8.76 (t, J=2.1 Hz, 1H), 8.22-8.26 (m, 2H), 7.95-7.98 (t, J=1.2 Hz, 1H), 4.19 (t, J=6.6 Hz, 1H), 2.69 (s, 3H), 1.50 (s, 9H), 1.08 (d, J=6.6 Hz, 6H)

Example 11

2-(2-Fluoropyridin-4-yl)-3-(isopropyl(methyl)amino)quinoxaline-6-carboxylic acid

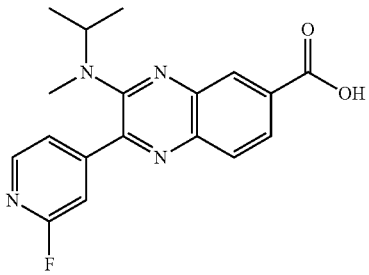

Step 1. Methyl 2-(2-fluoropyridin-4-yl)-3-(isopropyl(methyl)amino)quinoxaline-6-carboxylate

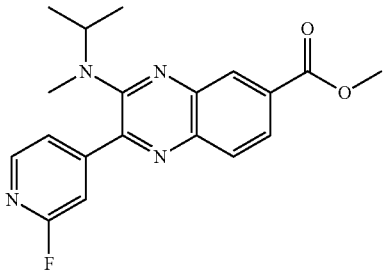 [SMILES: COC(=O)c1ccc2nc(-c3ccnc(F)c3)c(N(C)C(C)C)nc2c1]

To a solution of methyl 2-chloro-3-(isopropyl(methyl)amino)quinoxaline-6-carboxylate (300.0 mg, 1.02 mmol) in dioxane (5 mL) was added 2-fluoropyridin-4-ylboronic acid (289.0 mg, 2.06 mmol), $K_3PO_4$ (435.0 mg, 2.05 mmol), Pd(PPh$_3$)$_4$ (60 mg, 0.05 mmol) and three drops water under an inert atmosphere of nitrogen. The resulting solution was stirred for 1 h at 90° C. and then quenched by the addition of water (50 mL). The resulting solution was extracted with dichloromethane (5×20 mL) and the organic layers combined, dried over anhydrous magnesium sulfate and concentrated under vacuum to give a residue, which was purified by a silica gel column with 1%-5% ethyl acetate in petroleum ether to afford methyl 2-(2-fluoropyridin-4-yl)-3-(isopropyl(methyl)amino)quinoxaline-6-carboxylate as a yellow solid (250 mg, 69%).

LC/MS (ES, m/z): [M+H]$^+$ 355.0

$^1$H-NMR (300 MHz, CDCl$_3$), δ 8.58 (d, J=1.5 Hz, 1H), 8.38 (d, J=5.1 Hz, 1H), 8.09-8.12 (m, 1H), 7.98 (d, J=8.7 Hz, 1H), 7.72-7.74 (m, 1H), 7.51 (s, 1H), 4.22-4.26 (t, J=6.6 Hz, 1H), 4.07 (s, 3H), 2.78 (s, 3H), 1.15 (d, J=6.6 Hz, 6H)

Step 2. 2-(2-Fluoropyridin-4-yl)-3-(isopropyl(methyl)amino)quinoxaline-6-carboxylic acid

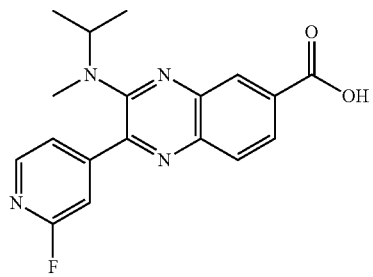 [SMILES: CC(C)N(C)c1nc2cc(C(=O)O)ccc2nc1-c1ccnc(F)c1]

To a solution of methyl 2-(2-fluoropyridin-4-yl)-3-(isopropyl(methyl)amino)quinoxaline-6-carboxylate (125.0 mg, 0.35 mmol) in methanol (25 mL) and chloroform (10 mL) was added sodium hydroxide (56.0 mg, 1.40 mmol) in water (1 mL). The resulting solution was stirred overnight at room temperature and concentrated under vacuum. The residue was dissolved in water (20 mL) and adjusted to pH 6 with hydrochloric acid (1N). The product was precipitated and collected by filtration to afford 2-(2-fluoropyridin-4-yl)-3-(isopropyl(methyl)amino)quinoxaline-6-carboxylic acid as a yellow solid (50 mg, 42%).

LC/MS (ES, m/z): [M+H]$^+$ 341.0

$^1$H-NMR (300 MHz, DMSO), δ 8.44 (d, J=8.1 Hz, 1H), 8.29 (d, J=1.2 Hz, 1H), 7.95-8.02 (m, 2H), 7.77-7.79 (m, 1H), 7.60 (s, 1H), 4.17-4.21 (t, J=6.6 Hz, 1H), 2.68 (s, 3H), 1.07 (d, J=6.6 Hz, 6H)

Example 12

3-(Isopropyl(methyl)amino)-2-(6-(pyrrolidin-1-yl)pyridin-3-yl)quinoxaline-6-carboxylic acid

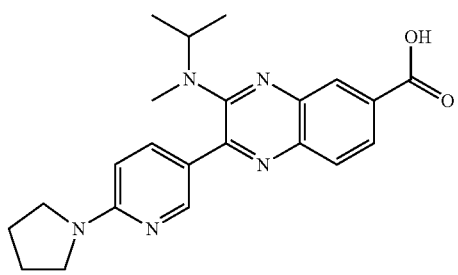 [SMILES: CC(C)N(C)c1nc2cc(C(=O)O)ccc2nc1-c1ccc(N2CCCC2)nc1]

Step 1. Methyl 3-(isopropyl(methyl)amino)-2-(6-(pyrrolidin-1-yl)pyridin-3-yl)quinoxaline-6-carboxylate

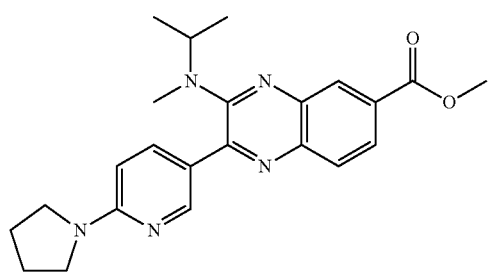 [SMILES: COC(=O)c1ccc2nc(-c3ccc(N4CCCC4)nc3)c(N(C)C(C)C)nc2c1]

To a solution of 6-(pyrrolidin-1-yl)pyridin-3-ylboronic acid (244.9 mg, 1.28 mmol) in N,N-dimethylformamide (6 mL) was added 2-chloro-3-(isopropyl(methyl)amino)quinoxaline-6-carboxylate (170.0 mg, 0.58 mmol), Pd(OAc)$_2$ (17.2 mg, 0.03 mmol), DPPF (28.3 mg, 0.05 mmol), CuCl (50.5 mg, 0.51 mmol) and Cs$_2$CO$_3$ (332.4 mg, 1.02 mmol) with stirring for 0.5 h at 100° C. with an inert atmosphere of nitrogen. The reaction mixture was cooled and extracted with ethyl acetate (3×80 mL), dried over anhydrous magnesium sulfate and concentrated under vacuum. The residue was purified by a silica gel column with 2.5% ethyl acetate in petroleum ether to afford methyl 3-(isopropyl(methyl)amino)-2-(6-(pyrrolidin-1-yl)pyridin-3-yl)quinoxaline-6-carboxylate as a light yellow solid (130.0 mg, 55%).

LC/MS (ES, m/z): [M+H]$^+$ 406.0

$^1$H-NMR (300 MHz, DMSO) δ 8.69 (d, J=2.1 Hz, 1H), 8.24 (d, J=0.9 Hz, 1H), 8.08 (d, J=2.4 Hz, 1H), 7.91-7.99 (m, 1H), 7.66-7.70 (m, 1H), 6.59 (d, J=9.0 Hz, 1H), 4.22-4.31 (m, 1H), 3.92 (s, 3H), 3.40-3.49 (m, 4H), 2.71 (s, 3H), 1.93-1.99 (m, 4H), 1.18 (d, J=6.6 Hz, 3H), 1.09 (d, J=6.6 Hz, 3H)

Step 2. 3-(Isopropyl(methyl)amino)-2-(6-(pyrrolidin-1-yl)pyridin-3-yl)quinoxaline-6-carboxylic acid

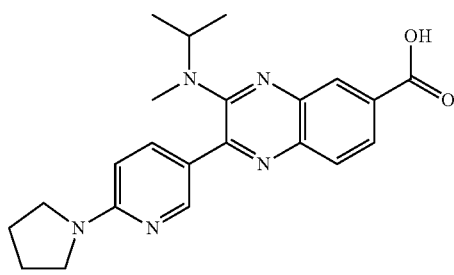 [SMILES: CC(C)N(C)c1nc2cc(C(=O)O)ccc2nc1-c1ccc(N2CCCC2)nc1]

To a solution of methyl 3-(isopropyl(methyl)amino)-2-(6-(pyrrolidin-1-yl)pyridin-3-yl)quinoxaline-6-carboxylate (130.0 mg, 0.32 mmol) in methanol (20 mL) was added sodium hydroxide (64.3 mg, 1.61 mmol) and water (1 mL) with stirring overnight at room temperature. The reaction mixture was concentrated under vacuum, dissolved in water (20 mL) and adjusted to pH 7 with hydrochloric acid (1N). The solids were collected to afford 3-(isopropyl(methyl)amino)-2-(6-(pyrrolidin-1-yl)pyridin-3-yl)quinoxaline-6-carboxylic acid as a light yellow solid (60.3 mg, 48%).

LC/MS (ES, m/z): [M+H]$^+$ 392.1

$^1$H-NMR (300 MHz, DMSO) δ 8.70 (d, J=2.1 Hz, 1H), 8.22 (d, J=1.2 Hz, 1H), 8.08 (d, J=9.0 Hz, 1H), 7.87-7.95 (m, 2H), 6.60 (d, J=8.7 Hz, 1H), 4.22-4.31 (m, 4H), 2.72 (s, 3H), 1.96-2.00 (t, J=6.3 Hz, 4H), 1.09 (d, J=6.6 Hz, 6H)

Example 13

2-(6-Fluoropyridin-3-yl)-3-(isopropyl(methyl)amino)quinoxaline-6-carboxylic acid

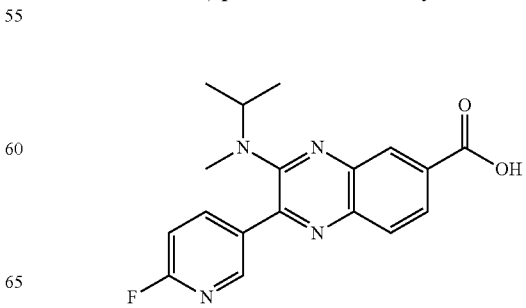

Step 1. Methyl 2-(6-fluoropyridin-2-yl)-3-(isopropyl(methyl)amino)quinoxaline-6-carboxylate

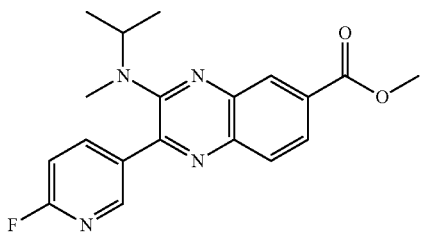 [SMILES: COC(=O)c1ccc2nc(-c3ccc(F)nc3)c(N(C)C(C)C)nc2c1]

To a solution of 6-fluoropyridin-2-ylboronic acid (289.0 mg, 2.05 mmol) in dioxane (1 mL) was added methyl 2-chloro-3-(isopropyl(methyl)amino)quinoxaline-6-carboxylate (300.0 mg, 1.02 mmol), K$_3$PO$_4$ (434.0 mg, 2.05 mmol), and Pd(PPh$_3$)$_4$ (27.6 mg, 0.02 mmol) under nitrogen atmosphere. After stirring 1 h at 90° C., the reaction mixture was dissolved in water (50 mL), extracted with dichloromethane (3×20 mL), dried over anhydrous magnesium sulfate and concentrated under reduced pressure to afford a residue, which was purified by a silica gel column with 0.05%-0.2% ethyl acetate in petroleum ether to afford methyl 2-(6-fluoropyridin-2-yl)-3-(isopropyl(methyl)amino)quinoxaline-6-carboxylate as a light yellow solid (260.0 mg, 72%).

LC/MS (ES, m/z): [M+H]$^+$ 355.0

$^1$H-NMR (300 MHz, DMSO) δ 8.56 (s, 1H), 8.42-8.44 (t, J=4.5 Hz, 1H), 8.29 (s, 1H), 7.94-8.01 (m, 2H), 7.32-7.39 (m, 1H), 4.12-4.21 (m, 1H), 3.93 (s, 3H), 2.67 (s, 3H), 1.05 (d, J=6.6 Hz, 6H)

Step 2. 2-(6-fluoropyridin-3-yl)-3-(isopropyl(methyl)amino)quinoxaline-6-carboxylic acid

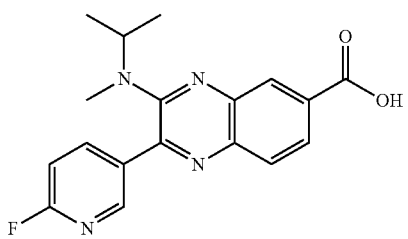 [SMILES: CC(C)N(C)c1nc2cc(C(=O)O)ccc2nc1-c1ccc(F)nc1]

To a solution of methyl 2-(6-fluoropyridin-3-yl)-3-(isopropyl(methyl)amino)quinoxaline-6-carboxylate (130 mg, 0.37 mmol) in tetrahydrofuran (10 mL) was added LiOH.H$_2$O (35 mg, 0.83 mmol) and water (1 mL). After stirring overnight at room temperature, the reaction mixture was concentrated under reduced pressure to afford a residue, which was dissolved in water (10 mL), adjusted the pH value to 6 with hydrochloric acid (1N). The solid was precipitated and filtered to afford 2-(6-fluoropyridin-3-yl)-3-(isopropyl(methyl)amino)quinoxaline-6-carboxylic acid as a light yellow solid (81.6 mg, 65%).

LC/MS (ES, m/z): [M+H]$^+$ 341.0

$^1$H-NMR (300 MHz, DMSO) δ 13.28 (s, 1H), 8.73 (d, J=2.4 Hz, 1H), 8.42-8.48 (m, 1H), 8.28 (s, 1H), 7.98 (d, J=0.9 Hz, 1H), 7.36-7.40 (m, 1H), 4.09-4.22 (m, 1H), 2.68 (s, 3H), 1.05 (d, J=6.6 Hz, 6H)

Example 14

(S)-2-(Benzofuran-2-yl)-3-(2-methylpyrrolidin-1-yl)quinoxaline-6-carboxylic acid

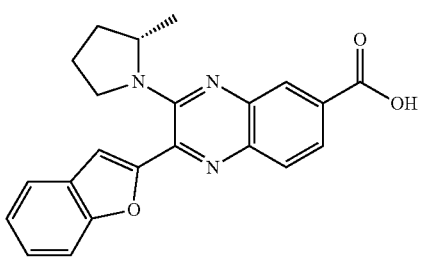 [SMILES: C[C@H]1CCCN1c1nc2cc(C(=O)O)ccc2nc1-c1cc2ccccc2o1]

Step 1. (S)-Methyl 3-(2-methylpyrrolidin-1-yl)-2-oxo-1,2-dihydroquinoxaline-6-carboxylate

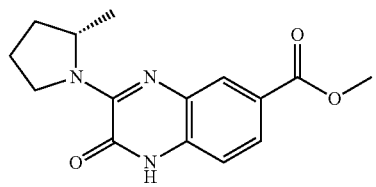 [SMILES: COC(=O)c1ccc2[nH]c(=O)c(N3CCC[C@@H]3C)nc2c1]

To a solution of methyl 3-chloro-2-oxo-1,2-dihydroquinoxaline-6-carboxylate (500.0 mg, crude) in DMSO (6 mL) was added DIEA (543.0 mg, 4.20 mmol), and (S)-2-methylpyrrolidine (268.0 mg, 3.15 mmol). The solution was stirred for 10 h at 100° C. and then quenched by the addition of water (25 mL), extracted with ethyl acetate (3×80 mL), dried over anhydrous sodium sulfate and concentrated under vacuum. The residue was purified by a silica gel column with 1%-5% ethyl acetate in petroleum ether to afford (S)-methyl 3-(2-methylpyrrolidin-1-yl)-2-oxo-1,2-dihydroquinoxaline-6-carboxylate as a yellow solid (216.0 mg).

LC/MS (ES, m/z): [M+H]$^+$ 288.0

$^1$H-NMR (300 MHz, CDCl$_3$) δ 10.87 (s, 1H), 8.24 (s, 1H), 7.77-7.81 (m, 1H), 7.11 (d, J=8.4 Hz, 1H), 4.10-4.23 (m, 1H), 3.93 (s, 3H), 1.98-2.12 (m, 4H), 1.74-1.76 (m, 2H), 1.35 (d, J=6.6 Hz, 3H)

Step 2. (S)-Methyl 3-(2-methylpyrrolidin-1-yl)-2-(trifluoromethylsulfonyloxy)quinoxaline-6-carboxylate

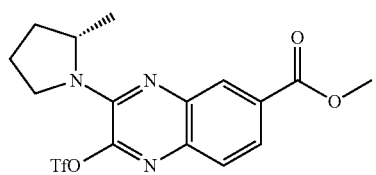 [SMILES: COC(=O)c1ccc2nc(OS(=O)(=O)C(F)(F)F)c(N3CCC[C@@H]3C)nc2c1]

To a solution of (S)-methyl 3-(2-methylpyrrolidin-1-yl)-2-oxo-1,2-dihydroquinoxaline-6-carboxylate (130.0 mg, 0.45 mmol) in dichloromethane (30 mL) was added pyridine (164.0 mg, 2.08 mmol) and then Tf₂O (293 mg, 1.04 mmol) was added dropwise with stirring at 0° C. The resulting solution was stirred for 12 h at room temperature and then quenched by the addition of ice-water (50 mL), extracted with dichloromethane (3×20 mL), dried over anhydrous sodium sulfate and concentrated under vacuum to afford (S)-methyl 3-(2-methylpyrrolidin-1-yl)-2-(trifluoromethylsulfonyloxy)quinoxaline-6-carboxylate as red oil (200 mg, crude).

Step 3. (S)-Methyl 2-(benzofuran-2-yl)-3-(2-methylpyrrolidin-1-yl)quinoxaline-6-carboxylate

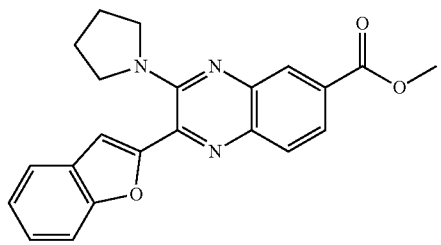 [SMILES: COC(=O)c1ccc2nc(-c3cc4ccccc4o3)c(N3CCCC3)nc2c1]

To a solution of (S)-methyl 3-(2-methylpyrrolidin-1-yl)-2-(trifluoromethylsulfonyloxy)quinoxaline-6-carboxylate (200 mg, crude) in dioxane (6 mL) was added benzofuran-2-ylboronic acid (113.0 mg, 0.70 mmol), K₃PO₄ (220.0 mg, 1.04 mmol), Pd(PPh₃)₄ (20.1 mg, 0.02 mmol) and water (3 drops). The resulting solution was stirred for 1 h at 90° C. and then concentrated under vacuum to give a residue, which was purified by a silica gel column with 1%-5% ethyl acetate in petroleum ether to afford (S)-methyl 2-(benzofuran-2-yl)-3-(2-methylpyrrolidin-1-yl)quinoxaline-6-carboxylate as a red oil (100.0 mg).

LC/MS (ES, m/z): [M+H]⁺ 388.0

¹H-NMR (300 MHz, CDCl₃): δ 9.27 (s, 1H), 8.16 (d, J=8.4 Hz, 1H), 8.06 (d, J=7.8 Hz, 1H), 7.75 (d, J=2.7 Hz, 1H), 7.73 (d, J=3.6 Hz, 1H), 7.35-7.67 (m, 4H), 5.10 (s, 1H), 4.02 (s, 3H), 3.69-3.77 (m, 1H), 3.41-3.51 (m, 1H), 2.31-2.37 (m, 2H), 1.77-1.98 (m, 2H), 1.42-1.69 (m, 3H)

Step 4. (S)-2-(Benzofuran-2-yl)-3-(2-methylpyrrolidin-1-yl)quinoxaline-6-carboxylic acid

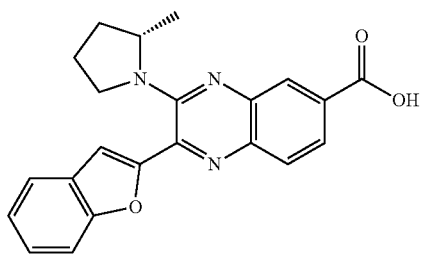 [SMILES: C[C@H]1CCCN1c1nc2cc(C(=O)O)ccc2nc1-c1cc2ccccc2o1]

To a solution of (S)-methyl 2-(benzofuran-2-yl)-3-(2-methylpyrrolidin-1-yl)quinoxaline-6-carboxylate (100.0 mg, 0.39 mmol) in MeOH (20 mL) was added sodium hydroxide (49.2 mg, 1.23 mmol) and water (1 mL). The resulting solution was stirred overnight at room temperature and concentrated under vacuum. The residue was dissolved in water (20 mL) and adjusted to pH 6 with hydrochloric acid (1N). The solids were collected by filtration to afford (S)-2-(benzofuran-2-yl)-3-(2-methylpyrrolidin-1-yl)quinoxaline-6-carboxylic acid as a yellow solid (50.9 mg, 53%).

LC/MS (ES, m/z): [M+H]⁺ 374.0

¹H-NMR (300 MHz, DMSO) δ 8.23 (d, J=1.8 Hz, 1H), 7.97 (d, J=8.7 Hz, 1H), 7.88-7.92 (m, 1H), 7.71-7.79 (m, 2H), 7.39-7.45 (m, 2H), 7.30-7.35 (m, 1H), 4.29-4.35 (m, 1H), 3.31-3.33 (m, 1H), 3.04-3.10 (t, J=8.1 Hz, 1H), 2.10-2.21 (m, 1H), 1.75-1.89 (m, 1H), 1.52-1.67 (m, 2H), 1.35 (d, J=6.6 Hz, 3H)

Example 15

2-(Benzofuran-2-yl)-3-(cyclopropyl(methyl)amino)quinoxaline-6-carboxylic acid

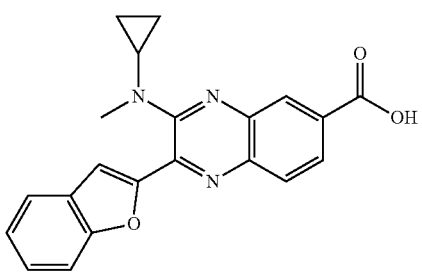 [SMILES: CN(c1nc2cc(C(=O)O)ccc2nc1-c1cc2ccccc2o1)C1CC1]

Step 1. Methyl 3-(cyclopropyl(methyl)amino)-2-oxo-1,2-dihydroquinoxaline-6-carboxylate

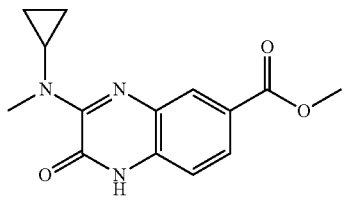

To a solution of methyl 3-chloro-2-oxo-1,2-dihydroquinoxaline-6-carboxylate (1.0 g, 4.20 mmol) in DMSO (6 mL) was added DIEA (1.35 g, 10.47 mmol), and N-methylcyclopropanamine hydrochloride (490 mg, 4.58 mmol). The solution was stirred 10 mins at room temperature and 2 h at 75° C. Then the reaction was quenched by the addition of water (100 mL) and the solids were collected by filtration to afford methyl 3-(cyclopropyl(methyl)amino)-2-oxo-1,2-dihydroquinoxaline-6-carboxylate as a yellow solid (405 mg, 35%).

LC/MS (ES, m/z): [M+H]⁺ 274.0

¹H-NMR (300 MHz, DMSO) δ 12.25 (s, 1H), 7.96 (d, J=1.8 Hz, 1H), 7.72-7.75 (m, 1H), 7.20 (d, J=8.4 Hz, 1H), 3.85 (d, J=5.4 Hz, 3H), 3.23 (s, 3H), 3.03-3.11 (m, 1H), 0.76-0.82 (m, 2H), 0.57-0.63 (m, 2H)

Step 2. Methyl 3-(cyclopropyl(methyl)amino)-2-(trifluoromethylsulfonyloxy)quinoxaline-6-carboxylate

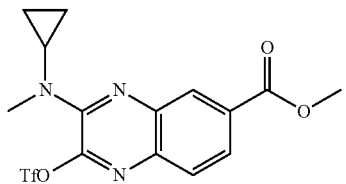

To a solution of methyl 3-(cyclopropyl(methyl)amino)-2-oxo-1,2-dihydroquinoxaline-6-carboxylate (126.0 mg, 0.46 mmol) in dichloromethane (34 mL) was added pyridine (145.0 mg, 1.84 mmol) and then Tf$_2$O (259 mg, 0.92 mmol) was added dropwise with stirring at 0° C. The resulting solution was stirred for 3 h at room temperature and then quenched by the addition of ice-water (50 mL), extracted with dichloromethane (2×20 mL), dried over anhydrous sodium sulfate and concentrated under vacuum to afford methyl 3-(cyclopropyl(methyl)amino)-2-(trifluoromethylsulfonyloxy)quinoxaline-6-carboxylate as red oil (180 mg, crude).

Step 3. Methyl 2-(benzofuran-2-yl)-3-(cyclopropyl(methyl)amino)quinoxaline-6-carboxylate

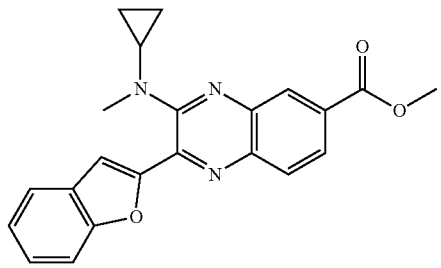 [SMILES: COC(=O)c1ccc2nc(-c3cc4ccccc4o3)c(N(C)C3CC3)nc2c1]

To a solution of methyl 3-(cyclopropyl(methyl)amino)-2-(trifluoromethylsulfonyloxy)quinoxaline-6-carboxylate (180.0 mg, crude) in dioxane (6 mL) was added benzofuran-2-ylboronic acid (149.0 mg, 0.92 mmol), K$_3$PO4 (195.0 mg, 0.92 mmol), Pd(PPh$_3$)$_4$ (30.0 mg, 0.03 mmol) and water (3 drops). The resulting solution was stirred for 1 h at 90° C. and then concentrated under vacuum to give a residue, which was purified by a silica gel column with 5%-20% ethyl acetate in petroleum ether to afford methyl 2-(benzofuran-2-yl)-3-(cyclopropyl(methyl)amino)quinoxaline-6-carboxylate as a yellow solid (95.0 mg, 39% 2 steps).

LC/MS (ES, m/z): [M+H]$^+$ 374.0

$^1$H-NMR (300 MHz, DMSO) δ 8.68 (s, 1H), 8.08-8.16 (m, 2H), 7.63-7.72 (m, 2H), 7.50 (d, J=0.6 Hz, 1H), 7.42-7.45 (m, 1H), 7.28-7.40 (m, 1H), 4.01 (s, 3H), 3.21 (s, 3H), 2.96-3.01 (m, 1H), 0.53-0.74 (m, 4H)

Step 4. 2-(Benzofuran-2-yl)-3-(cyclopropyl(methyl)amino)quinoxaline-6-carboxylic acid

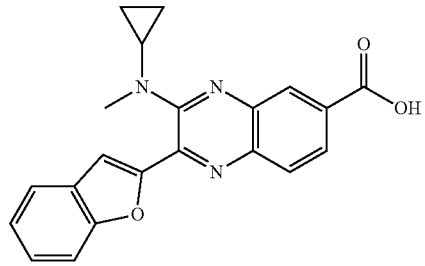 [SMILES: CN(c1nc2cc(C(=O)O)ccc2nc1-c1cc2ccccc2o1)C1CC1]

To a solution of methyl 3-(cyclopropyl(methyl)amino)-2-(2,3-dihydro-1H-inden-2-yl)quinoxaline-6-carboxylate (95.0 mg, 0.25 mmol) in methanol (15 mL) and CHCl$_3$ (10 mL) was added LiOH.H$_2$O (35.0 mg, 0.83 mmol) and water (1 mL). The resulting solution was stirred overnight at room temperature and concentrated under vacuum. The residue was dissolved in water (10 mL) and adjusted pH to 6 with hydrochloric acid (1N). The solids were collected by filtration to afford 2-(benzofuran-2-yl)-3-(cyclopropyl(methyl)amino) quinoxaline-6-carboxylic acid as a yellow solid (43.6 mg, 48%).

LC/MS (ES, m/z): [M+H]$^+$ 360.0

$^1$H-NMR (300 MHz, DMSO) δ 8.28 (d, J=1.2 Hz, 1H), 7.97-8.06 (m, 2H), 7.50 (d, J=0.6 Hz, 1H), 7.42-7.45 (m, 1H), 7.28-7.40 (m, 2H), 7.75-7.80 (t, J=8.4 Hz, 1H), 7.63 (s, 1H), 7.41-7.46 (t, J=7.2 Hz, 1H), 7.31-7.36 (t, J=7.2 Hz, 2H), 3.01 (s, 3H), 2.87-2.90 (t, J=3.6 Hz, 1H), 0.51-0.55 (t, J=7.2 Hz, 4H)

Example 16

2-(6-Aminopyridin-3-yl)-3-(isopropyl(methyl)amino)quinoxaline-6-carboxylic acid

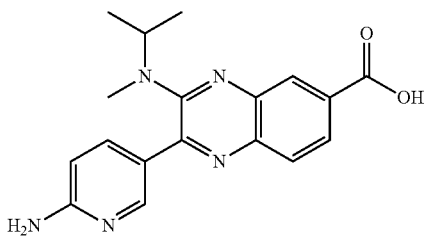 [SMILES: CC(C)N(C)c1nc2cc(C(=O)O)ccc2nc1-c1ccc(N)nc1]

To a solution of 2-(6-(tert-butoxycarbonylamino)pyridin-3-yl)-3-(isopropyl(methyl)amino)quinoxaline-6-carboxylic acid (140.0 mg, 0.32 mmol) in dichloromethane (50 mL) was added CF$_3$COOH (182.6 mg, 1.60 mmol) with stirring overnight at room temperature. The reaction mixture was concentrated under vacuum, dissolved in water (10 mL) and adjusted to pH 6 with sodium bicarbonate. The product were collected by filtration to afford 2-(6-aminopyridin-3-yl)-3-(isopropyl(methyl)amino)quinoxaline-6-carboxylic acid as a light yellow solid (88.6 mg, 78%).

LC/MS (ES, m/z): [M+H]$^+$ 338.0

$^1$H-NMR (300 MHz, DMSO) δ 8.54 (d, J=1.8 Hz, 1H), 8.23 (d, J=1.5 Hz, 1H), 7.87-7.98 (m, 3H), 6.51-6.59 (m, 3H), 4.18-4.25 (m, 1H), 2.73 (s, 3H), 1.08 (d, J=6.6 Hz, 6H)

Example 17

3-(Isopropyl(methyl)amino)-2-(5-methoxybenzofuran-2-yl)quinoxaline-6-carboxylic acid

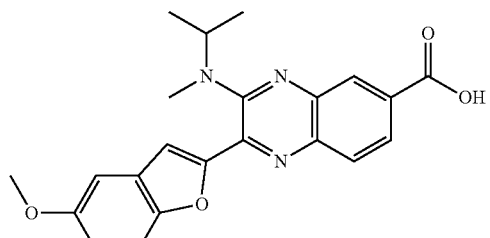

Step 1. 5-Methoxybenzofuran-2-ylboronic acid

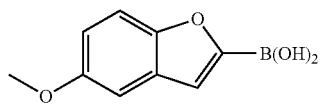

The solution of 5-methoxybenzofuran (1.0 g, 6.76 mmol) in dry tetrahydrofuran (50 mL) was kept below −60° C. under nitrogen, while BuLi (8.10 mmol, 2.5M solution in hexane) was added dropwise. It was warmed to −10° C. during 45 min and stirred at this temperature for another 30 min. The mixture was cooled again below −60° C., followed by dropwise addition of triisopropyl borate (3.8 g, 20.21 mmol). After warming to room temperature the mixture was quenched with hydrochloric acid (30 mL, 2N) and stirred for 1 h. The alkaline aqueous layer was brought to pH 5 and extracted with ethyl acetate (3×80 mL). All organic layers were combined, dried over sodium sulfate, and concentrated in vacuo to give 5-methoxybenzofuran-2-ylboronic acid (986 mg, 76%), which was used for the next step without further purification.

$^1$H-NMR (300 MHz, CDCl$_3$): δ 8.52 (s, 2H), 7.45 (d, J=9.0 Hz, 1H), 7.39 (d, J=0.9 Hz, 1H), 7.18 (d, J=2.7 Hz, 1H), 6.91-6.95 (m, 1H), 3.78 (s, 3H)

Step 2. Methyl 3-(isopropyl(methyl)amino)-2-(5-methoxybenzofuran-2-yl)-4a,8a-dihydroquinoxaline-6-carboxylate

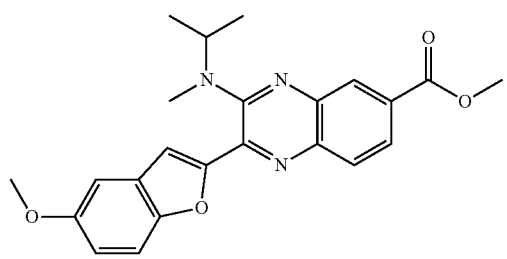

To a solution of 5-methoxybenzofuran-2-ylboronic acid (275.0 mg, 1.43 mmol) in dioxane (5.0 mL) was added ethyl 2-chloro-3-(isopropyl(methyl)amino)quinoxaline-6-carboxylate (140.0 mg, 0.48 mmol), K$_3$PO$_4$ (302.0 mg, 1.43 mmol) and Pd(PPh$_3$)$_4$ (27.5 mg, 0.02 mmol) and water (3 drops) with stirring for 1 h at 90° C. in an oil bath maintained with an inert atmosphere of nitrogen. The reaction mixture was concentrated under vacuum to give a residue, which was purified by a silica gel column with 1% ethyl acetate in petroleum ether to afford methyl 3-(isopropyl(methyl)amino)-2-(5-methoxybenzofuran-2-yl)-4a,8a-dihydroquinoxaline-6-carboxylate as a light yellow solid (150.0 mg, 73%).

LC/MS (ES, m/z): [M+H]$^+$ 406.0

$^1$H-NMR (300 MHz, CDCl$_3$): δ 8.56 (d, J=0.9 Hz, 1H), 8.05-8.12 (m, 2H), 7.54-7.58 (t, J=9.3 Hz, 2H), 7.13 (d, J=2.4 Hz, 1H), 7.01-7.05 (m, 1H), 4.32-4.36 (m, 1H), 4.01 (s, 3H), 390 (s, 3H), 2.93 (s, 3H), 1.23 (d, J=6.6 Hz, 6H)

Step 3. 3-(Isopropyl(methyl)amino)-2-(5-methoxy-benzofuran-2-yl)quinoxaline-6-carboxylic acid

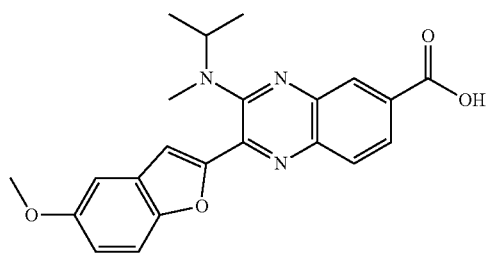 [SMILES: COc1ccc2oc(-c3nc4ccc(C(=O)O)cc4nc3N(C)C(C)C)cc2c1]

To a solution of methyl 3-(isopropyl(methyl)amino)-2-(5-methoxybenzofuran-2-yl)quinoxaline-6-carboxylate (150.0 mg, 0.37 mmol) in methanol (30 mL) and water (1 mL) was added sodium hydroxide (44.4 mg, 1.11 mmol) with stirring overnight at room temperature. The reaction mixture was concentrated under vacuum, dissolved in water (30 mL) and adjusted to pH 5 with HCl (3N). The solids were collected by filtration to afford 2-(5-fluorobenzofuran-2-yl)-3-(isopropyl(methyl)amino)quinoxaline-6-carboxylic acid as a light yellow solid (100.0 mg, 66%).

LC/MS (ES, m/z): [M+H]$^+$ 392.1

$^1$H-NMR (300 MHz, DMSO): δ 8.26 (s, 1H), 7.95-7.99 (m, 2H), 7.62-7.66 (t, J=2.7 Hz, 2H), 7.30 (d, J=2.4 Hz, 1H), 7.02-7.05 (m, 1H), 4.15-4.23 (m, 1H), 3.82 (s, 3H), 2.82 (s, 3H), 1.16 (d, J=6.6 Hz, 6H)

Example 18

2-(5-Fluorobenzofuran-2-yl)-3-(isopropyl(methyl)amino)quinoxaline-6-carboxylic acid

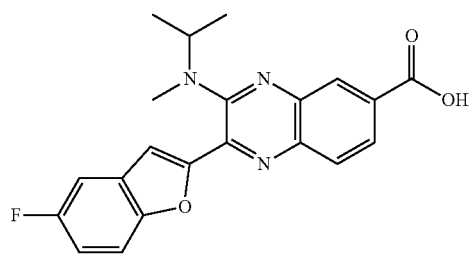 [SMILES: CC(C)N(C)c1nc2cc(C(=O)O)ccc2nc1-c1cc2cc(F)ccc2o1]

Step 1. 1-(Diethoxymethoxy)-4-fluorobenzene

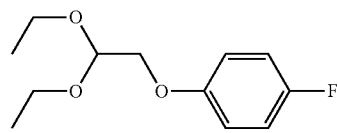 [SMILES: CCOC(COc1ccc(F)cc1)OCC]

To a suspension of sodium hydride (11.24 g, 281.00 mmol) in anhydrous N,N-dimethylformamide (500 mL) was added 4-fluorophenol (26.21 g, 233.96 mmol) at 0° C. After hydrogen evolution had ceased, bromo-acetaldehyde diethyl acetal (55 g, 280.60 mmol) was added. The reaction was heated at 120° C. overnight. The mixture was poured into ice-water, extracted with ethyl acetate (3×150 mL), washed with 1N sodium hydroxide (3×100 mL), and brine (3×100 mL). The organic layer was dried over anhydrous sodium sulfate and filtered. The solvent was removed under vacuum to give the residue, which was purified by a silica gel column with 1% ethyl acetate in petroleum ether to afford 1-(diethoxymethoxy)-4-fluorobenzene as oil (45 g, 84%).

$^1$H-NMR (300 MHz, CDCl$_3$): δ 6.84-7.01 (m, 4H), 4.81-4.85 (t, J=5.1 Hz, 1H), 3.99 (d, J=5.1 Hz, 2H), 3.69-3.83 (m, 2H), 3.59-3.67 (m, 2H), 1.24-1.31 (m, 6H)

Step 2. 5-Fluorobenzofuran

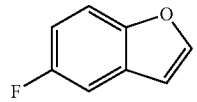

To a mixture of benzene (200 mL) containing polyphosphoric acid (80 g, 236.69 mmol) was added 2-(4-fluorophenoxy)-acetaldehyde diethyl acetal (45 g, 197.37 mmol). The mixture was stirred vigorously while being heated to reflux for 2.5 hours. The reaction mixture was cooled to room temperature and decanted from the polyphosphoric acid. The solvent was removed under vacuum to give the residue, which was purified by a silica gel column with 1% ethyl acetate in petroleum ether to afford 5-fluorobenzofuran as colorless oil (14.0 g, crude).

$^1$H-NMR (300 MHz, CDCl$_3$): δ 7.67 (d, J=2.1 Hz, 1H), 7.44-7.48 (m, 1H), 7.27-7.30 (m, 1H), 7.01-7.08 (m, 1H), 6.76-6.77 (m, 1H)

Step 3. 5-Fluorobenzofuran-2-ylboronic acid

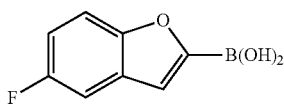

To a solution of 5-fluorobenzofuran (10 g, 73.53 mmol) in dry tetrahydrofuran (250 mL) were added tetramethylethylenediamine (10.2 g, 87.93 mmol). The solution was kept below −60° C. under nitrogen, while BuLi (93.75 mmol, 2.5M solution in hexane) was added dropwise. It was warmed to −10° C. during 45 min and stirred at this temperature for another 30 min. The mixture was cooled again below −60° C. followed by dropwise addition of triisopropyl borate (41.4 g, 220.21 mmol). After warming to room temperature the mixture was quenched with hydrochloric acid (70 mL, 2N) and stirred for 1 h. The alkaline aqueous layer was brought to pH 5 and extracted with ethyl acetate (3×80 mL). All organic layers were combined, dried over sodium sulfate, and concentrated in vacuo to give 5-fluorobenzofuran-2-ylboronic acid (3.5 g, 26%) which was used for the next step without further purification.

$^1$H-NMR (300 MHz, CDCl$_3$): δ 8.63 (s, 2H), 7.58-7.62 (m, 1H), 7.44-7.49 (m, 2H), 7.15-7.22 (m, 1H)

Step 4. Methyl 2-(5-fluorobenzofuran-2-yl)-3-(isopropyl(methyl)amino)quinoxaline-6-carboxylate

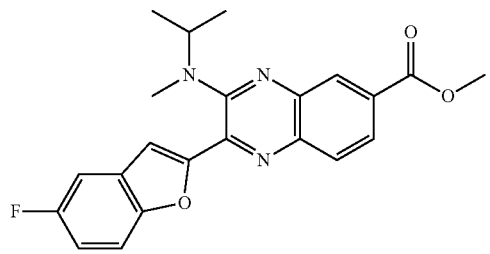 [SMILES: COC(=O)c1ccc2nc(-c3cc4cc(F)ccc4o3)c(N(C)C(C)C)nc2c1]

To a solution of 5-fluorobenzofuran-2-ylboronic acid (258.0 mg, 1.43 mmol) in dioxane (5.5 mL) was added ethyl 2-chloro-3-(isopropyl(methyl)amino)quinoxaline-6-carboxylate (140.0 mg, 0.48 mmol), K$_3$PO$_4$ (302.0 mg, 1.43 mmol) and Pd(PPh$_3$)$_4$ (27.5 mg, 0.02 mmol) and water (3 drops) with stirring for 1 h at 90° C. in an oil bath maintained with an inert atmosphere of nitrogen. The reaction mixture was concentrated under vacuum to give a residue, which was purified by a silica gel column with 1% ethyl acetate in petroleum ether to afford methyl 2-(5-fluorobenzofuran-2-yl)-3-(isopropyl(methyl)amino)quinoxaline-6-carboxylate as a light yellow solid (160.0 mg, 81%).

LC/MS (ES, m/z): [M+H]$^+$ 394.0

$^1$H-NMR (300 MHz, CDCl$_3$): δ 8.61 (d, J=1.5 Hz, 1H), 8.05-8.14 (m, 2H), 7.57-7.62 (m, 2H), 7.34-7.37 (m, 1H), 7.11-7.18 (m, 1H), 4.29-4.38 (m, 1H), 4.01 (s, 3H), 2.94 (s, 3H), 1.21 (d, J=6.6 Hz, 6H)

Step 5. 2-(5-Fluorobenzofuran-2-yl)-3-(isopropyl(methyl)amino)quinoxaline-6-carboxylic acid

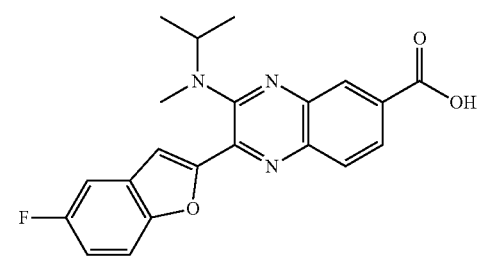 [SMILES: CC(C)N(C)c1nc2cc(C(=O)O)ccc2nc1-c1cc2cc(F)ccc2o1]

To a solution of methyl 2-(5-fluorobenzofuran-2-yl)-3-(isopropyl(methyl)amino)quinoxaline-6-carboxylate (160 mg, 0.41 mmol) in methanol (30 mL) and water (1 mL) was added sodium hydroxide (48.85 mg, 1.22 mmol) with stirring overnight at room temperature. The reaction mixture was concentrated under vacuum, dissolved in water (30 mL) and adjusted to pH 5 with HCl (3N). The solids were collected by filtration to afford 2-(5-fluorobenzofuran-2-yl)-3-(isopropyl(methyl)amino)quinoxaline-6-carboxylic acid as a light yellow solid (120.0 mg, 74%).

LC/MS (ES, m/z): [M+H]$^+$ 380.1

¹H-NMR (300 MHz, DMSO): δ 13.28 (s, 1H), 8.27 (s, 1H), 7.96-8.03 (m, 2H), 7.77-7.82 (m, 1H), 7.59-7.64 (m, 1H), 7.26-7.34 (m, 1H), 4.15-4.24 (m, 1H), 2.83 (s, 3H), 1.16 (d, J=6.6 Hz, 6H)

Example 19

2-(5-Chlorobenzofuran-2-yl)-3-(isopropyl(methyl)amino)quinoxaline-6-carboxylic acid

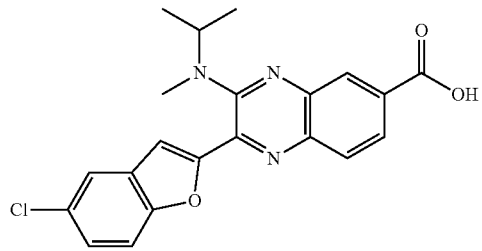 [SMILES: CC(C)N(C)c1nc2cc(C(=O)O)ccc2nc1-c1cc2cc(Cl)ccc2o1]

Step 1. 1-Chloro-4-(2,2-diethoxyethoxy)benzene

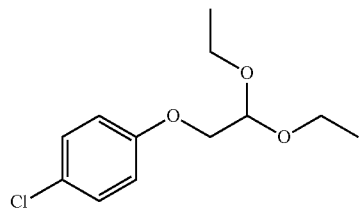 [SMILES: CCOC(COc1ccc(Cl)cc1)OCC]

To a suspension of sodium hydride (11.24 g, 281 mmol) in anhydrous N,N-dimethylformamide (500 mL) was added 4-chlorophenol (30 g, 234 mmol) at 0° C. After hydrogen evolution had ceased, bromo-acetaldehyde diethyl acetal (55 g, 281 mmol) was added. The mixture was heated at 120° C. overnight. The mixture was poured into ice-water, extracted with ethyl acetate (3×150 ml), washed with 1N sodium hydroxide (3×100 ml), and brine (3×100 ml). The organic layer was dried over anhydrous sodium sulfate and filtered. The solvent was removed under vacuum. The residue was purified by a silica gel column with 1% ethyl acetate in petroleum ether to afford 1-chloro-4-(2,2-diethoxyethoxy)benzene as oil (45 g, 75%).

¹H-NMR (300 MHz, CDCl₃): δ 7.24-7.28 (m, 1H), 7.21-7.23 (m, 1H), 6.84-6.89 (m, 2H), 4.81-4.85 (t, J=5.1 Hz, 1H), 3.99 (d, J=5.1 Hz, 2H), 3.69-3.83 (m, 2H), 3.59-3.67 (m, 2H), 1.23-1.30 (m, 6H)

Step 2. 5-Chlorobenzofuran

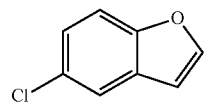

To a solution of 1-chloro-4-(2,2-diethoxyethoxy)benzene (45 g, 184 mmol,) in benzene (200 mL) was added polyphosphoric acid (25 g, 221 mmol) with stirring for 2.5 h at 90° C. in an oil bath. The reaction mixture was cooled to room temperature and decanted from the polyphosphoric acid. The solvent was removed under vacuum. The residue was applied onto a silica gel column with 1% ethyl acetate in petroleum ether to afford 5-chlorobenzofuran as colorless oil (14.0 g, crude).

¹H-NMR (300 MHz, CDCl₃): δ 7.66 (d, J=2.1 Hz, 1H), 7.59 (d, J=2.1 Hz, 1H), 7.45 (d, J=8.7 Hz, 1H), 7.26-7.29 (m, 1H), 6.73-7.75 (m, 1H)

Step 3. 5-Chlorobenzofuran-2-ylboronic acid

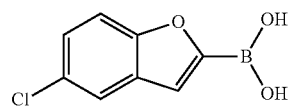 [SMILES: OB(O)c1cc2cc(Cl)ccc2o1]

To a solution of 5-chlorobenzofuran (14 g, crude) in dry tetrahydrofuran (250 mL) were added tetramethylethylenediamine (12.82 g, 110 mmol). The solution was kept below −60° C. under argon, while the solution of butyllithium in hexane (44 ml, 2.5 M) was added dropwise. It was warmed to −10° C. during 45 min and stirred at this temperature for another 30 min. The mixture was cooled again below −60° C. followed by dropwise addition of triisopropyl borate (51.88 g, 276 mmol). After warming to room temperature the mixture was quenched with hydrochloric acid (70 ml, 2N) and stirred for 1 h. The alkaline aqueous layer was brought to pH 5 and extracted with ethyl acetate (3×80 ml). All organic layers were combined, dried over sodium sulfate, and concentrated in vacuo to give 5-chlorobenzofuran-2-ylboronic acid (7.5 g) which was used for the next step without further purification.

¹H-NMR (300 MHz, DMSO): δ 8.66 (s, 2H), 7.78 (d, J=2.1 Hz, 1H), 7.58-7.71 (m, 1H), 7.42-7.44 (m, 1H), 7.27-7.37 (m, 1H)

Step 4. Methyl 2-(5-chlorobenzofuran-2-yl)-3-(isopropyl(methyl)amino)quinoxaline-6-carboxylate

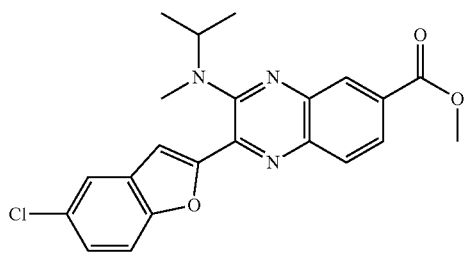 [SMILES: COC(=O)c1ccc2nc(-c3cc4cc(Cl)ccc4o3)c(N(C)C(C)C)nc2c1]

To a solution of 5-chlorobenzofuran-2-ylboronic acid (281 mg, 1.43 mmol) in dioxane (6 mL) was added ethyl 2-chloro-3-(isopropyl(methyl)amino)quinoxaline-6-carboxylate (140 mg, 0.48 mmol), K₃PO₄ (303 mg, 1.44 mmol), Pd(PPh₃)₄ (27.5 mg, 0.02 mmol) and water (3 drops) with stirring for 3 h at 90° C. in an oil bath maintained with an inert atmosphere of nitrogen. The reaction mixture was concentrated under vacuum to give a residue, which was applied onto a silica gel column with 1% ethyl acetate in petroleum ether to afford methyl 2-(5-chlorobenzofuran-2-yl)-3-(isopropyl(methyl)amino)quinoxaline-6-carboxylate as a light yellow solid (152 mg, 78%).

¹H-NMR (300 MHz, CDCl₃): δ 8.58 (s, 1H), 8.04-8.13 (m, 2H), 7.67 (d, J=2.1 Hz, 1H), 7.56-7.60 (t, J=8.7 Hz, 2H), 7.35-7.39 (m, 1H), 4.26-4.34 (m, 1H), 4.01 (s, 3H), 2.92 (s, 3H), 1.22 (d, J=6.6 Hz, 6H)

Step 5. 2-(5-Chlorobenzofuran-2-yl)-3-(isopropyl (methyl)amino)quinoxaline-6-carboxylic acid

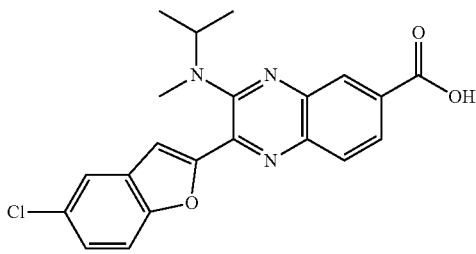 [SMILES: CC(C)N(C)c1nc2cc(C(=O)O)ccc2nc1-c1cc2cc(Cl)ccc2o1]

To a solution of methyl 2-(5-chlorobenzofuran-2-yl)-3-(isopropyl(methyl)amino)quinoxaline-6-carboxylate (152 mg, 0.37 mmol) in tetrahydrofuran (30 mL) was added sodium hydroxide (48.6 mg, 1.22 mmol) and water (2 ml) with stirring overnight at room temperature. The reaction mixture was concentrated under vacuum, dissolved in water (30 mL), and adjusted to pH 5 with HCl (3N). The solids were collected by filtration to afford 2-(5-chlorobenzofuran-2-yl)-3-(isopropyl(methyl)amino)quinoxaline-6-carboxylic acid as a light yellow solid (60 mg, 41%).

LC/MS (ES, m/z): [M+H]$^+$ 396.0

$^1$H-NMR (300 MHz, DMSO): δ 13.28 (s, 1H), 8.26-8.27 (t, J=1.2 Hz, 1H), 7.96-8.03 (m, 2H), 7.89 (d, J=2.1 Hz, 1H), 7.80 (d, J=8.7 Hz, 1H), 7.66 (d, J=0.9 Hz, 1H), 7.45-7.48 (m, 1H), 4.14-4.23 (m, 1H), 2.82 (s, 3H), 1.16 (d, J=6.6 Hz, 6H)

Example 20

2-(3,4-Dihydro-2H-benzo[b][1,4]dioxepin-7-yl)-3-(isopropyl(methyl)amino)quinoxaline-6-carboxylic acid

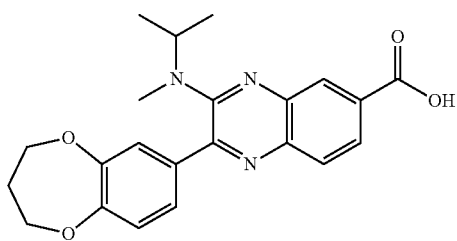 [SMILES: CC(C)N(C)c1nc2cc(C(=O)O)ccc2nc1-c1ccc2c(c1)OCCCO2]

Step 1. Methyl 2-(3,4-dihydro-2H-benzo[b][1,4]dioxepin-7-yl)-3-(isopropyl(methyl)amino)quinoxaline-6-carboxylate

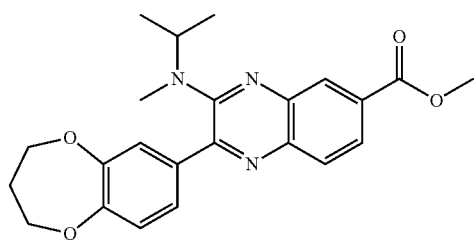 [SMILES: COC(=O)c1ccc2nc(-c3ccc4c(c3)OCCCO4)c(N(C)C(C)C)nc2c1]

To a solution of 3,4-dihydro-2H-benzo[b][1,4]dioxepin-7-ylboronic acid (200.0 mg, 1.03 mmol in dioxane (5.0 mL) was added methyl 2-chloro-3-(isopropyl(methyl)amino)quinoxaline-6-carboxylate (Scheme I, 150.0 mg, 0.52 mmol), K$_3$PO$_4$ (325.9 mg, 1.54 mmol) and Pd(PPh$_3$)$_4$ (29.7 mg, 0.03 mmol) and water (3 drops) with stirring for 1 h at 90° C. in an oil bath maintained with an inert atmosphere of nitrogen. The reaction mixture was concentrated under vacuum to give a residue, which was purified by a silica gel column with 1% ethyl acetate in petroleum ether to afford methyl 2-(3,4-dihydro-2H-benzo[b][1,4]dioxepin-7-yl)-3-(isopropyl(methyl)amino)quinoxaline-6-carboxylate as a light yellow solid (140.0 mg, 63%).

LC/MS (ES, m/z): [M+H]$^+$ 408.0

$^1$H-NMR (300 MHz, CDCl$_3$): δ 8.56 (d, J=1.5 Hz, 1H), 8.03-8.07 (dd, J$_1$=J$_2$=1.8 Hz, 1H), 7.95 (d, J=8.7 Hz, 1H), 7.56 (d, J=2.4 Hz, 1H), 7.47-7.51 (m, J$_1$=2.4 Hz, 1H), 7.08 (d, J=8.4 Hz, 1H), 4.23-4.31 (m, 5H), 3.99 (s, 3H), 390 (s, 3H), 2.79 (s, 3H), 2.24-2.29 (m, 2H), 1.22 (d, J=6.6 Hz, 6H)

Step 2. 2-(3,4-Dihydro-2H-benzo[b][1,4]dioxepin-7-yl)-3-(isopropyl(methyl)amino)quinoxaline-6-carboxylic acid

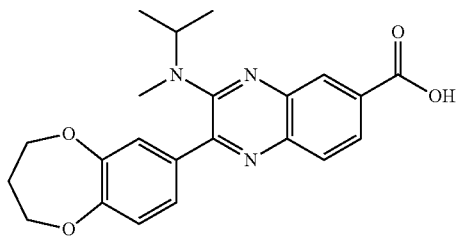 [SMILES: CC(C)N(C)c1nc2cc(C(=O)O)ccc2nc1-c1ccc2c(c1)OCCCO2]

To a solution of methyl 2-(3,4-dihydro-2H-benzo[b][1,4]dioxepin-7-yl)-3-(isopropyl(methyl)amino)quinoxaline-6-carboxylate (140.0 mg, 0.34 mmol) in methanol (30 mL) and water (1 mL) was added sodium hydroxide (42.0 mg, 1.03 mmol) with stirring overnight at room temperature. The reaction mixture was concentrated under vacuum, dissolved in water (30 mL) and adjusted to pH 5 with HCl (3N). The solids were collected by filtration to afford 2-(3,4-dihydro-2H-benzo[b][1,4]dioxepin-7-yl)-3-(isopropyl(methyl)amino) quinoxaline-6-carboxylic acid as a light yellow solid (120.0 mg, 84%).

LC/MS (ES, m/z): [M+H]$^+$ 392.1

$^1$H-NMR (300 MHz, DMSO): δ 8.23-8.24 (t, J=1.2 Hz, 1H), 7.92 (s, 2H), 7.45-7.49 (m, 2H), 7.09 (d, J=8.1 Hz, 1H), 4.17-4.22 (m, 5H), 2.69 (s, 3H), 2.13-2.17 (t, J=5.1 Hz, 3H), 1.04 (d, J=6.6 Hz, 6H)

Example 21

2-(Chroman-6-yl)-3-(isopropyl(methyl)amino)quinoxaline-6-carboxylic acid

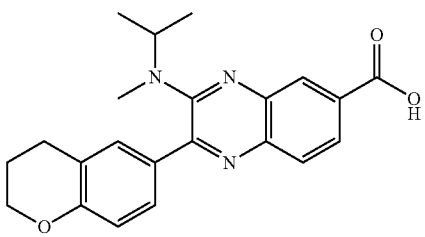 [SMILES: CC(C)N(C)c1nc2cc(C(=O)O)ccc2nc1-c1ccc2c(c1)CCCO2]

Step 1. 2-(Chroman-6-yl)-4,4,5,5-tetramethyl-1,3,2-dioxaborolane

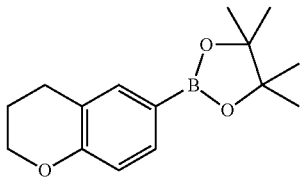 [SMILES: CC1(C)OB(c2ccc3c(c2)CCCO3)OC1(C)C]

To a solution of 6-bromochromane (400 mg, 1.88 mmol) in N,N-dimethylformamide (50 mL) was added 4,4,4',4',5,5,5',5'-octamethyl-2,2'-bi(1,3,2-dioxaborolane) (620 mg, 2.44 mmol), KOAc (552.1 mg, 5.63 mmol) and Pd(dppf)Cl₂ (155 mg, 0.19 mmol) with stirring for 3 h at 95° C. maintained with an inert atmosphere of nitrogen in an oil bath. The reaction mixture was diluted with water, extracted with ethyl acetate (80 mL×3) and the organic layers combined, dried over anhydrous magnesium sulfate, concentrated under vacuum to give the residue, which was applied onto a silica gel column with 1% ethyl acetate in petroleum ether to afford 2-(chroman-6-yl)-4,4,5,5-tetramethyl-1,3,2-dioxaborolane as colorless oil (320 mg, 59%).

¹H-NMR (300 MHz, CDCl₃): δ 7.54 (d, J=7.5 Hz, 2H), 6.78 (d, J=8.4 Hz, 1H), 4.19-4.23 (t, J=5.4 Hz, 2H), 2.78-2.83 (t, J=6.3 Hz, 2H), 1.98-2.05 (m, 2H), 1.28 (s, 12H)

Step 2. Methyl 2-(chroman-6-yl)-3-(isopropyl(methyl)amino)quinoxaline-6-carboxylate

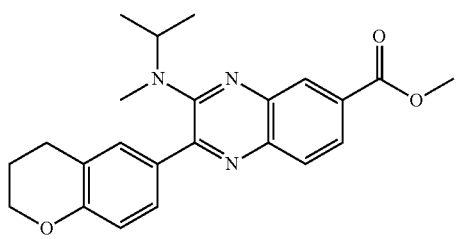 [SMILES: COC(=O)c1ccc2nc(-c3ccc4c(c3)CCCO4)c(N(C)C(C)C)nc2c1]

To a solution of 2-(chroman-6-yl)-4,4,5,5-tetramethyl-1,3,2-dioxaborolane (320 mg, 1.23 mmol) in dioxane (5.0 mL) was added methyl 2-chloro-3-(isopropyl(methyl)amino)quinoxaline-6-carboxylate (Scheme I, 180 mg, 0.61 mmol), K₃PO₄ (392 mg, 1.86 mmol), Pd(PPh₃)₄ (35.8 mg, 0.03 mmol) and water (3 drops) with stirring for 4 h at 95° C. maintained with an inert atmosphere of nitrogen in an oil bath. The reaction mixture was concentrated under vacuum to give the residue, which was applied onto a silica gel column with 2% ethyl acetate in petroleum ether to afford methyl 2-(chroman-6-yl)-3-(isopropyl(methyl)amino)quinoxaline-6-carboxylate as a light yellow solid (130 mg, 51%).

LC/MS (ES, m/z): [M+H]⁺ 392.0

¹H-NMR (300 MHz, CDCl₃): δ 8.76 (s, 1H), 8.07-8.16 (m, 2H), 7.71 (s, 1H), 7.62 (d, J=8.7 Hz, 1H), 6.89 (d, J=8.4 Hz, 1H), 4.42-4.47 (t, J=6.6 Hz, 1H), 4.27-4.30 (t, J=5.1 Hz, 2H), 4.00 (s, 3H), 2.88-2.94 (m, 5H), 2.05-2.12 (m, 2H), 1.16 (d, J=6.60 Hz, 6H)

Step 3. 2-(Chroman-6-yl)-3-(isopropyl(methyl)amino)quinoxaline-6-carboxylic acid

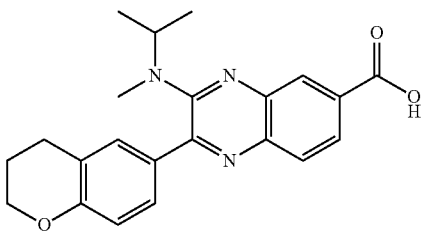 [SMILES: CC(C)N(C)c1nc2cc(C(=O)O)ccc2nc1-c1ccc2c(c1)CCCO2]

To a solution of methyl 2-(chroman-6-yl)-3-(isopropyl(methyl)amino)quinoxaline-6-carboxylate (130 mg, 0.33 mmol) in water (1 mL) and tetrahydrofuran (5 mL) was added sodium hydroxide (53 mg, 1.33 mmol) with stirring overnight at room temperature. The reaction mixture was concentrated under vacuum, dissolved in water (30 mL), adjusted to pH 4 with HCl (3N) to give the precipitate, which was collected by filtration to afford 2-(chroman-6-yl)-3-(isopropyl(methyl)amino)quinoxaline-6-carboxylic acid as a light yellow solid (80 mg, 61%).

LC/MS (ES, m/z): [M+H]⁺ 378.0

¹H-NMR (300 MHz, DMSO): δ 13.06 (s, 1H), 8.23 (s, 1H), 7.88-7.95 (m, 2H), 7.61-7.65 (t, J=2.1 Hz, 1H), 6.85 (d, J=8.4 Hz, 1H), 4.15-4.23 (m, 3H), 2.81-2.85 (t, J=6.3 Hz, 2H), 2.70 (d, J=7.8 Hz, 3H), 1.95-2.01 (m, 2H), 1.05 (d, J=6.6 Hz, 6H)

Example 22

2-(Benzo[d]oxazol-2-yl)-3-(isopropyl(methyl)amino)quinoxaline-6-carboxylic acid

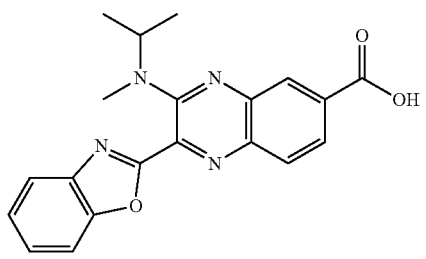 [SMILES: CC(C)N(C)c1nc2cc(C(=O)O)ccc2nc1-c1nc2ccccc2o1]

Step 1. Methyl 2-(benzo[d]oxazol-2-yl)-3-(isopropyl(methyl)amino)quinoxaline-6-carboxylate

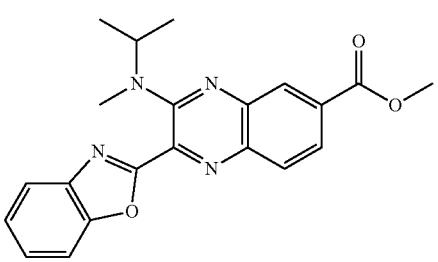 [SMILES: COC(=O)c1ccc2nc(-c3nc4ccccc4o3)c(N(C)C(C)C)nc2c1]

To a 10-mL sealed tube was placed methyl 2-chloro-3-(isopropyl(methyl)amino)quinoxaline-6-carboxylate (Scheme I, 400 mg, 1.36 mmol), 6,7-dihydrobenzo[d]oxazole (400 mg, 3.31 mmol), AcOK (268 mg, 3.31 mmol), and Pd(PPh₃)₄ (40 mg, 0.03 mmol) under nitrogen atmosphere.

After stirring 2 h at 150° C., the reaction mixture was dissolved in water (10 mL), extracted with dichloromethane (3×30 mL), dried over anhydrous magnesium sulfate and concentrated under reduced pressure to afford a residue, which was purified by a silica gel column with 10% ethyl acetate in petroleum ether to afford methyl 2-(benzo[d]oxazol-2-yl)-3-(isopropyl(methyl)amino)quinoxaline-6-carboxylate as a light yellow solid (100 mg, 21%).

LC/MS (ES, m/z): [M+H]$^+$ 377.0

$^1$H-NMR (300 MHz, CDCl$_3$) δ 8.52 (d, J=1.2 Hz, 1H), 8.03-8.11 (m, 2H), 7.87-7.90 (m, 1H), 7.69-7.72 (m, 1H), 7.41-7.46 (m, 2H), 4.37-4.46 (m, 1H), 4.00 (s, 3H), 2.87 (s, 3H), 1.23 (d, J=6.6 Hz, 6H)

Step 2. 2-(Benzo[d]oxazol-2-yl)-3-(isopropyl(methyl)amino)quinoxaline-6-carboxylic acid

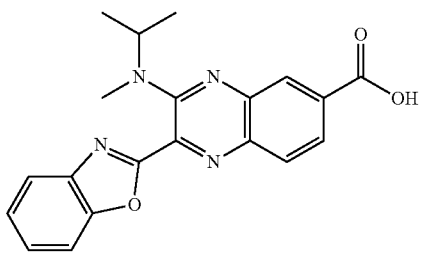 [SMILES: CC(C)N(C)c1nc2cc(C(=O)O)ccc2nc1-c1nc2ccccc2o1]

To a solution of methyl 2-(benzo[d]oxazol-2-yl)-3-(isopropyl(methyl)amino)quinoxaline-6-carboxylate (100 mg, 0.27 mmol) in tetrahydrofuran (20 mL) and water (2 mL) was added sodium hydroxide (21 mg, 0.53 mmol). After stirring overnight at room temperature, the reaction mixture was concentrated under reduced pressure to afford a residue, which was dissolved in water (20 mL), adjusted the pH to 6 with hydrochloric acid (3N) and filtered to give 2-(benzo[d]oxazol-2-yl)-3-(isopropyl(methyl)amino)quinoxaline-6-carboxylic acid as a light yellow solid (21.9 mg, 23%).

LC/MS (ES, m/z): [M+H]$^+$ 363.0.0

$^1$H-NMR (300 MHz, DMSO) δ 13.31 (s, 1H), 8.27 (d, J=1.5 Hz, 1H), 8.04 (d, J=8.7 Hz, 1H), 7.92-7.97 (m, 3H), 7.50-7.56 (m, 2H), 4.33-4.42 (m, 1H), 2.77 (s, 3H), 1.16 (d, J=6.6 Hz, 6H)

Example 23

2-(Benzo[b]thiophen-2-yl)-3-(isopropyl(methyl)amino)quinoxaline-6-carboxylic acid

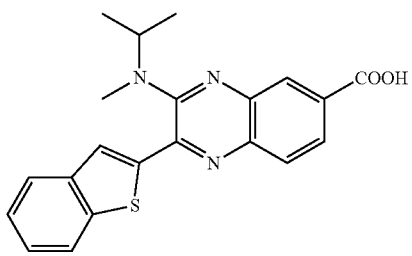 [SMILES: CC(C)N(C)c1nc2cc(C(=O)O)ccc2nc1-c1cc2ccccc2s1]

Step 1. Methyl 6-(benzo[b]thiophen-2-yl)-7-(isopropyl(methyl)amino)-2-naphthoate

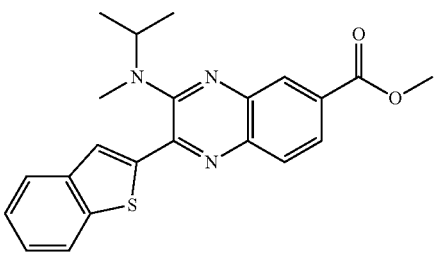 [SMILES: COC(=O)c1ccc2nc(-c3cc4ccccc4s3)c(N(C)C(C)C)nc2c1]

To a solution of benzo[b]thiophen-2-ylboronic acid (180 mg, 1.01 mmol) in dioxane (6 mL) was added methyl 6-chloro-7-(isopropyl(methyl)amino)-2-naphthoate (120 mg, 0.41 mmol), K$_3$PO$_4$ (259 mg, 1.23 mmol), Pd(PPh$_3$)$_4$ (24.0 mg, 0.02 mmol) and water (3 drops) with stirring for 1 h at 90° C. in an oil bath with an inert atmosphere of nitrogen. The reaction mixture was concentrated under vacuum and then purified by a silica gel column with 1% to 4% ethyl acetate in petroleum ether to afford methyl 6-(benzo[b]thiophen-2-yl)-7-(isopropyl(methyl)amino)-2-naphthoate as a light yellow solid (140 mg, 87.5%).

LC/MS (ES, m/z): [M+H]$^+$ 392.0

$^1$H-NMR (300 MHz, CDCl$_3$) δ 8.57 (d, J=1.2 Hz, 1H), 8.21 (s, 1H), 8.09-8.13 (m, 1H), 8.00 (d, J=8.4 Hz, 1H), 7.90-7.93 (m, 1H), 7.83-7.87 (m, 1H), 7.39-7.43 (m, 2H), 7.32-4.41 (m, 1H), 4.01 (s, 3H), 2.93 (s, 3H), 1.24 (d, J=6.6 Hz, 6H)

Step 2. 2-(Benzo[b]thiophen-2-yl)-3-(isopropyl(methyl)amino)quinoxaline-6-carboxylic acid

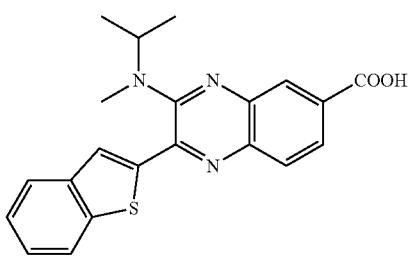 [SMILES: CC(C)N(C)c1nc2cc(C(=O)O)ccc2nc1-c1cc2ccccc2s1]

To a solution of methyl 2-(benzo[b]thiophen-2-yl)-3-(isopropyl(methyl)amino)quinoxaline-6-carboxylate (140 mg, 0.36 mmol) in tetrahydrofuran (25 mL) was added sodium hydroxide (43.2 mg, 1.08 mmol) and water (2 mL) with stirring overnight at room temperature. The reaction mixture was concentrated under vacuum, dissolved in water (20 mL) and adjusted to pH 5 with hydrochloric acid (3 N). The solids were collected by filtration to afford 2-(benzo[b]thiophen-2-yl)-3-(isopropyl(methyl)amino)quinoxaline-6-carboxylic acid as a yellow solid (80 mg, 59%).

LC/MS (ES, m/z): [M+H]$^+$ 378.1

$^1$H-NMR (300 MHz, DMSO) δ 8.28 (s, 1H), 7.98-8.05 (m, 3H), 7.90-7.94 (m, 1H), 7.42-7.45 (m, 2H), 4.18-4.27 (m, 1H), 2.85 (s, 3H), 1.17 (d, J=6.6 Hz, 6H)

Example 24

2-(5-Fluorobenzo[b]thiophen-2-yl)-3-(isopropyl(methyl)amino)quinoxaline-6-carboxylic acid

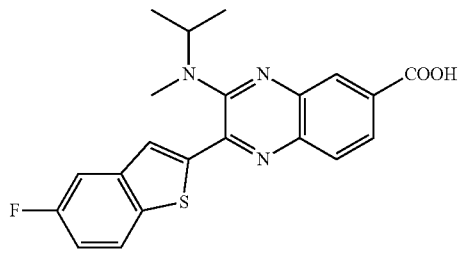 [SMILES: CC(C)N(C)c1nc2cc(C(=O)O)ccc2nc1-c1cc2cc(F)ccc2s1]

Step 1. Methyl 2-(5-fluorobenzo[b]thiophen-2-yl)-3-(isopropyl(methyl)amino)quinoxaline-6-carboxylate

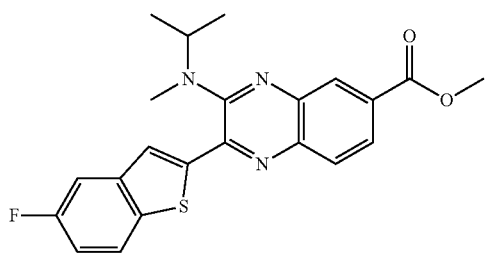 [SMILES: COC(=O)c1ccc2nc(-c3cc4cc(F)ccc4s3)c(N(C)C(C)C)nc2c1]

To a solution of 5-fluorobenzo[b]thiophen-2-ylboronic acid (202 mg, 1.03 mmol) in dioxane (6 mL) was added methyl 2-chloro-3-(isopropyl(methyl)amino)quinoxaline-6-carboxylate (120 mg, 0.41 mmol), $K_3PO_4$ (259 mg, 1.23 mmol), Pd(PPh$_3$)$_4$ (24.0 mg, 0.02 mmol) and water (3 drops) with stirring for 0.5 h at 90° C. in an oil bath with an inert atmosphere of nitrogen. The reaction mixture was concentrated under vacuum and then purified by a silica gel column with 1% to 2% ethyl acetate in petroleum ether to afford methyl 2-(5-fluorobenzo[b]thiophen-2-yl)-3-(isopropyl(methyl)amino)quinoxaline-6-carboxylate as a light yellow solid (148 mg, 88%).

LC/MS (ES, m/z): [M+H]$^+$ 410.0

$^1$H-NMR (300 MHz, CDCl$_3$) δ 8.54 (d, J=1.5 Hz, 1H), 8.10-8.15 (m, 2H), 8.00 (d, J=8.4 Hz, 1H), 7.81-7.86 (m, 1H), 7.43-7.53 (m, 1H), 7.14-7.21 (m, 1H), 4.27-4.36 (m, 1H), 4.01 (s, 3H), 2.91 (s, 3H), 1.23 (d, J=6.6 Hz, 6H)

Step 2. 2-(5-Fluorobenzo[b]thiophen-2-yl)-3-(isopropyl(methyl)amino)quinoxaline-6-carboxylic acid

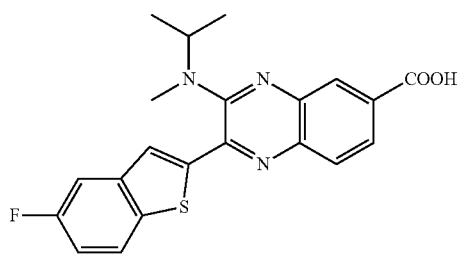 [SMILES: CC(C)N(C)c1nc2cc(C(=O)O)ccc2nc1-c1cc2cc(F)ccc2s1]

To a solution of methyl 2-(5-fluorobenzo[b]thiophen-2-yl)-3-(isopropyl(methyl)amino)quinoxaline-6-carboxylate (148 mg, 0.36 mmol) in tetrahydrofuran (25 mL) was added sodium hydroxide (43.4 mg, 1.08 mmol) and water (2 mL) with stirring overnight at room temperature. The reaction mixture was concentrated under vacuum, dissolved in water (20 mL) and adjusted to pH 5 with hydrochloric acid (3N). The solids were collected by filtration to afford 2-(5-fluorobenzo[b]thiophen-2-yl)-3-(isopropyl(methyl)amino)quinoxaline-6-carboxylic acid (69 mg, 49%).

LC/MS (ES, m/z): [M+H]$^+$ 396.0

$^1$H-NMR (300 MHz, DMSO) δ 8.29 (d, J=1.5 Hz, 1H), 8.25 (s, 1H), 8.06-8.11 (m, 1H), 7.95-8.03 (m, 2H), 7.84-7.89 (dd, J=2.7 Hz, J=2.4 Hz, 1H), 7.31-7.38 (m, 1H), 4.19-4.28 (m, 1H), 2.84 (s, 3H), 1.17 (d, J=6.3 Hz, 6H)

Example 25

3-(Isopropyl(methyl)amino)-2-(1-methyl-1H-indazol-5-yl)quinoxaline-6-carboxylic acid

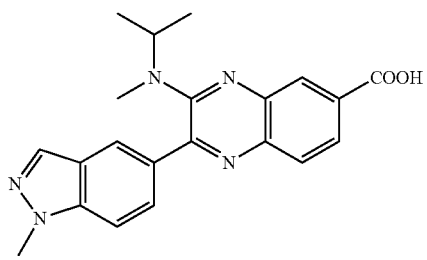 [SMILES: CC(C)N(C)c1nc2cc(C(=O)O)ccc2nc1-c1ccc2c(cnn2C)c1]

Step 1. Methyl 3-(isopropyl(methyl)amino)-2-(1-methyl-1H-indazol-5-yl)quinoxaline-6-carboxylate

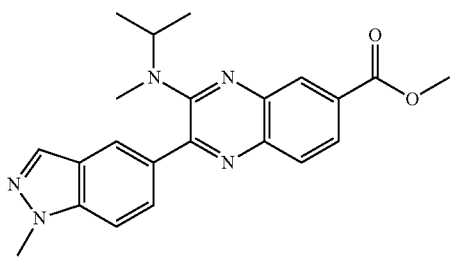 [SMILES: COC(=O)c1ccc2nc(-c3ccc4c(cnn4C)c3)c(N(C)C(C)C)nc2c1]

To a solution of 1-methyl-1H-indazol-5-ylboronic acid (180 mg, 1.02 mmol) in dioxane (3 mL) was added methyl 2-chloro-3-(isopropyl(methyl)amino)quinoxaline-6-carboxylate (Scheme I, 109 mg, 0.37 mmol), $K_3PO_4$ (175 mg, 0.83 mmol), Pd(PPh$_3$)$_4$ (29 mg, 0.03 mmol) and water (3 drops) with stirring for 1 h at 90° C. in an oil bath with an inert atmosphere of nitrogen. The reaction mixture was concentrated under vacuum and then purified by a silica gel column with 10% ethyl acetate in petroleum ether to afford methyl 3-(isopropyl(methyl)amino)-2-(1-methyl-1H-indazol-5-yl)quinoxaline-6-carboxylate as a light yellow solid (110 mg, 76%).

LC/MS (ES, m/z): [M+H]$^+$ 390.0

¹H-NMR (300 MHz, CDCl₃) δ 8.68 (s, 1H), 8.35 (d, J=0.9 Hz, 1H), 8.07-8.11 (m, 3H), 7.96-8.00 (m, 1H), 7.52 (d, J=6.0 Hz, 1H), 4.30-4.39 (m, 1H), 4.16 (s, 3H), 4.01 (s, 3H), 2.81 (s, 3H), 1.09 (d, J=6.6 Hz, 6H)

Step 2. 3-(Isopropyl(methyl)amino)-2-(1-methyl-1H-indazol-5-yl)quinoxaline-6-carboxylic acid

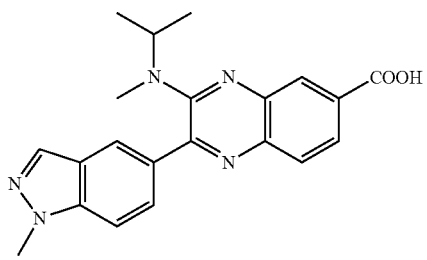 [SMILES: CC(C)N(C)c1nc2cc(C(=O)O)ccc2nc1-c1ccc2c(cnn2C)c1]

To a solution of methyl 3-(isopropyl(methyl)amino)-2-(1-methyl-1H-indazol-5-yl)quinoxaline-6-carboxylate (110 mg, 0.28 mmol) in methanol (20 mL) and CHCl₃ (6 mL) was added sodium hydroxide (20 mg, 0.50 mmol) and water (1 mL). The resulting solution was stirred overnight at room temperature and concentrated under vacuum. The residue was dissolved in water (10 mL) and adjusted to pH 6 with hydrochloric acid (3N). The solids were collected by filtration to afford 3-(isopropyl(methyl)amino)-2-(1-methyl-1H-indazol-5-yl)quinoxaline-6-carboxylic acid (50 mg, 47%).

LC/MS (ES, m/z): [M+H]⁺ 376.1
¹H-NMR (300 MHz, DMSO): δ 8.31 (d, J=0.6 Hz, 1H), 8.27-8.28 (t, J=1.2 Hz, 1H), 8.19 (d, J=0.9 Hz, 1H), 7.91-7.95 (m, 3H), 7.79 (d, J=8.7 Hz, 1H), 4.19-4.23 (m, 1H), 4.11 (s, 3H), 2.69 (s, 3H), 1.01 (d, J=6.6 Hz, 6H)

Example 26

2-(1-Ethyl-1H-indazol-5-yl)-3-(isopropyl(methyl)amino)quinoxaline-6-carboxylic acid

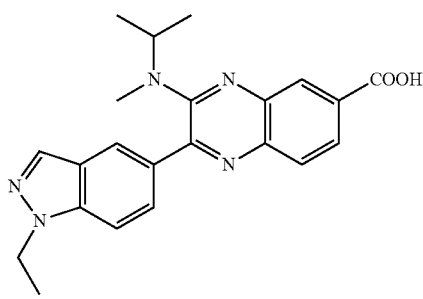 [SMILES: CCn1ncc2cc(-c3nc4ccc(C(=O)O)cc4nc3N(C)C(C)C)ccc21]

Step 1. 5-Bromo-1-ethyl-1H-indazole

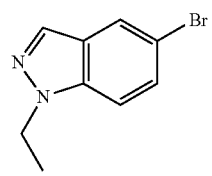

To a solution of 5-bromo-1H-indazole (1 g, 5.10 mmol) in tetrahydrofuran (30 mL) was added sodium hydride (330 mg, 8.25 mmol) at 0° C. with stirring for 30 min, iodoethane (1.72 g, 11.04 mmol) was added dropwise. The reaction mixture was stirred overnight at room temperature. The reaction was then quenched with water (50 mL), extracted with ethyl acetate (3×80 mL) and the organic layers combined, dried over anhydrous magnesium sulfate and concentrated under vacuum to give the residue, which was purified by a silica gel column with 1% to 5% ethyl acetate in petroleum ether to afford 5-bromo-1-ethyl-1H-indazole as yellow oil (598 mg, 52%).

LC/MS (ES, m/z): [M+H]⁺ 225
¹H-NMR (300 MHz, CDCl₃): δ 7.95 (d, J=0.3 Hz, 1H), 7.88-7.89 (t, J=1.2 Hz, 1H), 7.44-7.48 (m, 1H), 7.28-7.33 (m, 1H), 4.40-4.47 (m, 2H), 1.48-1.55 (m, 3H)

Step 2. 1-Ethyl-1H-indazol-5-ylboronic acid

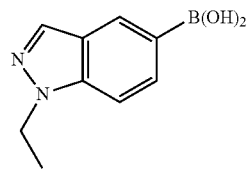

A solution of 5-bromo-1-ethyl-1H-indazole (598 mg, 2.67 mmol) in dry tetrahydrofuran (30 mL) was cooled below −60° C. Then a solution of butyllithium in hexane (2.5 ml, 2.5M) was added dropwise. It was warmed to −10° C. during 45 min and stirred at this temperature for another 30 min. The mixture was cooled again below −60° C. followed by dropwise addition of triisopropyl borate (1.5 g, 7.98 mmol). After warming to room temperature the mixture was quenched with hydrochloric acid (3N) and stirred for 1 h. The alkaline aqueous layer was brought to pH 5 and extracted with ethyl acetate (3×80 ml). All organic layers were combined, dried over sodium sulfate, and concentrated in vacuum to give 1-ethyl-1H-indazol-5-ylboronic acid (450 mg, 89%) which was used for the next step without further purification.

¹H-NMR (300 MHz, DMSO) δ 8.29 (d, J=1.5 Hz, 1H), 8.24 (s, 1H), 8.07 (d, J=0.6 Hz, 1H), 7.77-7.80 (m, 1H), 7.59 (d, J=8.4 Hz, 1H), 4.39-4.46 (m, 2H), 1.29-1.41 (m, 3H)

Step 3. Methyl 2-(1-ethyl-1H-indazol-5-yl)-3-(isopropyl(methyl)amino)quinoxaline-6-carboxylate

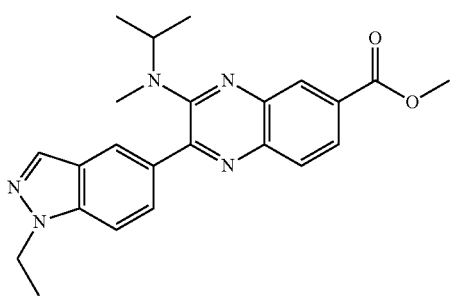 [SMILES: CCn1ncc2cc(-c3nc4ccc(C(=O)OC)cc4nc3N(C)C(C)C)ccc21]

To a solution of 1-ethyl-1H-indazol-5-ylboronic acid (196 mg, 1.03 mmol) in dioxane (6 mL) was added methyl 2-chloro-3-(isopropyl(methyl)amino)quinoxaline-6-carboxylate (Scheme I, 120 mg, 0.41 mmol), K₃PO₄ (259 mg, 1.23 mmol), Pd(PPh₃)₄ (20 mg, 0.02 mmol) and water (5 drops) with stirring for 4 h at 90° C. in an oil bath under an inert atmosphere of nitrogen. The reaction mixture was concentrated under vacuum and then purified by a silica gel column with 1% to 5% ethyl acetate in petroleum ether to afford methyl 2-(1-ethyl-1H-indazol-5-yl)-3-(isopropyl(methyl)amino)quinoxaline-6-carboxylate as a light yellow solid (80 mg, 49%).

LC/MS (ES, m/z): [M+H]⁺ 404.0

¹H-NMR (300 MHz, CDCl₃) δ 8.80 (s, 1H), 8.34 (s, 1H), 8.10-8.13 (m, 3H), 7.93-7.97 (m, 1H), 7.58 (d, J=8.7 Hz, 1H), 4.42-4.55 (m, 3H), 4.01 (s, 3H), 2.87 (s, 3H), 1.55-1.61 (t, J=7.2 Hz, 3H), 1.13 (d, J=6.6 Hz, 6H)

Step 4. 2-(1-Ethyl-1H-indazol-5-yl)-3-(isopropyl (methyl)amino)quinoxaline-6-carboxylic acid

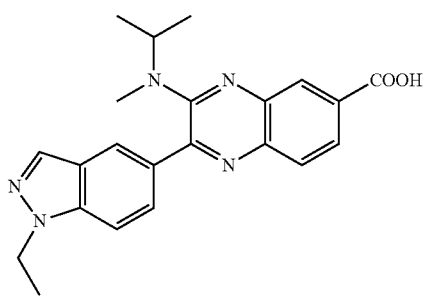 [SMILES: CCn1ncc2cc(-c3nc4ccc(C(=O)O)cc4nc3N(C)C(C)C)ccc21]

To a solution of methyl 2-(1-ethyl-1H-indazol-5-yl)-3-(isopropyl(methyl)amino)quinoxaline-6-carboxylate (80 mg, 0.20 mmol) in tetrahydrofuran (25 mL) was added sodium hydroxide (34 mg, 0.85 mmol) and water (2 mL) with stirring overnight at room temperature. The reaction mixture was concentrated under vacuum, dissolved in water (20 mL) and adjusted to pH 5 with HCl (3N). The solids were collected by filtration to afford 2-(1-ethyl-1H-indazol-5-yl)-3-(isopropyl(methyl)amino)quinoxaline-6-carboxylic acid as yellow solid (18.6 mg, 24%).

LC/MS (ES, m/z): [M+H]⁺ 390.0

¹H-NMR (300 MHz, DMSO) δ 8.32 (s, 1H), 8.26 (s, 1H), 8.20 (s, 1H), 7.79-7.98 (m, 4H), 4.46-4.53 (m, 2H), 4.13-4.21 (m, 1H), 2.69 (s, 1H), 1.42-1.47 (t, J=7.2 Hz, 3H), 1.01 (d, J=6.3 Hz, 6H)

Example 27

2-(1-Benzofuran-2-yl)-3-(diethylamino)quinoxaline-6-carboxylic acid

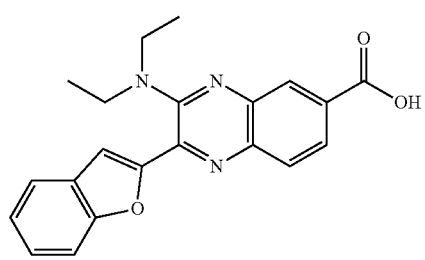 [SMILES: CCN(CC)c1nc2cc(C(=O)O)ccc2nc1-c1cc2ccccc2o1]

Step 1. Methyl 3-(diethylamino)-2-hydroxyquinoxaline-6-carboxylate

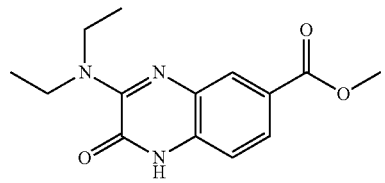 [SMILES: CCN(CC)c1nc2cc(C(=O)OC)ccc2[nH]c1=O]

To a solution of methyl 3-chloro-2-hydroxyquinoxaline-6-carboxylate (450 mg, crude) in DMSO (5 mL) was added diethylamine (550 mg, 7.52 mmol), DIEA (492 mg, 3.81 mmol). After stirring for 2 h at 70° C., the resulting solution was diluted with water (50 mL), extracted with ethyl acetate (4×20 mL), dried over anhydrous magnesium sulfate and concentrated under reduced pressure to afford a residue, which was purified by a silica gel column with 5% ethyl acetate in petroleum ether to afford methyl 3-(diethylamino)-2-hydroxyquinoxaline-6-carboxylate as a yellow solid (160 mg).

LC/MS (ES, m/z): [M+H]⁺ 276.0

¹H-NMR (300 MHz, CDCl₃) δ 9.86 (s, 1H), 8.24 (s, 1H), 7.77-7.81 (m, 1H), 7.03 (d, J=8.4 Hz, 1H), 3.92 (s, 1H), 3.85-3.89 (m, 4H), 1.29-1.34 (m, 6H)

Step 2. Methyl 3-(diethylamino)-2-[(trifluoromethane)sulfonyloxy]quinoxaline-6-carboxylate

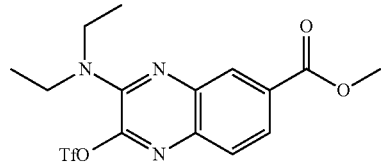 [SMILES: CCN(CC)c1nc2cc(C(=O)OC)ccc2nc1OS(=O)(=O)C(F)(F)F]

To a solution of methyl 3-(diethylamino)-2-hydroxyquinoxaline-6-carboxylate (150 mg, 0.54 mmol) in dichloromethane (20 mL) was added pyridine (260 mg, 3.29 mmol) and Tf₂O (460 mg, 1.63 mmol). After stirring overnight at room temperature, the reaction was quenched by the addition water/ice (50 mL), extracted with dichloromethane (2×10 mL), dried over anhydrous magnesium sulfate and concentrated under vacuum to give methyl 3-(diethylamino)-2-[(trifluoromethane)sulfonyloxy]quinoxaline-6-carboxylate as red oil (200 mg, crude).

Step 3. Methyl 2-(1-benzofuran-2-yl)-3-(diethylamino)quinoxaline-6-carboxylate

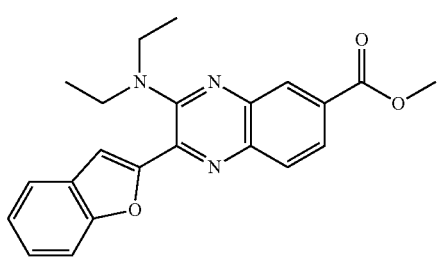 [SMILES: CCN(CC)c1nc2cc(C(=O)OC)ccc2nc1-c1cc2ccccc2o1]

To a solution of methyl 3-(diethylamino)-2-[(trifluoromethane)sulfonyloxy]quinoxaline-6-carboxylate (200 mg, crude) in dioxane (4 mL) was added (1-benzofuran-2-yl)boronic acid (170 mg, 1.05 mmol), K₃PO₄ (230 mg, 1.08 mmol), Pd(PPh₃)₄ (30 mg, 0.03 mmol) and water (3 drops) under nitrogen atmosphere. After stirring 1 h at 90° C., the reaction mixture was dissolved in water (40 mL), extracted with dichloromethane (3×20 mL), dried over anhydrous magnesium sulfate and concentrated under reduced pressure to afford a residue, which was purified by a silica gel column with 2% ethyl acetate in petroleum ether to afford methyl 2-(1-benzofuran-2-yl)-3-(diethylamino)quinoxaline-6-carboxylate as a light yellow solid (70 mg, 38%).

LC/MS (ES, m/z): [M+H]⁺ 376.0

¹H-NMR (300 MHz, CDCl₃) δ 8.59 (s, 1H), 8.12 (d, J=1.8 Hz, 2H), 7.68-7.76 (m, 3H), 7.40-7.45 (m, 1H), 7.30-7.35 (t, J=7.2 Hz, 1H), 3.99 (s, 3H), 3.49-3.56 (m, 4H), 1.18-1.22 (m, 6H)

Step 4. 2-(1-Benzofuran-2-yl)-3-(diethylamino)quinoxaline-6-carboxylic acid

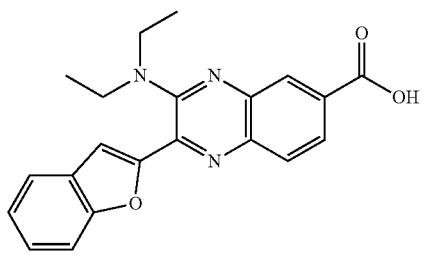 [SMILES: CCN(CC)c1nc2cc(C(=O)O)ccc2nc1-c1cc2ccccc2o1]

To a solution of methyl 2-(1-benzofuran-2-yl)-3-(diethylamino)quinoxaline-6-carboxylate (65 mg, 0.17 mmol) in methanol (10 mL) and water (1 mL) was added sodium hydroxide (13 mg, 0.33 mmol). After stirring overnight at room temperature, the reaction mixture was concentrated under reduced pressure to afford a residue, which was dissolved in water (10 mL), adjusted the pH to 6 with 3N HCl and filtered to give 2-(1-benzofuran-2-yl)-3-(diethylamino)quinoxaline-6-carboxylic acid as a light yellow solid (32.2 mg, 51%).

LC/MS (ES, m/z): [M+H]⁺ 362.0

¹H-NMR (300 MHz, DMSO) δ 13.23 (s, 1H), 8.29 (s, 1H), 7.99-8.05 (m, 2H), 7.74-7.83 (m, 3H), 7.43-7.49 (m, 1H), 7.33-7.38 (t, J=7.2 Hz, 1H), 3.43-3.47 (m, 4H), 1.10-1.15 (m, 6H)

Example 28

2-(6-Fluoro-1-benzofuran-2-yl)-3-[(2S)-2-methylpiperidin-1-yl]quinoxaline-6-carboxylic acid

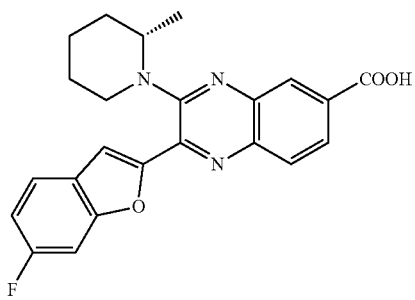 [SMILES: C[C@H]1CCCCN1c1nc2cc(C(=O)O)ccc2nc1-c1cc2ccc(F)cc2o1]

Step 1. Methyl 3-[(2S)-2-methylpiperidin-1-yl]-2-oxo-1,2-dihydroquinoxaline-6-carboxylate

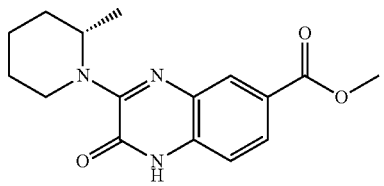 [SMILES: COC(=O)c1ccc2[nH]c(=O)c(N3CCCC[C@@H]3C)nc2c1]

To a solution of methyl 3-chloro-2-oxo-1,2-dihydroquinoxaline-6-carboxylate (500 mg, crude) in DMSO (6 mL) was added DIEA (543 mg, 4.20 mmol), (2S)-2-methylpiperidine (104 mg, 1.05 mmol). The solution was stirred for 6 h at 100° C. Then the reaction was quenched by the addition of water (50 mL). The resulting solution was extracted with ethyl acetate (4×30 mL) and the organic layers were concentrated under vacuum. The residue was purified by a silica gel column with 1%-5% ethyl acetate in petroleum ether to afford methyl 3-[(2S)-2-methylpiperidin-1-yl]-2-oxo-1,2-dihydroquinoxaline-6-carboxylate as a yellow solid (98 mg).

LC/MS (ES, m/z): [M+H]⁺ 302.0

¹H-NMR (300 MHz, CDCl₃) δ 9.39 (s, 1H), 8.28 (s, 1H), 7.83-7.86 (m, 1H), 7.05 (d, J=8.4 Hz, 1H), 5.36-5.40 (m, 1H), 4.88 (d, J=13.5 Hz, 1H), 3.94 (s, 1H), 3.16-3.25 (t, J=13.2 Hz, 1H), 1.50-1.94 (m, 6H), 1.44 (d, J=6.6 Hz, 3H)

Step 2. (S)-Methyl 3-(2-methylpiperidin-1-yl)-2-(trifluoromethylsulfonyloxy)quinoxaline-6-carboxylate

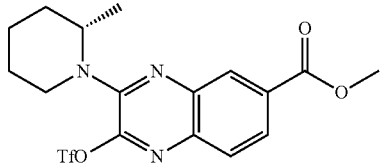 [SMILES: COC(=O)c1ccc2nc(OS(=O)(=O)C(F)(F)F)c(N3CCCC[C@@H]3C)nc2c1]

To a solution of methyl 3-[(2S)-2-methylpiperidin-1-yl]-2-oxo-1,2-dihydroquinoxaline-6-carboxylate (98 mg, 0.33 mmol) in dichloromethane (30 mL) was added pyridine (104 mg, 1.31 mmol), and then Tf₂O (186 mg, 0.66 mmol) was added dropwise with stirring at 0° C. The resulting solution was stirred overnight at room temperature and then quenched by the addition of ice-water (20 mL), extracted with dichloromethane (3×10 mL), dried over anhydrous sodium sulfate and concentrated under vacuum to afford (S)-methyl 3-(2-methylpiperidin-1-yl)-2-(trifluoromethylsulfonyloxy)quinoxaline-6-carboxylate as red oil (200 mg, crude).

Step 3. Methyl 2-(6-fluoro-M-inden-2-yl)-3-[(2S)-2-methylpiperidin-1-yl]quinoxaline-6-carboxylate

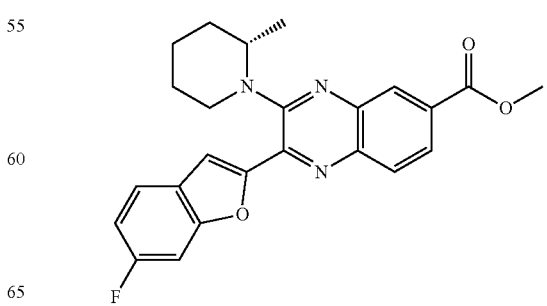

To a solution of methyl 3-[(2S)-2-methylpiperidin-1-yl]-2-[(trifluoromethane)sulfonyloxy]quinoxaline-6-carboxylate (200 mg, crude) in dioxane (5 mL) was added 2-(6-fluoro-1-benzofuran-2-yl)-4,4,5,5-tetramethyl-1,3,2-dioxaborolane (250 mg, 0.95 mmol), Pd(PPh$_3$)$_4$ (27 mg, 0.02 mmol), K$_3$PO$_4$ (291 mg, 1.37 mmol) and water (5 drops) with stirring for 1 h at 90° C. maintained with an inert atmosphere of nitrogen in an oil bath. The reaction mixture was concentrated under vacuum to give the residue, which was applied onto a silica gel column with 1% to 2% ethyl acetate in petroleum to afford methyl 2-(6-fluoro-1H-inden-2-yl)-3-[(2S)-2-methylpiperidin-1-yl]quinoxaline-6-carboxylate as a yellow solid (50 mg).

LC/MS (ES, m/z): [M+H]$^+$ 420.0

$^1$H-NMR (300 MHz, CDCl$_3$) δ 8.67 (s, 1H), 8.12-8.20 (m, 2H), 7.97 (s, 1H), 7.63-7.68 (m, 1H), 7.39-7.43 (m, 1H), 7.07-7.15 (m, 1H), 4.19 (s, 1H), 4.02 (s, 3H), 3.39 (s, 1H), 1.65-1.85 (m, 6H), 1.19 (d, J=6.3 Hz, 3H)

Step 4. 2-(6-Fluoro-1-benzofuran-2-yl)-3-[(2S)-2-methylpiperidin-1-yl]quinoxaline-6-carboxylic acid

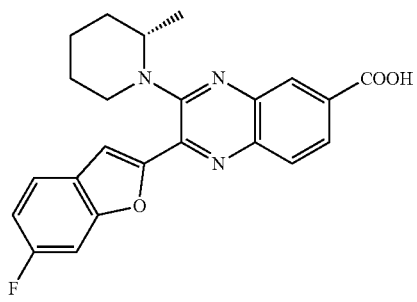 [SMILES: C[C@H]1CCCCN1c1nc2cc(C(=O)O)ccc2nc1-c1cc2ccc(F)cc2o1]

To a solution of methyl 2-(6-fluoro-1-benzofuran-2-yl)-3-[(2S)-2-methylpiperidin-1-yl]quinoxaline-6-carboxylate (50 mg, 0.12 mmol) in methanol (25 mL) and water (5 mL) was added sodium hydroxide (14.4 mg, 0.36 mmol) with stirring overnight at room temperature. The reaction mixture was concentrated under vacuum, dissolved in water (30 mL), adjusted pH to 5 with HCl (3N) to give the precipitate, which was collected by filtration to afford 2-(6-fluoro-1-benzofuran-2-yl)-3-[(2S)-2-methylpiperidin-1-yl]quinoxaline-6-carboxylic acid (36.6 mg, 76%).

LC/MS (ES, m/z): [M+H]$^+$ 406.0

$^1$H-NMR (300 MHz, DMSO) δ 8.29 (s, 1H), 8.03 (s, 2H), 7.96 (s, 1H), 7.81-7.86 (m, 1H), 7.65 (d, J=9.0 Hz, 1H), 7.18-7.25 (m, 1H), 4.00 (d, J=9.0 Hz, 1H), 3.27 (s, 1H), 1.80-1.95 (m, 1H), 1.47-1.66 (m, 5H), 1.05 (d, J=6.6 Hz, 3H)

Example 29

3-(Cyclopropyl(methyl)amino)-2-(1H-indazol-5-yl)quinoxaline-6-carboxylic acid

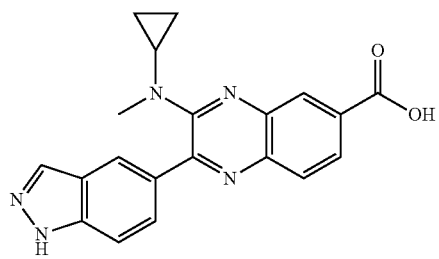 [SMILES: CN(c1nc2cc(C(=O)O)ccc2nc1-c1ccc2[nH]ncc2c1)C1CC1]

Step 1. Methyl 3-(cyclopropyl(methyl)amino)-2-(trifluoromethylsulfonyloxy)quinoxaline-6-carboxylate

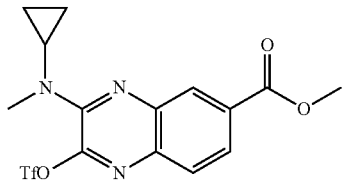

To a solution of methyl 3-(cyclopropyl(methyl)amino)-2-oxo-1,2-dihydroquinoxaline-6-carboxylate (240 mg, 0.88 mmol) in DCM (50 mL) was added pyridine (280 mg, 3.54 mmol) and Tf$_2$O (496 mg, 1.76 mmol). The resulting solution was stirred 3 h at room temperature and then dissolved in water/ice (100 mL), extracted with dichloromethane (3×20 mL), dried over anhydrous magnesium sulfate and concentrated under vacuum to afford methyl 3-(cyclopropyl(methyl)amino)-2-(trifluoromethylsulfonyloxy)quinoxaline-6-carboxylate as a red oil (300 mg, crude), which was used to the next step directly.

Step 2. 3-(Cyclopropyl(methyl)amino)-2-(1H-indazol-5-yl)quinoxaline-6-carboxylate

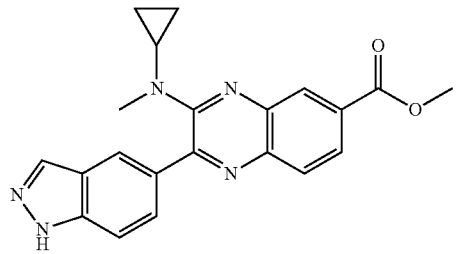 [SMILES: COC(=O)c1ccc2nc(-c3ccc4[nH]ncc4c3)c(N(C)C3CC3)nc2c1]

To a solution of methyl 3-(cyclopropyl(methyl)amino)-2-(trifluoromethylsulfonyloxy)quinoxaline-6-carboxylate (300 mg, crude) in dioxane (10 mL), 1H-indazol-5-ylboronic acid (430 mg, 1.76 mmol), K$_3$PO$_4$ (370 mg, 1.76 mmol), and Pd(PPh$_3$)$_4$ (51 mg, 0.04 mmol). The resulting solution was stirred for 1 h at 90° C. The resulting mixture was concentrated under vacuum to give a residue, which was purified by a silica gel column with 5%-50% ethyl acetate in petroleum ether to afford methyl 3-(cyclopropyl(methyl)amino)-2-(1H-indazol-5-yl)quinoxaline-6-carboxylate as a yellow solid (40 mg).

LC/MS (ES, m/z): [M+H]$^+$ 374.0

$^1$H-NMR (300 MHz, CDCl$_3$) δ 8.96 (s, 1H), 8.28 (s, 2H), 8.10-8.18 (m, 2H), 7.88 (d, J=7.8 Hz, 1H), 7.68 (d, J=8.7 Hz, 2H), 4.02 (s, 3H), 2.70-2.80 (m, 1H), 0.83-0.92 (m, 4H)

Step 3. 3-(Cyclopropyl(methyl)amino)-2-(1H-indazol-5-yl)quinoxaline-6-carboxylic acid

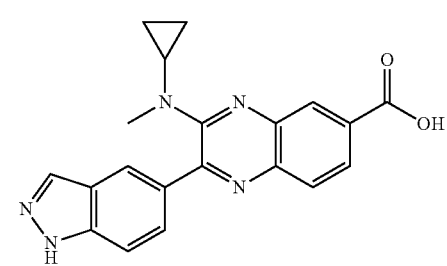 [SMILES: CN(c1nc2cc(C(=O)O)ccc2nc1-c1ccc2[nH]ncc2c1)C1CC1]

To a solution of 3-(cyclopropyl(methyl)amino)-2-(1H-indazol-5-yl)quinoxaline-6-carboxylate (40.0 mg, 0.11 mmol,) in methanol (15 mL) and water (1 mL) was added a solution of NaOH (20 mg, 0.50 mmol). The resulting solution was stirred overnight at room temperature and concentrated under vacuum. The residue was dissolved in water (5 mL) and adjusted to pH 6 with hydrochloric acid (3N). The solids were collected by filtration to afford 3-(cyclopropyl(methyl) amino)-2-(1H-indazol-5-yl)quinoxaline-6-carboxylic acid as a yellow solid (18.2 mg, 47%).

LC/MS (ES, m/z): [M+H]+ 360.0

$^1$H-NMR (300 MHz, CD$_3$OD), δ 8.48 (d, J=1.8 Hz, 1H), 8.27 (d, J=0.3 Hz, 1H), 8.19 (d, J=0.6 Hz, 1H), 8.05-8.08 (m, 1H), 7.91-7.99 (m, 2H), 7.68 (d, J=8.7 Hz, 1H), 3.07 (s, 3H), 2.55 (d, J=5.4 Hz, 1H), 0.50 (d, J=5.4 Hz, 4H)

Example 30

2-(1-Benzofuran-5-yl)-3-[methyl(propan-2-yl) amino]quinoxaline-6-carboxylic acid

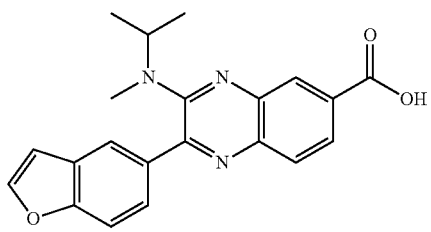 [SMILES: CC(C)N(C)c1nc2cc(C(=O)O)ccc2nc1-c1ccc2occc2c1]

Step 1. (1-Benzofuran-5-yl)boronic acid

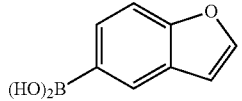

The solution of 5-bromo-1-benzofuran (1.0 g, 5.08 mmol) in dry tetrahydrofuran (50 mL) was kept below −60° C. under nitrogen, while BuLi (6.09 mmol, 2.5M solution in hexane) was added dropwise. It was warmed to −30° C. during 45 min and stirred at this temperature for another 30 min. The mixture was cooled again below −60° C. followed by dropwise addition of triisopropyl borate (1.44 g, 7.66 mmol). After warming to room temperature the mixture was quenched with hydrochloric acid (30 mL, 2N) and stirred for 1 h. The alkaline aqueous layer was brought to pH 5 and extracted with ethyl acetate (3×80 mL). All organic layers were combined, dried over sodium sulfate, and concentrated in vacuo to give (1-benzofuran-5-yl)boronic acid (500 mg, crude), which was used for the next step without further purification.

Step 2. Methyl 2-(1-benzofuran-5-yl)-3-[methyl(propan-2-yl)amino]quinoxaline-6-carboxylate

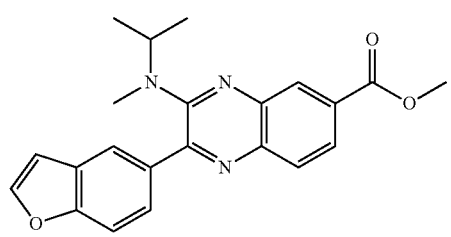 [SMILES: COC(=O)c1ccc2nc(-c3ccc4occc4c3)c(N(C)C(C)C)nc2c1]

To a solution of methyl 2-chloro-3-[methyl(propan-2-yl) amino]quinoxaline-6-carboxylate (100 mg, 0.34 mmol) in dioxane (5.0 mL) was added (1-benzofuran-5-yl)boronic acid (215.6 mg, 1.33 mmol), K$_3$PO$_4$ (280.6 mg, 1.33 mmol), Pd(PPh$_3$)$_4$ (25.56 mg, 0.02 mmol) and water (3 drops) with stirring for 1 h at 90° C. in an oil bath under an inert atmosphere of nitrogen. The reaction mixture was concentrated under vacuum to give a residue, which was purified by a silica gel column with 1% ethyl acetate in petroleum ether to afford methyl 2-(1-benzofuran-5-yl)-3-[methyl(propan-2-yl) amino]quinoxaline-6-carboxylate as a light yellow solid (105 mg, crude). LC/MS (ES, m/z): 376.0

Step 3. 2-(1-Benzofuran-5-yl)-3-[methyl(propan-2-yl)amino]quinoxaline-6-carboxylic acid

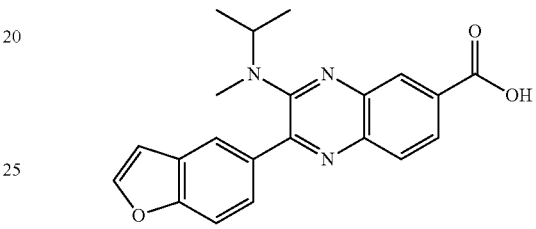

To a solution of methyl 2-(1-benzofuran-5-yl)-3-[methyl (propan-2-yl)amino]quinoxaline-6-carboxylate (105 mg, crude) in methanol (30 mL) was added sodium hydroxide (59.7 mg, 1.49 mmol) with stirring overnight at room temperature. The reaction mixture was concentrated under vacuum, dissolved in water (30 mL) and adjusted to pH 5 with HCl (3N), extracted with ethyl acetate (3×80 mL) and the organic layers combined, dried over anhydrous magnesium sulfate and concentrated under vacuum to give the residue, which was purified by Prep-HPLC under the following conditions [(Agilent 1200 prep HPLC): Column, SunFire Prep C18, 19*50 mm 5 um; mobile phase, water with 0.05% NH$_3$H$_2$O and CH$_3$CN (10% CH$_3$CN up to 45% in 10 min); Detector, UV 220 nm] to afford 2-(1-benzofuran-5-yl)-3-[methyl(propan-2-yl)amino]quinoxaline-6-carboxylic acid as a yellow solid (26.3 mg).

LC/MS (ES, m/z): [M+H]$^+$ 362.0

$^1$H-NMR (300 MHz, DMSO): δ 8.23 (d, J=1.5 Hz, 1H), 8.17 (d, J=1.5 Hz, 1H), 8.08 (d, J=2.1 Hz, 1H), 7.95-7.98 (dd, J$_1$=1.8 Hz, J$_2$=1.5 Hz, 1H), 7.81-7.88 (m, 2H), 7.72 (d, J=9.0 Hz, 1H), 7.08-7.09 (m, 1H), 4.09-4.16 (m, 1H), 2.69 (s, 3H), 1.00 (d, J=6.6 Hz, 6H)

Example 31

2-(6-Chloro-1-benzofuran-2-yl)-3-[methyl(propan-2-yl)amino]quinoxaline-6-carboxylic acid

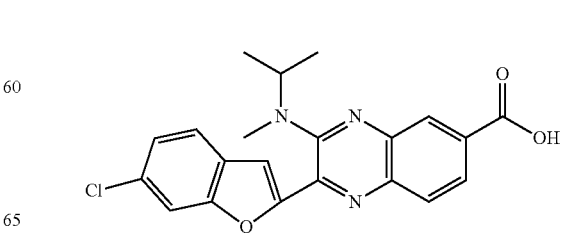

Step 1. Methyl 4-chloro-2-hydroxybenzoate

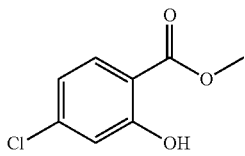

To a solution of 4-chloro-2-hydroxybenzoic acid (20 g, 115.90 mmol) in methanol (500 mL) was added thionyl chloride (26 mL). After refluxing for 3 h, the reaction mixture was concentrated under vacuum, dissolved in petroleum ether (300 mL) and filtered to give methyl 4-chloro-2-hydroxybenzoate as a white solid (21 g, 95%).

$^1$H-NMR (300 MHz, CDCl$_3$) δ 10.88 (s, 1H), 7.77 (d, J=8.4 Hz, 1H), 7.02 (d, J=2.1 Hz, 1H), 6.86-6.90 (m, 1H), 3.97 (s, 3H)

Step 2. Methyl 4-chloro-2-(2-ethoxy-2-oxoethoxy)benzoate

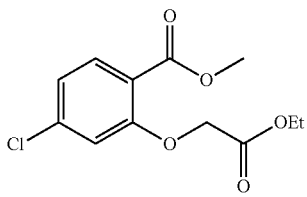 [SMILES: CCOC(=O)COc1cc(Cl)ccc1C(=O)OC]

To a solution of methyl 4-chloro-2-hydroxybenzoate (21 g, 112.55 mmol) in acetone (200 mL) was added ethyl 2-bromoacetate (28.3 g, 169.46 mmol) and potassium carbonate (23.4 g, 169.31 mmol). After refluxing for 3 h, the solids were collected by filtration. The resulting mixture was concentrated under vacuum, dissolved in petroleum ether (300 mL) and filtered to give methyl 4-chloro-2-(2-ethoxy-2-oxoethoxy)benzoate as a red solid (26 g, 85%).

Step 3. 2-(Carboxymethoxy)-4-chlorobenzoic acid

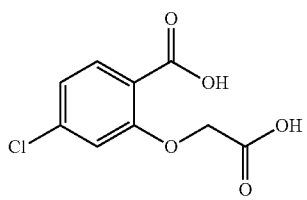 [SMILES: O=C(O)COc1cc(Cl)ccc1C(=O)O]

To a solution of methyl 4-chloro-2-(2-ethoxy-2-oxoethoxy)benzoate (10 g, 36.67 mmol) in methanol (250 mL) and water (50 mL) was added potassium hydroxide (4 g, 71.43 mmol). After stirring for 1.5 h at 25° C., the resulting mixture was concentrated under vacuum, dissolved in water (50 mL), adjusted to pH 6 with HCl (3N) and filtered to give 2-(carboxymethoxy)-4-chlorobenzoic acid as a white solid (7 g, 80%).

$^1$H-NMR (300 MHz, DMSO) δ 7.50 (d, J=8.1 Hz, 1H), 7.39 (d, J=1.8 Hz, 1H), 7.08-7.11 (m, 1H), 4.62 (s, 2H)

Step 4. 6-Methyl-1-benzofuran-3-yl acetate

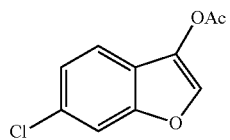

To a solution of 4-chloro-2-(2,3-dioxobutoxy)benzoic acid (5 g, 19.48 mmol) in HOAc (80 mL) and Ac$_2$O (100 mL) was added NaOAc (4.2 g, 51.22 mmol). After stirring for 3 h at 150° C., the resulting mixture was dissolved in water (1000 mL), extracted with ethyl acetate (3×200 mL), dried over anhydrous magnesium sulfate and concentrated in vacuo to give 6-methyl-1-benzofuran-3-yl acetate as off-white oil (3.8 g, 85%).

$^1$H-NMR (300 MHz, DMSO) δ 8.25 (s, 1H), 7.82 (d, J=1.8 Hz, 1H), 7.60 (d, J=8.4 Hz, 1H), 7.35-7.39 (m, 1H), 2.38 (s, 3H)

Step 5. 6-Methyl-2,3-dihydro-1-benzofuran-3-one

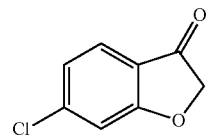 [SMILES: O=C1COc2cc(Cl)ccc21]

A solution of 6-methyl-1-benzofuran-3-yl acetate (3.8 g, 19.98 mmol) in HCl (4 mL, conc), methanol (160 mL), and water (40 mL) was heated under reflux for 1.5 h, the reaction mixture was cooled to room temperature, dissolved in water (200 mL) and filtered to give 6-methyl-2,3-dihydro-1-benzofuran-3-one as a white solid (2.5 g, 82%).

$^1$H-NMR (300 MHz, DMSO) δ 7.65-7.69 (t, J=8.1 Hz, 1H), 7.50 (d, J=1.5 Hz, 1H), 7.18-7.22 (m, 1H), 4.85 (s, 2H)

Step 6. 6-Chloro-1-benzofuran

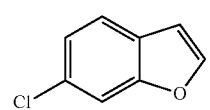

To a solution of 6-chloro-2,3-dihydro-1-benzofuran-3-one (2.5 g, 14.83 mmol) in methanol (50 mL) was treated with NaBH$_4$ (1.2 g, 31.58 mmol) in four equivalent portions at room temperature, until the reaction was complete, as monitored by TLC (1 h). The reaction mixture was quenched by the addition of acetone (10 mL). This mixture was then treated with HCl (3N, 20 mL). After stirring for another 1 h, the resulting solution was extracted with ethyl acetate (3×50 mL) dried over anhydrous magnesium sulfate and concentrated under vacuum to give 6-chloro-1-benzofuran as oil (2 g, crude).

Step 7. 2-(6-Chloro-1-benzofuran-2-yl)-4,4,5,5-tetramethyl-1,3,2-dioxaborolane

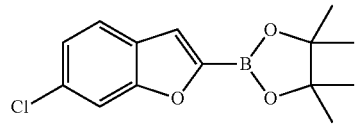 [SMILES: CC1(C)OB(c2cc3ccc(Cl)cc3o2)OC1(C)C]

To a solution of 6-chloro-1-benzofuran (2 g, 13.11 mmol) in tetrahydrofuran (30 mL) was added n-BuLi (10 mL, 2.5N) at −78° C. and stirred for 1.5 h. Then 4,4,5,5-tetramethyl-2-(propan-2-yloxy)-1,3,2-dioxaborolane (4.4 g, 23.65 mmol) was added and stirred for 1.5 h. The reaction solution was quenched by water (100 mL), extracted with ethyl acetate (3×50 mL), dried over anhydrous magnesium sulfate and concentrated under vacuum to give 2-(6-chloro-1-benzofuran-2-yl)-4,4,5,5-tetramethyl-1,3,2-dioxaborolane as a reddish crude solid (3 g, crude).

Step 8. Methyl 2-(6-chloro-1-benzofuran-2-yl)-3-[methyl(propan-2-yl)amino]quinoxaline-6-carboxylate

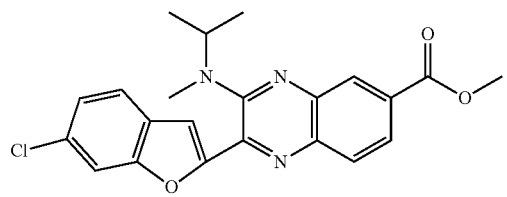 [SMILES: COC(=O)c1ccc2nc(-c3cc4ccc(Cl)cc4o3)c(N(C)C(C)C)nc2c1]

To a solution of methyl 2-chloro-3-[methyl(propan-2-yl)amino]quinoxaline-6-carboxylate (100 mg, 0.34 mmol) in 1,4-dioxane (1 mL) was added 2-(6-chloro-1-benzofuran-2-yl)-4,4,5,5-tetramethyl-1,3,2-dioxaborolane (300 mg, crude), and $K_3PO_4$ (140 mg, 0.66 mmol), $Pd(PPh_3)_4$ (20 mg, 0.02 mmol) under nitrogen atmosphere. After stirring 1 h at 95° C., the reaction mixture was dissolved in water (50 mL), extracted with dichloromethane (3×30 mL), dried over anhydrous magnesium sulfate and concentrated under reduced pressure to afford a residue, which was purified by a silica gel column with 2% ethyl acetate in petroleum ether to afford methyl 2-(6-chloro-1-benzofuran-2-yl)-3-[methyl(propan-2-yl)amino]quinoxaline-6-carboxylate as a light yellow solid (60 mg, 43%).

LC/MS (ES, m/z): $[M+H]^+$ 410.0

$^1$H-NMR (300 MHz, $CDCl_3$) δ 8.60 (d, J=1.5 Hz, 1H), 8.04-8.13 (m, 2H), 7.60-7.67 (m, 3H), 7.30-7.33 (m, 1H), 4.31-4.35 (t, J=6.6 Hz, 1H), 4.01 (s, 3H), 2.93 (s, 3H), 1.23 (d, J=6.6 Hz, 6H)

Step 9. 2-(6-Chloro-1-benzofuran-2-yl)-3-[methyl(propan-2-yl)amino]quinoxaline-6-carboxylic acid

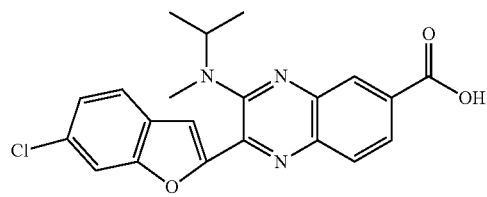 [SMILES: CC(C)N(C)c1nc2cc(C(=O)O)ccc2nc1-c1cc2ccc(Cl)cc2o1]

To a solution of methyl 2-(6-chloro-1-benzofuran-2-yl)-3-[methyl(propan-2-yl)amino]quinoxaline-6-carboxylate (60 mg, 0.15 mmol) in methanol (20 mL) and water (1 mL) was added sodium hydroxide (16 mg, 0.40 mmol). After stirring overnight at room temperature, the reaction mixture was concentrated under reduced pressure to afford a residue, which was dissolved in water (20 mL), adjusted the pH to 6 with 3N HCl and filtered to give 2-(6-chloro-1-benzofuran-2-yl)-3-[methyl(propan-2-yl)amino]quinoxaline-6-carboxylic acid as a light yellow solid (25.2 mg, 43%).

LC/MS (ES, m/z): $[M+H]^+$ 396.0

$^1$H-NMR (300 MHz, DMSO) δ 8.28 (s, 1H), 7.96-8.00 (m, 3H), 7.81 (d, J=8.4 Hz, 1H), 7.70 (d, J=0.9 Hz, 1H), 7.38-7.42 (m, 1H), 4.16-4.21 (t, J=6.6 Hz, 1H), 2.82 (s, 3H), 1.15 (d, J=6.6 Hz, 6H)

Example 32

(S)-2-(6-Fluorobenzofuran-2-yl)-3-(2-methylpyrrolidin-1-yl)quinoxaline-6-carboxylic acid

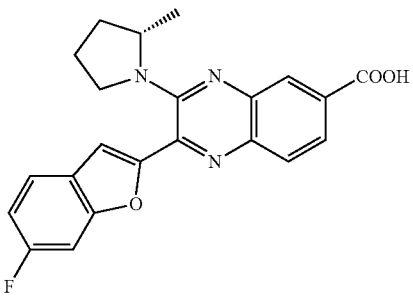 [SMILES: C[C@H]1CCCN1c1nc2cc(C(=O)O)ccc2nc1-c1cc2ccc(F)cc2o1]

Step 1. (S)-Methyl 3-(2-methylpyrrolidin-1-yl)-2-(trifluoromethylsulfonyloxy)quinoxaline-6-carboxylate

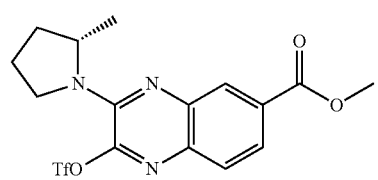 [SMILES: COC(=O)c1ccc2nc(OS(=O)(=O)C(F)(F)F)c(N3CCC[C@@H]3C)nc2c1]

To a solution of (S)-methyl 3-(2-methylpyrrolidin-1-yl)-2-oxo-1,2-dihydroquinoxaline-6-carboxylate (200 mg, 0.70 mmol) in dichloromethane (30 mL) was added pyridine (220 mg, 2.78 mmol), followed by dropwise addition of $Tf_2O$ (393 mg, 1.39 mmol) with stirring at 0° C. The resulting solution was stirred overnight at room temperature and then quenched by the addition of ice-water (50 mL), extracted with dichloromethane (3×10 mL), dried over anhydrous sodium sulfate and concentrated under vacuum to afford (S)-methyl 3-(2- methylpyrrolidin-1-yl)-2-(trifluoromethylsulfonyloxy)quinoxaline-6-carboxylate as red oil (292 mg, crude).

Step 2. Methyl 2-(6-fluoro-1-benzofuran-2-yl)-3-[(2S)-2-methylpyrrolidin-1-yl]quinoxaline-6-carboxylate

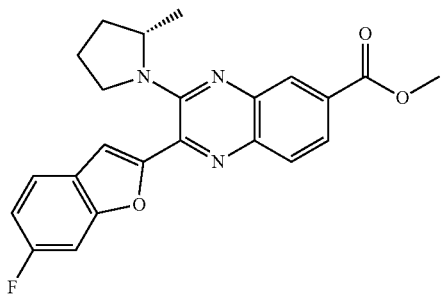 [SMILES: COC(=O)c1ccc2nc(-c3cc4ccc(F)cc4o3)c(N3CCC[C@@H]3C)nc2c1]

To a solution of methyl 3-[(2S)-2-methylpyrrolidin-1-yl]-2-[(trifluoromethane)sulfonyloxy]quinoxaline-6-carboxylate (292 mg, crude) in 1,2-dimethoxyethane (6 mL) was added 2-(6-fluoro-1-benzofuran-2-yl)-4,4,5,5-tetramethyl-1,3,2-dioxaborolane (365 mg, 1.39 mmol), Pd(PPh$_3$)$_4$ (40 mg, 0.03 mmol), K$_3$PO$_4$ (440 mg, 2.07 mmol) and water (5 drops) with stirring for 1 h at 90° C. under an inert atmosphere of nitrogen in an oil bath. The reaction mixture was concentrated under vacuum to give the residue, which was applied onto a silica gel column with 1% to 5% ethyl acetate in petroleum to afford methyl 2-(6-fluoro-1-benzofuran-2-yl)-3-[(2S)-2-methylpyrrolidin-1-yl]quinoxaline-6-carboxylate as a yellow solid (78 mg).

LC/MS (ES, m/z): [M+H]$^+$ 406.0

$^1$H-NMR (300 MHz, CDCl$_3$) δ 8.52 (s, 1H), 8.04 (s, 2H), 7.60-7.65 (m, 1H), 7.37-7.41 (m, 1H), 7.29 (s, 1H), 7.06-7.13 (m, 1H), 4.44-4.53 (m, 1H), 4.01 (s, 3H), 3.51-3.60 (m, 1H), 3.06-3.12 (m, 1H), 2.22-2.32 (m, 1H), 1.89-1.94 (m, 1H), 1.70-1.73 (m, 2H), 1.45 (d, J=6.0 Hz, 3H)

Step 3. (S)-2-(6-Fluorobenzofuran-2-yl)-3-(2-methylpyrrolidin-1-yl)quinoxaline-6-carboxylic acid

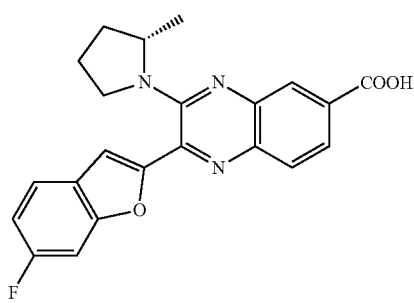 [SMILES: C[C@H]1CCCN1c1nc2cc(C(=O)O)ccc2nc1-c1cc2ccc(F)cc2o1]

To a solution of methyl 2-(6-fluoro-1-benzofuran-2-yl)-3-[(2S)-2-methylpyrrolidin-1-yl]quinoxaline-6-carboxylate (78 mg, 0.19 mmol) in methanol (25 mL) and water (5 mL) was added sodium hydroxide (23 mg, 0.57 mmol) with stirring overnight at room temperature. The reaction mixture was concentrated under vacuum, dissolved in water (10 mL), adjusted to pH 5 with HCl (3N) to give the precipitate, which was collected by filtration to afford (S)-2-(6-fluorobenzofuran-2-yl)-3-(2-methylpyrrolidin-1-yl)quinoxaline-6-carboxylic acid (37.3 mg, 52%).

LC/MS (ES, m/z): [M+H]$^+$ 392.0

$^1$H-NMR (300 MHz, CD$_3$OD) δ 8.39 (s, 1H), 8.02-8.14 (m, 1H), 7.93 (d, J=8.4 Hz, 1H), 7.60-7.80 (m, 1H), 7.43-7.47 (m, 1H), 7.40 (s, 1H), 7.12-7.19 (m, 1H), 4.42-4.53 (m, 1H), 3.50-3.62 (m, 1H), 3.11-3.17 (m, 1H), 2.18-2.26 (m, 1H), 1.83-1.94 (m, 1H), 1.63-1.79 (m, 2H), 1.41 (d, J=6.0 Hz, 3H)

Example 33

2-(5,6-Difluorobenzofuran-2-yl)-3-(isopropyl(methyl)amino)quinoxaline-6-carboxylic acid

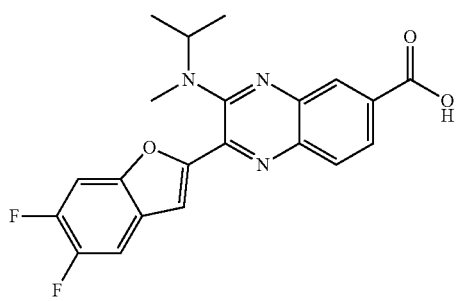 [SMILES: CC(C)N(C)c1nc2cc(C(=O)O)ccc2nc1-c1cc2cc(F)c(F)cc2o1]

LC/MS (ES, m/z): [M+H]+ 398.0.

Example 34

(S)-2-(2,2-Difluorobenzo[d][1,3]dioxol-5-yl)-3-(2-methylpyrrolidin-1-yl)quinoxaline-6-carboxylic acid

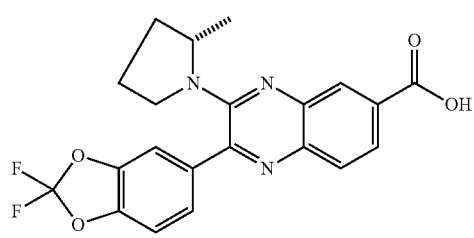 [SMILES: C[C@H]1CCCN1c1nc2cc(C(=O)O)ccc2nc1-c1ccc2c(c1)OC(F)(F)O2]

LC/MS (ES, m/z): [M+H]+ 414.0

Example 35

2-(1H-Indazol-5-yl)-3-(piperidin-1-yl)quinoxaline-6-carboxylic acid

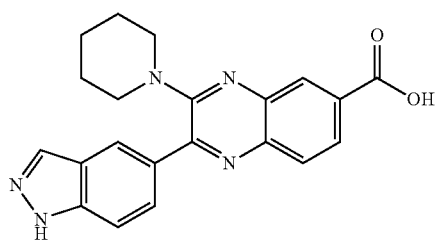 [SMILES: O=C(O)c1ccc2nc(-c3ccc4[nH]ncc4c3)c(N3CCCCC3)nc2c1]

LC/MS (ES, m/z): [M+H]+ 374.0

Example 36

3-(Azepan-1-yl)-2-(1H-indazol-5-yl)quinoxaline-6-carboxylic acid

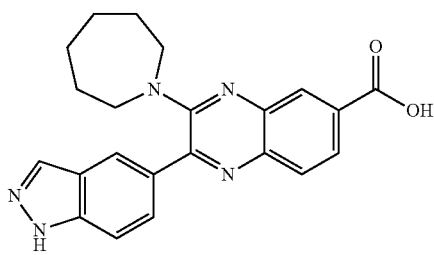 [SMILES: O=C(O)c1ccc2nc(-c3ccc4[nH]ncc4c3)c(N3CCCCCC3)nc2c1]

LC/MS (ES, m/z): [M+H]+ 388.0

Example 37

3-(Azepan-1-yl)-2-(1H-indol-5-yl)quinoxaline-6-carboxylic acid

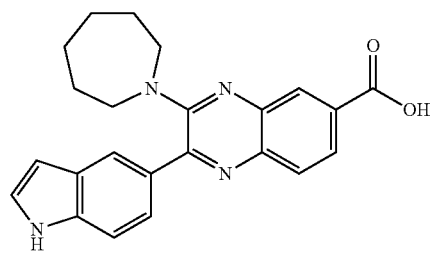 [SMILES: O=C(O)c1ccc2nc(-c3ccc4[nH]ccc4c3)c(N3CCCCCC3)nc2c1]

LC/MS (ES, m/z): [M+H]+ 387.0

Example 38

3-(Diethylamino)-2-(1H-indol-5-yl)quinoxaline-6-carboxylic acid

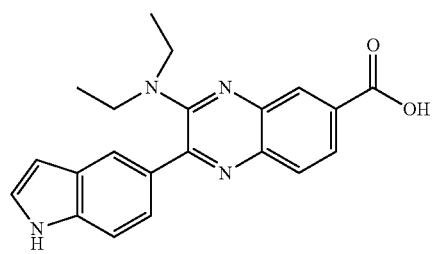 [SMILES: CCN(CC)c1nc2cc(C(=O)O)ccc2nc1-c1ccc2[nH]ccc2c1]

LC/MS (ES, m/z): [M+H]+ 361.0

Example 39

3-(Azepan-1-yl)-2-(5-fluorobenzofuran-2-yl)quinoxaline-6-carboxylic acid

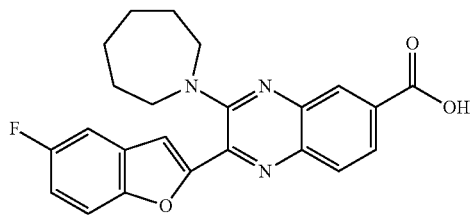 [SMILES: O=C(O)c1ccc2nc(-c3cc4cc(F)ccc4o3)c(N3CCCCCC3)nc2c1]

LC/MS (ES, m/z): [M+H]+ 406.0

Example 40

(S)-2-(1H-Indol-5-yl)-3-(2-methylpyrrolidin-1-yl)quinoxaline-6-carboxylic acid

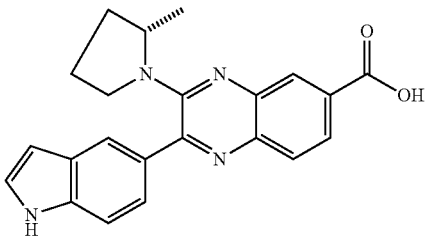 [SMILES: C[C@H]1CCCN1c1nc2cc(C(=O)O)ccc2nc1-c1ccc2[nH]ccc2c1]

LC/MS (ES, m/z): [M+H]+ 373.0

Example 41

(S)-2-(5-Fluorobenzofuran-2-yl)-3-(2-methylpyrrolidin-1-yl)quinoxaline-6-carboxylic acid

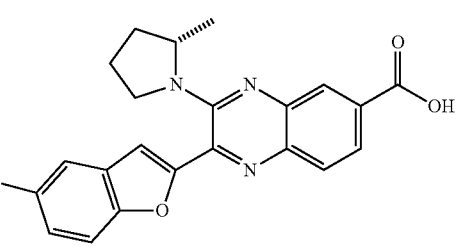

LC/MS (ES, m/z): [M+H]+ 392.0

Example 42

2-(2,2-Difluorobenzo[d][1,3]dioxol-5-yl)-3-(isopropyl(methyl)amino)quinoxaline-6-carboxylic acid

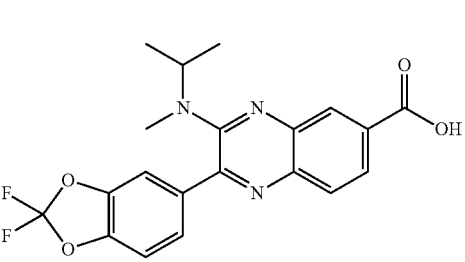 [SMILES: CC(C)N(C)c1nc2cc(C(=O)O)ccc2nc1-c1ccc2c(c1)OC(F)(F)O2]

LC/MS (ES, m/z): [M+H]+ 402.0

Example 43

3-(Isopropyl(methyl)amino)-2-(1H-pyrazol-5-yl)quinoxaline-6-carboxylic acid

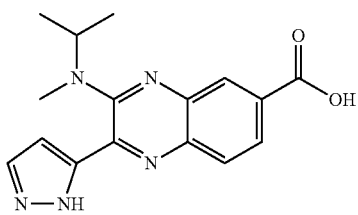 [SMILES: CC(C)N(C)c1nc2cc(C(=O)O)ccc2nc1-c1ccn[nH]1]

LC/MS (ES, m/z): [M+H]+ 312.0

Example 44

2-(3-Methyl-M-indazol-5-yl)-3-(isopropyl(methyl)amino)quinoxaline-6-carboxylic acid

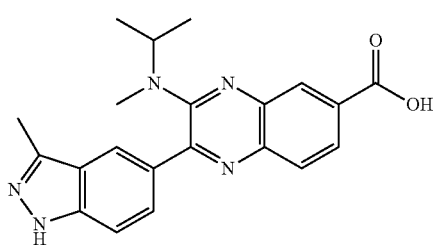 [SMILES: Cc1n[nH]c2ccc(-c3nc4ccc(C(=O)O)cc4nc3N(C)C(C)C)cc12]

Step 1. 5-Bromo-3-methyl-1H-indazole

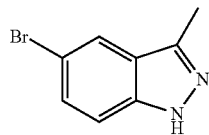

To a solution of 4-bromo-2-ethylbenzenamine (1.5 g, 7.50 mmol) in AcOH (20 mL) was added NaNO$_2$ (570 mg, 8.14 mmol). After stirring for 2.5 h at room temperature, the resulting mixture was concentrated under reduced pressure to afford a residue, which was purified by a silica gel column with 1% methanol in dichloromethane to afford 5-bromo-3-methyl-1H-indazole as a light red solid (700 mg, 44%).

$^1$H-NMR (300 MHz, CDCl$_3$) δ 8.35 (s, 1H), 7.45-7.49 (m, 1H), 7.33 (d, J=8.7 Hz, 1H), 2.59 (s, 3H)

Step 2. 3-Methyl-5-(tetramethyl-1,3,2-dioxaborolan-2-yl)-1H-indazole

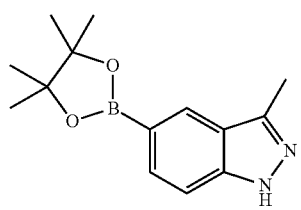 [SMILES: Cc1n[nH]c2ccc(B3OC(C)(C)C(C)(C)O3)cc12]

To a solution of 5-bromo-3-methyl-1H-indazole (400 mg, 1.90 mmol) in DMSO (10 mL) was added 4,4,5,5-tetramethyl-2-(tetramethyl-1,3,2-dioxaborolan-2-yl)-1,3,2-dioxaborolane (959 mg, 3.78 mmol), KOAc (400 mg, 4.08 mmol), Pd(dppf)Cl$_2$ (100 mg). After stirring for 6 h at 85° C., the mixture was dissolved in water (50 mL), extracted with ethyl acetate (3×20 mL), dried over anhydrous magnesium sulfate and concentrated under reduced pressure to afford a residue, which was purified by a silica gel column with 10% ethyl acetate in petroleum ether to afford 3-methyl-5-(tetramethyl-1,3,2-dioxaborolan-2-yl)-1H-indazole as a off-white solid (700 mg, crude).

Step 3. Methyl 3-(isopropyl(methyl)amino)-2-(3-methyl-1H-indazol-5-yl)quinoxaline-6-carboxylate

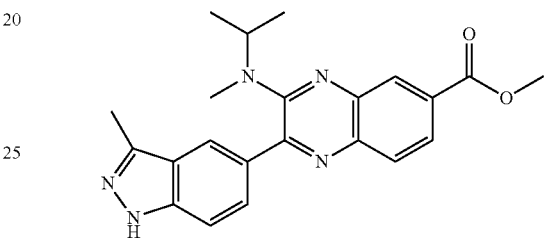

To a solution of methyl 2-chloro-3-(isopropyl(methyl)amino)quinoxaline-6-carboxylate (180 mg, 0.61 mmol) in 1,4-dioxane (1 mL) was added 3-methyl-5-(4,4,5,5-tetramethyl-1,3,2-dioxaborolan-2-yl)-1H-indazole (440 mg, crude), K$_3$PO$_4$ (360 mg, 1.71 mmol), Pd(PPh$_3$)$_4$ (40 mg, 0.03 mmol) under nitrogen atmosphere. After stirring 4 h at 95° C., the reaction mixture was dissolved in water (50 mL), extracted with dichloromethane (3×30 mL), dried over anhydrous magnesium sulfate and concentrated under reduced pressure to afford a residue, which was purified by a silica gel column with 0.5% methanol in dichloromethane to afford methyl 3-(isopropyl(methyl)amino)-2-(3-methyl-1H-indazol-5-yl)quinoxaline-6-carboxylate as a light yellow solid (85 mg, 35%).

LC/MS (ES, m/z): [M+H]$^+$ 390.0

$^1$H-NMR (300 MHz, DMSO) δ 12.85 (s, 1H), 8.26-8.29 (t, J=2.1 Hz, 2H), 7.92-7.99 (m, 2H), 7.85-7.88 (m, 1H), 7.60 (d, J=9.0 Hz, 2H), 4.18-4.24 (m, 1H), 3.93 (s, 3H), 2.72 (s, 3H), 2.54 (s, 3H), 0.88 (d, J=6.6 Hz, 6H)

Step 4. 2-(3-Methyl-1H-indazol-5-yl)-3-(isopropyl(methyl)amino)quinoxaline-6-carboxylic acid

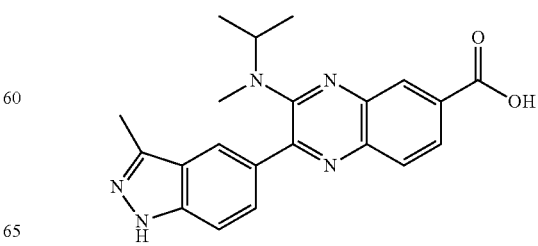

To a solution of methyl 2-(3-methyl-1H-indazol-5-yl)-3-(3-methylbutan-2-yl)quinoxaline-6-carboxylate (85 mg, 0.22 mmol) in methanol (20 mL) and water (1 mL) was added sodium hydroxide (18 mg, 0.45 mmol). After stirring overnight at room temperature, the reaction mixture was concentrated under reduced pressure to afford a residue, which was dissolved in water (20 mL), adjusted the pH value to 6 with 3N HCl and filtered to give 2-(3-methyl-1H-indazol-5-yl)-3-(isopropyl(methyl)amino)quinoxaline-6-carboxylic acid as a light yellow solid (50.1 mg, 61%).

LC/MS (ES, m/z): [M+H]+ 376.0

$^1$H-NMR (300 MHz, DMSO) δ 8.27 (s, 2H), 7.85-7.94 (m, 3H), 7.57-7.60 (d, J=9.3 Hz, 1H), 4.17-4.21 (t, J=6.6 Hz, 1H), 2.72 (s, 3H), 2.54 (s, 3H), 1.02 (d, J=6.6 Hz, 6H)

Example 45

2-(6-Fluoro-1-benzofuran-2-yl)-3-[methyl(propan-2-yl)amino]quinoxaline-6-carboxylic acid

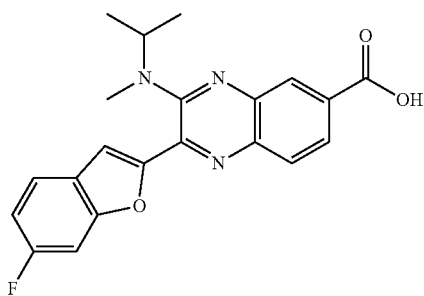 [SMILES: CC(C)N(C)c1nc2cc(C(=O)O)ccc2nc1-c1cc2ccc(F)cc2o1]

Step 1. 2-(2,2-Dibromoethenyl)-5-fluorophenol

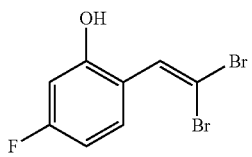 [SMILES: Oc1cc(F)ccc1C=C(Br)Br]

To a solution of CBr$_4$ (5.6 g, 17.1 mmoL) in dichloromethane (100 mL) was added PPh$_3$ (7 g, 26.69 mmol) at 0° C., 30 min later, NEt$_3$ (4.3 g, 42.6 mmol) and 4-fluoro-2-hydroxybenzaldehyde (1 g, 7.14 mmol) was added slowly. After stirring for 30 mins at room temperature, the resulting mixture was concentrated under reduced pressure to afford a residue, which was purified by a silica gel column with 5% ethyl acetate in petroleum ether to afford 2-(2,2-dibromoethenyl)-5-fluorophenol as a white solid (0.58 g, 27%).

$^1$H-NMR (300 MHz, CDCl$_3$) δ 7.47-7.72 (m, 4H)

Step 2. 2-Bromo-6-fluoro-1-benzofuran

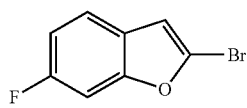

To a solution of 2-(2,2-dibromoethenyl)-5-fluorophenol (580 mg, 1.96 mmol) in tetrahydrofuran (20 mL) was added CuI (30 mg, 0.16 mmol), K$_3$PO$_4$ (800 mg, 3.77 mmol) under nitrogen atmosphere. After stirring overnight at 80° C., the reaction mixture was dissolved in water (50 mL), extracted with dichloromethane (3×30 mL), dried over anhydrous magnesium sulfate and concentrated under reduced pressure to afford a residue, which was purified by a silica gel column with petroleum ether to afford 6-fluoro-1-benzofuran as a white solid (0.16 g, 38%).

$^1$H-NMR (300 MHz, DMSO) δ 7.59-7.65 (m, 2H). 7.15-7.22 (m, 2H)

Step 3. 2-(6-Fluoro-1-benzofuran-2-yl)-4,4,5,5-tetramethyl-1,3,2-dioxaborolane

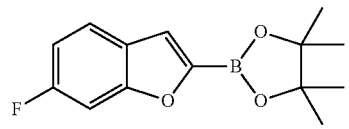 [SMILES: CC1(C)OB(c2cc3ccc(F)cc3o2)OC1(C)C]

To a solution of 2-bromo-6-fluoro-1-benzofuran (450 mg, 2.09 mmol) in DMSO (10 mL) was added KOAc (410 mg, 4.18 mmol), Pd(dppf)Cl$_2$ (150 mg, 0.21 mmol), 15 min later was added 4,4,5,5-tetramethyl-2-(tetramethyl-1,3,2-dioxaborolan-2-yl)-1,3,2-dioxaborolane (1 g, 3.94 mmol) at room temperature. After stirring for 2 h at 85° C., the reaction mixture was dissolved in water (100 mL), extracted with ethyl acetate (3×20 mL), dried over anhydrous magnesium sulfate and concentrated under reduced pressure to afford 2-(6-fluoro-1-benzofuran-2-yl)-4,4,5,5-tetramethyl-1,3,2-dioxaborolane as a black solid (0.6 g, crude).

Step 4. Methyl 2-(6-fluoro-1-benzofuran-2-yl)-3-[methyl(propan-2-yl)amino]quinoxaline-6-carboxylate

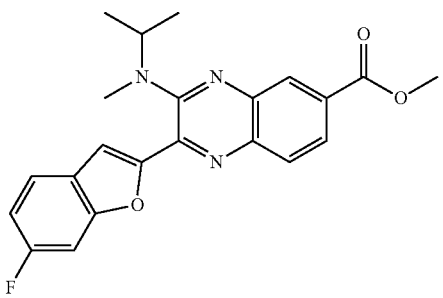 [SMILES: COC(=O)c1ccc2nc(-c3cc4ccc(F)cc4o3)c(N(C)C(C)C)nc2c1]

To a solution of methyl 2-chloro-3-[methyl(propan-2-yl)amino]quinoxaline-6-carboxylate (100 mg, 0.34 mmol) in dioxane (2 mL) was added 2-(6-fluoro-1-benzofuran-2-yl)-4,4,5,5-tetramethyl-1,3,2-dioxaborolane (600 mg, crude), Pd(PPh$_3$)$_4$ (20 mg, 0.02 mmol), K$_3$PO$_4$ (140 mg, 0.66 mmol) under nitrogen atmosphere. After stirring 40 min at 95° C., the reaction mixture was dissolved in water (50 mL), extracted with dichloromethane (3×20 mL), dried over anhydrous magnesium sulfate and concentrated under reduced pressure to afford a residue, which was purified by a silica gel column with 2% ethyl acetate in petroleum ether to afford methyl 2-(6-fluoro-1-benzofuran-2-yl)-3-[methyl(propan-2-yl) amino]quinoxaline-6-carboxylate as a light yellow solid (55 mg).

LC/MS (ES, m/z): [M+H]+ 394.0

$^1$H-NMR (300 MHz, CDCl$_3$) δ 8.59 (s, 1H), 8.08-8.12 (m, 2H), 7.61-7.66 (m, 2H), 7.37-7.40 (t, J=1.8 Hz, 1H), 7.10 (d, J=2.1 Hz, 1H), 4.31-4.35 (t, J=6.6 Hz, 1H), 4.01 (s, 3H), 2.93 (s, 3H), 1.26 (d, J=6.6 Hz, 6H)

Step 5. 2-(6-Fluoro-1-benzofuran-2-yl)-3-[methyl (propan-2-yl)amino]quinoxaline-6-carboxylic acid

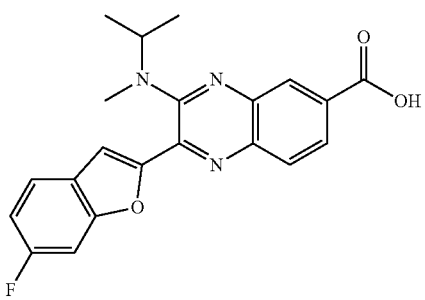 [SMILES: CC(C)N(C)c1nc2cc(C(=O)O)ccc2nc1-c1cc2ccc(F)cc2o1]

To a solution of methyl 2-(6-fluoro-1-benzofuran-2-yl)-3-[methyl(propan-2-yl)amino]quinoxaline-6-carboxylate (55 mg, 0.14 mmol) in methanol (20 mL) and water (1 mL) was added sodium hydroxide (12 mg, 0.30 mmol). After stirring overnight at room temperature, the reaction mixture was concentrated under reduced pressure to afford a residue, which was dissolved in water (10 mL), adjusted the pH value to 5 with 3N HCl and filtered to give 2-(6-fluoro-1-benzofuran-2-yl)-3-[methyl(propan-2-yl)amino]quinoxaline-6-carboxylic acid as a light yellow solid (28.8 mg, 54%).

LC/MS (ES, m/z): [M+H]+ 380.0

$^1$H-NMR (300 MHz, DMSO) δ 8.23 (s, 1H), 8.00-8.03 (t, J=4.5 Hz, 1H), 7.87 (d, J=8.7 Hz, 1H), 7.80-7.82 (t, J=2.7 Hz, 1H), 7.72-7.76 (m, 1H), 7.69 (s, 1H), 7.20-7.27 (m, 1H), 4.11-4.16 (t, J=6.6 Hz, 1H), 2.82 (s, 3H), 1.14-1.17 (d, J=6.6 Hz, 6H)

Example 46

3-(Isopropyl(methyl)amino)-2-(quinolin-6-yl)qui-noxaline-6-carboxylic acid

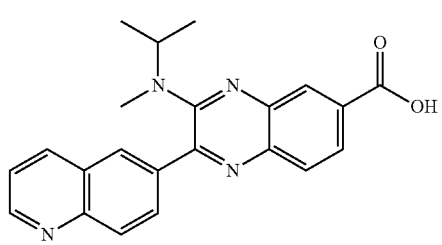 [SMILES: CC(C)N(C)c1nc2cc(C(=O)O)ccc2nc1-c1ccc2ncccc2c1]

LC/MS (ES, m/z): [M+H]+ 373.00

Example 47

2-(1H-Indazol-5-yl)-3-[(2S)-2-methylpyrrolidin-1-yl]quinoxaline-6-carboxylic acid

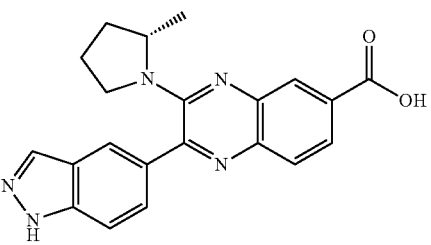 [SMILES: C[C@H]1CCCN1c1nc2cc(C(=O)O)ccc2nc1-c1ccc2[nH]ncc2c1]

Step 1. tert-Butyl 5-bromo-1H-indazole-1-carboxylate

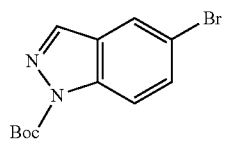

To a solution of 5-bromo-1H-indazole (3 g, 15.23 mmol) in acetonitrile (40 mL) was added 4-dimethylaminopyridine (373 mg, 3.05 mmol), (Boc)$_2$O (3.67 g, 16.82 mmol) and triethylamine (1.55 g, 15.32 mmol). The solution was stirred overnight at room temperature and concentrated under vacuum. The residue was dissolved in ethyl acetate (200 mL), washed with water (3×50 mL) and the organic layers were dried over anhydrous magnesium sulfate, concentrated under vacuum. The residue was purified by a silica gel column with 1%-2% ethyl acetate in petroleum ether to afford tert-butyl 5-bromo-1H-indazole-1-carboxylate as yellow oil (3.88 g, 86%).

$^1$H-NMR (300 MHz, CDCl$_3$) δ 8.08-8.13 (m, 2H), 7.89-7.90 (m, 1H), 7.61-7.65 (m, 1H), 1.74 (s, 9H)

Step 2. tert-Butyl 5-(tetramethyl-1,3,2-dioxaborolan-2-yl)-1H-indazole-1-carboxylate

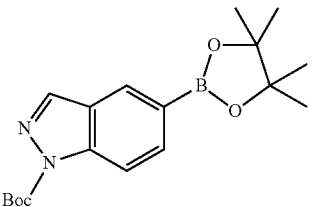 [SMILES: CC(C)(C)OC(=O)n1ncc2cc(B3OC(C)(C)C(C)(C)O3)ccc21]

To a solution of tert-butyl 5-bromo-1H-indazole-1-carboxylate (750 mg, 2.52 mmol) in DMSO (10 mL), was added KOAc (666 mg, 6.79 mmol) and Pd(dppf)Cl$_2$ (250 mg, 0.34 mmol). The solution was stirred for 15 mins at room temperature and then added 4,4,5,5-tetramethyl-2-(tetramethyl-1,3,2-dioxaborolan-2-yl)-1,3,2-dioxaborolane (1.72 g, 6.77 mmol). The resulting solution was stirred for 2.5 h at 85° C. Then the reaction was quenched by the addition of water (100 mL) and extracted with ethyl acetate (3×50 mL), dried over anhydrous sodium sulfate and concentrated under vacuum to give a residue, which was purified by a silica gel column with 1%-2% ethyl acetate in petroleum ether to afford tert-butyl 5-(tetramethyl-1,3,2-dioxaborolan-2-yl)-1H-indazole-1-carboxylate as a white solid (500 mg, crude).

$^1$H-NMR (300 MHz, CDCl$_3$) δ 8.25 (s, 1H), 8.17-8.20 (m, 2H), 7.94-7.98 (m, 1H), 2.14 (s, 9H), 1.38 (s, 12H)

Step 3. (S)-Methyl 3-(2-methylpyrrolidin-1-yl)-2-(trifluoromethylsulfonyloxy)quinoxaline-6-carboxylate

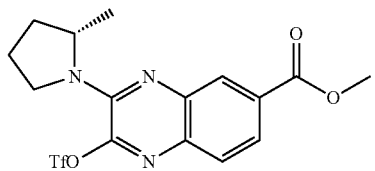 [SMILES: COC(=O)c1ccc2nc(OS(=O)(=O)C(F)(F)F)c(N3CCC[C@@H]3C)nc2c1]

To a solution of (S)-methyl 3-(2-methylpyrrolidin-1-yl)-2-oxo-1,2-dihydroquinoxaline-6-carboxylate (200 mg, 0.70 mmol) in dichloromethane (30 mL) was added pyridine (220 mg, 2.78 mmol), and then Tf$_2$O (393 mg, 1.39 mmol) was added dropwise with stirring at 0° C. The resulting solution was stirred overnight at room temperature and then quenched by the addition of ice-water (20 mL), extracted with dichloromethane (2×20 mL), dried over anhydrous sodium sulfate and concentrated under vacuum to afford (S)-methyl 3-(2-methylpyrrolidin-1-yl)-2-(trifluoromethylsulfonyloxy)quinoxaline-6-carboxylate as red oil (292 mg, crude).

Step 4. Methyl 2-[1-[(tert-butoxy)carbonyl]-1H-indazol-5-yl]-3-[(2S)-2-methylpyrrolidin-1-yl]quinoxaline-6-carboxylate

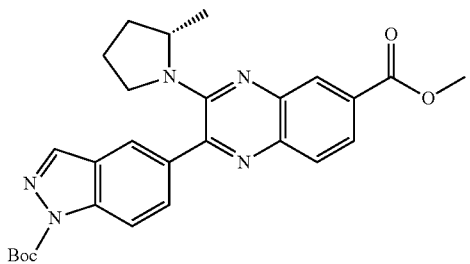 [SMILES: COC(=O)c1ccc2nc(-c3ccc4c(cnn4C(=O)OC(C)(C)C)c3)c(N3CCC[C@@H]3C)nc2c1]

To a solution of methyl 3-[(2S)-2-methylpyrrolidin-1-yl]-2-[(trifluoromethane)sulfonyloxy]quinoxaline-6-carboxylate (292 mg, crude) in dioxane (12 mL) was added tert-butyl 5-(tetramethyl-1,3,2-dioxaborolan-2-yl)-1H-indazole-1-carboxylate (300 mg), Pd(PPh$_3$)$_4$ (40 mg, 0.03 mmol), K$_3$PO$_4$ (221 mg, 1.05 mmol) and water (3 mL). The resulting solution was stirred for 1 h at 90° C. and then quenched by the addition of water (50 mL), extracted with dichloromethane (3×20 mL), dried over anhydrous sodium sulfate and concentrated under vacuum to give a residue, which was purified by a silica gel column with 25% ethyl acetate in petroleum ether to afford methyl 2-[1-[(tert-butoxy)carbonyl]-1H-indazol-5-yl]-3-[(2S)-2-methylpyrrolidin-1-yl]quinoxaline-6-carboxylate as a yellow solid (105 mg, crude).

LC/MS (ES, m/z): [M+H]$^+$ 488.0

$^1$H-NMR (300 MHz, CDCl$_3$): δ 8.63 (s, 1H), 8.29-8.34 (t, J=8.7 Hz, 2H), 8.20 (s, 1H), 7.96-8.07 (m, 3H), 4.44 (d, J=4.8 Hz, 1H), 4.01 (s, 3H), 3.09 (s, 1H), 2.97 (s, 1H), 2.20 (s, 1H), 1.78 (s, 9H), 1.38-1.44 (m, 3H), 1.25-1.30 (m, 3H)

Step 5. Methyl 2-(1H-indazol-5-yl)-3-[(2S)-2-methylpyrrolidin-1-yl]quinoxaline-6-carboxylate

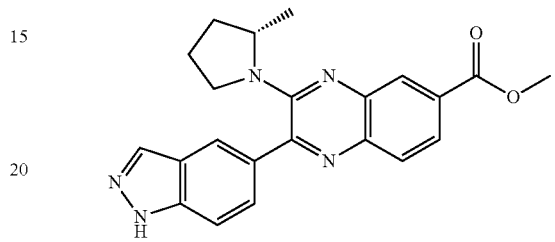

To a solution of methyl 2-[1-[(tert-butoxy)carbonyl]-1H-indazol-5-yl]-3-[(2S)-2-methylpyrrolidin-1-yl]quinoxaline-6-carboxylate (105 mg, crude) in dichloromethane (20 mL) was added 2,2,2-trifluoroacetic acid (4 mL), The solution was stirred for 3 h at room temperature and concentrated under vacuum. The residue was quenched by the addition of water (50 mL) and adjusted pH to 9 with NaHCO$_3$ (aq.), extracted with dichloromethane (3×30 mL), dried over anhydrous sodium sulfate and concentrated under vacuum to afford methyl 2-(1H-indazol-5-yl)-3-[(2S)-2-methylpyrrolidin-1-yl]quinoxaline-6-carboxylate as a light yellow solid (69 mg, crude).

LC/MS (ES, m/z): [M+H]$^+$ 388.0

Step 6. 2-(1H-Indazol-5-yl)-3-[(2S)-2-methylpyrrolidin-1-yl]quinoxaline-6-carboxylic acid

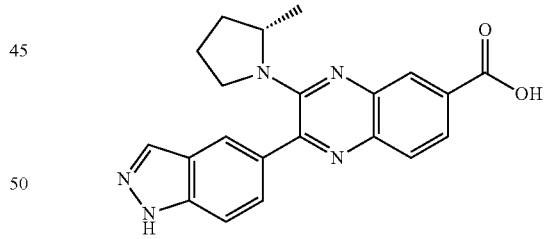

To a solution of methyl 2-(1H-indazol-5-yl)-3-[(2S)-2-methylpyrrolidin-1-yl]quinoxaline-6-carboxylate (69 mg, 0.18 mmol) in MeOH (20 mL) was added sodium hydroxide (21.6 mg, 0.54 mmol) and water (2 mL). The resulting solution was stirred overnight at room temperature and concentrated under vacuum. The residue was dissolved in water (5 mL) and adjusted pH to 5 with hydrochloric acid (1N). The solids were collected by filtration to afford 2-(1H-indazol-5-yl)-3-[(2S)-2-methylpyrrolidin-1-yl]quinoxaline-6-carboxylic acid as a yellow solid (29 mg, 43%).

LC/MS (ES, m/z): [M+H]$^+$ 374.0

$^1$H-NMR (300 MHz, DMSO) δ 13.27 (s, 1H), 8.25 (d, J=1.2 Hz, 1H), 8.22 (s, 1H), 8.15 (s, 1H), 7.86-7.95 (m, 2H), 7.76-7.79 (t, J=1.5 Hz, 1H), 7.67 (d, J=8.7 Hz, 1H), 4.19-4.26

(m, 1H), 2.92-3.06 (m, 2H), 2.07-2.16 (m, 1H), 1.60-1.68 (m, 1H), 1.52-1.57 (m, 2H), 1.36 (d, J=6.6 Hz, 3H)

Example 48

3-(Azepan-1-yl)-2-(6-fluoro-1-benzofuran-2-yl)quinoxaline-6-carboxylic acid

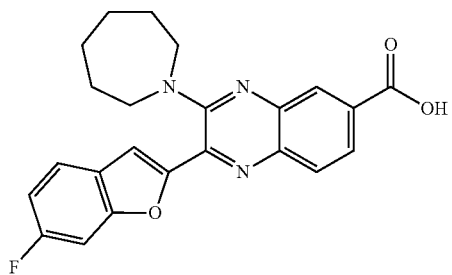 [SMILES: O=C(O)c1ccc2nc(-c3cc4ccc(F)cc4o3)c(N3CCCCCC3)nc2c1]

Step 1. Methyl 3-(azepan-1-yl)-2-oxo-1,2-dihydroquinoxaline-6-carboxylate

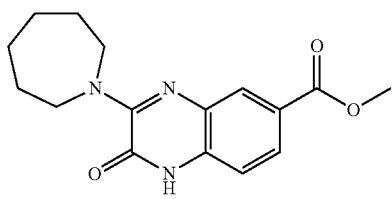 [SMILES: COC(=O)c1ccc2[nH]c(=O)c(N3CCCCCC3)nc2c1]

To a solution of methyl 3-chloro-2-oxo-1,2-dihydroquinoxaline-6-carboxylate (500 mg, crude) in DMSO (6 mL) was added DIEA (543 mg, 4.20 mmol) and azepane (208 mg, 2.10 mmol). The solution was stirred overnight at 90° C. Then the reaction was quenched by the addition of water (50 mL), extracted with ethyl acetate (5×20 mL) and the organic layers were concentrated under vacuum to give a residue, which was purified by a silica gel column with 1%-5% ethyl acetate in petroleum ether to afford methyl 3-(azepan-1-yl)-2-oxo-1,2-dihydroquinoxaline-6-carboxylate as a yellow solid (165 mg).

LC/MS (ES, m/z): [M+H]$^+$ 302.0

$^1$H-NMR (300 MHz, CDCl$_3$) δ 9.74 (s, 1H), 8.16 (d, J=1.5 Hz, 1H), 7.78-7.82 (m, 1H), 7.02 (d, J=8.4 Hz, 1H), 4.04 (s, 4H), 3.94 (s, 3H), 1.91 (s, 4H), 1.54-1.66 (m, 4H)

Step 2. Methyl 3-(azepan-1-yl)-2-(trifluoromethylsulfonyloxy)quinoxaline-6-carboxylate

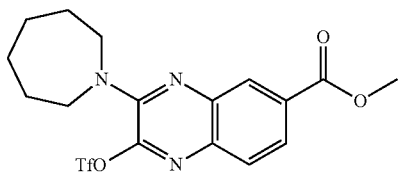 [SMILES: COC(=O)c1ccc2nc(OS(=O)(=O)C(F)(F)F)c(N3CCCCCC3)nc2c1]

To a solution of methyl 3-(azepan-1-yl)-2-oxo-1,2-dihydroquinoxaline-6-carboxylate (100 mg, 0.33 mmol) in dichloromethane (30 mL) was added pyridine (104 mg, 1.31 mmol) and then Tf$_2$O (186 mg, 0.66 mmol) was added dropwise with stirring at 0° C. The resulting solution was stirred overnight at room temperature and then quenched by the addition of ice-water (20 mL), extracted with dichloromethane (3×10 mL), dried over anhydrous sodium sulfate and concentrated under vacuum to afford methyl 3-(azepan-1-yl)-2-(trifluoromethylsulfonyloxy)quinoxaline-6-carboxylate as red oil (200 mg, crude).

Step 3. Methyl 3-(azepan-1-yl)-2-(6-fluoro-1-benzofuran-2-yl)quinoxaline-6-carboxylate

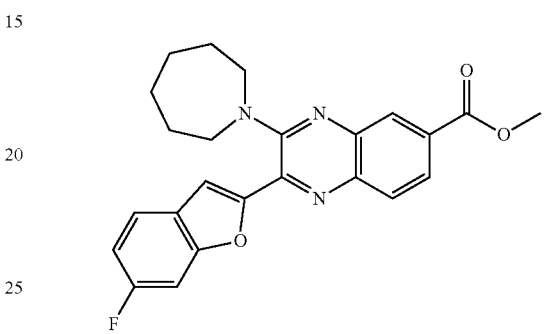

To a solution of methyl 3-(azepan-1-yl)-2-[(trifluoromethane)sulfonyloxy]quinoxaline-6-carboxylate (200 mg, crude) in 1,2-dimethoxyethane (5 mL) was added 2-(6-fluoro-1-benzofuran-2-yl)-4,4,5,5-tetramethyl-1,3,2-dioxaborolane (250 mg, 0.95 mmol), Pd(PPh$_3$)$_4$ (27 mg, 0.02 mmol), K$_3$PO$_4$ (291 mg, 1.37 mmol) and water (5 drops) with stirring for 1 h at 90° C. maintained with an inert atmosphere of nitrogen in an oil bath. The reaction mixture was concentrated under vacuum to give the residue, which was applied onto a silica gel column with 1% to 2% ethyl acetate in petroleum to afford methyl 3-(azepan-1-yl)-2-(6-fluoro-1-benzofuran-2-yl)quinoxaline-6-carboxylate as a yellow solid (73 mg).

LC/MS (ES, m/z): [M+H]$^+$ 420.0

$^1$H-NMR (300 MHz, CDCl$_3$) δ 8.59 (s, 1H), 8.00-8.08 (m, 2H), 7.60-7.65 (m, 1H), 7.41 (s, 1H), 7.34-7.38 (m, 1H), 7.06-7.13 (m, 1H), 4.01 (s, 3H), 3.64-3.68 (t, J=6.0 Hz, 4H), 1.83-1.90 (m, 4H), 1.60-1.76 (m, 4H)

Step 4. 3-(Azepan-1-yl)-2-(6-fluoro-1-benzofuran-2-yl)quinoxaline-6-carboxylic acid

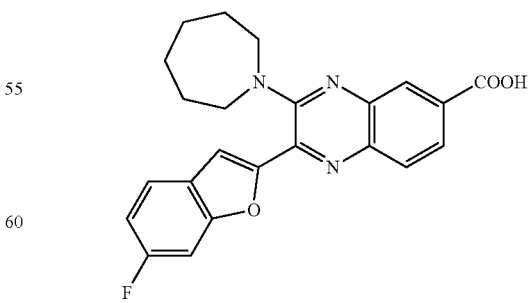

To a solution of methyl 3-(azepan-1-yl)-2-(6-fluoro-1-benzofuran-2-yl)quinoxaline-6-carboxylate (73 mg, 0.17 mmol) in methanol (25 mL) and chloroform (5 mL) was added sodium hydroxide (13.6 mg, 0.34 mmol) and water (2 mL) with stirring overnight at room temperature. The reaction mixture was concentrated under vacuum, dissolved in water (15 mL), adjusted pH to 5 with HCl (3 N) to give the precipitate, which was collected by filtration to afford 3-(azepan-1-yl)-2-(6-fluoro-1-benzofuran-2-yl)quinoxaline-6-carboxylic acid (39 mg, 55%).

LCMS (ES, m/z): [M+H]$^+$ 406.0

$^1$H-NMR (300 MHz, CD$_3$OD) δ 8.38 (s, 1H), 8.01-8.04 (m, 1H), 7.93 (d, J=8.4 Hz, 1H), 7.72-7.77 (m, 1H), 7.48 (s, 1H), 7.41-7.45 (m, 1H), 7.12-7.19 (m, 1H), 3.62-3.66 (t, J=5.7 Hz, 4H), 1.82-1.90 (m, 4H), 1.58-1.62 (m, 4H)

Example 49

3-(Cyclopropyl(methyl)amino)-2-(6-fluorobenzofuran-2-yl)quinoxaline-6-carboxylic acid

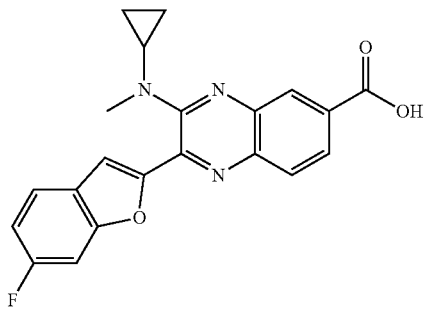 [SMILES: CN(c1nc2cc(C(=O)O)ccc2nc1-c1cc2ccc(F)cc2o1)C1CC1]

Step 1. Methyl 3-(cyclopropyl(methyl)amino)-2-(trifluoromethylsulfonyloxy)quinoxaline-6-carboxylate

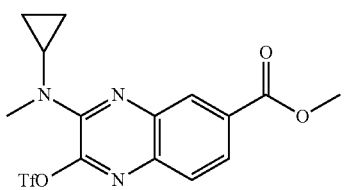

To a solution of methyl 3-(cyclopropyl(methyl)amino)-2-oxo-1,2-dihydroquinoxaline-6-carboxylate (120 mg, 0.44 mmol) in dichloromethane (10 mL) was added pyridine (135 mg, 1.71 mmol) and Tf$_2$O (230 mg, 0.82 mmol) under nitrogen atmosphere. After stirring overnight at room temperature, the reaction was quenched by the addition water/ice (50 mL), extracted with dichloromethane (2×10 mL), dried over anhydrous magnesium sulfate and concentrated under vacuum to give methyl 3-(cyclopropyl(methyl)amino)-2-(trifluoromethylsulfonyloxy)quinoxaline-6-carboxylate as red oil (130 mg, crude).

Step 2. Methyl 3-[cyclopropyl(methyl)amino]-2-(6-fluoro-1-benzofuran-2-yl)quinoxaline-6-carboxylate

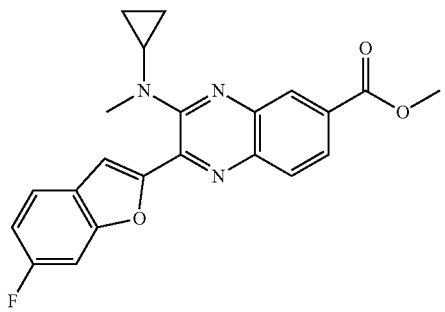 [SMILES: COC(=O)c1ccc2nc(-c3cc4ccc(F)cc4o3)c(N(C)C3CC3)nc2c1]

To a solution of methyl 3-[cyclopropyl(methyl)amino]-2-[(trifluoromethane)sulfonyloxy]quinoxaline-6-carboxylate (130 mg, crude) in dioxane (2 mL) was added 2-(6-fluoro-2,3,5,6-tetrahydro-1-benzofuran-2-yl)-4,4,5,5-tetramethyl-1,3,2-dioxaborolane (175 mg, 0.66 mmol), K$_3$PO$_4$ (140 mg, 0.66 mmol), Pd(PPh$_3$)$_4$ (20 mg, 0.02 mmol) and water (3 drops) under nitrogen atmosphere. After stirring 40 min at 90° C., the reaction mixture was dissolved in water (40 mL), extracted with dichloromethane (3×20 mL), dried over anhydrous magnesium sulfate and concentrated under reduced pressure to afford a residue, which was purified by a silica gel column with 2% ethyl acetate in petroleum ether to afford methyl 3-[cyclopropyl(methyl)amino]-2-(6-fluoro-1-benzofuran-2-yl)quinoxaline-6-carboxylate as a yellow solid (55 mg).

LC/MS (ES, m/z): [M+H]$^+$ 392.0

$^1$H-NMR (300 MHz, DMSO) δ 8.30 (d, J=1.5 Hz, 1H), 7.98-8.08 (m, 2H), 7.73-7.83 (m, 2H), 7.65 (s, 1H), 7.20-7.27 (m, 1H), 3.94 (s, 3H), 3.09 (s, 3H), 2.89 (s, 1H), 0.51-0.57 (m, 4H)

Step 3. 3-(Cyclopropyl(methyl)amino)-2-(6-fluorobenzofuran-2-yl)quinoxaline-6-carboxylic acid

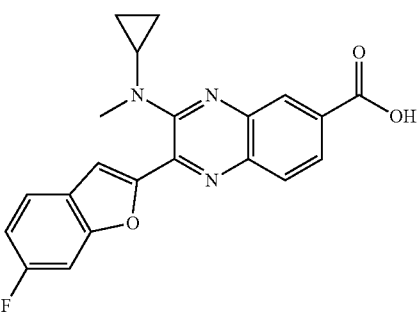 [SMILES: CN(c1nc2cc(C(=O)O)ccc2nc1-c1cc2ccc(F)cc2o1)C1CC1]

To a solution of methyl 3-[cyclopropyl(methyl)amino]-2-(6-fluoro-1-benzofuran-3-yl)quinoxaline-6-carboxylate (55 mg, 0.15 mmol) in methanol (20 mL) and water (1 mL) was added sodium hydroxide (10 mg, 0.25 mmol). After stirring overnight at room temperature, the reaction mixture was concentrated under reduced pressure to afford a residue, which was dissolved in water (10 mL), adjusted the pH to 5 with 3N HCl and filtered to give 3-(cyclopropyl(methyl)amino)-2-(6-fluorobenzofuran-2-yl)quinoxaline-6-carboxylic acid as a light yellow solid (28.7 mg, 50%).

LC/MS (ES, m/z): [M+H]$^+$ 378.0

$^1$H-NMR (300 MHz, DMSO) δ 8.28 (s, 1H), 7.98-8.05 (m, 2H), 7.72-7.82 (m, 2H), 7.63 (s, 1H), 7.19-7.27 (m, 1H), 3.07 (s, 3H), 2.87-2.91 (m, 1H), 0.47-0.60 (m, 4H)

Example 50

2-(1,2-Benzoxazol-5-yl)-3-[methyl(propan-2-yl)amino]quinoxaline-6-carboxylic acid

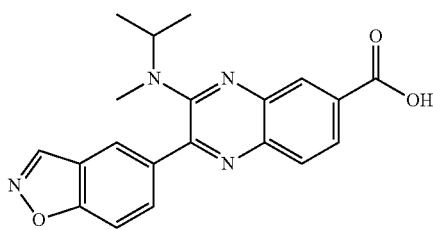

Step 1. 2-Hydroxy-5-(tetramethyl-1,3,2-dioxaborolan-2-yl)benzaldehyde

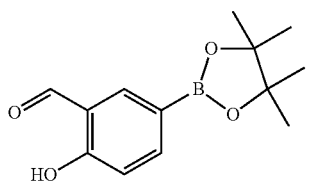 [SMILES: CC1(C)OB(c2ccc(O)c(C=O)c2)OC1(C)C]

To a solution of 5-bromo-2-hydroxybenzaldehyde (5 g, 24.87 mmol) in 1,4-dioxane (20 mL) was added KOAc (6.2 g, 63.18 mmol) and Pd(dppf)Cl$_2$ (1.6 g, 2.19 mmol). The solution was stirred for 15 min at room temperature and then 4,4,5,5-tetramethyl-2-(tetramethyl-1,3,2-dioxaborolan-2-yl)-1,3,2-dioxaborolane (7.7 g, 30.32 mmol) was added. The resulting solution was stirred for 2 h at 85° C. Then the reaction was quenched by the addition of water (300 mL). The resulting solution was extracted with ethyl acetate (4×60 mL), dried over anhydrous sodium sulfate and concentrated in vacuo to give a residue, which was purified by silica gel column chromatography eluting with petroleum ether to afford 2-hydroxy-5-(tetramethyl-1,3,2-dioxaborolan-2-yl)benzaldehyde (4.8 g, 78%).

$^1$H-NMR (300 MHz, CDCl$_3$) δ 11.23 (s, 1H), 9.93 (s, 1H), 8.06 (d, J=1.5 Hz, 1H), 7.94-7.97 (m, 1H), 6.98 (d, J=8.4 Hz, 1H), 1.36 (s, 12H)

Step 2. (4-Methoxyphenyl)methyl 2-bromo-3-[methyl(propan-2-yl)amino]quinoxaline-6-carboxylate

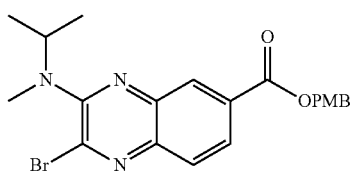

To a solution of (4-methoxyphenyl)methyl 3-[methyl(propan-2-yl)amino]-2-[(trifluoromethane)sulfonyloxy]quinoxaline-6-carboxylate (550 mg, 1.07 mmol) in toluene (10 mL) was added TBAB (350 mg, 1.17 mmol). The solution was stirred for 3 h at 110° C. Then the reaction was quenched by the addition of water (100 mL). The resulting solution was extracted with dichloromethane (3×30 mL), dried over anhydrous sodium sulfate and concentrated in vacuo to give a residue, which was purified by silica gel column chromatography with dichloromethane to afford (4-methoxyphenyl)methyl 2-bromo-3-[methyl(propan-2-yl)amino]quinoxaline-6-carboxylate (400 mg, 84%).

$^1$H-NMR (300 MHz, CDCl$_3$) δ 8.48 (d, J=1.8 Hz, 1H), 8.07-8.11 (m, 1H), 7.88 (d, J=8.7 Hz, 1H), 7.43 (d, J=8.7 Hz, 2H), 6.94 (d, J=8.7 Hz, 2H), 5.36 (s, 2H), 4.46-4.55 (m, 1H), 3.84 (s, 3H), 3.74 (s, 3H), 2.98 (s, 3H), 1.28 (d, J=6.6 Hz, 6H)

Step 3. (4-Methoxyphenyl)methyl 2-(3-formyl-4-hydroxyphenyl)-3-[methyl(propan-2-yl)amino]quinoxaline-6-carboxylate

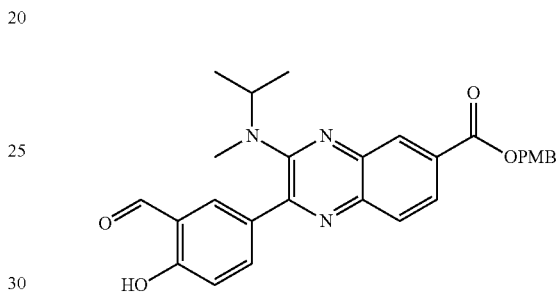

To a solution of (4-methoxyphenyl)methyl 2-bromo-3-[methyl(propan-2-yl)amino]quinoxaline-6-carboxylate (400 mg, 0.90 mmol) in 1,2-dimethoxyethane (10 mL) was added 2-hydroxy-5-(tetramethyl-1,3,2-dioxaborolan-2-yl)benzaldehyde (444 mg, 2.26 mmol), Et$_3$N (273 mg, 2.7 mmol), Pd(dppf)Cl$_2$ (58 mg, 0.08 mmol) and water (5 drops). The resulting solution was stirred for 1 h at 90° C. and maintained under an inert atmosphere of nitrogen in an oil bath. The reaction mixture was concentrated in vacuo to give the residue, which was purified by silica gel column chromatography eluting with 1% to 5% ethyl acetate in petroleum to afford (4-methoxyphenyl)methyl 2-(3-formyl-4-hydroxyphenyl)-3-[methyl(propan-2-yl)amino]quinoxaline-6-carboxylate as a yellow solid (190 mg, 43%).

LC/MS (ES, m/z): [M+H]$^+$ 486.0

$^1$H-NMR (300 MHz, CDCl$_3$) δ 11.24 (s, 1H), 10.03 (s, 1H), 8.57 (s, 1H), 8.31 (s, 1H), 8.18 (d, J=9.0 Hz, 1H), 8.10 (d, J=8.7 Hz, 1H), 7.98 (d, J=8.4 Hz, 1H), 7.38-7.48 (m, 2H), 7.12-7.18 (m, 1H), 6.95-7.01 (m, 2H), 5.38 (s, 2H), 4.09-4.35 (m, 1H), 3.86 (s, 3H), 2.81 (s, 3H), 1.10 (d, J=6.3 Hz, 6H)

Step 4. (4-Methoxyphenyl)methyl 2-(1,2-benzoxazol-5-yl)-3-[methyl(propan-2-yl)amino]quinoxaline-6-carboxylate

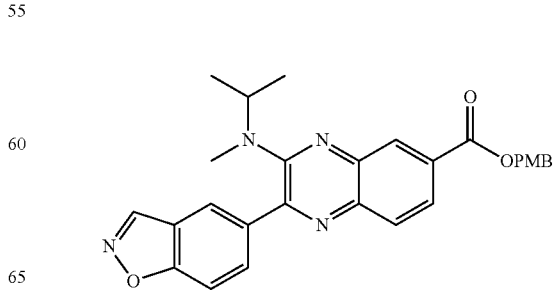

To a solution of (4-methoxyphenyl)methyl 2-(3-formyl-4-hydroxyphenyl)-3-[methyl(propan-2-yl)amino]quinoxaline-6-carboxylate (190 mg, 0.39 mmol) in water (5 mL) was added aminooxysulfonic acid (83 mg, 0.48 mmol) and methanol (5 mL). The resulting solution was stirred overnight at 25° C. Then the reaction was quenched by the addition of water (200 mL) and extracted with ethyl acetate (3×50 mL), dried over anhydrous sodium sulfate and concentrated in vacuo to give a residue, which was purified by silica gel column chromatography eluting with 1% to 5% ethyl acetate in petroleum to afford (4-methoxyphenyl)methyl 2-(1,2-benzoxazol-5-yl)-3-[methyl(propan-2-yl)amino]quinoxaline-6-carboxylate as a yellow solid (50 mg, 26%).

LC/MS (ES, m/z): [M+H]$^+$ 483.0

$^1$H-NMR (300 MHz, CDCl$_3$) δ 8.83 (s, 1H), 8.61 (s, 1H), 8.38 (s, 1H), 8.09-8.19 (m, 2H), 7.99 (d, J=8.4 Hz, 1H), 7.75 (d, J=7.8 Hz, 1H), 7.46 (d, J=8.4 Hz, 1H), 6.93-6.98 (m, 2H), 5.39 (s, 2H), 4.15-4.21 (m, 1H), 3.86 (s, 3H), 2.79 (s, 3H), 1.10 (d, J=6.6 Hz, 6H)

Step 5. 2-(1,2-Benzoxazol-5-yl)-3-[methyl(propan-2-yl)amino]quinoxaline-6-carboxylic acid

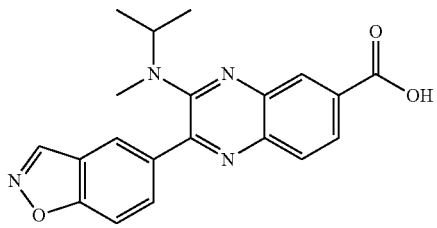 [SMILES: CC(C)N(C)c1nc2cc(C(=O)O)ccc2nc1-c1ccc2oncc2c1]

To a solution of (4-methoxyphenyl)methyl 2-(1,2-benzoxazol-5-yl)-3-[methyl(propan-2-yl)amino]quinoxaline-6-carboxylate (50 mg, 0.10 mmol) in dichloromethane (10 mL) was added 2,2,2-trifluoroacetic acid (1 mL). The solution was stirred for 30 min at room temperature. Then the reaction was quenched by the addition of water (100 mL), extracted with dichloromethane (3×30 mL), dried over anhydrous sodium sulfate and concentrated in vacuo to give a residue, which was purified by silica gel column chromatography eluting with 5% dichloromethane in methanol to afford 2-(1,2-benzoxazol-5-yl)-3-[methyl(propan-2-yl)amino]quinoxaline-6-carboxylic acid as a yellow solid (12.3 mg, 33%).

LC/MS (ES, m/z): [M+H]$^+$ 363.0

$^1$H-NMR (300 MHz, DMSO) δ 13.15 (s, 1H), 9.37 (s, 1H), 8.42 (d, J=0.9 Hz, 1H), 8.29 (s, 1H), 8.15-8.19 (m, 1H), 7.93-7.97 (m, 3H), 4.12-4.17 (m, 1H), 2.69 (s, 3H), 1.02 (d, J=6.6 Hz, 6H)

Example 51

3-(Azepan-1-yl)-2-(2,2-difluoro-2H-1,3-benzodioxol-5-yl)quinoxaline-6-carboxylic acid

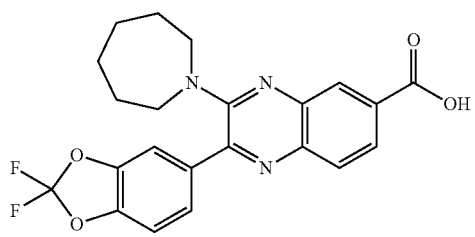 [SMILES: O=C(O)c1ccc2nc(-c3ccc4c(c3)OC(F)(F)O4)c(N3CCCCCC3)nc2c1]

Step 1. Methyl 3-(azepan-1-yl)-2-[(trifluoromethane)sulfonyloxy]quinoxaline-6-carboxylate

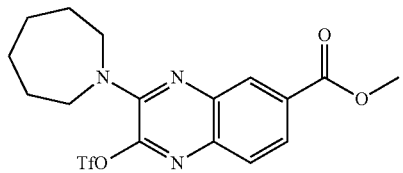 [SMILES: COC(=O)c1ccc2nc(OS(=O)(=O)C(F)(F)F)c(N3CCCCCC3)nc2c1]

To a solution of methyl 3-(azepan-1-yl)-2-oxo-1,2-dihydroquinoxaline-6-carboxylate (190 mg, 0.63 mmol) in dichloromethane (20 mL) was added pyridine (300 mg, 3.79 mmol) and Tf$_2$O (534 mg, 1.89 mmol) with stirring overnight under atmosphere of nitrogen at room temperature. The resulting solution was diluted with water (50 mL), extracted with dichloromethane (3×20 mL) and the organic layers combined and dried over anhydrous sodium sulfate and concentrated in vacuo to afford methyl 3-(azepan-1-yl)-2-[(trifluoromethane)sulfonyloxy]quinoxaline-6-carboxylate as yellow oil (273 mg, crude).

Step 2. Methyl 3-(azepan-1-yl)-2-(2,2-difluoro-2H-1,3-benzodioxol-5-yl)quinoxaline-6-carboxylate

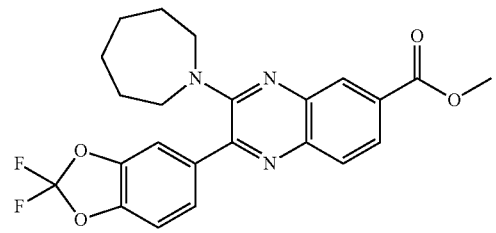 [SMILES: COC(=O)c1ccc2nc(-c3ccc4c(c3)OC(F)(F)O4)c(N3CCCCCC3)nc2c1]

To a solution of methyl 3-(azepan-1-yl)-2-[(trifluoromethane)sulfonyloxy]quinoxaline-6-carboxylate (273 mg, 0.63 mmol) in dioxane (5.0 mL) and water (3 drops) was added 2-(2,2-difluoro-2H-1,3-benzodioxol-5-yl)-4,4,5,5-tetramethyl-1,3,2-dioxaborolane (358 mg, 1.26 mmol), Pd(PPh$_3$)$_4$ (37 mg, 0.03 mmol), K$_3$PO$_4$ (266 mg, 1.25 mmol) with stirring for 1 hour at 90° C. under atmosphere of nitrogen. The resulting mixture was concentrated in vacuo to give a residue, which was applied onto silica gel column chromatography eluting with 1% ethyl acetate in petroleum ether to give methyl 3-(azepan-1-yl)-2-(2,2-difluoro-2H-1,3-benzodioxol-5-yl)quinoxaline-6-carboxylate as a yellow solid (110 mg, 40%).

LC/MS (ES, m/z): [M+H]$^+$ 442.0

Step 3. 3-(Azepan-1-yl)-2-(2,2-difluoro-2H-1,3-benzodioxol-5-yl)quinoxaline-6-carboxylic acid

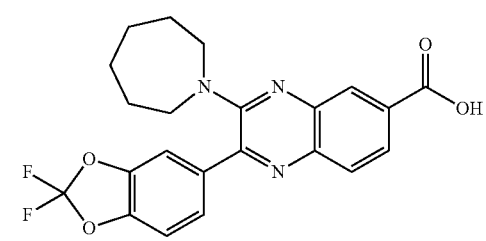 [SMILES: O=C(O)c1ccc2nc(-c3ccc4c(c3)OC(F)(F)O4)c(N3CCCCCC3)nc2c1]

To a solution of methyl 3-(azepan-1-yl)-2-(2,2-difluoro-2H-1,3-benzodioxol-5-yl)quinoxaline-6-carboxylate (110 mg, 0.25 mmol) in methanol (30 mL) and water (1 mL) was added sodium hydroxide (40 mg, 1.00 mmol) with stirring overnight at room temperature. The resulting mixture was concentrated in vacuo and dissolved in water (10 mL), adjusted to 6 with HCl (3 N) and collected by filtration to give 3-(azepan-1-yl)-2-(2,2-difluoro-2H-1,3-benzodioxol-5-yl)quinoxaline-6-carboxylic acid as a yellow solid (70 mg, 66%).

LC/MS (ES, m/z): [M+H]$^+$ 428.0

$^1$H-NMR (300 MHz, DMSO) δ 8.23 (s, 1H), 7.87 (d, J=9.0 Hz, 2H), 7.82 (d, J=0.9 Hz, 1H), 7.53-7.60 (m, 2H), 3.41-3.45 (m, 4H), 1.65-1.75 (m, 4H), 1.42-1.50 (s, 4H)

Example 52

3-[Methyl(propan-2-yl)amino]-2-(4-phenylfuran-2-yl)quinoxaline-6-carboxylic acid

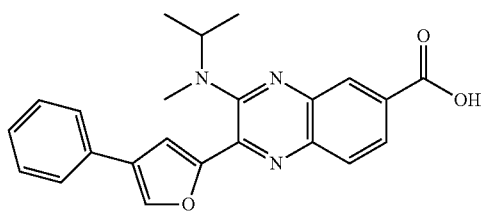 [SMILES: CC(C)N(C)c1nc2cc(C(=O)O)ccc2nc1-c1cc(-c2ccccc2)co1]

Step 1. 3-Phenylfuran

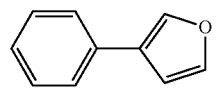

To a solution of phenylboronic acid (15 g, 123.02 mmol) in dioxane (150.0 mL) and water (3.0 mL) was added 3-bromofuran (16.3 g, 110.91 mmol), K$_3$PO$_4$ (43 g, 202.57 mmol) and Pd(PPh$_3$)$_4$ (6.0 g, 5.19 mmol) with stirring for 2 h at 90° C. in an oil bath maintained with an inert atmosphere of nitrogen. The reaction mixture was concentrated under reduced pressure to give the residue, which was purified by silica gel column chromatography eluting with 1% ethyl acetate in petroleum ether to afford 3-phenylfuran as a white solid (15 g, 85%).

$^1$H-NMR (300 MHz, CDCl$_3$): δ 7.76 (s, 1H), 7.51-7.54 (m, 3H), 7.40-7.47 (m, 2H), 7.29-7.38 (m, 1H), 6.73 (d, J=0.9 Hz, 1H)

Step 2. 4,4,5,5-Tetramethyl-2-(4-phenylfuran-2-yl)-1,3,2-dioxaborolane

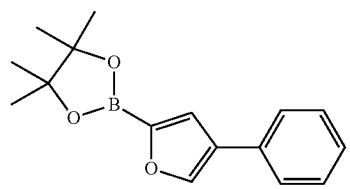 [SMILES: CC1(C)OB(c2cc(-c3ccccc3)co2)OC1(C)C]

A solution of n-BuLi (6.2 mL, 2.5 M solution in hexane) was added drop-wise to a solution of 3-phenylfuran (1.5 g, 10.40 mmol) in dry tetrahydrofuran (100 mL) at −78° C. under nitrogen. It was warmed slowly to −40° C. over 45 min and stirred at this temperature for another 30 min. The mixture was cooled again to −78° C. followed by the dropwise addition of 4,4,5,5-tetramethyl-2-(propan-2-yloxy)-1,3,2-dioxaborolane (3.72 g, 19.99 mmol). After warming to room temperature, the mixture was quenched with NH$_4$Cl (aq) and extracted with ethyl acetate (3×80 mL). The combined organic layers were dried over anhydrous sodium sulfate, filtered and concentrated in vacuo to give the residue, which was precipitated by cooling to afford 4,4,5,5-tetramethyl-2-(3-phenylfuran-2-yl)-1,3,2-dioxaborone as a white solid (400 mg, 14.0%). The mother liquid was purified by silica gel column chromatography eluting with 2% ethyl acetate in petroleum ether to afford 4,4,5,5-tetramethyl-2-(4-phenylfuran-2-yl)-1,3,2-dioxaborolane (200 mg, crude), which was used to the next step without further purification.

Step 3. Methyl 3-[methyl(propan-2-yl)amino]-2-(4-phenylfuran-2-yl)quinoxaline-6-carboxylate

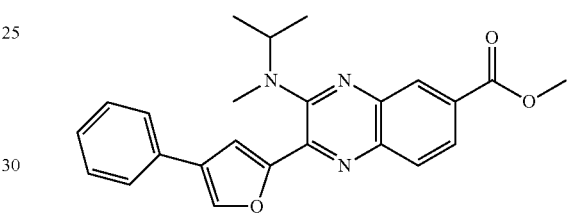

To a solution of 4,4,5,5-tetramethyl-2-(4-phenylfuran-2-yl)-1,3,2-dioxaborolane (200 mg, crude) in dioxane (5.5 mL) and water (3 drops) was added methyl 2-chloro-3-[methyl(propan-2-yl)amino]quinoxaline-6-carboxylate (72 mg, 0.25 mmol), K$_3$PO$_4$ (156 mg, 0.73 mmol) and Pd(PPh$_3$)$_4$ (14 mg, 0.01 mmol) with stirring for 1 h at 95° C. in an oil bath which was maintained under an inert atmosphere of nitrogen. The reaction mixture was concentrated under reduced pressure to give the residue, which was purified by silica gel column chromatography eluting with 2% ethyl acetate in petroleum ether to afford methyl 3-[methyl(propan-2-yl)amino]-2-(5-phenylfuran-2-yl)quinoxaline-6-carboxylate as a light yellow solid (50 mg).

LC/MS (ES, m/z): [M+H]$^+$ 401.0

$^1$H-NMR (300 MHz, CDCl$_3$): δ 8.54 (s, 1H), 8.03-8.13 (m, 2H), 7.96 (s, 1H), 7.58-7.63 (m, 3H), 7.43-7.47 (m, 3H), 4.28-4.32 (m, 1H), 4.00 (s, 1H), 2.93 (s, 3H), 1.25 (d, J=6.6 Hz, 6H)

Step 4. 3-[Methyl(propan-2-yl)amino]-2-(4-phenylfuran-2-yl)quinoxaline-6-carboxylic acid

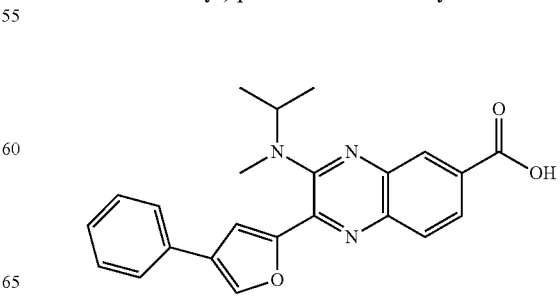

To a solution of methyl 3-[methyl(propan-2-yl)amino]-2-(4-phenylfuran-2-yl)quinoxaline-6-carboxylate (50 mg, 0.12 mmol) in methanol (30 mL) and water (2 mL) was added sodium hydroxide (19.9 mg, 0.50 mmol) with stirring overnight at room temperature. The reaction mixture was concentrated in vacuo, dissolved in water (30 mL) and adjusted to pH 5 with HCl (3 N). The solids were collected by filtration to afford 3-[methyl(propan-2-yl)amino]-2-(5-phenylfuran-2-yl)quinoxaline-6-carboxylic acid as a light yellow solid (40 mg, 83%).

LC/MS (ES, m/z): [M+H]$^+$ 388.0

$^1$H-NMR (300 MHz, DMSO): δ 13.23 (s, 1H), 8.50 (s, 1H), 8.26 (s, 1H), 7.94-7.99 (m, 2H), 7.71-7.76 (m, 3H), 7.42-7.47 (m, 2H), 7.30-7.35 (m, 1H), 4.15-4.24 (m, 1H), 2.83 (s, 3H), 1.18 (d, J=6.6 Hz, 6H)

Example 53

2-(Benzo[b]thiophen-2-yl)-3-(piperidin-1-yl)quinoxaline-6-carboxylic acid

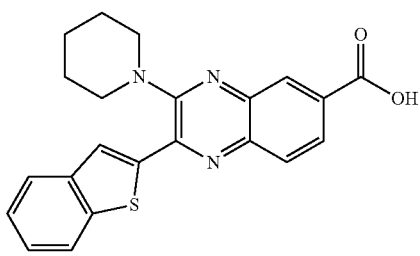 [SMILES: O=C(O)c1ccc2nc(-c3cc4ccccc4s3)c(N3CCCCC3)nc2c1]

Step 1. Methyl 3-(piperidin-1-yl)-2-(trifluoromethylsulfonyloxy)quinoxaline-6-carboxylate

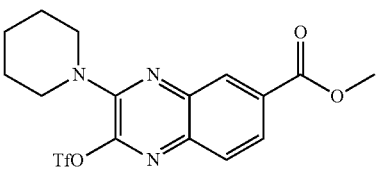 [SMILES: COC(=O)c1ccc2nc(OS(=O)(=O)C(F)(F)F)c(N3CCCCC3)nc2c1]

To a solution of methyl 2-oxo-3-(piperidin-1-yl)-1,2-dihydroquinoxaline-6-carboxylate (200 mg, 0.70 mmol) in dichloromethane (30 mL) was added pyridine (220 mg, 2.8 mmol) and then Tf$_2$O (393 mg, 1.4 mmol) was added dropwise with stirring at 0° C. The resulting solution was stirred overnight at room temperature and then quenched by the addition of water (50 mL), extracted with dichloromethane (3×10 mL), dried over anhydrous sodium sulfate and concentrated in vacuo to afford methyl 3-(piperidin-1-yl)-2-(trifluoromethylsulfonyloxy)quinoxaline-6-carboxylate as red solid (280 mg, crude).

Step 2. Methyl 2-(benzo[b]thiophen-2-yl)-3-(piperidin-1-yl)quinoxaline-6-carboxylate

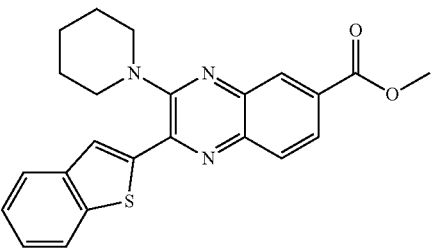 [SMILES: COC(=O)c1ccc2nc(-c3cc4ccccc4s3)c(N3CCCCC3)nc2c1]

To a solution of methyl 3-(piperidin-1-yl)-2-(trifluoromethylsulfonyloxy)quinoxaline-6-carboxylate (280 mg, crude) in dioxane (5 mL) was added benzo[b]thiophen-2-ylboronic acid (357 mg, 2.0 mmol), K$_3$PO$_4$ (425 mg, 2.0 mmol), Pd(PPh$_3$)$_4$ (39 mg, 0.033 mmol) and water (3 drops). The resulting solution was stirred for 1 h at 90° C. and then concentrated in vacuo to give a residue, which was purified by silica gel column chromatography eluting with 3.3% ethyl acetate in petroleum ether to afford methyl 2-(benzo[b]thiophen-2-yl)-3-(piperidin-1-yl)quinoxaline-6-carboxylate as a yellow solid (100.0 mg, 37% 2 steps).

LC/MS (ES, m/z): [M+H]$^+$ 404.0

$^1$H-NMR (300 MHz, CDCl$_3$): δ 8.75 (d, J=1.5 Hz, 1H), 8.42 (s, 1H), 8.15-8.19 (m, 1H), 8.04 (d, J=8.7 Hz, 1H), 7.88-7.94 (m, 2H), 7.37-7.47 (m, 2H), 4.01 (s, 3H), 3.50-3.47 (m, 4H), 1.82-1.71 (m, 6H)

Step 3. 2-(Benzo[b]thiophen-2-yl)-3-(piperidin-1-yl)quinoxaline-6-carboxylic acid

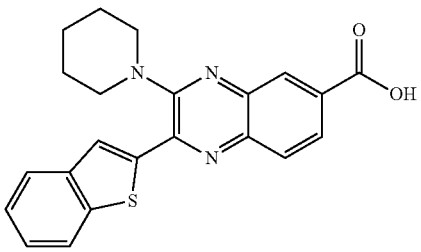 [SMILES: O=C(O)c1ccc2nc(-c3cc4ccccc4s3)c(N3CCCCC3)nc2c1]

To a solution of methyl 2-(benzo[b]thiophen-2-yl)-3-(piperidin-1-yl)quinoxaline-6-carboxylate (70 mg, 0.17 mmol) in MeOH (20 mL) was added sodium hydroxide (28 mg, 0.69 mmol) and water (1 mL). The resulting solution was stirred overnight at room temperature and concentrated in vacuo. The residue was dissolved in water (10 mL) and adjusted to pH 4 with HCl (1N). The solids were collected by filtration to afford 2-(benzo[b]thiophen-2-yl)-3-(piperidin-1-yl)quinoxaline-6-carboxylic acid as a yellow solid (60 mg, 89%).

LC/MS (ES, m/z): [M+H]$^+$ 390.0

$^1$H-NMR (300 MHz, DMSO+D$_2$O) δ 8.50 (s, 1H), 8.31 (d, J=1.5 Hz, 1H), 7.96-8.06 (m, 4H), 7.43-7.46 (m, 2H), 3.38-3.32 (m, 4H), 1.63-1.73 (m, 6H)

Example 54

3-(Azepan-1-yl)-2-(benzo[b]thiophen-2-yl)quinoxaline-6-carboxylic acid

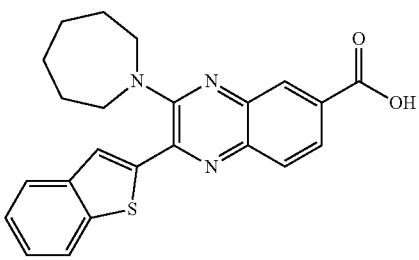 [SMILES: O=C(O)c1ccc2nc(-c3cc4ccccc4s3)c(N3CCCCCC3)nc2c1]

Step 1. Methyl 3-(azepan-1-yl)-2-(trifluoromethylsulfonyloxy)quinoxaline-6-carboxylate

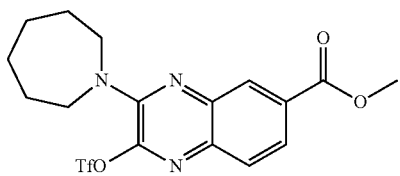 [SMILES: COC(=O)c1ccc2nc(OS(=O)(=O)C(F)(F)F)c(N3CCCCCC3)nc2c1]

To a solution of methyl 3-(azepan-1-yl)-2-oxo-1,2,4a,8a-tetrahydroquinoxaline-6-carboxylate (150.0 mg, 0.50 mmol) in dichloromethane (50 mL) was added pyridine (210 mg, 2.64 mmol) and Tf$_2$O (375 mg, 1.32 mmol) with stirring overnight under atmosphere of nitrogen at room temperature. The reaction mixture was then quenched with water (50 mL), extracted with dichloromethane (3×15 mL), the organic layers combined and dried over anhydrous magnesium sulfate, concentrated in vacuo to afford methyl 3-(azepan-1-yl)-2-(trifluoromethylsulfonyloxy)quinoxaline-6-carboxylate as red oil (250 mg, crude), which was used directly in the next step.

Step 2. Methyl 3-(azepan-1-yl)-2-(benzo[b]thiophen-2-yl)quinoxaline-6-carboxylate

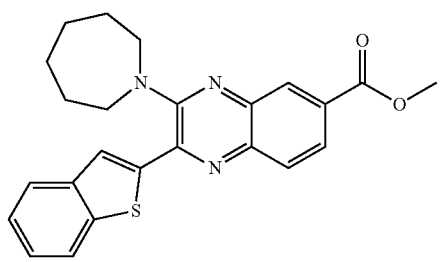 [SMILES: COC(=O)c1ccc2nc(-c3cc4ccccc4s3)c(N3CCCCCC3)nc2c1]

To a solution of methyl 3-(azepan-1-yl)-2-(trifluoromethylsulfonyloxy)quinoxaline-6-carboxylate (250 mg, crude) in dioxane (2 mL) was added benzo[b]thiophen-2-ylboronic acid (180 mg, 1.00 mmol), K$_3$PO$_4$ (210 mg, 1.00 mmol) and Pd(PPh$_3$)$_4$ (29 mg, 0.025 mmol) under nitrogen atmosphere. After stirring 1 h at 90° C., the reaction mixture was dissolved in water (25 mL), extracted with dichloromethane (3×30 mL), dried over anhydrous magnesium sulfate and concentrated under reduced pressure to afford a residue, which was purified by silica gel column chromatography eluting with 2% ethyl acetate in petroleum ether to afford methyl 3-(azepan-1-yl)-2-(benzo[b]thiophen-2-yl)quinoxaline-6-carboxylate as a light yellow solid (82 mg).

LC/MS (ES, m/z): [M+H]$^+$ 417.0

$^1$H-NMR (300 MHz, CDCl$_3$) δ 8.65 (s, 1H), 8.06-8.10 (m, 1H), 7.98 (d, J=5.4 Hz, 1H) 7.84-7.93 (m, 3H), 7.36-7.48 (m, 2H), 4.00 (s, 3H), 3.58-3.61 (t, J=6.0 Hz, 4H), 1.82-1.90 (m, 4H), 1.52-1.65 (m, 4H)

Step 3. 3-(Azepan-1-yl)-2-(benzo[b]thiophen-2-yl)quinoxaline-6-carboxylic acid

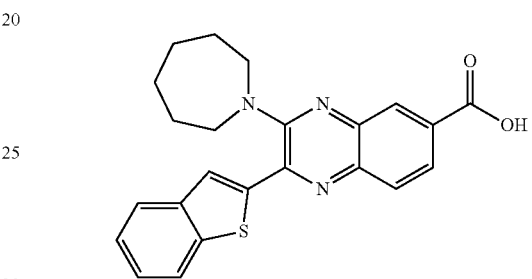

To a solution of methyl 3-(azepan-1-yl)-2-(benzo[b]thiophen-2-yl)quinoxaline-6-carboxylate (82 mg, 0.2 mmol) in methanol (15 mL) was added sodium hydroxide (80 mg, 2 mmol) and water (1 mL). After stirring overnight at room temperature, the reaction mixture was concentrated under reduced pressure to afford a residue, which was dissolved in water (10 mL), adjusted the pH value to 6 with HCl (3 N) and filtered to give 3-(azepan-1-yl)-2-(benzo[b]thiophen-2-yl)quinoxaline-6-carboxylic acid as a light yellow solid (70.1 mg, 88%).

LC/MS (ES, m/z): [M+H]$^+$ 404.0

$^1$H-NMR (300 MHz, DMSO) δ 8.21 (s, 1H), 7.95-8.21 (m, 4H), 7.85-7.87 (m, 1H), 7.36-7.48 (m, 2H), 3.58-3.61 (t, J=6.0 Hz, 4H), 1.74-1.80 (m, 4H), 1.45-1.55 (m, 4H)

Example 55

(S)-2-(5-Fluorobenzo[b]thiophen-2-yl)-3-(2-methylpyrrolidin-1-yl)quinoxaline-6-carboxylic acid

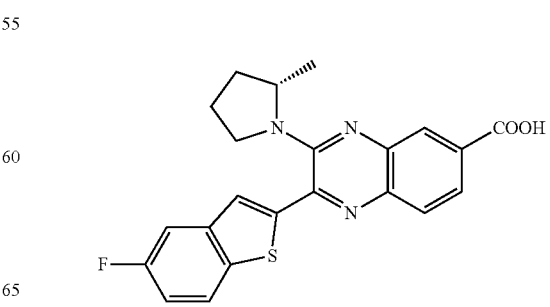

Step 1. (S)-Methyl 3-(2-methylpyrrolidin-1-yl)-2-(trifluoromethylsulfonyloxy)quinoxaline-6-carboxylate

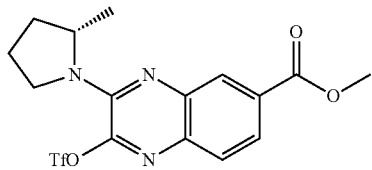 [SMILES: COC(=O)c1ccc2nc(OS(=O)(=O)C(F)(F)F)c(N3CCC[C@@H]3C)nc2c1]

To a solution of (S)-methyl 3-(2-methylpyrrolidin-1-yl)-2-oxo-1,2-dihydroquinoxaline-6-carboxylate (200 mg, 0.70 mmol) in dichloromethane (30 mL) was added pyridine (220 mg, 2.78 mmol) and then Tf$_2$O (393 mg, 1.39 mmol) was added dropwise with stirring at 0° C. The resulting solution was stirred overnight at room temperature and then quenched by the addition of ice-water (20 mL), extracted with dichloromethane (3×20 mL), dried over anhydrous sodium sulfate and concentrated in vacuo to afford (S)-methyl 3-(2-methylpyrrolidin-1-yl)-2-(trifluoromethylsulfonyloxy)quinoxaline-6-carboxylate as red oil (300 mg, crude).

Step 2. (S)-Methyl 2-(5-fluorobenzo[b]thiophen-2-yl)-3-(2-methylpyrrolidin-1-yl)quinoxaline-6-carboxylate

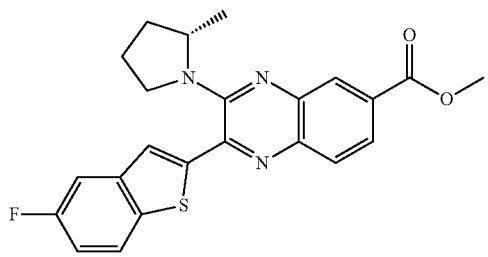 [SMILES: COC(=O)c1ccc2nc(-c3cc4cc(F)ccc4s3)c(N3CCC[C@@H]3C)nc2c1]

To a solution of methyl 3-[(2S)-2-methylpyrrolidin-1-yl]-2-[(trifluoromethane)sulfonyloxy]quinoxaline-6-carboxylate (300 mg, crude) in 1,4-dioxane (6 mL) was added 5-fluorobenzo[b]thiophen-2-ylboronic acid (176 mg, 0.90 mmol), Pd(PPh$_3$)$_4$ (21 mg, 0.018 mmol), K$_3$PO$_4$ (228 mg, 1.08 mmol) and water (5 drops) with stirring for 1 h at 90° C. maintained with an inert atmosphere of nitrogen in an oil bath. The reaction mixture was concentrated in vacuo to give the residue, which was applied onto silica gel column chromatography eluting with 1% to 5% ethyl acetate in petroleum to afford (S)-methyl 2-(5-fluorobenzo[b]thiophen-2-yl)-3-(2-methylpyrrolidin-1-yl)quinoxaline-6-carboxylate as a yellow solid (89 mg).

LC/MS (ES, m/z): [M+H]$^+$ 422.0

$^1$H-NMR (300 MHz, CDCl$_3$) δ 8.60 (s, 1H), 7.98-8.08 (m, 2H), 7.82-7.86 (m, 1H), 7.71 (s, 1H), 7.49-7.54 (m, 1H), 7.15-7.22 (m, 1H), 4.54-4.61 (m, 1H), 4.01 (s, 3H), 3.54-3.63 (m, 1H), 3.03-3.09 (m, 1H), 2.28-2.3 (m, 1H), 1.89-1.95 (m, 1H), 1.65-1.78 (m, 2H), 1.44 (d, J=6.0 Hz, 3H)

Step 3. (S)-2-(5-Fluorobenzo[b]thiophen-2-yl)-3-(2-methylpyrrolidin-1-yl)quinoxaline-6-carboxylic acid

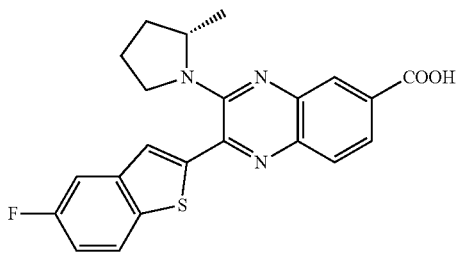 [SMILES: C[C@H]1CCCN1c1nc2cc(C(=O)O)ccc2nc1-c1cc2cc(F)ccc2s1]

To a solution of (S)-methyl 2-(5-fluorobenzo[b]thiophen-2-yl)-3-(2-methylpyrrolidin-1-yl)quinoxaline-6-carboxylate (89 mg, 0.21 mmol) in methanol (25 mL) and chloroform (5 mL) was added sodium hydroxide (25.2 mg, 0.63 mmol) with stirring overnight at room temperature. The reaction mixture was concentrated in vacuo, dissolved in water (15 mL), adjusted pH to 5 with HCl (3 N) to give the precipitate, which was collected by filtration to afford (S)-2-(5-fluorobenzo[b]thiophen-2-yl)-3-(2-methylpyrrolidin-1-yl)quinoxaline-6-carboxylic acid (56 mg, 65%).

LC/MS (ES, m/z): [M+H]$^+$ 408.0

$^1$H-NMR (300 MHz, DMSO) δ 8.27 (s, 1H), 8.06-8.11 (m, 1H), 7.94 (s, 2H), 7.87 (s, 1H), 7.80-7.85 (m, 1H), 7.30-7.37 (m, 1H), 4.37-4.43 (m, 1H), 3.46-3.55 (m, 1H), 2.96-3.01 (t, J=6.9 Hz, 1H), 2.22-2.67 (m, 1H), 1.50-1.68 (m, 2H), 1.39 (d, J=6.0 Hz, 3H)

Example 56

2-(Benzo[d]thiazol-5-yl)-3-(isopropyl(methyl)amino)quinoxaline-6-carboxylic acid

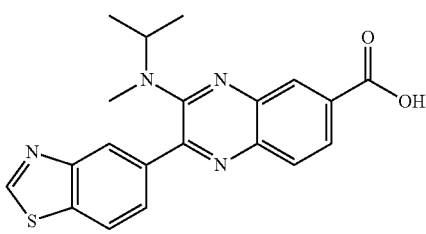 [SMILES: CC(C)N(C)c1nc2cc(C(=O)O)ccc2nc1-c1ccc2scnc2c1]

Step 1. Methyl 2-(benzo[d]thiazol-5-yl)-3-(isopropyl(methyl)amino)quinoxaline-6-carboxylate

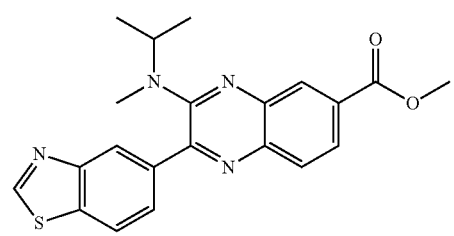 [SMILES: COC(=O)c1ccc2nc(-c3ccc4scnc4c3)c(N(C)C(C)C)nc2c1]

To a solution of methyl 3-(isopropyl(methyl)amino)-2-(trifluoromethylsulfonyloxy)quinoxaline-6-carboxylate (150 mg, 0.37 mmol) in dioxane (5 mL) was added 5-(4,4,5,5-tetramethyl-1,3,2-dioxaborolan-2-yl)benzo[d]thiazole (288 mg, 1.1 mmol), K$_3$PO$_4$ (234 mg, 1.1 mmol), Pd(PPh$_3$)$_4$ (21 mg, 0.018 mmol) and water (3 drops). The resulting solution was stirred for 1 h at 90° C. and then concentrated in vacuo to give a residue, which was purified by silica gel column chromatography eluting with 2%-5% ethyl acetate in petroleum ether to afford methyl 2-(benzo[d]thiazol-5-yl)-3-(isopropyl (methyl)amino)quinoxaline-6-carboxylate as a yellow solid (120 mg, 83%).

LC/MS (ES, m/z): [M+H]$^+$ 393.0

$^1$H-NMR (300 MHz, CDCl$_3$): δ 9.10 (s, 1H), 8.70 (d, J=0.9 Hz, 1H), 8.63 (d, J=1.5 Hz, 1H), 8.00-8.13 (m, 4H), 4.29-4.38 (m, 1H), 4.01 (s, 3H), 2.81 (s, 3H), 1.10 (d, J=6.6 Hz, 6H)

Step 2. 2-(Benzo[d]thiazol-5-yl)-3-(isopropyl(methyl)amino)quinoxaline-6-carboxylic acid

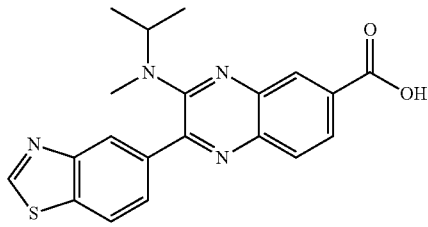 [SMILES: CC(C)N(C)c1nc2cc(C(=O)O)ccc2nc1-c1ccc2scnc2c1]

To a solution of methyl 2-(benzo[d]thiazol-5-yl)-3-(isopropyl(methyl)amino)quinoxaline-6-carboxylate (120 mg, 0.31 mmol) in MeOH (10 mL) was added sodium hydroxide (49 mg, 1.2 mmol) and water (1 mL). The resulting solution was stirred overnight at room temperature and concentrated in vacuo. The residue was dissolved in water (10 mL) and adjusted to pH 6 with HCl (1 N). The solids were collected by filtration to afford 2-(benzo[d]thiazol-5-yl)-3-(isopropyl(methyl)amino)quinoxaline-6-carboxylic acid as a yellow solid (99 mg, 86%).

LC/MS (ES, m/z): [M+H]$^+$ 379.1

$^1$H-NMR (300 MHz, DMSO) δ 9.49 (s, 1H), 8.56 (d, J=1.2 Hz, 1H), 8.29-8.35 (t, J=8.4 Hz, 2H), 7.93-8.00 (m, 3H), 4.18-4.23 (m, 1H), 2.69 (s, 3H), 1.01 (d, J=6.6 Hz, 6H)

Example 57

2-(1,3-Benzothiazol-5-yl)-3-[(2S)-2-methylpyrrolidin-1-yl]quinoxaline-6-carboxylic acid

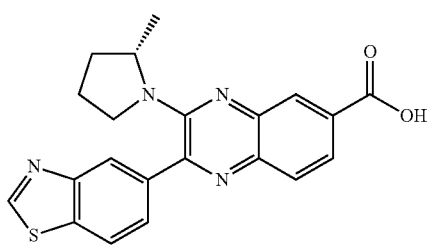 [SMILES: C[C@H]1CCCN1c1nc2cc(C(=O)O)ccc2nc1-c1ccc2scnc2c1]

Step 1. Methyl 2-(1,3-benzothiazol-5-yl)-3-[(2S)-2-methylpyrrolidin-1-yl]quinoxaline-6-carboxylate

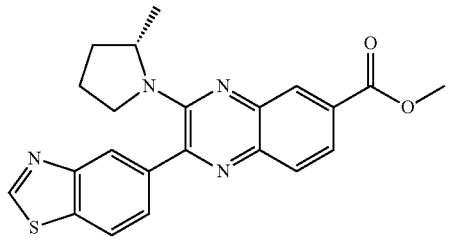 [SMILES: COC(=O)c1ccc2nc(-c3ccc4scnc4c3)c(N3CCC[C@@H]3C)nc2c1]

To a solution of methyl 3-[(2S)-2-methylpyrrolidin-1-yl]-2-[(trifluoromethane)sulfonyloxy]quinoxaline-6-carboxylate (150 mg, 0.36 mmol) in dioxane (6 mL) was added 5-(tetramethyl-1,3,2-dioxaborolan-2-yl)-1,3-benzothiazole (280 mg, 1.07 mmol), Pd(PPh$_3$)$_4$ (21 mg, 0.02 mmol), K$_3$PO$_4$ (228 mg, 1.07 mmol) and water (5 drops). The resulting solution was stirred for 1 h at 90° C. maintained with an inert atmosphere of nitrogen in an oil bath. The reaction mixture was concentrated in vacuo to give the residue, which was applied onto silica gel column chromatography eluting with 1% to 5% ethyl acetate in petroleum to afford methyl 2-(1,3-benzothiazol-5-yl)-3-[(2S)-2-methylpyrrolidin-1-yl]quinoxaline-6-carboxylate as a yellow solid (100 mg, 69%).

LC/MS (ES, m/z): [M+H]$^+$ 405.0

$^1$H-NMR (300 MHz, CDCl$_3$) δ 9.12 (s, 1H), 8.73 (s, 1H), 8.52 (s, 1H), 7.92-8.14 (m, 4H), 4.50-4.60 (m, 1H), 4.01 (s, 3H), 3.17-3.24 (m, 1H), 2.95-3.05 (m, 1H), 2.15-2.25 (m, 1H), 1.81-1.91 (m, 1H), 1.60-1.75 (m, 2H), 1.45 (d, J=5.7 Hz, 3H)

Step 2. 2-(1,3-Benzothiazol-5-yl)-3-[(2S)-2-methylpyrrolidin-1-yl]quinoxaline-6-carboxylic acid

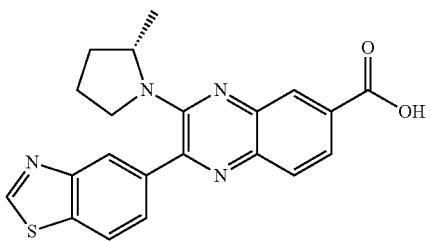 [SMILES: C[C@H]1CCCN1c1nc2cc(C(=O)O)ccc2nc1-c1ccc2scnc2c1]

To a solution of methyl 2-(1,3-benzothiazol-5-yl)-3-[(2S)-2-methylpyrrolidin-1-yl]quinoxaline-6-carboxylate (100 mg, 0.25 mmol) in methanol (15 mL) was added sodium hydroxide (30.0 mg, 0.75 mmol) and water (1 mL). The resulting solution was stirred overnight at room temperature and concentrated in vacuo. The residue was dissolved in water (15 mL) and adjusted pH to 5 with hydrochloric acid (3 N). The solids were collected by filtration to afford 2-(1,3-benzothiazol-5-yl)-3-[(2S)-2-methylpyrrolidin-1-yl]quinoxaline-6-carboxylic acid as a yellow solid (80 mg, 82%).

LC/MS (ES, m/z): [M+H]$^+$ 391.0

$^1$H-NMR (300 MHz, CD$_3$OD) δ 9.37 (s, 1H), 8.43-8.48 (m, 2H), 8.25 (d, J=8.4 Hz, 1H), 7.93-8.03 (m, 3H), 4.36-4.43 (m,

1H), 2.96-3.11 (m, 2H), 2.15-2.25 (m, 1H), 1.75-1.80 (m, 1H), 1.59-1.69 (m, 2H), 1.43 (d, J=6.0 Hz, 3H)

Example 58

2-(1,3-Benzothiazol-2-yl)-3-[methyl(propan-2-yl)amino]quinoxaline-6-carboxylic acid

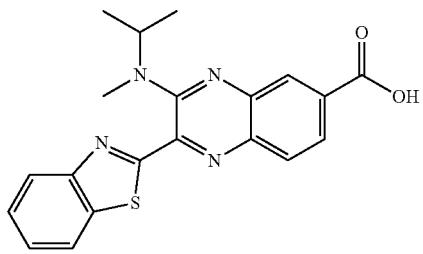 [SMILES: CC(C)N(C)c1nc2cc(C(=O)O)ccc2nc1-c1nc2ccccc2s1]

Step 1. Methyl 2-(1,3-benzothiazol-2-yl)-3-[methyl(propan-2-yl)amino]quinoxaline-6-carboxylate

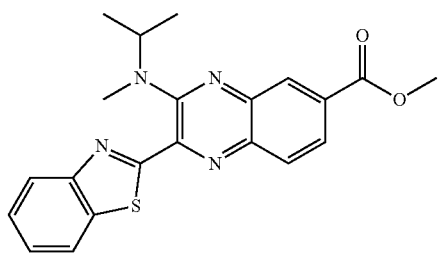 [SMILES: COC(=O)c1ccc2nc(-c3nc4ccccc4s3)c(N(C)C(C)C)nc2c1]

Into a 10-mL sealed was placed methyl 2-chloro-3-[methyl(propan-2-yl)amino]quinoxaline-6-carboxylate (400 mg, 1.36 mmol), 1,3-benzothiazole (368 mg, 2.72 mmol), Pd(PPh$_3$)$_4$ (80 mg, 0.06 mmol) and AcOK (272 mg, 2.72 mmol) under nitrogen atmosphere. After stirring 4 h at 150° C., the reaction mixture was purified by silica gel column chromatography eluting with 10% ethyl acetate in petroleum ether to afford methyl 2-(1,3-benzothiazol-2-yl)-3-[methyl(propan-2-yl)amino]quinoxaline-6-carboxylate as a light yellow solid (50 mg, 9.4%).

LC/MS (ES, m/z): [M+H]$^+$ 393.0

$^1$H-NMR (300 MHz, CDCl$_3$) δ 8.81 (s, 1H), 8.01-8.19 (m, 4H), 7.51-7.63 (m, 2H), 4.51-4.64 (m, 1H), 4.02 (s, 3H), 3.08 (s, 3H), 1.31 (d, J=6.6 Hz, 6H)

Step 2. 2-(1,3-Benzothiazol-2-yl)-3-[methyl(propan-2-yl)amino]quinoxaline-6-carboxylic acid

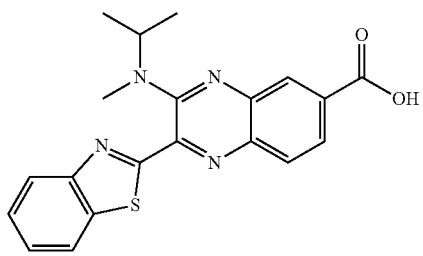 [SMILES: CC(C)N(C)c1nc2cc(C(=O)O)ccc2nc1-c1nc2ccccc2s1]

To a solution of methyl 2-(1,3-benzothiazol-2-yl)-3-[methyl(propan-2-yl)amino]quinoxaline-6-carboxylate (50 mg, 0.13 mmol) in methanol (30 mL), was added sodium hydroxide (50 mg, 1.25 mmol). After stirring overnight at room temperature, the reaction mixture was concentrated under reduced pressure to afford a residue, which was dissolved in water (10 mL), adjusted the pH value to 6 with 3 N HCl and filtered to give 2-(1,3-benzothiazol-2-yl)-3-[methyl(propan-2-yl)amino]quinoxaline-6-carboxylic acid as a light yellow solid (19.4 mg, 40%).

LC/MS (ES, m/z): [M+H]$^+$ 379.0

$^1$H-NMR (300 MHz, DMSO) δ 8.20-8.27 (m, 2H), 8.12 (d, J=7.5 Hz, 1H), 7.98 (s, 1H), 7.53-7.63 (m, 2H), 4.36-4.43 (m, 1H), 2.86 (s, 3H), 1.20 (d, J=6.6 Hz, 6H)

Example 59

2-(1,3-Benzothiazol-2-yl)-3-[(2S)-2-methylpyrrolidin-1-yl]quinoxaline-6-carboxylic acid

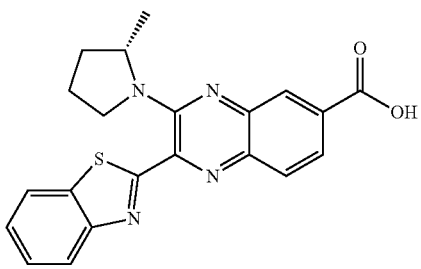 [SMILES: C[C@H]1CCCN1c1nc2cc(C(=O)O)ccc2nc1-c1nc2ccccc2s1]

Step 1. Methyl 2-chloro-3-[(2S)-2-methylpyrrolidin-1-yl]quinoxaline-6-carboxylate

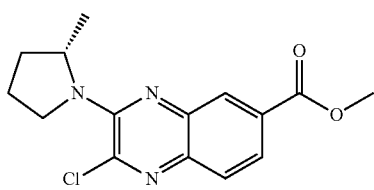 [SMILES: COC(=O)c1ccc2nc(Cl)c(N3CCC[C@@H]3C)nc2c1]

The solution of methyl 3-[(2S)-2-methylpyrrolidin-1-yl]-2-oxo-1,2-dihydroquinoxaline-6-carboxylate (5.9 g, 20.54 mmol,) in phosphorus oxychloride (100 mL) was stirred overnight at 120° C. in an oil bath. The reaction mixture was concentrated in vacuo and diluted with dichloromethane (500 mL) and ice-water (500 mL), adjusted to pH 7 with NaHCO$_3$ solution. The solution was extracted with dichloromethane (3×200 mL) and the organic layers combined, dried over anhydrous sodium sulfate and concentrated in vacuo to give a residue, which was purified by silica gel column chromatography eluting with 2% ethyl acetate in petroleum ether to afford methyl 2-chloro-3-[(2S)-2-methylpyrrolidin-1-yl]quinoxaline-6-carboxylate as a yellow solid (5 g, 80%).

LC/MS (ES, m/z): [M+H]$^+$ 306.1

$^1$H-NMR (300 MHz, CDCl$_3$) δ 8.46 (d, J=1.5 Hz, 1H), 7.98-8.02 (m, 1H), 7.82 (d, J=8.7 Hz, 1H), 4.62-6.69 (m, 1H), 4.04-4.14 (m, 1H), 3.99 (s, 3H), 3.78-3.88 (m, 1H), 2.20-2.29 (m, 1H), 2.03-2.12 (m, 1H), 1.81-1.95 (m, 1H), 1.72-1.79 (m, 1H), 1.32-1.42 (m, 3H)

Step 2. Methyl 2-(1,3-benzothiazol-2-yl)-3-[(2S)-2-methylpyrrolidin-1-yl]quinoxaline-6-carboxylate

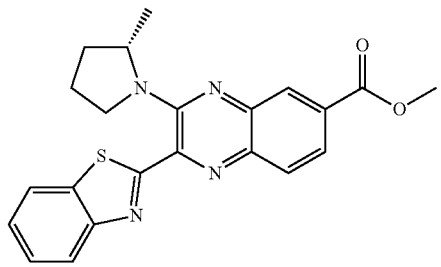 [SMILES: COC(=O)c1ccc2nc(-c3nc4ccccc4s3)c(N3CCC[C@@H]3C)nc2c1]

To a solution of methyl 2-chloro-3-[(2S)-2-methylpyrrolidin-1-yl]quinoxaline-6-carboxylate (300 mg, 0.98 mmol) in 1,3-benzothiazole (266 mg, 1.97 mmol) was added Pd(PPh₃)₄ (57 mg, 0.05 mmol,) and potassium acetate (193 mg, 1.97 mmol) under an atmosphere of nitrogen. The resulting solution was stirred for 2 h at 170° C. and then quenched by the addition of NH₄Cl solution (150 mL), extracted with dichloromethane (3×20 mL) and the organic layers combined and dried over anhydrous sodium sulfate and concentrated in vacuo to give a residue, which was purified by silica gel column chromatography eluting with 1%-5% ethyl acetate in petroleum ether to afford methyl 2-(1,3-benzothiazol-2-yl)-3-[(2S)-2-methylpyrrolidin-1-yl]quinoxaline-6-carboxylate as a yellow solid (80 mg, 20%).

¹H-NMR (300 MHz, CDCl₃) δ 8.55 (s, 1H), 8.16 (d, J=7.5 Hz, 1H), 7.98-8.02 (m, 3H), 7.47-7.59 (m, 2H), 4.53-4.60 (m, 1H), 4.01 (s, 3H), 3.68-3.77 (m, 1H), 2.26-2.31 (m, 1H), 1.92-1.93 (m, 1H), 1.75-1.77 (m, 2H), 1.45 (d, J=6.0 Hz, 3H).

Step 3. 2-(1,3-Benzothiazol-2-yl)-3-[(2S)-2-methylpyrrolidin-1-yl]quinoxaline-6-carboxylic acid

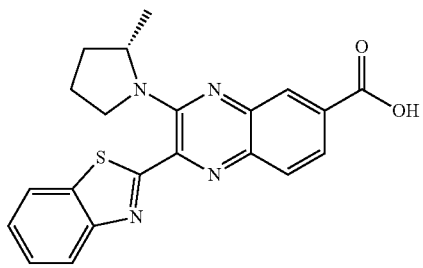 [SMILES: C[C@H]1CCCN1c1nc2cc(C(=O)O)ccc2nc1-c1nc2ccccc2s1]

To a solution of methyl 2-(1,3-benzothiazol-2-yl)-3-[(2S)-2-methylpyrrolidin-1-yl]quinoxaline-6-carboxylate (80 mg, 0.20 mmol) in tetrahydrofuran (20 mL) was added NaOH (23.8 mg, 0.60 mmol) and water (1 mL). The resulting solution was stirred overnight at room temperature and then concentrated in vacuo, adjusted the pH to 7 with HCl (3 N). The product was collected and filtered to afford 2-(1,3-benzothiazol-2-yl)-3-[(2S)-2-methylpyrrolidin-1-yl]quinoxaline-6-carboxylic acid as a light yellow solid (43.8 mg, 57%).

LC/MS (ES, m/z): [M+H]⁺ 391.0

¹H-NMR (300 MHz, CD₃OD) δ 8.40 (d, J=1.2 Hz, 1H), 8.10-8.14 (m, 2H), 7.92-8.02 (m, 2H), 7.51-7.62 (m, 2H), 4.49-4.55 (m, 1H), 3.60-3.69 (m, 1H), 3.05-3.10 (m, 1H), 2.25-2.31 (m, 1H), 1.91-1.92 (m, 1H), 1.65-1.80 (m, 2H), 1.42 (d, J=6.0 Hz, m, 3H)

Example 60

3-(isopropyl(methyl)amino)-2,7'-biquinoxaline-6-carboxylic acid

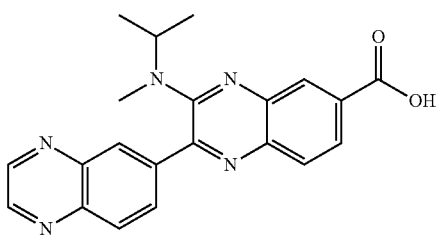 [SMILES: CC(C)N(C)c1nc2cc(C(=O)O)ccc2nc1-c1ccc2nccnc2c1]

Step 1. Methyl 3-(isopropyl(methyl)amino)-2,7'-biquinoxaline-6-carboxylate

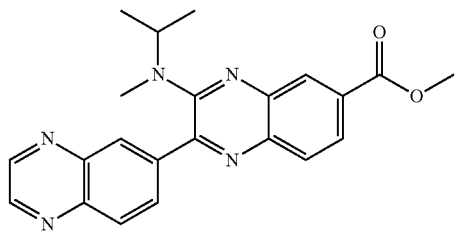 [SMILES: COC(=O)c1ccc2nc(-c3ccc4nccnc4c3)c(N(C)C(C)C)nc2c1]

To a solution of methyl 3-[methyl(propan-2-yl)amino]-2-[(trifluoromethane)sulfonyloxy]quinoxaline-6-carboxylate (150 mg, 0.37 mmol) in dioxane (5 ml) was added 6-(tetramethyl-1,3,2-dioxaborolan-2-yl)quinoxaline (141.5 mg, 0.55 mmol), Pd(PPh₃)₄ (21.3 mg, 0.02 mmol), K₃PO₄ (155.5 mg, 0.73 mmol) and water (3 drops) under a nitrogen atmosphere. After stirring 1 h at 90° C., the reaction mixture was concentrated in vacuo and purified by silica gel column chromatography eluting with 2%-10% ethyl acetate in petroleum ether to afford methyl 3-(isopropyl(methyl)amino)-2,7'-biquinoxaline-6-carboxylate as a light yellow solid (90 mg, 63%).

LC/MS (ES, m/z): [M+H]⁺ 388.0

¹H-NMR (300 MHz, DMSO) δ 9.00-9.04 (m, 2H), 8.58 (d, J=1.8 Hz, 1H), 8.25-8.39 (m, 3H), 7.96-8.07 (m, 2H), 4.20-4.26 (m, 1H), 3.95 (s, 3H), 2.70 (s, 3H), 1.06 (d, J=6.6 Hz, 6H)

Step 2. 3-(Isopropyl(methyl)amino)-2,7'-biquinoxaline-6-carboxylic acid

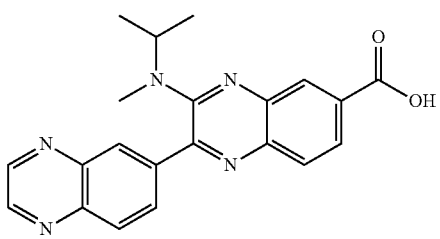 [SMILES: CC(C)N(C)c1nc2cc(C(=O)O)ccc2nc1-c1ccc2nccnc2c1]

To a solution of methyl 3-(isopropyl(methyl)amino)-2,7'-biquinoxaline-6-carboxylate (90 mg, 0.23 mmol) in methanol (30 mL) and water (1 ml), was added sodium hydroxide (54 mg, 1.35 mmol). After stirring overnight at room temperature, the reaction mixture was concentrated under reduced pressure to afford a residue, which was dissolved in water (10 ml), adjusted the pH value to 6 with HCl (3N) and filtered to give 3-(isopropyl(methyl)amino)-2,7'-biquinoxaline-6-carboxylic acid as a light yellow solid (43.6 mg, 50%).

LC/MS (ES, m/z): [M+H]$^+$ 374.0

$^1$H-NMR (300 MHz, DMSO) δ 8.57 (d, J=2.1 Hz, 2H), 8.57 (d, J=4.2 Hz, 1H), 8.26-8.38 (m, 3H), 7.96-8.04 (m, 2H), 4.17-4.26 (m, 1H), 2.71 (s, 3H), 1.03 (d, J=6.6 Hz, 6H)

Example 61

3-[Cyclopropyl(methyl)amino]-2-(5-fluoro-1-benzofuran-2-yl)quinoxaline-6-carboxylic acid

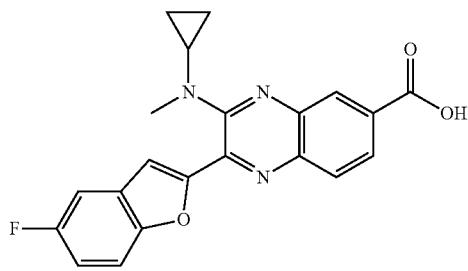 [SMILES: CN(c1nc2cc(C(=O)O)ccc2nc1-c1cc2cc(F)ccc2o1)C1CC1]

Step 1. Methyl 3-(cyclopropyl(methyl)amino)-2-(trifluoromethylsulfonyloxy)quinoxaline-6-carboxylate

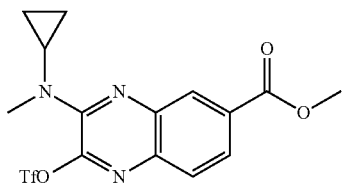

To a solution of methyl 3-(cyclopropyl(methyl)amino)-2-oxo-1,2-dihydroquinoxaline-6-carboxylate (120 mg, 0.44 mmol) in dichloromethane (10 mL) was added pyridine (139 mg, 1.76 mmol) and Tf$_2$O (248 mg, 0.88 mmol) under a nitrogen atmosphere. After stirring overnight at room temperature, the reaction was quenched by the addition water/ice (50 mL), extracted with dichloromethane (2×10 mL), dried over anhydrous magnesium sulfate and concentrated in vacuo to give methyl 3-(cyclopropyl(methyl)amino)-2-(trifluoromethylsulfonyloxy)quinoxaline-6-carboxylate as red oil (150 mg, crude).

Step 2. Methyl 3-[cyclopropyl(methyl)amino]-2-(5-fluoro-1-benzofuran-2-yl)quinoxaline-6-carboxylate

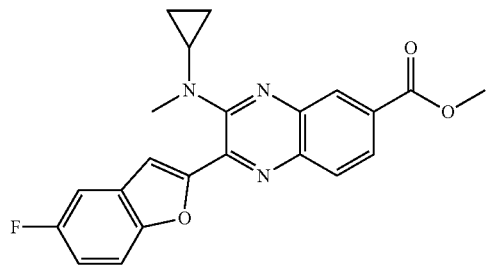 [SMILES: COC(=O)c1ccc2nc(-c3cc4cc(F)ccc4o3)c(N(C)C3CC3)nc2c1]

To a solution of methyl 3-[cyclopropyl(methyl)amino]-2-[(trifluoromethane)sulfonyloxy]quinoxaline-6-carboxylate (150 mg, crude) in dioxane (5 mL) was added (5-fluoro-1-benzofuran-2-yl)boronic acid (167 mg, 0.93 mmol), K$_3$PO$_4$ (234 mg, 1.11 mmol), Pd(PPh$_3$)$_4$ (22 mg, 0.02 mmol) under a nitrogen atmosphere. After stirring 1 h at 90° C., the reaction mixture was dissolved in water (10 mL), extracted with dichloromethane (3×30 mL), dried over anhydrous magnesium sulfate and concentrated under reduced pressure to afford a residue, which was purified by silica gel column chromatography eluting with 2% ethyl acetate in petroleum ether to afford methyl 3-[cyclopropyl(methyl)amino]-2-(5-fluoro-1-benzofuran-2-yl)quinoxaline-6-carboxylate as a yellow solid (79 mg).

LC/MS (ES, m/z): [M+H]$^+$ 392.0

$^1$H-NMR (300 MHz, CDCl$_3$) δ 8.61 (s, 1H), 8.07-8.15 (m, 2H), 7.58-7.63 (m, 1H), 7.44 (s, 1H), 7.33-7.36 (m, 1H), 7.07-7.17 (m, 1H), 4.01 (s, 3H), 3.19 (s, 3H), 2.84-2.94 (m, 1H), 0.61-0.70 (m, 2H), 0.54-0.55 (m, 2H)

Step 3. 3-[Cyclopropyl(methyl)amino]-2-(5-fluoro-1-benzofuran-2-yl)quinoxaline-6-carboxylic acid To a solution of methyl 3-[cyclopropyl(methyl)amino]-2-(5-fluoro-1-benzofuran-2-yl)quinoxaline-6-carboxylate (79 mg, 0.20 mmol) in methanol (15 mL) and water (1 mL) was added sodium hydroxide (24 mg, 0.60 mmol). After stirring overnight at room temperature, the reaction mixture was concentrated under reduced pressure to afford a residue, which was dissolved in water (20 mL), adjusted the pH value to 5 with 3N HCl and filtered to give 3-[cyclopropyl(methyl)amino]-2-(5-fluoro-1-benzofuran-2-yl)quinoxaline-6-carboxylic acid as a light yellow solid (60 mg, 79%).

LC/MS (ES, m/z): [M+H]$^+$ 378.0

$^1$H-NMR (300 MHz, DMSO) δ 13.25 (s, 1H), 8.28 (s, 1H), 7.98-8.05 (m, 2H), 7.78-7.83 (m, 1H), 7.56-7.60 (m, 2H), 7.24-7.32 (m, 1H), 3.10 (s, 3H), 2.87-2.95 (m, 1H), 0.50-0.55 (m, 4H)

Example 62

2-(5-Fluoro-1-benzofuran-2-yl)-3-(pyrrolidin-1-yl)quinoxaline-6-carboxylic acid

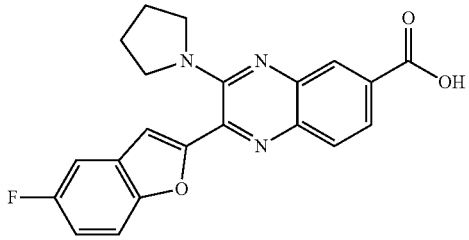 [SMILES: O=C(O)c1ccc2nc(-c3cc4cc(F)ccc4o3)c(N3CCCC3)nc2c1]

Step 1. Methyl 2-oxo-3-(pyrrolidin-1-yl)-1,2-dihydroquinoxaline-6-carboxylate

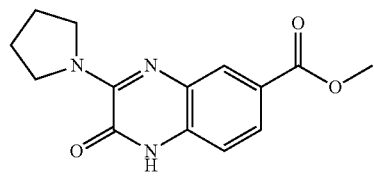 [SMILES: COC(=O)c1ccc2[nH]c(=O)c(N3CCCC3)nc2c1]

To a solution of methyl 3-chloro-2-oxo-1,2-dihydroquinoxaline-6-carboxylate (200 mg, 0.84 mmol) in DMSO (2 mL) was added pyrrolidine (90 mg, 1.27 mmol) and DIEA (163 mg, 1.26 mmol). After stirring overnight at 70° C., the reaction mixture was dissolved in water (50 mL), then filtered to afford methyl 2-oxo-3-(pyrrolidin-1-yl)-1,2-dihydroquinoxaline-6-carboxylate as a light yellow solid (200 mg, 87%).

LC/MS (ES, m/z): [M+H]+ 274.0

$^1$H-NMR (300 MHz, DMSO) δ 12.15 (s, 1H), 7.82 (d, J=1.8 Hz, 1H), 7.61 (d, J=8.4 Hz, 1H), 7.13 (d, J=8.4 Hz, 1H), 3.83 (s, 3H), 3.35-3.40 (m, 4H), 1.85-1.95 (m, 4H)

Step 2. Methyl 3-(pyrrolidin-1-yl)-2-[(trifluoromethane)sulfonyloxy]quinoxaline-6-carboxylate

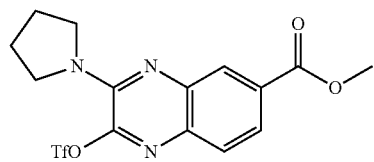 [SMILES: COC(=O)c1ccc2nc(OS(=O)(=O)C(F)(F)F)c(N3CCCC3)nc2c1]

To a solution of methyl 2-oxo-3-(pyrrolidin-1-yl)-1,2-dihydroquinoxaline-6-carboxylate (200 mg, 0.73 mmol) in dichloromethane (40 mL) was added pyridine (400 mg, 5.06 mmol) and Tf$_2$O (400 mg, 1.42 mmol), which was added dropwise with stirring at 0° C. After stirring overnight at room temperature under a nitrogen atmosphere, the reaction mixture was dissolved in water (100 mL), extracted with dichloromethane (3×20 mL), dried over anhydrous magnesium sulfate and concentrated under reduced pressure to afford methyl 3-(pyrrolidin-1-yl)-2-[(trifluoromethane)sulfonyloxy]quinoxaline-6-carboxylate as a light yellow solid (500 mg, crude).

Step 3. Methyl 2-(5-fluoro-1-benzofuran-2-yl)-3-(pyrrolidin-1-yl)quinoxaline-6-carboxylate

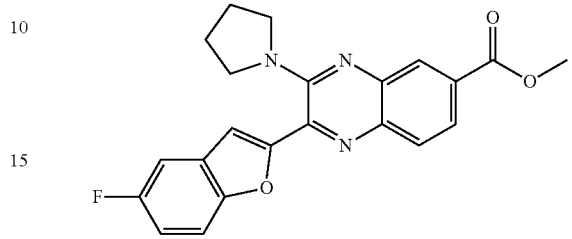

To a solution of methyl 3-(pyrrolidin-1-yl)-2-[(trifluoromethane)sulfonyloxy]quinoxaline-6-carboxylate (500 mg, crude) in dioxane (2 mL) was added (5-fluoro-1-benzofuran-2-yl)boronic acid (264 mg, 1.47 mmol), Pd(PPh$_3$)$_4$ (309 mg, 0.27 mmol), K$_3$PO$_4$ (42 mg, 0.20 mmol), and water (5 drops). After stirring 40 min at 90° C. under nitrogen atmosphere, the reaction mixture was dissolved in water (100 mL), extracted with dichloromethane (3×30 mL), dried over anhydrous magnesium sulfate and concentrated under reduced pressure to afford a residue, which was purified by silica gel column chromatography eluting with 2% ethyl acetate in petroleum ether to afford methyl 2-(5-fluoro-1-benzofuran-2-yl)-3-(pyrrolidin-1-yl)quinoxaline-6-carboxylate as a light yellow solid (150 mg).

LC/MS (ES, m/z): [M+H]+ 392.0

$^1$H-NMR (300 MHz, CDCl$_3$) δ 8.58 (s, 1H), 7.98-8.06 (m, 2H), 7.55-7.62 (m, 1H), 7.33-7.37 (m, 1H), 7.26 (s, 1H), 7.09-7.16 (m, 1H), 4.00 (s, 3H), 3.53-3.57 (m, 4H), 1.93-1.97 (m, 4H)

Step 4. 2-(5-Fluoro-1-benzofuran-2-yl)-3-(pyrrolidin-1-yl)quinoxaline-6-carboxylic acid

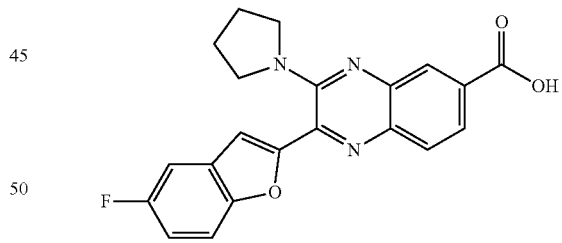

To a solution of methyl 2-(5-fluoro-1-benzofuran-2-yl)-3-(pyrrolidin-1-yl)quinoxaline-6-carboxylate (150 mg, 0.38 mmol) in methanol (50 mL) was added sodium hydroxide (150 mg, 3.75 mmol) and water (2 mL). After stirring overnight at room temperature, the reaction mixture was concentrated under reduced pressure to afford a residue, which was dissolved in water (10 mL), adjusted to pH 6 with HCl (3N) and filtered to give 2-(5-fluoro-1-benzofuran-2-yl)-3-(pyrrolidin-1-yl)quinoxaline-6-carboxylic acid as a light yellow solid (36.5 mg, 25%).

LC/MS (ES, m/z): [M+H]+ 378.0

$^1$H-NMR (300 MHz, CDCl$_3$) δ 8.77 (s, 1H), 8.02-8.10 (m, 2H), 7.56-7.62 (m, 1H), 7.35-7.38 (m, 1H), 7.31 (s, 1H), 7.11-7.18 (m, 1H), 3.55-3.61 (m, 4H), 1.97-2.05 (m, 4H)

Example 63

2-(1H-Benzo[d]imidazol-1-yl)-3-(isopropyl(methyl)amino)quinoxaline-6-carboxylic acid

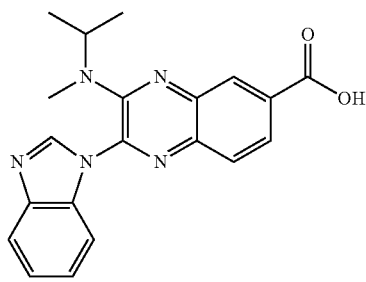 [SMILES: CC(C)N(C)c1nc2cc(C(=O)O)ccc2nc1-n1cnc2ccccc21]

The mixture of methyl 2-chloro-3-(isopropyl(methyl)amino)quinoxaline-6-carboxylate (200 mg, 0.68 mmol), 1H-benzo[d]imidazole (500 mg, 4.24 mmol), AcOK (200 mg, 2.05 mmol) and Pd(PPh$_3$)$_4$ (39 mg, 0.03 mmol) was stirred for 3 h at 170° C. and then purified by silica gel chromatography eluting with 2%-5% methanol in dichloromethane to afford 2-(1H-benzo[d]imidazol-1-yl)-3-(isopropyl(methyl)amino)quinoxaline-6-carboxylic acid as a yellow solid (18.0 mg, 7%).

LC/MS (ES, m/z): [M+H]$^+$ 362.0

$^1$H-NMR (300 MHz, CDCl$_3$): δ 8.69 (d, J=9.0 Hz, 2H), 8.20 (d, J=8.1 Hz, 1H), 7.92-8.03 (m, 3H), 7.44-7.47 (t, J=4.2 Hz, 2H), 4.13-4.17 (m, 1H), 2.69 (s, 3H), 1.15 (d, J=6.3 Hz, 6H)

Example 64

3-[Cyclopropyl(methyl)amino]-2-(1H-indol-5-yl)quinoxaline-6-carboxylic acid

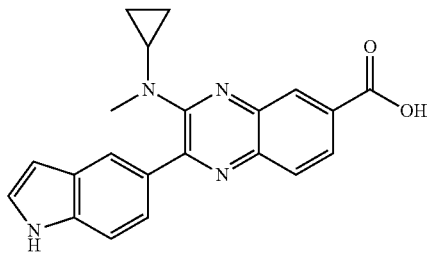 [SMILES: CN(c1nc2cc(C(=O)O)ccc2nc1-c1ccc2[nH]ccc2c1)C1CC1]

Step 1. Methyl 3-[cyclopropyl(methyl)amino]-2-oxo-1,2-dihydroquinoxaline-6-carboxylate

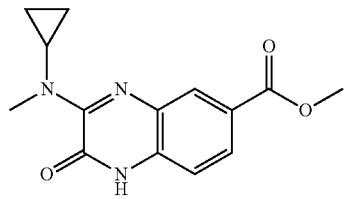

To a solution of methyl 3-chloro-2-oxo-1,2-dihydroquinoxaline-6-carboxylate (300 mg, 1.26 mmol) in DMSO (2 mL), was added N-methylcyclopropanamine hydrochloride (175 mg, 1.63 mmol) and DIEA (325 mg, 2.52 mmol) with stirring for 2 h at 75° C. in an oil bath. Then the reaction was quenched by the addition of water (10 mL) to give the precipitate, which was collected by filtration to afford methyl 3-[cyclopropyl(methyl)amino]-2-oxo-1,2-dihydroquinoxaline-6-carboxylate as an off-white solid (297 mg, 86%).

LC/MS (ES, m/z): [M+H]$^+$ 273.0

$^1$H-NMR (300 MHz, DMSO) δ 12.26 (s, 1H), 7.92 (d, J=1.8 Hz 1H), 7.71-7.75 (m, 1H), 7.19 (d, J=10.5 Hz, 1H), 3.85 (s, 3H), 3.23 (s, 3H), 3.05-3.12 (m, 1H), 0.76-0.82 (m, 2H), 0.60-0.63 (m, 1H)

Step 2. Methyl 3-[cyclopropyl(methyl)amino]-2-[(trifluoromethane)sulfonyloxy]quinoxaline-6-carboxylate

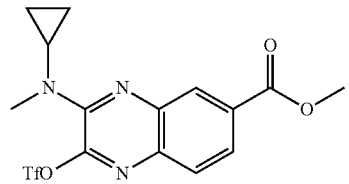

To a solution of methyl 3-[cyclopropyl(methyl)amino]-2-oxo-1,2-dihydroquinoxaline-6-carboxylate (150 mg, 0.55 mmol) in dichloromethane (30 mL) was added pyridine (173.8 mg, 2.20 mmol) under an inert atmosphere of nitrogen. This was followed by the addition of Tf$_2$O (316 mg, 1.12 mmol) with stirring overnight at room temperature. The reaction mixture was then quenched with water (50 mL), extracted with dichloromethane (3×20 mL), the organic layers combined and dried over anhydrous magnesium sulfate, and concentrated in vacuo to afford methyl 3-[cyclopropyl(methyl)amino]-2-[(trifluoromethane)sulfonyloxy]quinoxaline-6-carboxylate as a yellow oil (200 mg, crude).

Step 3. Methyl 3-[cyclopropyl(methyl)amino]-2-(1H-indol-5-yl)quinoxaline-6-carboxylate

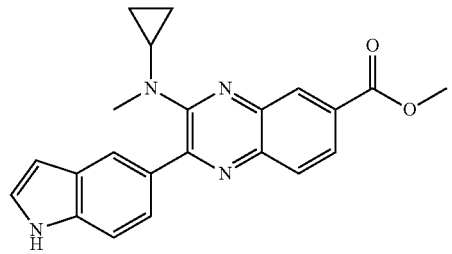 [SMILES: COC(=O)c1ccc2nc(-c3ccc4[nH]ccc4c3)c(N(C)C3CC3)nc2c1]

To a solution of methyl 3-[cyclopropyl(methyl)amino]-2-[(trifluoromethane)sulfonyloxy]quinoxaline-6-carboxylate (200 mg, crude) in 1,4-dioxane (4.0 mL) and water (three drops) was added (1H-indol-5-yl)boronic acid (238 mg, 1.48 mmol), K$_3$PO$_4$ (312 mg, 1.47 mmol) and Pd(PPh$_3$)$_4$ (28 mg, 0.02 mmol) with stirring for 1 h at 90° C. maintained under an inert atmosphere of nitrogen in an oil bath. The reaction mixture was concentrated in vacuo to give the residue, which was purified by silica gel column chromatography eluting with 2%-10% ethyl acetate in petroleum to afford methyl 3-[cyclopropyl(methyl)amino]-2-(1H-indol-5-yl)quinoxaline-6-carboxylate as a yellow solid (71 mg, 35% 2 steps).

LC/MS (ES, m/z): [M+H]$^+$ 372.0

$^1$H-NMR (300 MHz, DMSO) δ11.29 (s, 1H), 8.29 (s, 1H), 7.92-8.04 (m, 3H), 7.62-7.71 (m, 1H), 7.48-7.59 (m, 1H), 7.41-7.48 (m, 1H), 6.60-6.84 (m, 1H), 6.21-6.22 (m, 1H), 4.02-4.07 (m, 1H), 3.93 (s, 3H), 2.96 (s, 3H), 0.43-0.45 (m, 4H)

Step 4. 3-[Cyclopropyl(methyl)amino]-2-(1H-indol-5-yl)quinoxaline-6-carboxylic acid

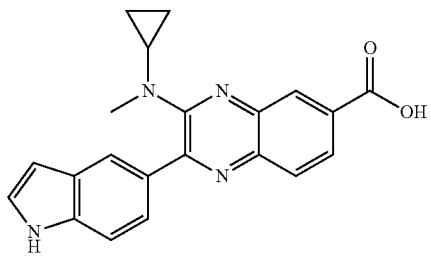 [SMILES: CN(c1nc2cc(C(=O)O)ccc2nc1-c1ccc2[nH]ccc2c1)C1CC1]

To a solution of methyl 3-[cyclopropyl(methyl)amino]-2-(1H-indol-5-yl)quinoxaline-6-carboxylate (71 mg, 0.19 mmol) in methanol (20 mL) and water (1.0 mL) was added sodium hydroxide (22.9 mg, 0.57 mmol) with stirring overnight at room temperature. The reaction mixture was concentrated in vacuo, dissolved in water (10 mL), adjusted pH to 4 with HCl (3N) to give the precipitate, which was collected by filtration to afford 3-[cyclopropyl(methyl)amino]-2-(1H-indol-5-yl)quinoxaline-6-carboxylic acid of as a yellow solid (20.4 mg, 30%).

LC/MS (ES, m/z): [M+H]$^+$ 358.0

$^1$H-NMR (300 MHz, CD$_3$OD) δ 8.47 (d, J=1.8 Hz, 1H), 8.03-8.06 (m, 2H), 7.94 (d, J=8.4 Hz, 1H), 7.59-7.63 (m, 1H), 7.41 (d, J=9.3 Hz, 1H), 7.33 (d, J=3.3 Hz, 1H), 6.58 (d, J=6.6 Hz, 1H), 3.01 (s, 3H), 2.55-2.59 (m, 1H), 0.51-0.54 (m, 4H)

Example 65

2-(1H-Indol-5-yl)-3-(piperidin-1-yl)quinoxaline-6-carboxylic acid

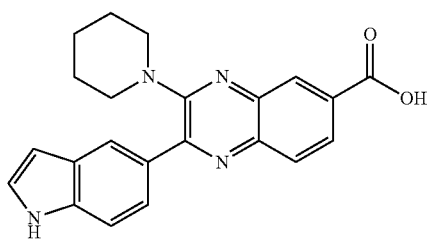 [SMILES: O=C(O)c1ccc2nc(-c3ccc4[nH]ccc4c3)c(N3CCCCC3)nc2c1]

Step 1. Methyl 3-(piperidin-1-yl)-2-(trifluoromethylsulfonyloxy)quinoxaline-6-carboxylate

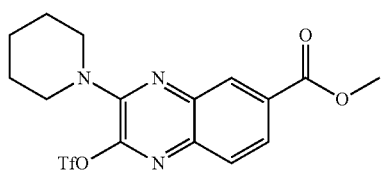 [SMILES: COC(=O)c1ccc2nc(OS(=O)(=O)C(F)(F)F)c(N3CCCCC3)nc2c1]

To a solution of methyl 2-oxo-3-(piperidin-1-yl)-1,2-dihydroquinoxaline-6-carboxylate (180 mg, 0.63 mmol) in dichloromethane (50 mL) was added pyridine (220 mg, 2.8 mmol) and then Tf$_2$O (393 mg, 1.4 mmol) was added dropwise with stirring at 0° C. The resulting solution was stirred overnight at room temperature and then washed with water (3×50 mL), dried over anhydrous sodium sulfate and concentrated in vacuo to afford methyl 3-(piperidin-1-yl)-2-(trifluoromethylsulfonyloxy)quinoxaline-6-carboxylate as yellow oil (290 mg, crude).

Step 2. Methyl 2-(1H-indol-5-yl)-3-(piperidin-1-yl)quinoxaline-6-carboxylate

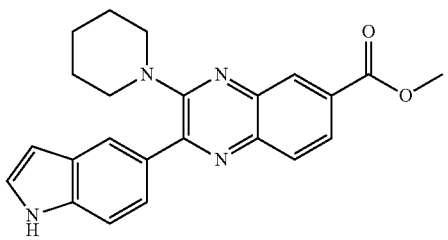 [SMILES: COC(=O)c1ccc2nc(-c3ccc4[nH]ccc4c3)c(N3CCCCC3)nc2c1]

To a solution of methyl 3-(piperidin-1-yl)-2-(trifluoromethylsulfonyloxy)quinoxaline-6-carboxylate (290 mg, crude) in dioxane (5 mL) was added 1H-indol-5-ylboronic acid (337 mg, 2.1 mmol), K$_3$PO$_4$ (443 mg, 2.1 mmol), Pd(PPh$_3$)$_4$ (40 mg, 0.03 mmol) and water (0.5 mL). The resulting solution was stirred for 1 h at 90° C. and then quenched by the addition of CH$_2$Cl$_2$ (100 mL), washed with water (3×50 mL), dried over anhydrous sodium sulfate and concentrated in vacuo to give a residue, which was purified by silica gel column chromatography eluting with 5% ethyl acetate in petroleum ether to afford methyl 2-(1H-indol-5-yl)-3-(piperidin-1-yl)quinoxaline-6-carboxylate as a yellow solid (90.0 mg, 33%).

LC/MS (ES, m/z): [M+H]$^+$ 387.0

$^1$H-NMR (300 MHz, CDCl$_3$): δ8.55 (d, J=1.8 Hz, 1H), 8.39 (s, 1H), 8.30 (s, 1H), 8.06-8.09 (m, 1H), 7.99 (d, J=8.7 Hz, 1H), 7.90-7.93 (m, 1H), 7.50 (d, J=8.7 Hz, 1H), 7.29-7.31 (m, 1H), 6.67-6.69 (t, J=2.4 Hz, 1H), 4.00 (s, 3H), 3.25-3.31 (m, 4H), 1.55-1.62 (m, 6H)

Step 3. 2-(1H-Indol-5-yl)-3-(piperidin-1-yl)quinoxaline-6-carboxylic acid

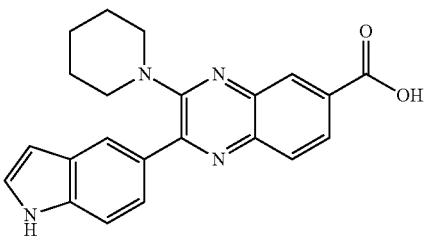 [SMILES: O=C(O)c1ccc2nc(-c3ccc4[nH]ccc4c3)c(N3CCCCC3)nc2c1]

To a solution of methyl 2-(1H-indol-5-yl)-3-(piperidin-1-yl)quinoxaline-6-carboxylate (90 mg, 0.23 mmol) in MeOH (20 mL) was added sodium hydroxide (40 mg, 0.93 mmol) and water (2 mL). The resulting solution was stirred overnight at room temperature and concentrated in vacuo. The residue was dissolved in water (5 mL) and adjusted to pH 6 with hydrochloric acid (1N). The solids were collected by filtration to afford 2-(1H-indol-5-yl)-3-(piperidin-1-yl)quinoxaline-6-carboxylic acid as a brown solid (65.8 mg, 76%).

LC/MS (ES, m/z): [M+H]$^+$ 373.0

¹H-NMR (300 MHz, DMSO) δ 11.32 (s, 1H), 8.27 (d, J=0.6 Hz, 1H), 7.92-7.99 (m, 2H), 7.77-7.81 (m, 1H), 7.51 (d, J=8.4 Hz, 1H), 7.42 (d, J=2.7 Hz, 1H), 6.58 (s, 1H), 3.15-3.24 (m, 4H), 1.45-1.53 (m, 6H)

Example 66

(S)-2-(1H-Indol-5-yl)-3-(3-methylmorpholino)quinoxaline-6-carboxylic acid

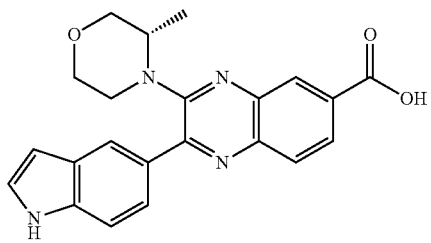

Step 1. (S)-Methyl 3-(3-methylmorpholino)-2-oxo-1,2-dihydroquinoxaline-6-carboxylate

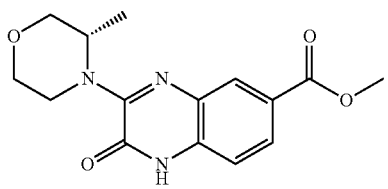 [SMILES: COC(=O)c1ccc2[nH]c(=O)c(N3CCOC[C@@H]3C)nc2c1]

To a solution of (3S)-3-methylmorpholine (127 mg, 1.26 mmol) in DMSO (2 mL) was added methyl 3-chloro-2-hydroxyquinoxaline-6-carboxylate (200 mg, 0.84 mmol) and DIEA (217 mg, 1.68 mmol). The resulting solution was stirred at 70° C. for 3 h and then quenched by water (10 mL). The solids were collected by filtration to afford (S)-methyl 3-(3-methylmorpholino)-2-oxo-1,2-dihydroquinoxaline-6-carboxylate as a light yellow solid (200 mg, crude).

LC/MS (ES, m/z): [M+H]⁺ 304.0

¹H-NMR (300 MHz, CDCl₃) δ 9.29 (s, 1H), 8.22 (d, J=1.5 Hz, 1H), 7.87-7.90 (m, 1H), 7.04 (d, J=8.4 Hz, 1H), 5.21-5.23 (m, 1H), 4.69-4.74 (m, 1H), 3.95-4.02 (m, 4H), 3.67-3.88 (m, 3H), 3.46-3.55 (m, 1H), 1.42 (d, J=6.6 Hz, 3H)

Step 2. (S)-Methyl 3-(3-methylmorpholino)-2-(trifluoromethylsulfonyloxy)quinoxaline-6-carboxylate

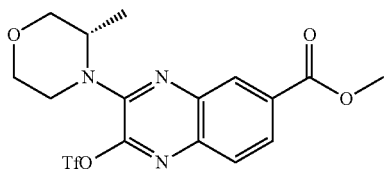 [SMILES: COC(=O)c1ccc2nc(OS(=O)(=O)C(F)(F)F)c(N3CCOC[C@@H]3C)nc2c1]

To a solution of (S)-methyl 3-(3-methylmorpholino)-2-oxo-1,2-dihydroquinoxaline-6-carboxylate (200 mg, crude) in dichloromethane (30 mL) was added pyridine (79 mg, 2.64 mmol). Then Tf₂O (372 mg, 1.32 mmol) was added and stirred overnight at room temperature. The reaction was then quenched by the addition of ice-water (100 mL) and extracted with dichloromethane (3×15 mL), the organic layers combined and dried over anhydrous magnesium sulfate and concentrated in vacuo to afford (S)-methyl 3-(3-methylmorpholino)-2-(trifluoromethylsulfonyloxy)quinoxaline-6-carboxylate as red oil (250 mg, crude).

Step 3. (S)-Methyl 2-(1H-indol-5-yl)-3-(3-methylmorpholino)quinoxaline-6-carboxylate

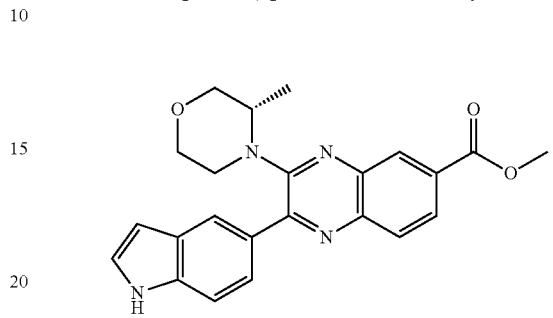

To a solution of (S)-methyl 3-(3-methylmorpholino)-2-(trifluoromethylsulfonyloxy)quinoxaline-6-carboxylate (250 mg, crude) in dioxane (5 mL) was added Pd(PPh₃)₄ (33 mg, 0.03 mmol), 1H-indol-5-ylboronic acid (230 mg, 1.43 mmol), K₃PO₄ (361 mg, 1.71 mmol) and water (5 drops). The resulting solution was stirred for 1 h at 90° C. under an inert atmosphere of nitrogen and then concentrated in vacuo to give a residue, which was purified by silica gel column chromatography eluting with 1%-10% ethyl acetate in petroleum ether to afford (S)-methyl 2-(1H-indol-5-yl)-3-(3-methylmorpholino)quinoxaline-6-carboxylate as a yellow solid (110 mg).

LC/MS (ES, m/z): [M+H]⁺ 403.0

¹H-NMR (300 MHz, CDCl₃) δ 8.56 (d, J=1.5 Hz, 1H), 8.36 (d, J=0.9 Hz, 1H), 8.34 (s, 1H), 8.02-8.14 (m, 2H), 7.87-7.91 (m, 1H), 7.52 (d, J=8.7 Hz, 1H), 7.30-7.33 (t, J=2.7 Hz, 1H), 6.68-6.70 (t, J=2.1 Hz, 1H), 4.01 (s, 3H), 3.91-3.96 (m, 1H), 3.81-3.86 (m, 1H), 3.64-3.76 (m, 2H), 3.41-3.51 (m, 3H), 1.17 (d, J=6.6 Hz, 3H)

Step 4. (S)-2-(1H-Indol-5-yl)-3-(3-methylmorpholino)quinoxaline-6-carboxylic acid

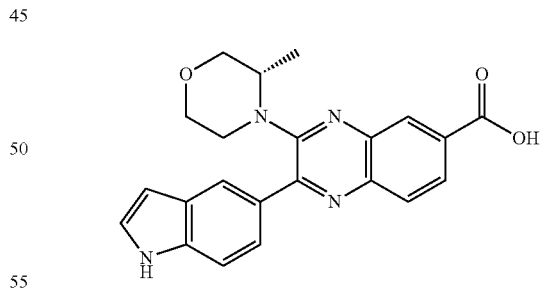

To a solution of (S)-methyl 2-(1H-indol-5-yl)-3-(3-methylmorpholino)quinoxaline-6-carboxylate (110 mg, 0.27 mmol) in methanol (15 mL) and CHCl₃ (5 mL) was added NaOH (32.4 mg, 0.81 mmol) and water (1 mL). The resulting solution was stirred overnight at room temperature and concentrated in vacuo. The residue was dissolved in water (15 mL) and adjusted to pH 5 with hydrochloric acid (1N). The solids were collected by filtration to afford (S)-2-(1H-indol-5-yl)-3-(3-methylmorpholino)quinoxaline-6-carboxylic acid as a yellow solid (81 mg, 76%).

LC/MS (ES, m/z): [M+H]+ 389.0

¹H-NMR (300 MHz, DMSO) δ 11.28 (s, 1H), 8.29 (s, 1H), 8.24 (s, 1H), 7.95-8.01 (m, 2H), 7.74-7.77 (m, 1H), 7.53 (d, J=8.7 Hz, 1H), 7.40-7.43 (t, J=2.4 Hz, 1H), 6.59 (d, J=2.4 Hz, 1H), 3.76-3.82 (m, 2H), 3.53-3.60 (m, 2H), 3.26-3.42 (m, 3H), 1.02 (d, J=6.6 Hz, 3H)

Example 67

2-(1H-Indol-5-yl)-3-[(2R)-2-(methoxymethyl)pyrrolidin-1-yl]quinoxaline-6-carboxylic acid

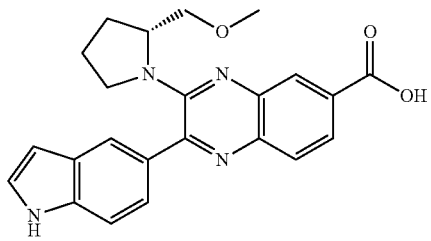 [SMILES: COC[C@H]1CCCN1c1nc2cc(C(=O)O)ccc2nc1-c1ccc2[nH]ccc2c1]

Step 1. Methyl 3-[(2R)-2-(methoxymethyl)pyrrolidin-1-yl]-2-oxo-1,2-dihydroquinoxaline-6-carboxylate

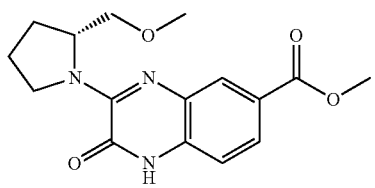 [SMILES: COC[C@H]1CCCN1c1nc2cc(C(=O)OC)ccc2[nH]c1=O]

To a solution of methyl 3-chloro-2-oxo-1,2-dihydroquinoxaline-6-carboxylate (600 mg, 2.51 mmol) in DMSO (8 mL) was added DIEA (650 mg, 5.03 mmol), and (2R)-2-(methoxymethyl)pyrrolidine (318 mg, 2.76 mmol). The solution was stirred for 4 h at 75° C. Then the reaction was quenched by the addition of water (50 mL) to give the precipitate, which was collected by filtration to afford methyl 3-[(2R)-2-(methoxymethyl)pyrrolidin-1-yl]-2-oxo-1,2-dihydroquinoxaline-6-carboxylate as a gray solid (650 mg, 81%).

LC/MS (ES, m/z): [M+H]⁺ 317.0

¹H-NMR (300 MHz, CDCl₃) δ 11.09 (s, 1H), 8.18 (s, 1H), 7.79-7.82 (m, 1H), 7.11 (d, J=8.4 Hz, 1H), 4.11-4.20 (m, 1H), 3.91-4.01 (m, 4H), 3.67-3.72 (m, 1H), 3.41-3.46 (m, 4H), 2.65 (s, 4H), 1.96-2.12 (m, 4H)

Step 2. Methyl 3-[(2R)-2-(methoxymethyl)pyrrolidin-1-yl]-2-[(trifluoromethane)sulfonyloxy]quinoxaline-6-carboxylate

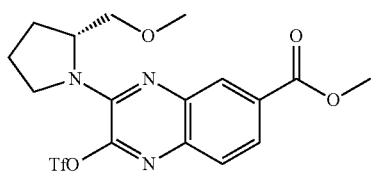 [SMILES: COC[C@H]1CCCN1c1nc2cc(C(=O)OC)ccc2nc1OS(=O)(=O)C(F)(F)F]

To a solution of methyl 3-[(2R)-2-(methoxymethyl)pyrrolidin-1-yl]-2-oxo-1,2-dihydroquinoxaline-6-carboxylate (600 mg, 1.89 mmol) in dichloromethane (120 mL) was added pyridine (598 mg, 7.56 mmol) and Tf₂O (1.06 g, 3.76 mmol) with stirring overnight maintained under an inert atmosphere of nitrogen at room temperature. The reaction was then quenched with water (100 mL), extracted with dichloromethane (3×50 mL), the organic layers combined and dried over anhydrous magnesium sulfate, and concentrated in vacuo to afford methyl 3-[(2R)-2-(methoxymethyl)pyrrolidin-1-yl]-2-[(trifluoromethane)sulfonyloxy]quinoxaline-6-carboxylate as red oil (850 mg, crude), which was used to the next step directly.

Step 3. Methyl 2-(1H-indol-5-yl)-3-[(2R)-2-(methoxymethyl)pyrrolidin-1-yl]quinoxaline-6-carboxylate

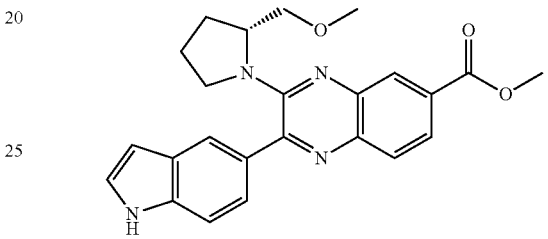

To a solution of methyl 3-[(2R)-2-(methoxymethyl)pyrrolidin-1-yl]-2-[(trifluoromethane)sulfonyloxy]quinoxaline-6-carboxylate (425 mg, crude) in dioxane (5.0 mL) and water (three drops) was added (1H-indol-5-yl)boronic acid (350 mg, 2.17 mmol), K₃PO₄ (458 mg, 2.16 mmol) and Pd(PPh₃)₄ (41.5 mg, 0.04 mmol) with stirring for 1 h at 90° C. under with an inert atmosphere of nitrogen in an oil bath. The reaction mixture was concentrated in vacuo to give the residue, which was purified by silica gel column chromatography eluting with 2% ethyl acetate in petroleum to afford methyl 2-(1H-indol-5-yl)-3-[(2R)-2-(methoxymethyl)pyrrolidin-1-yl]quinoxaline-6-carboxylate as a red solid (200 mg).

LC/MS (ES, m/z): [M+H]⁺ 417.0

¹H-NMR (300 MHz, CDCl₃) δ 8.51 (s, 1H), 8.37 (s, 1H), 8.10 (s, 1H), 7.97-8.04 (m, 2H), 7.65-7.68 (m, 1H), 7.48 (d, J=8.7 Hz, 1H), 7.30 (d, J=3.0 Hz, 1H), 6.65-6.66 (m, 1H), 4.67-4.69 (m, 1H), 4.01 (s, 3H), 3.82-3.86 (m, 1H), 3.62-3.81 (m, 1H), 3.46 (s, 3H), 2.96-3.09 (m, 2H), 2.12-2.17 (m, 1H), 1.87-1.94 (m, 2H), 1.75-1.79 (m, 1H)

Step 4. 2-(1H-Indol-5-yl)-3-[(2R)-2-(methoxymethyl)pyrrolidin-1-yl]quinoxaline-6-carboxylic acid

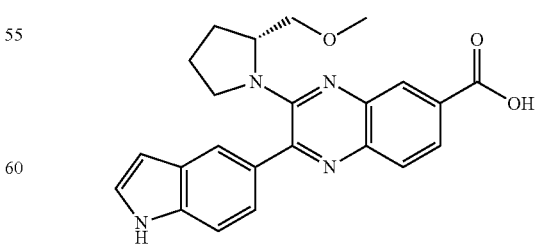

To a solution of methyl 2-(1H-indol-5-yl)-3-[(2R)-2-(methoxymethyl)pyrrolidin-1-yl]quinoxaline-6-carboxylate (200 mg, 0.48 mmol) in methanol (35.0 mL) and water (1.0 mL) was added sodium hydroxide (76.9 mg, 1.92 mmol) with stirring overnight at room temperature. The reaction mixture was concentrated in vacuo, dissolved in water (30.0 mL), adjusted pH to 4 with HCl (3N) to give the precipitate, which was collected by filtration to afford 2-(1H-indol-5-yl)-3-[(2R)-2-(methoxymethyl)pyrrolidin-1-yl]quinoxaline-6-carboxylic acid (80 mg, 41%).

LC/MS (ES, m/z): [M+H]$^+$ 403.0

$^1$H-NMR (300 MHz, DMSO) δ 11.32 (s, 1H), 8.24 (s, 1H), 7.86-8.24 (m, 3H), 7.43-7.55 (m, 3H), 6.54-6.56 (t, J=2.1 Hz, 1H), 4.45-4.50 (m, 1H), 3.67-3.71 (m, 1H), 3.49-3.55 (m, 1H), 3.32 (s, 1H), 2.93-2.99 (m, 2H), 2.00-2.08 (m, 1H), 1.81-1.93 (m, 2H), 1.56-1.69 (m, 1H)

Example 68

2-(5-Fluoro-1-benzofuran-2-yl)-3-[(2R)-2-(methoxymethyl)pyrrolidin-1-yl]quinoxaline-6-carboxylic acid

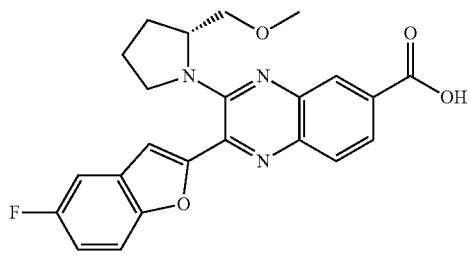 [SMILES: COC[C@H]1CCCN1c1nc2cc(C(=O)O)ccc2nc1-c1cc2cc(F)ccc2o1]

Step 1. Methyl 2-(5-fluoro-1-benzofuran-2-yl)-3-[(2R)-2-(methoxymethyl)pyrrolidin-1-yl]quinoxaline-6-carboxylate

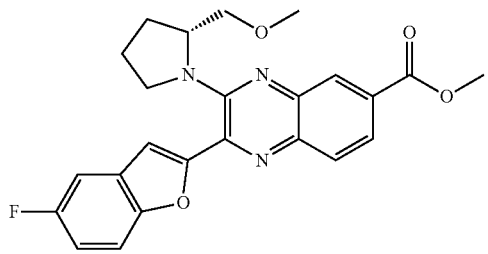 [SMILES: COC[C@H]1CCCN1c1nc2cc(C(=O)OC)ccc2nc1-c1cc2cc(F)ccc2o1]

To a solution of methyl 3-[(2R)-2-(methoxymethyl)pyrrolidin-1-yl]-2-[(trifluoromethane)sulfonyloxy]quinoxaline-6-carboxylate (325 mg, 0.72 mmol) in dioxane (5.0 mL) and water (three drops) was added (5-fluoro-1-benzofuran-2-yl)boronic acid (391 mg, 2.17 mmol), Pd(PPh$_3$)$_4$ (41.7 mg, 0.04 mmol), and K$_3$PO$_4$ (458.0 mg, 2.16 mmol) with stirring for 1 h at 90° C. under an inert atmosphere of nitrogen in an oil bath. The reaction mixture was cooled down to room temperature, concentrated in vacuo to give the residue, which was purified by silica gel column chromatography eluting with 1% ethyl acetate in petroleum ether to afford methyl 2-(5-fluoro-1-benzofuran-2-yl)-3-[(2R)-2-(methoxymethyl)pyrrolidin-1-yl]quinoxaline-6-carboxylate as a yellow solid (135 mg).

LC/MS (ES, m/z): [M+H]$^+$ 436.0

$^1$H-NMR (300 MHz, CDCl$_3$) δ 8.50 (s, 1H), 8.06 (s, 2H), 7.58-7.62 (m, 1H), 7.31-7.37 (m, 2H), 7.10-7.17 (m, 1H), 4.78-4.80 (m, 1H), 4.15 (s, 3H), 3.77-3.81 (m, 1H), 3.63-3.68 (m, 1H), 3.50-3.56 (m, 1H), 3.48 (s, 3H), 3.05-3.10 (m, 1H), 2.17-2.21 (m, 1H), 1.92-2.01 (m, 2H), 1.59-1.71 (m, 1H)

Step 2. 2-(5-Fluoro-1-benzofuran-2-yl)-3-[(2R)-2-(methoxymethyl)pyrrolidin-1-yl]quinoxaline-6-carboxylic acid

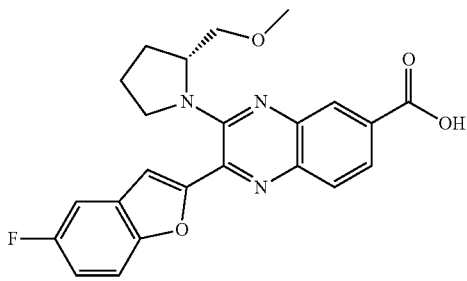 [SMILES: COC[C@H]1CCCN1c1nc2cc(C(=O)O)ccc2nc1-c1cc2cc(F)ccc2o1]

To a solution of methyl 2-(5-fluoro-1-benzofuran-2-yl)-3-[(2R)-2-(methoxymethyl)pyrrolidin-1-yl]quinoxaline-6-carboxylate (135 mg, 0.31 mmol) in methanol (35.0 mL) and water (1.0 mL) was added sodium hydroxide (55 mg, 1.38 mmol) with stirring overnight at room temperature. The reaction mixture was concentrated in vacuo, dissolved in water (30.0 mL), adjusted pH to 4 with HCl (3N) to give the precipitate, which was collected by filtration to afford 2-(5-fluoro-1-benzofuran-2-yl)-3-[(2R)-2-(methoxymethyl)pyrrolidin-1-yl]quinoxaline-6-carboxylic acid (100 mg, 77%).

LC/MS (ES, m/z): [M+H]$^+$ 422.0

$^1$H-NMR (300 MHz, DMSO) δ 13.21 (s, 1H), 8.26 (s, 1H), 7.93-8.02 (m, 2H), 7.77-7.81 (m, 1H), 7.58-7.63 (m, 1H), 7.44 (s, 1H), 7.26-7.33 (m, 1H), 4.59-4.64 (m, 1H), 3.68-3.72 (m, 1H), 3.47-3.52 (m, 1H), 3.36-3.43 (m, 1H), 3.10-3.16 (m, 1H), 2.17-2.27 (m, 1H), 1.81-1.93 (m, 2H), 1.56-1.71 (m, 1H)

Example 69

(S)-3-(sec-Butyl(methyl)amino)-2-(5-fluorobenzofuran-2-yl)quinoxaline-6-carboxylic acid

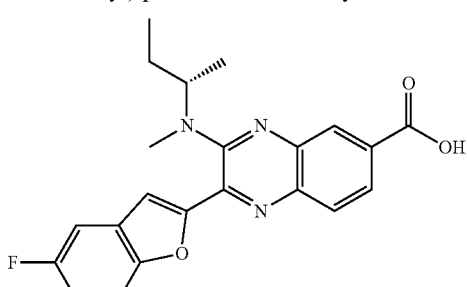

Step 1. (S)-methyl 3-(sec-butylamino)-2-oxo-1,2-dihydroquinoxaline-6-carboxylate

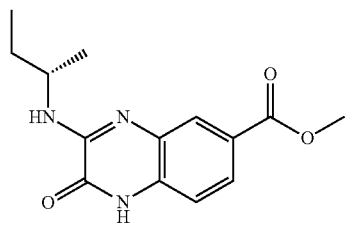 [SMILES: CC[C@H](C)Nc1nc2cc(C(=O)OC)ccc2[nH]c1=O]

To a solution of methyl 3-chloro-2-oxo-1,2-dihydroquinoxaline-6-carboxylate (200 mg, 0.84 mmol) in DMSO (2 mL) was added (S)-butan-2-amine (93 mg, 1.27 mmol) and DIEA (163 mg, 1.26 mmol). The resulting solution was stirred for 3 hours at 70° C. and then quenched by the addition of water (10 mL). The solids were collected by filtration to afford (S)-methyl 3-(sec-butylamino)-2-oxo-1,2-dihydroquinoxaline-6-carboxylate as light yellow solid (150 mg, 65%).

LC/MS (ES, m/z): [M+H]+ 276.0

Step 2. (S)-Methyl 3-(sec-butylamino)-2-(trifluoromethylsulfonyloxy)quinoxaline-6-carboxylate

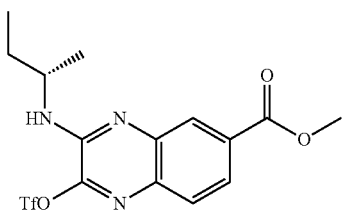 [SMILES: CC[C@H](C)Nc1nc2cc(C(=O)OC)ccc2nc1OS(=O)(=O)C(F)(F)F]

To a solution of (S)-methyl 3-(sec-butylamino)-2-oxo-1,2-dihydroquinoxaline-6-carboxylate (300 mg, 1.10 mmol) in dichloromethane (40 mL) was added pyridine (344 mg, 4.36 mmol). Tf$_2$O (615 mg, 2.18 mmol) was added drop-wise with stirring at 0° C. The resulting solution was stirred for 2 h at room temperature and then washed with water (3×50 mL), dried over anhydrous sodium sulfate and concentrated in vacuo to afford (S)-methyl 3-(sec-butylamino)-2-(trifluoromethylsulfonyloxy)quinoxaline-6-carboxylate as red oil (390 mg, crude).

Step 3. (S)-Methyl 3-(sec-butylamino)-2-(5-fluorobenzofuran-2-yl)quinoxaline-6-carboxylate

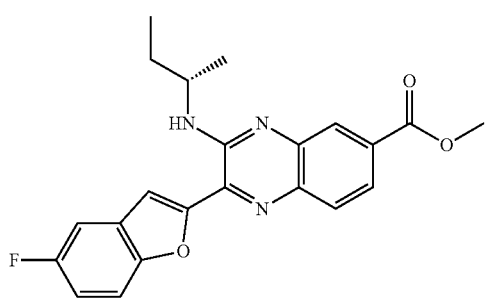 [SMILES: CC[C@H](C)Nc1nc2cc(C(=O)OC)ccc2nc1-c1cc2cc(F)ccc2o1]

To a solution of (S)-methyl 3-(sec-butylamino)-2-(trifluoromethylsulfonyloxy)quinoxaline-6-carboxylate (390 mg, crude) in dioxane (6 mL) was added 5-fluorobenzofuran-2-ylboronic acid (353 mg, 1.96 mmol), K$_3$PO$_4$ (416 mg, 1.96 mmol), Pd(PPh$_3$)$_4$ (64 mg, 0.06 mmol) and water (5 drops). The resulting solution was stirred for 1 h at 90° C. and then quenched by the addition of dichloromethane (100 mL). The resulting mixture washed with water (3×50 mL), dried over anhydrous sodium sulfate and concentrated in vacuo to give a residue, which was purified by silica gel column chromatography eluting with 3.3% ethyl acetate in petroleum ether to afford (S)-methyl 3-(sec-butylamino)-2-(5-fluorobenzofuran-2-yl)quinoxaline-6-carboxylate as a red solid (130.0 mg, 30% 2 steps).

LC/MS (ES, m/z): [M+H]+ 394.1

$^1$H-NMR (300 MHz, CDCl$_3$): δ 8.59 (s, 1H), 8.01-8.04 (m, 1H), 7.91 (d, J=8.7 Hz, 1H), 7.79 (s, 1H), 7.55-7.59 (m, 1H), 7.39-7.42 (m, 1H), 6.95-7.22 (m, 1H), 4.56-4.60 (m, 1H), 4.00 (s, 3H), 1.71-1.85 (m, 2H), 1.40 (d, J=6.6 Hz, 3H), 1.08-1.13 (t, J=7.2 Hz, 3H)

Step 4. (S)-3-(sec-Butyl(methyl)amino)-2-(5-fluorobenzofuran-2-yl)quinoxaline-6-carboxylic acid

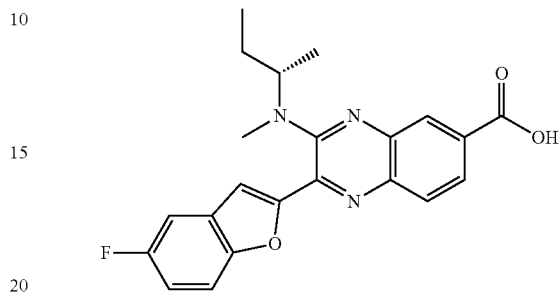

To a solution of (S)-methyl 3-(sec-butylamino)-2-(5-fluorobenzofuran-2-yl)quinoxaline-6-carboxylate (130 mg, 0.33 mmol) in THF (20 mL) was added NaH (52 mg, 1.32 mmol) and CH$_3$I (188 mg, 1.32 mmol). The resulting solution was stirred overnight at room temperature and then the reaction mixture was poured into water/ice solution (20 mL). The mixture was evaporated until about 10 mL of water remained and adjusted to pH 5 with hydrochloric acid (1N). The product was collected by filtration to afford (S)-3-(sec-butyl(methyl)amino)-2-(5-fluorobenzofuran-2-yl)quinoxaline-6-carboxylic acid as a yellow solid (34.4 mg, 27%).

LC/MS (ES, m/z): [M+H]+ 3940

$^1$H-NMR (300 MHz, DMSO): δ 8.22 (s, 1H), 7.92-7.99 (m, 2H), 7.74-7.78 (m, 1H), 7.60-7.63 (m, 2H), 7.25-7.32 (m, 1H), 3.89-3.96 (m, 1H), 2.81 (s, 3H), 1.61-1.70 (m, 1H), 1.42-1.51 (m, 1H), 1.17 (d, J=6.6 Hz, 3H), 0.69-0.71 (t, J=7.2 Hz, 3H)

Example 70

2-(1-Benzofuran-2-yl)-3-[(propan-2-yl)amino]quinoxaline-6-carboxylic acid

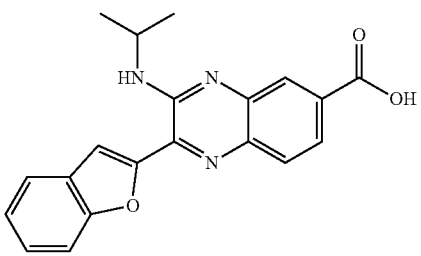 [SMILES: CC(C)Nc1nc2cc(C(=O)O)ccc2nc1-c1cc2ccccc2o1]

Step 1. Methyl 2-oxo-3-[(propan-2-yl)amino]-1,2-dihydroquinoxaline-6-carboxylate

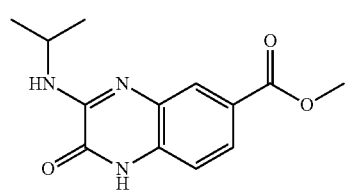 [SMILES: COC(=O)c1ccc2[nH]c(=O)c(NC(C)C)nc2c1]

To a solution of methyl 3-chloro-2-oxo-1,2-dihydroquinoxaline-6-carboxylate (500 mg, 2.1 mmol) in DMSO (2 mL) was added propan-2-amine (186 mg, 3.15 mmol) and DIEA (540 mg, 3.15 mmol). After stirring for overnight at 50° C., the reaction mixture was dissolved in water (20 mL), then filtered to afford methyl 2-oxo-3-[(propan-2-yl)amino]-1,2-dihydroquinoxaline-6-carboxylate as a white solid (430 mg, 78%).

LC/MS (ES, m/z): [M+H]$^+$ 262.0

$^1$H-NMR (300 MHz, DMSO) δ 12.42 (s, 1H), 7.88 (d, J=1.8 Hz, 1H), 7.66-7.70 (m, 1H), 7.34 (d, J=8.1 Hz, 1H), 7.34 (d, J=8.4 Hz, 1H), 4.21-4.30 (m, 1H), 3.84 (s, 3H), 1.22 (d, J=6.6 Hz, 6H)

Step 2. Methyl 3-[(propan-2-yl)amino]-2-[(trifluoromethane)sulfonyloxy]quinoxaline-6-carboxylate

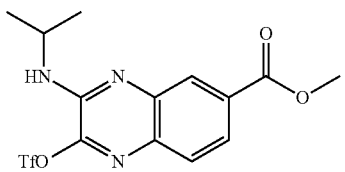 [SMILES: COC(=O)c1ccc2nc(OS(=O)(=O)C(F)(F)F)c(NC(C)C)nc2c1]

To a solution of methyl 2-oxo-3-[(propan-2-yl)amino]-1,2-dihydroquinoxaline-6-carboxylate (330 mg, 1.26 mmol) in dichloromethane (50 mL) was added pyridine (600 mg, 7.59 mmol) and Tf$_2$O (1100 mg, 3.90 mmol), which was added dropwise with stirring at 0° C. After stirring 3 h at room temperature under nitrogen atmosphere, the reaction mixture was dissolved in water (100 mL), extracted with dichloromethane (2×20 mL), dried over anhydrous magnesium sulfate and concentrated under reduced pressure to afford methyl 3-[(propan-2-yl)amino]-2-[(trifluoromethane)sulfonyloxy]quinoxaline-6-carboxylate as a light yellow solid (650 mg, crude).

Step 3. Methyl 2-(1-benzofuran-2-yl)-3-[(propan-2-yl)amino]quinoxaline-6-carboxylate

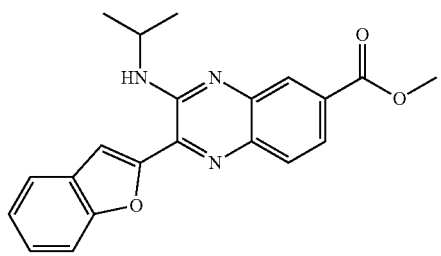 [SMILES: COC(=O)c1ccc2nc(-c3cc4ccccc4o3)c(NC(C)C)nc2c1]

To a solution of methyl 3-[(propan-2-yl)amino]-2-[(trifluoromethane)sulfonyloxy]quinoxaline-6-carboxylate (650 mg, crude) in dioxane (5 mL) was added (1-benzofuran-2-yl)boronic acid (537 mg, 3.32 mmol), K$_3$PO$_4$ (700 mg, 3.30 mmol) and Pd(PPh$_3$)$_4$ (95 mg, 0.08 mmol). After stirring 40 min at 95° C. under a nitrogen atmosphere, the reaction mixture was dissolved in water (10 mL), extracted with dichloromethane (3×30 mL), dried over anhydrous magnesium sulfate and concentrated under reduced pressure to afford a residue, which was purified by silica gel column chromatography eluting with 2% ethyl acetate in petroleum ether to afford methyl 2-(1-benzofuran-2-yl)-3-[(propan-2-yl)amino]quinoxaline-6-carboxylate as a light yellow solid (60 mg).

LC/MS (ES, m/z): [M+H]$^+$ 362.0

$^1$H-NMR (300 MHz, DMSO) δ 8.17 (d, J=1.5 Hz, 1H), 7.80-7.96 (m, 5H), 7.47-7.53 (m, 1H), 7.36-7.42 (m, 1H), 7.13 (d, J=7.2 Hz, 1H), 4.39-4.50 (m, 1H), 3.92 (s, 3H), 1.34 (d, J=6.6 Hz, 6H)

Step 4. 2-(1-Benzofuran-2-yl)-3-[(propan-2-yl)amino]quinoxaline-6-carboxylic acid

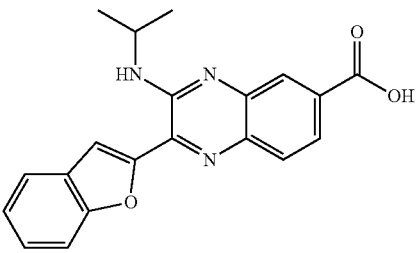 [SMILES: CC(C)Nc1nc2cc(C(=O)O)ccc2nc1-c1cc2ccccc2o1]

To a solution of methyl 2-(1-benzofuran-2-yl)-3-[(propan-2-yl)amino]quinoxaline-6-carboxylate (60 mg, 0.17 mmol) in methanol (30 mL) was added sodium hydroxide (60 mg, 1.50 mmol). After stirring overnight at room temperature, the reaction mixture was concentrated under reduced pressure to afford a residue, which was dissolved in water (10 mL), adjusted pH to 6 with HCl (3N) and filtered to give 2-(1-benzofuran-2-yl)-3-[(propan-2-yl)amino]quinoxaline-6-carboxylic acid as a light yellow solid (30.1 mg, 52%).

LC/MS (ES, m/z): [M+H]$^+$ 348.1

$^1$H-NMR (300 MHz, DMSO) δ 8.15 (d, J=1.5 Hz, 1H), 7.80-7.94 (m, 5H), 7.47-7.53 (m, 1H), 7.36-7.42 (m, 1H), 7.10 (d, J=7.5 Hz, 1H), 4.42-4.51 (m, 1H), 1.34 (d, J=6.6 Hz, 6H)

Example 71

3-[Methyl(propan-2-yl)amino]-2-[5-(trifluoromethyl)-1-benzofuran-3-yl]quinoxaline-6-carboxylic acid

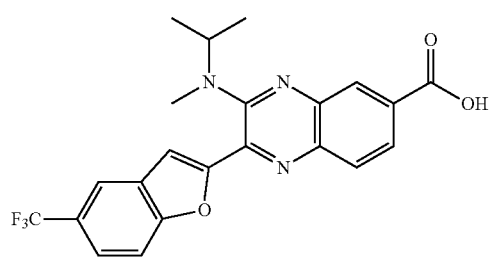 [SMILES: CC(C)N(C)c1nc2cc(C(=O)O)ccc2nc1-c1cc2cc(C(F)(F)F)ccc2o1]

Step 1.
1-(2,2-Diethoxyethoxy)-4-(trifluoromethyl)benzene

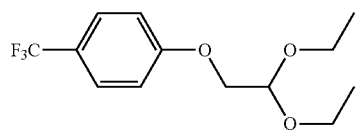 [SMILES: CCOC(COc1ccc(C(F)(F)F)cc1)OCC]

To a suspension of sodium hydride (12.0 g, 500.00 mmol) in anhydrous DMF (500 mL) was added 4-(trifluoromethyl)phenol (35.0 g, 215.90 mmol) at 0° C. After hydrogen evolution had ceased, 2-bromo-1,1-diethoxyethane (55.0 g, 279.09 mmol) was added. The reaction was heated at 120° C. overnight. The mixture was poured into ice-water (2 L), extracted with ethyl acetate (3×150 mL), washed with 1N sodium hydroxide (3×100 mL) and brine (3×100 mL). The organic layer was dried over anhydrous sodium sulfate and filtered. The solvent was removed under vacuum to give the residue, which was purified by silica gel column chromatography eluting with 1% ethyl acetate in petroleum ether to afford 1-(2,2-diethoxyethoxy)-4-(trifluoromethyl)benzene as oil (8.0 g, 13%).

$^1$H-NMR (300 MHz, CDCl$_3$): δ 7.54 (d, J=8.4 Hz, 2H), 6.99 (d, J=8.4 Hz, 2H), 4.85-4.88 (t, J=5.10 Hz, 1H), 4.06 (d, J=5.10 Hz, 2H), 3.69-3.85 (m, 4H), 1.22-1.29 (m, 6H)

Step 2. 5-(Trifluoromethyl)-1-benzofuran

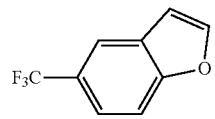

To a mixture of benzene (100 mL) containing polyphosphoric acid (19.45 g, 57.54 mmol) was added 1-(2,2-diethoxyethoxy)-4-(trifluoromethyl)benzene (8.0 g, 28.75 mmol). The mixture was stirred vigorously while being heated to reflux for 2.5 hours. The reaction mixture was cooled to room temperature and decanted from the polyphosphoric acid. The solvent was removed under vacuum to give the residue, which was purified by silica gel column chromatography eluting with 1% ethyl acetate in petroleum ether to afford 5-(trifluoromethyl)-1-benzofuran (5.0 g, crude) as colorless oil.

$^1$H-NMR (300 MHz, CDCl$_3$): δ 7.93 (s, 1H), 7.75 (d, J=2.4 Hz, 1H), 7.56-7.64 (m, 2H), 6.87-6.88 (m, 1H)

Step 3.
[5-(Trifluoromethyl)-1-benzofuran-2-yl]boronic acid

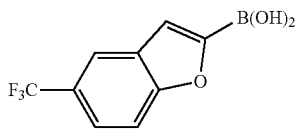

To a solution of 5-(trifluoromethyl)-1-benzofuran (5.0 g, 26.86 mmol) in dry tetrahydrofuran (120 mL) were added tetramethylethylenediamine (3.74 g, 32.2 mmol). The solution was kept below −60° C. under nitrogen, while n-BuLi (12.8 mL, 32.2 mmol, 2.5 M solution in hexane) was added dropwise. The solution was warmed to −10° C. over 45 min and stirred at this temperature for another 30 min. The mixture was cooled again below −60° C. followed by dropwise addition of triisopropyl borate (10.0 g, 53.19 mmol). After warming to room temperature the mixture was quenched with hydrochloric acid (70 mL, 2N) and stirred for 1 h. The alkaline aqueous layer was brought to pH 5 and extracted with ethyl acetate (3×80 mL). All organic layers were combined, dried over sodium sulfate, and concentrated in vacuo to give [5-(trifluoromethyl)-1-benzofuran-2-yl]boronic acid (2.0 g, crude) as light yellow oil; which was used for the next step without further purification.

Step 4. Methyl 3-[methyl(propan-2-yl)amino]-2-[5-(trifluoromethyl)-1-benzofuran-2-yl]quinoxaline-6-carboxylate

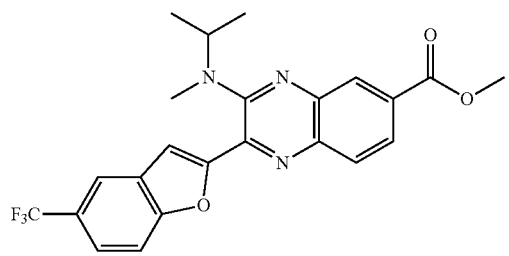 [SMILES: COC(=O)c1ccc2nc(-c3cc4cc(C(F)(F)F)ccc4o3)c(N(C)C(C)C)nc2c1]

To a solution of [5-(trifluoromethyl)-1-benzofuran-2-yl]boronic acid (305.1 mg, 1.33 mmol) in dioxane (5.0 mL) and water (3 drops) was added methyl 3-[methyl(propan-2-yl)amino]-2-[(trifluoromethane)sulfonyloxy]quinoxaline-6-carboxylate (180 mg, 0.44 mmol), K$_3$PO$_4$ (279 mg, 1.31 mmol) and Pd(PPh$_3$)$_4$ (25.38 mg, 0.02 mmol) with stirring for 1 h at 90° C. in an oil bath under an inert atmosphere of nitrogen. The reaction mixture was concentrated in vacuo to give a residue, which was purified by silica gel column chromatography eluting with 1% ethyl acetate in petroleum ether to afford methyl 3-[methyl(propan-2-yl)amino]-2-[5-(trifluoromethyl)-1-benzofuran-2-yl]quinoxaline-6-carboxylate as a light yellow solid (135 mg, 71%).

LC/MS (ES, m/z): [M+H]$^+$ 444.0

$^1$H-NMR (300 MHz, CDCl$_3$): δ 8.54 (d, J=1.2 Hz, 1H), 7.97-8.14 (m, 3H), 7.72-7.78 (m, 1H), 7.63-7.69 (m, 2H), 4.26-4.35 (m, 1H), 4.02 (s, 3H), 2.91 (s, 3H), 1.26 (d, J=6.6 Hz, 6H)

Step 5. 3-[Methyl(propan-2-yl)amino]-2-[5-(trifluoromethyl)-1-benzofuran-3-yl]quinoxaline-6-carboxylic acid

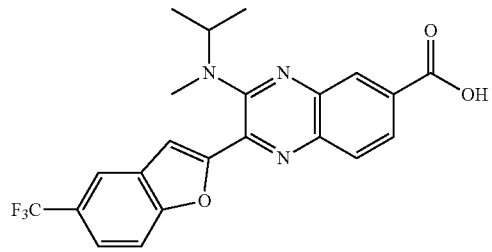 [SMILES: CC(C)N(C)c1nc2cc(C(=O)O)ccc2nc1-c1cc2cc(C(F)(F)F)ccc2o1]

To a solution of methyl 3-[methyl(propan-2-yl)amino]-2-[5-(trifluoromethyl)-1-benzofuran-3-yl]quinoxaline-6-carboxylate (135 mg, 0.30 mmol) in methanol (30 mL) and water (1.0 mL) was added sodium hydroxide (48.8 mg, 1.22 mmol) with stirring overnight at room temperature. The reaction mixture was concentrated in vacuo, dissolved in water (20 mL) and adjusted to pH 5 with HCl (3N). The solids were collected by filtration to afford 3-[methyl(propan-2-yl)amino]-2-[5-(trifluoromethyl)-1-benzofuran-3-yl]quinoxaline-6-carboxylic acid as a light yellow solid (42.6 mg, 33%).

LC/MS (ES, m/z): [M+H]+ 430.0

1H-NMR (300 MHz, DMSO): δ 8.27-8.28 (t, J=0.6 Hz, 2H), 7.98-8.05 (m, 3H), 7.77-7.81 (m, 2H), 4.17-4.26 (m, 1H), 2.83 (s, 3H), 1.17 (d, J=6.6 Hz, 6H)

Example 72

2-(1-Benzofuran-3-yl)-3-[(2S)-2-methylpyrrolidin-1-yl]quinoxaline-6-carboxylic acid

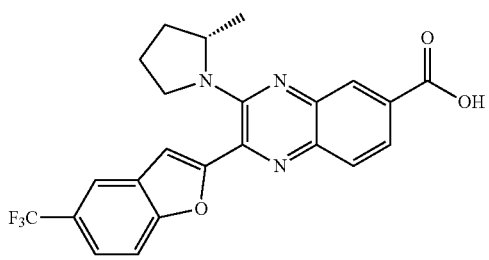 [SMILES: C[C@H]1CCCN1c1nc2cc(C(=O)O)ccc2nc1-c1cc2cc(C(F)(F)F)ccc2o1]

Step 1. Methyl 3-[(2S)-2-methylpyrrolidin-1-yl]-2-[6-(trifluoromethyl)-1-benzofuran-2-yl]quinoxaline-6-carboxylate

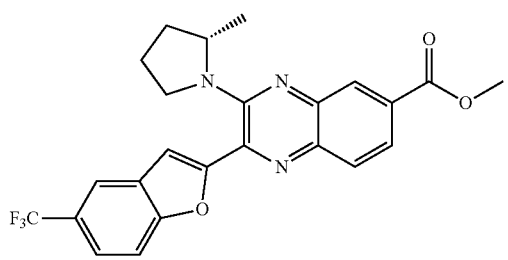 [SMILES: COC(=O)c1ccc2nc(-c3cc4cc(C(F)(F)F)ccc4o3)c(N3CCC[C@@H]3C)nc2c1]

To a solution of 3-[(2S)-2-methylpyrrolidin-1-yl]-2-[(trifluoromethane)sulfonyloxy]quinoxaline-6-carboxylate (200 mg, 0.48 mmol) in dioxane (3.0 mL) and water (2 drops) was added [6-(trifluoromethyl)-1-benzofuran-2-yl]boronic acid (331 mg, 1.44 mmol,), Pd(PPh3)4 (28 mg, 0.02 mmol), K3PO4 (304 mg, 1.43 mmol) with stirring for 2 hour at 90° C. under an atmosphere of nitrogen. The resulting mixture was concentrated in vacuo to give a residue, which was purified by silica gel column chromatography eluting with 1% ethyl acetate in petroleum ether to give methyl methyl 3-[(2S)-2-methylpyrrolidin-1-yl]-2-[6-(trifluoromethyl)-1-benzofuran-2-yl]quinoxaline-6-carboxylate (150 mg, 69%) as a yellow solid.

LC/MS (ES, m/z): [M+H]+ 456.1

1H-NMR (300 MHz, CDCL3) δ 8.52-8.53 (t, J=0.9 Hz, 1H), 8.01-8.06 (m, 3H), 7.76 (d, J=8.7 Hz, 1H), 7.65-7.69 (m, 1H), 7.36 (d, J=0.6 Hz, 1H), 4.46-4.53 (m, 1H), 4.02 (s, 3H), 3.49-3.55 (m, 1H), 3.06-3.11 (m, 1H), 2.27-2.31 (m, 1H), 1.92-1.94 (m, 1H), 1.67-1.74 (m, 2H), 1.44-1.48 (d, J=6.0 Hz, 3H)

Step 2. 2-(1-Benzofuran-3-yl)-3-[(2S)-2-methylpyrrolidin-1-yl]quinoxaline-6-carboxylic acid

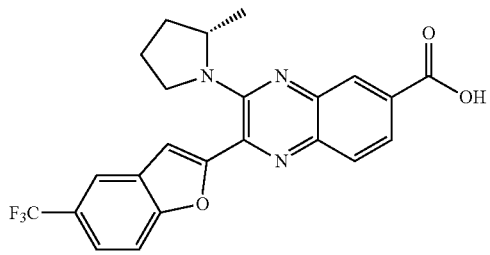 [SMILES: C[C@H]1CCCN1c1nc2cc(C(=O)O)ccc2nc1-c1cc2cc(C(F)(F)F)ccc2o1]

To a solution of methyl 3-[(2S)-2-methylpyrrolidin-1-yl]-2-[5-(trifluoromethyl)-1-benzofuran-2-yl]quinoxaline-6-carboxylate (150 mg, 0.33 mmol) in methanol (30 mL) and water (1 mL) was added sodium hydroxide (53 mg, 1.33 mmol) with stirring overnight at room temperature. The resulting mixture was concentrated in vacuo and dissolved in water (15 mL), adjusted to pH 7 with HCl (3N). The product was collected by filtration to give 3-[(2S)-2-methylpyrrolidin-1-yl]-2-[5-(trifluoromethyl)-1-benzofuran-2-yl]quinoxaline-6-carboxylic acid as a yellow solid (72.8 mg, 50%).

LC/MS (ES, m/z): [M+H]+ 442.0

1H-NMR (300 MHz, DMSO) δ 8.24-8.27 (t, J=1.5 Hz, 2H), 7.92-8.06 (m, 3H), 7.77-7.80 (m, 1H), 7.59 (s, 1H), 4.33-4.40 (m, 1H), 3.34-3.44 (m, 1H), 3.11-3.13 (m, 1H), 2.15-2.20 (m, 1H), 1.85-1.90 (m, 1H), 1.60-1.70 (m, 2H), 1.38 (d, J=6.0 Hz, 3H)

Example 73

(S)-2-(1H-Indol-5-yl)-3-(2-methylpiperidin-1-yl)quinoxaline-6-carboxylic acid

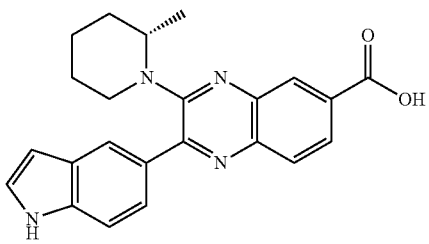 [SMILES: C[C@H]1CCCCN1c1nc2cc(C(=O)O)ccc2nc1-c1ccc2[nH]ccc2c1]

Step 1. (S)-Methyl 3-(2-methylpiperidin-1-yl)-2-oxo-1,2-dihydroquinoxaline-6-carboxylate

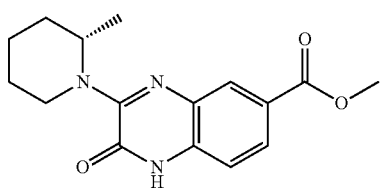 [SMILES: COC(=O)c1ccc2[nH]c(=O)c(N3CCCC[C@@H]3C)nc2c1]

To a solution of methyl 3-chloro-2-oxo-1,2-dihydroquinoxaline-6-carboxylate (200 mg, 0.84 mmol) in DMSO (2 mL) was added (S)-2-methylpiperidine (166 mg, 1.7 mmol) and DIEA (217 mg, 1.7 mmol). The resulting solution was stirred at 70° C. for 3 h and then quenched by water (10 mL), the solids were collected by filtration to afford (S)-methyl 3-(2-methylpiperidin-1-yl)-2-oxo-1,2-dihydroquinoxaline-6-carboxylate as a light yellow solid (200 mg, 79%).

LC/MS (ES, m/z): [M+H]⁺ 302.0

¹H-NMR (300 MHz, CDCl₃): δ 10.11 (s, 1H), 8.29 (s, 1H), 7.83-7.86 (m, 1H), 7.09 (d, J=8.4 Hz, 1H), 5.39-5.41 (m, 1H), 4.86 (d, J=13.8 Hz, 1H), 3.94 (s, 3H), 3.18-3.26 (t, J=12.6 Hz, 1H), 1.65-1.94 (m, 6H), 1.35 (d, J=6.9 Hz, 3H)

Step 2. (S)-Methyl 3-(2-methylpiperidin-1-yl)-2-(trifluoromethylsulfonyloxy)quinoxaline-6-carboxylate

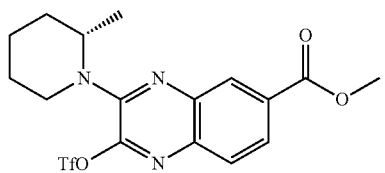 [SMILES: COC(=O)c1ccc2nc(OS(=O)(=O)C(F)(F)F)c(N3CCCC[C@@H]3C)nc2c1]

To a solution of (S)-methyl 3-(2-methylpiperidin-1-yl)-2-oxo-1,2-dihydroquinoxaline-6-carboxylate (200 mg, 0.66 mmol) in dichloromethane (30 mL) was added pyridine (208 mg, 2.64 mmol). Then Tf₂O (372 mg, 1.32 mmol) was added and stirred overnight at room temperature. The reaction was then quenched by the addition of ice-water (100 mL) and extracted with dichloromethane (3×15 mL), the organic layers combined and dried over anhydrous magnesium sulfate and concentrated in vacuo to afford (S)-methyl 3-(2-methylpiperidin-1-yl)-2-(trifluoromethylsulfonyloxy)quinoxaline-6-carboxylate as red oil (250 mg, crude).

Step 3. (S)-Methyl 2-(1H-indol-5-yl)-3-(2-methylpiperidin-1-yl)quinoxaline-6-carboxylate

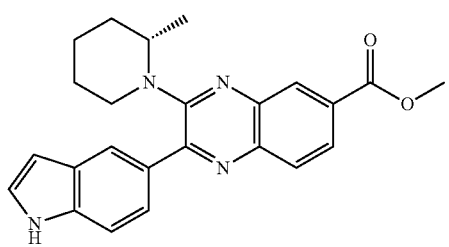 [SMILES: COC(=O)c1ccc2nc(-c3ccc4[nH]ccc4c3)c(N3CCCC[C@@H]3C)nc2c1]

To a solution of (S)-methyl 3-(2-methylpiperidin-1-yl)-2-(trifluoromethylsulfonyloxy)quinoxaline-6-carboxylate (250 mg, crude) in dioxane (5 mL) was added Pd(PPh₃)₄ (33 mg, 0.03 mmol), 1H-indol-5-ylboronic acid (234 mg, 1.45 mmol), K₃PO₄ (367 mg, 1.74 mmol) and water (5 drops). The resulting solution was stirred for 1 h at 90° C. with an inert atmosphere of nitrogen and then concentrated in vacuo to give a residue, which was purified by silica gel column chromatography eluting with 1%-10% ethyl acetate in petroleum ether to afford (S)-methyl 2-(1H-indol-5-yl)-3-(2-methylpiperidin-1-yl)quinoxaline-6-carboxylate as a yellow solid (79 mg).

LC/MS (ES, m/z): [M+H]⁺ 401.0

¹H-NMR (300 MHz, CDCl₃) δ 8.53 (d, J=1.5 Hz, 1H), 8.38 (s, 1H), 8.29 (s, 1H), 8.05-8.08 (d, J=1.8 Hz, 2H), 7.98 (d, J=8.7 Hz, 1H), 7.88-7.92 (m, 1H), 7.50 (d, J=8.7 Hz, 1H), 7.30 (d, J=3.0 Hz, 1H), 6.67 (d, J=2.1 Hz, 1H), 4.17-4.21 (m, 1H), 4.00 (s, 3H), 3.58-3.63 (m, 1H), 3.12-3.16 (m, 1H), 1.60-1.76 (m, 4H), 1.28-1.39 (m, 2H), 1.10 (d, J=6.9 Hz, 3H)

Step 4. (S)-2-(1H-indol-5-yl)-3-(2-methylpiperidin-1-yl)quinoxaline-6-carboxylic acid

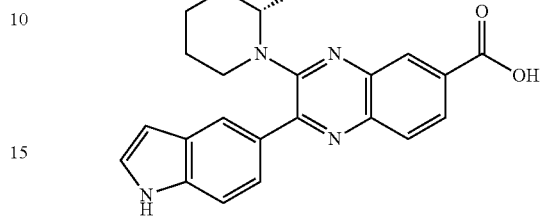

To a solution of (S)-methyl 2-(1H-indol-5-yl)-3-(2-methylpiperidin-1-yl)quinoxaline-6-carboxylate (79 mg, 0.20 mmol) in methanol (15 mL) and CHCl₃ (5 mL) was added NaOH (24 mg, 0.60 mmol) and water (1 mL). The resulting solution was stirred overnight at room temperature and concentrated in vacuo. The residue was dissolved in water (15 mL) and adjusted to pH 5 with hydrochloric acid (1N). The solids were collected by filtration to afford (S)-2-(1H-indol-5-yl)-3-(2-methylpiperidin-1-yl)quinoxaline-6-carboxylic acid as a yellow solid (70 mg, 92%).

LC/MS (ES, m/z): [M+H]⁺ 387.0

¹H-NMR (300 MHz, DMSO) δ 11.33 (s, 1H), 8.28 (d, J=16.2 Hz, 2H), 7.89-7.98 (m, 2H), 7.77 (d, J=8.4 Hz, 1H), 7.53 (d, J=8.4 Hz, 1H), 7.44 (s, 1H), 6.57 (s, 1H), 4.05-4.11 (m, 1H), 3.54 (d, J=12.3 Hz, 1H), 3.04-3.08 (m, 1H), 1.54-1.64 (m, 5H), 1.32 (d, J=8.7 Hz, 1H), 1.02 (d, J=6.6 Hz, 3H)

Example 74

(R)-3-(sec-Butyl(methyl)amino)-2-(5-fluorobenzofuran-2-yl)quinoxaline-6-carboxylic acid

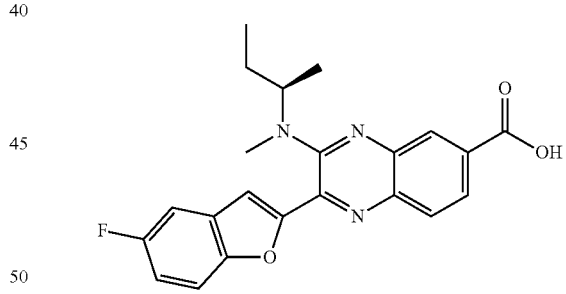

Step 1. (R)-Methyl 3-(sec-butylamino)-2-oxo-1,2-dihydroquinoxaline-6-carboxylate

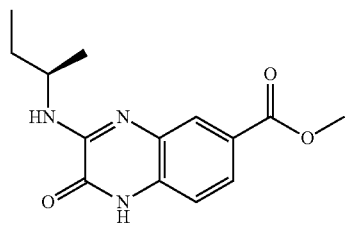 [SMILES: CC[C@@H](C)Nc1nc2cc(C(=O)OC)ccc2[nH]c1=O]

To a solution of methyl 3-chloro-2-oxo-1,2-dihydroquinoxaline-6-carboxylate (0.5 g, 2.1 mmol) in DMSO (10 mL) was added (R)-butan-2-amine (570 mg, 7.79 mmol) and DIEA (850 mg, 6.58 mmol). The resulting solution was stirred for 4 hours at 70° C. and then quenched by the addition of water (50 mL). The solids were collected by filtration to afford (R)-methyl 3-(sec-butylamino)-2-oxo-1,2-dihydroquinoxaline-6-carboxylate as a white solid (425 mg, 75%).

LC/MS (ES, m/z): [M+H]$^+$ 276.0

$^1$H-NMR (300 MHz, DMSO): δ12.43 (s, 1H), 7.87 (d, J=1.8 Hz, 1H), 7.66-7.70 (m, 1H), 7.33 (d, J=8.4 Hz, 1H), 7.20 (d, J=8.4 Hz, 1H), 4.04-4.14 (m, 1H), 3.85 (s, 3H), 1.51-1.71 (m, 2H), 1.19 (d, J=6.6 Hz, 3H), 0.88-0.91 (t, J=7.5 Hz, 3H)

Step 2. (R)-Methyl 3-(sec-butylamino)-2-(trifluoromethylsulfonyloxy)quinoxaline-6-carboxylate

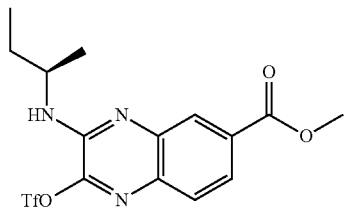 [SMILES: CC[C@@H](C)Nc1nc2cc(C(=O)OC)ccc2nc1OS(=O)(=O)C(F)(F)F]

To a solution of (R)-methyl 3-(sec-butylamino)-2-oxo-1,2-dihydroquinoxaline-6-carboxylate (300 mg, 1.10 mmol) in dichloromethane (40 mL) was added pyridine (344 mg, 4.36 mmol) and then Tf$_2$O (615 mg, 2.18 mmol) was added dropwise with stirring at 0° C. The resulting solution was stirred for 2 h at room temperature and then washed with water (3×50 mL), dried over anhydrous sodium sulfate and concentrated in vacuo to afford (R)-methyl 3-(sec-butylamino)-2-(trifluoromethylsulfonyloxy)quinoxaline-6-carboxylate as red oil (400 mg, crude).

Step 3. (R)-Methyl 3-(sec-butylamino)-2-(5-fluorobenzofuran-2-yl)quinoxaline-6-carboxylate

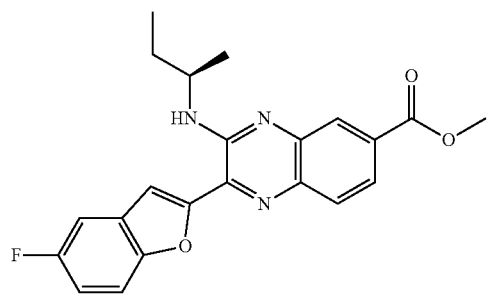 [SMILES: CC[C@@H](C)Nc1nc2cc(C(=O)OC)ccc2nc1-c1cc2cc(F)ccc2o1]

To a solution of (R)-methyl 3-(sec-butylamino)-2-(trifluoromethylsulfonyloxy)quinoxaline-6-carboxylate (400 mg, crude) in dioxane (5 mL) was added 5-fluorobenzofuran-2-ylboronic acid (441 mg, 2.45 mmol), K$_3$PO$_4$ (620 mg, 2.94 mmol), and Pd(PPh$_3$)$_4$ (57 mg, 0.05 mmol). The resulting solution was stirred for 1 h at 90° C. and then quenched by the addition of dichloromethane (200 mL) and washed with water (3×50 mL). The organic layer was dried over anhydrous sodium sulfate and concentrated in vacuo to give a residue, which was purified by silica gel column chromatography (5% ethyl acetate in petroleum ether) to afford (R)-methyl 3-(sec-butylamino)-2-(5-fluorobenzofuran-2-yl)quinoxaline-6-carboxylate as a yellow solid (100 mg, 24% 2 steps).

LC/MS (ES, m/z): [M+H]$^+$ 394.1

$^1$H-NMR (300 MHz, CDCl$_3$): δ 8.53 (s, 1H), 8.02 (d, J=8.1 Hz, 1H), 7.93 (d, J=8.7 Hz, 1H), 7.78 (s, 1H), 7.55-7.59 (m, 1H), 7.39-7.43 (m, 1H), 6.87 (s, 1H), 4.53-4.55 (m, 1H), 4.01 (s, 3H), 1.73-1.85 (m, 2H), 1.40 (d, J=6.6 Hz, 3H), 1.08-1.13 (t, J=7.5 Hz, 3H)

Step 4. (R)-3-(sec-Butyl(methyl)amino)-2-(5-fluorobenzofuran-2-yl)quinoxaline-6-carboxylic acid

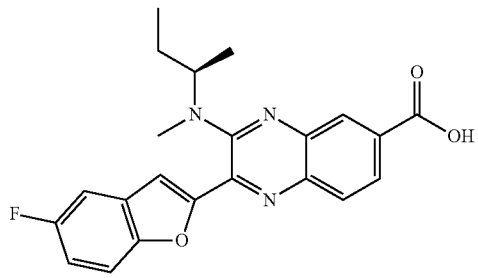 [SMILES: CC[C@@H](C)N(C)c1nc2cc(C(=O)O)ccc2nc1-c1cc2cc(F)ccc2o1]

To a solution of (R)-methyl 3-(sec-butylamino)-2-(5-fluorobenzofuran-2-yl)quinoxaline-6-carboxylate (100 mg, 0.33 mmol) in THF (20 mL) was added NaH (90 mg, 2.24 mmol) and CH$_3$I (159 mg, 1.12 mmol). The resulting solution was stirred overnight at room temperature and concentrated in vacuo. The residue was dissolved in water (10 mL) and adjusted to pH 5 with hydrochloric acid (1N). The resulting solution was extracted with dichloromethane (3×10 mL), dried over anhydrous sodium sulfate and then concentrated in vacuo to give a residue, which was purified by silica gel column chromatography eluting (10% dichloromethane in methanol) to afford (R)-3-(sec-butyl(methyl)amino)-2-(5-fluorobenzofuran-2-yl)quinoxaline-6-carboxylic acid as a yellow solid (25 mg, 23%).

LC/MS (ES, m/z): [M+H]$^+$ 394.1

$^1$H-NMR (300 MHz, CDCl$_3$): δ 8.38 (s, 1H), 8.06 (d, J=8.7 Hz, 1H), 7.92 (d, J=8.4 Hz, 1H), 7.59-7.63 (m, 1H), 7.55 (s, 1H), 7.44-7.48 (m, 1H), 7.15-7.23 (m, 1H), 3.97-4.05 (m, 1H), 2.89 (s, 3H), 1.70-1.80 (m, 1H), 1.48-1.57 (m, 1H), 1.23 (d, J=6.6 Hz, 3H), 0.75-0.81 (t, J=7.5 Hz, 3H)

Example 75

2-(2-Methyl-1H-indol-5-yl)-3-[(2S)-2-methylpyrrolidin-1-yl]quinoxaline-6-carboxylic acid

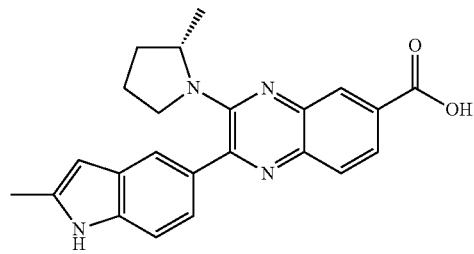 [SMILES: Cc1cc2cc(-c3nc4ccc(C(=O)O)cc4nc3N3CCC[C@@H]3C)ccc2[nH]1]

Step 1. 5-Bromo-2-methyl-1H-indole

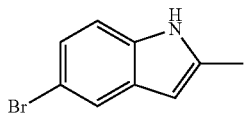

To a solution of 2-methyl-1H-indole (5.0 g, 38.12 mmol) in sulfuric acid (80 mL) was added Ag$_2$SO$_4$ (12.5 g, 40.06 mmol) with ice cooling, and the solution was stirred for 30 min. Then Br$_2$ (6.4 g, 40.05 mmol) was added to the solution dropwise over 30 min. After the solution was stirred for 4 h at room temperature, the reaction was then quenched by the addition of water/ice (300 mL). The reaction mixture was extracted with dichloromethane (3×200 mL) and the organic layers combined, dried over anhydrous sodium sulfate and concentrated in vacuo to afford 5-bromo-2-methyl-1H-indole as a light brown solid (6 g, 75%).

LC/MS (ES, m/z): [M+H]$^+$ 211.0

$^1$H-NMR (300 MHz, CDCl$_3$): δ 11.23 (s, 1H), 7.56 (s, 1H), 7.21 (d, J=8.7 Hz, 1H), 7.07-7.09 (m, 1H), 6.11 (s, 1H), 2.38 (s, 3H)

Step 2. 2-Methyl-6-(tetramethyl-1,3,2-dioxaborolan-2-yl)-1H-indole

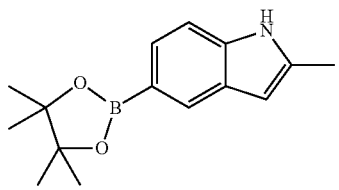

To a solution of 6-bromo-2-methyl-1H-indole (2.0 g, 9.52 mmol) in dry tetrahydrofuran (100 mL) was added sodium hydride (381 mg, 9.53 mmol) with ice-cooling. After stirring for about 30 min, a solution of n-BuLi (15 mL, 2.5 M solution in hexane) was added dropwise with stirring at −78° C. under nitrogen. It was warmed slowly to −40° C. during 45 min and stirred at this temperature for another 30 min. The mixture was cooled again below −78° C. followed by dropwise addition of 4,4,5,5-tetramethyl-2-(propan-2-yloxy)-1,3,2-dioxaborolane (3.54 g, 19.03 mmol). After warming to room temperature, the mixture was quenched with NH$_4$Cl (aq) and extracted with ethyl acetate (3×80 mL). The combined organic layers were dried over anhydrous sodium sulfate, filtered and concentrated under reduced pressure to give the residue, which was purified by silica gel column chromatography (2% ethyl acetate in petroleum ether) to afford 2-methyl-6-(tetramethyl-1,3,2-dioxaborolan-2-yl)-1H-indole (1.2 g, 49%).

$^1$H-NMR (300 MHz, CDCl$_3$): δ 8.06 (s, 1H), 7.91 (s, 1H), 7.58-7.60 (t, J=7.5 Hz, 1H), 7.31 (d, J=8.1 Hz, 1H), 6.24 (s, 1H), 2.46 (s, 3H), 1.39 (s, 12H)

Step 3. Methyl 2-(2-methyl-1H-indol-5-yl)-3-[(2S)-2-methylpyrrolidin-1-yl]quinoxaline-6-carboxylate

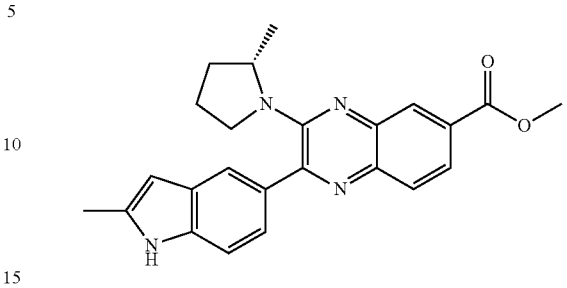

To a solution of 2-methyl-6-(tetramethyl-1,3,2-dioxaborolan-2-yl)-1H-indole (378 mg, 1.47 mmol) in ethylene glycol dimethyl ether (5.5 mL) and water (3 drops) was added methyl 2-chloro-3-[(2S)-2-methylpyrrolidin-1-yl]quinoxaline-6-carboxylate (150 mg, 0.49 mmol), sodium carbonate (156 mg, 1.47 mmol) and Pd(PPh$_3$)$_4$ (29 mg, 0.03 mmol) with stirring for 2 h at 90° C. in an oil bath under an inert atmosphere of nitrogen. The reaction mixture was concentrated under reduced pressure to give the residue, which was purified by silica gel column chromatography (2% ethyl acetate in petroleum ether) to afford methyl 2-(2-methyl-1H-indol-5-yl)-3-[(2S)-2-methylpyrrolidin-1-yl]quinoxaline-6-carboxylate as light yellow solid (140 mg, 71%).

LC/MS (ES, m/z): [M+H]$^+$ 401.0

$^1$H-NMR (300 MHz, CDCl$_3$): δ 8.92 (s, 1H), 8.13 (s, 1H), 8.06 (s, 2H), 7.89 (s, 1H), 7.48 (d, J=8.4 Hz, 1H), 7.39 (d, J=8.40 Hz, 1H), 6.34 (s, 1H), 4.72 (s, 1H), 4.01 (s, 1H), 3.06-3.19 (m, 2H), 2.51 (s, 3H), 2.21-2.25 (m, 1H), 1.73-1.80 (m, 1H), 1.55-1.62 (m, 2H), 1.43-1.49 (m, 3H)

Step 4. 2-(2-Methyl-1H-indol-5-yl)-3-[(2S)-2-methylpyrrolidin-1-yl]quinoxaline-6-carboxylic acid

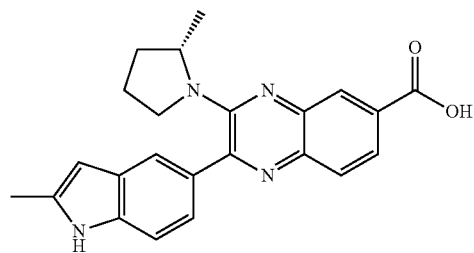 [SMILES: Cc1cc2cc(-c3nc4ccc(C(=O)O)cc4nc3N3CCC[C@@H]3C)ccc2[nH]1]

To a solution of methyl 2-(2-methyl-1H-indol-5-yl)-3-[(2S)-2-methylpyrrolidin-1-yl]quinoxaline-6-carboxylate (140 mg, 0.35 mmol) in methanol (30 mL) and water (2 mL) was added sodium hydroxide (56 mg, 1.40 mmol) with stirring overnight at room temperature. The reaction mixture was concentrated in vacuo, dissolved in water (30 mL) and adjusted to pH 5 with acetic acid. The solids were collected by filtration to afford 2-(2-methyl-1H-indol-5-yl)-3-[(2S)-2-methylpyrrolidin-1-yl]quinoxaline-6-carboxylic acid as a light yellow solid (100 mg, 74%).

LC/MS (ES, m/z): [M+H]$^+$ 387.1

$^1$H-NMR (300 MHz, DMSO): δ 13.05 (s, 1H), 11.14 (s, 1H), 8.23 (s, 1H), 7.81-7.88 (m, 3H), 7.36-7.44 (m, 2H), 6.25 (s, 1H), 4.19-4.21 (m, 1H), 2.96-3.32 (m, 2H), 2.42 (s, 3H), 2.09-2.21 (m, 1H), 1.69-1.72 (m, 1H), 1.51-1.54 (m, 2H), 1.31 (d, J=6.0 Hz, 3H)

Example 76

3-[Methyl(propan-2-yl)amino]-2-(2-methyl-M-indol-5-yl)quinoxaline-6-carboxylic acid

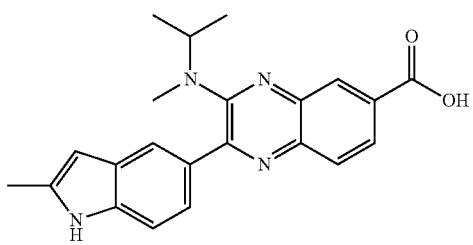 [SMILES: Cc1cc2cc(-c3nc4ccc(C(=O)O)cc4nc3N(C)C(C)C)ccc2[nH]1]

Step 1. Methyl 3-[methyl(propan-2-yl)amino]-2-(2-methyl-1H-indol-5-yl)quinoxaline-6-carboxylate

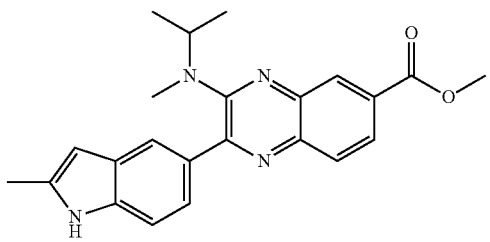

To a solution of methyl 2-chloro-3-[methyl(propan-2-yl)amino]quinoxaline-6-carboxylate (200 mg, 0.68 mmol) in DME (5.0 mL) and water (2 drops) was added 2-methyl-6-(tetramethyl-1,3,2-dioxaborolan-2-yl)-1H-indole (352 mg, 1.37 mmol), Pd(PPh₃)₄ (39 mg, 0.03 mmol), and K₂CO₃ (189 mg, 1.37 mmol) with stirring for 1 hour at 90° C. under atmosphere of nitrogen. The resulting mixture was concentrated in vacuo to give a residue, which was purified by silica gel column chromatography (1% ethyl acetate in petroleum ether) to give methyl 3-[methyl(propan-2-yl)amino]-2-(2-methyl-1H-indol-5-yl)quinoxaline-6-carboxylate as a light yellow solid (180 mg, 68%).

LC/MS (ES, m/z): [M+H]⁺ 389.1

¹H-NMR (300 MHz, DMSO) δ 11.14 (s, 1H), 8.27 (s, 1H), 7.93-7.97 (m, 3H), 7.54-7.57 (m, 1H), 7.37 (d, J=9.0 Hz, 1H), 6.25 (s, 1H), 4.21-4.25 (m, 1H), 3.93 (s, 3H), 2.70 (s, 3H), 2.42 (s, 3H), 1.00-1.02 (d, J=6.6 Hz, 6H)

Step 2. 3-[Methyl(propan-2-yl)amino]-2-(2-methyl-1H-indol-5-yl)quinoxaline-6-carboxylic acid

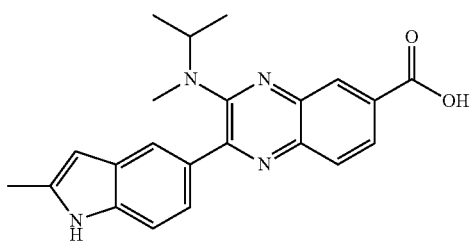 [SMILES: Cc1cc2cc(-c3nc4ccc(C(=O)O)cc4nc3N(C)C(C)C)ccc2[nH]1]

To a solution of methyl 3-[methyl(propan-2-yl)amino]-2-(2-methyl-1H-indol-5-yl)quinoxaline-6-carboxylate (120 mg, 0.31 mmol) in methanol (20 mL) and water (1 mL) was added sodium hydroxide (66 mg, 1.65 mmol) with stirring 1 h at reflux. The resulting mixture was concentrated in vacuo and dissolved in water (30 ml), adjusted to pH 7 with HCl (3N), and collected by filtration to give 3-[methyl(propan-2-yl)amino]-2-(2-methyl-M-indol-5-yl)quinoxaline-6-carboxylic acid as a light yellow solid (50.1 mg, 43%).

LC/MS (ES, m/z): [M+H]⁺ 375.1

¹H-NMR (300 MHz, DMSO) δ 13.00 (s, 1H), 11.13 (s, 1H), 8.25 (s, 1H), 7.91-7.97 (m, 3H), 7.54-7.57 (m, 1H), 7.37 (d, J=8.4 Hz, 1H), 6.25 (s, 1H), 4.21-4.31 (m, 1H), 2.70 (s, 3H), 2.50 (s, 3H), 1.00 (d, J=6.6 Hz, 6H)

Example 77

3-[Methyl(propan-2-yl)amino]-2-(5-phenylfuran-2-yl)quinoxaline-6-carboxylic acid

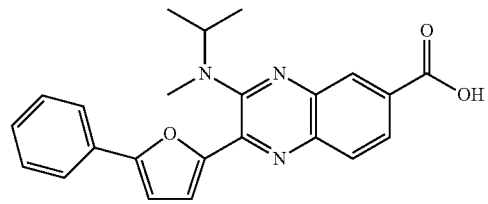 [SMILES: CC(C)N(C)c1nc2cc(C(=O)O)ccc2nc1-c1ccc(-c2ccccc2)o1]

Step 1. 2-Phenylfuran

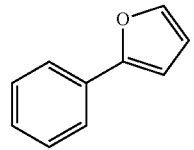 [SMILES: c1ccc(-c2ccco2)cc1]

To a solution of (furan-2-yl)boronic acid (3.0 g, 26.81 mmol) in dioxane (50.0 mL) and water (1.0 mL) was added bromobenzene (2.10 g, 13.38 mmol), K₃PO₄ (9.3 g, 43.81 mmol) and Pd(PPh₃)₄ (767 mg, 0.66 mmol) with stirring for 3 h at 95° C. in an oil bath under an inert atmosphere of nitrogen. The reaction mixture was concentrated under reduced pressure to give the residue, which was purified by silica gel column chromatography (1% ethyl acetate in petroleum ether) to afford 2-phenylfuran as colorless oil (1.20 g, 62%).

¹H-NMR (300 MHz, CDCl₃): δ 7.69-7.72 (m, 2H), 7.50 (d, J=0.6 Hz, 1H), 7.38-7.49 (m, 2H), 7.26-7.31 (m, 2H), 6.68-6.69 (m, 1H), 6.47-6.49 (m, 1H)

Step 2. 4,4,5,5-Tetramethyl-2-(5-phenylfuran-2-yl)-1,3,2-dioxaborolane

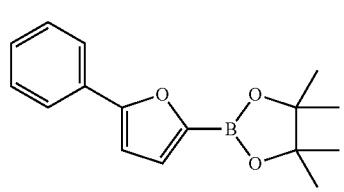 [SMILES: CC1(C)OB(c2ccc(-c3ccccc3)o2)OC1(C)C]

To a solution of 2-phenylfuran (1.20 g, 8.32 mmol) in dry tetrahydrofuran (100 mL) was added a solution of n-BuLi (4.9 mL, 2.5 M solution in hexane) dropwise with stirring at −78° C. under nitrogen. The resulting solution was warmed slowly to −40° C. during 45 min and stirred at this temperature for another 30 min. The mixture was cooled again below −78° C. followed by dropwise addition of 4,4,5,5-tetramethyl-2-(propan-2-yloxy)-1,3,2-dioxaborolane (3.10 g, 16.66 mmol). After warming to room temperature, the mixture was quenched with NH$_4$Cl (aq) and extracted with ethyl acetate (3×80 mL). The combined organic layers were dried over anhydrous sodium sulfate, filtered and concentrated under reduced pressure to give the residue, which was purified by silica gel column chromatography (2% ethyl acetate in petroleum ether) to afford 4,4,5,5-tetramethyl-2-(5-phenylfuran-2-yl)-1,3,2-dioxaborolane (560 mg, 25%).

$^1$H-NMR (300 MHz, CDCl$_3$): δ 7.79-7.83 (m, 2H), 7.37-7.43 (m, 2H), 7.30-7.33 (m, 1H), 7.16 (d, J=3.6 Hz, 1H), 6.71 (d, J=3.3 Hz, 1H), 1.34-1.42 (m, 12H)

Step 3. Methyl 3-[methyl(propan-2-yl)amino]-2-(5-phenylfuran-2-yl)quinoxaline-6-carboxylate

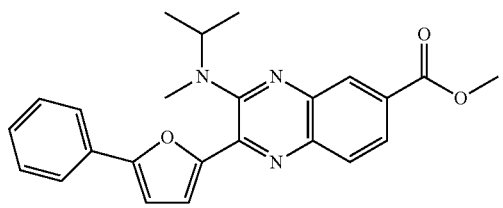 [SMILES: COC(=O)c1ccc2nc(-c3ccc(-c4ccccc4)o3)c(N(C)C(C)C)nc2c1]

To a solution of 4,4,5,5-tetramethyl-2-(5-phenylfuran-2-yl)-1,3,2-dioxaborolane (553 mg, 2.05 mmol) in dioxane (5.5 mL) and water (3 drops) was methyl 2-chloro-3-[methyl(propan-2-yl)amino]quinoxaline-6-carboxylate (200 mg, 0.68 mmol), K$_3$PO$_4$ (430 mg, 2.03 mmol) and Pd(PPh$_3$)$_4$ (39.3 mg, 0.03 mmol) with stirring for 1 h at 95° C. in an oil bath under an inert atmosphere of nitrogen. The reaction mixture was concentrated under reduced pressure to give the residue, which was purified by silica gel column chromatography (2% ethyl acetate in petroleum ether) to afford methyl 3-[methyl (propan-2-yl)amino]-2-(5-phenylfuran-2-yl)quinoxaline-6-carboxylate as light yellow solid (150 mg, 55%).

LC/MS (ES, m/z): [M+H]$^+$ 401.0

$^1$H-NMR (300 MHz, CDCl$_3$): δ 8.51 (s, 1H), 8.02-8.09 (m, 2H), 7.80-7.99 (m, 2H), 7.48-7.56 (m, 2H), 7.42-7.46 (m, 2H), 6.87 (d, J=3.6 Hz, 1H), 4.41-4.47 (m, 1H), 4.00 (s, 1H), 2.88 (s, 3H), 1.26 (d, J=6.6 Hz, 6H)

Step 4. 3-[Methyl(propan-2-yl)amino]-2-(5-phenylfuran-2-yl)quinoxaline-6-carboxylic acid

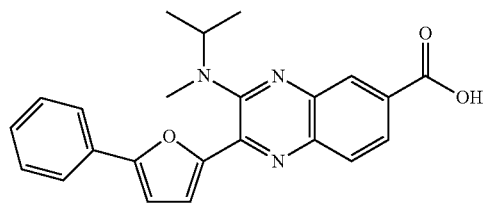 [SMILES: CC(C)N(C)c1nc2cc(C(=O)O)ccc2nc1-c1ccc(-c2ccccc2)o1]

To a solution of methyl 3-[methyl(propan-2-yl)amino]-2-(5-phenylfuran-2-yl)quinoxaline-6-carboxylate (150 mg, 0.37 mmol) in methanol (30 mL) and water (2 mL) was added sodium hydroxide (59.8 mg, 1.50 mmol) with stirring overnight at room temperature. The reaction mixture was concentrated in vacuo, dissolved in water (30 mL) and adjusted to pH 5 with HCl (3N). The solids were collected by filtration to afford 3-[methyl(propan-2-yl)amino]-2-(5-phenylfuran-2-yl)quinoxaline-6-carboxylic acid as a light yellow solid (100 mg, 69%).

LC/MS (ES, m/z): [M+H]$^+$ 388.0

$^1$H-NMR (300 MHz, DMSO): δ 8.24 (d, J=1.5 Hz, 1H), 7.87-8.01 (m, 4H), 7.51-7.62 (m, 2H), 7.36-7.48 (m, 2H), 7.25 (d, J=3.3 Hz, 1H), 4.25-4.33 (m, 1H), 2.80 (s, 3H), 1.17 (d, J=6.6 Hz, 6H)

Example 78

2-(Furan-3-yl)-3-[(2S)-2-methylpyrrolidin-1-yl]quinoxaline-6-carboxylic acid

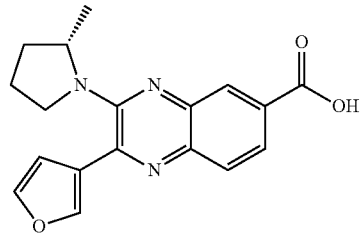 [SMILES: C[C@H]1CCCN1c1nc2cc(C(=O)O)ccc2nc1-c1ccoc1]

Step 1. Methyl 2-(furan-3-yl)-3-[(2S)-2-methylpyrrolidin-1-yl]quinoxaline-6-carboxylate

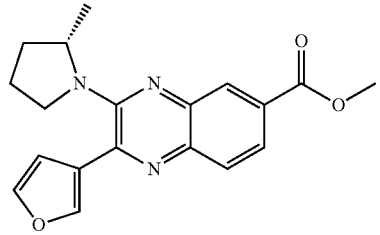 [SMILES: COC(=O)c1ccc2nc(-c3ccoc3)c(N3CCC[C@@H]3C)nc2c1]

To a solution of methyl 3-[(2S)-2-methylpyrrolidin-1-yl]-2-[(trifluoromethane)sulfonyloxy]quinoxaline-6-carboxylate (200 mg, 0.48 mmol) in 1,4-dioxane (4.0 mL) and water (3 drops) was added (furan-3-yl)boronic acid (116 mg, 1.04 mmol), K$_3$PO$_4$ (304 mg, 1.43 mmol) and Pd(PPh$_3$)$_4$ (28 mg, 0.02 mmol) with stirring for 1 h at 90° C. under an inert atmosphere of nitrogen in an oil bath. The reaction mixture was concentrated in vacuo to give the residue, which was purified by silica gel column chromatography (2% ethyl acetate in petroleum ether) to afford methyl 2-(furan-3-yl)-3-[(2S)-2-methylpyrrolidin-1-yl]quinoxaline-6-carboxylate as a light yellow solid (111 mg, 69%).

LC/MS (ES, m/z): [M+H]$^+$ 337.0

$^1$H-NMR (300 MHz, CDCl$_3$) δ 8.51 (d, J=1.8 Hz, 1H), 7.93-8.06 (m, 3H), 7.54-7.55 (t, J=0.9 Hz, 1H), 7.00 (d, J=0.6 Hz, 1H), 4.44-4.51 (m, 1H), 4.00 (s, 3H), 3.51-3.60 (m, 1H), 3.02-3.08 (m, 1H), 2.20-2.26 (m, 1H), 1.90-1.95 (m, 1H), 1.60-1.66 (m, 2H), 1.24-1.29 (m, 3H)

Step 2. 2-(Furan-3-yl)-3-[(2S)-2-methylpyrrolidin-1-yl]quinoxaline-6-carboxylic acid

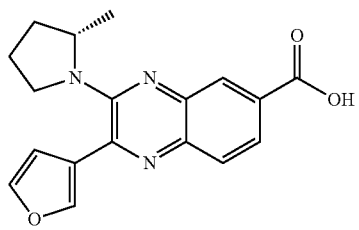 [SMILES: C[C@H]1CCCN1c1nc2cc(C(=O)O)ccc2nc1-c1ccoc1]

To a solution of methyl 2-(furan-3-yl)-3-[(2S)-2-methylpyrrolidin-1-yl]quinoxaline-6-carboxylate (111 mg, 0.33 mmol) in methanol (20 mL) and water (1.0 mL) was added sodium hydroxide (52.9 mg, 1.32 mmol) with stirring overnight at room temperature. The reaction mixture was concentrated in vacuo, dissolved in water (10 mL), adjusted pH to 4 with HCl (3N) to give the precipitate, which was collected by filtration to afford 2-(furan-3-yl)-3-[(2S)-2-methylpyrrolidin-1-yl]quinoxaline-6-carboxylic acid as a light yellow solid (72 mg, 68%).

LC/MS (ES, m/z): [M+H]$^+$ 323.0

$^1$H-NMR (300 MHz, DMSO) δ 8.23 (s, 2H), 7.84-7.94 (m, 3H), 7.01-7.02 (m, 1H), 4.31-4.38 (m, 1H), 3.47-3.50 (m, 2H), 2.98-3.04 (m, 1H), 2.10-2.17 (m, 1H), 1.80-1.90 (m, 1H), 1.58-1.64 (m, 2H), 1.29 (d, J=6.0 Hz, 3H)

Example 79

3-(Isopropyl(methyl)amino)-2-(4-phenylfuran-2-yl)quinoxaline-6-carboxylic acid

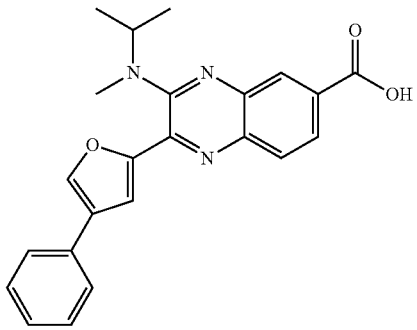 [SMILES: CC(C)N(C)c1nc2cc(C(=O)O)ccc2nc1-c1cc(-c2ccccc2)co1]

Step 1. 1-Phenyl-4-(tetrahydro-2H-pyran-2-yloxy)but-2-yn-1-ol

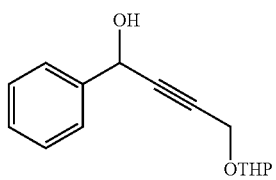

To a solution of 2-(prop-2-ynyloxy)-tetrahydro-2H-pyran (10.0 g, 71.4 mmol) in THF (40 mL) was added n-BuLi (2.5M, 31.4 mL, 78.6 mmol) at −78° C. The reaction mixture was kept for 1 h at −78° C. and then benzaldehyde (8.3 g, 78.6 mmol) was added at −78° C. The reaction mixture was stirred for 2 h and then slowly warmed to −30° C. before being poured into NaHCO$_3$ (aq., 500 mL), extracted with ethyl acetate (3×200 mL), dried over anhydrous sodium sulfate and then concentrated in vacuo to afford 1-phenyl-4-(tetrahydro-2H-pyran-2-yloxy)but-2-yn-1-ol as a colorless oil (17.0 g, crude).

$^1$H-NMR (300 MHz, CDCl$_3$) δ 7.54-7.57 (m, 2H), 7.40-7.43 (m, 3H), 5.43 (s, 1H), 4.83-4.85 (m, 1H), 4.36-4.38 (m, 2H), 3.80-3.90 (m, 1H), 3.45-3.56 (m, 1H), 1.54-1.84 (m, 6H)

Step 2. 1-Phenyl-4-(tetrahydro-2H-pyran-2-yloxy)but-2-yn-1-one

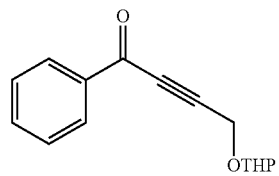

To a solution of 1-phenyl-4-(tetrahydro-2H-pyran-2-yloxy)but-2-yn-1-ol (3.0 g, 12.2 mmol) in DCM (50 mL) was added DMP (10.0 g, 24.4 mmol). The resulting solution was stirred for 30 min at room temperature and then the reaction mixture was poured into NaHCO$_3$/NaS$_2$O$_3$ solution and stirred for overnight, extracted with DCM (3×150 mL), dried over anhydrous sodium sulfate and then concentrated in vacuo to give a residue. The residue was purified by silica gel column chromatography (3% ethyl acetate in petroleum ether) to afford 1-phenyl-4-(tetrahydro-2H-pyran-2-yloxy)but-2-yn-1-one as a light yellow oil (2.4 g).

$^1$H-NMR (300 MHz, CDCl$_3$): δ 8.14-8.17 (m, 2H), 7.61-7.66 (m, 1H), 7.48-7.53 (m, 1H), 4.90-4.92 (m, 1H), 4.57 (s, 2H), 3.86-3.92 (m, 1H), 3.58-3.61 (m, 1H), 1.55-1.86 (m, 6H)

Step 3. 4-Hydroxy-1-phenylbut-2-yn-1-one

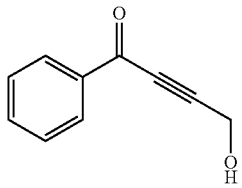 [SMILES: O=C(C#CCO)c1ccccc1]

To a solution of (1-phenyl-4-(tetrahydro-2H-pyran-2-yloxy)but-2-yn-1-one (3.0 g, 12.3 mmol) in EtOH (20 mL) was added pyridinium p-toluenesulfonate (0.62 g, 2.5 mmol). The resulting solution was stirred for 1 h at 50° C. and then the reaction mixture was poured into water (150 mL), extracted with Et$_2$O (3×50 mL), dried over anhydrous sodium sulfate and then concentrated in vacuo to afford 4-hydroxy-1-phenylbut-2-yn-1-one as a dark red oil (3.2 g, crude).

Step 4. 4-Bromo-2-phenylfuran

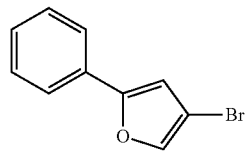 [SMILES: Brc1coc(-c2ccccc2)c1]

To a solution of 4-hydroxy-1-phenylbut-2-yn-1-one (3.2 g, crude) in toluene (60 mL) was added HBr (40%, 15 mL). The resulting solution was stirred for 40 min at 50° C. and then the reaction mixture was poured into water (300 mL), extracted with Et₂O (4×100 mL), dried over anhydrous sodium sulfate and then concentrated in vacuo to give a residue, which was purified by silica gel column chromatography (petroleum ether) to afford 4-bromo-2-phenylfuran as a yellow solid (1.3 g, 50%).

¹H-NMR (300 MHz, CDCl₃): δ 7.63-7.66 (m, 2H), 7.48 (s, 1H), 7.41-7.46 (m, 2H), 7.28-7.34 (m, 1H), 6.70 (s, 1H)

Step 5. 4,4,5,5-Tetramethyl-2-(5-phenylfuran-3-yl)-1,3,2-dioxaborolane

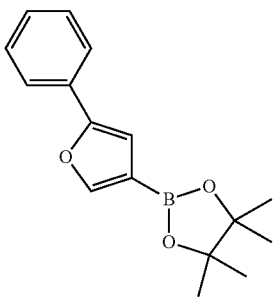 [SMILES: CC1(C)OB(c2coc(-c3ccccc3)c2)OC1(C)C]

To a solution of 4-bromo-2-phenylfuran (1.3 g, 5.8 mmol) in THF (15 mL) was added n-BuLi (2.5M, 2.8 mL, 7.0 mmol) at −78° C. The reaction mixture was kept at −55° C. for 15 min and then 2-isopropoxy-4,4,5,5-tetramethyl-1,3,2-dioxaborolane (1.3 g, 7.0 mmol) was added at −78° C. The reaction mixture was stirred for 1.5 h and then poured into water/ice solution, extracted with petroleum ether (3×50 mL), dried over anhydrous sodium sulfate and then concentrated in vacuo to give a residue, which was purified by silica gel column chromatography (1% ethyl acetate in petroleum ether) to afford 4,4,5,5-tetramethyl-2-(5-phenylfuran-3-yl)-1,3,2-dioxaborolane as a red oil (300 mg, 19%).

¹H-NMR (300 MHz, CDCl₃): δ 7.81 (s, 1H), 7.67-7.70 (m, 2H), 7.37-7.42 (t, J=7.5 Hz, 2H), 7.24-7.29 (m, 1H), 6.87 (s, 1H), 1.36 (s, 12H)

Step 6. Methyl 3-(isopropyl(methyl)amino)-2-(4-phenylfuran-2-yl)quinoxaline-6-carboxylate

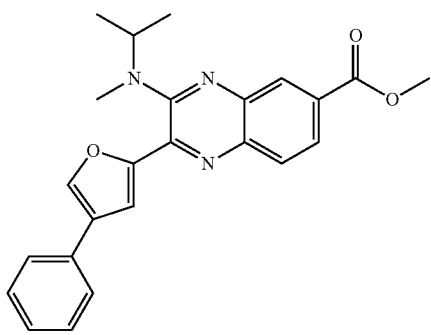 [SMILES: COC(=O)c1ccc2nc(-c3cc(-c4ccccc4)co3)c(N(C)C(C)C)nc2c1]

To a solution of methyl 2-chloro-3-(isopropyl(methyl)amino)quinoxaline-6-carboxylate (150 mg, 0.51 mmol) in dioxane (5 mL) was added 4,4,5,5-tetramethyl-2-(5-phenyl-furan-3-yl)-1,3,2-dioxaborolane (276 mg, 1.02 mmol), Na₂CO₃ (54 mg, 0.51 mmol), Pd(PPh₃)₄ (30 mg, 0.03 mmol). The resulting solution was stirred for 1 h at 90° C. and then concentrated in vacuo to give a residue, which was purified by silica gel column chromatography (3.3% ethyl acetate in petroleum ether) to afford methyl 3-(isopropyl(methyl)amino)-2-(4-phenylfuran-2-yl)quinoxaline-6-carboxylate as a red solid (140 mg, 68%).

LC/MS (ES, m/z): [M+H]⁺ 402.0

¹H-NMR (300 MHz, CDCl₃): δ 8.55 (d, J=0.9 Hz, 1H), 8.30 (s, 1H), 8.10-8.13 (m, 1H), 7.98-8.00 (d, J=8.4 Hz, 1H), 7.77-7.80 (m, 2H), 7.40-7.48 (m, 4H), 4.27-4.31 (m, 1H), 4.00 (s, 3H), 2.89 (s, 3H), 1.20-1.22 (d, J=6.6 Hz, 6H)

Step 7. 3-(Isopropyl(methyl)amino)-2-(4-phenylfuran-2-yl)quinoxaline-6-carboxylic acid

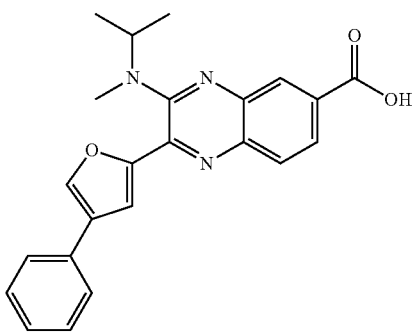 [SMILES: CC(C)N(C)c1nc2cc(C(=O)O)ccc2nc1-c1cc(-c2ccccc2)co1]

To a solution of methyl 3-(isopropyl(methyl)amino)-2-(4-phenylfuran-2-yl)quinoxaline-6-carboxylate (70 mg, 0.17 mmol) in MeOH (20 mL) was added sodium hydroxide (28 mg, 0.70 mmol) and water (2 mL). The resulting solution was stirred overnight at room temperature and concentrated in vacuo. The residue was dissolved in water (3 mL) and adjusted to pH 6 with HCl (1N). The solids were collected by filtration to afford 3-(isopropyl(methyl)amino)-2-(4-phenyl-furan-2-yl)quinoxaline-6-carboxylic acid (43 mg, 64%).

LC/MS (ES, m/z): [M+H]⁺ 388.1

¹H-NMR (300 MHz, DMSO): δ 8.48 (s, 1H), 8.27 (d, J=1.5 Hz, 2H), 7.99-8.03 (m, 1H), 7.91-7.94 (d, J=8.7 Hz, 1H), 7.82-7.85 (d, J=7.5 Hz, 2H), 7.56 (s, 1H), 7.46-7.51 (m, 2H), 7.34-7.39 (m, 1H), 4.19-4.23 (m, 1H), 2.81 (s, 3H), 1.14-1.16 (d, J=6.6 Hz, 6H)

Example 80

3-[(2S)-2-methylpyrrolidin-1-yl]-2-(1H-pyrrol-3-yl)quinoxaline-6-carboxylic acid

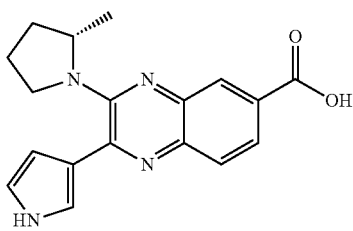 [SMILES: C[C@H]1CCCN1c1nc2cc(C(=O)O)ccc2nc1-c1cc[nH]c1]

Step 1. Methyl 3-[(2S)-2-methylpyrrolidin-1-yl]-2-[1-[tris(propan-2-yl)silyl]-1H-pyrrol-3-yl]quinoxaline-6-carboxylate

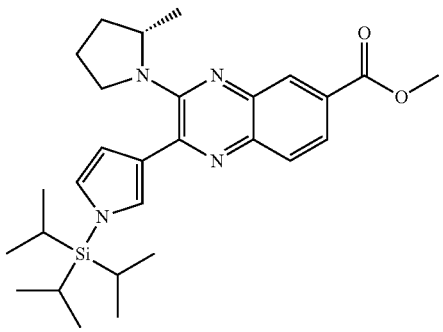 [SMILES: COC(=O)c1ccc2nc(-c3ccn([Si](C(C)C)(C(C)C)C(C)C)c3)c(N3CCC[C@@H]3C)nc2c1]

To a solution of methyl 2-chloro-3-[(2S)-2-methylpyrrolidin-1-yl]quinoxaline-6-carboxylate (180 mg, 0.59 mmol) in ethylene glycol dimethyl ether (6 ml) and water (2 ml) was added 3-(tetramethyl-1,3,2-dioxaborolan-2-yl)-1-[tris(propan-2-yl)silyl]-1H-pyrrole (618 mg, 1.77 mmol), sodium carbonate (188 mg, 1.77 mmol) and Pd(PPh$_3$)$_4$ (34 mg, 0.03 mmol) with stirring for 1 h at 95° C. in an oil bath maintained under an inert atmosphere of nitrogen. The reaction mixture was concentrated under vacuum to give a residue, which was purified via silica gel chromatography (2% ethyl acetate in petroleum ether) to afford methyl 3-[(2S)-2-methylpyrrolidin-1-yl]-2-[1-[tris(propan-2-yl)silyl]-1H-pyrrol-3-yl]quinoxaline-6-carboxylate as a light yellow solid (150 mg, 52%).

LC/MS (ES, m/z): [M+H]$^+$ 493.0

$^1$H-NMR (300 MHz, CDCl$_3$): δ 8.47 (d, J=1.2 Hz, 1H), 7.91-8.01 (m, 2H), 7.43 (s, 1H), 6.92 (s, 1H), 6.84-6.86 (m, 1H), 4.42-4.45 (m, 1H), 3.98 (s, 3H), 3.53-3.60 (m, 1H), 3.06-3.09 (m, 1H), 2.20-2.22 (m, 1H), 1.85-1.87 (m, 1H), 1.64-1.85 (m, 2H), 1.50-1.60 (m, 4H), 1.25-1.31 (m, 3H), 1.07-1.18 (m, 18H)

Step 2. Methyl 3-[(2S)-2-methylpyrrolidin-1-yl]-2-(1H-pyrrol-3-yl)quinoxaline-6-carboxylate

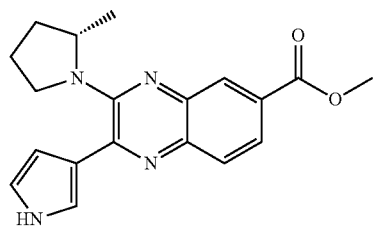 [SMILES: COC(=O)c1ccc2nc(-c3cc[nH]c3)c(N3CCC[C@@H]3C)nc2c1]

To a solution of methyl 3-[(2S)-2-methylpyrrolidin-1-yl]-2-[1-[tris(propan-2-yl)silyl]-1H-pyrrol-3-yl]quinoxaline-6-carboxylate (150 mg, 0.30 mmol) in tetrahydrofuran (30 ml) was added Tetra-n-butylammonium fluoride (TBAF) (80 mg, 0.31 mmol) with stirring for 10 min at room temperature. The reaction was then quenched with water (10 ml). The resulting solution was extracted with dichloromethane (3×10 ml) and the organic layers combined and dried over anhydrous magnesium sulfate, concentrated under vacuum to afford methyl 3-[(2S)-2-methylpyrrolidin-1-yl]-2-(1H-pyrrol-3-yl)quinoxaline-6-carboxylate as a light yellow solid (100 mg, 98%).

LC/MS (ES, m/z): [M+H]$^+$ 337.0

$^1$H-NMR (300 MHz, CDCl$_3$): δ 8.71 (s, 1H), 8.48 (d, J=1.5 Hz, 1H), 7.92-8.02 (m, 2H), 7.50 (s, 1H), 6.81-6.88 (m, 2H), 4.45-4.48 (m, 1H), 3.98 (s, 3H), 3.56-3.58 (m, 1H), 3.08-3.10 (m, 1H), 2.15-2.25 (m, 1H), 1.82-1.93 (m, 1H), 160-1.69 (m, 2H), 1.33 (d, J=6.0 Hz, 3H)

Step 3. 3-[(2S)-2-Methylpyrrolidin-1-yl]-2-(1H-pyrrol-3-yl)quinoxaline-6-carboxylic acid

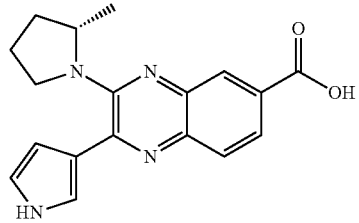 [SMILES: C[C@H]1CCCN1c1nc2cc(C(=O)O)ccc2nc1-c1cc[nH]c1]

To a solution of methyl 3-[(2S)-2-methylpyrrolidin-1-yl]-2-(1H-pyrrol-3-yl)quinoxaline-6-carboxylate (100 mg, 0.30 mmol) in methanol (30 ml) and water (2.0 ml) was added sodium hydroxide (48 mg, 1.20 mmol) with stirring overnight at room temperature. The reaction mixture was concentrated under vacuum, dissolved in water (30 mL1) and adjusted to pH 4 with HCl (3 N). The solids were collected by filtration to afford 3-[(2S)-2-methylpyrrolidin-1-yl]-2-(1H-pyrrol-3-yl)quinoxaline-6-carboxylic acid as a light yellow solid (70 mg, 73%).

LC/MS (ES, m/z): [M+H]$^+$ 323.0

$^1$H-NMR (300 MHz, CDCl$_3$): δ 11.25 (s, 1H), 8.18 (s, 1H), 7.79-7.88 (m, 2H), 7.41-7.42 (t, J=1.2 Hz, 1H), 6.87-6.89 (m, 1H), 6.65 (d, J=1.5 Hz, 1H), 4.31-4.38 (m, 1H), 3.48-3.54 (m, 1H), 2.95-3.00 (m, 1H), 2.11-2.19 (m, 1H), 1.81-1.85 (m, 1H), 1.56-1.62 (m, 2H), 1.27 (d, J=6.0 Hz, 3H)

Example 81

3-[Methyl(propan-2-yl)amino]-2-(1H-pyrrol-3-yl)quinoxaline-6-carboxylic acid

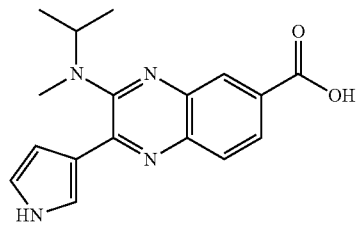 [SMILES: CC(C)N(C)c1nc2cc(C(=O)O)ccc2nc1-c1cc[nH]c1]

Step 1. Methyl 3-[methyl(propan-2-yl)amino]-2-[1-[tris(propan-2-yl)silyl]-1H-pyrrol-3-yl]quinoxaline-6-carboxylate

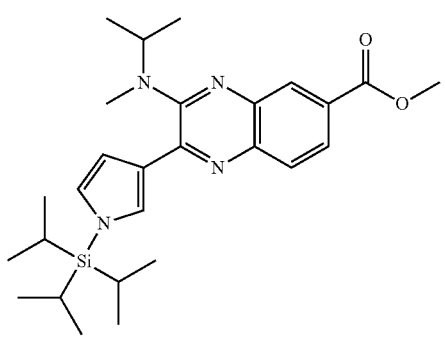 [SMILES: COC(=O)c1ccc2nc(-c3ccn([Si](C(C)C)(C(C)C)C(C)C)c3)c(N(C)C(C)C)nc2c1]

To a solution of methyl 2-chloro-3-[methyl(propan-2-yl) amino]quinoxaline-6-carboxylate (150 mg, 0.51 mmol) in 1,4-dioxane (5.0 mL) and water (3 drops) was added 3-(tetramethyl-1,3,2-dioxaborolan-2-yl)-1-[tris(propan-2-yl)silyl]-1H-pyrrole (356 mg, 1.02 mmol), Pd(PPh$_3$)$_4$ (29.4 mg, 0.03 mmol), and sodium carbonate (108.1 mg, 1.01 mmol) with stirring for 1 hour at 90° C. under an atmosphere of nitrogen. The resulting mixture was concentrated under vacuum to give a residue, which was purified by silica gel chromatography (1% ethyl acetate in petroleum ether) to give methyl 3-[methyl(propan-2-yl)amino]-2-[1-[tris(propan-2-yl)silyl]-1H-pyrrol-3-yl]quinoxaline-6-carboxylate as a yellow solid (130 mg, 53%).

LC/MS (ES, m/z): [M+H]$^+$ 481.0

Step 2. Methyl 3-[methyl(propan-2-yl)amino]-2-(1H-pyrrol-3-yl)quinoxaline-6-carboxylate

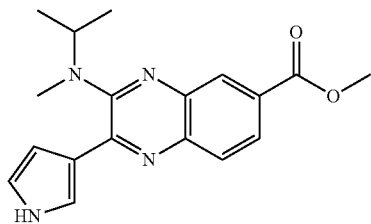 [SMILES: COC(=O)c1ccc2nc(-c3cc[nH]c3)c(N(C)C(C)C)nc2c1]

To a solution of 3-[methyl(propan-2-yl)amino]-2-[1-[tris (propan-2-yl)silyl]-1H-pyrrol-3-yl]quinoxaline-6-carboxylate (130 mg, 0.27 mmol) in THF (10 mL) was added TBAF (71 mg, 0.27 mmol) with stirring for 10 min at room temperature. The resulting mixture was concentrated under vacuum, diluted with water (30 mL), and extracted with ethyl acetate (2×30 mL). The organic layers were combined, dried over anhydrous sodium sulfate, and the solids were collected via filtration. The resulting mixture was concentrated under vacuum to give methyl 3-[methyl(propan-2-yl)amino]-2-(1H-pyrrol-3-yl)quinoxaline-6-carboxylate (70 mg, 80%) as yellow oil.

LC/MS (ES, m/z): [M+H]$^+$ 325.0

$^1$H-NMR (300 MHz, DMSO) δ 11.26 (s, 1H), 8.24 (d, J=1.8 Hz, 1H), 7.92-8.23 (m, 1H), 7.83 (d, J=8.4 Hz, 1H), 7.61-7.62 (t, J=0.9 Hz, 1H), 6.87-6.90 (m, 1H), 6.77-6.78 (t, J=1.5 Hz, 1H), 4.25-4.34 (m, 1H), 3.92 (s, 1H), 2.73-2.78 (s, 3H), 1.09-1.12 (m, 6H)

Step 3. 3-[Methyl(propan-2-yl)amino]-2-(1H-pyrrol-3-yl)quinoxaline-6-carboxylic acid

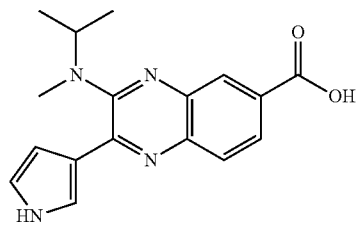 [SMILES: CC(C)N(C)c1nc2cc(C(=O)O)ccc2nc1-c1cc[nH]c1]

To a solution of methyl 3-[methyl(propan-2-yl)amino]-2-(1H-pyrrol-3-yl)quinoxaline-6-carboxylate (70 mg, 0.22 mmol) in methanol (40 mL) was added NaOH (34.6 mg, 0.87 mmol) with stirring for 2 h at room temperature. The resulting mixture was concentrated under vacuum and extracted with dichloromethane (20 mL). The aqueous layers were combined, adjusted to pH 6 with HCl (3 N), and the product was collected by filtration to give 3-[methyl(propan-2-yl)amino]-2-(1H-pyrrol-3-yl)quinoxaline-6-carboxylic acid as a yellow solid (18.6 mg, 28%).

LC/MS (ES, m/z): [M+H]$^+$ 311.0

$^1$H-NMR (300 MHz, DMSO) δ 11.26 (s, 1H), 8.21 (d, J=1.5 Hz, 1H), 7.91-7.95 (m, 1H), 7.81 (d, J=8.7 Hz, 1H), 7.62 (s, 1H), 6.88 (t, J=2.4 Hz, 1H), 6.77 (d, J=1.5 Hz, 1H), 4.25-4.30 (t, J=6.6 Hz, 1H), 2.78 (s, 3H), 1.10 (d, J=6.6 Hz, 6H)

Example 82

2-(1-Benzofuran-3-yl)-3-[(2S)-2-methylpyrrolidin-1-yl]quinoxaline-6-carboxylic acid

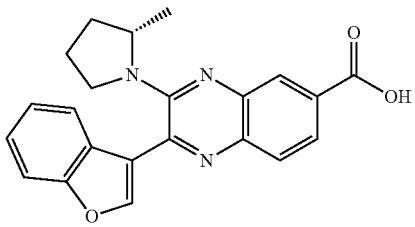 [SMILES: C[C@H]1CCCN1c1nc2cc(C(=O)O)ccc2nc1-c1coc2ccccc12]

Step 1. Methyl 2-(1-benzofuran-3-yl)-3-[(2S)-2-methylpyrrolidin-1-yl]quinoxaline-6-carboxylate

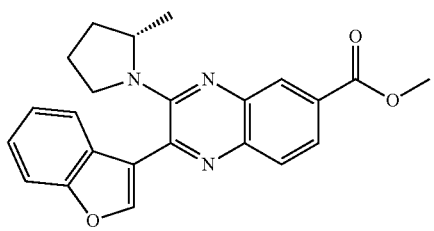 [SMILES: COC(=O)c1ccc2nc(-c3coc4ccccc34)c(N3CCC[C@@H]3C)nc2c1]

To a solution of 3-[(2S)-2-methylpyrrolidin-1-yl]-2-[(trifluoromethane)sulfonyloxy]quinoxaline-6-carboxylate (150 mg, 0.36 mmol) in dioxane (5.0 mL) and water (3 drops) was added 2-(1-benzofuran-3-yl)-4,4,5,5-tetramethyl-1,3,2-dioxaborolane (174.7 mg, 0.72 mmol), Pd(PPh$_3$)$_4$ (20.7 mg, 0.02 mmol), and K$_3$PO$_4$ (151 mg, 0.71 mmol) with stirring for 1 hour at 90° C. under an atmosphere of nitrogen. The resulting mixture was concentrated under vacuum to give a residue, which was purified via silica gel chromatography (1% ethyl acetate in petroleum ether) to give methyl 2-(1-benzofuran-3-yl)-3-[(2S)-2-methylpyrrolidin-1-yl]quinoxaline-6-carboxylate as a yellow solid (97 mg, 70%).

LC/MS (ES, m/z): [M+H]$^+$ 388.0

$^1$H-NMR (300 MHz, CDCL3) δ 8.54 (d, J=1.5 Hz, 1H), 8.14 (d, J=2.4 Hz, 1H), 8.12 (d, J=1.8 Hz, 1H), 7.98-8.07 (m, 2H), 7.59 (d, J=1.8 Hz, 1H), 7.35-7.58 (m, 2H), 4.43-4.50 (m, 1H), 4.01 (s, 3H), 3.33-3.38 (m, 1H), 3.07-3.13 (m, 1H), 2.16-2.21 (m, 1H), 1.80-1.85 (m, 1H), 1.58-1.71 (m, 2H), 1.40 (d, J=6.0 Hz, 3H)

Step 2. 2-(1-Benzofuran-3-yl)-3-[(2S)-2-methylpyrrolidin-1-yl]quinoxaline-6-carboxylic acid

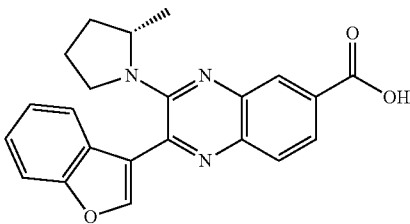 [SMILES: C[C@H]1CCCN1c1nc2cc(C(=O)O)ccc2nc1-c1coc2ccccc12]

To a solution of methyl 2-(1-benzofuran-3-yl)-3-[(2S)-2-methylpyrrolidin-1-yl]quinoxaline-6-carboxylate (80 mg, 0.21 mmol) in methanol (40 mL) and water (1 mL) was added sodium hydroxide (33 mg, 0.83 mmol) with stirring overnight at room temperature. The resulting mixture was concentrated under vacuum, dissolved in water (50 ml) adjusted to pH 6 with HCl (3N), and collected by filtration to give 2-(1-benzofuran-3-yl)-3-[(2S)-2-methylpyrrolidin-1-yl]quinoxaline-6-carboxylic acid as a yellow solid (60.1 mg, 78%).

LC/MS (ES, m/z): [M+H]+ 374.0
$^1$H-NMR (300 MHz, DMSO) δ 8.52 (s, 1H), 8.27 (s, 1H), 8.08-8.11 (t, J=1.5 Hz, 1H), 7.92-7.98 (t, J=8.4 Hz, 1H), 7.72 (d, J=7.2 Hz, 1H), 7.38-7.47 (m, 2H), 4.30-4.37 (m, 1H), 3.24-3.32 (m, 1H), 3.03-3.09 (m, 1H), 2.04-2.14 (m, 1H), 1.78-1.85 (m, 1H), 1.53-1.63 (m, 2H), 1.33 (d, J=6.0 Hz, 3H)

Example 83

3-[Methyl(propan-2-yl)amino]-2-(3-phenylfuran-2-yl)quinoxaline-6-carboxylic acid

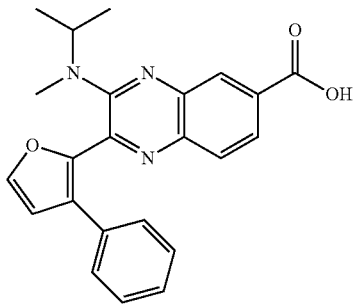 [SMILES: CC(C)N(C)c1nc2cc(C(=O)O)ccc2nc1-c1occc1-c1ccccc1]

Step 1. Methyl 3-[methyl(propan-2-yl)amino]-2-(3-phenylfuran-2-yl)quinoxaline-6-carboxylate

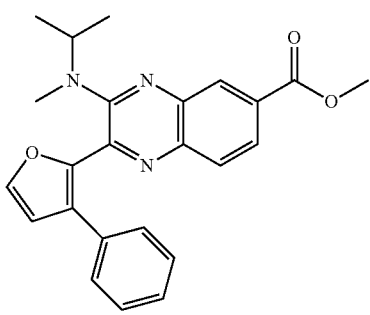 [SMILES: COC(=O)c1ccc2nc(-c3occc3-c3ccccc3)c(N(C)C(C)C)nc2c1]

To a solution of methyl 2-chloro-3-[methyl(propan-2-yl)amino]quinoxaline-6-carboxylate (140 mg, 0.48 mmol) in dioxane (5.0 mL) and water (3 drops) was added 4,4,5,5-tetramethyl-2-(3-phenylfuran-2-yl)-1,3,2-dioxaborolane (270 mg, 1.00 mmol), K$_3$PO$_4$ (211 mg, 0.99 mmol) and Pd(PPh$_3$)$_4$ (28 mg, 0.02 mmol) with stirring for 1 h at 95° C. in an oil bath maintained under an inert atmosphere of nitrogen. The reaction mixture was concentrated under vacuum to give a residue, which was purified by silica gel chromatography (2% ethyl acetate in petroleum ether) to afford methyl 3-[methyl(propan-2-yl)amino]-2-(3-phenylfuran-2-yl)quinoxaline-6-carboxylate as a light yellow solid (140.0 mg, 73%).

LC/MS (ES, m/z): [M+H]+ 402.0
$^1$H-NMR (300 MHz, CDCl$_3$): δ 8.47 (t, J=1.2 Hz, 1H), 8.00-8.05 (m, 2H), 7.70 (d, J=2.1 Hz, 2H), 7.28-7.31 (m, 2H), 7.19-7.27 (m, 2H), 6.80 (d, J=1.8 Hz 1H), 4.24-4.28 (m, 1H), 4.00 (s, 3H), 2.44 (s, 3H), 0.85 (d, J=6.6 Hz, 6H)

Step 2. 3-[Methyl(propan-2-yl)amino]-2-(3-phenylfuran-2-yl)quinoxaline-6-carboxylic acid

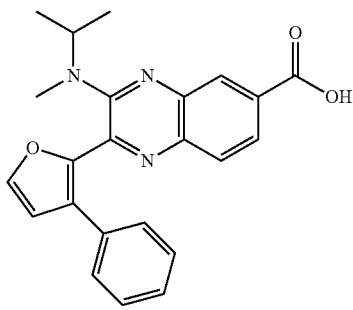 [SMILES: CC(C)N(C)c1nc2cc(C(=O)O)ccc2nc1-c1occc1-c1ccccc1]

To a solution of methyl 3-[methyl(propan-2-yl)amino]-2-(3-phenylfuran-2-yl)quinoxaline-6-carboxylate (140 mg, 0.35 mmol) in methanol (35 mL) and water (2.0 mL) was added sodium hydroxide (55 mg, 1.38 mmol) with stirring overnight at room temperature. The reaction mixture was concentrated under vacuum, dissolved in water (30 mL) and adjusted to pH 4 with HCl (3N). The solids were collected by filtration to afford 3-[methyl(propan-2-yl)amino]-2-(3-phenylfuran-2-yl)quinoxaline-6-carboxylic acid as a light yellow solid (100 mg, 74%).

LC/MS (ES, m/z): [M+H]+ 388.0
$^1$H-NMR (300 MHz, DMSO): δ 8.23 (s, 1H), 8.02 (d, J=1.8 Hz, 1H), 7.89-7.95 (m, 2H), 7.22-7.35 (m, 5H), 7.06 (d, J=1.8 Hz, 1H), 4.15-4.24 (m, 1H), 2.66 (s, 3H), 2.43 (s, 1H), 0.85 (d, J=6.6 Hz, 6H)

Example 84

2-[5-(4-Fluorophenyl)furan-2-yl]-3-[methyl(propan-2-yl)amino]quinoxaline-6-carboxylic acid

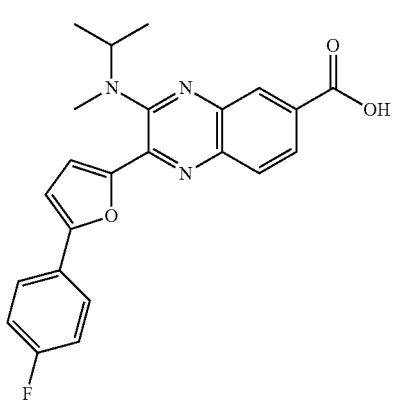 [SMILES: CC(C)N(C)c1nc2cc(C(=O)O)ccc2nc1-c1ccc(-c2ccc(F)cc2)o1]

Step 1. 2-(4-Fluorophenyl)furan

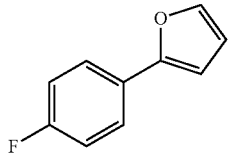

To a solution of 1-bromo-4-fluorobenzene (3.0 g, 17.14 mmol) in dioxane (100.0 mL) and water (3.0 mL) was added (furan-2-yl)boronic acid (5.76 g, 51.48 mmol), $K_3PO_4$ (10.76 g, 50.69 mmol) and $Pd(PPh_3)_4$ (980 mg, 0.85 mmol) with stirring for 2 h at 90° C. in an oil bath maintained under an inert atmosphere of nitrogen. The reaction mixture was concentrated under reduced pressure to give the residue, which was purified via silica gel chromatography (1% ethyl acetate in petroleum ether) to afford 2-(4-fluorophenyl)furan as colorless oil (2.5 g, 90%).

$^1$H-NMR (300 MHz, $CDCl_3$): δ 7.66-7.71 (m, 2H), 7.45-7.48 (m, 1H), 7.11-7.14 (m, 2H), 6.60-6.61 (m, 1H), 6.48-6.49 (m, 1H)

Step 2. 2-[5-(4-Fluorophenyl)furan-2-yl]-4,4,5,5-tetramethyl-1,3,2-dioxaborolane

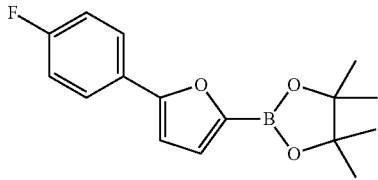 [SMILES: CC1(C)OB(c2ccc(-c3ccc(F)cc3)o2)OC1(C)C]

To a solution of 2-(4-fluorophenyl)furan (1.50 g, 9.25 mmol) in dry tetrahydrofuran (100 mL) was added a solution of n-BuLi (4.4 mL, 2.5M solution in hexane) dropwise with stirring at −78° C. under nitrogen. The resulting solution was warmed slowly to −40° C. over 45 min and stirred at this temperature for another 30 min. The mixture was cooled again below −78° C. followed by dropwise addition of 4,4,5,5-tetramethyl-2-(propan-2-yloxy)-1,3,2-dioxaborolane (3.42 g, 18.38 mmol). After warming to room temperature, the mixture was quenched with $NH_4Cl$ (aq) and extracted with ethyl acetate (3×80 mL). The combined organic layers were dried over anhydrous sodium sulfate, filtered and concentrated under reduced pressure to give the residue (1.20 g crude), which was used to the next step without further purification.

Step 3. Methyl 2-[5-(4-fluorophenyl)furan-2-yl]-3-[methyl(propan-2-yl)amino]quinoxaline-6-carboxylate

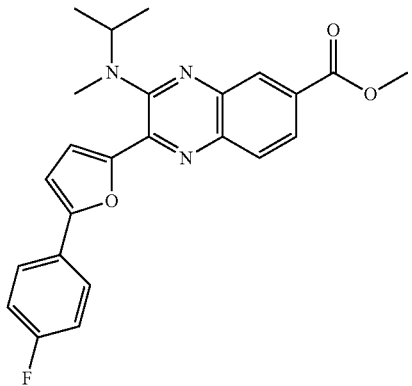 [SMILES: COC(=O)c1ccc2nc(-c3ccc(-c4ccc(F)cc4)o3)c(N(C)C(C)C)nc2c1]

To a solution of 2-[5-(4-fluorophenyl)furan-2-yl]-4,4,5,5-tetramethyl-1,3,2-dioxaborolane (442 mg, crude) in dioxane (5.5 mL) and water (3 drops) was added methyl 2-chloro-3-[methyl(propan-2-yl)amino]quinoxaline-6-carboxylate (150 mg, 0.51 mmol), $K_3PO_4$ (324.9 mg, 1.53 mmol) and $Pd(PPh_3)_4$ (29.5 mg, 0.03 mmol) with stirring for 40 min at 90° C. in an oil bath maintained under an inert atmosphere of nitrogen. The reaction mixture was concentrated under reduced pressure to give the residue, which was purified via silica gel chromatography (2% ethyl acetate in petroleum ether) to afford methyl 2-[5-(4-fluorophenyl)furan-2-yl]-3-[methyl(propan-2-yl)amino]quinoxaline-6-carboxylate as light yellow solid (150 mg, 55%).

LC/MS (ES, m/z): [M+H]$^+$ 420.0

$^1$H-NMR (300 MHz, $CDCl_3$): δ 8.50 (d, J=1.8 Hz, 1H), 8.06-8.09 (m, 1H), 7.98 (d, J=8.7 Hz, 1H), 7.75-7.82 (m, 2H), 7.36 (d, J=3.3 Hz, 1H), 7.15-7.19 (m, 2H), 6.80 (d, J=3.6 Hz, 1H), 4.35-4.44 (m, 1H), 4.00 (s, 3H), 2.88 (s, 3H), 1.26 (d, J=6.6 Hz, 6H)

Step 4. 2-[5-(4-Fluorophenyl)furan-2-yl]-3-[methyl(propan-2-yl)amino]quinoxaline-6-carboxylic acid

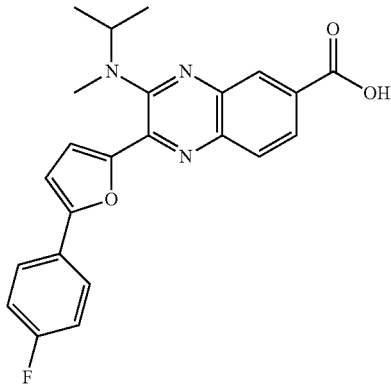 [SMILES: CC(C)N(C)c1nc2cc(C(=O)O)ccc2nc1-c1ccc(-c2ccc(F)cc2)o1]

To a solution of methyl 2-[5-(4-fluorophenyl)furan-2-yl]-3-[methyl(propan-2-yl)amino]quinoxaline-6-carboxylate (110 mg, 0.26 mmol) in methanol (30 mL) and water (2 mL) was added sodium hydroxide (42 mg, 1.05 mmol) with stirring overnight at room temperature. The reaction mixture was concentrated under vacuum, dissolved in water (30 mL) and adjusted to pH 5 with HCl (3N). The solids were collected by filtration to afford 3-[methyl(propan-2-yl)amino]-2-(5-phenylfuran-2-yl)quinoxaline-6-carboxylic acid as a light yellow solid (19.3 mg, 18%).

LC/MS (ES, m/z): [M+H]$^+$ 406.1

$^1$H NMR (300 MHz, DMSO): δ 8.58 (d, J=1.8 Hz, 1H), 8.48 (d, J=1.5 Hz, 1H), 8.12-8.17 (m, 1H), 7.80-7.99 (m, 2H), 7.38 (d, J=3.6 Hz, 1H), 7.12-7.19 (m, 2H), 6.81 (d, J=3.6 Hz, 1H), 4.37-4.46 (m, 1H), 2.89 (s, 3H), 1.24 (d, J=6.6 Hz, 6H)

Example 85

3-[Methyl(propan-2-yl)amino]-2-(3-methyl-1-benzofuran-5-yl)quinoxaline-6-carboxylic acid

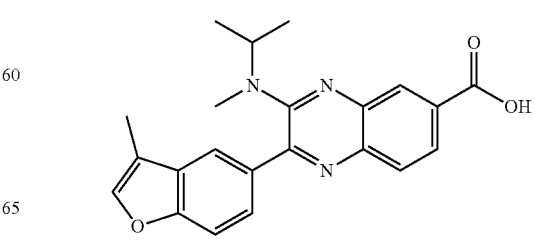

Step 1. Ethyl 2-(2-acetyl-4-bromophenoxy)acetate

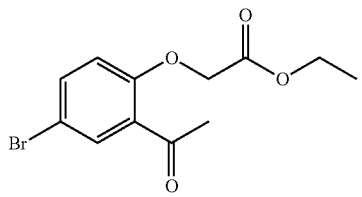 [SMILES: CCOC(=O)COc1ccc(Br)cc1C(C)=O]

To a solution of 1-(5-bromo-2-hydroxyphenyl)ethan-1-one (10 g, 46.50 mmol) in N,N-dimethylformamide (80 mL) was added sodium hydroxide (2.23 g, 92.92 mmol) and then stirred for 1 hour at room temperature. Ethyl 2-bromoacetate (8.24 g, 49.34 mmol) was added dropwise and stirred overnight at room temperature. The reaction mixture was quenched by the addition of water (200 mL), adjusted to pH 5 with HCl (3N), extracted with ethyl acetate (50 mL×3), dried over anhydrous sodium sulfate, and concentrated under vacuum to give a residue which was purified by silica gel chromatography (5% ethyl acetate in petroleum ether) to afford ethyl 2-(2-acetyl-4-bromophenoxy)acetate as a light yellow oil (8.9 g, 64%).
$^1$H-NMR (300 MHz, CDCl$_3$) δ 7.87 (d, J=2.7 Hz, 1H), 7.52-7.55 (m, 1H), 6.74 (d, J=8.7 Hz, 1H), 4.72 (s, 2H), 4.24-4.30 (m, 2H), 2.71 (s, 3H), 1.28-1.36 (m, 3H)

Step 2. 2-(2-Acetyl-4-bromophenoxy)acetic acid

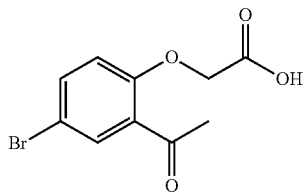

To a solution of ethyl 2-(2-acetyl-4-bromophenoxy)acetate (8.9 g, 29.56 mmol) in THF (60 mL) was added sodium hydroxide (1.43 g, 35.75 mmol) and water (10 mL). The resulting solution was stirred overnight at room temperature and concentrated under vacuum. The residue was dissolved in water (30 mL) and adjusted to pH 2 with HCl (3N). The solids were collected by filtration to afford 2-(2-acetyl-4-bromophenoxy)acetic acid as a light yellow solid (6.3 g, 78%).
$^1$H-NMR (300 MHz, CDCl$_3$) δ 7.62-7.69 (m, 2H), 7.10 (d, J=8.7 Hz, 1H), 4.86 (s, 2H), 2.63 (s, 3H)

Step 3. 5-Bromo-3-methyl-1-benzofuran

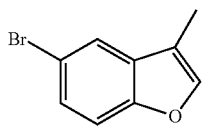

To a solution of 2-(2-acetyl-4-bromophenoxy)acetic acid (5.3 g, 19.41 mmol) in acetic anhydride (100 mL) was added NaOAc (3.19 g, 38.90 mmol). The resulting solution was heated to reflux overnight. The pH value of the resulting solution was adjusted to 7 with aqueous sodium hydroxide, extracted with ether (50 mL×3), dried over anhydrous sodium sulfate and concentrated under vacuum to give a residue, which was purified by silica gel chromatography (petroleum ether) to afford 5-bromo-3-methyl-1-benzofuran as a light yellow oil (3.8 g, 93%).
$^1$H-NMR (300 MHz, CDCl$_3$) δ 7.67 (d, J=1.8 Hz, 1H), 7.33-7.43 (m, 3H), 2.28 (d, J=1.5 Hz, 3H)

Step 4. 4,4,5,5-Tetramethyl-2-(3-methyl-1-benzofuran-5-yl)-1,3,2-dioxaborolane

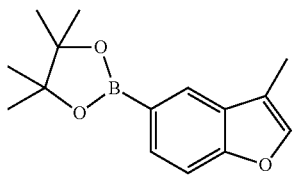 [SMILES: Cc1coc2ccc(B3OC(C)(C)C(C)(C)O3)cc12]

To a solution of 5-bromo-3-methyl-1-benzofuran (1.9 g, 9.00 mmol) in 1,4-dioxane (30 mL) was added KOAc (2.2 g, 22.42 mmol) and Pd(dppf)Cl$_2$ (600 mg, 0.82 mmol). The solution was stirred for 15 minutes at room temperature and then 4,4,5,5-tetramethyl-2-(tetramethyl-1,3,2-dioxaborolan-2-yl)-1,3,2-dioxaborolane (2.7 g, 10.63 mmol) was added. The resulting solution was stirred overnight at 85° C., followed by quenching via the addition of water (100 mL). The resulting solution was extracted with ethyl acetate (3×30 mL), dried over anhydrous sodium sulfate and concentrated under vacuum to give a residue, which was purified by silica gel chromatography (petroleum ether) to afford 4,4,5,5-tetramethyl-2-(3-methyl-1-benzofuran-5-yl)-1,3,2-dioxaborolane as a light yellow solid (1.5 g, 65%).
$^1$H-NMR (300 MHz, CDCl$_3$) δ 8.05 (s, 1H), 7.76-7.79 (m, 1H), 7.41-7.48 (m, 2H), 2.28 (d, J=1.5 Hz, 3H), 1.39 (s, 12H)

Step 5. Methyl 3-[methyl(propan-2-yl)amino]-2-(3-methyl-1-benzofuran-5-yl)quinoxaline-6-carboxylate

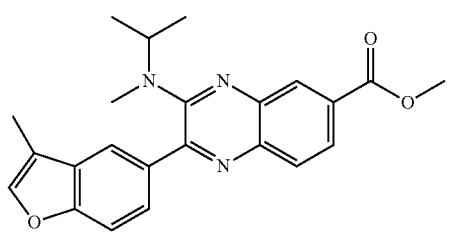 [SMILES: COC(=O)c1ccc2nc(-c3ccc4occ(C)c4c3)c(N(C)C(C)C)nc2c1]

To a solution of methyl 2-chloro-3-[methyl(propan-2-yl)amino]quinoxaline-6-carboxylate (150 mg, 0.36 mmol) in 1,4-dioxane (6 mL) was added 4,4,5,5-tetramethyl-2-(3-methyl-1-benzofuran-5-yl)-1,3,2-dioxaborolane (350 mg, 1.36 mmol), Pd(PPh$_3$)$_4$ (40 mg, 0.034 mmol), K$_3$PO$_4$ (430 mg, 2.04 mmol) and water (5 drops) with stirring for 5 h at 90° C. under an inert atmosphere of nitrogen in an oil bath. The reaction mixture was concentrated under vacuum to give the residue, which was purified via silica gel chromatography (1% to 5% ethyl acetate in petroleum ether) to afford methyl 3-[methyl(propan-2-yl)amino]-2-(3-methyl-1-benzofuran-5-yl)quinoxaline-6-carboxylate as a yellow solid (110 mg, 63%).

LC/MS (ES, m/z): [M+H]+ 390.0

¹H-NMR (300 MHz, CDCl₃) δ 8.56 (d, J=1.5 Hz, 1H), 7.99-8.12 (m, 3H), 7.83-7.86 (m, 1H), 7.49-7.62 (m, 2H), 4.25-4.39 (m, 1H), 4.00 (s, 3H), 3.00 (s, 3H), 2.54 (s, 3H), 1.08 (d, J=6.6 Hz, 6H)

Step 6. 3-[Methyl(propan-2-yl)amino]-2-(3-methyl-1-benzofuran-5-yl)quinoxaline-6-carboxylic acid

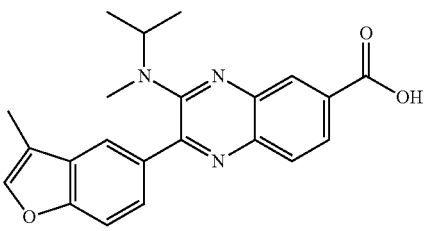 [SMILES: Cc1coc2ccc(-c3nc4ccc(C(=O)O)cc4nc3N(C)C(C)C)cc12]

To a solution of methyl 3-[methyl(propan-2-yl)amino]-2-(3-methyl-1-benzofuran-5-yl)quinoxaline-6-carboxylate (110 mg, 0.28 mmol) in methanol (25 mL) and chloroform (5 mL) was added sodium hydroxide (468 mg, 1.17 mmol) and water (2 mL) with stirring for 3 h at room temperature. The reaction mixture was concentrated under vacuum, dissolved in water (15 mL), and adjusted pH to 5 with HCl (3N) to give the precipitate, which was collected by filtration to afford 3-[methyl(propan-2-yl)amino]-2-(3-methyl-1-benzofuran-5-yl)quinoxaline-6-carboxylic acid (62 mg, 59%).

LC/MS (ES, m/z): [M+H]+ 376.1

¹H-NMR (300 MHz, DMSO) δ 8.28 (t, J=0.9 Hz, 1H), 8.12 (d, J=1.5 Hz, 1H), 7.96 (s, 2H), 7.81-7.87 (m, 2H), 7.68 (d, J=8.4 Hz, 1H), 4.16-4.20 (m, 1H), 2.69 (s, 3H), 2.28 (s, 3H), 1.02 (d, J=6.6 Hz, 6H)

Example 86

3-(Isopropyl(methyl)amino)-2-(3-methyl-1H-indol-5-yl)quinoxaline-6-carboxylic acid

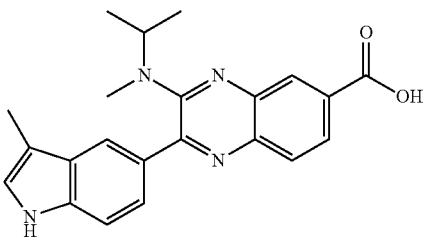 [SMILES: Cc1c[nH]c2ccc(-c3nc4ccc(C(=O)O)cc4nc3N(C)C(C)C)cc12]

Step 1. 5-Bromo-1H-indole-3-carbaldehyde

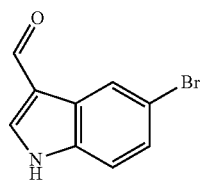 [SMILES: O=Cc1c[nH]c2ccc(Br)cc12]

To a solution of POCl₃ (8.58 g, 55.96 mmol) in N,N-dimethylformamide (14.9 g, 203.9 mmol) was added a solution of 5-bromo-1H-indole (10.0 g, 51.0 mmol) in N,N-dimethylformamide (100 mL) dropwise at 0-10° C. The reaction mixture was stirred for 1 h at 0-35° C. and then poured into water/ice solution, adjusted the pH to 10 with aqueous sodium hydroxide and filtered to afford 5-bromo-1H-indole-3-carbaldehyde as a white solid (8.0 g, 70%).

¹H-NMR (300 MHz, CD₃OD): δ: 9.90 (s, 1H), 8.32 (s, 1H), 8.14 (s, 1H), 7.38-7.44 (m, 2H)

Step 2. 5-Bromo-3-methyl-1H-indole

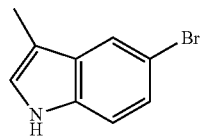

To a solution of 5-bromo-1H-indole-3-carbaldehyde (5.0 g, 22.3 mmol) in THF (80 mL) was added LiAlH₄ (1.70 g, 44.6 mmol). The resulting solution was stirred for 2 h under reflux, then poured into 1N NaOH solution (150 mL), extracted with ethyl acetate (3×100 mL), dried over anhydrous sodium sulfate, and then concentrated under vacuum to give a residue, which was purified via silica gel chromatography (3% ethyl acetate in petroleum ether) to afford 5-bromo-3-methyl-1H-indole as a white solid (3.4 g, 73%).

¹H-NMR (300 MHz, CDCl₃): δ:7.91 (s, 1H), 7.72-7.73 (t, J=0.9 Hz, 1H), 7.21-7.30 (m, 2H), 6.99 (d, J=0.9 Hz, 1H), 2.31 (s, 3H)

Step 3. 3-Methyl-5-(4,4,5,5-tetramethyl-1,3,2-dioxaborolan-2-yl)-1H-indole

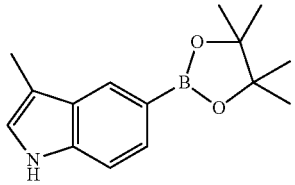 [SMILES: Cc1c[nH]c2ccc(B3OC(C)(C)C(C)(C)O3)cc12]

To a solution of 5-bromo-3-methyl-1H-indole (1.5 g, 7.14 mmol) in dioxane (40 mL) was added 4,4,4',4',5,5,5',5'-octamethyl-2,2'-bi(1,3,2-dioxaborolane) (2.18 g, 8.57 mmol), AcOK (1.40 g, 14.3 mmol) and Pd(dppf)Cl₂ (262 mg, 0.36 mmol). The resulting solution was stirred overnight at 90° C. The reaction mixture was poured into water (200 mL), extracted with DCM (3×100 mL), dried over anhydrous sodium sulfate, and concentrated under vacuum to give a residue, which was purified via silica gel chromatography (3% ethyl acetate in petroleum ether) to afford 3-methyl-5-(4,4,5,5-tetramethyl-1,3,2-dioxaborolan-2-yl)-1H-indole as a white solid (1.1 g, 60%).

$^1$H-NMR (300 MHz, CDCl$_3$): δ: 8.14 (s, 1H), 7.95 (s, 1H), 7.65-7.68 (m, 1H), 7.34-7.37 (m, 1H), 6.97 (d, J=0.9 Hz, 2H), 2.37 (s, 3H), 1.40 (s, 12H)

Step 4. Methyl 3-(isopropyl(methyl)amino)-2-(3-methyl-1H-indol-5-yl)quinoxaline-6-carboxylate

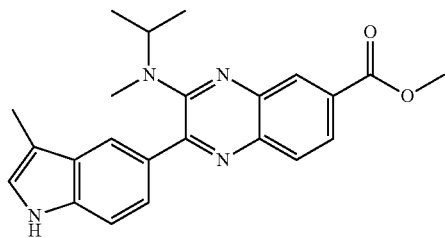 [SMILES: COC(=O)c1ccc2nc(-c3ccc4[nH]cc(C)c4c3)c(N(C)C(C)C)nc2c1]

To a solution of methyl 2-chloro-3-(isopropyl(methyl)amino)quinoxaline-6-carboxylate (150 mg, 0.51 mmol) in dioxane (5 mL) was added 3-methyl-5-(4,4,5,5-tetramethyl-1,3,2-dioxaborolan-2-yl)-1H-indole (395 mg, 1.54 mmol), K$_2$CO$_3$ (106 g, 0.77 mmol), Pd(PPh$_3$)$_4$ (30 mg, 0.03 mmol) and water (5 drops). The resulting solution was stirred for 5 h at 90° C., and then poured into water (100 mL), extracted with DCM (4×50 mL), dried over anhydrous sodium sulfate and then concentrated under vacuum to give a residue. The residue was purified via silica gel chromatography (25% ethyl acetate in petroleum ether) to afford methyl 3-(isopropyl(methyl)amino)-2-(3-methyl-1H-indol-5-yl)quinoxaline-6-carboxylate as a yellow solid (80 mg, 45%).

$^1$H-NMR (300 MHz, CDCl$_3$): δ 8.96-9.09 (m, 1H), 8.51-8.61 (m, 2H), 8.15-8.22 (m, 3H), 7.62-7.70 (m, 1H), 4.60-4.70 (m, 1H), 4.03 (s, 3H), 2.95 (s, 3H), 2.41 (s, 3H), 1.99 (s, 6H)

Step 5. 3-(Isopropyl(methyl)amino)-2-(3-methyl-1H-indol-5-yl)quinoxaline-6-carboxylic acid

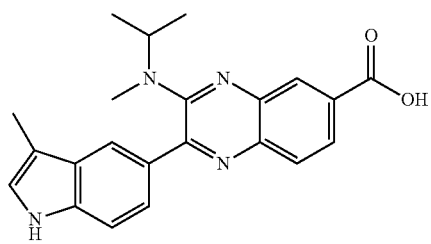 [SMILES: Cc1c[nH]c2ccc(-c3nc4ccc(C(=O)O)cc4nc3N(C)C(C)C)cc12]

To a solution of methyl 3-(isopropyl(methyl)amino)-2-(3-methyl-1H-indol-5-yl)quinoxaline-6-carboxylate (80 mg, 0.21 mmol) in MeOH (10 mL) was added sodium hydroxide (52 mg, 0.29 mmol) and water (1 mL). The resulting solution was stirred for 2 h at room temperature and concentrated under vacuum. The residue was dissolved in water (3 mL) and adjusted to pH 6 with hydrochloric acid (1N). The solids were collected by filtration to afford 3-(isopropyl(methyl)amino)-2-(3-methyl-1H-indol-5-yl)quinoxaline-6-carboxylic acid as a yellow solid (45.8 mg, 59%).

LC/MS (ES, m/z): [M+H]$^+$ 375.1

$^1$H-NMR (300 MHz, DMSO): δ 13.05 (s, 1H), 10.98 (s, 1H), 8.25 (s, 1H), 8.08 (s, 1H), 7.93 (s, 2H), 7.64-7.68 (m, 2H), 7.44-7.46 (d, J=8.4 Hz, 1H), 7.20 (s, 1H), 4.20-4.29 (m, 1H), 2.71 (s, 3H), 2.31 (s, 3H), 1.10-1.13 (d, J=6.6 Hz, 6H)

Example 87

(R)-2-(Benzo[d][1,3]dioxol-5-yl)-3-(2-methylpyrrolidin-1-yl)quinoxaline-6-carboxylic acid

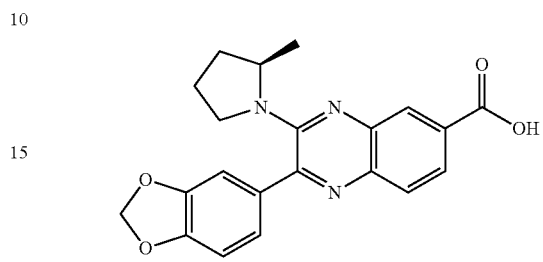

Step 1. (R)-Methyl 3-(2-methylpyrrolidin-1-yl)-2-oxo-1,2-dihydroquinoxaline-6-carboxylate

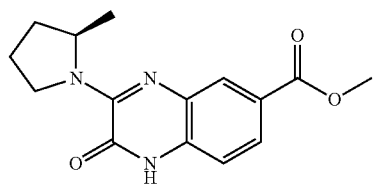 [SMILES: COC(=O)c1ccc2[nH]c(=O)c(N3CCC[C@H]3C)nc2c1]

To a solution of methyl 3-chloro-2-oxo-1,2-dihydroquinoxaline-6-carboxylate (250 mg, 1.05 mmol) in DMSO (2 mL) was added DIEA (850 mg, 4.2 mmol), and (R)-2-methylpyrrolidine hydrochloride (300 mg, 2.35 mmol), and the resulting mixture was stirred for 3 h at 70° C. Then the reaction was quenched by the addition of water (10 mL). The solids were collected by filtration to afford (R)-methyl 3-(2-methylpyrrolidin-1-yl)-2-oxo-1,2-dihydroquinoxaline-6-carboxylate as a light yellow solid (216 mg, 72%).

LC/MS (ES, m/z): [M+H]$^+$ 288.0

Step 2. (R)-Methyl 3-(2-methylpyrrolidin-1-yl)-2-(trifluoromethylsulfonyloxy)quinoxaline-6-carboxylate

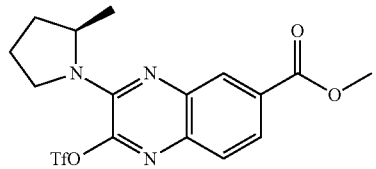 [SMILES: COC(=O)c1ccc2nc(OS(=O)(=O)C(F)(F)F)c(N3CCC[C@H]3C)nc2c1]

To a solution of (R)-methyl 3-(2-methylpyrrolidin-1-yl)-2-oxo-1,2-dihydroquinoxaline-6-carboxylate (200 mg, 0.70 mmol) in dichloromethane (30 mL) was added pyridine (221 mg, 2.79 mmol) and then Tf$_2$O (395 mg, 1.40 mmol) dropwise with stirring at 0° C. The resulting solution was stirred overnight at room temperature, then quenched by the addition of ice-water (50 mL), extracted with dichloromethane (3×20 mL), dried over anhydrous sodium sulfate and concentrated under vacuum to afford (R)-methyl 3-(2-methylpyrrolidin-1-yl)-2-(trifluoromethylsulfonyloxy)quinoxaline-6-carboxylate as red oil (250 mg, crude).

Step 3. (R)-Methyl 2-(benzo[d][1,3]dioxol-5-yl)-3-(2-methylpyrrolidin-1-yl)quinoxaline-6-carboxylate

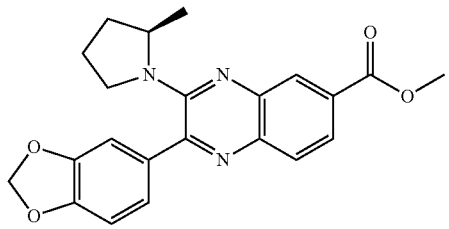 [SMILES: COC(=O)c1ccc2nc(-c3ccc4c(c3)OCO4)c(N3CCC[C@H]3C)nc2c1]

To a solution of (R)-methyl 3-(2-methylpyrrolidin-1-yl)-2-(trifluoromethylsulfonyloxy)quinoxaline-6-carboxylate (250 mg, crude) in dioxane (5 mL) was added 2-(benzo[d][1,3]dioxol-5-yl)-4,4,5,5-tetramethyl-1,3,2-dioxaborolane (250 mg, 1.51 mmol), $K_3PO_4$ (380 mg, 1.79 mmol), Pd(PPh$_3$)$_4$ (35 mg, 0.03 mmol) and water (5 drops). The resulting solution was stirred for 1 h at 90° C. and then concentrated under vacuum to give a residue, which was purified via silica gel chromatography (1%-5% ethyl acetate in petroleum ether) to afford (R)-methyl 2-(benzo[d][1,3]dioxol-5-yl)-3-(2-methylpyrrolidin-1-yl)quinoxaline-6-carboxylate as a yellow solid (120 mg).

LC/MS (ES, m/z)[M+H]$^+$ 392.0

$^1$H-NMR (300 MHz, CDCl$_3$): δ 8.56 (s, 1H), 7.93-8.03 (m, 2H), 7.28-7.32 (s, 2H), 6.93 (d, J=7.8 Hz, 1H), 6.07 (s, 2H), 4.35-4.42 (m, 1H), 4.00 (s, 3H), 3.25 (d, J=6.3 Hz, 1H), 2.95-3.04 (m, 1H), 2.15-2.25 (m, 1H), 1.86-1.91 (m, 1H), 1.53-1.70 (m, 2H), 1.39 (d, J=5.4 Hz, 3H)

Step 4. (R)-2-(Benzo[d][1,3]dioxol-5-yl)-3-(2-methylpyrrolidin-1-yl)quinoxaline-6-carboxylic acid

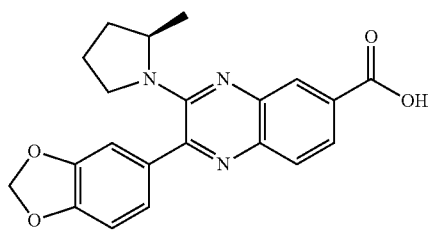 [SMILES: C[C@@H]1CCCN1c1nc2cc(C(=O)O)ccc2nc1-c1ccc2c(c1)OCO2]

To a solution of (R)-methyl 2-(benzo[d][1,3]dioxol-5-yl)-3-(2-methylpyrrolidin-1-yl)quinoxaline-6-carboxylate (120 mg, 0.31 mmol) in methanol (25 mL) was added sodium hydroxide (37.2 mg, 0.93 mmol) and water (2 mL). The resulting solution was stirred overnight at room temperature and concentrated under vacuum. The residue was dissolved in water (20 mL) and adjusted pH to 5 with hydrochloric acid (3N). The solids were collected by filtration to afford (R)-2-(benzo[d][1,3]dioxol-5-yl)-3-(2-methylpyrrolidin-1-yl)quinoxaline-6-carboxylic acid as a yellow solid (90 mg, 78%).

LC/MS (ES, m/z): [M+H]$^+$ 378.1

$^1$H-NMR (300 MHz, CD$_3$OD) δ 8.38 (d, J=1.8 Hz, 1H), 7.96-7.99 (m, 1H), 7.86 (d, J=8.7 Hz, 1H), 7.26-7.29 (m, 2H), 6.98 (d, J=8.4 Hz, 1H), 6.06-6.08 (m, 2H), 4.32-4.87 (m, 1H), 3.19-3.33 (m, 1H), 3.01-3.07 (m, 1H), 2.18-2.22 (m, 1H), 1.83-1.87 (m, 1H), 1.59-1.70 (m, 2H), 1.37 (d, J=6.6 Hz, 3H)

Example 88

(S)-2-(2-Methyl-1H-indol-5-yl)-3-(2-methylpiperidin-1-yl)quinoxaline-6-carboxylic acid

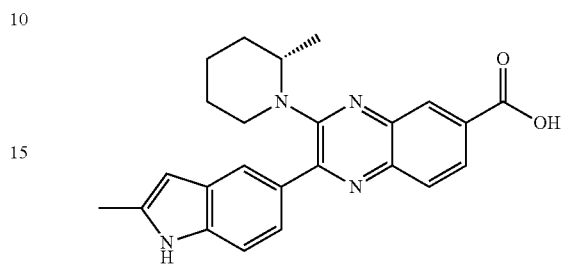

Step 1. (S)-Methyl 3-(2-methylpiperidin-1-yl)-2-oxo-1,2-dihydroquinoxaline-6-carboxylate

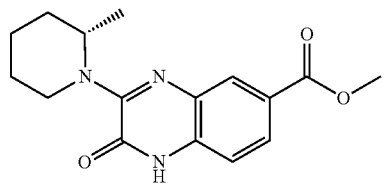 [SMILES: COC(=O)c1ccc2[nH]c(=O)c(N3CCCC[C@@H]3C)nc2c1]

To a solution of methyl 3-chloro-2-oxo-1,2-dihydroquinoxaline-6-carboxylate (1 g, 4.2 mmol) in DMSO (20 ml) was added (S)-2-methylpiperidine (500 mg, 5.04 mmol) and DIEA (1.09 g, 8.4 mmol). The resulting solution was stirred for 2 hours at 80° C. and then quenched by the addition of water (100 ml). The product was collected by filtration to afford (S)-methyl 3-(2-methylpiperidin-1-yl)-2-oxo-1,2-dihydroquinoxaline-6-carboxylate as white solid (840 mg, 66%).

LC/MS (ES, m/z): [M+H]$^+$ 302.0

$^1$H-NMR (300 MHz, CDCl$_3$): δ 10.11 (s, 1H), 8.29 (s, 1H), 7.83-7.86 (m, 1H), 7.09 (d, J=8.4 Hz, 1H), 5.39-5.41 (m, 1H), 4.86-4.91 (m 1H), 3.94 (s, 3H), 3.18-3.26 (t, J=12.6 Hz, 1H), 1.65-1.94 (m, 6H), 1.35 (d, J=6.9 Hz, 3H)

Step 2. (S)-Methyl 3-(2-methylpiperidin-1-yl)-2-(trifluoromethylsulfonyloxy)quinoxaline-6-carboxylate

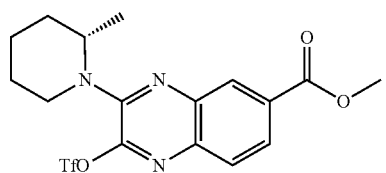 [SMILES: COC(=O)c1ccc2nc(OS(=O)(=O)C(F)(F)F)c(N3CCCC[C@@H]3C)nc2c1]

To a solution of (S)-methyl 3-(2-methylpiperidin-1-yl)-2-oxo-1,2-dihydroquinoxaline-6-carboxylate (840 mg, 2.79 mmol) in dichloromethane (60 ml) was added pyridine (1.19 g, 14.98 mmol) and then Tf$_2$O (2.12 g, 7.52 mmol) dropwise with stirring at 0° C. The resulting solution was stirred overnight at room temperature, then washed with water (3×50 ml), dried over anhydrous sodium sulfate and concentrated under vacuum to give a residue, which was purified via silica gel chromatography (1% to 2% ethyl acetate in petroleum ether) to afford (S)-methyl 3-(2-methylpiperidin-1-yl)-2-(trifluoromethylsulfonyloxy)quinoxaline-6-carboxylate as red oil (990 mg, crude).

Step 3. (S)-Methyl 2-bromo-3-(2-methylpiperidin-1-yl)quinoxaline-6-carboxylate

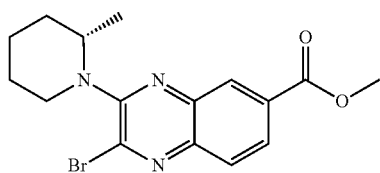 [SMILES: COC(=O)c1ccc2nc(Br)c(N3CCCC[C@@H]3C)nc2c1]

To a solution of (S)-methyl 3-(2-methylpiperidin-1-yl)-2-(trifluoromethylsulfonyloxy)quinoxaline-6-carboxylate (990 mg, crude) in toluene (30 ml) was added Bu$_4$NBr (1.3 g, 4.05 mmol) with stirring for 5 h at 120° C. The resulting solution was extracted with ethyl acetate (3×50 ml), and the organic layers were combined and dried over anhydrous magnesium sulfate and concentrated under vacuum to give (S)-methyl 2-bromo-3-(2-methylpiperidin-1-yl)quinoxaline-6-carboxylate as a yellow solid (900 mg).

LC/MS (ES, m/z): [M+H]$^+$ 364.0

Step 4. (S)-Methyl 2-(2-methyl-1H-indol-5-yl)-3-(2-methylpiperidin-1-yl)quinoxaline-6-carboxylate

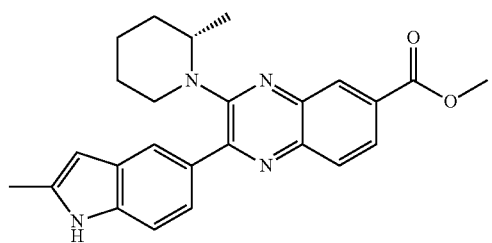

To a solution of (S)-methyl 2-bromo-3-(2-methylpiperidin-1-yl)quinoxaline-6-carboxylate (200 mg, 0.55 mmol) in ethylene glycol dimethyl ether (7 ml) was added 2-methyl-5-(tetramethyl-1,3,2-dioxaborolan-2-yl)-1H-indole (141 mg, 0.55 mmol), sodium carbonate (116 mg, 1.09 mmol), water (2 mL), and Pd(PPh$_3$)$_4$ (32 mg, 0.03 mmol). The resulting solution was stirred for 3 h at 90° C. and concentrated under vacuum to give a residue, which was purified via silica gel chromatography (2% ethyl acetate in petroleum ether) to afford (S)-methyl 2-(2-methyl-1H-indol-5-yl)-3-(2-methylpiperidin-1-yl)quinoxaline-6-carboxylate as a light yellow solid (142.1 mg, 62%).

LC/MS (ES, m/z): [M+H]$^+$ 415.0

$^1$H-NMR (300 MHz, CDCl$_3$): δ 8.67 (s, 1H), 8.15-8.30 (m, 4H), 8.08-8.11 (m, 1H), 7.73-7.77 (m, 1H), 7.37 (d, J=8.7 Hz, 1H), 6.32 (s, 1H), 4.22-4.35 (m, 1H), 4.01 (s, 3H), 3.62-3.70 (m, 1H), 3.11-3.30 (m, 1H), 2.67 (s, 3H), 1.62-1.72 (m, 4H), 1.38-1.45 (m, 2H), 1.12 (d, J=6.6 Hz, 3H)

Step 5. (S)-2-(2-Methyl-1H-indol-5-yl)-3-(2-methylpiperidin-1-yl)quinoxaline-6-carboxylic acid

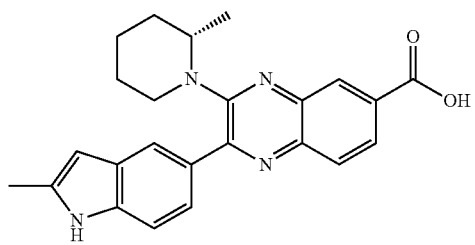 [SMILES: Cc1cc2cc(-c3nc4ccc(C(=O)O)cc4nc3N3CCCC[C@@H]3C)ccc2[nH]1]

To a solution of (S)-methyl 2-(2-methyl-1H-indol-5-yl)-3-(2-methylpiperidin-1-yl)quinoxaline-6-carboxylate (142.1 mg, 0.34 mmol) in methanol (30 ml) was added NaOH (55 mg, 1.38 mmol) and water (2 ml). The resulting solution was stirred overnight at room temperature and concentrated under vacuum to give a residue, which was dissolved in water (20 ml), and the pH adjusted to 4 with HCl (3N). The solids were collected by filtration to afford (S)-2-(2-methyl-1H-indol-5-yl)-3-(2-methylpiperidin-1-yl)quinoxaline-6-carboxylic acid as a yellow solid (11.9 mg, 9%).

LC/MS (ES, m/z): [M+H]$^+$ 401.1

$^1$H-NMR (300 MHz, CDCl$_3$): δ 8.44 (d, J=1.5 Hz, 1H), 8.03-8.09 (m, 2H), 7.91 (d, J=8.7 Hz, 1H), 7.63-7.67 (m, 1H), 7.40 (d, J=8.4 Hz, 1H), 6.26 (s, 1H), 4.14-4.21 (m, 1H), 3.50-3.64 (m, 1H), 3.09-3.22 (m, 1H), 2.48 (s, 3H), 1.62-1.72 (m, 4H), 1.32-1.37 (m, 2H), 1.12 (d, J=6.6 Hz, 3H)

Example 89

3-[Cyclopropyl(methyl)amino]-2-(2-methyl-1H-indol-5-yl)quinoxaline-6-carboxylic acid

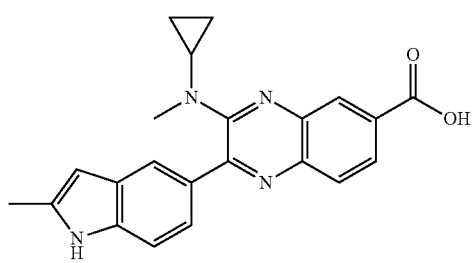 [SMILES: Cc1cc2cc(-c3nc4ccc(C(=O)O)cc4nc3N(C)C3CC3)ccc2[nH]1]

Step 1. Methyl 3-(cyclopropyl(methyl)amino)-2-oxo-1,2-dihydroquinoxaline-6-carboxylate

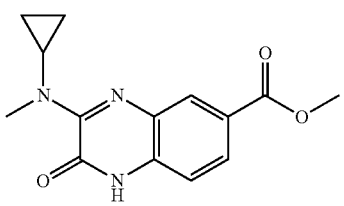

To a solution of methyl 3-chloro-2-oxo-1,2-dihydroquinoxaline-6-carboxylate (750 mg, 3.14 mmol) in DMSO (5 ml) was added DIEA (812.7 mg, 6.29 mmol), N-methylcyclopropanamine hydrochloride (450 mg, 4.18 mmol) with stirring for 3 h at 75° C. in an oil bath. The resulting solution was diluted with water (200 ml), and the product was collected by filtration to give methyl 3-[cyclopropyl(methyl)amino]-2-oxo-1,2-dihydroquinoxaline-6-carboxylate as a solid (780 mg, 91%).

LC/MS (ES, m/z)[M+H]+ 274.1

1H-NMR (300 MHz, DMSO) δ 12.17 (s, 1H), 7.93 (d, J=1.8 Hz, 1H), 7.67-7.75 (m, 1H), 7.20 (d, J=8.4 Hz, 1H), 3.85 (s, 3H), 3.23 (s, 3H), 3.05-3.11 (m, 1H), 0.76-0.82 (m, 2H), 0.50-0.63 (m, 2H)

Step 2. Methyl 3-[cyclopropyl(methyl)amino]-2-[(trifluoromethane)sulfonyloxy]quinoxaline-6-carboxylate

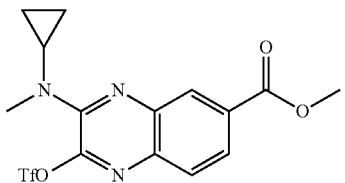

To a solution of methyl 3-[cyclopropyl(methyl)amino]-2-oxo-1,2-dihydroquinoxaline-6-carboxylate (780 mg, 2.85 mmol) in dichloromethane (100 ml) was added pyridine (900 mg, 11.38 mmol), Tf2O (1645 mg, 5.83 mmol) with stirring under an inert atmosphere of nitrogen for 2 h at room temperature. The resulting solution was diluted with water (300 ml), extracted with dichloromethane (2×50 ml), dried over anhydrous magnesium sulfate and concentrated under vacuum to give a residue, which was purified via silica gel chromatography (1%-5% ethyl acetate in petroleum ether) to give methyl 3-[cyclopropyl(methyl)amino]-2-[(trifluoromethane)sulfonyloxy]quinoxaline-6-carboxylate as a yellow solid (700 mg, 61%).

Step 3. Methyl 2-bromo-3-[cyclopropyl(methyl)amino]quinoxaline-6-carboxylate

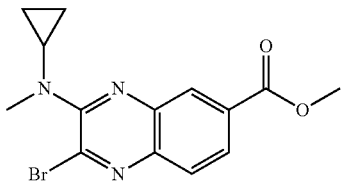

To a solution of methyl 3-[cyclopropyl(methyl)amino]-2-[(trifluoromethane)sulfonyloxy]quinoxaline-6-carboxylate (700 mg, 1.73 mmol) in toluene (80 mL) was added tetrabutylammonium bromide (TBAB) (668 mg, 2.07 mmol) with stirring overnight at 120° C. in an oil bath. The resulting solution was diluted with water (300 ml), extracted with dichloromethane (3×30 ml), dried over anhydrous magnesium sulfate, concentrated under vacuum to get residue, which was purified via silica gel chromatography (1%-10% ethyl acetate in petroleum ether) to give methyl 2-bromo-3-[cyclopropyl(methyl)amino]quinoxaline-6-carboxylate as a yellow solid (480 mg, 82%).

LC/MS (ES, m/z): [M+H]+ 336.1.0

1H-NMR (300 MHz, DMSO) δ 8.26 (d, J=1.5 Hz, 2H), 7.98-8.01 (m, 1H), 7.88 (d, J=8.7 Hz, 1H), 3.93 (s, 3H), 3.19 (s, 3H), 3.10-3.18 (m, 1H), 0.70-0.90 (m, 4H)

Step 4. Methyl 3-[cyclopropyl(methyl)amino]-2-(2-methyl-1H-indol-5-yl)quinoxaline-6-carboxylate

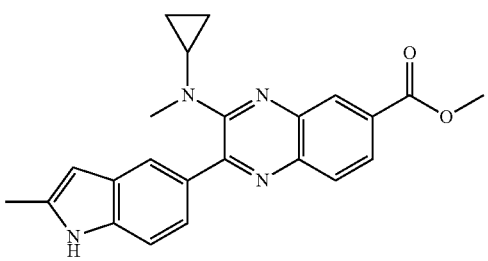

To a solution of methyl 2-bromo-3-[cyclopropyl(methyl)amino]quinoxaline-6-carboxylate (200 mg, 0.59 mmol) in DME (5 ml) and water (2 ml) was added Pd(PPh3)4 (35 mg, 0.03 mmol), potassium carbonate (164 mg, 1.19 mmol), 2-methyl-5-(tetramethyl-1,3,2-dioxaborolan-2-yl)-1H-indole (305 mg, 1.19 mmol) with stirring for 2 h at 90° C. in an oil bath. The resulting solution was diluted with water (150 ml), extracted with dichloromethane (2×40 ml), dried over anhydrous sodium sulfate, then concentrated under vacuum to give a residue, which was purified via silica gel chromatography (1%-20% ethyl acetate in petroleum ether) to give methyl 3-[cyclopropyl(methyl)amino]-2-(2-methyl-M-indol-5-yl)quinoxaline-6-carboxylate as a yellow solid (74.4 mg, 32%).

LC/MS (ES, m/z): [M+H]+ 387.1

1H-NMR (300 MHz, CD3OD) δ 8.46 (d, J=1.5 Hz, 1H), 8.01-8.05 (m, 1H), 7.90-7.96 (m, 1H), 7.89 (s, 1H), 7.49-7.52 (m, 1H), 7.37-7.40 (m, 1H), 6.25 (s, 1H), 4.00 (s, 3H), 3.01 (s, 3H), 2.55-2.59 (m, 1H), 2.46 (s, 3H), 0.47-0.55 (m, 4H)

Step 5. 3-[Cyclopropyl(methyl)amino]-2-(2-methyl-1H-indol-5-yl)quinoxaline-6-carboxylic acid

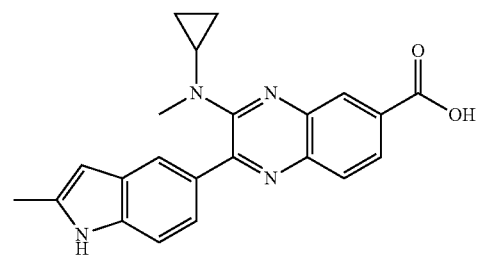 [SMILES: Cc1cc2cc(-c3nc4ccc(C(=O)O)cc4nc3N(C)C3CC3)ccc2[nH]1]

To a solution of methyl 3-[cyclopropyl(methyl)amino]-2-(2-methyl-1H-indol-5-yl)quinoxaline-6-carboxylate (74.7 mg, 0.19 mmol) in methanol (30 ml) was added NaOH (32 mg, 0.80 mmol), water (1 ml) with stirring overnight at room temperature. The resulting solution was extracted ethyl acetate (2×50 ml), and adjusted pH to 5 with AcOH. The resulting solution was extracted with ethyl acetate (3×30 ml), dried over anhydrous sodium sulfate, concentrated under vacuum to give a residue, which was purified via silica gel chromatography (20% methanol in ethyl acetate) to afford 3-[cyclopropyl(methyl)amino]-2-(2-methyl-1H-indol-5-yl)quinoxaline-6-carboxylic acid as a yellow solid (13.6 mg, 19%).

LC/MS (ES, m/z): [M+H]$^+$ 373.1

$^1$H-NMR (300 MHz, CD$_3$OD) δ 8.46 (d, J=1.8 Hz, 1H), 8.02-8.06 (m, 1H), 7.89-7.95 (m, 2H), 7.49-7.53 (m, 1H), 7.38-7.40 (m, 1H), 6.25 (s, 1H), 3.00 (s, 3H), 2.57-2.60 (m, 1H), 2.47 (s, 3H), 1.32 (m, 1H), 0.50-0.55 (m, 4H)

Example 90

3-[Methyl(propan-2-yl)amino]-2-(1-methyl-1H-pyrazol-4-yl)quinoxaline-6-carboxylic acid

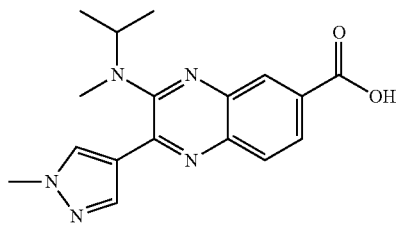 [SMILES: CC(C)N(C)c1nc2cc(C(=O)O)ccc2nc1-c1cnn(C)c1]

Step 1. Methyl 3-[methyl(propan-2-yl)amino]-2-(1-methyl-1H-pyrazol-4-yl)quinoxaline-6-carboxylate

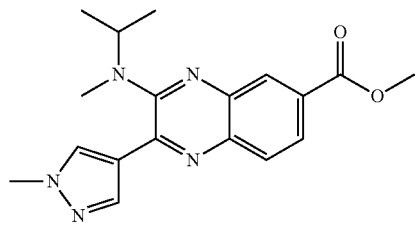

To a solution of methyl 3-[methyl(propan-2-yl)amino]-2-[(trifluoromethane)sulfonyloxy]quinoxaline-6-carboxylate (200 mg, 0.49 mmol) in ethylene glycol dimethyl ether (3 mL) was added Pd(PPh$_3$)$_4$ (28 mg, 0.02 mmol), 1-methyl-4-(tetramethyl-1,3,2-dioxaborolan-2-yl)-1H-pyrazole (205 mg, 0.99 mmol), Na$_2$CO$_3$ (130 mg, 1.23 mmol) and water (5 drops). The resulting solution was stirred for 1 h at 90° C. under an inert atmosphere of nitrogen, and then concentrated under vacuum to give a residue. The residue was purified via silica gel chromatography (1%-10% ethyl acetate in petroleum ether) to afford methyl 3-[methyl(propan-2-yl)amino]-2-(1-methyl-1H-pyrazol-4-yl)quinoxaline-6-carboxylate as a yellow solid (80 mg, 48%).

LC/MS (ES, m/z): [M+H]$^+$ 340.0

$^1$H-NMR (300 MHz, CDCl$_3$) δ 8.52 (d, J=1.8 Hz, 1H), 8.21 (d, J=6.3 Hz, 2H), 8.07-8.11 (m, 1H), 7.94 (d, J=8.7 Hz, 1H), 4.18-4.27 (m, 1H), 4.00 (d, J=6.6 Hz, 6H), 2.85 (s, 3H), 1.18 (d, J=6.6 Hz, 6H)

Step 2. 3-[Methyl(propan-2-yl)amino]-2-(1-methyl-1H-pyrazol-4-yl)quinoxaline-6-carboxylic acid

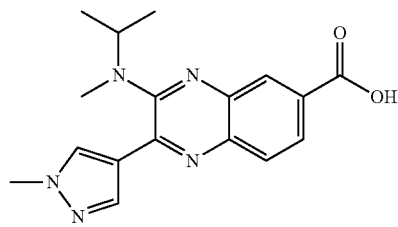 [SMILES: CC(C)N(C)c1nc2cc(C(=O)O)ccc2nc1-c1cnn(C)c1]

To a solution of methyl 3-[methyl(propan-2-yl)amino]-2-(1-methyl-1H-pyrazol-4-yl)quinoxaline-6-carboxylate (80 mg, 0.24 mmol) in methanol (20 mL) and CHCl$_3$ (5 mL) was added sodium hydroxide (75 mg, 0.72 mmol) and water (1 mL). The resulting solution was stirred for overnight at room temperature and concentrated under vacuum. The residue was dissolved in water (15 mL) and adjusted to pH 5 with hydrochloric acid (3N). The solids were collected by filtration to afford 3-[methyl(propan-2-yl)amino]-2-(1-methyl-1H-pyrazol-4-yl)quinoxaline-6-carboxylic acid as a yellow solid (70 mg, 91%).

LC/MS (ES, m/z): [M+H]$^+$ 326.1

$^1$H-NMR (300 MHz, DMSO) δ 13.10 (s, 1H), 8.41 (s, 1H), 8.25 (d, J=1.8 Hz, 1H), 8.08 (s, 1H), 7.95-7.99 (m, 1H), 7.88 (d, J=8.7 Hz, 1H), 4.11-4.20 (m, 1H), 3.95 (s, 3H), 2.74 (s, 3H), 1.13 (d, J=6.6 Hz, 6H)

Example 91

3-[Methyl(propan-2-yl)amino]-2-(1-phenyl-1H-pyrazol-4-yl)quinoxaline-6-carboxylic acid

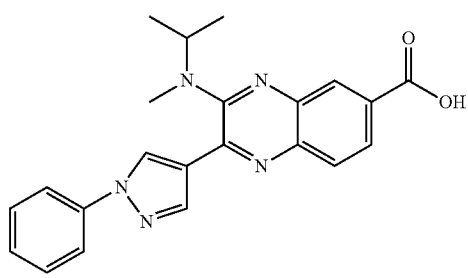 [SMILES: CC(C)N(C)c1nc2cc(C(=O)O)ccc2nc1-c1cnn(-c2ccccc2)c1]

Step 1. Methyl 3-[methyl(propan-2-yl)amino]-2-(1H-pyrazol-4-yl)quinoxaline-6-carboxylate

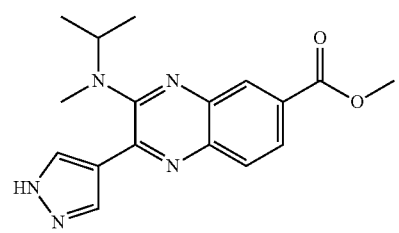 [SMILES: COC(=O)c1ccc2nc(-c3cn[nH]c3)c(N(C)C(C)C)nc2c1]

To a solution of methyl 2-chloro-3-[methyl(propan-2-yl)amino]quinoxaline-6-carboxylate (170 mg, 0.58 mmol) in 1,4-dioxane (6 ml) was added (1H-pyrazol-4-yl)boronic acid (130 mg, 1.16 mmol), Pd(PPh$_3$)$_4$ (34 mg, 0.029 mmol), K$_3$PO$_4$ (367 mg, 1.74 mmol) and water (5 drops) with stirring for 1 h at 90° C. under an inert atmosphere of nitrogen in an oil bath. The reaction mixture was concentrated under vacuum to give the residue, which was purified via silica gel chromatography (1% to 10% ethyl acetate in petroleum ether) to afford methyl 3-[methyl(propan-2-yl)amino]-2-(1H-pyrazol-4-yl)quinoxaline-6-carboxylate as a yellow solid (150 mg, 79%).

LC/MS (ES, m/z): [M+H]$^+$ 326.0

$^1$H-NMR (300 MHz, CDCl$_3$) δ 8.53 (d, J=1.8 Hz, 1H), 8.40 (s, 2H), 8.08-8.12 (m, 1H), 7.94 (d, J=8.4 Hz, 1H), 4.16-4.25 (m, 1H), 4.00 (s, 3H), 2.85 (m, 3H), 1.19 (d, J=6.6 Hz, 6H)

Step 2. Methyl 3-[methyl(propan-2-yl)amino]-2-(1-phenyl-1H-pyrazol-4-yl)quinoxaline-6-carboxylate

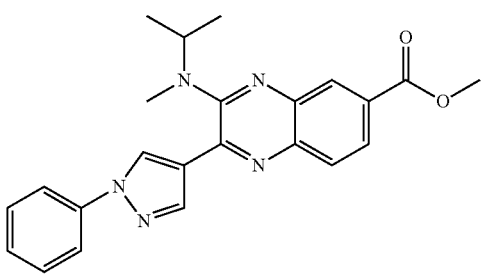 [SMILES: COC(=O)c1ccc2nc(-c3cnn(-c4ccccc4)c3)c(N(C)C(C)C)nc2c1]

To a solution of methyl 3-[methyl(propan-2-yl)amino]-2-(1H-pyrazol-4-yl)quinoxaline-6-carboxylate (150 mg, 0.46 mmol) in dioxane (10 mL) was added phenylboronic acid (112 mg, 0.92 mmol), Cu(OAc)$_2$ (123 mg, 0.68 mmol), pyridine (31 mg, 0.39 mmol) and Et$_3$N (310 mg, 2.3 mmol). The resulting solution was stirred for 36 h at room temperature and concentrated under vacuum. The residue was purified via silica gel chromatography (1% to 5% ethyl acetate in petroleum ether) to afford methyl 3-[methyl(propan-2-yl)amino]-2-(1-phenyl-1H-pyrazol-4-yl)quinoxaline-6-carboxylate as a yellow solid (80 mg, 43%).

LC/MS (ES, m/z): [M+H]$^+$ 402.0

$^1$H-NMR (300 MHz, CDCl$_3$) δ 8.77 (s, 1H), 8.55 (d, J=1.8 Hz, 1H), 8.45 (s, 1H), 8.10-8.13 (m, 1H), 7.97 (d, J=8.7 Hz, 1H), 7.82 (d, J=7.8 Hz, 2H), 7.50-7.56 (m, 2H), 7.34-7.40 (m, 1H), 4.22-4.31 (m, 1H), 4.00 (s, 3H), 2.90 (s, 3H), 1.22 (d, J=6.6 Hz, 6H)

Step 3. 3-[Methyl(propan-2-yl)amino]-2-(1-phenyl-1H-pyrazol-4-yl)quinoxaline-6-carboxylic acid

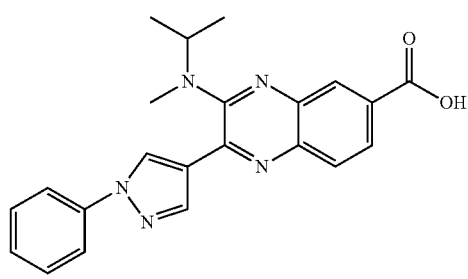 [SMILES: CC(C)N(C)c1nc2cc(C(=O)O)ccc2nc1-c1cnn(-c2ccccc2)c1]

To a solution of methyl 3-[methyl(propan-2-yl)amino]-2-(1-phenyl-1H-pyrazol-4-yl)quinoxaline-6-carboxylate (80 mg, 0.20 mmol) in methanol (25 ml) and chloroform (5 ml) was added sodium hydroxide (24 mg, 0.60 mmol) with stirring overnight at room temperature. The reaction mixture was concentrated under vacuum, dissolved in water (15 ml), and the pH adjusted to 5 with HCl (3N) to give the precipitate, which was collected by filtration to afford 3-[methyl(propan-2-yl)amino]-2-(1-phenyl-1H-pyrazol-4-yl)quinoxaline-6-carboxylic acid (56 mg, 73%).

LC/MS (ES, m/z): [M+H]$^+$ 388.1

$^1$H-NMR (300 MHz, CDCl$_3$) δ 9.11 (s, 1H), 8.37 (s, 1H), 8.28 (d, J=1.8 Hz, 1H), 7.92-8.03 (m, 4H), 7.53-7.59 (t, J=7.8 Hz, 2H), 7.36-7.41 (t, J=7.5 Hz, 1H), 4.15-4.24 (m, 1H), 2.82 (s, 3H), 1.14 (d, J=6.6 Hz, 6H)

Example 92

(S)-2-(1H-indazol-5-yl)-3-(2-methyl-4-(pyridin-2-yl)piperazin-1-yl)quinoxaline-6-carboxylic acid

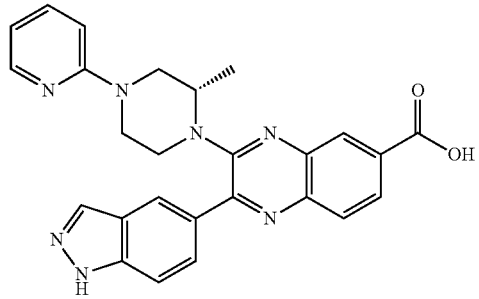 [SMILES: C[C@H]1CN(c2ccccn2)CCN1c1nc2cc(C(=O)O)ccc2nc1-c1ccc2[nH]ncc2c1]

Step 1. (S)-tert-Butyl 2-methyl-4-(pyridin-2-yl)piperazine-1-carboxylate

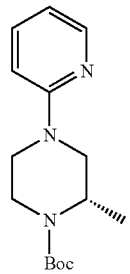

To a solution of tert-butyl (2S)-2-methylpiperazine-1-carboxylate (8 g, 39.94 mmol) in DMSO (25 ml) was added 2-bromopyridine (6.594 g, 41.74 mmol), and DIEA (15.48 g, 119.78 mmol). After stirring 2 days at 120° C., the resulting solution was quenched by the addition of DCM (200 ml), washed with water (3×300 ml), dried over anhydrous magnesium sulfate and concentrated under reduced pressure to afford a residue, which was purified via silica gel chromatography (3% ethyl acetate in petroleum ether) to afford (S)-tert-butyl 2-methyl-4-(pyridin-2-yl)piperazine-1-carboxylate as a red oil (5.2 g, 47%).

LC/MS (ES, m/z): [M+H]$^+$ 278.0

$^1$H-NMR (300 MHz, CDCl$_3$) δ 8.18-8.20 (t, J=1.8 Hz, 1H), 7.46-7.52 (m, 1H), 6.60-6.64 (m, 2H), 4.33-4.35 (m, 1H), 4.08-4.15 (m, 1H), 3.91-4.00 (m, 2H), 3.19-3.31 (m, 2H), 2.92-3.01 (m, 1H), 1.50 (s, 9H), 1.27-1.30 (t, J=4.5 Hz, 3H)

Step 2. (S)-3-Methyl-1-(pyridin-2-yl)piperazine

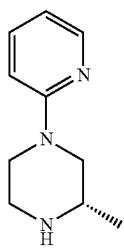

To a solution of (S)-tert-butyl 2-methyl-4-(pyridin-2-yl)piperazine-1-carboxylate (5.2 g, 18.75 mmol,) in dichloromethane (30 ml) was added trifluoroacetic acid (5 ml). After stirring overnight at room temperature, the pH was adjusted to 8 with an aqueous sodium carbonate solution, extracted with dichloromethane (3×150 ml), dried over anhydrous magnesium sulfate and concentrated under vacuum to afford (S)-3-methyl-1-(pyridin-2-yl)piperazine as yellow oil (3.1 g, 93%).

LC/MS (ES, m/z): [M+H]+ 178.0

Step 3. (S)-Methyl 3-(2-methyl-4-(pyridin-2-yl)piperazin-1-yl)-2-oxo-1,2-dihydroquinoxaline-6-carboxylate

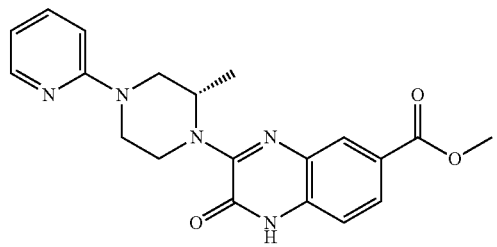 [SMILES: COC(=O)c1ccc2[nH]c(=O)c(N3CCN(c4ccccn4)C[C@@H]3C)nc2c1]

To a solution of (S)-3-methyl-1-(pyridin-2-yl)piperazine (748 mg, 4.22 mmol) in NMP (5 ml), was added methyl 3-chloro-2-oxo-1,2-dihydroquinoxaline-6-carboxylate (1 g, 4.19 mmol). After stirring 1 h at 140° C., the resulting solution was quenched by the addition of water (100 ml) and filtered to give (S)-methyl 3-(2-methyl-4-(pyridin-2-yl)piperazin-1-yl)-2-oxo-1,2-dihydroquinoxaline-6-carboxylate as a yellow solid (1.07 g, 67%).

LC/MS (ES, m/z): [M+H]+ 380

$^1$H-NMR (300 MHz, CDCl$_3$) δ 9.86 (s, 1H), 8.24 (d, J=1.2 Hz, 2H), 7.87-7.91 (m, 1H), 7.51-7.56 (m, 1H), 7.08 (d, J=8.4 Hz, 2H), 6.64-6.70 (t, J=8.7 Hz, 2H), 5.40 (s, 1H), 4.89-4.50 (m, 1H), 4.15-4.25 (m, 1H), 4.07-4.14 (m, 1H), 3.96 (s, 3H), 3.63-3.72 (m, 1H), 3.45-3.50 (m, 1H), 3.20-3.25 (m, 1H), 1.41 (d, J=6.6 Hz, 3H)

Step 4. (S)-Methyl 3-(2-methyl-4-(pyridin-2-yl)piperazin-1-yl)-2-(trifluoromethylsulfonyloxy)quinoxaline-6-carboxylate

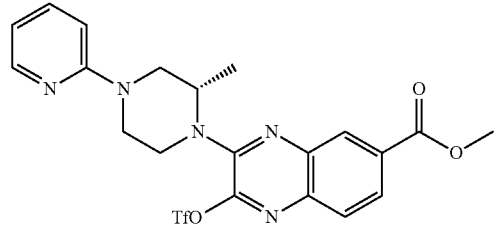 [SMILES: COC(=O)c1ccc2nc(OS(=O)(=O)C(F)(F)F)c(N3CCN(c4ccccn4)C[C@@H]3C)nc2c1]

To a solution of (S)-methyl 3-(2-methyl-4-(pyridin-2-yl)piperazin-1-yl)-2-oxo-1,2-dihydroquinoxaline-6-carboxylate (800 mg, 2.11 mmol) in dichloromethane (20 ml) under an inert atmosphere of nitrogen, was added TEA (958 mg, 9.47 mmol) followed by addition of Tf$_2$O (1.19 g, 4.22 mmol) dropwise at −60° C. After stirring 5 min at this temperature, the reaction was quenched by the addition of water (100 ml), extracted with dichloromethane (2×30 ml), dried over anhydrous magnesium sulfate and concentrated under vacuum to give a residue, which was purified via silica gel chromatography (2% ethyl acetate in petroleum ether) to afford (S)-methyl 3-(2-methyl-4-(pyridin-2-yl)piperazin-1-yl)-2-(trifluoromethylsulfonyloxy)quinoxaline-6-carboxylate as red oil (0.9 g, 83.4%).

Step 5. (S)-Methyl 2-(1-(tert-butoxycarbonyl)-1H-indazol-5-yl)-3-(2-methyl-4-(pyridin-2-yl)piperazin-1-yl)quinoxaline-6-carboxylate

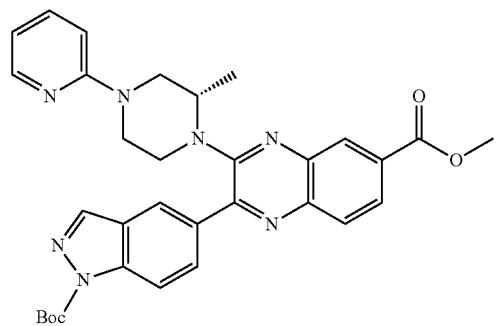 [SMILES: COC(=O)c1ccc2nc(-c3ccc4c(cnn4C(=O)OC(C)(C)C)c3)c(N3CCN(c4ccccn4)C[C@@H]3C)nc2c1]

To a solution of (S)-methyl 3-(2-methyl-4-(pyridin-2-yl)piperazin-1-yl)-2-(trifluoromethylsulfonyloxy)quinoxaline-6-carboxylate (240 mg, 0.38 mmol) in ethylene glycol dimethyl ether (20 ml) was added Pd(PPh$_3$)$_4$ (27 mg, 0.02 mmol), sodium carbonate (74.3 mg, 0.69 mmol) in water (6 ml), and tert-butyl 5-(tetramethyl-1,3,2-dioxaborolan-2-yl)-1H-indazole-1-carboxylate (300 mg, 0.87 mmol). After stirring 90 minutes at 90° C. in an oil bath, the reaction was then quenched by the addition of water (200 ml), extracted with dichloromethane (3×30 ml), dried over anhydrous magnesium sulfate and concentrated under vacuum to afford a residue, which was purified via silica gel chromatography (20% ethyl acetate in petroleum ether) to afford (S)-methyl 2-(1-(tert-butoxycarbonyl)-1H-indazol-5-yl)-3-(2-methyl-4-(pyridin-2-yl)piperazin-1-yl)quinoxaline-6-carboxylate as a yellow solid (134 mg, 60%).

LC/MS (ES, m/z): [M+H]+ 580

¹H-NMR (300 MHz, CDCl₃) δ 8.59 (d, J=1.5 Hz, 1H), 8.49 (s, 1H), 8.19-8.29 (m, 3H), 8.14-8.18 (m, 2H), 8.03 (d, J=8.7 Hz, 1H), 7.50-7.51 (m, 1H), 6.63-6.66 (m, 2H), 4.13-4.18 (t, J=7.2 Hz, 2H), 4.06 (s, 3H), 3.78-3.85 (m, 1H), 3.61-3.70 (m, 1H), 3.40-3.55 (m, 1H), 3.10-3.35 (m, 2H), 1.78 (s, 9H), 1.21 (d, J=6.3 Hz, 3H)

Step 6. (S)-Methyl 2-(1H-indazol-5-yl)-3-(2-methyl-4-(pyridin-2-yl)piperazin-1-yl)quinoxaline-6-carboxylate

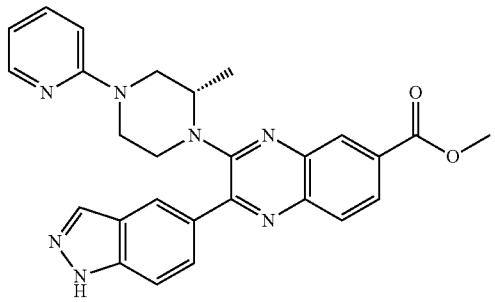 [SMILES: COC(=O)c1ccc2nc(-c3ccc4[nH]ncc4c3)c(N3CCN(c4ccccn4)C[C@@H]3C)nc2c1]

To a solution of (S)-methyl 2-(1-(tert-butoxycarbonyl)-M-indazol-5-yl)-3-(2-methyl-4-(pyridin-2-yl)piperazin-1-yl)quinoxaline-6-carboxylate (112 mg, 0.19 mmol) in dichloromethane (20 ml), was added trifluoroacetic acid (2 ml). After stirring 100 min at room temperature, the pH was adjusted to 8 with saturated sodium bicarbonate, extracted with dichloromethane (3×20 mL), dried over anhydrous magnesium sulfate and concentrated under vacuum to afford a residue, which was purified via silica gel chromatography (30% petroleum ether in ethyl acetate) to afford (S)-methyl 2-(1H-indazol-5-yl)-3-(2-methyl-4-(pyridin-2-yl)piperazin-1-yl)quinoxaline-6-carboxylate as a yellow solid (78 mg, 84%).

LC/MS (ES, m/z): [M+H]⁺ 480.1

¹H-NMR (300 MHz, CDCl₃) δ 8.58 (d, J=1.5 Hz, 1H), 8.53 (s, 1H), 8.13-8.19 (m, 3H), 8.03 (d, J=8.7 Hz, 1H), 7.63 (d, J=8.1 Hz, 1H), 7.45-7.60 (m, 1H), 6.66 (d, J=6.0 Hz, 2H), 4.20 (s, 1H), 4.08 (s, 1H), 4.02 (s, 3H), 3.80-3.85 (m, 1H), 3.65-3.69 (m, 1H), 3.43-3.51 (m, 1H), 3.19-3.32 (m, 2H), 1.22-1.28 (m, 3H)

Step 7. (S)-2-(1H-Indazol-5-yl)-3-(2-methyl-4-(pyridin-2-yl)piperazin-1-yl)quinoxaline-6-carboxylic acid

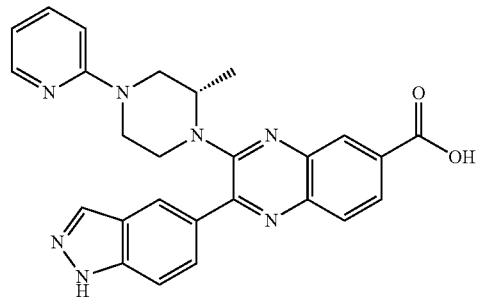 [SMILES: C[C@H]1CN(c2ccccn2)CCN1c1nc2cc(C(=O)O)ccc2nc1-c1ccc2[nH]ncc2c1]

To a solution of (S)-methyl 2-(1H-indazol-5-yl)-3-(2-methyl-4-(pyridin-2-yl)piperazin-1-yl)quinoxaline-6-carboxylate (47 mg, 0.10 mmol) in methanol (15 ml) was added NaOH (15.6 mg, 0.39 mmol) and water (1 mL). After stirring 6 h at room temperature, the reaction mixture was concentrated under reduced pressure to afford a residue, which was dissolved in water (10 ml), adjusted to pH 6 with HCl (3N). The solids were filtered to give (S)-2-(1H-indazol-5-yl)-3-(2-methyl-4-(pyridin-2-yl)piperazin-1-yl)quinoxaline-6-carboxylic acid as a yellow solid (40 mg, 88%).

LC/MS (ES, m/z): [M+H]⁺ 466.2

¹H-NMR (300 MHz, CD₃OD) δ 8.52 (d, J=1.8 Hz, 2H), 8.23 (s, 1H), 7.87-8.17 (m, 5H), 7.74 (d, J=8.7 Hz, 1H), 7.21 (d, J=9.0 Hz, 1H), 6.89-6.93 (t, J=6.3 Hz, 1H), 4.29-4.32 (m, 1H), 3.97-4.01 (m, 1H), 3.73-3.86 (m, 2H), 3.34-3.59 (m, 3H), 1.21 (d, J=6.6 Hz, 3H)

Example 93

(S)-7-Hydroxy-2-(1H-indazol-5-yl)-3-(2-methylpyrrolidin-1-yl)quinoxaline-6-carboxylic acid

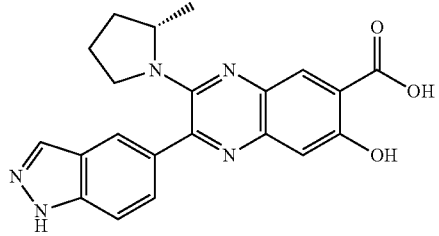 [SMILES: C[C@H]1CCCN1c1nc2cc(C(=O)O)c(O)cc2nc1-c1ccc2[nH]ncc2c1]

Step 1. (S)-Methyl 2-(1-(tert-butoxycarbonyl)-1H-indazol-5-yl)-7-methoxy-3-(2-methylpyrrolidin-1-yl)quinoxaline-6-carboxylate

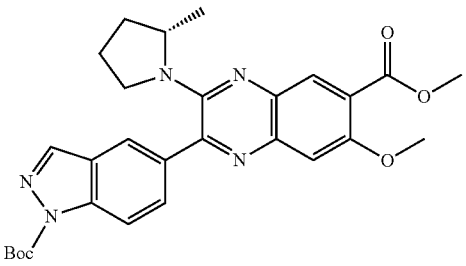 [SMILES: COC(=O)c1cc2nc(N3CCC[C@@H]3C)c(-c3ccc4c(cnn4C(=O)OC(C)(C)C)c3)nc2cc1OC]

To a solution of methyl 7-methoxy-3-[(2S)-2-methylpyrrolidin-1-yl]-2-[(trifluoromethane)sulfonyloxy]quinoxaline-6-carboxylate (359 mg, 0.80 mmol) in DME (4 ml) and water (1 ml) was added tert-butyl 5-(tetramethyl-1,3,2-dioxaborolan-2-yl)-1H-indazole-1-carboxylate (275 mg, 0.80 mmol), sodium carbonate (200 mg, 1.87 mmol) and Pd(PPh₃)₄ (43 mg, 0.04 mmol) under nitrogen atmosphere. After stirring 30 min at 90° C., the reaction mixture was dissolved in water (100 ml), extracted with dichloromethane (3×30 ml), dried over anhydrous magnesium sulfate and concentrated under reduced pressure to afford a residue, which was purified via silica gel chromatography (2% ethyl acetate in petroleum ether) to afford (S)-methyl 2-(1-(tert-butoxycarbonyl)-1H-indazol-5-yl)-7-methoxy-3-(2-methylpyrrolidin-1-yl)quinoxaline-6-carboxylate as a light yellow solid (310 mg, crude).

LC/MS (ES, m/z): [M+H]⁺ 518.0

Step 2. (S)-Methyl 2-(1H-indazol-5-yl)-7-methoxy-3-(2-methylpyrrolidin-1-yl)quinoxaline-6-carboxylate

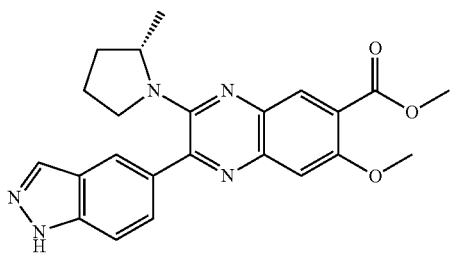 [SMILES: COC(=O)c1cc2nc(N3CCC[C@@H]3C)c(-c3ccc4[nH]ncc4c3)nc2cc1OC]

To a solution of (S)-methyl 2-(1-(tert-butoxycarbonyl)-1H-indazol-5-yl)-7-methoxy-3-(2-methylpyrrolidin-1-yl)quinoxaline-6-carboxylate (310 mg, crude) in dichloromethane (32 ml) was added trifluoroacetic acid (8 ml). After stirring overnight at room temperature, the pH value was adjusted to 7 with aqueous sodium bicarbonate and extracted with dichloromethane (2×25 ml). The organic layers were combined, dried over anhydrous magnesium sulfate and concentrated under vacuum to give a residue, which was purified via silica gel chromatography (10% ethyl acetate in petroleum ether) to give (S)-methyl 2-(1H-indazol-5-yl)-7-methoxy-3-(2-methylpyrrolidin-1-yl)quinoxaline-6-carboxylate (240 mg) as yellow solid.

LC/MS (ES, m/z): [M+H]$^+$ 418.1

$^1$H-NMR (300 MHz, CDCl$_3$) δ 8.28 (s, 1H), 8.20-8.22 (m, 2H), 7.87-7.90 (m, 1H), 7.60 (d, J=8.7 Hz, 1H), 7.43 (s, 1H), 4.28-4.39 (m, 1H), 4.00 (s, 6H), 3.05-3.15 (m, 1H), 2.89-2.96 (m, 1H), 2.10-2.20 (m, 1H), 1.59-1.76 (m, 3H), 1.48 (d, J=6.9 Hz, 3H)

Step 3. (S)-Methyl 7-hydroxy-2-(1H-indazol-5-yl)-3-(2-methylpyrrolidin-1-yl)quinoxaline-6-carboxylate

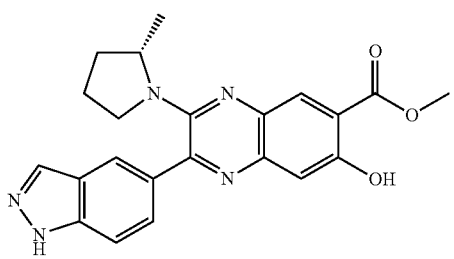 [SMILES: COC(=O)c1cc2nc(N3CCC[C@@H]3C)c(-c3ccc4[nH]ncc4c3)nc2cc1O]

To a solution of (S)-methyl 2-(1H-indazol-5-yl)-7-methoxy-3-(2-methylpyrrolidin-1-yl)quinoxaline-6-carboxylate (208 mg, 0.50 mmol) in dichloromethane (20 ml) was added BBr$_3$ (0.37 g, 0.75 mmol) at −60° C. The resulting solution was stirred for 0.5 h at −60° C. The reaction was then quenched by the addition of water/ice (200 ml), extracted with dichloromethane (4×50 ml), and the organic layers combined, dried over anhydrous magnesium sulfate, and concentrated under vacuum to give the residue, which was purified via silica gel chromatography (10% ethyl acetate in petroleum ether) to afford (S)-methyl 7-hydroxy-2-(1H-indazol-5-yl)-3-(2-methylpyrrolidin-1-yl)quinoxaline-6-carboxylate as a yellow solid (180 mg, 90%).

LC/MS (ES, m/z): [M+H]+ 404.0

$^1$H-NMR (300 MHz, CDCl$_3$) δ10.46 (s, 1H), 8.43 (s, 1H), 8.25 (d, J=0.6 Hz, 1H), 8.20 (s, 1H), 7.90-7.94 (m 1H), 7.60 (d, J=8.7 Hz, 1H), 7.48 (s, 1H), 4.26-4.33 (m, 1H), 4.00 (s, 3H), 3.04-3.13 (m, 1H), 2.89-2.96 (m, 1H), 2.14 (d, J=6.9 Hz, 1H), 1.50-1.80 (m, 3H), 1.38 (d, J=6.0 Hz, 3H)

Step 4. (S)-7-Hydroxy-2-(1H-indazol-5-yl)-3-(2-methylpyrrolidin-1-yl)quinoxaline-6-carboxylic acid

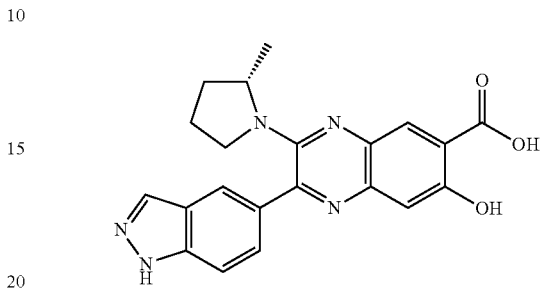

To a solution of (S)-methyl 7-hydroxy-2-(1H-indazol-5-yl)-3-(2-methylpyrrolidin-1-yl)quinoxaline-6-carboxylate (120 mg, 0.30 mmol) in methanol (10 ml) was added NaOH (48 mg, 1.27 mmol) and water (1 ml). The resulting solution was stirred overnight at room temperature and concentrated under vacuum. The residue was dissolved in water (15 ml) and adjusted to pH 5 with hydrochloric acid (1N). The solids were collected by filtration to afford (S)-7-hydroxy-2-(1H-indazol-5-yl)-3-(2-methylpyrrolidin-1-yl)quinoxaline-6-carboxylic acid as a yellow solid (65.6 mg, 56%).

LC/MS (ES, m/z): [M+H]+ 390.1

$^1$H-NMR (300 MHz, DMSO) δ 13.24 (s, 1H), 8.21 (s, 1H), 8.16 (d, J=3.3 Hz, 1H), 7.77-7.80 (m, 1H), 7.64 (d, J=8.7 Hz, 1H), 7.13 (s, 1H), 4.12-4.18 (m, 1H), 2.87-3.01 (m, 1H), 2.72-2.84 (m, 1H), 2.01-2.18 (m, 1H), 1.69-1.80 (m, 1H), 1.47-1.57 (m, 2H), 1.30 (s, 3H)

Example 94

2-(1H-Benzo[d][1,2,3]triazol-5-yl)-3-(isopropyl(methyl)amino)quinoxaline-6-carboxylic acid

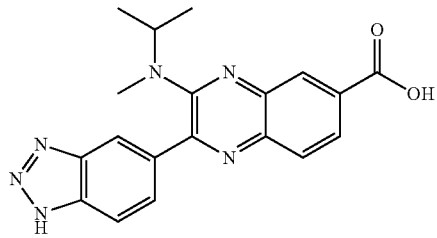 [SMILES: CC(C)N(C)c1nc2cc(C(=O)O)ccc2nc1-c1ccc2[nH]nnc2c1]

Step 1. 2-Nitro-4-(4,4,5,5-tetramethyl-1,3,2-dioxaborolan-2-yl)aniline

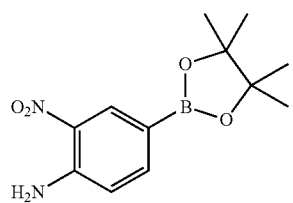 [SMILES: CC1(C)OB(c2ccc(N)c([N+](=O)[O-])c2)OC1(C)C]

To a solution of 4-bromo-2-nitrobenzenamine (4 g, 18.43 mmol) in 1,4-dioxane (100 mL) was added KOAc (5.4 g, 55.02 mmol), Pd(dppf)Cl$_2$ (405 mg, 0.55 mmol), dppf (307 mg, 0.55 mmol) and 4,4,4',4',5,5,5',5'-octamethyl-2,2'-bi(1,3,2-dioxaborolane (5.15 g, 20.28 mmol). The resulting solution was stirred overnight at 85° C. Then the reaction was quenched by the addition of water (200 mL), extracted with ethyl acetate (3×80 mL), dried over anhydrous sodium sulfate, and concentrated under vacuum to give a residue, which was purified via silica gel chromatography (petroleum ether) to afford 2-nitro-4-(4,4,5,5-tetramethyl-1,3,2-dioxaborolan-2-yl)aniline as a yellow solid (4.2 g, 86%).

$^1$H-NMR (300 MHz, CDCl$_3$) δ 8.60 (d, J=0.9 Hz, 1H), 7.72-7.75 (m, 1H), 6.79 (d, J=8.4 Hz, 1H), 6.24 (s, 2H), 1.35 (s, 12H)

Step 2. Methyl 2-(4-amino-3-nitrophenyl)-3-(isopropyl(methyl)amino)quinoxaline-6-carboxylate

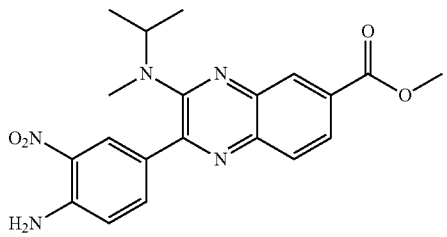

To a solution of methyl 3-(isopropyl(methyl)amino)-2-(trifluoromethylsulfonyloxy)quinoxaline-6-carboxylate (1.0 g, 2.46 mmol) in DME (10 mL) was added 2-nitro-4-(4,4,5,5-tetramethyl-1,3,2-dioxaborolan-2-yl)aniline (0.97 g, 3.69 mmol), Pd(PPh$_3$)$_4$ (90 mg, 0.12 mmol), Na$_2$CO$_3$ (781 mg, 7.38 mmol) and water (2 mL) with stirring for 40 minutes at 90° C. under an inert atmosphere of nitrogen in an oil bath. The reaction mixture was concentrated under vacuum to give the residue, which was purified via silica gel chromatography (1% to 5% ethyl acetate in petroleum ether) to afford methyl 2-(4-amino-3-nitrophenyl)-3-(isopropyl(methyl)amino)quinoxaline-6-carboxylate as a yellow solid (900 mg, 93%).

LC/MS (ES, m/z): [M+H]$^+$ 396.0

$^1$H-NMR (300 MHz, DMSO) δ 8.89 (d, J=1.8 Hz, 1H), 8.54 (d, J=1.8 Hz, 1H), 8.06-8.14 (m, 2H), 7.96 (d, J=8.7 Hz, 1H), 6.90-6.98 (m, 1H), 6.32 (s, 2H), 4.23-4.32 (m, 1H), 4.00 (s, 3H), 2.82 (s, 3H), 1.15 (d, J=6.6 Hz, 6H)

Step 3. Methyl 2-(3,4-diaminophenyl)-3-(isopropyl(methyl)amino)quinoxaline-6-carboxylate

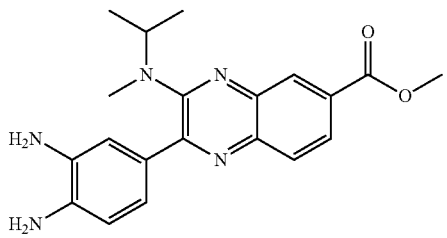 [SMILES: COC(=O)c1ccc2nc(-c3ccc(N)c([N+](=O)[O-])c3)c(N(C)C(C)C)nc2c1]

To a solution of methyl 2-(4-amino-3-nitrophenyl)-3-(isopropyl(methyl)amino)quinoxaline-6-carboxylate (900 mg, 2.28 mmol) in methanol (40 mL) was added iron (1.28 g, 22.8 mmol) and NH$_4$Cl (1.81 g, 34.2 mmol). After stirring for 6 h at 60° C., the solids were filtered out. The filtrate was concentrated under vacuum to give a residue which was dissolved in water (200 mL), extracted with dichloromethane (3×50 mL), dried over anhydrous sodium sulfate and concentrated under vacuum to afford methyl 2-(3,4-diaminophenyl)-3-(isopropyl(methyl)amino)quinoxaline-6-carboxylate as yellow solid (635 mg, crude).

LC/MS (ES, m/z): [M+H]$^+$ 366.0

Step 4. Methyl 2-(1H-benzo[d][1,2,3]triazol-5-yl)-3-(isopropyl(methyl)amino)quinoxaline-6-carboxylate

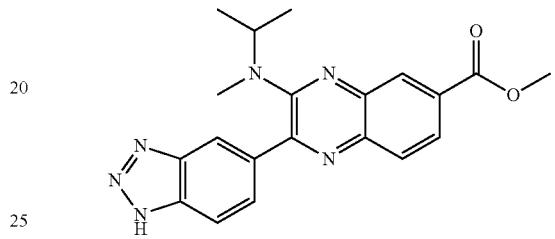

To a solution of methyl 2-(3,4-diaminophenyl)-3-(isopropyl(methyl)amino)quinoxaline-6-carboxylate (635 mg, crude) in HCl (1N, 150 mL) was added sodium nitrite (132 mg, 1.91 mmol) in water (1 mL) at 0° C. After stirring for 15 min at 0° C., the reaction mixture was extracted with dichloromethane (3×50 mL), dried over anhydrous sodium sulfate and concentrated under vacuum to give a residue, which was purified via silica gel chromatography (3% methanol in dichloromethane) to afford methyl 2-(1H-benzo[d][1,2,3]triazol-5-yl)-3-(isopropyl(methyl)amino)quinoxaline-6-carboxylate as a yellow solid (140 mg).

LC/MS (ES, m/z): [M+H]$^+$ 377.1

$^1$H-NMR (300 MHz, DMSO) δ 8.40 (s, 1H), 8.31 (d, J=1.2 Hz, 1H), 7.94-8.03 (m, 4H), 4.16-4.25 (m, 1H), 3.94 (s, 3H), 2.67 (s, 3H), 1.02 (d, J=6.6 Hz, 6H)

Step 5. 2-(1H-Benzo[d][1,2,3]triazol-5-yl)-3-(isopropyl(methyl)amino)quinoxaline-6-carboxylic acid

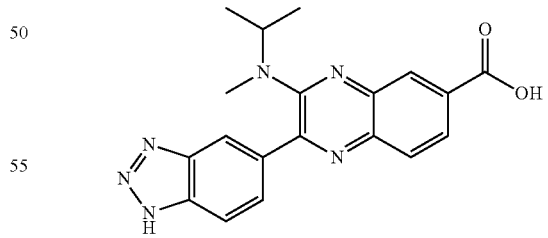

To a solution of methyl 2-(1H-benzo[d][1,2,3]triazol-5-yl)-3-(isopropyl(methyl)amino)quinoxaline-6-carboxylate (140 mg, 0.37 mmol) in methanol (25 mL) and water (5 mL) was added sodium hydroxide (45 mg, 1.11 mmol) with stirring for overnight at room temperature. The reaction mixture was concentrated under vacuum, dissolved in water (20 mL), and adjusted to pH 5 with HCl (3N) to give the precipitate, which was collected by filtration to afford 2-(1H-benzo[d][1, 2,3]triazol-5-yl)-3-(isopropyl(methyl)amino)quinoxaline-6-carboxylic acid as a yellow solid (110 mg, 82%).

LC/MS (ES, m/z): [M+H]+ 363.1

¹H-NMR (300 MHz, CD₃OD) δ 8.46 (d, J=1.5 Hz, 2H), 7.95-8.08 (m, 4H), 4.19-4.28 (m, 1H), 2.79 (s, 3H), 1.08 (d, J=6.6 Hz, 6H)

Example 95

3-(Isopropyl(methyl)amino)-2-(1-methyl-1H-benzo[d][1,2,3]triazol-5-yl)quinoxaline-6-carboxylic acid

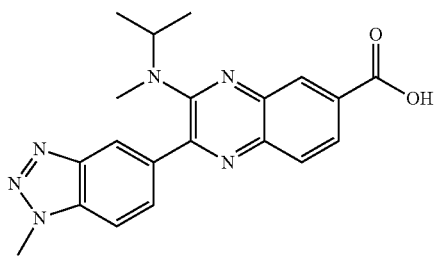 [SMILES: CC(C)N(C)c1nc2cc(C(=O)O)ccc2nc1-c1ccc2c(c1)nnn2C]

Step 1. 4-Bromo-N-methyl-2-nitroaniline

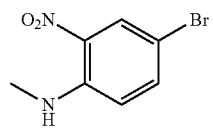

To a solution of 4-bromo-1-fluoro-2-nitrobenzene (6 g, 27.27 mmol) in dichloromethane (100 ml) was added potassium carbonate (7.5 g, 54.27 mmol). This was followed by the addition of CH₃NH₂ (20 ml, 33% aqueous), which was added dropwise with stirring at room temperature. The resulting solution was stirred for 2 h at room temperature, extracted with dichloromethane (2×200 ml), and the organic layers combined and concentrated under vacuum to afford 4-bromo-N-methyl-2-nitroaniline as a red solid (6.1 g, 97%).

LC/MS (ES, m/z): [M+H]+ 231.1

¹H-NMR (300 MHz, CDCl₃) δ 8.34 (d, J=2.4 Hz, 1H), 8.05 (s, 1H), 7.47-7.56 (m, 1H), 6.79 (d, J=3.3 Hz, 1H), 3.03 (d, J=8.1 Hz, 3H)

Step 2. 4-Bromo-N¹-methylbenzene-1,2-diamine

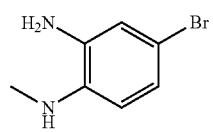

To a solution of 4-bromo-N-methyl-2-nitroaniline (6 g, 25.97 mmol) in ethanol (100 ml) was added SnCl₂.2H₂O (29 g, 128.52 mmol). The resulting solution was stirred for 3 h at 70° C., adjusted to pH 8 with potassium hydroxide (4M), extracted with ethyl acetate (2×200 ml), and the organic layers combined and concentrated under vacuum to afford 4-bromo-N¹-methylbenzene-1,2-diamine as a white solid (5 g, 96%).

LC/MS (ES, m/z): [M+H]+ 202.1

¹H-NMR (300 MHz, CDCl₃) δ 6.93-6.96 (m, 1H), 6.84 (d, J=2.1 Hz, 1H), 6.50 (d, J=8.4 Hz, 1H), 2.85 (s, 3H)

Step 3.
5-Bromo-1-methyl-1H-benzo[d][1,2,3]triazole

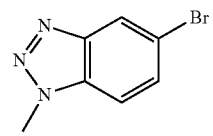

To a solution of 4-bromo-N¹-methylbenzene-1,2-diamine (4.2 g, 21 mmol) in hydrochloric acid (2N, 50 ml) was added a solution of NaNO₂ (1.52 g, 22 mmol) in water (5 ml) at 0° C. The resulting solution was stirred for 4 h at 0-10° C., adjusted to pH 8 with potassium hydroxide (3N), extracted with dichloromethane (2×200 ml), and the organic layers combined and concentrated under vacuum to give a residue, which was purified via silica gel chromatography (50% dichloromethane in petroleum ether) to afford 5-bromo-1-methyl-1H-benzo[d][1,2,3]triazole as a red solid (1.5 g, 31%).

LC/MS (ES, m/z): [M+H]+.213.1

¹H-NMR (300 MHz, CDCl₃) δ 8.24-8.25 (m, 1H), 7.60-7.63 (m, 1H), 7.42-7.46 (m, 1H), 4.32 (d, J=5.4 Hz, 3H)

Step 4. 1-Methyl-5-(4,4,5,5-tetramethyl-1,3,2-dioxaborolan-2-yl)-1H-benzo[d][1,2,3]triazole

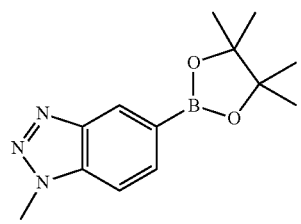 [SMILES: Cn1nnc2cc(B3OC(C)(C)C(C)(C)O3)ccc21]

To a solution of 5-bromo-1-methyl-1H-benzo[d][1,2,3]triazole (600 mg, 2.84 mmol) in dioxane (20 ml) was added Pd(dppf)Cl₂ (86 mg, 0.12 mmol), AcOK (0.575 g, 5.86 mmol), and 4,4,4',4',5,5,5',5'-octamethyl-2,2'-bi(1,3,2-dioxaborolane) (658 mg, 2.59 mmol) under an N₂ atmosphere. The resulting solution was stirred for 12 h at 90° C. and then concentrated under vacuum to give a residue, which was purified via silica gel chromatography (2% ethyl acetate in petroleum ether) to afford 1-methyl-5-(4,4,5,5-tetramethyl-1,3,2-dioxaborolan-2-yl)-1H-benzo[d][1,2,3]triazole as a white solid (0.56 g, 74%).

LC/MS (ES, m/z): [M+H]+.260.1

¹H-NMR (300 MHz, CDCl₃) δ 8.57 (s, 1H), 7.90-7.93 (m, 1H), 7.50-7.55 (m, 1H), 4.33 (s, 3H), 1.36 (s, 12H)

Step 5. Methyl 3-(isopropyl(methyl)amino)-2-(1-methyl-1H-benzo[d][1,2,3]triazol-5-yl)quinoxaline-6-carboxylate

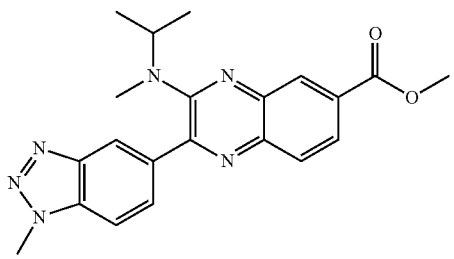 [SMILES: COC(=O)c1ccc2nc(-c3ccc4c(c3)nnn4C)c(N(C)C(C)C)nc2c1]

To a solution of 1-methyl-5-(4,4,5,5-tetramethyl-1,3,2-dioxaborolan-2-yl)-1H-benzo[d][1,2,3]triazole (168 mg, 0.65 mmol) in dioxane (10 ml) was added K₃PO₄ (316 mg, 1.49 mmol), Pd(PPh3)4 (28 mg, 0.02 mmol), and methyl 3-[methyl(propan-2-yl)amino]-2-[(trifluoromethane)sulfonyloxy]quinoxaline-6-carboxylate (203.5 mg, 0.50 mmol). The resulting solution was stirred for 1 h at 90° C. under an N₂ atmosphere. The resulting mixture was concentrated under vacuum to give a residue, which was purified via silica gel chromatography (50% dichloromethane in petroleum ether) to afford methyl 3-(isopropyl(methyl)amino)-2-(1-methyl-1H-benzo[d][1,2,3]triazol-5-yl)quinoxaline-6-carboxylate as a yellow solid (110 mg, 56%).

LC/MS (ES, m/z): [M+H]⁺ 391.1

¹H-NMR (300 MHz, CDCl₃) δ 8.65 (s, 1H), 8.55 (d, J=1.8 Hz, 1H), 7.98-8.17 (m, 3H), 7.65 (d, J=8.7 Hz, 1H), 4.39 (s, 3H), 4.24-4.28 (m, 1H), 4.01 (s, 3H), 2.76 (s, 3H), 1.08 (d, J=6.6 Hz, 6H)

Step 6. 3-(Isopropyl(methyl)amino)-2-(1-methyl-1H-benzo[d][1,2,3]triazol-5-yl)quinoxaline-6-carboxylic acid

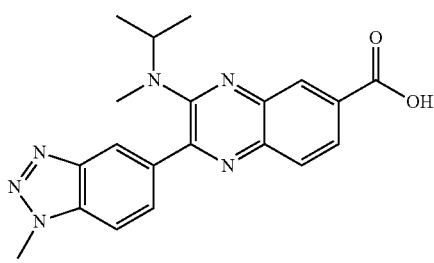 [SMILES: CC(C)N(C)c1nc2cc(C(=O)O)ccc2nc1-c1ccc2c(c1)nnn2C]

To a solution of methyl 3-(isopropyl(methyl)amino)-2-(1-methyl-1H-benzo[d][1,2,3]triazol-5-yl)quinoxaline-6-carboxylate (110 mg, 0.28 mmol) in methanol (10 ml) was added sodium hydroxide (45 mg, 1.12 mmol) and water (2 ml). The resulting solution was stirred for 2 h at room temperature and concentrated under vacuum, diluted with water (10 ml), and the pH adjusted to 4 with HCl (3N). The solid was collected by filtration to afford 3-(isopropyl(methyl)amino)-2-(1-methyl-1H-benzo[d][1,2,3]triazol-5-yl)quinoxaline-6-carboxylic acid as a yellow solid (56.2 mg, 53%).

LC/MS (ES, m/z): [M+H]⁺ 377.1

¹H-NMR (300 MHz, DMSO) δ 13.1 (s, 1H), 8.51 (s, 1H), 8.29 (s, 1H), 7.94-8.08 (m, 4H), 4.38 (s, 3H), 4.15-4.24 (m, 1H), 2.68 (s, 3H), 1.01 (d, J=6.6 Hz, 6H)

Example 96

(S)-2-(1H-Benzo[d][1,2,3]triazol-5-yl)-3-(2-methylpyrrolidin-1-yl)quinoxaline-6-carboxylic acid

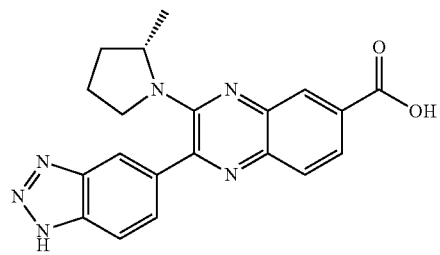 [SMILES: C[C@H]1CCCN1c1nc2cc(C(=O)O)ccc2nc1-c1ccc2[nH]nnc2c1]

Step 1. (S)-Methyl 2-(4-amino-3-nitrophenyl)-3-(2-methylpyrrolidin-1-yl)quinoxaline-6-carboxylate

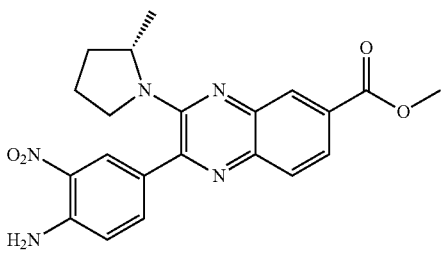

To a solution of 2-nitro-4-(4,4,5,5-tetramethyl-1,3,2-dioxaborolan-2-yl)aniline (1.30 g, 4.92 mmol) in ethylene glycol dimethyl ether (100 mL) was added (S)-methyl 2-chloro-3-(2-methylpyrrolidin-1-yl)quinoxaline-6-carboxylate (1.0 g, 3.27 mmol), sodium carbonate (1.05 g, 9.91 mmol), and Pd(dppf)₂Cl₂ (0.12 g, 0.17 mmol). The resulting solution was stirred for 40 min at 90° C. under an N₂ atmosphere, and then concentrated under vacuum to give a residue, which was purified via silica gel chromatography (2% to 10% ethyl acetate in petroleum ether) to afford (S)-methyl 2-(4-amino-3-nitrophenyl)-3-(2-methylpyrrolidin-1-yl)quinoxaline-6-carboxylate as an orange solid (1.0 g, 57%).

LC/MS (ES, m/z): [M+H]⁺ 408.0

¹H-NMR (300 MHz, CDCl₃) δ 8.68 (d, J=2.1 Hz, 1H), 8.50 (d, J=1.5 Hz, 1H), 7.93-7.98 (m, 2H), 6.94 (d, J=8.7 Hz, 1H), 6.30 (s, 1H), 4.37-4.44 (m, 1H), 3.94 (s, 3H), 3.23-3.32 (m, 1H), 2.97-3.03 (m, 1H), 2.15-2.25 (m, 1H), 1.82-1.90 (m, 1H), 1.58-1.68 (m, 2H), 1.40 (d, J=6.0 Hz, 3H).

Step 2. (S)-Methyl 2-(3,4-diaminophenyl)-3-(2-methylpyrrolidin-1-yl)quinoxaline-6-carboxylate

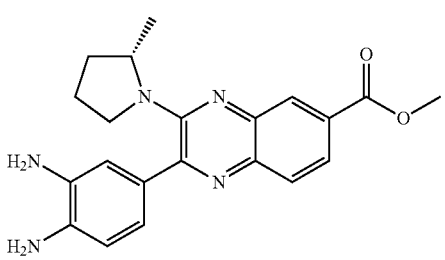 [SMILES: COC(=O)c1ccc2nc(-c3ccc(N)c([N+](=O)[O-])c3)c(N3CCC[C@@H]3C)nc2c1]

To a solution of (S)-methyl 2-(4-amino-3-nitrophenyl)-3-(2-methylpyrrolidin-1-yl)quinoxaline-6-carboxylate (1.0 g, 2.45 mmol) in methanol (40 mL) was added Fe (1.38 g, 24.6 mmol) and NH$_4$Cl (1.3 g, 24.30 mmol). After the resulting solution was stirred for 6 h at 60° C., the solids were filtered out. The filtrate was concentrated under vacuum and dissolved in water (200 mL), extracted with dichloromethane (3×80 mL), dried over anhydrous sodium sulfate and concentrated under vacuum to afford (S)-methyl 2-(3,4-diaminophenyl)-3-(2-methylpyrrolidin-1-yl)quinoxaline-6-carboxylate as yellow solid (970 mg, crude).

LC/MS (ES, m/z): [M+H]$^+$ 378.0

Step 3. (S)-Methyl 2-(1H-benzo[d][1,2,3]triazol-5-yl)-3-(2-methylpyrrolidin-1-yl)quinoxaline-6-carboxylate

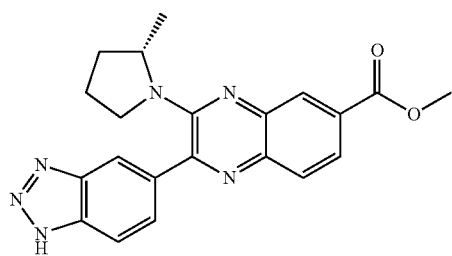 [SMILES: COC(=O)c1ccc2nc(-c3ccc4[nH]nnc4c3)c(N3CCC[C@@H]3C)nc2c1]

To a solution of (S)-methyl 2-(3,4-diaminophenyl)-3-(2-methylpyrrolidin-1-yl)quinoxaline-6-carboxylate (600 mg, crude) in HCl (60 mL, 2N) was added sodium nitrite (164.7 mg, 2.39 mmol) in water (1 mL) dropwise at 0-5° C. The resulting solution was stirred for 15 min at 0° C., then diluted with water (150 mL), extracted with dichloromethane (3×80 mL), dried over anhydrous sodium sulfate and concentrated under vacuum to give a residue, which was purified via silica gel chromatography (1.25% methanol in dichloromethane) to afford (S)-methyl 2-(1H-benzo[d][1,2,3]triazol-5-yl)-3-(2-methylpyrrolidin-1-yl)quinoxaline-6-carboxylate (130 mg).

LC/MS (ES, m/z): [M+H]$^+$ 389.0

$^1$H-NMR (300 MHz, DMSO) δ 8.29 (d, J=1.5 Hz, 1H), 7.98-8.25 (m, 3H), 7.90-7.94 (m, 2H), 7.80-7.90 (m, 1H), 4.25-4.27 (m, 1H), 3.94 (s, 3H), 2.89-2.95 (m, 2H), 2.05-2.15 (m, 1H), 1.65-1.73 (m, 1H), 1.45-1.57 (m, 2H), 1.37 (d, J=6.0 Hz, 3H)

Step 4. (S)-2-(1H-Benzo[d][1,2,3]triazol-5-yl)-3-(2-methylpyrrolidin-1-yl)quinoxaline-6-carboxylic acid

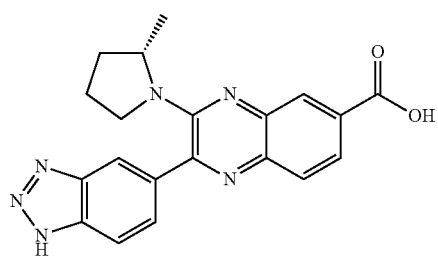 [SMILES: C[C@H]1CCCN1c1nc2cc(C(=O)O)ccc2nc1-c1ccc2[nH]nnc2c1]

To a solution of (S)-methyl 2-(1H-benzo[d][1,2,3]triazol-5-yl)-3-(2-methylpyrrolidin-1-yl)quinoxaline-6-carboxylate (130 mg, 0.33 mmol) in methanol (30 mL) was added sodium hydroxide (40.2 mg, 1.00 mmol) and water (1 mL) with stirring for overnight at room temperature. The resulting mixture was concentrated under vacuum and dissolved in water (25 mL), and adjusted to pH 4 with HCl (3N) to give the precipitate, which was collected by filtration to afford (S)-2-(1H-benzo[d][1,2,3]triazol-5-yl)-3-(2-methylpyrrolidin-1-yl)quinoxaline-6-carboxylic acid as a yellow solid (90.3 mg, 72%).

LC/MS (ES, m/z): [M+H]$^+$ 375.1

$^1$H-NMR (300 MHz, CD$_3$OD) δ 8.27 (d, J=1.5 Hz, 1H), 8.24 (s, 1H), 8.04 (d, J=8.7 Hz, 1H), 7.90-7.98 (m, 2H), 7.83 (d, J=8.4 Hz, 1H), 4.22-4.29 (m, 1H), 2.93-2.97 (m, 2H), 2.05-2.16 (m, 1H), 1.68-1.72 (m, 1H), 1.45-1.60 (m, 2H), 1.36 (d, J=6.0 Hz, 3H)

Example 97

3-(Benzyl(methyl)amino)-2-(1H-indazol-5-yl)quinoxaline-6-carboxylic acid

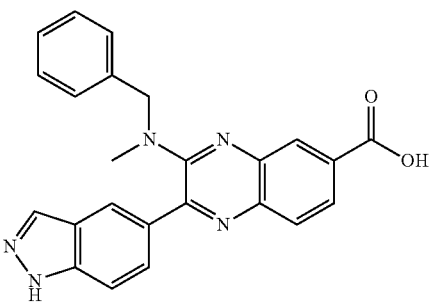 [SMILES: CN(Cc1ccccc1)c1nc2cc(C(=O)O)ccc2nc1-c1ccc2[nH]ncc2c1]

Step 1. Methyl 3-(benzyl(methyl)amino)-2-oxo-1,2-dihydroquinoxaline-6-carboxylate

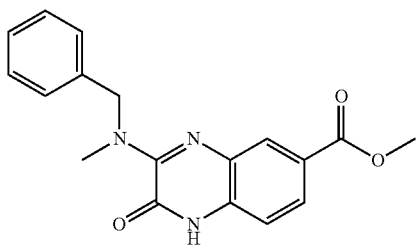 [SMILES: COC(=O)c1ccc2[nH]c(=O)c(N(C)Cc3ccccc3)nc2c1]

To a solution of methyl 3-chloro-2-oxo-1,2-dihydroquinoxaline-6-carboxylate (500 mg, 2.10 mmol) in DMSO (6 mL) was added benzyl(methyl)amine (305 mg, 2.52 mmol), and DIEA (542 mg, 4.19 mmol). The resulting solution was stirred for 2 h at 85° C., then water (50 mL) was added, causing a precipitate to form which was collected by filtration to afford methyl 3-(benzyl(methyl)amino)-2-oxo-1,2-dihydroquinoxaline-6-carboxylate as a yellow solid (0.55 g, 81%).

LC/MS (ES, m/z): [M+H]$^+$ 324.0

$^1$H-NMR (300 MHz, CDCl$_3$): δ 10.01 (s, 1H), 8.23 (d, J=1.8 Hz, 1H), 7.81-7.84 (m, 1H), 7.25-7.37 (m, 5H), 6.68 (d, J=8.1 Hz, 1H), 5.21 (s, 2H), 3.95 (s, 3H), 3.34 (s, 3H)

Step 2. Methyl 3-(benzyl(methyl)amino)-2-(trifluoromethylsulfonyloxy)quinoxaline-6-carboxylate

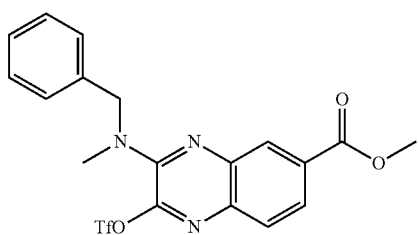 [SMILES: COC(=O)c1ccc2nc(OS(=O)(=O)C(F)(F)F)c(N(C)Cc3ccccc3)nc2c1]

To a solution of methyl 3-[benzyl(methyl)amino]-2-oxo-1,2-dihydroquinoxaline-6-carboxylate (200 mg, 0.62 mmol) in dichloromethane (30 mL) was added pyridine (196 mg, 2.48 mmol), followed by Tf$_2$O (349 mg, 1.24 mmol) at room temperature. The mixture was stirred overnight at room temperature, then quenched with water (100 mL), extracted with dichloromethane (3×20 mL1), and the organic layers combined and dried over anhydrous magnesium sulfate and concentrated under vacuum to afford methyl 3-(benzyl(methyl)amino)-2-(trifluoromethylsulfonyloxy)quinoxaline-6-carboxylate as a red solid (300 mg, crude).

Step 3. Methyl 3-(benzyl(methyl)amino)-2-(1-(tert-butoxycarbonyl)-1H-indazol-5-yl)quinoxaline-6-carboxylate

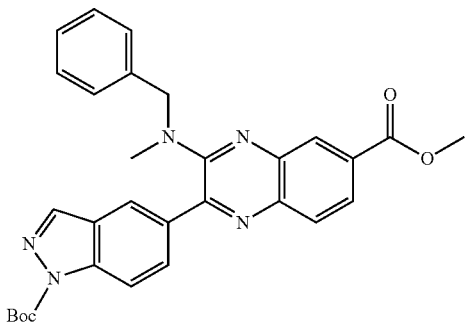 [SMILES: COC(=O)c1ccc2nc(-c3ccc4c(cnn4C(=O)OC(C)(C)C)c3)c(N(C)Cc3ccccc3)nc2c1]

To a solution of methyl 3-(benzyl(methyl)amino)-2-(trifluoromethylsulfonyloxy)quinoxaline-6-carboxylate (300 mg, crude) in ethylene glycol dimethyl ether (7 mL) was added tert-butyl 5-(4,4,5,5-tetramethyl-1,3,2-dioxaborolan-2-yl)-1H-indazole-1-carboxylate (181 mg, 0.53 mmol), sodium carbonate (93 mg, 0.88 mmol), and Pd(PPh$_3$)$_4$ (25 mg, 0.02 mmol). The resulting solution was stirred for 1 h at 90° C. under an inert atmosphere of nitrogen, quenched with water (100 mL) and extracted with dichloromethane (3×50 mL), dried over anhydrous magnesium sulfate, and concentrated under vacuum to give a residue, which was purified via silica gel chromatography (3% ethyl acetate in petroleum ether) to afford methyl 3-(benzyl(methyl)amino)-2-(1-(tert-butoxycarbonyl)-1H-indazol-5-yl)quinoxaline-6-carboxylate as a yellow solid (120 mg).
LC/MS (ES, m/z): [M+H]$^+$ 524.0

Step 4. Methyl 3-(benzyl(methyl)amino)-2-(1H-indazol-5-yl)quinoxaline-6-carboxylate

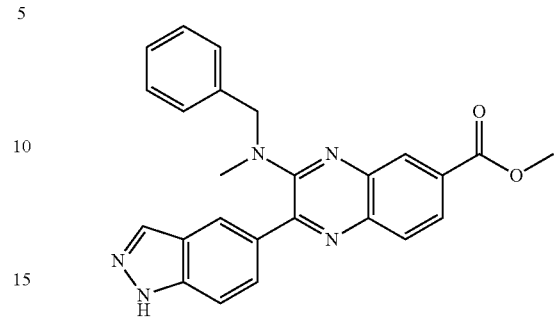

To a solution of methyl 3-(benzyl(methyl)amino)-2-(1-(tert-butoxycarbonyl)-M-indazol-5-yl)quinoxaline-6-carboxylate (120 mg, 0.23 mmol) in dichloromethane (10 mL) was added trifluoroacetic acid (0.5 mL). The resulting solution was stirred for 2 h at room temperature, adjusted to pH 7 with saturated aqueous sodium bicarbonate, extracted with dichloromethane (3×50 mL), and the organic layers combined and concentrated under vacuum to give a residue, which was purified via silica gel chromatography (4% ethyl acetate in petroleum ether) to afford methyl 3-(benzyl(methyl)amino)-2-(1H-indazol-5-yl)quinoxaline-6-carboxylate as a yellow solid (70 mg, 72%).
LC/MS (ES, m/z): [M+H]$^+$ 424.0
$^1$H-NMR (300 MHz, CDCl$_3$): δ 8.58 (d, J=1.2 Hz, 1H), 8.38 (s, 1H), 8.18 (s, 1H), 8.01-8.12 (m, 3H), 7.62 (d, J=8.7 Hz, 1H), 7.21-7.33 (m, 4H), 4.60 (s, 2H), 4.01 (s, 3H), 2.76 (s, 3H)

Step 5. 3-(Benzyl(methyl)amino)-2-(1H-indazol-5-yl)quinoxaline-6-carboxylic acid

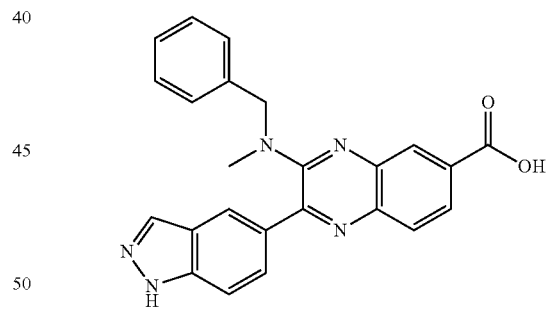

To a solution of methyl 3-(benzyl(methyl)amino)-2-(1H-indazol-5-yl)quinoxaline-6-carboxylate (70 mg, 0.17 mmol) in methanol (20 ml) was added sodium hydroxide (33 mg, 0.82 mmol) in water (5 ml). The resulting solution was stirred overnight at room temperature and then concentrated under vacuum to give a residue, which was dissolved in water (20 ml), and adjusted to pH 4 with HCl (3N). The solids were collected by filtration to afford 3-(benzyl(methyl)amino)-2-(1H-indazol-5-yl)quinoxaline-6-carboxylic acid as a yellow solid (64.1 mg, 89%).
LC/MS (ES, m/z): [M+H]$^+$ 410.1
$^1$H-NMR (300 MHz, DMSO): δ 8.47 (d, J=1.8 Hz, 1H), 8.36 (s, 1H), 8.15 (s, 1H), 8.06-8.10 (m, 1H), 7.95-7.99 (m, 2H), 7.68 (d, J=8.7 Hz, 1H), 7.18-7.30 (m, 5H), 4.54 (s, 2H), 2.81 (s, 3H)

Example 98

(S)-2-(1H-Indazol-5-yl)-3-(methyl(1-phenylethyl)amino)quinoxaline-6-carboxylic acid

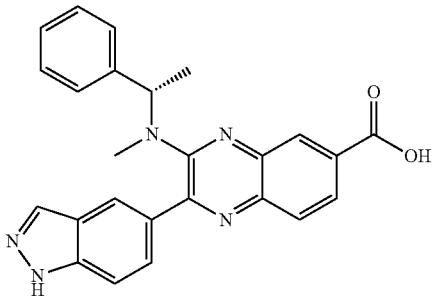 [SMILES: C[C@@H](c1ccccc1)N(C)c1nc2cc(C(=O)O)ccc2nc1-c1ccc2[nH]ncc2c1]

Step 1. (S)-Methyl 3-(methyl(1-phenylethyl)amino)-2-oxo-1,2-dihydroquinoxaline-6-carboxylate

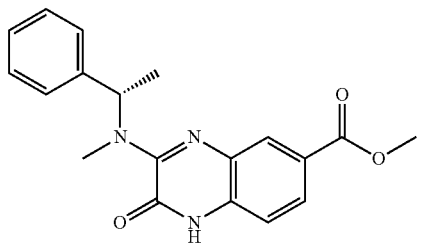 [SMILES: COC(=O)c1ccc2[nH]c(=O)c(N(C)[C@@H](C)c3ccccc3)nc2c1]

To a solution of methyl 3-chloro-2-oxo-1,2-dihydroquinoxaline-6-carboxylate (300 mg, 1.26 mmol) in DMSO (2 mL) was added DIEA (244 mg, 1.89 mmol), and (S)—N-methyl-1-phenylethanamine (204 mg, 1.51 mmol) with stirring for 3 h at 85° C. in an oil bath. The reaction was then quenched by the addition of water (50 mL). The product was precipitated via the addition of water and collected by filtration to give (S)-methyl 3-(methyl(1-phenylethyl)amino)-2-oxo-1,2-dihydroquinoxaline-6-carboxylate as a gray solid (323 mg, 76%).

LC/MS (ES, m/z): [M+H]+ 338.1

$^1$H-NMR (300 MHz, CD$_3$OD) δ 8.09 (d, J=1.8 Hz, 1H), 7.79-7.82 (m, 1H), 7.33-7.43 (m, 5H), 7.19-7.29 (m, 1H), 6.66-6.73 (m, 1H), 3.92 (s, 3H), 2.94 (s, 3H), 1.66 (d, J=6.9 Hz, 3H)

Step 2. (S)-Methyl 3-(methyl(1-phenylethyl)amino)-2-(trifluoromethylsulfonyloxy)quinoxaline-6-carboxylate

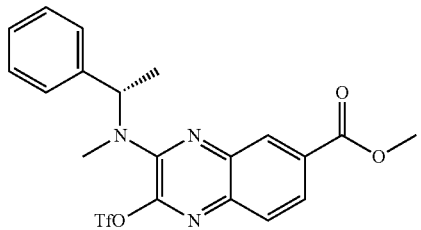 [SMILES: COC(=O)c1ccc2nc(OS(=O)(=O)C(F)(F)F)c(N(C)[C@@H](C)c3ccccc3)nc2c1]

To a solution of (S)-methyl 3-(methyl(1-phenylethyl)amino)-2-oxo-1,2-dihydroquinoxaline-6-carboxylate (320 mg, 0.95 mmol) in dichloromethane (30 mL) was added pyridine (313 mg, 3.96 mmol), and Tf$_2$O (559 mg, 1.98 mmol). The resulting solution was stirred overnight at room temperature and then concentrated under vacuum to get a residue, which was purified via silica gel chromatography (1% to 5% ethyl acetate in petroleum ether) to give (S)-methyl 3-(methyl(1-phenylethyl)amino)-2-(trifluoromethylsulfonyloxy)quinoxaline-6-carboxylate as a yellow solid (432 mg, crude).

Step 3. (S)-Methyl 2-(1H-indazol-5-yl)-3-(methyl(1-phenylethyl)amino)quinoxaline-6-carboxylate

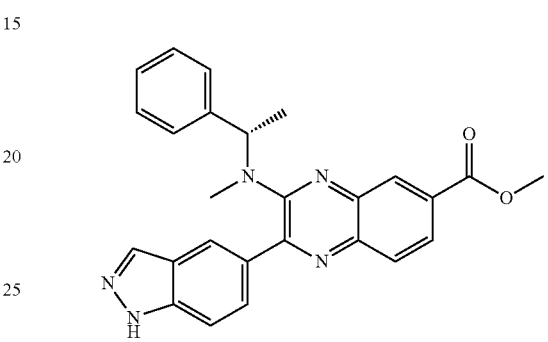

To a solution of (S)-methyl 3-(methyl(1-phenylethyl)amino)-2-(trifluoromethylsulfonyloxy)quinoxaline-6-carboxylate (432 mg, crude) in ethylene glycol dimethyl ether (5 mL) was added tert-butyl 5-(4,4,5,5-tetramethyl-1,3,2-dioxaborolan-2-yl)-1H-indazole-1-carboxylate (201 mg, 0.58 mmol), K$_2$CO$_3$ (55 mg, 0.40 mmol), Pd(PPh$_3$)$_4$ (392 mg, 0.34 mmol) and water (1.5 mL) with stirring overnight at 90° C. in an oil bath. The resulting mixture was concentrated under vacuum, dissolved in water (100 mL), extracted with ethyl acetate (3×30 mL), dried over anhydrous sodium sulfate and concentrated under vacuum to give a residue, which was purified via silica gel chromatography (10% ethyl acetate in petroleum ether) to afford (S)-methyl 2-(1H-indazol-5-yl)-3-(methyl(1-phenylethyl)amino)quinoxaline-6-carboxylate as a yellow solid (144 mg).

LC/MS (ES, m/z): [M+H]+ 438.1

$^1$H-NMR (300 MHz, CD$_3$OD) δ 8.43 (d, J=1.8 Hz, 1H), 8.34 (s, 1H), 8.15 (s, 1H), 7.93-8.08 (m, 3H), 7.68 (d, J=8.7 Hz, 1H), 7.21-7.30 (m, 5H), 5.51-5.53 (m, 1H), 4.00 (s, 3H), 2.60 (s, 3H), 1.50 (d, J=6.9 Hz, 3H)

Step 4. (S)-2-(1H-Indazol-5-yl)-3-(methyl(1-phenylethyl)amino)quinoxaline-6-carboxylic acid

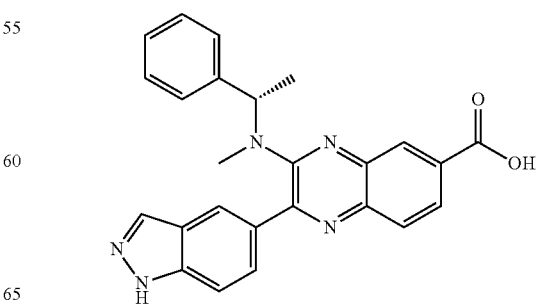

To a solution of (S)-methyl 2-(1H-indazol-5-yl)-3-(methyl(1-phenylethyl)amino)quinoxaline-6-carboxylate (100 mg, 0.23 mmol) in methanol (20 mL) was added NaOH (37 mg, 0.93 mmol) and water (1 mL) with stirring for 1 day at room temperature. The resulting mixture was concentrated under vacuum, diluted with water (20 mL), and adjusted to pH 5 with HCl (3N). The product was precipitated from solution via the addition of water and collected by filtration to give (S)-2-(1H-indazol-5-yl)-3-(methyl(1-phenylethyl)amino)quinoxaline-6-carboxylic acid as a yellow solid (48.9 mg, 51%).

LC/MS (ES, m/z): [M+H]+ 424.2

1H-NMR (300 MHz, CD3OD) δ 8.40 (d, J=1.5 Hz, 1H), 8.33 (s, 1H), 8.15 (d, J=0.6 Hz, 1H), 8.06-8.10 (m, 1H), 7.91-7.96 (m, 2H), 7.67-7.70 (m, 1H), 7.19-7.26 (m, 5H), 5.43-5.45 (m, 1H), 2.59 (s, 3H), 1.48 (d, J=6.9 Hz, 3H)

Example 99

(S)-2-(2-Methyl-1H-indol-5-yl)-3-(2-methyl-4-(pyridin-2-yl)piperazin-1-yl)quinoxaline-6-carboxylic acid

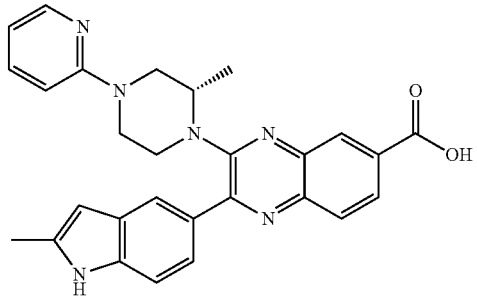 [SMILES: Cc1cc2cc(-c3nc4ccc(C(=O)O)cc4nc3N3CCN(c4ccccn4)C[C@@H]3C)ccc2[nH]1]

Step 1. (S)-Methyl 2-bromo-3-(2-methyl-4-(pyridin-2-yl)piperazin-1-yl)quinoxaline-6-carboxylate

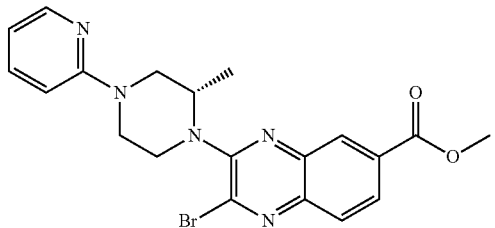 [SMILES: COC(=O)c1ccc2nc(Br)c(N3CCN(c4ccccn4)C[C@@H]3C)nc2c1]

To a solution of (S)-methyl 3-(2-methyl-4-(pyridin-2-yl)piperazin-1-yl)-2-(trifluoromethylsulfonyloxy)quinoxaline-6-carboxylate (900 mg, 1.76 mmol) in toluene (25 ml) was added Bu4NBr (0.85 g, 2.64 mmol). The resulting solution was stirred for 2 h at 110° C. Then the mixture was concentrated under vacuum to give a residue, which was purified via silica gel chromatography (2.5% ethyl acetate in petroleum ether) to afford (S)-methyl 2-bromo-3-(2-methyl-4-(pyridin-2-yl)piperazin-1-yl)quinoxaline-6-carboxylate as a yellow solid (632 mg, 81%).

LC/MS (ES, m/z): [M+H]+ 442.0

Step 2. (S)-Methyl 2-(2-methyl-1H-indol-5-yl)-3-(2-methyl-4-(pyridin-2-yl)piperazin-1-yl)quinoxaline-6-carboxylate

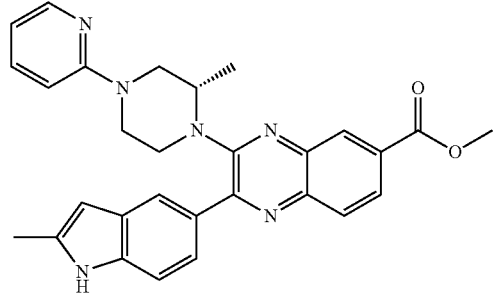 [SMILES: COC(=O)c1ccc2nc(-c3ccc4[nH]c(C)cc4c3)c(N3CCN(c4ccccn4)C[C@@H]3C)nc2c1]

To a solution of (S)-methyl 2-bromo-3-(2-methyl-4-(pyridin-2-yl)piperazin-1-yl)quinoxaline-6-carboxylate (200 mg, 0.45 mmol) in dioxane (7 ml) was added 2-methyl-5-(4,4,5,5-tetramethyl-1,3,2-dioxaborolan-2-yl)-1H-indole (140 mg, 0.54 mmol), K3PO4 (190 mg, 0.90 mmol), and Pd(PPh3)4 (26 mg, 0.02 mmol). The resulting solution was stirred for 2 h at 90° C. Then the mixture was concentrated under vacuum, and the residue was purified via silica gel column chromatography (5% ethyl acetate in petroleum ether) to afford (S)-methyl 2-(2-methyl-1H-indol-5-yl)-3-(2-methyl-4-(pyridin-2-yl)piperazin-1-yl)quinoxaline-6-carboxylate as a yellow solid (202 mg, 91%).

LC/MS (ES, m/z): [M+H]+ 493.0

1H-NMR (300 MHz, DMSO) δ 11.19 (s, 1H), 8.32 (t, J=1.2 Hz, 1H), 8.14 (s, 1H), 8.07-8.09 (m, 1H), 7.99 (s, 2H), 7.70-7.73 (m, 1H), 7.50-7.60 (m, 1H), 7.40-7.45 (m, 1H), 6.80-6.83 (m, 1H), 6.63-6.64 (m, 1H), 6.30 (s, 1H), 3.99-4.02 (m, 2H), 3.94 (s, 3H), 3.33-3.38 (m, 1H), 2.99-3.20 (m, 2H), 3.19-3.25 (m, 1H), 2.49-2.52 (m, 3H), 1.05 (t, J=6.6 Hz, 3H)

Step 3. (S)-2-(2-Methyl-1H-indol-5-yl)-3-(2-methyl-4-(pyridin-2-yl)piperazin-1-yl)quinoxaline-6-carboxylic acid

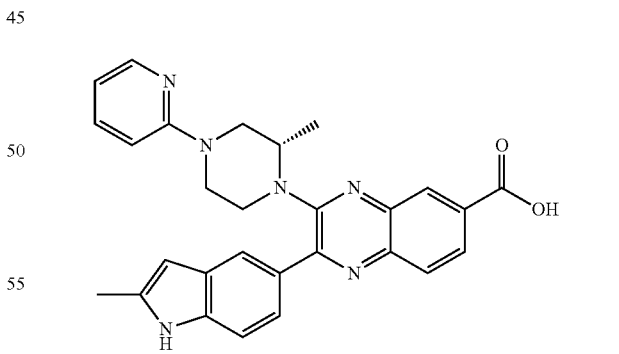

To a solution of (S)-methyl 2-(2-methyl-1H-indol-5-yl)-3-(2-methyl-4-(pyridin-2-yl)piperazin-1-yl)quinoxaline-6-carboxylate (150 mg, 0.30 mmol) in methanol (20 ml) was added sodium hydroxide (36 mg, 0.90 mmol) and water (1 ml) The resulting solution was stirred overnight at room temperature and the mixture was concentrated under vacuum dissolved in water (30 ml), adjusted to pH 5 with hydrochloric acid (3N) to give the precipitate, which was collected by filtration to afford (S)-2-(2-methyl-1H-indol-5-yl)-3-(2-methyl-4-(pyridin-2-yl)piperazin-1-yl)quinoxaline-6-carboxylic acid as a yellow solid (44 mg, 30%).

LC/MS (ES, m/z): [M+H]+ 479.2

¹H-NMR (300 MHz, CD₃OD) δ 8.48 (d, J=1.5 Hz, 1H), 8.06-8.47 (m, 3H), 7.95 (d, J=8.7 Hz, 1H), 7.67-7.70 (m, 1H), 7.51-7.57 (m, 1H), 7.43-7.46 (m, 1H), 6.79-6.82 (m, 1H), 6.64-6.68 (m, 1H), 6.28 (s, 1H), 4.18-4.21 (m, 1H), 3.98-4.03 (m, 1H), 3.70-3.75 (m, 2H), 3.31-3.34 (m, 1H), 3.12-3.23 (m, 2H), 2.48 (s, 3H), 1.13 (d, J=6.6 Hz, 3H)

Example 100

(S)-2-(5-Fluorobenzofuran-2-yl)-3-(2-methylpiperidin-1-yl)quinoxaline-6-carboxylic acid

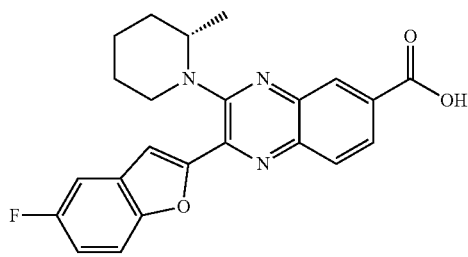 [SMILES: C[C@H]1CCCCN1c1nc2cc(C(=O)O)ccc2nc1-c1cc2cc(F)ccc2o1]

Step 1. (S)-Methyl 3-(2-methylpiperidin-1-yl)-2-oxo-1,2-dihydroquinoxaline-6-carboxylate

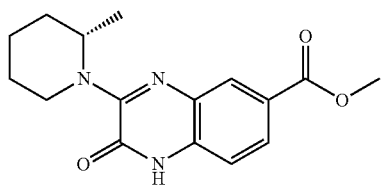 [SMILES: COC(=O)c1ccc2[nH]c(=O)c(N3CCCC[C@@H]3C)nc2c1]

To a solution of methyl 3-chloro-2-oxo-1,2-dihydroquinoxaline-6-carboxylate (150 mg, 0.63 mmol) in DMSO (2 mL) was added (S)-2-methylpiperidine (166 mg, 1.7 mmol) and DIEA (217 mg, 1.7 mmol). The resulting solution was stirred for 3 hours at 80° C. and then quenched by the addition of water (250 mL), extracted with dichloromethane (3×100 mL), dried over anhydrous sodium sulfate, and then concentrated under vacuum to give a residue, which was purified via silica gel column chromatography (9% ethyl acetate in petroleum ether) to afford (S)-methyl 3-(2-methylpiperidin-1-yl)-2-oxo-1,2-dihydroquinoxaline-6-carboxylate as white solid (165 mg, 87%).

(ES, m/z): [M+H]+ 302.0

¹H-NMR (300 MHz, CDCl₃): δ 10.11 (s, 1H), 8.29 (s, 1H), 7.83-7.86 (m, 1H), 7.09 (d, J=8.4 Hz, 1H), 5.39-5.41 (m, 1H), 4.86-4.91 (m 1H), 3.94 (s, 3H), 3.18-3.26 (t, J=12.6 Hz, 1H), 1.65-1.94 (m, 6H), 1.35 (d, J=6.9 Hz, 3H)

Step 2. (S)-Methyl 3-(2-methylpiperidin-1-yl)-2-(trifluoromethylsulfonyloxy)quinoxaline-6-carboxylate

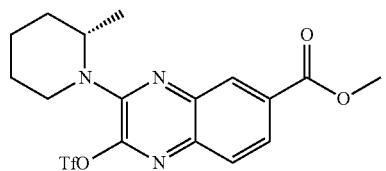 [SMILES: COC(=O)c1ccc2nc(OS(=O)(=O)C(F)(F)F)c(N3CCCC[C@@H]3C)nc2c1]

To a solution of (S)-methyl 3-(2-methylpiperidin-1-yl)-2-oxo-1,2-dihydroquinoxaline-6-carboxylate (165 mg, 0.55 mmol) in dichloromethane (40 mL) was added pyridine (231 mg, 2.92 mmol) followed by the addition of Tf₂O (412 mg, 1.46 mmol) dropwise with stirring at 0° C. The resulting solution was stirred overnight at room temperature and then washed with water (3×50 mL), dried over anhydrous sodium sulfate and concentrated under vacuum to afford (S)-methyl 3-(2-methylpiperidin-1-yl)-2-(trifluoromethylsulfonyloxy)quinoxaline-6-carboxylate as red oil (240 mg, crude).

Step 3. (S)-Methyl 2-(5-fluorobenzofuran-2-yl)-3-(2-methylpiperidin-1-yl)quinoxaline-6-carboxylate

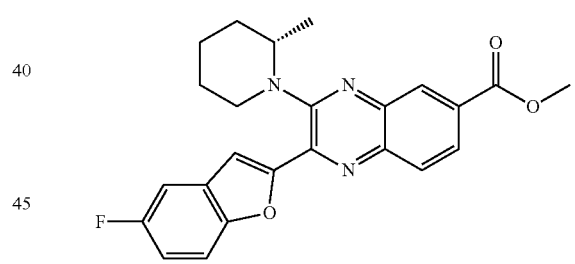

To a solution of (S)-methyl 3-(2-methylpiperidin-1-yl)-2-(trifluoromethylsulfonyloxy)quinoxaline-6-carboxylate (240 mg, crude) in dioxane (5 mL) was added 5-fluorobenzofuran-2-ylboronic acid (337 mg, 1.87 mmol), K₃PO₄ (397 mg, 1.87 mmol), Pd(PPh₃)₄ (36 mg, 0.03 mmol) and water (5 drops). The resulting solution was stirred for 1 hour at 90° C. and then concentrated under vacuum to give a residue, which was purified via silica gel column chromatography (2% ethyl acetate in petroleum ether) to afford (S)-methyl 2-(5-fluorobenzofuran-2-yl)-3-(2-methylpiperidin-1-yl)quinoxaline-6-carboxylate as a yellow solid (135.0 mg, 59% 2 steps).

(ES, m/z): [M+H]+ 420.1

¹H-NMR (300 MHz, CDCl₃): δ 8.71 (d, J=1.2 Hz, 1H), 8.12-8.21 (m, 2H), 7.91 (s, 1H), 7.60-7.65 (m, 1H), 7.36-7.40 (m, 1H), 7.13-7.19 (m, 1H), 4.21-4.25 (m, 1H), 4.02 (s, 3H), 3.40-3.43 (m, 2H), 1.95-2.06 (m, 1H), 1.59-1.90 (m, 1H), 1.19 (d, J=6.6 Hz, 3H)

Step 4. (S)-2-(5-Fluorobenzofuran-2-yl)-3-(2-methylpiperidin-1-yl)quinoxaline-6-carboxylic acid

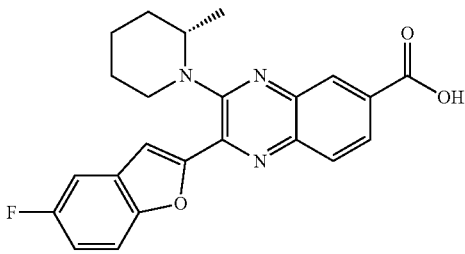 [SMILES: C[C@H]1CCCCN1c1nc2cc(C(=O)O)ccc2nc1-c1cc2cc(F)ccc2o1]

To a solution of (S)-methyl 2-(5-fluorobenzofuran-2-yl)-3-(2-methylpiperidin-1-yl)quinoxaline-6-carboxylate (120 mg, 0.29 mmol) in MeOH (20 mL) was added sodium hydroxide (46 mg, 1.15 mmol) and water (3 mL). The resulting solution was stirred overnight at room temperature and concentrated under vacuum. The residue was dissolved in water (10 mL) and adjusted to pH 5 with hydrochloric acid (1N). The solids were collected by filtration to afford (S)-2-(5-fluorobenzofuran-2-yl)-3-(2-methylpiperidin-1-yl)quinoxaline-6-carboxylic acid as a yellow solid (113 mg, 97%).

(ES, m/z): [M+H]$^+$ 406.0

$^1$H-NMR (300 MHz, DMSO+D$_2$O) δ 8.30 (s, 1H), 8.01-8.08 (m, 2H), 7.93 (s, 1H), 7.76-7.81 (m, 1H), 7.63-7.67 (m, 1H), 7.26-7.33 (m, 1H), 4.04-4.06 (m, 1H), 3.22-3.36 (m, 2H), 1.80-1.90 (m, 1H), 1.49-1.75 (m, 5H), 1.08 (d, J=6.6 Hz, 3H)

Example 101

(R)-2-(4-Fluorophenyl)-3-(2-(trifluoromethyl)pyrrolidin-1-yl)quinoxaline-6-carboxylic acid

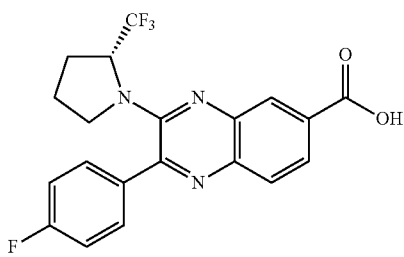 [SMILES: O=C(O)c1ccc2nc(-c3ccc(F)cc3)c(N3CCC[C@@H]3C(F)(F)F)nc2c1]

Step 1. (R)-Methyl 2-(4-fluorophenyl)-3-(2-(trifluoromethyl)pyrrolidin-1-yl)quinoxaline-6-carboxylate

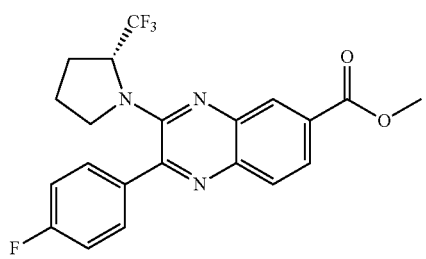 [SMILES: COC(=O)c1ccc2nc(-c3ccc(F)cc3)c(N3CCC[C@@H]3C(F)(F)F)nc2c1]

To a solution of methyl 3-chloro-2-(4-fluorophenyl)quinoxaline-6-carboxylate (270 mg, 0.85 mmol) in DMSO (1 mL) was added (R)-2-(trifluoromethyl)pyrrolidine (275 mg, 1.99 mmol). The resulting solution was stirred 7 days at 130° C. and then evaporated in vacuo. The residue was diluted with petroleum ether (15 mL) and filtered. The filtrate was concentrated and purified by a silica gel column chromatography with 2%-10% ethyl acetate in petroleum ether to afford (R)-methyl 2-(4-fluorophenyl)-3-(2-(trifluoromethyl)pyrrolidin-1-yl)quinoxaline-6-carboxylate as a yellow solid (35 mg, crude).

LC/MS (ES, m/z): [M+H]$^+$ 420.0

Step 2. (R)-2-(4-Fluorophenyl)-3-(2-(trifluoromethyl)pyrrolidin-1-yl)quinoxaline-6-carboxylic acid

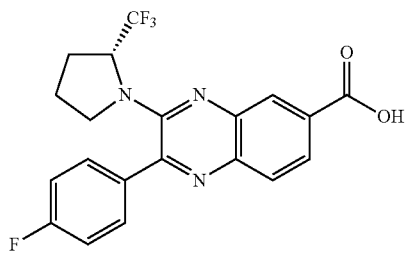

To a solution of (R)-methyl 2-(4-fluorophenyl)-3-(2-(trifluoromethyl)pyrrolidin-1-yl)quinoxaline-6-carboxylate (35 mg, crude) in methanol (15 mL) was added a solution of sodium hydroxide (10 mg, 0.25 mmol) in water (1 mL). The resulting solution was stirred overnight at room temperature and then concentrated in vacuo. The residue was dissolved in water (5 mL) and adjusted to pH 6 with aqueous hydrochloric acid (1N). The product was collected by filtration and purified by Prep-HPLC under the following conditions: Column, silica gel 19 mm*100 mm; mobile phase, A:B=0.05% TFA: ACN B %=35%~100% 0~8 mins; Detector, 5 um. 18.2 mg. (R)-2-(4-Fluorophenyl)-3-(2-(trifluoromethyl)pyrrolidin-1-yl)quinoxaline-6-carboxylic acid was obtained as a yellow solid (2 steps yield=5.3%).

LC/MS (ES, m/z): [M+H]$^+$ 406.1

$^1$H-NMR (300 MHz, CD$_3$OD) δ 8.48 (d, J=1.5 Hz, 1H), 8.11-8.14 (m, 1H), 8.00 (d, J=8.7 Hz, 1H), 7.29-7.35 (t, J=8.7 Hz, 2H), 5.73-5.81 (m, 1H), 3.00-3.17 (m, 2H), 2.26-2.34 (m, 1H), 2.05-2.17 (m, 1H), 1.89-1.95 (m, 1H), 1.71-1.80 (m, 1H)

Example 102

2-(4-Fluorophenyl)-3-(methyl(tetrahydro-2H-pyran-4-yl)amino)quinoxaline-6-carboxylic acid

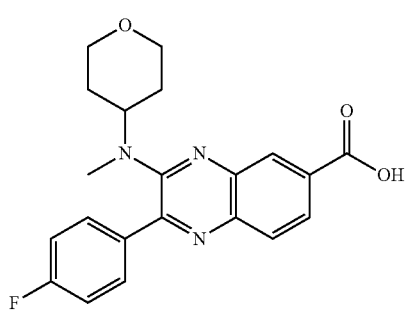 [SMILES: CN(c1nc2cc(C(=O)O)ccc2nc1-c1ccc(F)cc1)C1CCOCC1]

Step 1. Methyl 2-(4-fluorophenyl)-3-(tetrahydro-2H-pyran-4-ylamino)quinoxaline-6-carboxylate

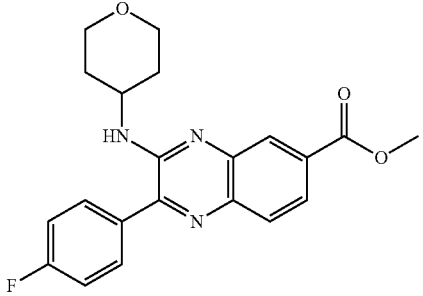 [SMILES: COC(=O)c1ccc2nc(-c3ccc(F)cc3)c(NC3CCOCC3)nc2c1]

To a solution of methyl 3-chloro-2-(4-fluorophenyl)quinoxaline-6-carboxylate (200.0 mg, 0.63 mmol) in DMSO (1.5 mL) was added tetrahydro-2H-pyran-4-amine (127.8 mg, 1.26 mmol), DIEA (163.3 mg, 1.27 mmol) under nitrogen atmosphere. After stirring overnight at 100° C., the reaction mixture was dissolved in dichloromethane (30 mL), washed with water (3×10 mL), dried over anhydrous magnesium sulfate and concentrated under reduced pressure to afford a residue, which was purified by a silica gel column with 0.01%-0.1% ethyl acetate in petroleum ether to afford methyl 2-(4-fluorophenyl)-3-(tetrahydro-2H-pyran-4-ylamino)quinoxaline-6-carboxylate as a light yellow solid (180.0 mg, 75%).

(ES, m/z): [M+H]$^+$ 382.0
$^1$H-NMR (300 MHz, DMSO) δ 8.17 (d, J=1.2 Hz, 1H), 7.82-7.89 (m, 4H), 7.37-7.43 (m, 2H), 6.65 (d, J=7.5 Hz, 1H), 4.24-4.34 (m, 1H), 3.86-3.91 (m, 5H), 3.42-3.49 (m, 2H), 1.86-1.92 (m, 2H), 1.57-1.68 (m, 2H)

Step 2. Methyl 2-(4-fluorophenyl)-3-(methyl(tetrahydro-2H-pyran-4-yl)amino)quinoxaline-6-carboxylate

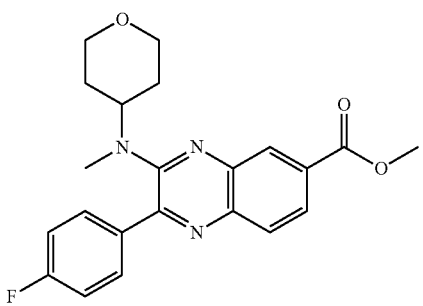 [SMILES: COC(=O)c1ccc2nc(-c3ccc(F)cc3)c(N(C)C3CCOCC3)nc2c1]

To a solution of ethyl 2-(4-fluorophenyl)-3-(tetrahydro-2H-pyran-4-ylamino)quinoxaline-6-carboxylate (180.0 mg, 0.47 mmol) in tetrahydrofuran (20 mL) was added sodium hydride (22.7 mg, 0.95 mmol) at 0° C. and stirred for 1 h at room temperature. Then CH$_3$I (134.0 mg, 0.94 mmol) was added at 0° C. and stirred overnight at room temperature. The reaction mixture was quenched by the addition of NH$_4$Cl solution (100 ml) and adjusted to pH 6 with hydrochloric acid (1N), extracted with dichloromethane (3×30 mL), dried over anhydrous magnesium sulfate and concentrated under vacuum to afford methyl 2-(4-fluorophenyl)-3-(methyl(tetrahydro-2H-pyran-4-yl)amino)quinoxaline-6-carboxylate as yellow oil (100 mg, crude).

(ES, m/z): [M+H]$^+$ 395.0

Step 3. 2-(4-Fluorophenyl)-3-(methyl(tetrahydro-2H-pyran-4-yl)amino)quinoxaline-6-carboxylic acid

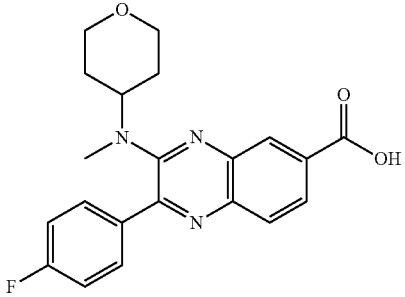 [SMILES: CN(c1nc2cc(C(=O)O)ccc2nc1-c1ccc(F)cc1)C1CCOCC1]

To a solution of methyl 2-(4-fluorophenyl)-3-(methyl(tetrahydro-2H-pyran-4-yl)amino)quinoxaline-6-carboxylate (100 mg) in methanol (20 mL) was added sodium hydroxide (40 mg, 1.00 mmol) and water (1 mL). After stirring overnight at room temperature, the reaction mixture was concentrated under reduced pressure to afford a residue, which was dissolved in water (10 mL), adjusted the pH value to 6 with hydrochloric acid (3 N) and the product was precipitated to afford 2-(4-fluorophenyl)-3-(methyl(tetrahydro-2H-pyran-4-yl)amino)quinoxaline-6-carboxylic acid as a light yellow solid (52 mg).

(ES, m/z): [M+H]$^+$ 382.0
$^1$H-NMR (300 MHz, DMSO) δ 8.27 (s, 1H), 7.85-7.95 (m, 4H), 7.35-7.41 (t, J=9.0 Hz, 2H), 3.98-4.06 (m, 1H), 3.83-3.88 (m, 2H), 3.11-3.18 (t, J=10.5 Hz, 2H), 2.69 (s, 3H), 1.69-1.82 (m, 2H), 1.5 (d, J=10.5 Hz, 1H)

Example 103

2-(4-Fluorophenyl)-3-(methyl(piperidin-4-yl)amino)quinoxaline-6-carboxylic acid

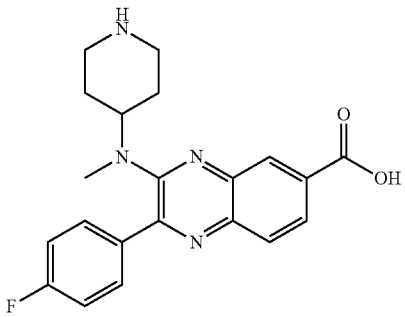 [SMILES: CN(c1nc2cc(C(=O)O)ccc2nc1-c1ccc(F)cc1)C1CCNCC1]

Step 1. Methyl 3-(1-(tert-butoxycarbonyl)piperidin-4-ylamino)-2-(4-fluorophenyl)quinoxaline-6-carboxylate

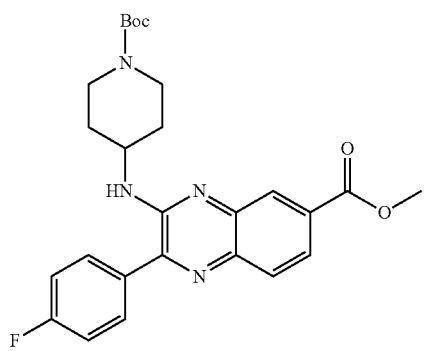 [SMILES: COC(=O)c1ccc2nc(-c3ccc(F)cc3)c(NC3CCN(C(=O)OC(C)(C)C)CC3)nc2c1]

To a solution of methyl 3-chloro-2-(4-fluorophenyl)quinoxaline-6-carboxylate (300.0 mg, 0.95 mmol) in DMSO (2 mL) was added tert-butyl 4-aminopiperidine-1-carboxylate (227.0 mg, 1.14 mmol), DIEA (367.0 mg, 2.82 mmol). The resulting solution was stirred overnight at 100° C. and then diluted with water (10 mL), extracted with dichloromethane (3×10 mL), dried over anhydrous magnesium sulfate and concentrated in vacuo. The residue was purified by a silica gel column chromatography with 20%-50% ethyl acetate in petroleum ether to afford methyl 3-(1-(tert-butoxycarbonyl)piperidin-4-ylamino)-2-(4-fluorophenyl)quinoxaline-6-carboxylate as a yellow solid (200 mg, 44%).

LC/MS (ES, m/z): [M+H]⁺ 481.0

¹H-NMR (300 MHz, CDCl₃) δ 8.47 (d, J=1.8 Hz, 1H), 8.01-8.04 (m, 1H), 7.92 (d, J=8.7 Hz, 1H), 4.15 (m, 2H), 4.00 (s, 3H), 3.00-3.08 (t, J=12 Hz, 2H), 2.12-2.17 (m, 2H), 1.51 (s, 9H), 1.34-1.48 (m, 2H)

Step 2. 3-((1-(tert-Butoxycarbonyl)piperidin-4-yl)(methyl)amino)-2-(4-fluorophenyl)quinoxaline-6-carboxylate

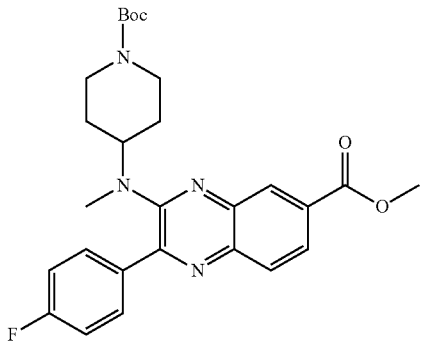

To a solution of methyl 3-(1-(tert-butoxycarbonyl)piperidin-4-ylamino)-2-(4-fluorophenyl)quinoxaline-6-carboxylate (200.0 mg, 0.42 mmol) in tetrahydrofuran (10 mL) was added sodium hydride (50.0 mg, 2.08 mmol) at 0° C. and stirred for 30 minutes at room temperature. Subsequently, iodomethane (350.0 mg, 2.47 mmol) was added and stirred overnight at room temperature. The reaction mixture was then quenched by the addition of NH₄Cl solution (100 mL), extracted with dichloromethane (3×15 mL), dried over anhydrous magnesium sulfate and concentrated in vacuo to afford methyl 3-((1-(tert-butoxycarbonyl)piperidin-4-yl)(methyl)amino)-2-(4-fluorophenyl)quinoxaline-6-carboxylate as a yellow solid (210 mg, crude).

(ES, m/z): [M+H]⁺ 495.0

Step 3. Methyl 2-(4-fluorophenyl)-3-(methyl(piperidin-4-yl)amino)quinoxaline-6-carboxylate

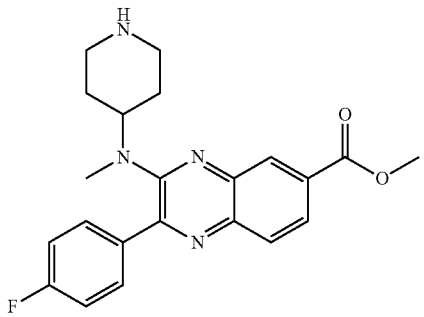 [SMILES: COC(=O)c1ccc2nc(-c3ccc(F)cc3)c(N(C)C3CCNCC3)nc2c1]

The solution of methyl 3-((1-(tert-butoxycarbonyl)piperidin-4-yl)(methyl)amino)- 2-(4-fluorophenyl)quinoxaline-6-carboxylate (210 mg, crude) in hydrogen chloride(g)/MeOH (50 mL) was stirred overnight at room temperature and then concentrated in vacuo. The residue was dissolved in water (50 mL) and adjusted to pH 8 with sodium bicarbonate, extracted with dichloromethane (5×30 mL), dried over anhydrous magnesium sulfate and concentrated in vacuo. The product was precipitated by the addition ether (20 mL) to afford methyl 2-(4-fluorophenyl)-3-(methyl(piperidin-4-yl)amino)quinoxaline-6-carboxylate as a yellow solid (100 mg).

LC/MS (ES, m/z): [M+H]⁺ 395.0

¹H-NMR (300 MHz, DMSO) δ 8.33 (s, 1H), 7.89-7.96 (m, 2H), 7.99 (d, J=8.4 Hz, 1H), 7.35-7.41 (t, J=8.7 Hz, 2H), 4.15-4.22 (t, J=9.3 Hz, 1H), 3.94 (s, 3H), 2.82-2.89 (t, J=11.8 Hz, 2H), 2.61 (s, 2H), 1.84-2.00 (m, 4H)

Step 4. 2-(4-Fluorophenyl)-3-(methyl(piperidin-4-yl)amino)quinoxaline-6-carboxylic acid

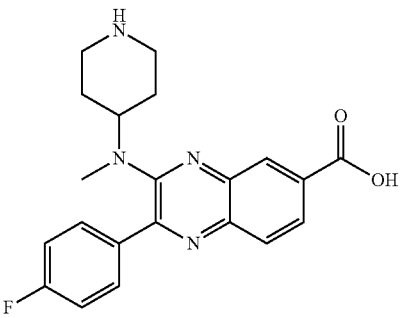 [SMILES: CN(c1nc2cc(C(=O)O)ccc2nc1-c1ccc(F)cc1)C1CCNCC1]

To a solution of 3-((1-(tert-butoxycarbonyl)piperidin-4-yl)(methyl)amino)-2-(4-fluorophenyl)quinoxaline-6-carboxylic acid (90.0 mg, 0.23 mmol) in MeOH (20 mL) was added sodium hydroxide (50 mg, 1.25 mol) and water (1 mL). The resulting solution was stirred overnight at room temperature and concentrated in vacuo. The residue was dissolved in water (5 mL) and adjusted to pH 6 with hydrochloric acid (1N) and concentrated in vacuo. The crude product was purified by Prep-HPLC with the following conditions (3#-Agilent 1200 prep HPLC): Column, X-Bridge Prep C18,19*150 mm; mobile phase, water with 0.5% TFA:CH₃CN=(25%-37% CH₃CN in 9.0 min); Detector, 5 μm to afford 2-(4-fluorophenyl)-3-(methyl(piperidin-4-yl)amino)quinoxaline-6-carboxylic acid as a yellow solid (22 mg, 25%).

LC/MS (ES, m/z): [M+H]⁺ 380.9

¹H-NMR (300 MHz, CD₃OD) δ 8.48 (s, 1H), 8.09 (d, J=6.3 Hz, 1H), 7.96-8.00 (t, J=5 Hz, 3H), 7.29-7.33 (t, J=6 Hz, 2H), 4.31 (s, 1H), 3.50 (d, J=9 Hz, 2H), 3.07-3.15 (m, 2H), 2.73 (s, 3H), 2.11 (s, 4H)

Example 104

(S)-3-(sec-Butyl(methyl)amino)-2-(4-fluorophenyl)quinoxaline-6-carboxylic acid

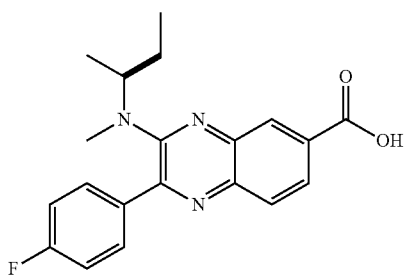

Step 1. (S)-Methyl 3-(sec-butylamino)-2-(4-fluorophenyl)quinoxaline-6-carboxylate

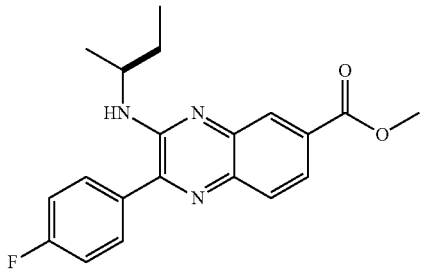 [SMILES: CC[C@H](C)Nc1nc2cc(C(=O)OC)ccc2nc1-c1ccc(F)cc1]

To a solution of methyl 3-chloro-2-(4-fluorophenyl)quinoxaline-6-carboxylate (400.0 mg, 1.26 mmol) in DMSO (3 mL) was added (S)-butan-2-amine (200 mg, 2.74 mmol). The resulting solution was stirred overnight at 90° C. and then diluted with water (50 mL), extracted with dichloromethane (5×20 mL), dried over anhydrous magnesium sulfate and concentrated in vacuo. The residue was purified by a silica gel column chromatography with 2% ethyl acetate in petroleum ether to afford (S)-methyl 3-(sec-butylamino)-2-(4-fluorophenyl)quinoxaline-6-carboxylate as a yellow solid (280.0 mg, 63%).

LC/MS (ES, m/z): [M+H]$^+$ 354.0

$^1$H-NMR (300 MHz, CDCl$_3$), δ 8.60 (s, 1H), 8.01-8.04 (m, 1H), 7.92 (d, J=8.7 Hz, 1H), 7.73-7.78 (m, 2H), 7.23-7.33 (m, 2H), 4.43-4.48 (t, J=6.9 Hz, 1H), 4.00 (s, 3H), 1.59-1.68 (m, 2H), 1.23-1.32 (m, 3H), 0.90-1.01 (m, 3H)

Step 2. (S)-3-(sec-Butyl(methyl)amino)-2-(4-fluorophenyl)quinoxaline-6-carboxylic acid

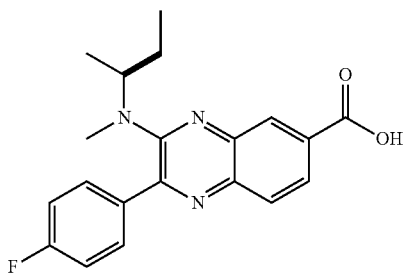 [SMILES: CC[C@H](C)N(C)c1nc2cc(C(=O)O)ccc2nc1-c1ccc(F)cc1]

To a solution of (S)-methyl 3-(sec-butylamino)-2-(4-fluorophenyl)quinoxaline-6-carboxylate (280.0 mg, 0.79 mmol) in tetrahydrofuran (30 mL) was added sodium hydride (127 mg, 3.17 mmol) and stirred for 1 h at room temperature. Subsequently, iodomethane (570 mg, 3.97 mmol) was added and stirred overnight at room temperature. The reaction was concentrated in vacuo and then quenched by the addition of water (20 mL), adjusted to pH 5 with hydrochloric acid (1N). The solids were collected by filtration to afford (S)-3-(sec-butyl(methyl)amino)-2-(4-fluorophenyl)quinoxaline-6-carboxylic acid as a yellow solid (124.3 mg, 44%).

LC/MS (ES, m/z): [M+H]$^+$ 354.0

$^1$H-NMR (300 MHz, CDCl$_3$), δ 8.58 (s, 1H), 8.08 (d, J=8.4 Hz, 1H), 7.97 (d, J=8.4 Hz, 1H), 7.86-7.91 (m, 2H), 7.18-7.28 (m, 2H), 4.04 (d, J=6.9 Hz, 1H), 2.74 (s, 3H), 1.56-1.65 (m, 2H), 1.09 (d, J=6.6 Hz, 3H), 0.73-0.78 (t, J=7.5 Hz, 3H)

Example 105

(S)-2-(4-Fluorophenyl)-3-(3-methylmorpholino)quinoxaline-6-carboxylic acid

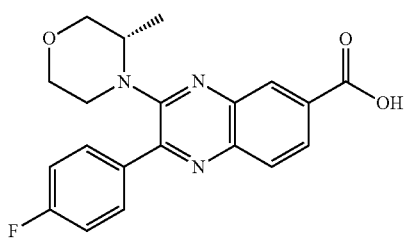 [SMILES: C[C@H]1COCCN1c1nc2cc(C(=O)O)ccc2nc1-c1ccc(F)cc1]

Step 1. (S)-Methyl 3-(3-methylmorpholino)-2-oxo-1,2-dihydroquinoxaline-6-carboxylate

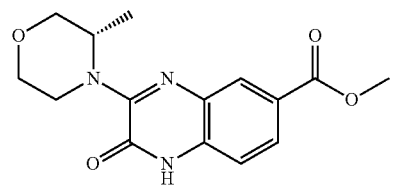 [SMILES: COC(=O)c1ccc2[nH]c(=O)c(N3CCOC[C@@H]3C)nc2c1]

To a solution of (3S)-3-methylmorpholine (200 mg, 1.98 mmol) in DMSO (10 mL) was added methyl 3-chloro-2-hydroxyquinoxaline-6-carboxylate (700 mg, 2.93 mmol), DIEA (510 mg, 3.95 mmol). The resulting solution was stirred overnight at 70° C. and then dissolved in water (100 mL), extracted with dichloromethane (4×30 mL), dried over anhydrous magnesium sulfate and concentrated in vacuo. The residue was purified by a silica gel column chromatography with 5%~50% ethyl acetate in petroleum ether to afford methyl 2-hydroxy-3-[(3S)-3-methylmorpholin-4-yl]quinoxaline-6-carboxylate as a light yellow solid (210.0 mg).

LC/MS (ES, m/z): [M+H]+ 304.0

$^1$H-NMR (300 MHz, CDCl$_3$), δ 9.34 (s, 1H), 8.22 (d, J=1.5 Hz, 1H), 7.87-7.90 (m, 1H), 7.04 (d, J=8.1 Hz, 1H), 3.95-4.03 (m, 4H), 3.67-3.87 (m, 3H), 3.50-3.56 (m, 1H), 1.43 (d, J=6.6 Hz, 3H)

Step 2. Methyl 3-[(3S)-3-methylmorpholin-4-yl]-2-[(trifluoromethane)sulfonyloxy]quinoxaline-6-carboxylate

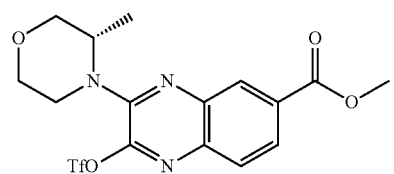 [SMILES: COC(=O)c1ccc2nc(OS(=O)(=O)C(F)(F)F)c(N3CCOC[C@@H]3C)nc2c1]

To a solution of methyl 3-[(3S)-3-methylmorpholin-4-yl]-2-oxo-1,2-dihydroquinoxaline-6-carboxylate (210 mg, 0.69 mmol) in dichloromethane (50 mL) was added pyridine (220 mg, 2.78 mmol), followed by Tf₂O (390 mg, 1.38 mmol), and the resulting mixture was stirred overnight at room temperature. The reaction was then quenched by the addition of ice-water (100 mL) and extracted with dichloromethane (2×20 mL), the organic layers were combined and dried over anhydrous magnesium sulfate and concentrated in vacuo to afford methyl 3-[(3S)-3-methylmorpholin-4-yl]-2-[(trifluoromethane)sulfonyloxy]quinoxaline-6-carboxylate as red oil (300 mg, crude).

Step 3. Methyl 2-(4-fluorophenyl)-3-[(3S)-3-methylmorpholin-4-yl]quinoxaline-6-carboxylate

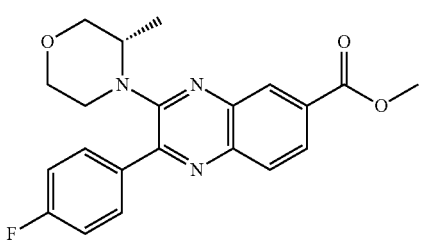 [SMILES: COC(=O)c1ccc2nc(-c3ccc(F)cc3)c(N3CCOC[C@@H]3C)nc2c1]

To a solution of methyl 3-[(3S)-3-methylmorpholin-4-yl]-2-[(trifluoromethane)sulfonyloxy]quinoxaline-6-carboxylate (300 mg, crude) in dioxane (10 mL) was added Pd(PPh₃)₄ (40 mg, 0.03 mmol), (4-fluorophenyl)boronic acid (200 mg, 1.43 mmol), K₃PO₄ (292 mg, 1.38 mmol) and water (1 mL). The resulting solution was stirred for 1 h at 90° C. with an inert atmosphere of nitrogen, and then concentrated in vacuo to give a residue, which was purified by a silica gel column chromatography (2%-4% ethyl acetate in petroleum ether) to afford methyl 2-(4-fluorophenyl)-3-[(3S)-3-methylmorpholin-4-yl]quinoxaline-6-carboxylate as a yellow solid (140 mg).

LC/MS (ES, m/z): [M+H]+ 382.0
¹H-NMR (300 MHz, CDCl₃), δ 8.56 (d, J=1.8 Hz, 1H), 8.00-8.16 (m, 4H), 7.20-7.26 (m, 2H), 4.01 (s, 3H), 3.84-3.89 (m, 2H), 3.64-3.76 (m, 2H), 3.31-3.56 (m, 3H), 1.17 (d, J=6.6 Hz, 3H)

Step 4. (S)-2-(4-Fluorophenyl)-3-(3-methylmorpholino)quinoxaline-6-carboxylic acid

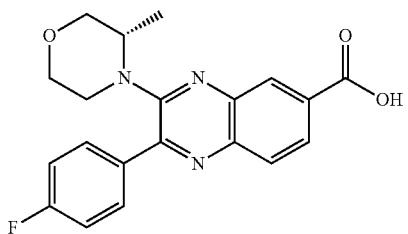 [SMILES: C[C@H]1COCCN1c1nc2cc(C(=O)O)ccc2nc1-c1ccc(F)cc1]

To a solution of (S)-methyl 2-(4-fluorophenyl)-3-(3-methylmorpholino)quinoxaline-6-carboxylate (140.0 mg, 0.37 mmol,) in methanol (15 mL) and CHCl₃ (5 mL) was added a solution of NaOH (45 mg, 1.12 mmol) in water (1 mL). The resulting solution was stirred overnight at room temperature and concentrated in vacuo. The residue was dissolved in water (10 mL) and adjusted to pH 6 with hydrochloric acid (1N). The solids were collected by filtration to afford (S)-2-(4-fluorophenyl)-3-(3-methylmorpholino)quinoxaline-6-carboxylic acid as a yellow solid (91.2 mg, 68%).

(ES, m/z): [M+H]+ 368.0
¹H-NMR (300 MHz, DMSO), δ 8.31 (d, J=0.6 Hz, 1H), 8.01-8.09 (m, 4H), 7.37-7.43 (t, J=8.7 Hz, 2H), 3.75-3.79 (m, 2H), 3.45-3.64 (m, 4H), 3.26-3.33 (m, 1H), 1.08 (d, J=6.6 Hz, 3H)

Example 106

2-(4-Fluorophenyl)-3-[(2R)-2-(trifluoromethyl)piperidin-1-yl]quinoxaline-6-carboxylic acid

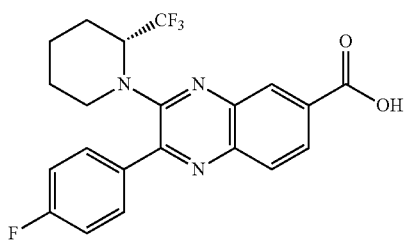

Step 1. (R)-2-(4-Fluorophenyl)-3-(2-(trifluoromethyl)piperidin-1-yl)quinoxaline-6-carboxylic acid

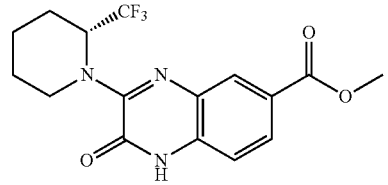 [SMILES: COC(=O)c1ccc2[nH]c(=O)c(N3CCCC[C@@H]3C(F)(F)F)nc2c1]

To a solution of methyl 3-chloro-2-oxo-1,2-dihydroquinoxaline-6-carboxylate (1 g, crude) in NMP (1 mL) was added (2R)-2-(trifluoromethyl)piperidine (700 mg, 4.57 mmol). The resulting solution was stirred for 5 h at 160° C. and then purified by a silica gel column chromatography (5% ethyl acetate in petroleum ether) to afford (R)-2-(4-fluorophenyl)-3-(2-(trifluoromethyl)piperidin-1-yl)quinoxaline-6-carboxylic acid as a yellow solid (55 mg, crude).
LC/MS (ES, m/z): [M+H]⁺ 356.0

Step 2. Methyl 2-[(trifluoromethane)sulfonyloxy]-3-[(2R)-2-(trifluoromethyl)piperidin-1-yl]quinoxaline-6-carboxylate

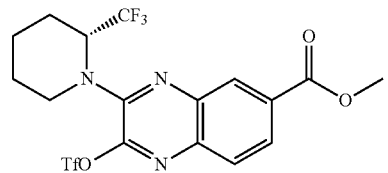 [SMILES: COC(=O)c1ccc2nc(OS(=O)(=O)C(F)(F)F)c(N3CCCC[C@@H]3C(F)(F)F)nc2c1]

To a solution of methyl 2-oxo-3-[(2R)-2-(trifluoromethyl)piperidin-1-yl]-1,2-dihydroquinoxaline-6-carboxylate (55 mg, crude) in dichloromethane (30 mL) was added pyridine (58 mg, 0.73 mmol) and Tf₂O (103 mg, 0.37 mmol). The resulting solution was stirred overnight at room temperature, and then quenched by the addition of water/ice (50 mL) and extracted with dichloromethane (2×20 mL). The organic layers were combined and dried over anhydrous magnesium sulfate and concentrated in vacuo to afford methyl 2-[(trifluoromethane)sulfonyloxy]-3-[(2R)-2-(trifluoromethyl)piperidin-1-yl]quinoxaline-6-carboxylate as red oil (80 mg, crude).

Step 3. Methyl 2-(4-fluorophenyl)-3-[(2R)-2-(trifluoromethyl)piperidin-1-yl]quinoxaline-6-carboxylate

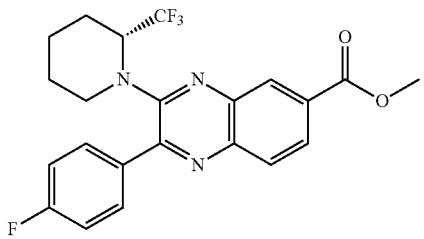 [SMILES: COC(=O)c1ccc2nc(-c3ccc(F)cc3)c(N3CCCC[C@@H]3C(F)(F)F)nc2c1]

To a solution of methyl 2-[(trifluoromethane)sulfonyloxy]-3-[(2R)-2-(trifluoromethyl)piperidin-1-yl]quinoxaline-6-carboxylate (80 mg, crude) in dioxane (2 mL) was added (4-fluorophenyl)boronic acid (69 mg, 0.49 mmol), K$_3$PO$_4$ (69 mg, 0.33 mmol), and Pd(PPh$_3$)$_4$ (9 mg, 0.01 mmol). The resulting solution was stirred for 1 h at 90° C. and then concentrated in vacuo. The residue was purified by a silica gel column chromatography (1%-5% ethyl acetate/petroleum ether) to afford methyl 2-(4-fluorophenyl)-3-[(2R)-2-(trifluoromethyl)piperidin-1-yl]quinoxaline-6-carboxylate as yellow oil (15 mg, crude).

LC/MS (ES, m/z): [M+H]$^+$ 434.0

Step 4. 2-(4-Fluorophenyl)-3-[(2R)-2-(trifluoromethyl)piperidin-1-yl]quinoxaline-6-carboxylic acid

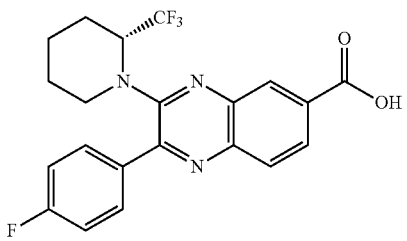 [SMILES: O=C(O)c1ccc2nc(-c3ccc(F)cc3)c(N3CCCC[C@@H]3C(F)(F)F)nc2c1]

To a solution of methyl 2-(4-fluorophenyl)-3-[(2R)-2-(trifluoromethyl)piperidin-1-yl]quinoxaline-6-carboxylate (15 mg, crude) in methanol (15 mL) was added sodium hydroxide (10 mg, 0.25 mmol) in water (1 mL). The resulting solution was stirred overnight at room temperature and concentrated in vacuo. The residue was dissolved in water (5 mL) and adjusted pH to 6 with HCl (1N), then extracted with dichloromethane (4×10 mL) and the organic layers combined and dried over anhydrous magnesium sulfate and concentrated in vacuo to give a residue. Purification via Prep-HPLC under the following conditions [(Agilent 1200 prep HPLC): Column, SunFire Prep C18, 19*50 mm 5 um; mobile phase, water with 0.05% NH3 and CH$_3$CN (10% CH$_3$CN up to 45% in 7 min); Detector, UV 220 nm] afforded 2-(4-fluorophenyl)-3-[(2R)-2-(trifluoromethyl)piperidin-1-yl]quinoxaline-6-carboxylic acid as a yellow solid (9 mg).

LC/MS (ES, m/z): [M+H]$^+$ 420.0

$^1$H-NMR (300 MHz, DMSO), δ; 8.47 (d, J=1.5 Hz, 1H), 8.13-8.17 (m, 1H) 7.95-8.03 (m, 1H), 7.28-7.36 (m, 2H), 4.93-4.99 (m, 1H), 3.50-3.56 (m, 1H), 3.16-3.25 (m, 1H), 1.94-2.00 (m, 2H), 1.66-1.71 (m, 3H), 1.51-1.55 (m, 1H)

Example 107

3-(tert-Butyl(methyl)amino)-2-(4-fluorophenyl)quinoxaline-6-carboxylic acid

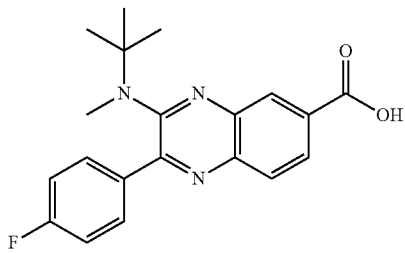 [SMILES: CN(c1nc2cc(C(=O)O)ccc2nc1-c1ccc(F)cc1)C(C)(C)C]

Step 1. Methyl 3-(tert-butylamino)-2-(4-fluorophenyl)quinoxaline-6-carboxylate

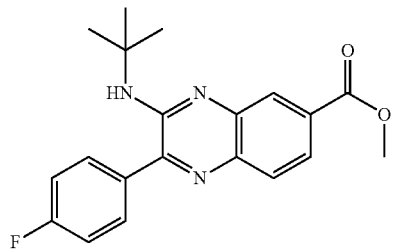 [SMILES: COC(=O)c1ccc2nc(-c3ccc(F)cc3)c(NC(C)(C)C)nc2c1]

To a solution of methyl 3-chloro-2-(4-fluorophenyl)quinoxaline-6-carboxylate (200 mg, 0.63 mmol) in DMSO (10 mL) was added DIEA (163 mg, 1.26 mmol) and 2-methylpropan-2-amine (461.3 mg, 6.32 mmol) with stirring overnight at 90° C. in an oil bath. The reaction mixture was cooled to room temperature, diluted with H$_2$O (150 mL), extracted with ethyl acetate (3×80 mL). The organic layers were combined, dried over magnesium sulfate, and concentrated in vacuo to give the residue, which was purified by silica gel column chromatography (1% ethyl acetate in petroleum ether) to afford methyl 3-(tert-butylamino)-2-(4-fluorophenyl)quinoxaline-6-carboxylate as a light yellow solid (115 mg, 51%).

(ES, m/z): [M+H]$^+$ 354.0

$^1$H-NMR (300 MHz, CDCl$_3$): δ 8.46 (d, J=1.5 Hz, 1H), 7.93-8.01 (m, 2H), 7.73-7.78 (m, 2H), 7.25-7.31 (m, 2H), 5.09 (s, 1H), 4.02 (s, 3H), 1.54 (s, 9H)

Step 2. 3-(tert-Butyl(methyl)amino)-2-(4-fluorophenyl)quinoxaline-6-carboxylic acid

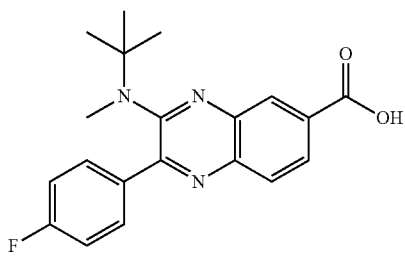 [SMILES: CN(c1nc2cc(C(=O)O)ccc2nc1-c1ccc(F)cc1)C(C)(C)C]

To a solution of methyl 3-(tert-butylamino)-2-(4-fluorophenyl)quinoxaline-6-carboxylate (115 mg, 0.33 mmol) in tetrahydrofuran (30 mL) was added sodium hydride (65 mg, 2.71 mmol) at 0° C. and then stirred for 10 minutes at room temperature. Methyliodide (185 mg, 1.30 mmol) was then added with stirring, and the reaction was allowed to proceed overnight at room temperature. The reaction was quenched with water (50 mL), adjusted to pH 5 with HCl (3N), extracted with ethyl acetate (3×80 mL) and the organic layers combined, dried over anhydrous magnesium sulfate and concentrated in vacuo to give the residue. Purification via Prep-HPLC under the following conditions [(Agilent 1200 prep HPLC): Column, SunFire Prep C18, 19*50 mm 5 um; mobile phase, water with 0.05% TFA and $CH_3CN$ (10% $CH_3CN$ up to 45% in 10 min); Detector, UV 220 nm] afforded 3-(tert-butyl(methyl)amino)-2-(4-fluorophenyl)quinoxaline-6-carboxylic acid as a light yellow solid (8.20 mg, 7.13%).

LC/MS (ES, m/z): $[M+H]^+$ 354.0

$^1$H-NMR (300 MHz, DMSO): δ 8.29 (d, J=1.2 Hz, 1H), 7.99-8.29 (m, 4H), 7.34-7.40 (t, J=9.0 Hz, 2H), 2.46 (s, 3H), 1.52 (s, 9H)

Example 108

3-(Cyclohexyl(methyl)amino)-2-(4-fluorophenyl)quinoxaline-6-carboxylic acid

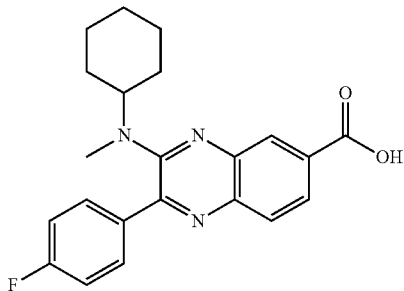 [SMILES: CN(c1nc2cc(C(=O)O)ccc2nc1-c1ccc(F)cc1)C1CCCCC1]

Step 1. Methyl 3-(cyclohexylamino)-2-(4-fluorophenyl)quinoxaline-6-carboxylate

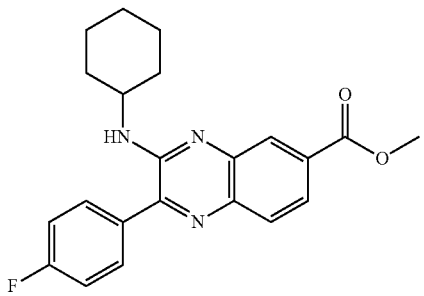 [SMILES: COC(=O)c1ccc2nc(-c3ccc(F)cc3)c(NC3CCCCC3)nc2c1]

To a solution of methyl 3-chloro-2-(4-fluorophenyl)quinoxaline-6-carboxylate (200 mg, 0.63 mmol) in DMSO (10 mL) was added DIEA (163.3 mg, 1.27 mmol) and cyclohexanamine (250.7 mg, 2.53 mmol), and the reaction was allowed to proceed with stirring overnight at 90° C. in an oil bath. The reaction mixture was cooled down to room temperature and diluted with water (150 mL). The mixture was extracted with ethyl acetate (3×80 mL), the organic layers combined and dried over magnesium sulfate, concentrated in vacuo to give the residue, which was purified by a silica gel column chromatography (1% ethyl acetate in petroleum ether) to afford methyl 3-(cyclohexylamino)-2-(4-fluorophenyl)quinoxaline-6-carboxylate as a light yellow solid (200 mg, 83%).

LC/MS (ES, m/z): $[M+H]^+$ 380.0

$^1$H-NMR (300 MHz, $CDCl_3$): δ 8.52 (s, 1H), 7.98 (d, J=8.4 Hz, 1H), 7.90 (d, J=8.4 Hz, 1H), 7.72-7.76 (t, J=5.7 Hz, 2H), 7.26-7.31 (t, J=7.5 Hz, 2H), 5.10 (s, 1H), 4.24 (s, 1H), 3.99 (s, 3H), 2.14 (d, J=7.5 Hz, 2H), 1.66-1.76 (m, 3H), 1.53-1.56 (d, J=7.8 Hz, 2H), 1.16 (s, 3H)

Step 2. 3-(Cyclohexyl(methyl)amino)-2-(4-fluorophenyl)quinoxaline-6-carboxylic acid

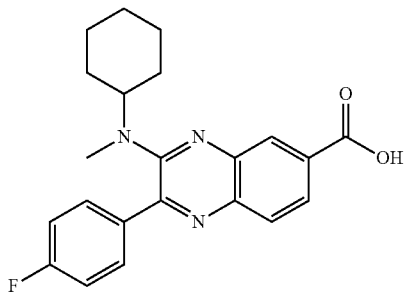 [SMILES: CN(c1nc2cc(C(=O)O)ccc2nc1-c1ccc(F)cc1)C1CCCCC1]

To a solution of methyl 3-(cyclohexylamino)-2-(4-fluorophenyl)quinoxaline-6-carboxylate (200 mg, 0.53 mmol) in tetrahydrofuran (30 mL) was added sodium hydride (105.5 mg, 4.40 mmol) and $CH_3I$ (299.9 mg, 2.11 mmol), and the reaction was allowed to proceed with stirring overnight at room temperature. The reaction was then quenched by the addition of water (50 mL), adjusted pH to 5 with HCl (3N). The resulting solution was extracted with ethyl acetate (3×80 mL) and the organic layers combined, dried over anhydrous magnesium sulfate, and concentrated in vacuo to give the crude product. The crude product was re-crystallized from ethyl acetate:petroleum ether (1:5) to afford 3-(cyclohexyl(methyl)amino)-2-(4-fluorophenyl)quinoxaline-6-carboxylic acid (100 mg, 48%) as a light yellow solid.

LC/MS (ES, m/z): $[M+H]^+$ 380.1

$^1$H-NMR (300 MHz, DMSO): δ 13.19 (s, 1H), 8.24-8.25 (t, J=1.20 Hz, 1H), 7.85-7.94 (m, 4H), 7.34-7.40 (t, J=8.7 Hz, 2H), 3.63-3.71 (m, 1H), 2.72 (s, 3H), 1.64 (d, J=9.6 Hz, 2H), 1.40-1.60 (m, 5H), 0.99-1.05 (t, J=7.80 Hz, 3H)

Example 109

2-(4-Fluorophenyl)-3-(methyl(o-tolyl)amino)quinoxaline-6-carboxylic acid

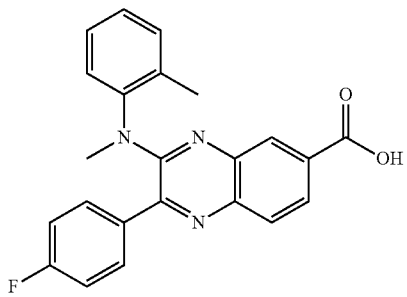 [SMILES: Cc1ccccc1N(C)c1nc2cc(C(=O)O)ccc2nc1-c1ccc(F)cc1]

Step 1. Methyl 3-(o-toluidino)-2-(4-fluorophenyl) quinoxaline-6-carboxylate

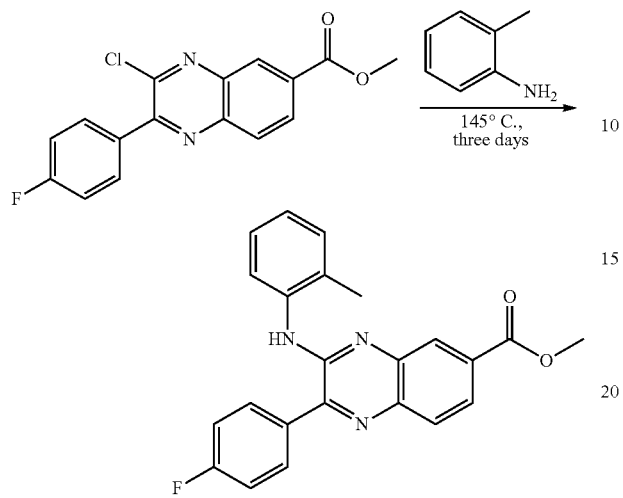

Methyl 3-chloro-2-(4-fluorophenyl)quinoxaline-6-carboxylate (300 mg, 0.95 mmol) was stirred in o-toluidine (10 mL) at 145° C. for 3 days in an oil bath. The reaction mixture was concentrated in vacuo to give a residue, which was purified by a silica gel column chromatography (1% ethyl acetate in petroleum ether) to afford methyl 3-(o-toluidino)-2-(4-fluorophenyl)quinoxaline-6-carboxylate as a light yellow solid (145 mg, 37%).

LC/MS (ES, m/z): [M+H]+ 388.0

1H-NMR (300 MHz, CDCl3): δ 8.55 (d, J=1.8 Hz, 2H), 8.49 (d, J=8.1 Hz, 2H), 8.08-8.12 (dd, J=1.8 Hz, 2H), 7.98 (d, J=8.7 Hz, 2H), 7.83-7.88 (m, 4H), 7.32-7.38 (m, 5H), 7.22 (d, J=6.9 Hz, 2H), 7.09-7.12 (t, J=0.9 Hz, 2H), 6.98 (s, 2H), 4.00-4.03 (t, J=5.4 Hz, 6H), 2.13 (s, 6H)

Step 2. 2-(4-Fluorophenyl)-3-(methyl(o-tolyl)amino) quinoxaline-6-carboxylic acid

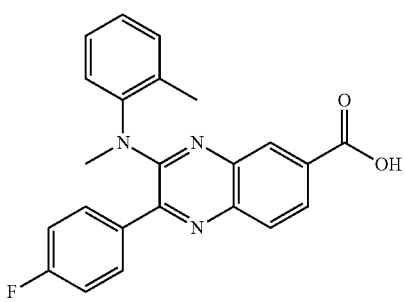 [SMILES: Cc1ccccc1N(C)c1nc2cc(C(=O)O)ccc2nc1-c1ccc(F)cc1]

To a solution of methyl 3-(o-toluidino)-2-(4-fluorophenyl) quinoxaline-6-carboxylate (145 mg, 0.37 mmol) in tetrahydrofuran (30 mL) was added sodium hydride (74.9 mg, 3.12 mmol) at 0° C. with stirring for 30 min, followed by the addition of CH3I (1.5 mL) dropwise. The reaction mixture was stirred overnight at room temperature. The reaction was then quenched with water (50 mL), adjusted to pH 5 with HCl (3N), and extracted with ethyl acetate (3×80 mL). The organic layers were combined, dried over anhydrous magnesium sulfate and concentrated in vacuo to give the residue, which was purified by Prep-HPLC under the following conditions [(Agilent 1200 prep HPLC): Column, SunFire Prep C18, 19*50 mm 5 um; mobile phase, water with 0.05% TFA and CH3CN (25% CH3CN up to 67% in 10 min); Detector, UV 220 nm] to afford 2-(4-fluorophenyl)-3-(methyl(o-tolyl)amino)quinoxaline-6-carboxylic acid as a light yellow solid (46.5 mg, 30%).

LC/MS (ES, m/z): [M+H]+ 388.0

1H-NMR (300 MHz, DMSO): δ 8.39 (d, J=1.2 Hz, 1H), 7.96-8.03 (m, 2H), 7.28-7.33 (m, 2H), 6.87-6.98 (m, 5H), 6.63-6.65 (t, J=3.6 Hz, 1H), 3.32 (s, 6H), 2.07 (s, 3H)

Example 110

3-(tert-Butylamino)-2-(4-fluorophenyl)quinoxaline-6-carboxylic acid

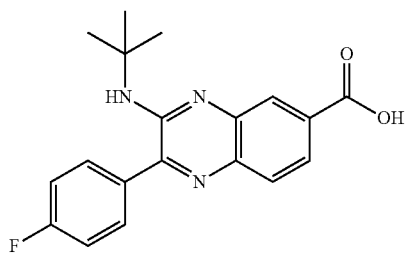 [SMILES: CC(C)(C)Nc1nc2cc(C(=O)O)ccc2nc1-c1ccc(F)cc1]

To a solution of methyl 3-(tert-butylamino)-2-(4-fluorophenyl)quinoxaline-6-carboxylate (120 mg, 0.34 mmol) in THF (20 mL) and water (2 mL) was added sodium hydroxide (54.39 mg, 1.36 mmol) with stirring overnight at room temperature. The reaction mixture was concentrated in vacuo, dissolved in water (30 mL), adjusted to pH 4 with HCl (3N) to give the precipitate, which was collected by filtration to afford 3-(tert-butylamino)-2-(4-fluorophenyl)quinoxaline-6-carboxylic acid as a light yellow solid (80 mg, 66%).

(ES, m/z): [M+H]+ 340.0

1H-NMR (300 MHz, DMSO): δ 8.18 (d, J=0.9 Hz, 1H), 7.84-7.89 (m, 4H), 7.38-7.44 (m, 2H), 5.77 (s, 1H), 4.02 (s, 3H), 1.49 (s, 9H)

Example 111

3-(Ethyl(isopropyl)amino)-2-(4-fluorophenyl)quinoxaline-6-carboxylic acid

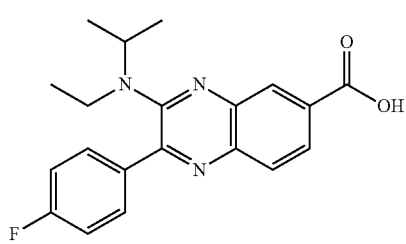

Step 1. Methyl 2-(4-fluorophenyl)-3-(isopropylamino)quinoxaline-6-carboxylate

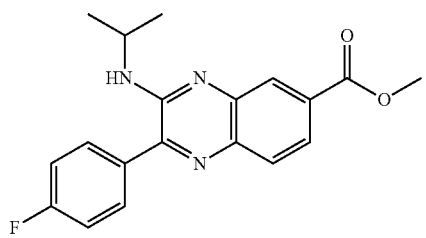 [SMILES: COC(=O)c1ccc2nc(-c3ccc(F)cc3)c(NC(C)C)nc2c1]

To a solution of methyl 3-chloro-2-(4-fluorophenyl)quinoxaline-6-carboxylate (200 mg, 0.63 mmol) in DMSO (10 mL) was added DIEA (489 mg, 3.79 mmol) and propan-2-amine (149.4 mg, 2.53 mmol) under nitrogen atmosphere. After stirring overnight at 70° C., the reaction mixture was dissolved in water (100 mL), extracted with dichloromethane (3×80 mL), dried over anhydrous magnesium sulfate and concentrated under reduced pressure to afford a residue. Purification via silica gel column chromatography (2% ethyl acetate in petroleum ether) afforded methyl 2-(4-fluorophenyl)-3-(isopropylamino)quinoxaline-6-carboxylate as a light yellow solid (100 mg, 44%).

LC/MS (ES, m/z): [M+H]+ 368.0

$^1$H-NMR (300 MHz, CDCl$_3$) δ 8.57 (s, 1H), 8.00-8.04 (m, 1H), 7.92 (d, J=8.7 Hz, 1H), 7.73-7.78 (m, 2H), 7.26-7.32 (m, 2H), 5.07 (s, 1H), 4.54 (d, J=6.6 Hz, 1H), 4.00 (s, 3H), 1.30 (d, J=6.6 Hz, 6H)

Step 2. 3-(Ethyl(isopropyl)amino)-2-(4-fluorophenyl)quinoxaline-6-carboxylic acid

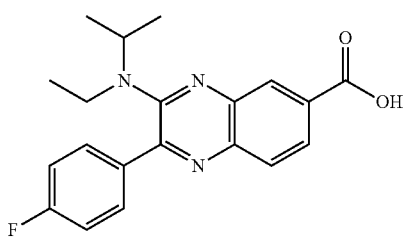 [SMILES: CCN(c1nc2cc(C(=O)O)ccc2nc1-c1ccc(F)cc1)C(C)C]

To a solution of methyl 2-(4-fluorophenyl)-3-(isopropylamino)quinoxaline-6-carboxylate (95 mg, 0.28 mmol) in tetrahydrofuran (20 mL) was added sodium hydride (23 mg, 0.96 mmol) and stirred for 10 minutes. Subsequently, iodoethane (43.7 mg, 0.28 mmol) was added and stirred overnight at room temperature. The reaction mixture was concentrated under reduced pressure to afford a residue, which was dissolved in water (25 mL) and the pH adjusted to 6 with hydrochloric acid (3N). The product precipitated and was filtered to afford 3-(ethyl(isopropyl)amino)-2-(4-fluorophenyl)quinoxaline-6-carboxylic acid as a light yellow solid (28.4 mg, 29%).

LC/MS (ES, m/z): [M+H]+ 354.0

$^1$H-NMR (300 MHz, CDCl$_3$) δ 8.63 (s, 1H), 7.95-8.11 (m, 3H), 7.15-7.21 (m, 3H), 3.81 (s, 1H), 3.36 (s, 2H), 1.18 (s, 3H), 0.96 (d, J=6.6 Hz, 6H)

Example 112

3-[Cyclohexyl(ethyl)amino]-2-(4-fluorophenyl)quinoxaline-6-carboxylic acid

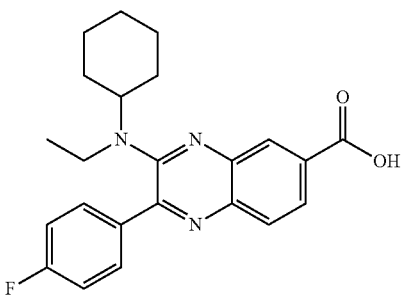 [SMILES: CCN(c1nc2cc(C(=O)O)ccc2nc1-c1ccc(F)cc1)C1CCCCC1]

To a solution of methyl 3-(cyclohexylamino)-2-(4-fluorophenyl)quinoxaline-6-carboxylate (130 mg, 0.34 mmol) in tetrahydrofuran (20 mL) was added sodium hydride (28 mg, 60%) and stirred for 10 minutes, followed by the addition of iodoethane (107 mg, 0.69 mmol).

After stirring overnight at room temperature, the reaction mixture was concentrated under reduced pressure to afford a residue, which was dissolved in water (10 mL), and the pH adjusted to 6 with hydrochloric acid (3N). The product precipitated and was filtered to afford 3-[cyclohexyl(ethyl)amino]-2-(4-fluorophenyl)quinoxaline-6-carboxylic acid as a light yellow solid (50.9 mg, 38%).

LC/MS (ES, m/z): [M+H]+ 394.0

$^1$H-NMR (300 MHz, CDCl$_3$) δ 8.61 (s, 1H), 8.09 (s, 1H), 7.90-7.97 (m, 3H), 7.16-7.22 (t, J=8.1 Hz, 1H), 3.43 (d, J=6.6 Hz, 3H), 1.63 (d, J=6.6 Hz, 2H), 1.39-1.49 (m, 5H), 1.19-1.27 (m, 3H), 0.85-0.97 (m, 3H)

Example 113

3-(Diethylamino)-2-(4-fluorophenyl)quinoxaline-6-carboxylic acid

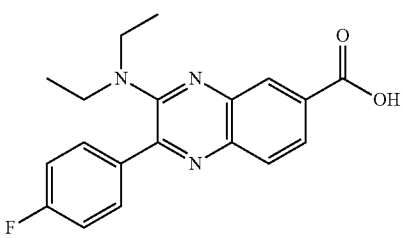 [SMILES: CCN(CC)c1nc2cc(C(=O)O)ccc2nc1-c1ccc(F)cc1]

Step 1. Methyl 3-(diethylamino)-2-(4-fluorophenyl)quinoxaline-6-carboxylate

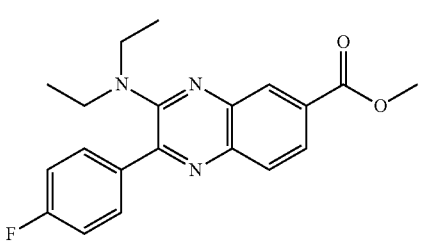 [SMILES: CCN(CC)c1nc2cc(C(=O)OC)ccc2nc1-c1ccc(F)cc1]

To a solution of methyl 3-chloro-2-(4-fluorophenyl)quinoxaline-6-carboxylate (150 mg, 0.47 mmol) in DMSO (2 mL) was added diethylamine (173 mg, 2.37 mmol) and DIEA (170 mg, 1.32 mmol). The resulting solution was stirred overnight at 70° C. and then quenched by the addition of water/ice (40 mL), extracted with ethyl acetate (3×20 mL), the organic layers combined and dried over anhydrous magnesium sulfate and concentrated in vacuo to give a residue. Purification via silica gel column chromatography (0.5%-4% ethyl acetate in petroleum ether) afforded methyl 3-(diethylamino)-2-(4-fluorophenyl)quinoxaline-6-carboxylate as a yellow solid (100 mg, 60%).

LC/MS (ES, m/z): [M+H]+ 354.0

$^1$H-NMR (300 MHz, CDCl$_3$), δ 8.68 (d, J=1.5 Hz, 1H), 8.11 (d, J=1.8 Hz, 1H), 8.08 (d, J=1.8 Hz, 1H), 7.99 (d, J=8.4 Hz, 1H), 7.90-7.95 (m, 1H), 7.19-7.25 (m, 2H), 4.01 (s, 3H), 3.38-3.45 (m, 4H), 1.10-1.15 (t, J=6.9 Hz, 6H)

Step 2. 3-(Diethylamino)-2-(4-fluorophenyl)quinoxaline-6-carboxylic acid

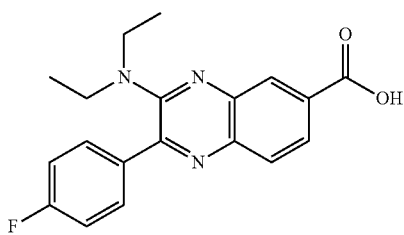 [SMILES: CCN(CC)c1nc2cc(C(=O)O)ccc2nc1-c1ccc(F)cc1]

To a solution of methyl 3-(diethylamino)-2-(4-fluorophenyl)quinoxaline-6-carboxylate (95.0 mg, 0.27 mmol,) in methanol (20 mL) was added a solution of NaOH (20 mg, 0.50 mmol) in water (1 mL). The resulting solution was stirred overnight at room temperature and concentrated in vacuo. The residue was dissolved in water (5 mL) and adjusted to pH 5 with hydrochloric acid (1N). The solids were collected by filtration to afford 3-(diethylamino)-2-(4-fluorophenyl)quinoxaline-6-carboxylic acid as a yellow solid (50 mg, 55%).

(ES, m/z): [M+H]+ 340.0

$^1$H-NMR (300 MHz, DMSO), δ 13.21 (s, 1H), 8.28 (t, J=1.2 Hz, 1H), 7.89-7.96 (m, 4H), 7.35-7.42 (t, J=9.0 Hz, 2H), 3.26-3.33 (m, 4H), 1.00-1.04 (m, 3H)

Example 114

2-(4-Fluorophenyl)-3-[(2S)-2-methylpiperazin-1-yl]quinoxaline-6-carboxylic acid

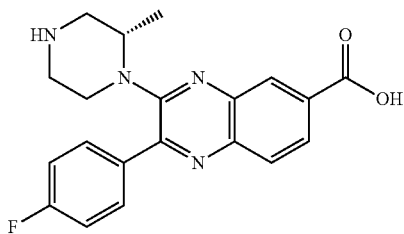 [SMILES: C[C@H]1CNCCN1c1nc2cc(C(=O)O)ccc2nc1-c1ccc(F)cc1]

Step 1. Methyl 3-[(2S)-4-[(tert-butoxy)carbonyl]-2-methylpiperazin-1-yl]-2-oxo-1,2-dihydroquinoxaline-6-carboxylate

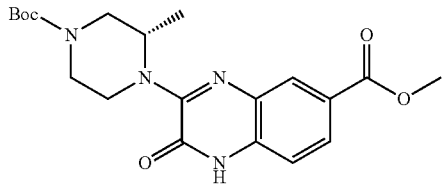 [SMILES: COC(=O)c1ccc2[nH]c(=O)c(N3CCN(C(=O)OC(C)(C)C)C[C@@H]3C)nc2c1]

To a solution of methyl 3-chloro-2-oxo-1,2-dihydroquinoxaline-6-carboxylate (1.0 g, crude) in DMSO (10 mL) was added tert-butyl-(3S)-3-methylpiperazine-1-carboxylate (1.0 g, 4.99 mmol) and DIEA (1.0 g, 7.74 mmol). The resulting solution was stirred overnight at 80° C. in an oil bath and then diluted with water (100 mL), extracted with ethyl acetate (4×40 mL) and the organic layers combined and dried over anhydrous magnesium sulfate. The solids were filtered out and filtrate was concentrated in vacuo to give a residue, which was purified by a silica gel column chromatography (2% ethyl acetate in petroleum ether) to afford methyl 3-[(2S)-4-[(tert-butoxy)carbonyl]-2-methylpiperazin-1-yl]-2-oxo-1,2-dihydroquinoxaline-6-carboxylate as a light yellow solid (310 mg).

LC/MS (ES, m/z): [M+H]$^+$ 403.0

$^1$H-NMR (300 MHz, CDCl$_3$) δ 8.43 (s, 1H), 8.26 (d, J=1.5 Hz, 1H), 7.87-7.91 (m, 1H), 7.07 (d, J=2.1 Hz, 1H), 4.79-4.84 (m, 1H), 3.94-4.01 (m, 5H), 3.45-3.46 (m, 1H), 3.25-3.41 (m, 3H), 1.52 (s, 9H), 1.24 (d, J=5.7 Hz, 3H)

Step 2. Methyl 3-[(2S)-4-[(tert-butoxy)carbonyl]-2-methylpiperazin-1-yl]-2-[(trifluoromethane)sulfonyloxy]quinoxaline-6-carboxylate

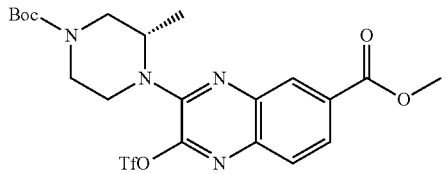 [SMILES: COC(=O)c1ccc2nc(OS(=O)(=O)C(F)(F)F)c(N3CCN(C(=O)OC(C)(C)C)C[C@@H]3C)nc2c1]

To a solution of methyl 3-[(2S)-4-[(tert-butoxy)carbonyl]-2-methylpiperazin-1-yl]-2-oxo-1,2-dihydroquinoxaline-6-carboxylate (300 mg, 0.75 mmol,) in dichloromethane (80 mL) was added pyridine (235.8 mg, 2.98 mmol) dropwise with stirring followed by Tf$_2$O (420.7 mg, 1.49 mmol), and the reaction was stirred overnight at room temperature. The resulting solution was diluted with water (50 mL), extracted with dichloromethane (3×20 mL), the organic layers combined and dried over anhydrous magnesium sulfate and concentrated in vacuo to afford methyl 3-[(2S)-4-[(tert-butoxy)carbonyl]-2-methylpiperazin-1-yl]-2-[(trifluoromethane)sulfonyloxy]quinoxaline-6-carboxylate as red oil (500 mg, crude).

Step 3. Methyl 3-[(2S)-4-[(tert-butoxy)carbonyl]-2-methylpiperazin-1-yl]-2-(4-fluorophenyl)quinoxaline-6-carboxylate

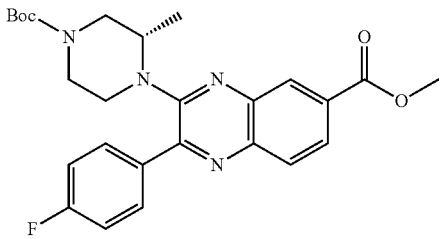 [SMILES: COC(=O)c1ccc2nc(-c3ccc(F)cc3)c(N3CCN(C(=O)OC(C)(C)C)C[C@@H]3C)nc2c1]

To a solution of methyl 3-[(2S)-4-[(tert-butoxy)carbonyl]-2-methylpiperazin-1-yl]-2-[(trifluoromethane)sulfonyloxy]quinoxaline-6-carboxylate (500 mg, crude) in dioxane (5 mL) and water (0.5 mL) was added 4-fluorophenyl)boronic acid (188.6 mg, 1.35 mmol), Pd(PPh$_3$)$_4$ (38.89 mg, 0.03 mmol,), and K$_3$PO$_4$ (426.6 mg, 2.01 mmol). The resulting solution was stirred for 1 h at 90° C. with an inert atmosphere of nitrogen and then concentrated in vacuo to give a residue. Purification via silica gel column chromatography (2%-5% ethyl acetate in petroleum ether) afforded methyl 3-[(2S)-4-[(tert-butoxy)carbonyl]-2-methylpiperazin-1-yl]-2-(4-fluorophenyl)quinoxaline-6-carboxylate as a light yellow solid (260 mg).

LC/MS (ES, m/z): [M+H]$^+$ 481.0

$^1$H-NMR (300 MHz, CDCl$_3$) δ 8.57 (d, J=1.8 Hz, 1H), 8.12-8.16 (m, 1H), 8.01-8.09 (m, 3H), 7.20-7.25 (m, 2H), 3.99-4.02 (m, 5H), 3.46-3.50 (m, 1H), 3.30-3.35 (m, 1H), 3.14-3.27 (m, 2H), 1.47 (s, 9H), 1.10 (d, J=6.6 Hz, 3H)

Step 4. 2-(4-Fluorophenyl)-3-[(2S)-2-methylpiperazin-1-yl]quinoxaline-6-carboxylic acid

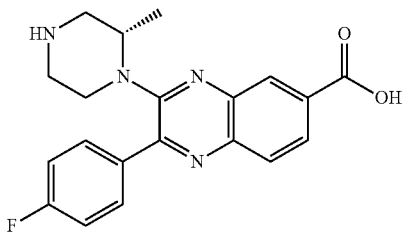 [SMILES: C[C@H]1CNCCN1c1nc2cc(C(=O)O)ccc2nc1-c1ccc(F)cc1]

To a solution of methyl 3-[(2S)-4-[(tert-butoxy)carbonyl]-2-methylpiperazin-1-yl]-2-(4-fluorophenyl)quinoxaline-6-carboxylate (260 mg, 0.54 mmol) in dichloromethane (30 mL) was added CF$_3$COOH (2 mL). The resulting solution was stirred overnight at room temperature and then concentrated in vacuo. The residue was dissolved in methanol (15 mL), and sodium hydroxide (20 mg, 0.50 mmol) in water (1 mL) was added. The resulting solution was stirred overnight at room temperature and concentrated in vacuo. The residue was dissolved in water (3 mL), the pH adjusted to 6, and the resulting solution concentrated in vacuo. The crude product (40 mg) was purified by Prep-HPLC with the following conditions (AGILENT Pre-HPLC(MS-Directed)): Column, 1#-PrepC-001(XBridge Shield RP18 19*150 186002987 111130103113 03), N; mobile phase, WATER WITH 0.03% NH$_3$H$_2$O and CH$_3$CN (10% CH$_3$CN up to 22% in 7 min, hold 100% in 2 min, hold 10% in 2 min); Detector, UV 220 nm) to afford 2-(4-fluorophenyl)-3-[(2S)-2-methylpiperazin-1-yl]quinoxaline-6-carboxylic acid as a yellow solid (31 mg, 59%).

LC/MS (ES, m/z): [M+H]$^+$ 367.0

$^1$H-NMR (300 MHz, CD$_3$OD) δ 8.42 (d, J=1.5 Hz, 1H), 8.05-8.14 (m, 3H), 7.89 (d, J=8.4 Hz, 3H), 7.26-7.32 (m, 2H), 3.79-3.82 (t, J=3.3 Hz, 1H), 3.26-3.30 (t, J=6.0 Hz, 2H), 2.94-3.00 (m, 1H), 2.84-2.88 (d, J=7.8 Hz, 2H), 2.61-2.66 (m, 1H), 1.14 (d, J=6.6 Hz, 3H)

Example 115

(S)-2-(2,4-Difluorophenyl)-3-(2-methylpyrrolidin-1-yl)quinoxaline-6-carboxylic acid

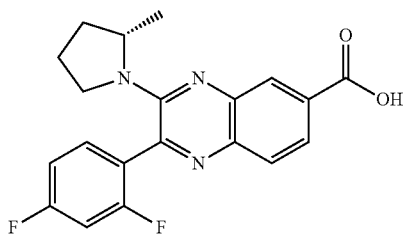

Step 1. (S)-Methyl 2-(2,4-difluorophenyl)-3-(2-methylpyrrolidin-1-yl)quinoxaline-6-carboxylate

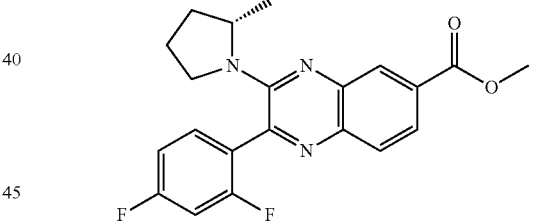

To a solution of (S)-methyl 3-(2-methylpyrrolidin-1-yl)-2-(trifluoromethylsulfonyloxy)quinoxaline-6-carboxylate (150 mg, 0.36 mmol) in dioxane (5 mL) was added 2,4-difluorophenylboronic acid (113 mg, 0.72 mmol), K$_3$PO$_4$ (152 mg, 0.72 mmol), Pd(PPh$_3$)$_4$ (20 mg, 0.02 mmol) and water (3 drops). The resulting solution was stirred for 1 hour at 90° C. and then concentrated in vacuo to give a residue, which was purified by silica gel column chromatography (5% ethyl acetate in petroleum ether) to afford (S)-methyl 2-(2,4-difluorophenyl)-3-(2-methylpyrrolidin-1-yl)quinoxaline-6-carboxylate as a yellow solid (115 mg, 84%).

LC/MS (ES, m/z): [M+H]$^+$ 384.0

$^1$H-NMR (300 MHz, CDCl$_3$): δ 8.66 (s, 1H), 8.02-8.05 (m, 1H), 7.94 (d, J=8.7 Hz, 1H), 7.65-7.80 (m, 1H), 7.04-7.10 (t, J=8.1 Hz, 1H), 6.92-6.99 (t, J=9.9 Hz, 1H), 4.51-4.53 (m, 1H), 4.00 (s, 3H), 3.05-3.08 (m, 2H), 2.17-2.21 (m, 1H), 1.85-1.95 (m, 1H), 1.65-1.75 (m, 2H), 1.41-1.47 (m, 3H)

Step 2. (S)-2-(2,4-Difluorophenyl)-3-(2-methylpyrrolidin-1-yl)quinoxaline-6-carboxylic acid

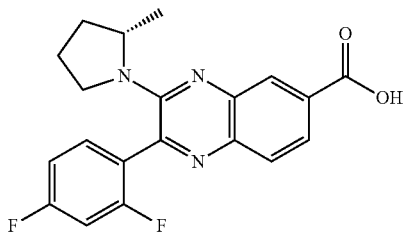 [SMILES: C[C@H]1CCCN1c1nc2cc(C(=O)O)ccc2nc1-c1ccc(F)cc1F]

To a solution of (S)-methyl 2-(2,4-difluorophenyl)-3-(2-methylpyrrolidin-1-yl)quinoxaline-6-carboxylate (100 mg, 0.39 mmol) in MeOH (20 mL) was added sodium hydroxide (63 mg, 1.57 mmol) and water (2 mL). The resulting solution was stirred overnight at room temperature and concentrated in vacuo. The residue was dissolved in water (2 mL) and adjusted to pH 6 with hydrochloric acid (1N). The solids were collected by filtration to afford (S)-2-(2,4-difluorophenyl)-3-(2-methylpyrrolidin-1-yl)quinoxaline-6-carboxylic acid as a brown solid (82.4 mg, 86%).

LC/MS (ES, m/z): [M+H]$^+$ 370.0

$^1$H-NMR (300 MHz, CD$_3$OD): δ 8.41 (d, J=1.8 Hz, 1H), 7.97-8.01 (m, 1H), 7.89 (d, J=8.4 Hz, 1H), 7.75-7.85 (m, 1H), 7.12-7.21 (m, 2H), 4.37-4.40 (m, 1H), 3.02-3.10 (m, 2H), 2.16-2.20 (m, 1H), 1.84-1.86 (m, 1H), 1.61-1.76 (m, 2H), 1.30-1.36 (t, J=6.0 Hz, 3H)

Example 116

(S)-2-(2,4-Difluorophenyl)-3-(2-methylpiperidin-1-yl)quinoxaline-6-carboxylic acid

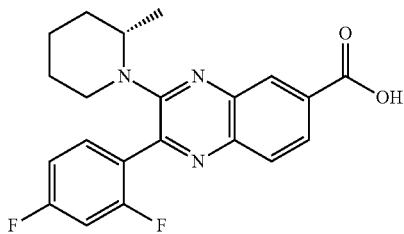 [SMILES: C[C@H]1CCCCN1c1nc2cc(C(=O)O)ccc2nc1-c1ccc(F)cc1F]

Step 1. (S)-Methyl 2-(2,4-difluorophenyl)-3-(2-methylpiperidin-1-yl)quinoxaline-6-carboxylate

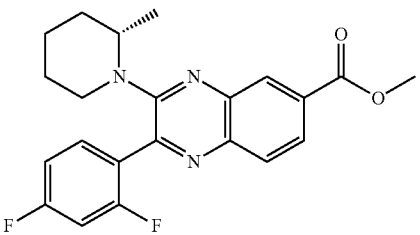 [SMILES: COC(=O)c1ccc2nc(-c3ccc(F)cc3F)c(N3CCCC[C@@H]3C)nc2c1]

To a solution of (2,4-difluorophenyl)boronic acid (218.9 mg, 1.39 mmol) in dioxane (5.0 mL) and water (3 drops) was added (S)-methyl 3-(2-methylpiperidin-1-yl)-2-(trifluoromethylsulfonyloxy)quinoxaline-6-carboxylate (300 mg, 0.69 mmol), K$_3$PO$_4$ (293 mg, 1.38 mmol) and Pd(PPh$_3$)$_4$ (39.97 mg, 0.03 mmol) with stirring for 1 hour at 95° C. in an oil bath under an inert atmosphere of nitrogen. The reaction mixture was concentrated in vacuo to give a residue, which was purified via silica gel column chromatography (2% ethyl acetate in petroleum ether) to afford (S)-methyl 2-(2,4-difluorophenyl)-3-(2-methylpiperidin-1-yl)quinoxaline-6-carboxylate as a light yellow solid (192.0 mg, 70%)

LC/MS (ES, m/z): [M+H]$^+$ 398.0

$^1$H-NMR (300 MHz, CDCl$_3$): δ 8.56 (d, J=1.50 Hz, 1H), 8.08-8.11 (m, 1H), 7.98 (d, J=8.70 Hz, 1H), 7.67-7.75 (m, 1H), 6.95-7.10 (m, 2H), 4.11-4.17 (m, 1H), 4.01 (s, 3H), 3.46-3.50 (m, 1H), 3.09-3.17 (m, 1H), 1.41-1.76 (m, 6H), 1.13 (d, J=6.60 Hz, 3H)

Step 2. (S)-2-(2,4-Difluorophenyl)-3-(2-methylpiperidin-1-yl)quinoxaline-6-carboxylic acid

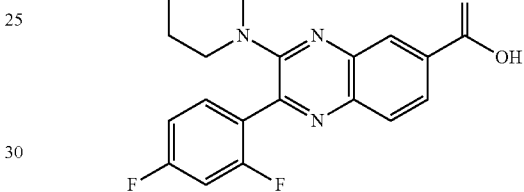

To a solution of (S)-methyl 2-(2,4-difluorophenyl)-3-(2-methylpiperidin-1-yl)quinoxaline-6-carboxylate (100 mg, 0.25 mmol) in methanol (30 mL) and water (1.0 mL) was added sodium hydroxide (40 mg, 1.00 mmol) with stirring overnight at room temperature. The reaction mixture was concentrated in vacuo, dissolved in water (10 mL) and adjusted to pH 5 with HCl (3N). The solids were collected by filtration to afford (S)-2-(2,4-difluorophenyl)-3-(2-methylpiperidin-1-yl)quinoxaline-6-carboxylic acid as a light yellow solid (55.5 mg, 57.5%).

LC/MS (ES, m/z): [M+H]$^+$ 366.0

$^1$H-NMR (300 MHz, DMSO): δ 8.29 (d, J=1.5 Hz 1H), 7.99-8.03 (m, 1H), 7.92 (d, J=8.4 Hz, 1H), 7.80-7.88 (m, 1H), 7.43-7.50 (m, 1H), 7.28-7.34 (m, 1H), 4.01-4.02 (m, 1H), 3.56-3.59 (m, 1H), 3.03-3.09 (m, 1H), 1.37-1.58 (m, 6H), 1.15 (d, J=6.6 Hz, 3H)

Example 117

(S)-2-(4-Fluoro-2-methylphenyl)-3-(2-methylpyrrolidin-1-yl)quinoxaline-6-carboxylic acid

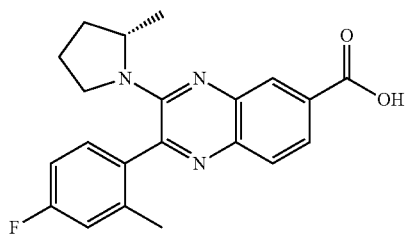

221

Step 1. (4-Fluoro-2-methylphenyl)boronic acid

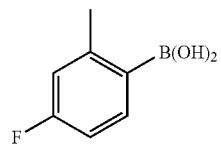

To a solution of 1-bromo-4-fluoro-2-methylbenzene (5 g, 26.45 mmol) in THF (100 mL) was added n-butyllithium (12.7 mL) dropwise at −78° C. Tris(propan-2-yl)borate (10 g, 53.17 mmol) was added dropwise and the reaction was stirred overnight at −78° C. in a liquid nitrogen bath. The resulting solution was diluted with aqueous sodium hydroxide (1N, 30 mL) and extracted with ether (2×50 mL). The aqueous layers were combined and adjusted to pH 3 with HCl (3N), extracted with ethyl acetate (3×50 mL), and the organic layers were combined and concentrated in vacuo to give (4-fluoro-2-methylphenyl)boronic acid as a white solid (2.1 g, 52%).

Step 2. (S)-Methyl 2-(4-fluoro-2-methylphenyl)-3-(2-methylpyrrolidin-1-yl)quinoxaline-6-carboxylate

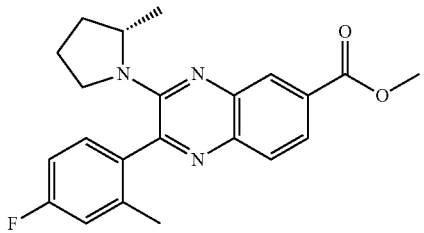 [SMILES: COC(=O)c1ccc2nc(-c3ccc(F)cc3C)c(N3CCC[C@@H]3C)nc2c1]

To a solution of (S)-methyl 3-(2-methylpyrrolidin-1-yl)-2-(trifluoromethylsulfonyloxy)quinoxaline-6-carboxylate (150 mg, 0.41 mmol) in dioxane (5.0 mL) and water (3 drops) was added (4-fluoro-2-methylphenyl)boronic acid (101 mg, 0.66 mmol), Pd(PPh$_3$)$_4$ (19.0 mg, 0.02 mmol), and K$_3$PO$_4$ (138.3 mg, 0.65 mmol). The reaction was stirred for 1 hour at 90° C. under a nitrogen atmosphere. The resulting solution was concentrated in vacuo, and then purified by silica gel column chromatography (1% ethyl acetate in petroleum ether) to provide (S)-methyl 2-(4-fluoro-2-methylphenyl)-3-(2-methylpyrrolidin-1-yl)quinoxaline-6-carboxylate as a yellow solid (120 mg, 78%).

LC/MS (ES, m/z): [M+H]$^+$ 380.0

$^1$H-NMR (300 MHz, DMSO) δ 8.27 (s, 1H), 7.87-7.95 (m, 2H), 7.66 (s, 1H), 7.20-7.30 (m, 2H), 4.23 (d, J=6.9 Hz, 1H), 3.93 (s, 3H), 3.00-3.05 (m, 1H), 2.73-2.80 (m, 1H), 2.30-2.40 (m, 1H), 1.99-2.12 (m, 3H), 1.75-1.85 (m, 1H), 1.46-1.65 (m, 2H), 1.18-1.30 (m, 3H)

Step 3. (S)-2-(4-Fluoro-2-methylphenyl)-3-(2-methylpyrrolidin-1-yl)quinoxaline-6-carboxylic acid

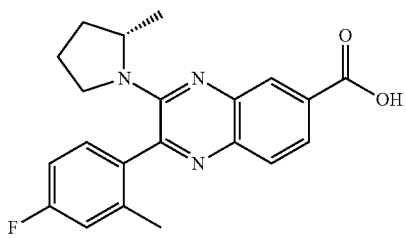 [SMILES: Cc1cc(F)ccc1-c1nc2ccc(C(=O)O)cc2nc1N1CCC[C@@H]1C]

To a solution of (S)-methyl 2-(4-fluoro-2-methylphenyl)-3-(2-methylpyrrolidin-1-yl)quinoxaline-6-carboxylate (120 mg, 0.32 mmol) in methanol (20 mL) and water (1 mL) was added sodium hydroxide (50.7 mg, 1.27 mmol,) and the reaction was stirred overnight at room temperature. The resulting mixture was concentrated in vacuo, adjusted to pH 6 with aqueous HCl (3N), collected by filtration to afford (S)-2-(4-fluoro-2-methylphenyl)-3-(2-methylpyrrolidin-1-yl)quinoxaline-6-carboxylic acid as a yellow solid (85.7 mg, 74%).

LC/MS (ES, m/z): [M+H]$^+$ 366.0

$^1$H-NMR (300 MHz, DMSO) δ 8.25 (s, 1H), 7.89 (s, 2H), 7.64 (s, 1H), 7.10-7.30 (m, 2H), 4.24-4.34 (m, 1H), 3.01-3.10 (m, 1H), 2.68-2.74 (m, 1H), 2.30-2.40 (m, 1H), 2.04-2.09 (m, 3H), 1.74-1.90 (m, 1H), 1.48-1.63 (m, 2H), 1.27 (d, J=6.0 Hz, 3H)

Example 118

2-(4-Fluoro-2-methylphenyl)-3-(isopropyl(methyl)amino)quinoxaline-6-carboxylic acid

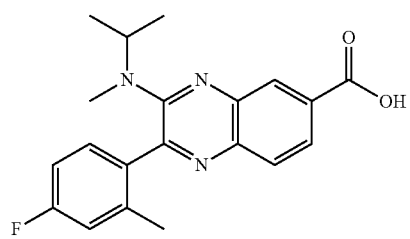

Step 1. Methyl 2-(4-fluoro-2-methylphenyl)-3-(isopropyl(methyl)amino)quinoxaline-6-carboxylate

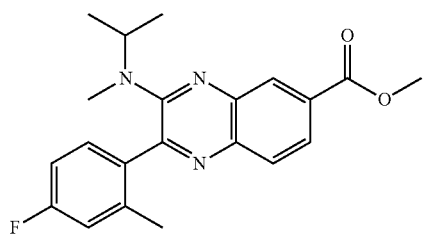 [SMILES: COC(=O)c1ccc2nc(-c3ccc(F)cc3C)c(N(C)C(C)C)nc2c1]

To a solution of (4-fluoro-2-methylphenyl)boronic acid (158 mg, 1.03 mmol) in dioxane (5.0 mL) and water (3 drops) was added methyl 2-chloro-3-[methyl(propan-2-yl)amino]quinoxaline-6-carboxylate (100 mg, 0.34 mmol), K$_3$PO$_4$ (215 mg, 1.01 mmol) and Pd(PPh$_3$)$_4$ (20 mg, 0.02 mmol), and the reaction was stirred for 1 hour at 95° C. under an inert atmosphere of nitrogen. The reaction mixture was concentrated in vacuo to provide a residue, which was purified via silica gel column chromatography (2% ethyl acetate in petroleum ether) to afford methyl 2-(4-fluoro-2-methylphenyl)-3-(isopropyl(methyl)amino)quinoxaline-6-carboxylate as a light yellow solid (53.0 mg, 42%).

LC/MS (ES, m/z): [M+H]$^+$ 368.0

$^1$H-NMR (300 MHz, CDCl$_3$): δ 8.55 (d, J=1.8 Hz, 1H), 8.04-8.08 (m, 1H), 7.95 (d, J=8.7 Hz, 1H), 7.43-7.49 (m, 1H), 7.02-7.07 (m, 2H), 4.21-4.30 (m, 1H), 4.01 (s, 3H), 2.69 (s, 3H), 2.30 (s, 3H), 1.09 (d, J=6.6 Hz, 6H)

Step 2. 2-(4-Fluoro-2-methylphenyl)-3-(isopropyl (methyl)amino)quinoxaline-6-carboxylic acid

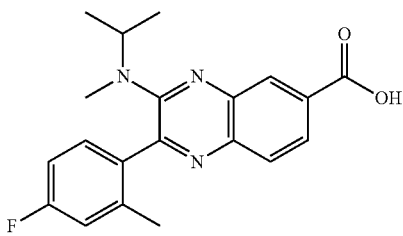 [SMILES: Cc1cc(F)ccc1-c1nc2ccc(C(=O)O)cc2nc1N(C)C(C)C]

To a solution of methyl 2-(4-fluoro-2-methylphenyl)-3-(isopropyl(methyl)amino)quinoxaline-6-carboxylate (45 mg, 0.12 mmol) in methanol (35 mL) and water (2.0 mL) was added sodium hydroxide (20 mg, 0.50 mmol) and the reaction was stirred overnight at room temperature. The reaction mixture was concentrated in vacuo, dissolved in water (20 mL) and adjusted to pH 4 with aqueous HCl (3N). The solids were collected by filtration to afford 2-(4-fluoro-2-methylphenyl)-3-(isopropyl(methyl)amino)quinoxaline-6-carboxylic acid as a light yellow solid (36 mg, 83%).

LC/MS (ES, m/z): [M+H]+ 354.0

$^1$H-NMR (300 MHz, DMSO): δ 13.12 (s, 1H), 8.27 (s, 1H), 7.90-7.97 (m, 2H), 7.51-7.56 (m, 1H), 7.16-7.26 (m, 2H), 4.13-4.22 (m, 1H), 2.61 (s, 3H), 2.22 (s, 3H), 0.99 (d, J=6.6 Hz, 6H)

Example 119

2-(4-Carbamoylphenyl)-3-(isopropyl(methyl)amino) quinoxaline-6-carboxylic acid

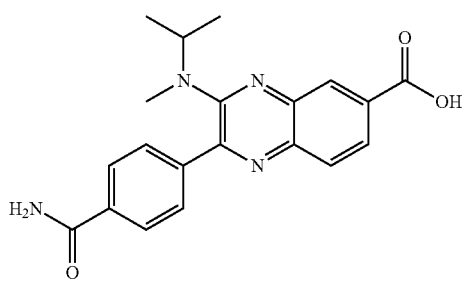 [SMILES: CC(C)N(C)c1nc2cc(C(=O)O)ccc2nc1-c1ccc(C(N)=O)cc1]

Step 1. Methyl 2-(4-carbamoylphenyl)-3-(isopropyl (methyl)amino)quinoxaline-6-carboxylate

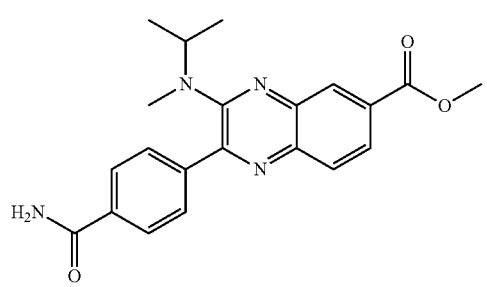 [SMILES: COC(=O)c1ccc2nc(-c3ccc(C(N)=O)cc3)c(N(C)C(C)C)nc2c1]

To a solution of methyl 2-chloro-3-(isopropyl(methyl) amino)quinoxaline-6-carboxylate (120 mg, 0.49 mmol) in dioxane (5 mL) was added 4-carbamoylphenylboronic acid (169 mg, 1.02 mmol), K$_3$PO$_4$ (217 mg, 1.02 mmol), Pd(PPh$_3$)$_4$ (30 mg, 0.03 mmol) and water (5 drops). The resulting solution was stirred for 1 hour at 90° C. and then concentrated in vacuo to give a residue, which was purified via silica gel column chromatography (9% ethyl acetate in petroleum ether) to afford methyl 2-(4-carbamoylphenyl)-3-(isopropyl(methyl)amino)quinoxaline-6-carboxylate as a yellow solid (103 mg, 66%).

LC/MS (ES, m/z): [M+H]+ 379.0

$^1$H-NMR (300 MHz, DMSO): δ 8.28 (d, J=1.2 Hz, 1H), 8.09 (s, 1H), 8.01 (d, J=8.4 Hz, 2H), 7.96-7.98 (m, 2H), 7.89-7.94 (m, 2H), 7.48 (s, 1H), 4.18-4.27 (m, 1H), 3.93 (s, 3H), 2.66 (s, 3H), 1.04 (d, J=6.6 Hz, 3H)

Step 2. 2-(4-Carbamoylphenyl)-3-(isopropyl(methyl) amino)quinoxaline-6-carboxylic acid

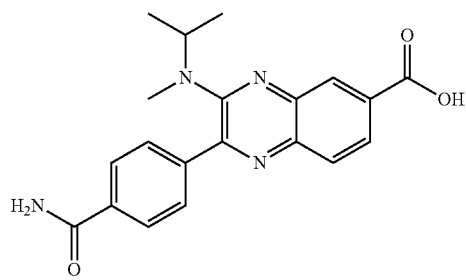 [SMILES: CC(C)N(C)c1nc2cc(C(=O)O)ccc2nc1-c1ccc(C(N)=O)cc1]

To a solution of methyl 2-(4-carbamoylphenyl)-3-(isopropyl(methyl)amino)quinoxaline-6-carboxylate (103 mg, 0.27 mmol) in MeOH (20 mL) was added sodium hydroxide (68 mg, 1.69 mmol) and water (2 mL). The resulting solution was stirred overnight at room temperature and concentrated in vacuo. The residue was dissolved in water (2 mL) and adjusted to pH 5 with hydrochloric acid (1N). The solids were collected by filtration to afford 2-(4-carbamoylphenyl)-3-(isopropyl(methyl)amino)quinoxaline-6-carboxylic acid as a brown solid (57.9 mg, 58%).

LC/MS (ES, m/z): [M+H]+ 365.0

$^1$H-NMR (300 MHz, DMSO): δ 13.18 (s, 1H), 8.27 (s, 1H), 8.10 (s, 1H), 8.01 (d, J=8.4 Hz, 2H), 7.90-7.98 (m, 4H), 7.48 (s, 1H), 4.18-4.22 (m, 1H), 2.66 (s, 3H), 1.03 (d, J=6.6 Hz, 3H)

Example 120

2-(4-Fluorophenyl)-7-hydroxy-3-(isopropyl(methyl) amino)quinoxaline-6-carboxylic acid

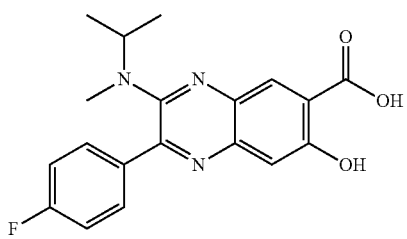 [SMILES: CC(C)N(C)c1nc2cc(C(=O)O)c(O)cc2nc1-c1ccc(F)cc1]

Step 1. Methyl 2,4-difluorobenzoate

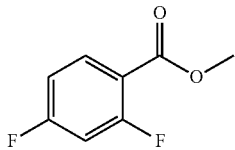

To a solution of 2,4-difluorobenzoic acid (50.0 g, 316.25 mmol) in methanol (500 mL) was added sulfuryl dichloride (112 g, 949.15 mmol) at 0° C. The resulting solution was heated to reflux overnight and concentrated in vacuo to afford methyl 2,4-difluorobenzoate as a colorless oil (50 g, 92%).

$^1$H-NMR (300 MHz, CDCl$_3$) δ 7.96-8.04 (m, 1H), 6.86-6.98 (m, 2H), 3.94 (s, 3H)

Step 2. Methyl 4-fluoro-2-methoxybenzoate

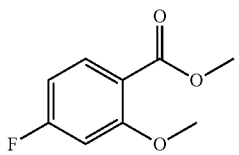

To a solution of methyl 2,4-difluorobenzoate (50 g, 290 mmol) in dioxane (300 mL) was added sodium methoxide (18.0 g, 333.21 mmol) and the reaction was stirred for 48 hours at 100° C. in an oil bath. The reaction mixture was cooled to room temperature and diluted with H$_2$O (200 mL). The mixture was extracted with ethyl acetate (3×150 mL). The organic layers were combined, dried over anhydrous magnesium sulfate, and concentrated in vacuo to afford methyl 4-fluoro-2-methoxybenzoate as colorless oil (50.0 g, 92%).

$^1$H-NMR (300 MHz, CDCl$_3$) δ 7.84-7.89 (m, 1H), 6.66-6.72 (m, 2H), 3.86-3.91 (m, 6H)

Step 3. Methyl 4-fluoro-2-methoxy-5-nitrobenzoate

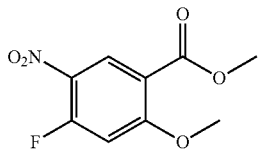 [SMILES: COC(=O)c1cc([N+](=O)[O-])c(F)cc1OC]

To a solution of methyl 4-fluoro-2-methoxybenzoate (50 g, 271.50 mmol) in sulfuric acid (150 mL) was added a solution of potassium nitrate (35.6 g, 352.48 mmol) in sulfuric acid (30 mL) dropwise with stirring for 45 min at 0-25° C. in an ice/water bath. The reaction was then quenched by the addition of water/ice. The solids were collected by filtration to afford methyl 4-fluoro-2-methoxy-5-nitrobenzoate as a white solid (40.0 g, 64%).

$^1$H-NMR (300 MHz, CDCl$_3$) δ 8.46-8.51 (m, 1H), 7.43 (d, J=13.8 Hz, 1H), 4.08 (s, 3H), 3.84 (s, 3H)

Step 4. Methyl 2-methoxy-4-(4-methoxybenzylamino)-5-nitrobenzoate

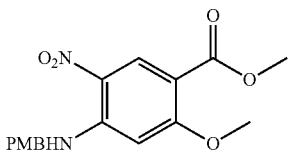

To a solution of methyl 4-fluoro-2-methoxy-5-nitrobenzoate (40 g, 174.55 mmol) in N,N-dimethylformamide (1000 mL) was added DIEA (45.2 g, 349.74 mmol). Then (4-methoxyphenyl)methanamine (31.1 g, 226.71 mmol) was added dropwise with stirring for 1 hour at 25° C. The reaction mixture was diluted with water (2 L). The solids were collected by filtration to afford methyl 2-methoxy-4-(4-methoxybenzylamino)-5-nitrobenzoate as a yellow solid (44 g, 75%).

$^1$H-NMR (300 MHz, CDCl$_3$) δ 8.97-9.01 (t, J=5.4 Hz, 1H), 8.55 (d, J=6.0 Hz, 1H), 7.36 (d, J=8.7 Hz, 2H), 6.92-6.96 (m, 2H), 6.35 (s, 1H), 4.62 (d, J=5.7 Hz, 2H), 3.72-3.81 (m, 9H)

Step 5. Methyl 5-amino-2-methoxy-4-(4-methoxybenzylamino)benzoate

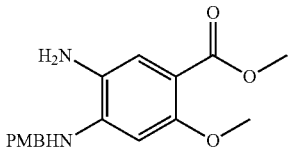

To a solution of methyl 2-methoxy-4-(4-methoxybenzylamino)-5-nitrobenzoate (544 g, 144.37 mmol) in methanol (1500 mL) was added palladium on carbon (15 g). The solution was allowed to react for 2 h at room temperature under an atmosphere of H$_2$ (g). The solids were filtered from the resulting solution, and the filtrate was concentrated in vacuo to afford methyl 5-amino-2-methoxy-4-(4-methoxybenzylamino)benzoate as a white solid (30.0 g, 75%).

$^1$H-NMR (300 MHz, DMSO) δ 7.30 (d, J=8.7 Hz, 2H), 7.04 (d, J=4.5 Hz, 1H), 6.88-6.93 (m, 2H), 6.07 (s, 1H), 5.89-5.92 (t, J=5.7 Hz, 1H), 4.40 (s, 2H), 4.31 (d, J=5.7 Hz, 2H), 3.71 (s, 3H), 3.83 (s, 3H), 3.65 (s, 1H)

Step 6. Methyl 7-methoxy-1-(4-methoxybenzyl)-2,3-dioxo-1,2,3,4-tetrahydroquinoxaline-6-carboxylate

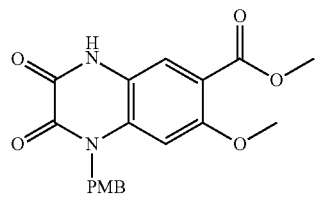

The solution of methyl 5-amino-2-methoxy-4-(4-methoxybenzylamino)benzoate (30 g, 94.83 mmol) in diethyl oxalate (100 mL) was stirred for 3 h at reflux and then cooled with a water/ice bath and diluted with ether (500 mL). The product was collected by filtration to afford methyl 7-methoxy-1-[(4-methoxyphenyl)methyl]-2,3-dioxo-1,2,3,4-tetrahydroquinoxaline-6-carboxylate as a light yellow solid (25.0 g, 71%).

¹H-NMR (300 MHz, DMSO) δ 12.03 (s, 1H), 7.56 (d, J=3.3 Hz, 1H), 7.32 (d, J=8.7 Hz, 2H), 6.88-6.92 (m, 3H), 5.38 (s, 2H), 3.91 (s, 3H), 3.71-3.79 (m, 6H)

Step 7. Methyl 3-chloro-7-methoxy-1-(4-methoxybenzyl)-2-oxo-1,2-dihydroquinoxaline-6-carboxylate

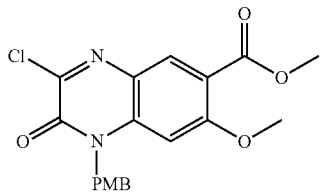

To a solution of methyl 7-methoxy-1-[(4-methoxyphenyl)methyl]-2,3-dioxo-1,2,3,4-tetrahydroquinoxaline-6-carboxylate (24 g, 64.80 mmol) in toluene (300 mL) was added POCl₃ (14.8 g, 96.52 mmol) and N,N-dimethylaniline (15.7 g, 129.75 mmol). The resulting solution was stirred overnight at 110° C. and concentrated in vacuo. The product was precipitated by the addition of methanol (150 mL) and collected by filtration to afford methyl 3-chloro-7-methoxy-1-(4-methoxybenzyl)-2-oxo-1,2-dihydroquinoxaline-6-carboxylate as a green solid (17 g, 65%).

¹H-NMR (300 MHz, DMSO) δ 8.02 (s, 1H), 7.34 (d, J=8.7 Hz, 2H), 7.03 (s, 1H), 6.88-6.92 (m, 2H), 5.52 (s, 2H), 3.85 (s, 3H), 3.81 (s, 3H), 3.72 (s, 3H)

Step 8. Methyl 3-chloro-7-methoxy-2-oxo-1,2-dihydroquinoxaline-6-carboxylate

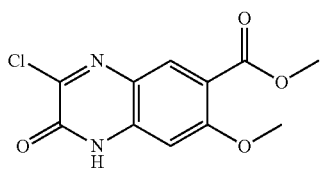 [SMILES: COC(=O)c1cc2nc(Cl)c(=O)[nH]c2cc1OC]

Methyl 3-chloro-7-methoxy-1-(4-methoxybenzyl)-2-oxo-1,2-dihydroquinoxaline-6-carboxylate (6.0 g, 15.43 mmol) was added to sulfuric acid (conc, 15 mL) in several batches with stirring at room temperature and then stirred for 10 minutes. The resulting solution was diluted with ice-water (100 mL) and extracted with ethyl acetate (3×200 mL). The organic layers were combined and dried over anhydrous magnesium sulfate and concentrated in vacuo to afford methyl 3-chloro-7-methoxy-2-oxo-1,2-dihydroquinoxaline-6-carboxylate as a yellow solid (2.5, 60%).

¹H-NMR (300 MHz, DMSO) δ 12.9 (s, 1H), 7.98-8.02 (m, 1H), 7.03 (s, 1H), 3.92 (s, 3H), 3.85 (s, 3H)

Step 9. Methyl 3-(isopropyl(methyl)amino)-7-methoxy-2-oxo-1,2-dihydroquinoxaline-6-carboxylate

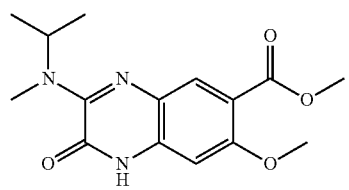

To a solution of methyl 3-chloro-7-methoxy-2-oxo-1,2-dihydroquinoxaline-6-carboxylate (1.2 g, 4.47 mmol) in DMSO (20 mL) was added DIEA (1.16 g, 8.98 mmol) and methyl(propan-2-yl)amine (490 mg, 6.70 mmol) with stirring at 85° C. overnight. The reaction mixture was cooled to room temperature. The product was precipitated by the addition water and the solids were collected by filtration to afford methyl 3-(isopropyl(methyl)amino)-7-methoxy-2-oxo-1,2-dihydroquinoxaline-6-carboxylate as a light yellow solid (1.0 g, 73%).

LC/MS (ES, m/z): [M+H]⁺ 306.0

¹H-NMR (300 MHz, DMSO) δ 12.10 (s, 1H), 7.69 (d, J=6.3 Hz, 1H), 6.78 (s, 1H), 5.14-5.22 (m, 1H), 3.71 (s, 6H), 2.99 (s, 3H), 1.21 (d, J=6.6 Hz, 6H)

Step 10. Methyl 3-(isopropyl(methyl)amino)-7-methoxy-2-(trifluoromethylsulfonyloxy)quinoxaline-6-carboxylate

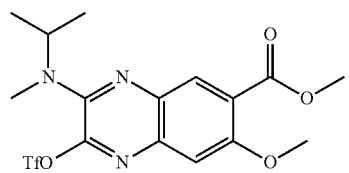

To a solution of methyl 3-(isopropyl(methyl)amino)-7-methoxy-2-oxo-1,2-dihydroquinoxaline-6-carboxylate (2.0 g, 6.55 mmol) in dichloromethane (80 mL) was added Pyridine (2.0 g, 25.28 mmol) and Tf₂O (3.66 g, 12.97 mmol) with stirring overnight under an atmosphere of nitrogen at room temperature. The reaction mixture was then quenched with water (50 mL) and extracted with dichloromethane (3×80 mL). The organic layers were combined and dried over anhydrous magnesium sulfate and concentrated in vacuo to afford methyl 3-(isopropyl(methyl)amino)-7-methoxy-2-(trifluoromethylsulfonyloxy)quinoxaline-6-carboxylate as red oil (2.50 g, crude), which was used in the next step directly.

Step 11. Methyl 2-(4-fluorophenyl)-3-(isopropyl(methyl)amino)-7-methoxyquinoxaline-6-carboxylate

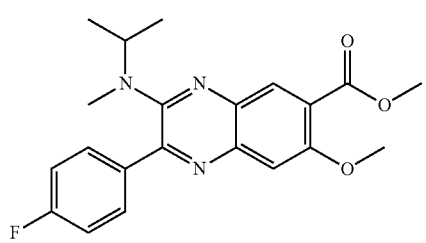 [SMILES: COC(=O)c1cc2nc(N(C)C(C)C)c(-c3ccc(F)cc3)nc2cc1OC]

To a solution of methyl 3-(isopropyl(methyl)amino)-7-methoxy-2-(trifluoromethylsulfonyloxy)quinoxaline-6-carboxylate (2.5 g, crude) in dioxane (5.0 mL) and water (3 drops) was added (4-fluorophenyl)boronic acid (2.40 g, 17.15 mmol), Pd(PPh$_3$)$_4$ (320 mg, 0.28 mmol), and K$_3$PO$_4$ (3.58 g, 16.87 mmol) with stirring for 1.5 h at 95° C. under an atmosphere of nitrogen. The reaction mixture was concentrated in vacuo to give a residue, which was purified via silica gel column chromatography (1% ethyl acetate in petroleum ether) to afford methyl 2-(4-fluorophenyl)-3-(isopropyl(methyl)amino)-7-methoxyquinoxaline-6-carboxylate as a light yellow solid (0.9 g, 36% 2 steps).

LC/MS (ES, m/z): [M+H]$^+$ 384.0

$^1$H-NMR (300 MHz, DMSO) δ 7.81-7.86 (m, 3H), 7.47 (s, 1H), 7.33-7.41 (m, 2H), 3.95-4.02 (m, 1H), 3.92 (s, 3H), 3.87 (s, 3H), 2.66 (s, 3H), 0.99 (d, J=6.6 Hz, 6H)

Step 12. Methyl 2-(4-fluorophenyl)-7-hydroxy-3-(isopropyl(methyl)amino)quinoxaline-6-carboxylate

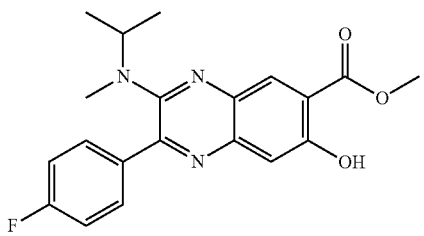 [SMILES: COC(=O)c1cc2nc(N(C)C(C)C)c(-c3ccc(F)cc3)nc2cc1O]

To a solution of methyl 2-(4-fluorophenyl)-3-(isopropyl(methyl)amino)-7-methoxyquinoxaline-6-carboxylate (500 mg, 1.31 mmol) in dichloromethane (80 mL) was added BBr$_3$ (2.0 mL) dropwise with stirring at −78° C. for 30 minutes. The reaction was then quenched by the addition of water/ice. The resulting solution was extracted with dichloromethane (3×80 mL), and the organic layers combined, dried over anhydrous magnesium sulfate, and concentrated in vacuo to give the residue, which was purified via silica gel column chromatography (2% ethyl acetate in petroleum ether) to afford methyl 2-(4-fluorophenyl)-7-hydroxy-3-(isopropyl(methyl)amino)quinoxaline-6-carboxylate as a yellow solid (145 mg, 30%).

LC/MS (ES, m/z): [M+H]$^+$ 370.0

$^1$H-NMR (300 MHz, DMSO) δ 10.35 (s, 1H), 8.15 (s, 1H), 7.91-8.14 (m, 2H), 7.33-7.39 (m, 3H), 3.89-4.04 (m, 4H), 2.65 (s, 3H), 0.95 (d, J=6.6 Hz, 6H)

Step 13. 2-(4-Fluorophenyl)-7-hydroxy-3-(isopropyl(methyl)amino)quinoxaline-6-carboxylic acid

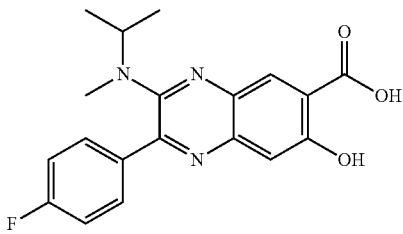 [SMILES: CC(C)N(C)c1nc2cc(C(=O)O)c(O)cc2nc1-c1ccc(F)cc1]

To a solution of methyl 2-(4-fluorophenyl)-7-hydroxy-3-(isopropyl(methyl)amino)quinoxaline-6-carboxylate (45 mg, 0.12 mmol) in methanol (30 mL) and water (1.0 mL) was added sodium hydroxide (19.5 mg, 0.49 mmol) with stirring overnight at room temperature. The reaction mixture was concentrated in vacuo, dissolved in water (30 mL), adjusted to pH 5 with hydrochloric acid (3N) to give the precipitate, which was collected by filtration to afford 2-(4-fluorophenyl)-7-hydroxy-3-(isopropyl(methyl)amino)quinoxaline-6-carboxylic acid as a light yellow solid (38.2 mg, 88%).

LC/MS (ES, m/z): [M+H]$^+$ 356.1

$^1$H-NMR (300 MHz, DMSO) δ 8.17 (s, 1H), 7.92-7.97 (m, 2H), 7.32-7.37 (t, J=9.0 Hz, 2H), 7.12 (s, 1H), 3.79-3.88 (m, 1H), 2.65 (s, 3H), 0.95 (d, J=6.6 Hz, 6H)

Example 121

(R)-2-(4-Fluorophenyl)-3-(2-methylpiperidin-1-yl)quinoxaline-6-carboxylic acid

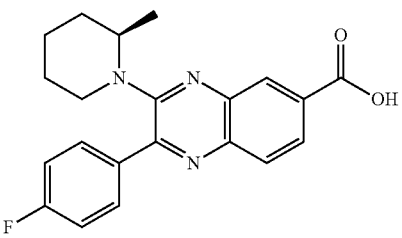 [SMILES: C[C@@H]1CCCCN1c1nc2cc(C(=O)O)ccc2nc1-c1ccc(F)cc1]

Step 1. Methyl 3-(2-methylpiperidin-1-yl)-2-oxo-1,2-dihydroquinoxaline-6-carboxylate

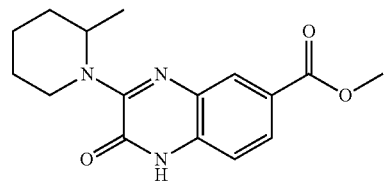 [SMILES: COC(=O)c1ccc2[nH]c(=O)c(N3CCCCC3C)nc2c1]

To a solution of methyl 3-chloro-2-oxo-1,2-dihydroquinoxaline-6-carboxylate (600 mg, 2.51 mmol) in DMSO (10 ml) was added 2-methylpiperidine (500 mg, 5.04 mmol) and DIEA (650 mg, 5.03 mmol). The resulting solution was stirred at 80° C. for 2 hours and then quenched by water (50 ml). The solids were collected by filtration to afford methyl 3-(2-methylpiperidin-1-yl)-2-oxo-1,2-dihydroquinoxaline-6-carboxylate as a light yellow solid (520 mg, 69%).

$^1$H-NMR (300 MHz, DMSO) δ 12.31 (s, 1H), 7.89 (d, J=1.8 Hz, 1H), 7.70-7.73 (m, 1H), 7.20 (d, J=8.4 Hz, 1H), 5.20-5.30 (m, 1H), 4.71-4.76 (m, 1H), 3.84 (s, 3H), 3.01-3.10 (m, 1H), 1.62-1.74 (m, 6H), 1.25 (d, J=6.6 Hz, 3H)

Step 2. Methyl 3-(2-methylpiperidin-1-yl)-2-(trifluoromethylsulfonyloxy)quinoxaline-6-carboxylate

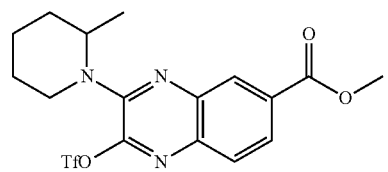 [SMILES: COC(=O)c1ccc2nc(OS(=O)(=O)C(F)(F)F)c(N3CCCCC3C)nc2c1]

To a solution of methyl 3-(2-methylpiperidin-1-yl)-2-oxo-1,2-dihydroquinoxaline-6-carboxylate (520 mg, 1.73 mmol) in dichloromethane (60 ml) was added pyridine (690 mg, 8.72 mmol) followed by the addition of Tf₂O (1.22 g, 4.32 mmol), and the resulting solution was stirred overnight at room temperature. The reaction was quenched by the addition of ice-water (200 ml) and extracted with dichloromethane (2×30 ml). The organic layers were combined, dried over anhydrous magnesium sulfate and concentrated in vacuo to afford methyl 3-(2-methylpiperidin-1-yl)-2-(trifluoromethylsulfonyloxy)quinoxaline-6-carboxylate as red oil (880 mg, crude).

Step 3. Methyl 2-(4-fluorophenyl)-3-(2-methylpiperidin-1-yl)quinoxaline-6-carboxylate

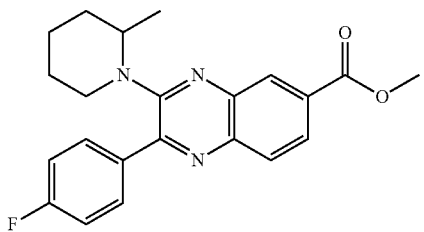 [SMILES: COC(=O)c1ccc2nc(-c3ccc(F)cc3)c(N3CCCCC3C)nc2c1]

To a solution of methyl 3-(2-methylpiperidin-1-yl)-2-(trifluoromethylsulfonyloxy)quinoxaline-6-carboxylate (880 mg, crude) in dioxane (25 ml) was added Pd(PPh₃)₄ (100 mg, 0.09 mmol), 4-fluorophenylboronic acid (485 mg, 3.47 mmol), K₃PO₄ (735 mg, 3.46 mmol) and water (3 ml). The resulting solution was stirred for 1 hour at 90° C. under an inert atmosphere of nitrogen, and then concentrated in vacuo to give a residue, which was purified via silica gel column chromatography (1%-10% ethyl acetate in petroleum ether) to afford methyl 2-(4-fluorophenyl)-3-(2-methylpiperidin-1-yl)quinoxaline-6-carboxylate as a yellow solid (330 mg).

LC/MS (ES, m/z): [M+H]⁺ 380.0

¹H-NMR (300 MHz, CDCl₃) δ 8.53 (d, J=1.5 Hz, 1H), 7.95-8.10 (m, 4H), 7.17-7.28 (m, 2H), 4.06-4.10 (m, 1H), 4.00 (s, 3H), 3.47-3.51 (m, 1H), 3.11-3.19 (m, 1H), 1.55-1.76 (m, 6H), 1.11 (d, J=6.6 Hz, 3H)

Step 4. (R)-2-(4-Fluorophenyl)-3-(2-methylpiperidin-1-yl)quinoxaline-6-carboxylic acid

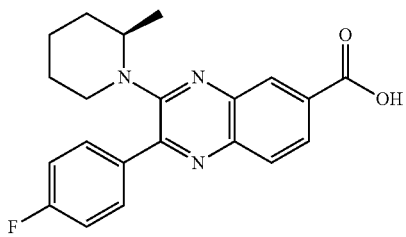 [SMILES: C[C@@H]1CCCCN1c1nc2cc(C(=O)O)ccc2nc1-c1ccc(F)cc1]

To a solution of methyl 2-(4-fluorophenyl)-3-(2-methylpiperidin-1-yl)quinoxaline-6-carboxylate (330 mg, 0.87 mmol) in methanol (15 ml) was added NaOH (104.4 mg, 2.61 mmol) and water (1 ml). The resulting solution was stirred overnight at room temperature and concentrated in vacuo. The residue was dissolved in water (15 ml) and adjusted to pH 5 with hydrochloric acid (3N) to yield a precipitate that was collected to afford yellow solid (250 mg). The solids was purified by Chiral-Prep-HPLC to afford (R)-2-(4-fluorophenyl)-3-(2-methylpiperidin-1-yl)quinoxaline-6-carboxylic acid as a yellow solid (53.2 mg, 17%).

LC/MS (ES, m/z): [M+H]⁺ 366.1

¹H-NMR (300 MHz, DMSO) δ 8.45 (s, 1H), 8.03-8.09 (m, 3H), 7.94 (d, J=8.7 Hz, 1H), 7.26-7.32 (t, J=8.7 Hz, 2H), 4.05-4.06 (m, 1H), 3.48-3.53 (m, 1H), 3.16-3.24 (m, 1H), 1.30-1.81 (m, 6H), 1.12 (d, J=6.6 Hz, 3H)

Example 122

2-(4-Fluorophenyl)-7-methoxy-3-[methyl(propan-2-yl)amino]quinoxaline-6-carboxylic acid

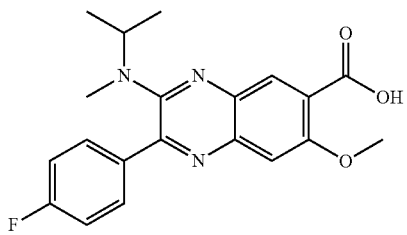 [SMILES: COc1cc2nc(-c3ccc(F)cc3)c(N(C)C(C)C)nc2cc1C(=O)O]

To a solution of methyl 2-(4-fluorophenyl)-7-methoxy-3-[methyl(propan-2-yl)amino]quinoxaline-6-carboxylate (120 mg, 0.31 mmol) in methanol (30 mL) and water (1.0 mL) was added sodium hydroxide (50 mg, 1.25 mmol) with stirring overnight at room temperature. The reaction mixture was concentrated in vacuo, dissolved in water (30 mL), and adjusted to pH 5 with hydrochloric acid (3N) to give the precipitate, which was collected by filtration to afford 2-(4-fluorophenyl)-7-methoxy-3-[methyl(propan-2-yl)amino]quinoxaline-6-carboxylic acid as a light yellow solid (38.2 mg, 88%).

LC/MS (ES, m/z): [M+H]⁺ 370.1

¹H-NMR (300 MHz, DMSO) δ 7.91-7.97 (m, 3H), 7.34-7.43 (m, 3H), 3.93-3.99 (m, 1H), 3.92 (s, 3H), 2.73 (s, 1H), 0.98 (d, J=6.6 Hz, 6H)

Example 123

7-Fluoro-2-(4-fluorophenyl)-3-[methyl(propan-2-yl)amino]quinoxaline-6-carboxylic acid

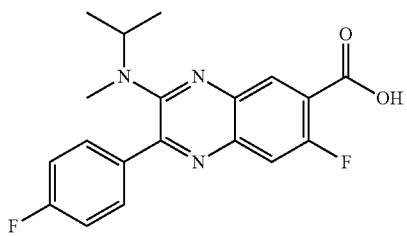

Step 1. Methyl 2,4-difluoro-5-nitrobenzoate

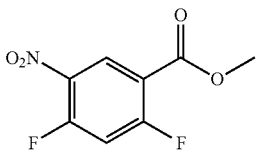

To a solution of methyl 2,4-difluorobenzoate (50.0 g, 290.48 mmol, 1.00 equiv) in sulfuric acid (150 ml) was added a solution of potassium nitrate (35.23 g, 348.81 mmol) in sulfuric acid (30 ml) dropwise in an ice-water bath with stirring for 1 h at 0-25° C. The reaction was then quenched by the addition of ice-water. The solids were collected by filtration to afford methyl 2,4-difluoro-5-nitrobenzoate as a white solid (40.0 g, 63%).

$^1$H-NMR (300 MHz, DMSO) δ 8.61-8.66 (m, 1H), 7.88-7.95 (m, 1H), 3.92 (s, 3H)

Step 2. Methyl 2-fluoro-4-(4-methoxybenzylamino)-5-nitrobenzoate

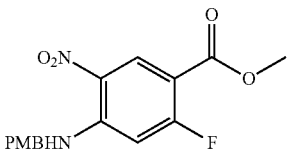

To a solution of methyl 2,4-difluoro-5-nitrobenzoate (35 g, 161.20 mmol) in N,N-dimethylformamide (1000 ml) was added DIEA (41.3 g, 319.56 mmol). Then (4-methoxybenzylamine (28.72 g, 209.64 mmol) was added dropwise with stirring for 1 hour at 25° C. The reaction mixture was diluted with water (2 L). The solids were collected by filtration to afford methyl 2-fluoro-4-(4-methoxybenzylamino)-5-nitrobenzoate as a yellow solid (44 g, 82%).

$^1$H-NMR (300 MHz, DMSO) δ 9.05-9.12 (m, 1H), 8.62-8.70 (m, 2H), 7.30-7.35 (m, 2H), 6.90-6.95 (m, 2H), 4.59 (d, J=6.0 Hz, 2H), 3.88 (s, 3H), 3.81 (s, 3H)

Step 3. Methyl 5-amino-2-fluoro-4-(4-methoxybenzylamino)benzoate

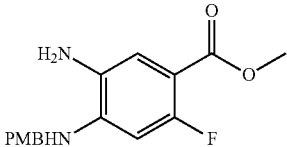

To a solution of methyl 2-fluoro-4-(4-methoxybenzylamino)-5-nitrobenzoate (50.0 g, 149.57 mmol) in methanol (1500 ml) was added palladium on carbon (15 g). The mixture was allowed to react for 2 hours at room temperature under an atmosphere of H$_2$ (g). The solids were filtered out and the filtrate was concentrated in vacuo to afford methyl 5-amino-2-fluoro-4-(4-methoxybenzylamino)benzoate as a gray solid (30.0 g, 66%).

$^1$H-NMR (300 MHz, DMSO) δ 7.27 (d, J=8.7 Hz, 2H), 7.04 (d, J=7.5 Hz, 1H), 6.88-6.93 (m, 2H), 6.12-6.21 (m, 2H), 4.72 (s, 2H), 4.30 (d, J=5.7 Hz, 2H), 3.68-3.73 (m, 6H)

Step 4. Methyl 7-fluoro-1-(4-methoxybenzyl)-2,3-dioxo-1,2,3,4-tetrahydroquinoxaline-6-carboxylate

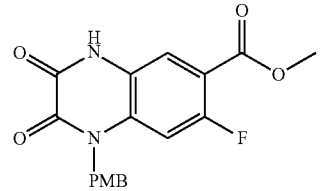

The solution of methyl 5-amino-2-fluoro-4-(4-methoxybenzylamino)benzoate (30 g, 98.58 mmol) in diethyl oxalate (100 ml) was stirred for 3 h at reflux and then cooled with a water/ice bath, diluted with ether (500 ml). The product was collected by filtration to afford methyl 7-fluoro-1-(4-methoxybenzyl)-2,3-dioxo-1,2,3,4-tetrahydroquinoxaline-6-carboxylate as a light yellow solid (35.0 g, 99%).

$^1$H-NMR (300 MHz, DMSO) δ 12.19 (s, 1H), 7.69 (d, J=6.9 Hz, 1H), 7.20-7.31 (m, 3H), 6.87-6.92 (m, 2H), 5.30 (s, 2H), 3.84 (s, 3H), 3.81 (s, 3H)

Step 5. Methyl 3-chloro-7-fluoro-1-(4-methoxybenzyl)-2-oxo-1,2-dihydroquinoxaline-6-carboxylate

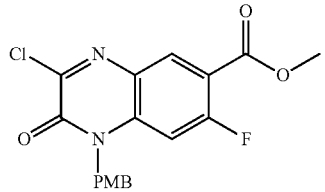

Methyl 7-fluoro-1-(4-methoxybenzyl)-2,3-dioxo-1,2,3,4-tetrahydroquinoxaline-6-carboxylate (35.0 g, 98 mmol) was added to POCl$_3$ with stirring overnight at 130° C. and concentrated in vacuo. The product was precipitated via the addition of methanol (150 ml) and collected by filtration to afford methyl 3-chloro-7-fluoro-1-(4-methoxybenzyl)-2-oxo-1,2-dihydroquinoxaline-6-carboxylate as a yellow solid (25.0 g, 68%).

$^1$H-NMR (300 MHz, DMSO) δ 8.21 (d, J=7.5 Hz, 1H), 7.50-7.55 (m, 1H), 7.23-7.32 (m, 2H), 6.88-6.92 (m, 2H), 5.43 (s, 2H), 3.96 (s, 3H), 3.74 (s, 3H)

Step 6. Methyl 3-chloro-7-fluoro-2-oxo-1,2-dihydroquinoxaline-6-carboxylate

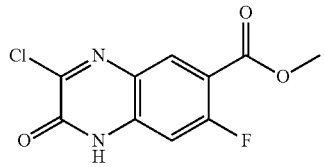 [SMILES: COC(=O)c1cc2nc(Cl)c(=O)[nH]c2cc1F]

Methyl 3-chloro-7-fluoro-1-(4-methoxybenzyl)-2-oxo-1,2-dihydroquinoxaline-6-carboxylate (4.0 g, 10.62 mmol) was added to sulfuric acid (conc, 15 ml) in several batches with stirring at room temperature, and then stirred for 10 minutes. The resulting solution was diluted with ice-water (100 ml) and extracted with ethyl acetate (3×200 ml). The organic layers were combined and dried over anhydrous magnesium sulfate and concentrated in vacuo to afford methyl 3-chloro-7-fluoro-2-oxo-1,2-dihydroquinoxaline-6-carboxylate as a yellow solid (2.0 g, crude), which was used in the next step without further purification.

Step 7. Methyl 7-fluoro-3-[methyl(propan-2-yl)amino]-2-oxo-1,2-dihydroquinoxaline-6-carboxylate

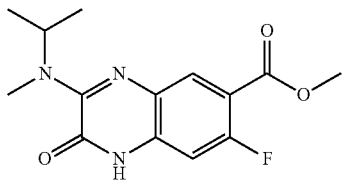

To a solution of methyl 3-chloro-7-fluoro-2-oxo-1,2-dihydroquinoxaline-6-carboxylate (2.0 g, crude) in DMSO (20 ml) was added DIEA (2.0 g, 15.48 mmol) and methyl(propan-2-yl)amine (790 mg, 10.80 mmol) with stirring at 85° C. overnight. The reaction mixture was cooled to room temperature. The product was precipitated by the addition water and the solids were collected by filtration to afford methyl 7-fluoro-3-[methyl(propan-2-yl)amino]-2-oxo-1,2-dihydroquinoxaline-6-carboxylate as a light yellow solid (800 mg).

LC/MS (ES, m/z): [M+H]$^+$ 294.0

$^1$H-NMR (300 MHz, DMSO) δ 12.28 (s, 1H), 7.78 (d, J=7.5 Hz, 1H), 6.91 (d, J=11.4 Hz, 1H), 5.22-5.29 (m, 1H), 3.84 (s, 3H), 3.04 (s, 3H), 1.17 (d, J=6.6 Hz, 6H)

Step 8. Methyl 7-fluoro-3-[methyl(propan-2-yl)amino]-2-[(trifluoromethane)sulfonyloxy]quinoxaline-6-carboxylate

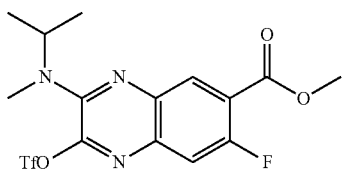

To a solution of methyl 7-fluoro-3-[methyl(propan-2-yl)amino]-2-oxo-1,2-dihydroquinoxaline-6-carboxylate (800 mg, 2.73 mmol) in dichloromethane (80 ml) was added pyridine (863 mg, 10.91 mmol) and Tf$_2$O (1.5 g, 5.32 mmol) with stirring overnight under atmosphere of nitrogen at room temperature. The reaction mixture was then quenched with water (50 ml), extracted with dichloromethane (3×80 ml), and the organic layers combined and dried over anhydrous magnesium sulfate and concentrated in vacuo to afford methyl 7-fluoro-3-[methyl(propan-2-yl)amino]-2-[(trifluoromethane)sulfonyloxy]quinoxaline-6-carboxylate as yellow oil (600 g, crude), which was used in the next step directly.

Step 9. Methyl 7-fluoro-2-(4-fluorophenyl)-3-[methyl(propan-2-yl)amino]quinoxaline-6-carboxylate

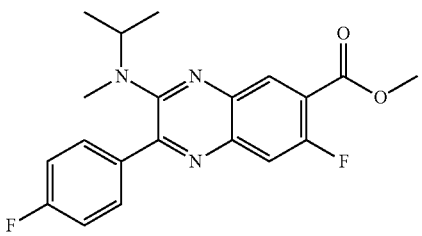 [SMILES: COC(=O)c1cc2nc(N(C)C(C)C)c(-c3ccc(F)cc3)nc2cc1F]

To a solution of methyl 7-fluoro-3-[methyl(propan-2-yl)amino]-2-[(trifluoromethane)sulfonyloxy]quinoxaline-6-carboxylate (400 mg, crude) in dioxane (5.0 ml) and water (3 drops) was added (4-fluorophenyl)boronic acid (389 mg, 2.78 mmol), Pd(PPh$_3$)$_4$ (163 mg, 0.14 mmol), and K$_3$PO$_4$ (595 mg, 2.80 mmol) with stirring for 40 min at 90° C. under an atmosphere of nitrogen. The reaction mixture was concentrated in vacuo to give a residue, which was purified via silica gel column chromatography (1% ethyl acetate in petroleum ether) to afford methyl 7-fluoro-2-(4-fluorophenyl)-3-[methyl(propan-2-yl)amino]quinoxaline-6-carboxylate as a light yellow solid (150 mg).

LC/MS (ES, m/z): [M+H]$^+$ 372.0

$^1$H-NMR (300 MHz, DMSO) δ 8.46 (d, J=7.2 Hz, 1H), 7.91-7.96 (m, 2H), 7.64 (d, J=11.1 Hz, 1H), 7.18-7.24 (m, 2H), 4.15-4.24 (m, 1H), 4.02 (s, 3H), 2.75 (s, 3H), 1.09 (d, J=6.6 Hz, 6H)

Step 10. 7-Fluoro-2-(4-fluorophenyl)-3-[methyl(propan-2-yl)amino]quinoxaline-6-carboxylic acid

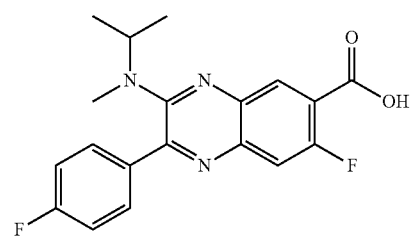

To a solution of methyl 7-fluoro-2-(4-fluorophenyl)-3-[methyl(propan-2-yl)amino]quinoxaline-6-carboxylate (150 mg, 0.40 mmol) in tetrahydrofuran (30 ml) and water (1.0 ml) was added lithium hydroxide (38.8 mg, 1.62 mmol) with stirring overnight at room temperature. The reaction mixture was concentrated in vacuo, dissolved in water (30 ml), and adjusted to pH 5 with hydrochloric acid (3N) to give the precipitate, which was collected by filtration to afford 7-fluoro-2-(4-fluorophenyl)-3-[methyl(propan-2-yl)amino]quinoxaline-6-carboxylic acid as a light yellow solid (120 mg, 83%).

LC/MS (ES, m/z): [M+H]$^+$ 358.1

$^1$H-NMR (300 MHz, DMSO) δ 8.16 (d, J=7.5 Hz, 1H), 7.89-7.94 (m, 2H), 7.72 (d, J=11.1 Hz, 1H), 7.35-7.41 (m, 2H), 4.07-4.16 (m, 1H), 2.66 (s, 3H), 1.02 (d, J=6.6 Hz, 6H)

Example 124

2-(4-Fluorophenyl)-3-[methyl(2,2,2-trifluoroethyl)amino]quinoxaline-6-carboxylic acid

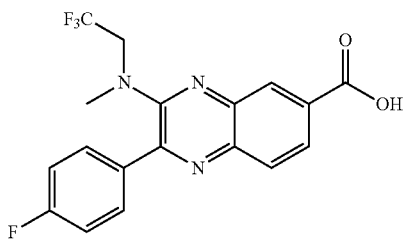 [SMILES: CN(CC(F)(F)F)c1nc2cc(C(=O)O)ccc2nc1-c1ccc(F)cc1]

Step 1. Methyl 2-(4-fluorophenyl)-3-[(2,2,2-trifluoroethyl)amino]quinoxaline-6-carboxylate

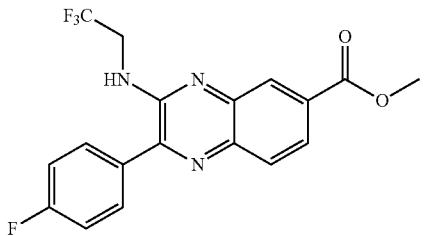 [SMILES: COC(=O)c1ccc2nc(-c3ccc(F)cc3)c(NCC(F)(F)F)nc2c1]

To a solution of methyl 3-chloro-2-(4-fluorophenyl)quinoxaline-6-carboxylate (500 mg, 1.58 mmol) in DMSO (23 ml) was added 2,2,2-trifluoroethan-1-amine (188 mg, 1.90 mmol) and DIEA (407 mg, 3.15 mmol,) with stirring, and the resulting mixture was allowed to react for 4 days at 110° C. in an oil bath. The reaction mixture was diluted with water (80 ml), extracted with dichloromethane (4×15 ml), dried over anhydrous sodium sulfate, and concentrated in vacuo to give the residue, which was purified via silica gel column chromatography (2% ethyl acetate in petroleum ether) to afford methyl 2-(4-fluorophenyl)-3-[(2,2,2-trifluoroethyl)amino]quinoxaline-6-carboxylate as a yellow solid (400 mg, 67%).

LC/MS (ES, m/z): [M+H]⁺ 380.1

¹H-NMR (300 MHz, CDCl₃) δ 8.52 (d, J=1.8 Hz, 1H), 8.08-812 (m, 1H), 7.99 (d, J=8.7 Hz, 1H), 7.76-7.82 (m, 2H), 7.28-7.35 (m, 2H), 5.33-5.37 (m, 1H), 4.33-4.44 (m, 2H), 4.02 (s, 3H)

Step 2. 2-(4-Fluorophenyl)-3-[methyl(2,2,2-trifluoroethyl)amino]quinoxaline-6-carboxylic acid

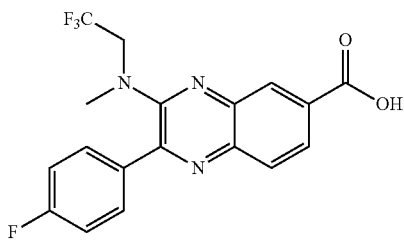 [SMILES: CN(CC(F)(F)F)c1nc2cc(C(=O)O)ccc2nc1-c1ccc(F)cc1]

To a solution of methyl 2-(4-fluorophenyl)-3-[(2,2,2-trifluoroethyl)amino]quinoxaline-6-carboxylate (400 mg, 1.05 mmol) in tetrahydrofuran (30 ml) was added sodium hydride (101 mg, 4.21 mmol) at 0° C. with stirring for 40 minutes and then iodomethane (899 mg, 6.33 mmol) was added to the reaction mixture, and the resulting mixture was allowed to react with stirring overnight at room temperature. The reaction mixture was adjusted pH to 4 with HCl to give the solid, which was collected by filtration to afford 2-(4-fluorophenyl)-3-[methyl(2,2,2-trifluoroethyl)amino]quinoxaline-6-carboxylic acid as a yellow solid (80.6 mg, 20%).

LC/MS (ES, m/z): [M+H]⁺ 380.0

¹H-NMR (300 MHz, DMSO) δ 11.19 (s, 1H), 8.35 (s, 1H), 8.04 (s, 2H), 7.84-7.89 (m, 2H), 7.41-7.47 (m, 2H), 4.49-4.52 (m, 2H), 2.84 (s, 3H)

Example 125

2-(4-Fluorophenyl)-3-(((1r,4r)-4-hydroxycyclohexyl)(methyl)amino)quinoxaline-6-carboxylic acid

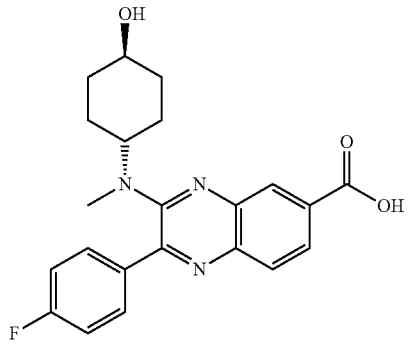

Step 1. Methyl 2-(4-fluorophenyl)-3-(((1r,4r)-4-hydroxycyclohexyl)(methyl)amino)quinoxaline-6-carboxylate

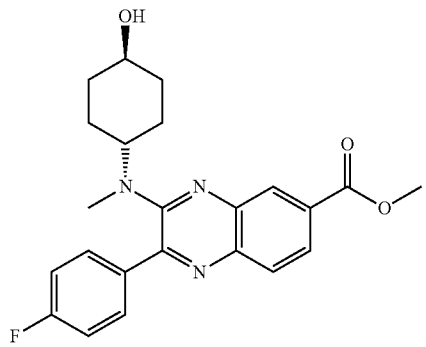

To a solution of methyl 3-chloro-2-(4-fluorophenyl)quinoxaline-6-carboxylate (408 mg, 1.29 mmol) in DMSO (20 ml) was added trans-4-(methylamino)cyclohexan-1-ol (200 mg, 1.55 mmol) and DIEA (499 mg, 3.86 mmol), and the reaction mixture was allowed to react with stirring overnight at 100° C. in an oil bath. The reaction mixture was diluted with water (200 ml), extracted with dichloromethane (4×50 ml). The organic layers were combined, dried over anhydrous magnesium sulfate, and concentrated in vacuo to give the residue, which was purified via silica gel column chromatography (5% ethyl acetate in petroleum ether) to afford methyl 2-(4-fluorophenyl)-3-(((1r,4r)-4-hydroxycyclohexyl)(methyl)amino)quinoxaline-6-carboxylate as a yellow solid (130 mg, 25%).

LC/MS (ES, m/z): [M+H]⁺ 410.0

¹H-NMR (300 MHz, DMSO) δ 8.27 (s, 1H), 7.93-7.99 (m, 2H), 7.85-7.90 (m, 2H), 7.36-7.41 (t, J=8.4 Hz, 2H), 3.93 (s, 3H), 3.65-3.69 (m, 1H), 3.26-3.29 (m, 1H), 2.74 (s, 3H), 1.76-1.79 (m, 2H), 1.51-1.58 (m, 4H), 0.97-1.01 (m, 2H)

Step 2. 2-(4-Fluorophenyl)-3-(((1r,4r)-4-hydroxycyclohexyl)(methyl)amino)quinoxaline-6-carboxylic acid

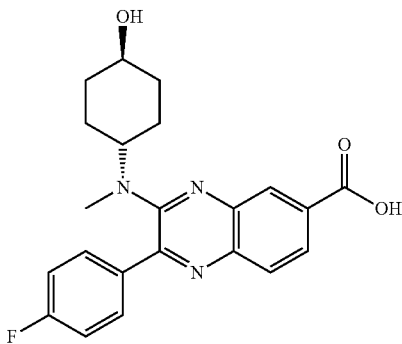

To a solution of methyl 2-(4-fluorophenyl)-3-(((1r,4r)-4-hydroxycyclohexyl)(methyl)amino)quinoxaline-6-carboxylate (130 mg, 0.32 mmol) in tetrahydrofuran (30 ml) and water (1.0 ml) was added sodium hydroxide (51.3 mg, 1.28 mmol), and the reaction mixture was allowed to react with stirring overnight at room temperature. The reaction mixture was concentrated in vacuo, dissolved in water (30 ml), and adjusted to pH 5 with hydrochloric acid (3N) to give the precipitate, which was collected by filtration to afford 2-(4-fluorophenyl)-3-(((1r,4r)-4-hydroxycyclohexyl)(methyl)amino)quinoxaline-6-carboxylic acid as a light yellow solid (100 mg, 80%).

LC/MS (ES, m/z): [M+H]⁺ 396.1

¹H-NMR (300 MHz, DMSO) δ 8.25 (s, 1H), 7.94 (s, 2H), 7.83-7.88 (m, 2H), 7.34-7.39 (t, J=8.7 Hz, 2H), 3.65-3.69 (m, 1H), 3.26-3.29 (m, 1H), 2.69 (s, 3H), 1.75-1.79 (m, 2H), 1.49-1.60 (m, 4H), 0.91-0.97 (m, 2H)

Example 126

2-(4-Fluorophenyl)-3-(methyl((1r,4r)-4-(methylamino)cyclohexyl)amino)quinoxaline-6-carboxylic acid

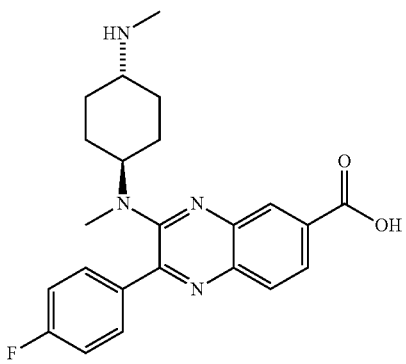 [SMILES: CN[C@H]1CC[C@H](N(C)c2nc3cc(C(=O)O)ccc3nc2-c2ccc(F)cc2)CC1]

Step 1. Methyl 3-(((1r,4r)-4-((tert-butoxycarbonyl)amino)cyclohexyl)amino)-2-(4-fluorophenyl)quinoxaline-6-carboxylate

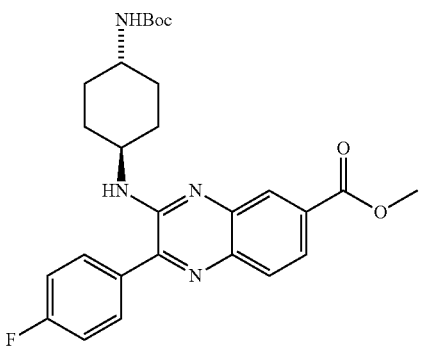 [SMILES: COC(=O)c1ccc2nc(-c3ccc(F)cc3)c(N[C@H]3CC[C@H](NC(=O)OC(C)(C)C)CC3)nc2c1]

To a solution of methyl 3-chloro-2-(4-fluorophenyl)quinoxaline-6-carboxylate (1.45 g, 4.74 mmol) in DMSO (25 ml) was added DIEA (1.22 g, 5.69 mmol), and tert-butyl (1r,4r)-4-aminocyclohexylcarbamate (1.3 g, 6 mmol). After stirring overnight at 100° C. in an oil bath, the reaction was quenched by the addition of water/ice (200 ml). The solids were collected via filtration and purified via silica gel column chromatography (1%-10% ethyl acetate in petroleum ether) to afford methyl 3-(((1r,4r)-4-((tert-butoxycarbonyl)amino)cyclohexyl)amino)-2-(4-fluorophenyl)quinoxaline-6-carboxylate as a light yellow solid (0.91 g, 42%).

LC/MS (ES, m/z): [M+H]⁺ 495.0

Step 2. Methyl 3-(((1r,4r)-4-((tert-butoxycarbonyl)(methyl)amino)cyclohexyl)(methyl)amino)-2-(4-fluorophenyl)quinoxaline-6-carboxylate

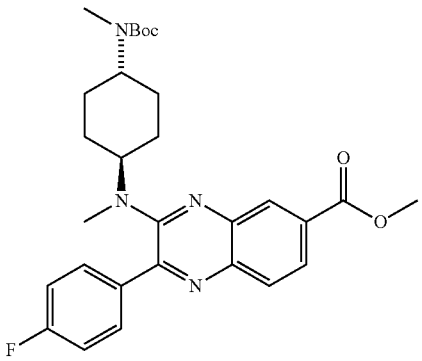 [SMILES: COC(=O)c1ccc2nc(-c3ccc(F)cc3)c(N(C)[C@H]3CC[C@H](N(C)C(=O)OC(C)(C)C)CC3)nc2c1]

To a solution of methyl 3-(((1r,4r)-4-((tert-butoxycarbonyl)amino)cyclohexyl)amino)-2-(4-fluorophenyl)quinoxaline-6-carboxylate (400 mg, 0.81 mmol) in tetrahydrofuran (20 ml) was added sodium hydride (140 mg, 5.83 mmol) and stirred for 10 minutes. Iodomethane (947 mg, 6.67 mmol) was added dropwise at 0° C. After stirring overnight, the reaction was quenched by the addition of NH₄Cl solution (100 ml), extracted with ethyl acetate (3×30 ml), dried over anhydrous magnesium sulfate, and concentrated in vacuo to afford methyl 3-(((1 r,4r)-4-((tert-butoxycarbonyl)(methyl)amino)cyclohexyl)(methyl)amino)-2-(4-fluorophenyl)quinoxaline-6-carboxylate as a yellow solid (360 mg, crude).

LC/MS (ES, m/z): [M+H]⁺ 523.1

Step 3. Methyl 2-(4-fluorophenyl)-3-(methyl((1r,4r)-4-(methylamino)cyclohexyl)amino)quinoxaline-6-carboxylate

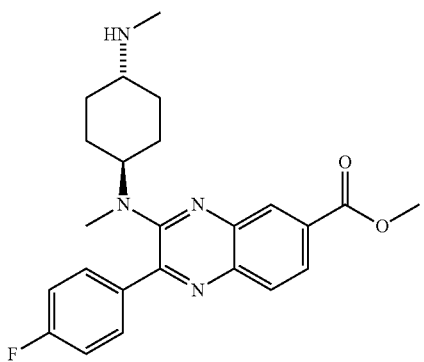 [SMILES: CN[C@H]1CC[C@H](N(C)c2nc3cc(C(=O)OC)ccc3nc2-c2ccc(F)cc2)CC1]

Methyl 3-(((1r,4r)-4-((tert-butoxycarbonyl)(methyl)amino)cyclohexyl)(methyl)amino)-2-(4-fluorophenyl)quinoxaline-6-carboxylate (360 mg, crude) in methanol (50 ml) was stirred for 4 hours at room temperature under an atmosphere of HCl (g). Then the reaction was concentrated in vacuo and the residue was dissolved in water (50 mL), adjusted pH to 8 with saturated sodium bicarbonate, extracted with dichloromethane (3×30 ml), dried over anhydrous magnesium sulfate, and concentrated in vacuo to afford methyl 2-(4-fluorophenyl)-3-(methyl((1r,4r)-4-(methylamino)cyclohexyl)amino)quinoxaline-6-carboxylate as a yellow solid (120 mg, 35% 2 steps).

LC/MS (ES, m/z): [M+H]$^+$ 423.2

$^1$H-NMR (300 MHz, CDCl$_3$) δ 8.50 (d, J=1.8 Hz, 1H), 8.05-8.09 (m, 1H), 7.95 (d, J=8.7 Hz, 1H), 7.86-7.91 (m, 2H), 7.18-7.23 (t, J=8.7 Hz, 2H), 4.00 (s, 3H), 3.86-3.94 (m, 1H), 2.81 (s, 3H), 2.43-2.60 (m, 4H), 2.14-2.18 (m, 2H), 1.80-1.90 (m, 2H), 1.60-1.75 (m, 2H), 1.27-1.38 (m, 2H)

Step 4. 2-(4-Fluorophenyl)-3-(methyl((1r,4r)-4-(methylamino)cyclohexyl)amino)quinoxaline-6-carboxylic acid

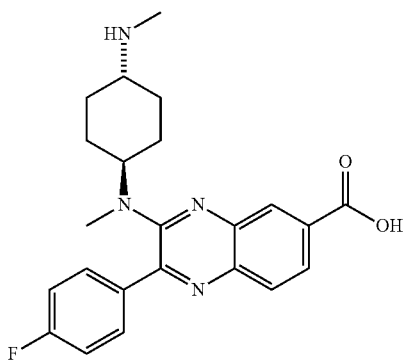 [SMILES: CN[C@H]1CC[C@H](N(C)c2nc3cc(C(=O)O)ccc3nc2-c2ccc(F)cc2)CC1]

To a solution of methyl 2-(4-fluorophenyl)-3-(methyl((1r,4r)-4-(methylamino)cyclohexyl)amino)quinoxaline-6-carboxylate (120 mg, 0.28 mmol) in methanol (40 ml) was added a solution of NaOH (34 mg, 0.85 mmol) in water (4 ml). After stirring overnight at room temperature, the resulting mixture was concentrated in vacuo. The residue was dissolved in water (10 ml) and adjusted pH to 6 with HCl (3N). The solids were collected by filtration to afford 2-(4-fluorophenyl)-3-(methyl((1r,4r)-4-(methylamino)cyclohexyl)amino)quinoxaline-6-carboxylic acid as a yellow solid (64 mg, 43%).

LC/MS (ES, m/z): [M+H]$^+$ 409.1

$^1$H-NMR (300 MHz, DMSO) δ 8.27 (s, 1H), 7.93 (d, J=9.0 Hz, 2H), 7.86-7.91 (m, 2H), 7.36-7.42 (t, J=9.0 Hz, 2H), 3.65-3.75 (m, 1H), 2.83-2.92 (m, 1H), 2.71 (s, 3H), 2.01-2.05 (m, 2H), 1.60-1.68 (m, 4H), 1.12-1.18 (m, 2H)

Example 127

3-(((1r,4r)-4-Acetamidocyclohexyl)(methyl)amino)-2-(4-fluorophenyl)quinoxaline-6-carboxylic acid

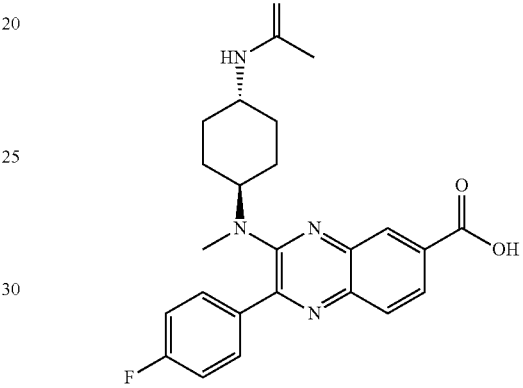

Step 1. Methyl 3-(((1r,4r)-4-((tert-butoxycarbonyl)amino)cyclohexyl)(methyl)amino)-2-(4-fluorophenyl)quinoxaline-6-carboxylate

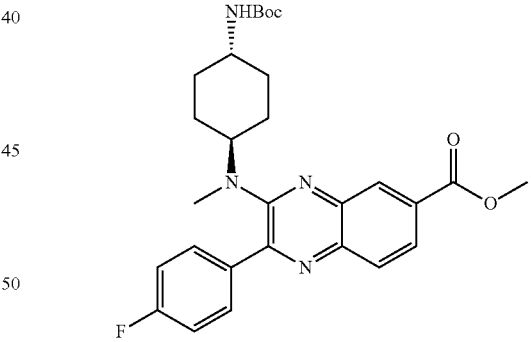

To a solution of methyl 3-((1r,4r)-4-(tert-butoxycarbonylamino)cyclohexylamino)-2-(4-fluorophenyl)quinoxaline-6-carboxylate (300 mg, 0.61 mmol) in DMF (18 ml) was added methyl iodide (300 mg), and t-BuOK (135 mg, 1.20 mmol), and the reaction mixture was stirred for 3 hours at room temperature. The resulting solution was quenched with water (100 ml) and extracted with ethyl acetate (3×50 mL). The organic layers were combined and dried over anhydrous magnesium sulfate and concentrated in vacuo to give a residue, which was purified via silica gel column chromatography (1% to 2% ethyl acetate in petroleum ether) to afford methyl 3-(((1r,4r)-4-((tert-butoxycarbonyl)amino)cyclohexyl)(methyl)amino)-2-(4-fluorophenyl)quinoxaline-6-carboxylate as a yellow solid (250 mg, 81%).

LC/MS (ES, m/z): [M+H]$^+$ 509.0

¹H-NMR (300 MHz, CDCl₃): δ 8.50 (d, J=1.5 Hz, 1H), 8.05-8.08 (m, 1H), 7.95-8.00 (m, 1H), 7.86-7.91 (m, 2H), 7.18-7.28 (m, 2H), 4.01 (s, 3H), 3.75-3.85 (m, 1H), 3.25-3.40 (m, 1H), 2.75 (s, 3H), 1.55-1.76 (m, 6H), 1.45 (s, 9H), 0.85-0.90 (m, 2H)

Step 2. Methyl 3-(((1r,4r)-4-aminocyclohexyl)(methyl)amino)-2-(4-fluorophenyl)quinoxaline-6-carboxylate

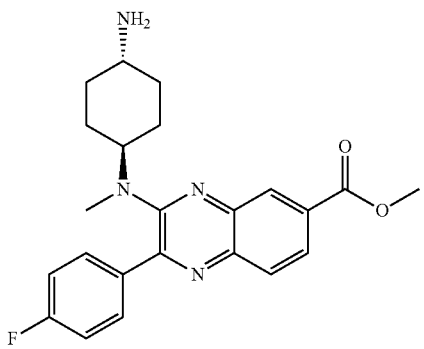 [SMILES: COC(=O)c1ccc2nc(-c3ccc(F)cc3)c(N(C)[C@H]3CC[C@H](N)CC3)nc2c1]

To a solution of methyl 3-(((1r,4r)-4-((tert-butoxycarbonyl)amino)cyclohexyl)(methyl)amino)-2-(4-fluorophenyl)quinoxaline-6-carboxylate (250 mg, 0.49 mmol) in dichloromethane (30 ml) was added trifluoroacetic acid (6 ml) and stirred for 3 hours at room temperature. The resulting solution was concentrated in vacuo to give a residue, which was dissolved in water (100 ml), adjusted to pH 8 with NaHCO₃ solution, and extracted with ethyl acetate (3×50 ml). The organic layers were combined, dried over anhydrous magnesium sulfate, and concentrated under reduced pressure to afford methyl 3-(((1r,4r)-4-aminocyclohexyl)(methyl)amino)-2-(4-fluorophenyl)quinoxaline-6-carboxylate as a yellow solid (150 mg, crude).
LC/MS (ES, m/z): [M+H]⁺ 409.1

Step 3. Methyl 3-(((1r,4r)-4-acetamidocyclohexyl)(methyl)amino)-2-(4-fluorophenyl)quinoxaline-6-carboxylate

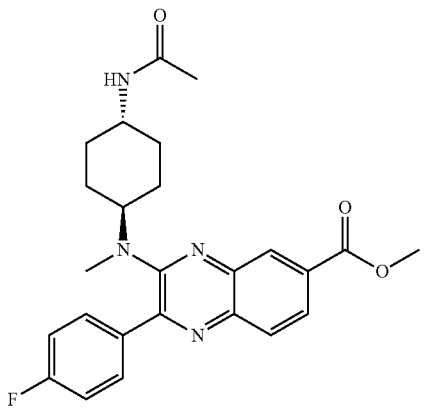 [SMILES: COC(=O)c1ccc2nc(-c3ccc(F)cc3)c(N(C)[C@H]3CC[C@H](NC(C)=O)CC3)nc2c1]

A solution of methyl 3-(((1r,4r)-4-aminocyclohexyl)(methyl)amino)-2-(4-fluorophenyl)quinoxaline-6-carboxylate (150 mg, crude) in acetic anhydride (30 ml) was stirred for 2 hours at room temperature. The resulting solution was diluted with water (200 mL) and stirred for 30 minutes. The pH was adjusted to 8 with sodium bicarbonate (3N) and extracted with ethyl acetate (3×50 ml). The organic layers combined and concentrated in vacuo to give a residue, which was purified via silica gel column chromatography (0.5% to 1% methanol in dichloromethane) to afford methyl 3-(((1r,4r)-4-acetamidocyclohexyl)(methyl)amino)-2-(4-fluorophenyl)quinoxaline-6-carboxylate as a yellow solid (142 mg).
LC/MS (ES, m/z): [M+H]⁺ 451.0
¹H-NMR (300 MHz, CDCl₃): δ 8.28 (s, 1H), 7.96-7.97 (d, J=1.5 Hz, 2H), 7.87-7.89 (m, 2H), 7.64-7.66 (d, J=8.4 Hz, 1H), 7.36-7.42 (m, 2H), 3.94 (s, 3H), 3.67 (s, 1H), 3.34 (s, 1H), 2.74 (s, 3H), 1.76 (s, 5H), 1.65 (s, 4H)

Step 4. 3-(((1r,4r)-4-Acetamidocyclohexyl)(methyl)amino)-2-(4-fluorophenyl)quinoxaline-6-carboxylic acid

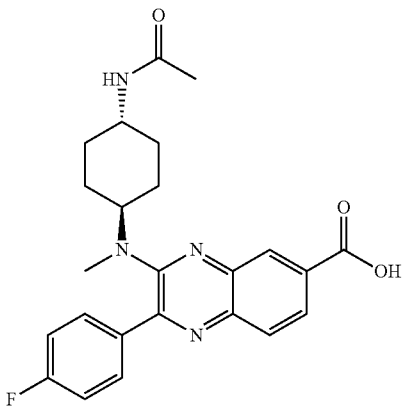 [SMILES: CC(=O)N[C@H]1CC[C@H](N(C)c2nc3cc(C(=O)O)ccc3nc2-c2ccc(F)cc2)CC1]

To a solution of methyl 3-(((1r,4r)-4-acetamidocyclohexyl)(methyl)amino)-2-(4-fluorophenyl)quinoxaline-6-carboxylate (142 mg, 0.32 mmol) in methanol (25 ml) was added solution of NaOH (51 mg, 1.28 mmol) in water (5 ml), and the resulting mixture was stirred overnight at room temperature. The resulting solution was concentrated in vacuo to give a residue, which was dissolved in water (10 ml) and adjusted to pH 4 with HCl (3N). The product was precipitated from water and filtered to afford 3-(((1r,4r)-4-acetamidocyclohexyl)(methyl)amino)-2-(4-fluorophenyl)quinoxaline-6-carboxylic acid as a yellow solid (115.7 mg, 81%).
LC/MS (ES, m/z): [M+H]⁺ 437.1
¹H-NMR (300 MHz, DMSO): δ 8.26 (s, 1H), 7.87-7.95 (m, 4H), 7.63 (d, J=8.8 Hz, 1H), 7.36-7.42 (m, 2H), 3.60-3.67 (m, 1H), 3.40-3.44 (m, 1H), 2.74 (s, 3H), 1.68-1.80 (m, 5H), 1.56-1.64 (m, 4H), 0.87-0.98 (m, 2H)

Example 128

3-(4-Acetylpiperazin-1-yl)-2-(4-fluorophenyl)quinoxaline-6-carboxylic acid

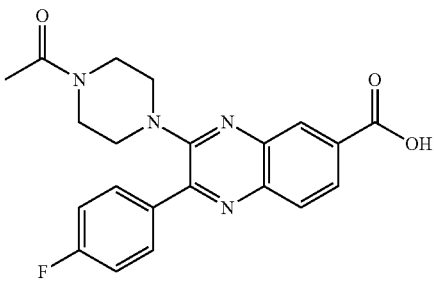 [SMILES: CC(=O)N1CCN(c2nc3cc(C(=O)O)ccc3nc2-c2ccc(F)cc2)CC1]

Step 1. Methyl 2-(4-fluorophenyl)-3-(piperazin-1-yl)quinoxaline-6-carboxylate

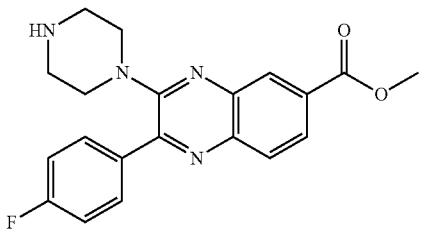 [SMILES: COC(=O)c1ccc2nc(-c3ccc(F)cc3)c(N3CCNCC3)nc2c1]

To a solution of methyl 3-chloro-2-(4-fluorophenyl)quinoxaline-6-carboxylate (632 mg, 2.00 mmol) in DMSO (10 ml) was added DIEA (516 mg, 3.99 mmol) and piperazine (688 mg, 7.99 mmol). The resulting solution was stirred for 3 hours at 80° C. and then quenched by the addition of water (100 ml). The solids were collected by filtration to afford methyl 2-(4-fluorophenyl)-3-(piperazin-1-yl)quinoxaline-6-carboxylate as a yellow solid (540 mg, 74%).

LC/MS (ES, m/z): [M+H]$^+$ 367.0

$^1$H-NMR (300 MHz, CDCl$_3$) δ 8.56 (d, J=1.5 Hz, 1H), 7.99-8.56 (m, 4H), 7.19-7.28 (m, 2H), 4.01 (s, 3H), 3.30-3.33 (t, J=4.5 Hz, 2H), 2.93-2.96 (t, J=4.8 Hz, 2H)

Step 2. Methyl 3-(4-acetylpiperazin-1-yl)-2-(4-fluorophenyl)quinoxaline-6-carboxylate

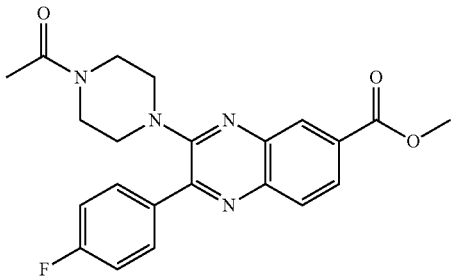 [SMILES: COC(=O)c1ccc2nc(-c3ccc(F)cc3)c(N3CCN(C(C)=O)CC3)nc2c1]

To a solution of methyl 2-(4-fluorophenyl)-3-(piperazin-1-yl)quinoxaline-6-carboxylate (180 mg, 0.49 mmol) in dichloromethane (10 ml) was added Et$_3$N (59 mg, 0.59 mmol) and then acetyl chloride (39 mg, 0.59 mmol) was added dropwise. The resulting solution was stirred for 1 hour at room temperature and then quenched by the addition of ice-water (100 ml) and extracted with dichloromethane (3×15 ml). The organic layers were combined and dried over anhydrous magnesium sulfate and concentrated in vacuo to afford methyl 3-(4-acetylpiperazin-1-yl)-2-(4-fluorophenyl)quinoxaline-6-carboxylate as a yellow solid (103 mg, 51%).

LC/MS (ES, m/z): [M+H]$^+$ 409.0

$^1$H-NMR (300 MHz, CDCl$_3$) δ 8.57 (d, J=1.5 Hz, 1H), 8.15-8.18 (m, 1H), 8.01-8.10 (m, 3H), 6.93-7.28 (m, 2H), 4.02 (s, 3H), 3.64-3.68 (t, J=5.4 Hz, 2H), 3.54-3.57 (t, J=5.7 Hz, 2H), 3.36-3.40 (t, J=4.8 Hz, 2H), 3.26-3.29 (t, J=5.1 Hz, 2H), 2.13 (s, 3H)

Step 3. 3-(4-Acetylpiperazin-1-yl)-2-(4-fluorophenyl)quinoxaline-6-carboxylic acid

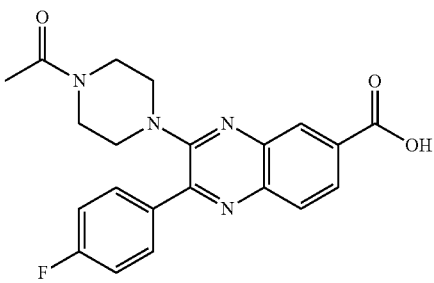 [SMILES: CC(=O)N1CCN(c2nc3cc(C(=O)O)ccc3nc2-c2ccc(F)cc2)CC1]

To a solution of methyl 3-(4-acetylpiperazin-1-yl)-2-(4-fluorophenyl)quinoxaline-6-carboxylate (103 mg, 0.25 mmol) in methanol (10 ml) was added NaOH (48 mg, 1.27 mmol). The resulting solution was stirred overnight at room temperature and concentrated in vacuo. The residue was dissolved in water (15 ml) and adjusted to pH 5 with hydrochloric acid (1N). The solids were collected by filtration to afford 3-(4-acetylpiperazin-1-yl)-2-(4-fluorophenyl)quinoxaline-6-carboxylic acid as a yellow solid (20.8 mg, 21%).

LC/MS (ES, m/z): [M+H]+ 395.1

$^1$H-NMR (300 MHz, DMSO) δ 8.32 (s, 1H), 8.07-8.12 (m, 2H), 8.02 (d, J=1.8 Hz, 2H) 7.37-7.43 (m, 2H), 3.50-3.60 (m, 4H), 3.20-3.30 (m, 4H), 2.00 (s, 3H)

Example 129

3-(4-Benzoylpiperazin-1-yl)-2-(4-fluorophenyl)quinoxaline-6-carboxylic acid

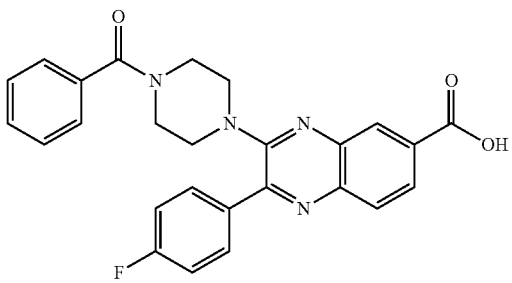 [SMILES: O=C(O)c1ccc2nc(-c3ccc(F)cc3)c(N3CCN(C(=O)c4ccccc4)CC3)nc2c1]

Step 1. Methyl 3-(4-benzoylpiperazin-1-yl)-2-(4-fluorophenyl)quinoxaline-6-carboxylate

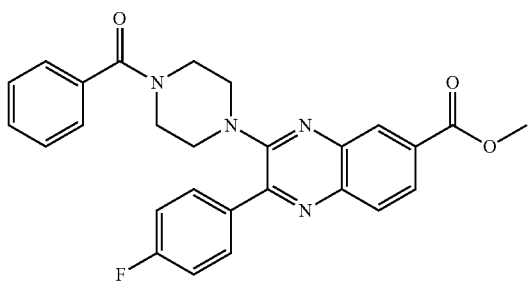 [SMILES: COC(=O)c1ccc2nc(-c3ccc(F)cc3)c(N3CCN(C(=O)c4ccccc4)CC3)nc2c1]

To a solution of methyl 2-(4-fluorophenyl)-3-(piperazin-1-yl)quinoxaline-6-carboxylate (180 mg, 0.49 mmol) in dichloromethane (10 ml) was added Et₃N (200 mg, 2 mmol) followed by benzoyl chloride (170 mg, 1.18 mmol) dropwise. The resulting solution was stirred for 1 hour at room temperature and then quenched by the addition of ice-water (150 ml) and extracted with dichloromethane (3×30 ml). The organic layers were combined, dried over anhydrous magnesium sulfate and concentrated in vacuo to afford methyl 3-(4-benzoylpiperazin-1-yl)-2-(4-fluorophenyl)quinoxaline-6-carboxylate as a yellow solid (130 mg, 56%).

¹H-NMR (300 MHz, CDCl₃) δ 8.57 (d, J=1.8 Hz, 1H), 8.02-8.56 (m, 4H), 7.40-7.48 (m, 5H), 7.20-7.28 (m, 2H), 4.05 (s, 3H), 3.20-3.90 (m, 8H)

Step 2. 3-(4-Benzoylpiperazin-1-yl)-2-(4-fluorophenyl)quinoxaline-6-carboxylic acid

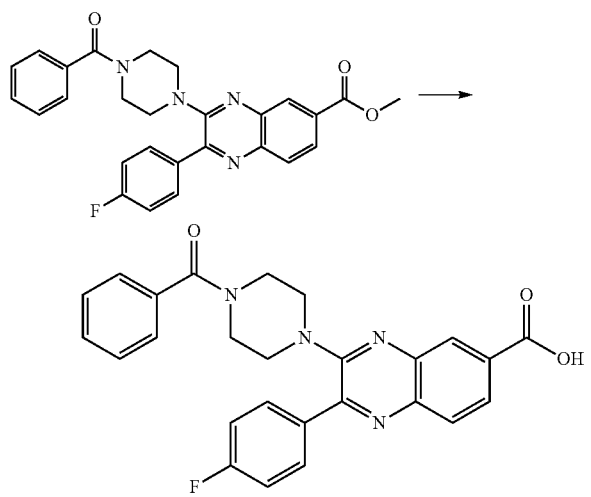

To a solution of methyl 3-(4-benzoylpiperazin-1-yl)-2-(4-fluorophenyl)quinoxaline-6-carboxylate (130 mg, 0.27 mmol) in methanol (15 ml) was added NaOH (37 mg, 0.93 mmol) in water (1 ml). The resulting solution was stirred overnight at room temperature and concentrated in vacuo. The residue was dissolved in water (15 ml) and adjusted to pH 5 with hydrochloric acid (1N). The solids were collected by filtration to afford 3-(4-benzoylpiperazin-1-yl)-2-(4-fluorophenyl)quinoxaline-6-carboxylic acid as a yellow solid (53.0 mg, 42%).

LC/MS (ES, m/z): [M+H]+ 457.1

¹H-NMR (300 MHz, DMSO) δ 8.30 (s, 1H), 7.90-8.01 (m, 4H), 7.35-7.43 (m, 7H), 3.55-3.82 (m, 2H), 3.10-3.52 (m, 6H)

Example 130

2-(4-Fluorophenyl)-3-(4-(methylsulfonyl)piperazin-1-yl)quinoxaline-6-carboxylic acid

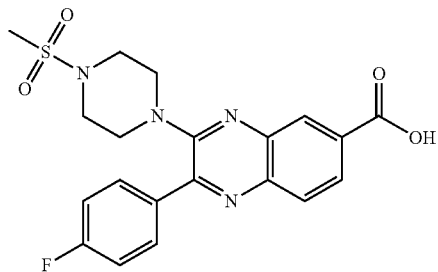 [SMILES: CS(=O)(=O)N1CCN(c2nc3cc(C(=O)O)ccc3nc2-c2ccc(F)cc2)CC1]

Step 1. Methyl 2-(4-fluorophenyl)-3-(4-(methylsulfonyl)piperazin-1-yl)quinoxaline-6-carboxylate

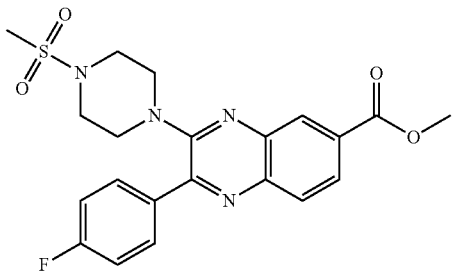

To a solution of methyl 2-(4-fluorophenyl)-3-(piperazin-1-yl)quinoxaline-6-carboxylate (180 mg, 0.59 mmol) in dichloromethane (10 ml) was added Et₃N (202 mg, 2 mmol) and methanesulfonyl chloride (110 mg, 0.98 mmol). The resulting solution was stirred for 1 hour at room temperature. The reaction was then quenched by the addition of ice-water (20 ml) and extracted with dichloromethane (3×15 ml). The organic layers were combined, dried over anhydrous magnesium sulfate, and concentrated in vacuo to afford methyl 2-(4-fluorophenyl)-3-(4-(methylsulfonyl)piperazin-1-yl)quinoxaline-6-carboxylate as a yellow solid (0.14 g, 70%).

LC/MS (ES, m/z): [M+H]⁺ 445.0

¹H-NMR (300 MHz, CDCl₃) δ 8.35 (d, J=1.2 Hz, 1H), 8.03-8.12 (m, 4H), 7.37-7.44 (m, 2H), 3.94 (s, 3H), 3.32-3.35 (m, 4H), 3.18-3.20 (m, 4H), 2.92 (s, 3H)

Step 2. 2-(4-Fluorophenyl)-3-(4-(methylsulfonyl)piperazin-1-yl)quinoxaline-6-carboxylic acid

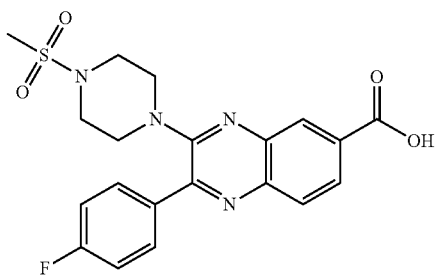 [SMILES: CS(=O)(=O)N1CCN(c2nc3cc(C(=O)O)ccc3nc2-c2ccc(F)cc2)CC1]

To a solution of methyl 2-(4-fluorophenyl)-3-(4-(methylsulfonyl)piperazin-1-yl)quinoxaline-6-carboxylate (100 mg, 0.22 mmol) in methanol (10 ml) was added NaOH (36 mg, 0.9 mmol) and water (1 ml). The resulting solution was stirred overnight at room temperature and concentrated in vacuo. The residue was dissolved in water (15 ml) and adjusted to pH 5 with hydrochloric acid (1N). The solids were collected by filtration to afford 2-(4-fluorophenyl)-3-(4-(methylsulfonyl)piperazin-1-yl)quinoxaline-6-carboxylic acid as a yellow solid (25.0 mg, 25%).

LC/MS (ES, m/z): [M+H]+ 431.1

¹H-NMR (300 MHz, DMSO) δ 8.33 (d, J=1.2 Hz, 1H), 7.99-8.11 (m, 4H), 7.37-7.43 (m, 2H), 3.30-3.34 (m, 4H), 3.18-3.20 (m, 4H), 2.91 (s, 3H)

Example 131

2-(4-Fluorophenyl)-3-[4-(pyridin-2-yl)piperidin-1-yl]quinoxaline-6-carboxylic acid

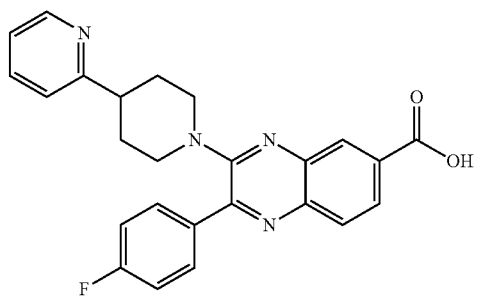 [SMILES: O=C(O)c1ccc2nc(-c3ccc(F)cc3)c(N3CCC(c4ccccn4)CC3)nc2c1]

Step 1. tert-Butyl 4-(trifluoromethylsulfonyloxy)-5,6-dihydropyridine-1(2H)-carboxylate

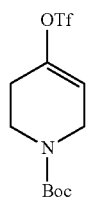

To a solution of diisopropylamine (14.5 mL, 2.00 equiv) in THF (100 ml) was added n-BuLi (36.1 mL, 2.4M) dropwise at −78° C. The mixture was then stirred for 15 min and followed by the addition of a solution of tert-butyl 4-oxopiperidine-1-carboxylate (10 g, 50.19 mmol) in tetrahydrofuran (100 ml). The mixture was stirred for 1 hour at this temperature and then 1,1,1-trifluoro-N-phenyl-N-(trifluoromethane) sulfonylmethane sulfonamide (23 g, 64.38 mmol) was added dropwise. The mixture was stirred overnight at room temperature and extracted with ethyl acetate (3×50 ml), dried over anhydrous magnesium sulfate, and concentrated in vacuo to give a residue, which was purified via silica gel column chromatography (1% ethyl acetate in petroleum ether) to afford tert-butyl 4-[(trifluoromethane)sulfonyloxy]-1,2,3,6-tetrahydropyridine-1-carboxylate as red oil (12 g, 72%).

Step 2. tert-Butyl 4-(4,4,5,5-tetramethyl-1,3,2-dioxaborolan-2-yl)-5,6-dihydropyridine-1(2H)-carboxylate

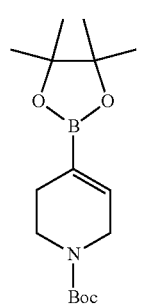

To a solution of tert-butyl 4-[(trifluoromethane)sulfonyloxy]-1,2,3,6-tetrahydropyridine-1-carboxylate (9 g, 27.16 mmol) in dioxane (150 ml) was added 4,4,4',4',5,5,5',5'-octamethyl-2,2'-bi(1,3,2-dioxaborolane) (7.6 g, 29.93 mmol), AcOK (7.9 g, 80.6 mmol), Pd(dppf)$_2$Cl$_2$ (0.59 g, 0.81 mmol), and dppf (450 mg, 0.81 mmol). The resulting solution was stirred overnight at 80° C. under an inert atmosphere of nitrogen, and then diluted with water (500 ml), extracted with ethyl acetate (4×100 ml), and the organic layers combined, dried over anhydrous magnesium sulfate, and concentrated in vacuo to give a residue, which was purified via silica gel column chromatography (1% to 4% ethyl acetate in petroleum ether) to afford tert-butyl 4-(4,4,5,5-tetramethyl-1,3,2-dioxaborolan-2-yl)-5,6-dihydropyridine-1(2H)-carboxylate as a pink solid (6.6 g, 79%).

$^1$H-NMR (300 MHz, CDCl$_3$): δ 6.47 (s, 1H), 3.95-3.98 (m, 2H), 3.43-3.47 (t, J=5.7 Hz, 2H), 2.21-2.26 (m, 2H), 1.451 (s, 9H), 1.25 (s, 12H)

Step 3. tert-Butyl 4-(pyridin-2-yl)-5,6-dihydropyridine-1(2H)-carboxylate

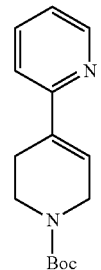 [SMILES: CC(C)(C)OC(=O)N1CC=C(c2ccccn2)CC1]

To a solution of tert-butyl 4-(4,4,5,5-tetramethyl-1,3,2-dioxaborolan-2-yl)-5,6-dihydropyridine-1(2H)-carboxylate (1 g, 3.23 mmol) in dioxane (35 ml) and water (2.0 ml) was added 2-bromopyridine (2.9 g, 18.35 mmol), K$_3$PO$_4$ (3.8 g, 17.90 mmol) and Pd(PPh$_3$)$_4$ (350 mg, 0.30 mmol), and the resulting mixture was allowed to react with stirring for 3 hours at 90° C. The reaction mixture was diluted with water (180 ml) and extracted with ethyl acetate (3×50 ml). The organic layers were combined, dried over anhydrous magnesium sulfate, and concentrated under reduced pressure to give the residue, which was purified via silica gel column chromatography (2% ethyl acetate in petroleum ether) to afford tert-butyl 4-(pyridin-2-yl)-5,6-dihydropyridine-1(2H)-carboxylate as pink oil (1.1 g, 70%).

LC/MS (ES, m/z): [M+H]$^+$ 261.0

$^1$H-NMR (300 MHz, CDCl$_3$): δ 8.58 (d, J=3.9 Hz, 1H), 7.65-7.71 (m, 1H), 7.38 (d, J=7.8 Hz, 1H), 7.16-7.19 (m, 1H), 6.63 (s, 1H), 4.13-4.17 (m, 2H), 3.65-3.69 (t, J=5.7 Hz, 2H), 2.65-2.69 (m, 2H), 1.51 (s, 9H)

Step 4. 2-(1,2,3,6-Tetrahydropyridin-4-yl)pyridine

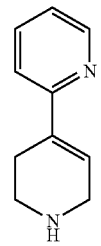

To a solution of tert-butyl 4-(pyridin-2-yl)-5,6-dihydropyridine-1(2H)-carboxylate (1.1 g, 4.23 mmol) in dichloromethane (50 ml) was added trifluoroacetic acid (4 ml), and the reaction mixture was allowed to react with stirring overnight at room temperature. The reaction mixture was concentrated in vacuo to afford 2-(1,2,3,6-tetrahydropyridin-4-yl)pyridine as a crude yellow oil (600 mg).

LC/MS (ES, m/z): [M+H]$^+$ 161.0.

Step 5. Methyl 2-(4-fluorophenyl)-3-(4-(pyridin-2-yl)-5,6-dihydropyridin-1(2H)-yl)quinoxaline-6-carboxylate

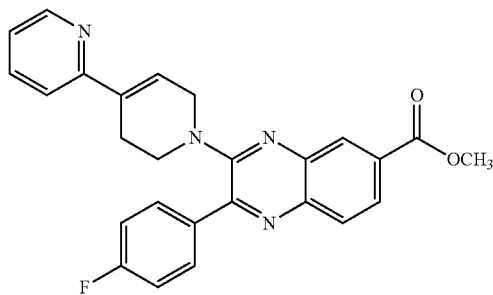 [SMILES: COC(=O)c1ccc2nc(-c3ccc(F)cc3)c(N3CC=C(c4ccccn4)CC3)nc2c1]

To a solution of methyl 3-chloro-2-(4-fluorophenyl)quinoxaline-6-carboxylate (450 mg, 1.42 mmol) in DMSO (5.0 ml) was added 2-(1,2,3,6-tetrahydropyridin-4-yl)pyridine (300 mg, 1.87 mmol) and DIEA (361 mg, 2.79 mmol), and the reaction mixture was stirred overnight at 90° C. The reaction mixture was extracted with ethyl acetate (3×50 ml), and the organic layers combined, dried over anhydrous magnesium sulfate, and concentrated under reduced pressure to give the residue, which was purified by preparative silica gel plate chromatography (dichloromethane:ethyl acetate:petroleum ether (40:1:12)) to afford methyl 2-(4-fluorophenyl)-3-(4-(pyridin-2-yl)-5,6-dihydropyridin-1(2H)-yl)quinoxaline-6-carboxylate as a yellow solid (410 mg).

LC/MS (ES, m/z): [M+H]$^+$ 441.0
$^1$H-NMR (300 MHz, CDCl$_3$): δ 8.58 (d, J=1.8 Hz, 2H), 7.99-8.14 (m, 4H), 7.63-7.72 (m, 1H), 7.42 (d, J=8.1 Hz, 1H), 7.17-7.26 (m, 3H), 6.78 (s, 1H), 4.15-4.16 (m, 2H), 4.02 (s, 3H), 3.52-3.55 (t, J=5.7 Hz, 2H), 2.63-2.66 (m, 2H)

Step 6. Methyl 2-(4-fluorophenyl)-3-[4-(pyridin-2-yl)piperidin-1-yl]quinoxaline-6-carboxylate

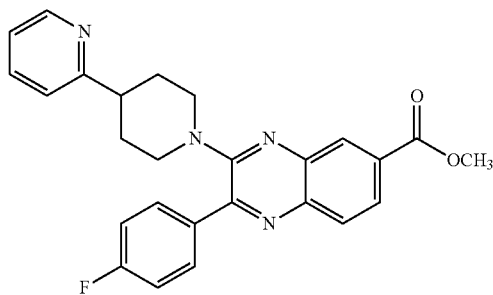 [SMILES: COC(=O)c1ccc2nc(-c3ccc(F)cc3)c(N3CCC(c4ccccn4)CC3)nc2c1]

To a solution of methyl 2-(4-fluorophenyl)-3-(4-(pyridin-2-yl)-5,6-dihydropyridin-1(2H)-yl)quinoxaline-6-carboxylate (150 mg, 0.34 mmol) in ethyl acetate (30 ml) was added PtO$_2$ (38 mg) and the reaction mixture was stirred at room temperature for 2 hours under an atmosphere of H$_2$(g). The reaction mixture was added to water (100 ml), extracted with dichloromethane (3×30 mL), and the organic layers combined, dried over anhydrous magnesium sulfate, and concentrated under reduced pressure to give the residue, which was purified via silica gel column chromatography (2% ethyl acetate in petroleum ether) to afford methyl 2-(4-fluorophenyl)-3-[4-(pyridin-2-yl)piperidin-1-yl]quinoxaline-6-carboxylate as a yellow solid (84 mg, 56%).

LC/MS (ES, m/z): [M+H]$^+$ 443.0
$^1$H-NMR (300 MHz, CDCl$_3$): δ 8.57-8.60 (t, J=6.6 Hz, 2H), 8.09-8.14 (m, 3H), 7.99 (d, J=8.7 Hz, 1H), 7.67-7.72 (m, 1H), 7.18-7.27 (m, 4H), 4.01 (s, 3H), 3.96-3.99 (m, 2H), 2.91-3.00 (m, 3H), 1.84-2.08 (m, 4H)

Step 7. 2-(4-Fluorophenyl)-3-[4-(pyridin-2-yl)piperidin-1-yl]quinoxaline-6-carboxylic acid

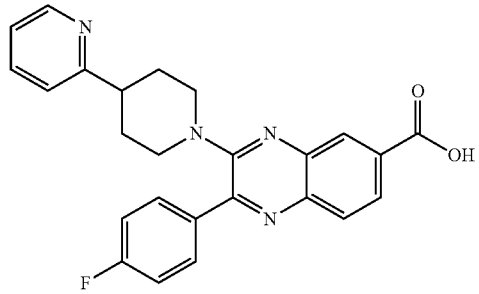 [SMILES: O=C(O)c1ccc2nc(-c3ccc(F)cc3)c(N3CCC(c4ccccn4)CC3)nc2c1]

To a solution of methyl 2-(4-fluorophenyl)-3-[4-(pyridin-2-yl)piperidin-1-yl]quinoxaline-6-carboxylate (84 mg, 0.19 mmol) in methanol (30 ml) and water (1.0 ml) was added sodium hydroxide (30 mg, 0.75 mmol), and the reaction mixture was stirred overnight at room temperature. The reaction mixture was concentrated in vacuo, dissolved in water (10 ml), and adjusted to pH 5 with hydrochloric acid (3N) to give the precipitate, which was collected by filtration to afford 2-(4-fluorophenyl)-3-[4-(pyridin-2-yl)piperidin-1-yl]quinoxaline-6-carboxylic acid as a light yellow solid (61.1 mg, 75%).

LC/MS (ES, m/z): [M+H]$^+$ 429.1
$^1$H-NMR (300 MHz, DMSO): δ 8.50 (d, J=4.8 Hz, 1H), 8.32 (s, 1H), 8.08-8.13 (m, 2H), 8.01 (s, 2H), 7.72-7.77 (m, 1H), 7.38-7.44 (m, 2H), 7.33 (d, J=7.5 Hz, 1H), 7.22-7.26 (m, 1H), 3.85-3.89 (m, 2H), 2.88-2.96 (m, 3H), 1.78-1.85 (m, 4H)

Example 132

(S)-2-(4-Fluorophenyl)-7-hydroxy-3-(2-methylpyrrolidin-1-yl)quinoxaline-6-carboxylic acid

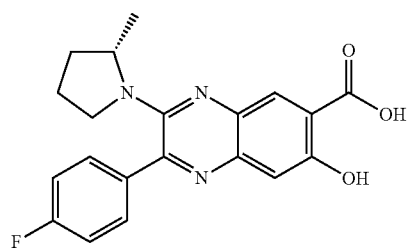 [SMILES: C[C@H]1CCCN1c1nc2cc(C(=O)O)c(O)cc2nc1-c1ccc(F)cc1]

Step 1. (S)-Methyl 7-methoxy-3-(2-methylpyrrolidin-1-yl)-2-oxo-1,2-dihydroquinoxaline-6-carboxylate

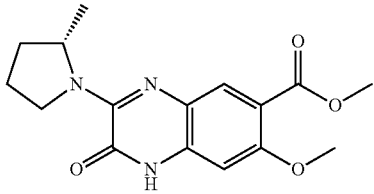 [SMILES: COC(=O)c1cc2nc(N3CCC[C@@H]3C)c(=O)[nH]c2cc1OC]

To a solution of methyl 3-chloro-7-methoxy-2-oxo-1,2-dihydroquinoxaline-6-carboxylate (1.2 g, 4.47 mmol) in DMSO (20 ml) was added DIEA (1.16 g, 8.98 mmol) and methylpyrrolidine hydrochloride (650 mg, 5.35 mmol), and the reaction was stirred at 85° C. overnight. The reaction mixture was cooled to room temperature. The product was precipitated by the addition water, and the solids were collected by filtration to afford (S)-methyl 7-methoxy-3-(2-methylpyrrolidin-1-yl)-2-oxo-1,2-dihydroquinoxaline-6-carboxylate as a light yellow solid (1.0 g, 71%).

LC/MS (ES, m/z): [M+H]$^+$ 318.0

$^1$H-NMR (300 MHz, DMSO) δ 12.04 (s, 1H), 7.63-7.67 (t, J=5.7 Hz, 1H), 6.76 (s, 1H), 4.73-4.78 (m, 1H), 3.91-3.96 (m, 1H), 3.83 (s, 6H), 2.53-2.54 (m, 1H), 1.87-1.99 (m, 3H), 1.63-1.65 (m, 1H), 1.12 (d, J=6.0 Hz, 3H)

Step 2. (S)-Methyl 7-methoxy-3-(2-methylpyrrolidin-1-yl)-2-(trifluoromethylsulfonyloxy)quinoxaline-6-carboxylate

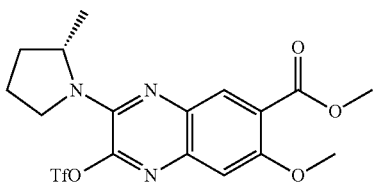 [SMILES: COC(=O)c1cc2nc(N3CCC[C@@H]3C)c(OS(=O)(=O)C(F)(F)F)nc2cc1OC]

To a solution of (S)-methyl 7-methoxy-3-(2-methylpyrrolidin-1-yl)-2-oxo-1,2-dihydroquinoxaline-6-carboxylate (1.0 g, 3.15 mmol) in dichloromethane (80 ml) was added pyridine (990 mg, 12.52 mmol) and Tf$_2$O (1.69 g, 5.99 mmol), and the reaction was stirred overnight under an atmosphere of nitrogen at room temperature. The reaction mixture was then quenched with water (200 ml), extracted with dichloromethane (3×30 mL), the organic layers combined, dried over anhydrous magnesium sulfate, and concentrated in vacuo to afford (S)-methyl 7-methoxy-3-(2-methylpyrrolidin-1-yl)-2-(trifluoromethylsulfonyloxy)quinoxaline-6-carboxylate as red oil (1.20 g, crude), which was used in the next step directly.

Step 3. (S)-Methyl 2-(4-fluorophenyl)-7-methoxy-3-(2-methylpyrrolidin-1-yl)quinoxaline-6-carboxylate

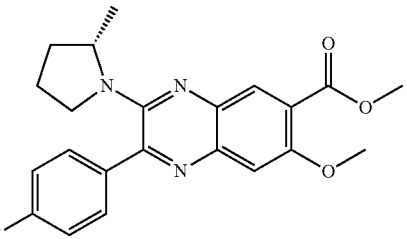

To a solution of (S)-methyl 7-methoxy-3-(2-methylpyrrolidin-1-yl)-2-(trifluoromethylsulfonyloxy)quinoxaline-6-carboxylate (300 mg, crude) in dioxane (5 ml) and water (3 drops) was added (4-fluorophenyl)boronic acid (280.6 mg, 2.01 mmol), Pd(PPh$_3$)$_4$ (38.5 mg, 0.03 mmol), and K$_3$PO$_4$ (422 mg, 1.99 mmol), and the reaction was stirred for 40 minutes at 95° C. under an atmosphere of nitrogen. The reaction mixture was concentrated in vacuo to give a residue, which was purified via silica gel column chromatography (1% ethyl acetate in petroleum ether) to afford (S)-methyl 2-(4-fluorophenyl)-7-methoxy-3-(2-methylpyrrolidin-1-yl)quinoxaline-6-carboxylate as a light yellow solid (200 mg).

LC/MS (ES, m/z): [M+H]$^+$ 396.1

$^1$H-NMR (300 MHz, DMSO) δ 8.27 (s, 1H), 7.78-7.83 (m, 2H), 7.48 (s, 1H), 7.14-7.23 (m, 2H), 4.31-4.35 (m, 1H), 3.98 (s, 6H), 3.19-3.24 (m, 1H), 2.85-2.92 (m, 1H), 2.18-2.25 (m, 1H), 1.81-1.86 (m, 1H), 1.55-1.69 (m, 3H), 1.36 (d, J=6.0 Hz, 3H)

Step 4. (S)-methyl 2-(4-fluorophenyl)-7-hydroxy-3-(2-methylpyrrolidin-1-yl)quinoxaline-6-carboxylate

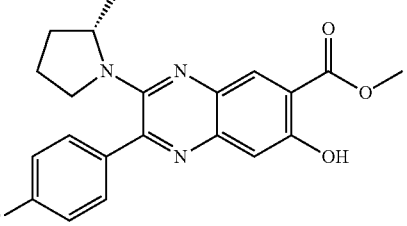

To a solution of (S)-methyl 2-(4-fluorophenyl)-7-methoxy-3-(2-methylpyrrolidin-1-yl)quinoxaline-6-carboxylate (200 mg, 0.51 mmol) in dichloromethane (80 ml) was added BBr$_3$ (2.0 ml) dropwise with stirring at −78° C., and the reaction was allowed to proceed for 40 minutes. The reaction was then quenched by the addition of water/ice. The resulting solution was extracted with dichloromethane (3×80 ml), and the organic layers combined, dried over anhydrous magnesium sulfate, and concentrated in vacuo to give the residue, which was purified via silica gel column chromatography (2% ethyl acetate in petroleum ether) to afford (S)-methyl 2-(4-fluorophenyl)-7-hydroxy-3-(2-methylpyrrolidin-1-yl)quinoxaline-6-carboxylate as a yellow solid (150 mg, 78%).

LC/MS (ES, m/z): [M+H]$^+$ 382.0

Step 5. (S)-2-(4-Fluorophenyl)-7-hydroxy-3-(2-methylpyrrolidin-1-yl)quinoxaline-6-carboxylic acid

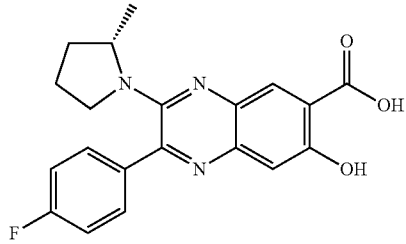 [SMILES: C[C@H]1CCCN1c1nc2cc(C(=O)O)c(O)cc2nc1-c1ccc(F)cc1]

To a solution of (S)-methyl 2-(4-fluorophenyl)-7-hydroxy-3-(2-methylpyrrolidin-1-yl)quinoxaline-6-carboxylate (150 mg, 0.39 mmol) in methanol (30 ml) and water (1 ml) was added sodium hydroxide (19.5 mg, 0.49 mmol), and the reaction was stirred overnight at room temperature. The reaction mixture was concentrated in vacuo, dissolved in water (30 mL), and adjusted to pH 5 with hydrochloric acid (3N) to give the precipitate, which was collected by filtration to afford (S)-2-(4-fluorophenyl)-7-hydroxy-3-(2-methylpyrrolidin-1-yl)quinoxaline-6-carboxylic acid as a light yellow solid (100 mg, 69%).

LC/MS (ES, m/z): [M+H]⁺ 368.1

¹H-NMR (300 MHz, DMSO) δ 8.18 (s, 1H), 7.78-7.83 (m, 2H), 7.32-7.39 (m, 2H), 7.26 (s, 1H), 4.12-4.22 (m, 1H), 2.99-3.11 (m, 1H), 2.86-2.95 (m, 1H), 2.07-2.14 (m, 1H), 1.69-1.76 (m, 1H), 1.55-1.59 (m, 2H), 1.25 (d, J=6.60 Hz, 3H)

Example 133

3-[Benzyl(methyl)amino]-2-(4-fluorophenyl)quinoxaline-6-carboxylic acid

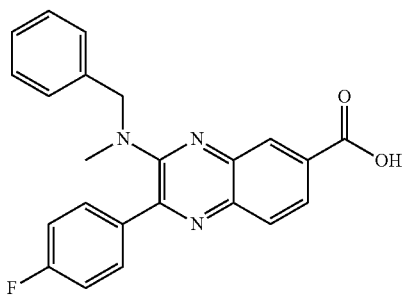 [SMILES: CN(Cc1ccccc1)c1nc2cc(C(=O)O)ccc2nc1-c1ccc(F)cc1]

Step 1. Methyl 3-[benzyl(methyl)amino]-2-(4-fluorophenyl)quinoxaline-6-carboxylate

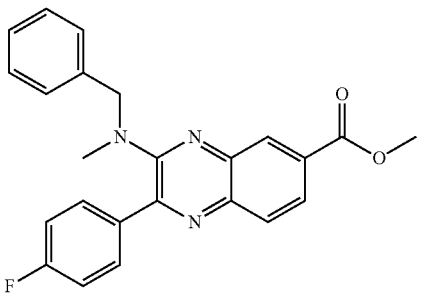 [SMILES: COC(=O)c1ccc2nc(-c3ccc(F)cc3)c(N(C)Cc3ccccc3)nc2c1]

To a solution of methyl 3-chloro-2-(4-fluorophenyl)quinoxaline-6-carboxylate (200 mg, 0.63 mmol) in DMSO (4 mL) was added benzyl(methyl)amine (92 mg, 0.76 mmol), and DIEA (163 mg, 1.26 mmol). The resulting solution was stirred for 2 hours at 85° C. Then the mixture was quenched of water (100 mL) and extracted with dichloromethane (3×50 mL) The organic layers were combined and concentrated in vacuo to give a residue, which was purified via silica gel column chromatography (2% ethyl acetate in petroleum ether) to afford methyl 3-[benzyl(methyl)amino]-2-(4-fluorophenyl)quinoxaline-6-carboxylate as yellow oil (100 mg, 39%).

LC/MS (ES, m/z): [M+H]⁺ 402.0.

Step 2. 3-[Benzyl(methyl)amino]-2-(4-fluorophenyl)quinoxaline-6-carboxylic acid

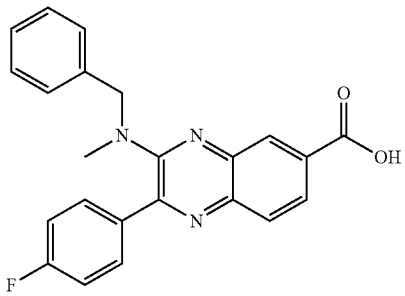

To a solution of methyl 3-[benzyl(methyl)amino]-2-(4-fluorophenyl)quinoxaline-6-carboxylate (100 mg, 0.25 mmol) in methanol (20 mL) was added sodium hydroxide (60 mg, 1.50 mmol) in water (5 mL). The resulting solution was stirred overnight at room temperature and the mixture was concentrated in vacuo to give a residue, which was dissolved in water (5 mL), and adjusted to pH to 5 with HCl (2N). The solids were collected by filtration and dried in an oven under reduced pressure to afford 3-[benzyl(methyl)amino]-2-(4-fluorophenyl)quinoxaline-6-carboxylic acid as a yellow solid (58.3 mg, 61%).

LC/MS (ES, m/z): [M+H]⁺ 388.1

¹H-NMR (300 MHz, DMSO): δ 8.26 (s, 1H), 7.92-7.98 (m, 4H), 7.22-7.39 (m, 7H), 4.55 (s, 2H), 2.70 (s, 3H)

Example 134

2-(4-Fluorophenyl)-3-[methyl(pyridin-2-ylmethyl)amino]quinoxaline-6-carboxylic acid

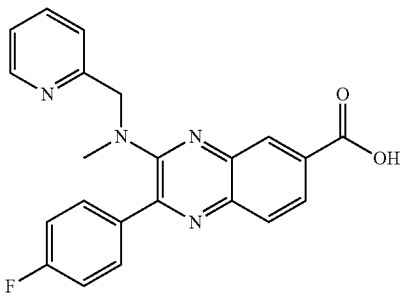

Step 1. Methyl 2-(4-fluorophenyl)-3-[(pyridin-2-ylmethyl)amino]quinoxaline-6-carboxylate

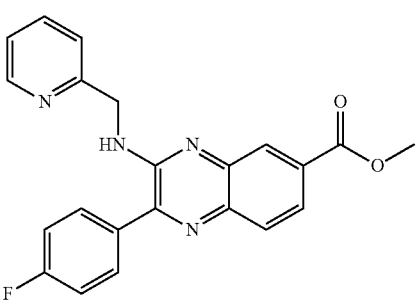 [SMILES: COC(=O)c1ccc2nc(-c3ccc(F)cc3)c(NCc3ccccn3)nc2c1]

To a solution of methyl 3-chloro-2-(4-fluorophenyl)quinoxaline-6-carboxylate (200 mg, 0.95 mmol) in DMSO (5 mL) was added DIEA (245 mg, 1.90 mmol) and pyridin-2-ylmethanamine (124 mg, 1.15 mmol), and the reaction was stirred overnight at 90° C. in an oil bath. The solids were precipitated from water (50 mL), collected by filtration, washed with AcOEt (10 mL), and dried to afford methyl 2-(4-fluorophenyl)-3-[(pyridin-2-ylmethyl)amino]quinoxaline-6-carboxylate as a yellow solid (200 mg, 81%).

LC/MS (ES, m/z): [M+H]+ 389.1

$^1$H-NMR (300 MHz, DMSO) δ 8.51 (d, J=4.2 Hz, 1H), 8.09 (s, 1H), 7.95-7.94 (m, 4H), 7.72-7.76 (m, 1H), 7.57-7.61 (t, J=5.4 Hz, 1H), 7.43-7.49 (t, J=9.0 Hz, 1H), 4.75 (d, J=5.7 Hz, 2H), 3.90 (s, 3H)

Step 2. Methyl 2-(4-fluorophenyl)-3-[methyl(pyridin-2-ylmethyl)amino]quinoxaline-6-carboxylate

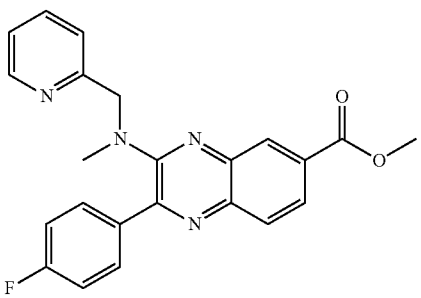 [SMILES: COC(=O)c1ccc2nc(-c3ccc(F)cc3)c(N(C)Cc3ccccn3)nc2c1]

To a solution of methyl 2-(4-fluorophenyl)-3-[(pyridin-2-ylmethyl)amino]quinoxaline-6-carboxylate (200 mg, 0.51 mmol) in tetrahydrofuran (50 mL) was added NaH (107 mg, 4.65 mmol) at 0° C., and the reaction mixture was stirred for 30 minutes. Iodomethane (954 mg, 6.72 mmol) was added, and the reaction mixture was stirred overnight at room temperature. The resulting solution was diluted with NH$_4$Cl solution (80 mL), extracted with ethyl acetate (3×40 mL), dried over anhydrous magnesium sulfate, and concentrated in vacuo to give methyl 2-(4-fluorophenyl)-3-[methyl(pyridin-2-ylmethyl)amino]quinoxaline-6-carboxylate as a yellow solid (120 mg, 57%).

LC/MS (ES, m/z): [M+H]+ 403.1

$^1$H-NMR (300 MHz, CDCl$_3$) δ 8.54 (d, J=4.5 Hz, 1H), 8.50 (d, J=1.8 Hz, 1H), 8.07-8.10 (m, 1H), 7.93-8.00 (m, 3H), 7.63-7.67 (t, J=7.5 Hz, 1H), 7.21-7.30 (m, 1H), 7.14-7.20 (m, 3H), 4.75 (s, 2H), 4.00 (s, 3H), 2.90 (s, 3H)

Step 3. 2-(4-Fluorophenyl)-3-[methyl(pyridin-2-ylmethyl)amino]quinoxaline-6-carboxylic acid

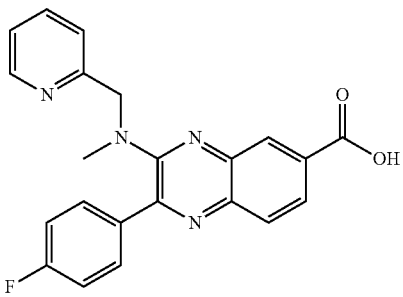 [SMILES: CN(Cc1ccccn1)c1nc2cc(C(=O)O)ccc2nc1-c1ccc(F)cc1]

To a solution of methyl 2-(4-fluorophenyl)-3-[methyl(pyridin-2-ylmethyl)amino]quinoxaline-6-carboxylate (120 mg, 0.30 mmol) in methanol (30 mL) was added sodium hydroxide (48 mg, 1.20 mmol), and the reaction mixture was stirred overnight at room temperature. The resulting mixture was concentrated in vacuo, diluted with water (20 mL), and adjusted to pH 6 with HCl (2N). The solids were collected by filtration to give 2-(4-fluorophenyl)-3-[methyl(pyridin-2-ylmethyl)amino]quinoxaline-6-carboxylic acid as a yellow solid (66 mg, 57%).

LC/MS (ES, m/z): [M+H]+ 389.1

$^1$H-NMR (300 MHz, CD$_3$OD) δ 8.41-8.47 (m, 2H), 8.06-8.09 (m, 1H), 7.94-7.98 (m, 3H), 7.77-7.82 (m, 1H), 7.42 (d, J=7.8 Hz, 1H), 7.20-7.33 (m, 3H), 4.70 (s, 2H), 2.89 (s, 3H)

Example 135

3-(Cyclopentyl(methyl)amino)-2-(4-fluorophenyl)quinoxaline-6-carboxylic acid

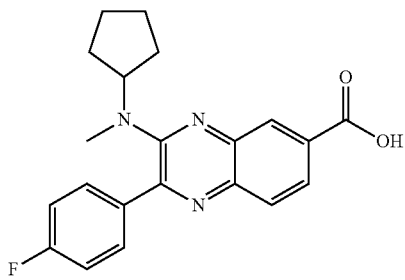

Step 1. Methyl 3-(cyclopentylamino)-2-(4-fluorophenyl)quinoxaline-6-carboxylate

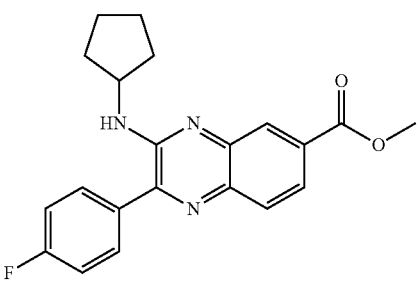 [SMILES: COC(=O)c1ccc2nc(-c3ccc(F)cc3)c(NC3CCCC3)nc2c1]

To a solution of methyl 3-chloro-2-(4-fluorophenyl)quinoxaline-6-carboxylate (250 mg, 0.79 mmol) in DMSO (3 mL) was added cyclopentylamine (402.6 mg, 4.73 mmol), and the resulting solution was stirred overnight at 100° C. The resulting mixture was diluted with water (15 mL) and extracted with dichloromethane (3×10 mL), and the organic layers combined, dried over anhydrous magnesium sulfate, and concentrated in vacuo to give a residue, which was purified via silica gel column chromatography (2%-5% ethyl acetate in petroleum ether) to afford methyl 3-(cyclopentylamino)-2-(4-fluorophenyl)quinoxaline-6-carboxylate as a yellow solid (240 mg, 69%).

LC/MS (ES, m/z): [M+H]+ 366.0

¹H-NMR (300 MHz, CDCl₃) δ 8.50 (d, J=1.8 Hz, 1H), 7.99-8.02 (m, 1H), 7.91 (d, J=8.4 Hz, 1H), 7.25-7.31 (m, 2H), 4.50-4.57 (m, 1H), 4.00 (s, 3H), 2.17-2.23 (m, 2H), 1.67-1.76 (m, 4H), 1.44-1.51 (m, 2H)

Step 2. Methyl 3-(cyclopentyl(methyl)amino)-2-(4-fluorophenyl)quinoxaline-6-carboxylate

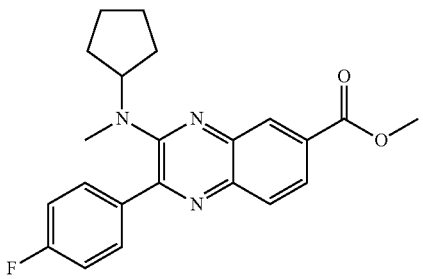

To a solution of methyl 3-(cyclopentylamino)-2-(4-fluorophenyl)quinoxaline-6-carboxylate (200 mg, 0.55 mmol) in tetrahydrofuran (15 mL) was added sodium hydride (96 mg, 4.00 mmol) at 0° C. After stirring for 1 h at room temperature, iodomethane (141.94 mg, 1.00 mmol) was added at 0° C. and the reaction mixture was stirred overnight. The reaction was then quenched by the addition of water (3 mL), extracted with dichloromethane (3×15 mL), and the organic layers combined, dried over anhydrous magnesium sulfate, and concentrated in vacuo to give methyl 3-(cyclopentyl(methyl)amino)-2-(4-fluorophenyl)quinoxaline-6-carboxylate as a yellow oil (120 mg, crude).

LC/MS (ES, m/z): [M+H]+ 380.0

Step 3. 3-(Cyclopentyl(methyl)amino)-2-(4-fluorophenyl)quinoxaline-6-carboxylic acid

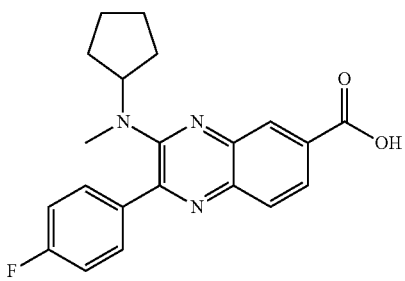 [SMILES: CN(c1nc2cc(C(=O)O)ccc2nc1-c1ccc(F)cc1)C1CCCC1]

To a solution of methyl 3-(cyclopentyl(methyl)amino)-2-(4-fluorophenyl)quinoxaline-6-carboxylate (120.0 mg, crude) in methanol (20 mL) was added sodium hydroxide (50.0 mg, 1.25 mmol) in water (1 mL). The resulting solution was stirred overnight at room temperature and then concentrated in vacuo. The residue was dissolved in water (15 mL) and adjusted to pH 6 with hydrochloric acid (1N). The product was precipitated and filtered to afford 3-(cyclopentyl(methyl)amino)-2-(4-fluorophenyl)quinoxaline-6-carboxylic acid (20 mg).

LC/MS (ES, m/z): [M+H]+ 366.0

¹H-NMR (300 MHz, CDCl₃) δ 8.61 (d, J=1.8 Hz, 1H), 8.11-8.14 (m, 1H), 7.95-7.99 (m, 2H), 7.18-7.24 (m, 2H), 4.31-4.36 (t, J=7.8 Hz, 1H), 2.77 (s, 3H), 1.54-1.81 (m, 8H)

Example 136

3-(Isopropyl(methyl)amino)-2-(4-(trifluoromethyl)phenyl)quinoxaline-6-carboxylic acid

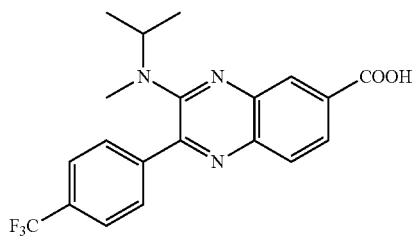 [SMILES: CC(C)N(C)c1nc2cc(C(=O)O)ccc2nc1-c1ccc(C(F)(F)F)cc1]

Step 1. Methyl 3-(isopropyl(methyl)amino)-2-(4-(trifluoromethyl)phenyl)quinoxaline-6-carboxylate

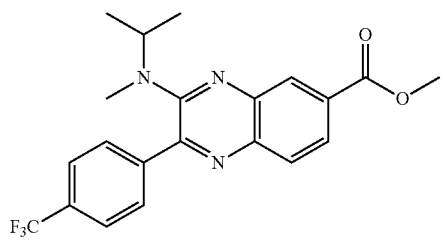 [SMILES: COC(=O)c1ccc2nc(-c3ccc(C(F)(F)F)cc3)c(N(C)C(C)C)nc2c1]

To a solution of 4-(trifluoromethyl)phenylboronic acid (273 mg, 1.44 mmol) in dioxane (6 mL) was added methyl 2-chloro-3-(isopropyl(methyl)amino)quinoxaline-6-carboxylate (140 mg, 0.48 mmol), K₃PO₄ (303 mg, 1.44 mmol), Pd(PPh₃)₄ (27.6 mg, 0.02 mmol) and water (3 drops), and the reaction mixture was stirred for 4 hours at 90° C. in an oil bath under an inert atmosphere of nitrogen. The reaction mixture was concentrated in vacuo and then purified via silica gel column chromatography (2%-10% ethyl acetate in petroleum ether) to afford methyl 3-(isopropyl(methyl)amino)-2-(4-(trifluoromethyl)phenyl)quinoxaline-6-carboxylate as a light yellow solid (158 mg, 82%).

LC/MS (ES, m/z): [M+H]+ 404.0

¹H-NMR (300 MHz, CDCl₃) δ 8.54 (d, J=1.8 Hz, 1H), 7.96-8.09 (m, 4H), 7.62-7.79 (m, 2H), 4.21-4.30 (m, 1H), 4.01 (s, 3H), 2.74 (s, 3H), 1.12 (d, J=6.6 Hz, 6H)

Step 2. 3-(Isopropyl(methyl)amino)-2-(4-(trifluoromethyl)phenyl)quinoxaline-6-carboxylic acid

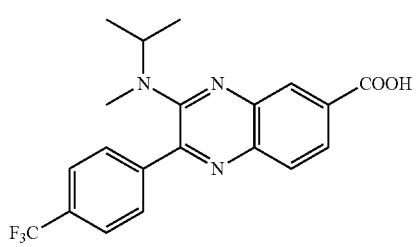 [SMILES: CC(C)N(C)c1nc2cc(C(=O)O)ccc2nc1-c1ccc(C(F)(F)F)cc1]

To a solution of methyl 3-(isopropyl(methyl)amino)-2-(4-(trifluoromethyl)phenyl)quinoxaline-6-carboxylate (158.0 mg, 0.39 mmol) in tetrahydrofuran (20 mL) was added sodium hydroxide (47.0 mg, 1.18 mmol) and water (2 mL), and the reaction mixture was stirred overnight at room temperature. The reaction mixture was concentrated in vacuo, dissolved in water (20 mL) and adjusted to pH 5 with hydrochloric acid (1N). The solids were collected by filtration to afford 3-(isopropyl(methyl)amino)-2-(4-(trifluoromethyl)phenyl)quinoxaline-6-carboxylic acid as a light yellow solid (89 mg, 58%). LC/MS (ES, m/z): [M+H]$^+$ 390.0

$^1$H-NMR (300 MHz, DMSO) δ 8.27-8.28 (t, J=1.2 Hz, 1H), 8.06 (d, J=8.1 Hz, 2H), 7.89-7.96 (m, 4H), 4.18 (t, J=6.6 Hz, 1H), 2.65 (s, 3H), 1.04-1.11 (m, 6H)

Example 137

3-[(1-Ethylpiperidin-4-yl)(methyl)amino]-2-(4-fluorophenyl)quinoxaline-6-carboxylic acid

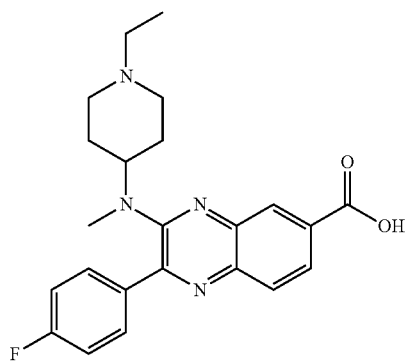 [SMILES: CCN1CCC(N(C)c2nc3cc(C(=O)O)ccc3nc2-c2ccc(F)cc2)CC1]

Step 1. Methyl 3-[(1-ethylpiperidin-4-yl)(methyl)amino]-2-(4-fluorophenyl)-1,4-dihydroquinoxaline-6-carboxylate

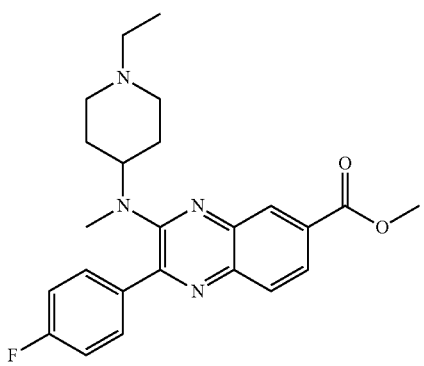 [SMILES: CCN1CCC(N(C)c2nc3cc(C(=O)OC)ccc3nc2-c2ccc(F)cc2)CC1]

To a solution of methyl 2-(4-fluorophenyl)-3-[methyl(piperidin-4-yl)amino]quinoxaline-6-carboxylate (100 mg, 0.25 mmol) in N,N-dimethylformamide (30 mL) was added potassium carbonate (157.6 mg, 1.14 mmol) and CH$_3$CH$_2$I (71.32 mg, 0.46 mmol), and the reaction mixture was stirred overnight at room temperature. The reaction mixture was then diluted with water (200 mL) and extracted with dichloromethane (4×50 mL). The organic layers were combined, dried over anhydrous magnesium sulfate, and concentrated in vacuo. The residue was purified by silica gel column chromatography (1% methanol in dichloromethane) to afford methyl 3-[(1-ethylpiperidin-4-yl)(methyl)amino]-2-(4-fluorophenyl)-1,4-dihydroquinoxaline-6-carboxylate as light yellow oil (53 mg, 46%).

LC/MS (ES, m/z): [M+H]$^+$ 423.0

$^1$H-NMR (300 MHz, CDCl$_3$) δ 8.49 (d, J=1.8 Hz, 1H), 8.05-8.09 (m, 1H), 7.95 (d, J=8.4 Hz, 1H), 7.87-7.92 (m, 2H), 7.18-7.23 (m, 2H), 4.01 (s, 3H), 3.95-3.98 (m, 1H), 3.07-3.15 (m, 2H), 2.77 (s, 3H), 2.41-2.49 (m, 2H), 1.82-2.01 (m, 4H), 1.74-1.78 (m, 2H), 0.85-0.89 (t, J=6.6 Hz, 3H)

Step 2. 3-[(1-Ethylpiperidin-4-yl)(methyl)amino]-2-(4-fluorophenyl)quinoxaline-6-carboxylic acid

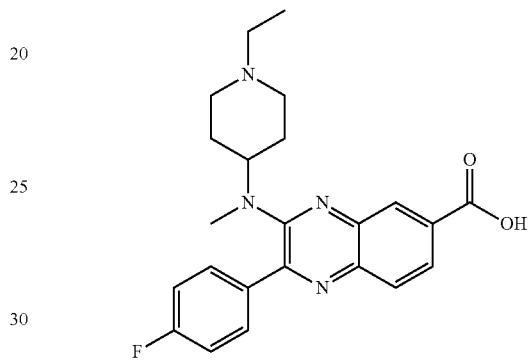

To a solution of methyl 3-[(1-ethylpiperidin-4-yl)(methyl)amino]-2-(4-fluorophenyl)quinoxaline-6-carboxylate (53 mg, 0.12 mmol) in methanol (30 mL) was added sodium hydroxide (26.5 mg, 0.66 mmol), and the resulting mixture was stirred overnight at room temperature. The reaction mixture was concentrated in vacuo, dissolved in water (10 mL), and adjusted to pH 5 with HCl (3N) to give the precipitate, which was collected by filtration to afford 3-[(1-ethylpiperidin-4-yl)(methyl)amino]-2-(4-fluorophenyl)quinoxaline-6-carboxylic acid as a light yellow solid (35.2 mg, 69%).

LC/MS (ES, m/z): [M+H]$^+$ 409.0

$^1$H-NMR (300 MHz, DMSO) δ 8.47 (d, J=1.8 Hz, 1H), 8.02-8.12 (m, 1H), 7.94-7.99 (m, 3H), 7.28-7.34 (t, J=8.7 Hz, 2H), 4.31-4.36 (t, J=7.5 Hz, 1H), 3.66-3.98 (m, 2H), 3.20 (d, J=6.9 Hz, 2H), 3.06-3.09 (t, J=6.9 Hz, 2H), 2.72 (s, 3H), 2.18 (s, 4H), 1.36-1.41 (t, J=7.5 Hz, 3H)

Example 138

(S)-3-(4-Ethyl-2-methylpiperazin-1-yl)-2-(4-fluorophenyl)quinoxaline-6-carboxylic acid

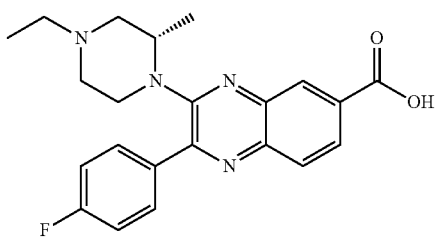 [SMILES: CCN1CCN(c2nc3cc(C(=O)O)ccc3nc2-c2ccc(F)cc2)[C@@H](C)C1]

Step 1. (S)-Methyl 3-(4-ethyl-2-methylpiperazin-1-yl)-2-(4-fluorophenyl)quinoxaline-6-carboxylate

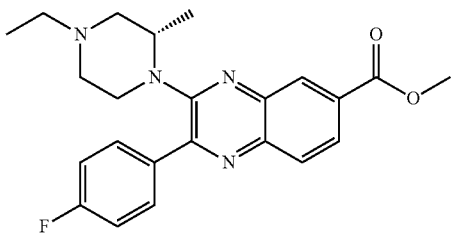 [SMILES: CCN1CCN(c2nc3cc(C(=O)OC)ccc3nc2-c2ccc(F)cc2)[C@@H](C)C1]

To a solution of (S)-methyl 2-(4-fluorophenyl)-3-(2-methylpiperazin-1-yl)quinoxaline-6-carboxylate (160 mg, 0.42 mmol) in N,N-dimethylformamide (30 mL) was added potassium carbonate (174 mg, 1.26 mmol) and $CH_3CH_2I$ (68.8 mg, 0.44 mmol), and the reaction was stirred overnight at room temperature. The reaction solution was diluted with water (150 mL), extracted with dichloromethane (3×30 mL), and the organic layers combined, dried over anhydrous magnesium sulfate, and concentrated in vacuo. The residue was purified by silica gel column chromatography (1% methanol in dichloromethane) to afford (S)-methyl 3-(4-ethyl-2-methylpiperazin-1-yl)-2-(4-fluorophenyl)quinoxaline-6-carboxylate as light yellow oil (80 mg, crude).
LC/MS (ES, m/z): $[M+H]^+$ 408.0

Step 2. (S)-3-(4-Ethyl-2-methylpiperazin-1-yl)-2-(4-fluorophenyl)quinoxaline-6-carboxylic acid

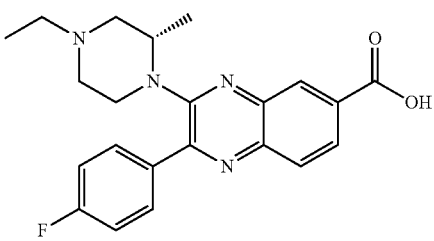 [SMILES: CCN1CCN(c2nc3cc(C(=O)O)ccc3nc2-c2ccc(F)cc2)[C@@H](C)C1]

To a solution of (S)-methyl 3-(4-ethyl-2-methylpiperazin-1-yl)-2-(4-fluorophenyl)quinoxaline-6-carboxylate (80 mg, crude) in methanol (30 mL) was added sodium hydroxide (31.0 mg, 0.78 mmol) and water (1 mL), and the reaction was stirred overnight at room temperature. The reaction mixture was concentrated in vacuo, dissolved in water (30 mL), and adjusted to pH 5 with HCl (3N) to give the precipitate, which was purified by Prep-HPLC with the following conditions [(Agilent 1200 prep HPLC): Column, SunFire Prep C18, 19*50 mm 5 um; mobile phase, water with 0.05% $NH_3·H_2O$ and $CH_3CN$ (10% $CH_3CN$ up to 45% in 10 min); Detector, UV 220 nm] to afford (S)-3-(4-ethyl-2-methylpiperazin-1-yl)-2-(4-fluorophenyl)quinoxaline-6-carboxylic acid (40 mg, 52.0%).
LC/MS (ES, m/z): $[M+H]^+$ 395.0
$^1$H-NMR (300 MHz, DMSO) δ 8.28 (d, J=1.50 Hz, 1H), 7.94-8.00 (m, 4H), 7.34-7.39 (t, J=9.00 Hz, 2H), 3.87-3.89 (t, J=3.30 Hz, 1H), 3.36-3.41 (m, 1H), 3.20-3.24 (m, 1H), 2.71-2.74 (m, 1H), 2.19-2.38 (m, 4H), 1.06 (d, J=6.60 Hz, 3H), 0.96-1.01 (t, J=6.90 Hz, 3H)

Example 139

3-[Ethyl(propyl)amino]-2-(4-fluorophenyl)quinoxaline-6-carboxylic acid

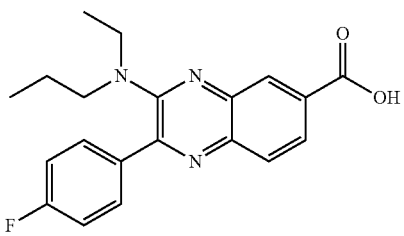 [SMILES: CCCN(CC)c1nc2cc(C(=O)O)ccc2nc1-c1ccc(F)cc1]

Step 1. Methyl 2-(4-fluorophenyl)-3-(propylamino)quinoxaline-6-carboxylate

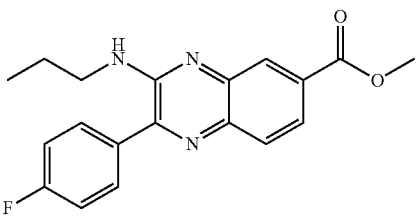 [SMILES: CCCNc1nc2cc(C(=O)OC)ccc2nc1-c1ccc(F)cc1]

To a solution of methyl 3-chloro-2-(4-fluorophenyl)quinoxaline-6-carboxylate (150 mg, 0.47 mmol) in DMSO (10 mL) was added DIEA (182 mg, 1.41 mmol) and propan-1-amine (56 mg, 0.95 mmol), and the reaction was stirred overnight at 80° C. in an oil bath. The reaction mixture was cooled to room temperature, diluted with water (150 mL), extracted with ethyl acetate (3×50 mL), and the organic layers combined, dried over magnesium sulfate, and concentrated in vacuo to give the residue, which was purified via silica gel column chromatography (1% ethyl acetate in petroleum ether) to afford 2-(4-fluorophenyl)-3-(propylamino)quinoxaline-6-carboxylate as a light yellow solid (70 mg, 45.0%).
LC/MS (ES, m/z): $[M+H]^+$ 340.0
$^1$H-NMR (300 MHz, $CDCl_3$): δ 8.51 (d, J=1.50 Hz, 1H), 7.91-8.02 (m, 2H), 7.73-7.79 (m, 2H), 7.25-7.32 (m, 2H), 5.20 (s, 1H), 4.00 (s, 3H), 3.54-3.60 (m, 2H), 1.64-1.76 (m, 2H), 0.95-1.54 (m, 3H)

Step 2. 3-(Ethyl(propyl)amino)-2-(4-fluorophenyl)quinoxaline-6-carboxylic acid

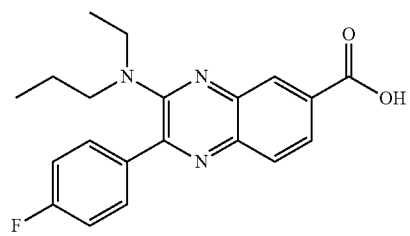 [SMILES: CCCN(CC)c1nc2cc(C(=O)O)ccc2nc1-c1ccc(F)cc1]

To a solution of methyl 2-(4-fluorophenyl)-3-(propylamino)quinoxaline-6-carboxylate (70 mg, 0.21 mmol) in tetrahydrofuran (30 mL) was added sodium hydride (32 mg, 1.32 mmol) and CH₃CH₂I (1.5 mL), and the reaction was stirred overnight at room temperature. The reaction was then quenched with water (50 mL), adjusted to pH 5 with HCl (3N), and extracted with ethyl acetate (3×40 mL). The organic layers were combined, dried over anhydrous magnesium sulfate, and concentrated in vacuo to give the residue, which was purified by Prep-HPLC under the following conditions [(Agilent 1200 prep HPLC): Column, SunFire Prep C18, 19*50 mm 5 um; mobile phase, water with 0.03% $NH_3H_2O$ and $CH_3CN$ (10% $CH_3CN$ up to 35% in 8 min); Detector, UV 220 nm] to afford 3-(ethyl(propyl)amino)-2-(4-fluorophenyl)quinoxaline-6-carboxylic acid as a light yellow solid (45.0 mg, 62.0%).

LC/MS (ES, m/z): [M+H]⁺ 354.0

¹H-NMR (300 MHz, DMSO): δ 8.21 (d, J=1.20 Hz, 1H), 7.83-7.98 (m, 4H), 7.34-7.40 (m, 2H), 3.36-3.39 (m, 2H), 3.27-3.32 (t, J=7.20 Hz, 2H), 1.45-1.52 (m, 2H), 0.98-1.02 (t, J=6.90 Hz, 3H), 0.69-0.74 (t, J=7.50 Hz, 3H)

Example 140

3-(Dipropylamino)-2-(4-fluorophenyl)quinoxaline-6-carboxylic acid

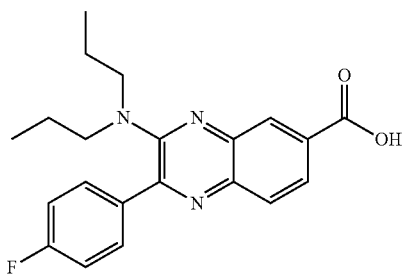 [SMILES: CCCN(CCC)c1nc2cc(C(=O)O)ccc2nc1-c1ccc(F)cc1]

Step 1. Methyl 3-(dipropylamino)-2-(4-fluorophenyl)quinoxaline-6-carboxylate

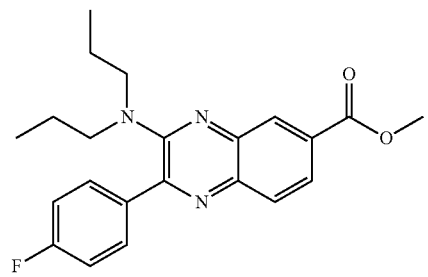 [SMILES: CCCN(CCC)c1nc2cc(C(=O)OC)ccc2nc1-c1ccc(F)cc1]

To a solution of methyl 3-chloro-2-(4-fluorophenyl)quinoxaline-6-carboxylate (100 mg, 0.32 mmol) in DMSO (3 mL) was added dipropylamine (100 mg, 0.99 mmol) and DIEA (100 mg, 0.77 mmol). The resulting solution was stirred overnight at 85° C. and then diluted with water (50 mL), extracted with ethyl acetate (3×20 mL), and the organic layers combined, dried over anhydrous magnesium sulfate, and concentrated in vacuo to give a residue, which was purified via silica gel column chromatography (2.5%-4% ethyl acetate in petroleum ether) to afford methyl 3-(dipropylamino)-2-(4-fluorophenyl)quinoxaline-6-carboxylate as a yellow solid (50 mg, 41%).

LC/MS (ES, m/z): [M+H]⁺ 382.0

¹H-NMR (300 MHz, CDCl₃), δ 8.60 (d, J=1.5 Hz, 1H), 8.06-8.09 (m, 1H), 7.91 (d, J=8.4 Hz, 1H), 7.86-7.91 (m, 2H), 7.18-7.24 (m, 2H), 4.00 (s, 3H), 3.26-3.31 (t, J=7.2 Hz, 4H), 1.51-1.63 (m, 4H), 0.77-0.82 (t, J=7.2 Hz, 6H)

Step 2. 3-(Dipropylamino)-2-(4-fluorophenyl)quinoxaline-6-carboxylic acid

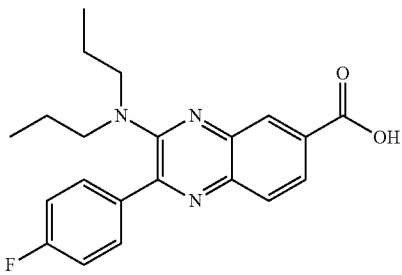 [SMILES: CCCN(CCC)c1nc2cc(C(=O)O)ccc2nc1-c1ccc(F)cc1]

To a solution of methyl 3-(dipropylamino)-2-(4-fluorophenyl)quinoxaline-6-carboxylate (50 mg, 0.13 mmol) in methanol (15 mL) was added a solution of sodium hydroxide (10 mg, 0.25 mmol) in water (1 mL). The resulting solution was stirred overnight at room temperature and then concentrated in vacuo. The residue was dissolved in water (20 mL) and adjusted to pH 5 with hydrochloric acid (3N). The resulting solution was extracted with dichloromethane (4×20 mL), and the organic layers combined, dried over anhydrous magnesium sulfate, and concentrated in vacuo to afford 3-(dipropylamino)-2-(4-fluorophenyl)quinoxaline-6-carboxylic acid as a yellow solid (22.4 mg, 46%).

LC/MS (ES, m/z): [M+H]⁺ 368.0

¹H-NMR (300 MHz, CD₃OD), δ 8.42 (d, J=1.5 Hz, 1H), 8.03-8.06 (m, 1H), 7.88-7.94 (m, 3H), 7.29-7.33 (m, 2H), 3.26 (d, J=7.5 Hz, 4H), 1.51-1.63 (m, 4H), 0.77-0.82 (t, J=7.2 Hz, 6H)

Example 141

2-(4-Fluorophenyl)-3-(isobutyl(methyl)amino)quinoxaline-6-carboxylic acid

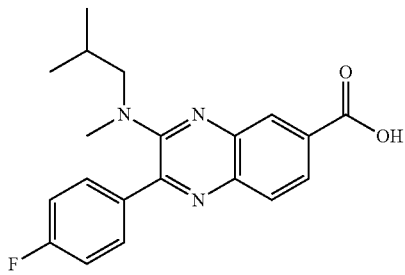 [SMILES: CC(C)CN(C)c1nc2cc(C(=O)O)ccc2nc1-c1ccc(F)cc1]

Step 1. Methyl 2-(4-fluorophenyl)-3-(isobutyl(methyl)amino)quinoxaline-6-carboxylate

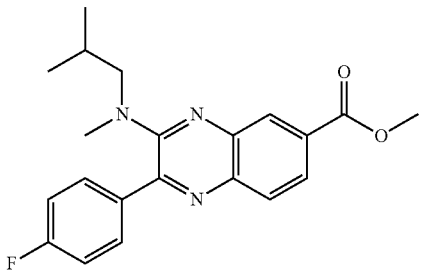 [SMILES: COC(=O)c1ccc2nc(-c3ccc(F)cc3)c(N(C)CC(C)C)nc2c1]

To a solution of methyl 3-chloro-2-(4-fluorophenyl)quinoxaline-6-carboxylate (100 mg, 0.32 mmol) in DMSO (3 mL) was added DIEA (81.5 mg, 0.63 mmol) and isobutyl (methyl)amine (41 mg, 0.47 mmol), and the reaction was stirred overnight at 70° C. in an oil bath. The reaction mixture was cooled to room temperature, diluted with water (50 mL), and extracted with ethyl acetate (3×20 mL). The organic layers were combined, dried over magnesium sulfate, and concentrated in vacuo to give the residue, which was purified via silica gel column chromatography (1% ethyl acetate in petroleum ether) to afford methyl 2-(4-fluorophenyl)-3-(isobutyl(methyl)amino)quinoxaline-6-carboxylate as a light yellow solid (80 mg, 69%).

LC/MS (ES, m/z): [M+H]$^+$ 368.0

$^1$H-NMR (300 MHz, CDCl$_3$): δ 8.54 (d, J=1.5 Hz, 1H), 8.04-8.08 (m, 1H), 7.96 (d, J=8.7 Hz, 1H), 7.86-7.91 (m, 2H), 7.19-7.28 (m, 2H), 4.00 (s, 3H), 3.16 (d, J=7.2 Hz, 2H), 2.89 (s, 3H), 1.99-2.09 (m, 1H), 0.82 (d, J=6.6 Hz, 6H)

Step 2. 2-(4-Fluorophenyl)-3-(isobutyl(methyl) amino)quinoxaline-6-carboxylic acid

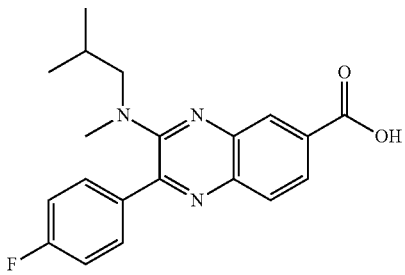 [SMILES: CC(C)CN(C)c1nc2cc(C(=O)O)ccc2nc1-c1ccc(F)cc1]

To a solution of methyl 2-(4-fluorophenyl)-3-(isobutyl (methyl)amino)quinoxaline-6-carboxylate (80 mg, 0.22 mmol) in methanol (20 mL) and water (1 mL) was added sodium hydroxide (34.8 mg, 0.87 mmol 1), and the reaction was stirred overnight at room temperature. The reaction mixture was concentrated in vacuo, dissolved in water (10 mL), and adjusted to pH 5 with HCl (3N) to give the precipitate, which was collected by filtration to afford 2-(4-fluorophenyl)-3-(isobutyl(methyl)amino)quinoxaline-6-carboxylic acid as a light yellow solid (50.0 mg, 65%).

LC/MS (ES, m/z): [M+H]$^+$ 354.0

$^1$H-NMR (300 MHz, DMSO) δ 13.19 (s, 1H), δ 8.25 (s, 1H), 7.83-7.96 (m, 4H), 7.36-7.42 (t, J=8.7 Hz, 2H), 3.09 (d, J=7.2 Hz, 2H), 2.84 (s, 3H), 1.92-2.01 (m, 1H), 0.71 (d, J=6.6 Hz, 6H)

Example 142

3-(2-Ethylpiperidin-1-yl)-2-(4-fluorophenyl)quinoxaline-6-carboxylic acid

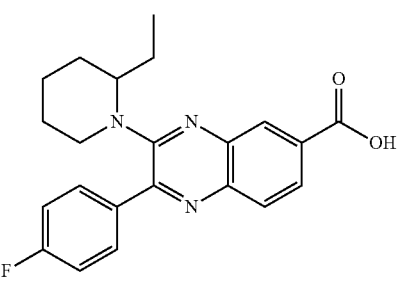 [SMILES: CCC1CCCCN1c1nc2cc(C(=O)O)ccc2nc1-c1ccc(F)cc1]

Step 1. Methyl 3-(2-ethylpiperidin-1-yl)-2-oxo-1,2-dihydroquinoxaline-6-carboxylate

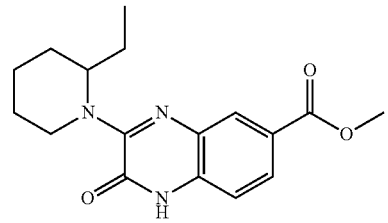 [SMILES: CCC1CCCCN1c1nc2cc(C(=O)OC)ccc2[nH]c1=O]

To a solution of methyl 3-chloro-2-oxo-1,2-dihydroquinoxaline-6-carboxylate (500 mg, crude) in DMSO (5 mL) was added 2-ethylpiperidine (475 mg, 4.20 mmol) and DIEA (542 mg, 4.19 mmol). The resulting solution was stirred overnight at 80° C. in an oil bath and then quenched by the addition of water (50 mL), extracted with dichloromethane (5×20 mL). The organic layers were combined, dried over magnesium sulfate, and concentrated in vacuo to give a residue, which was purified via silica gel column chromatography (1%-10% ethyl acetate in petroleum ether) to afford methyl 3-(2-ethylpiperidin-1-yl)-2-oxo-1,2-dihydroquinoxaline-6-carboxylate as yellow oil (150 mg).

LC/MS (ES, m/z): [M+H]$^+$ 316.0

$^1$H-NMR (300 MHz, CDCl$_3$), δ 9.78 (s, 1H), 9.27 (s, 1H), 7.82-7.86 (m, 1H), 7.06 (d, J=8.4 Hz, 1H), 5.27 (s, 1H), 4.86-4.91 (s, 1H), 3.94 (s, 3H), 3.14-3.19 (m, 1H), 1.60-1.80 (m, 6H), 0.92-0.98 (m, 3H)

Step 2. Methyl 3-(2-ethylpiperidin-1-yl)-2-[(trifluoromethane)sulfonyloxy]quinoxaline-6-carboxylate

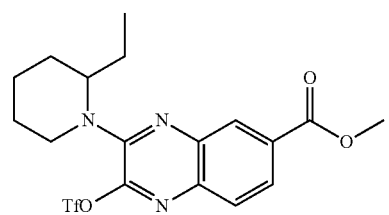 [SMILES: CCC1CCCCN1c1nc2cc(C(=O)OC)ccc2nc1OS(=O)(=O)C(F)(F)F]

To a solution of methyl 3-(2-ethylpiperidin-1-yl)-2-oxo-1,2-dihydroquinoxaline-6-carboxylate (150 mg, 0.48 mmol) in dichloromethane (20 mL) was added pyridine (151 mg, 1.91 mmol) and Tf$_2$O (270 mg, 0.96 mmol,). The resulting solution was stirred overnight at room temperature, and then washed with water (30 mL), dried over anhydrous magnesium sulfate, and concentrated in vacuo to afford methyl 3-(2-ethylpiperidin-1-yl)-2-[(trifluoromethane)sulfonyloxy]quinoxaline-6-carboxylate as yellow oil (210 mg crude).

Step 3. Methyl 3-(2-ethylpiperidin-1-yl)-2-(4-fluorophenyl)quinoxaline-6-carboxylate

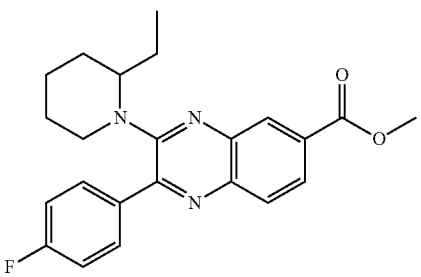 [SMILES: CCC1CCCCN1c1nc2cc(C(=O)OC)ccc2nc1-c1ccc(F)cc1]

To a solution of methyl 3-(2-ethylpiperidin-1-yl)-2-[(trifluoromethane)sulfonyloxy]quinoxaline-6-carboxylate (210 mg, crude) in dioxane (5 mL) was added (4-fluorophenyl)boronic acid (133 mg, 0.95 mmol), K$_3$PO$_4$ (200 mg, 0.94 mmol), Pd(PPh$_3$)$_4$ (27 mg, 0.02 mmol) and water (5 drops). The resulting solution was stirred for 1 hour at 90° C. under an inert atmosphere of nitrogen and then concentrated in vacuo to give a residue, which was purified via silica gel column chromatography (2%-10% ethyl acetate in petroleum ether) to afford methyl 3-(2-ethylpiperidin-1-yl)-2-(4-fluorophenyl)quinoxaline-6-carboxylate as a yellow solid (140 mg).

LC/MS (ES, m/z): [M+H]$^+$ 394.0

Step 4. 3-(2-Ethylpiperidin-1-yl)-2-(4-fluorophenyl)quinoxaline-6-carboxylic acid

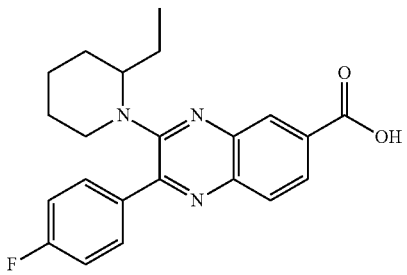

To a solution of methyl 3-(2-ethylpiperidin-1-yl)-2-(4-fluorophenyl)quinoxaline-6-carboxylate (45 mg, 0.11 mmol) in methanol (15 mL) was added sodium hydroxide (10 mg, 0.25 mmol) in water (1 mL). The resulting solution was stirred overnight at room temperature and concentrated in vacuo. The residue was dissolved in water (3 mL), adjusted to pH 5 with hydrochloric acid (3M), and collected by filtration to afford 3-(2-ethylpiperidin-1-yl)-2-(4-fluorophenyl)quinoxaline-6-carboxylic acid as a yellow solid (23.3 mg, 54%).

LC/MS (ES, m/z): [M+H]$^+$ 380.0

$^1$H-NMR (300 MHz, DMSO), 68.57 (d, J=1.2 Hz, 1H), 8.09-8.13 (m, 1H), 7.98-8.04 (m, 3H), 7.19-7.28 (m, 1H), 3.80-3.90 (m, 1H), 3.68-3.72 (m, 1H), 3.08-3.18 (m, 1H), 1.60-1.73 (m, 6H), 0.66-0.71 (t, J=7.5 Hz, 3H)

Example 143

(S)-2-(4-Fluorophenyl)-3-(methyl(1-phenylethyl)amino)quinoxaline-6-carboxylic acid

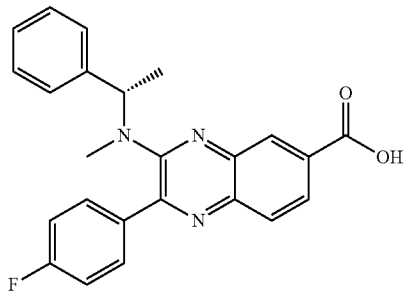 [SMILES: C[C@@H](c1ccccc1)N(C)c1nc2cc(C(=O)O)ccc2nc1-c1ccc(F)cc1]

Step 1. (S)-Methyl 2-(4-fluorophenyl)-3-(1-phenylethylamino)quinoxaline-6-carboxylate

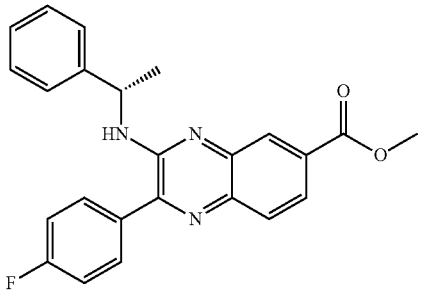 [SMILES: COC(=O)c1ccc2nc(-c3ccc(F)cc3)c(N[C@@H](C)c3ccccc3)nc2c1]

The solution of methyl 3-chloro-2-(4-fluorophenyl)quinoxaline-6-carboxylate (180 mg, 0.57 mmol) in (S)-1-phenylethanamine (2 mL) was stirred overnight at 95° C., and then purified via silica gel column chromatography (1%-2% ethyl acetate in petroleum ether) to afford (S)-methyl 2-(4-fluorophenyl)-3-(1-phenylethylamino)quinoxaline-6-carboxylate as yellow oil (100 mg, 44%).

LC/MS (ES, m/z): [M+H]$^+$ 402.0

$^1$H-NMR (300 MHz, CDCl$_3$), δ 8.27-8.28 (t, J=1.5 Hz, 1H), 7.82-7.95 (m, 4H), 7.44-7.47 (t, J=7.8 Hz, 1H), 7.30-7.38 (m, 4H), 7.21-7.24 (m, 1H), 5.45 (d, J=4.8 Hz, 1H), 3.97 (s, 3H), 1.57 (d, J=6.9 Hz, 3H)

Step 2. (S)-2-(4-Fluorophenyl)-3-(methyl(1-phenylethyl)amino)quinoxaline-6-carboxylic acid

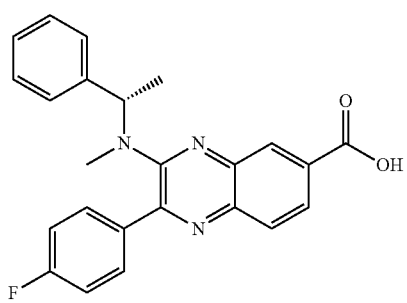 [SMILES: C[C@@H](c1ccccc1)N(C)c1nc2cc(C(=O)O)ccc2nc1-c1ccc(F)cc1]

To a solution of (S)-methyl 2-(4-fluorophenyl)-3-(1-phenylethylamino)quinoxaline-6-carboxylate (100 mg, 0.25 mmol) in tetrahydrofuran (15 mL) was added sodium hydride (30 mg, 0.75 mmol), and the reaction mixture was stirred for 10 minutes. CH₃I (106 mg, 0.75 mmol) was added, and the resulting mixture was stirred overnight. The reaction was then quenched by the addition of NH₄Cl solution (50 mL) and adjusted pH to 5 with hydrochloric acid (3N). The solids were collected by filtration to afford (S)-2-(4-fluorophenyl)-3-(methyl(1-phenylethyl)amino)quinoxaline-6-carboxylic acid as a yellow solid (47.5 mg, 48%).

LC/MS (ES, m/z): [M+H]⁺ 402.0

¹H-NMR (300 MHz, CD₃OD), δ 8.40 (d, J=1.8 Hz, 1H), 8.05-8.08 (m, 1H), 7.90-7.95 (m, 3H), 7.20-7.28 (m, 7H), 5.43-5.50 (m, 1H), 2.58 (s, 3H), 1.53 (d, J=6.9 Hz, 3H)

Example 144

2-(4-Fluorophenyl)-3-(pyrrolidin-1-yl)quinoxaline-6-carboxylic acid

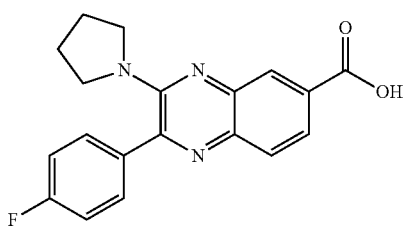 [SMILES: O=C(O)c1ccc2nc(-c3ccc(F)cc3)c(N3CCCC3)nc2c1]

Step 1. Methyl 2-(4-fluorophenyl)-3-(pyrrolidin-1-yl)quinoxaline-6-carboxylate

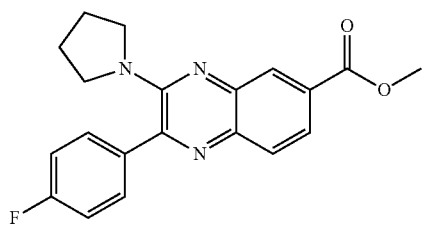 [SMILES: COC(=O)c1ccc2nc(-c3ccc(F)cc3)c(N3CCCC3)nc2c1]

To a solution of methyl 3-chloro-2-(4-fluorophenyl)quinoxaline-6-carboxylate (130 mg, 0.41 mmol) in DMSO (2 mL) was added pyrrolidine (58 mg, 0.82 mmol) and DIEA (106 mg, 0.82 mmol). After stirring 2 h at 70° C., the reaction mixture was dissolved in water (100 mL), extracted with dichloromethane (3×30 mL), dried over anhydrous magnesium sulfate and concentrated under reduced pressure to afford a residue, which was purified via silica gel column chromatography (2% dichloromethane in petroleum ether) to afford methyl 2-(4-fluorophenyl)-3-(pyrrolidin-1-yl)quinoxaline-6-carboxylate as a light yellow solid (72 mg, 50%).

LC/MS (ES, m/z): [M+H]⁺ 352.0

¹H-NMR (300 MHz, CDCl₃) δ 8.69 (s, 1H), 7.94-8.05 (m, 2H), 7.71-7.76 (m, 2H), 7.19-7.28 (m, 2H), 4.02 (s, 3H), 3.32-3.40 (m, 4H), 1.88-1.93 (m, 4H)

Step 2. 2-(4-Fluorophenyl)-3-(pyrrolidin-1-yl)quinoxaline-6-carboxylic acid

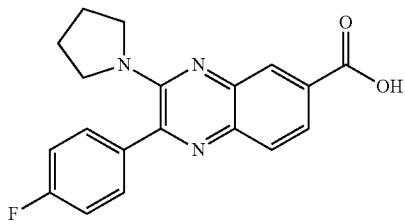 [SMILES: O=C(O)c1ccc2nc(-c3ccc(F)cc3)c(N3CCCC3)nc2c1]

To a solution of methyl 2-(4-fluorophenyl)-3-(pyrrolidin-1-yl)quinoxaline-6-carboxylate (72 mg, 0.20 mmol) in methanol (20 mL) was added sodium hydroxide (50 mg, 1.25 mmol). After stirring overnight at room temperature, the reaction mixture was concentrated under reduced pressure to afford a residue, which was dissolved in water (10 mL), adjusted to pH 6 with hydrochloric acid (3N). The product formed a precipitate and was filtered to give 2-(4-fluorophenyl)-3-(pyrrolidin-1-yl)quinoxaline-6-carboxylic acid as a light yellow solid (41.5 mg, 60%).

LC/MS (ES, m/z): [M+H]⁺ 338.0

¹H-NMR (300 MHz, DMSO) δ 8.23 (s, 1H), 7.85-7.92 (m, 2H), 7.73-7.76 (m, 2H), 7.34-7.38 (t, J=6.6 Hz, 2H), 3.23 (s, 4H), 1.80 (s, 4H)

Example 145

3-(Azetidin-1-yl)-2-(4-fluorophenyl)quinoxaline-6-carboxylic acid

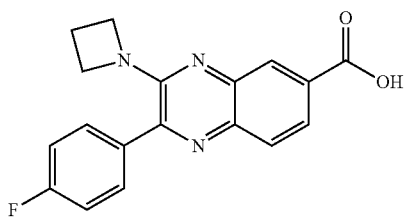 [SMILES: O=C(O)c1ccc2nc(-c3ccc(F)cc3)c(N3CCC3)nc2c1]

Step 1. Methyl 3-(azetidin-1-yl)-2-(4-fluorophenyl)quinoxaline-6-carboxylate

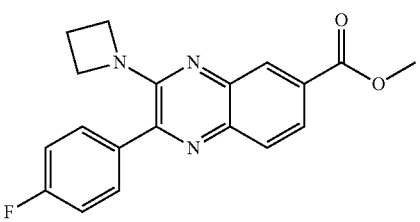 [SMILES: COC(=O)c1ccc2nc(-c3ccc(F)cc3)c(N3CCC3)nc2c1]

To a solution of methyl 3-chloro-2-(4-fluorophenyl)quinoxaline-6-carboxylate (100 mg, 0.32 mmol) in DMSO (2 mL) was added azetidine (37 mg, 0.65 mmol) and DIEA (81 mg, 0.63 mmol). After stirring for 2 hours at 70° C., the reaction mixture was dissolved in water (50 mL), extracted with dichloromethane (3×30 mL), dried over anhydrous magnesium sulfate, and concentrated under reduced pressure to afford a residue, which was purified via silica gel column chromatography (2% dichloromethane in petroleum ether) to afford methyl 3-(azetidin-1-yl)-2-(4-fluorophenyl)quinoxaline-6-carboxylate as a light yellow solid (60 mg, 56%).

LC/MS (ES, m/z): [M+H]$^+$ 338.0

$^1$H-NMR (300 MHz, DMSO) δ 8.24 (s, 1H), 7.88-7.95 (m, 2H), 7.75-7.80 (m, 2H), 7.34-7.48 (m, 2H), 3.97 (s, 3H), 3.70-3.85 (t, J=7.5 Hz, 4H), 2.13-2.23 (m, 2H)

Step 2. 3-(Azetidin-1-yl)-2-(4-fluorophenyl)quinoxaline-6-carboxylic acid

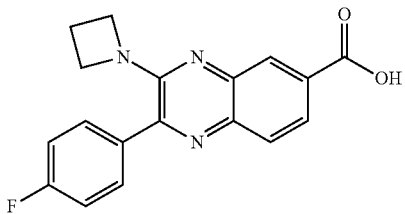 [SMILES: O=C(O)c1ccc2nc(-c3ccc(F)cc3)c(N3CCC3)nc2c1]

To a solution of methyl 3-(azetidin-1-yl)-2-(4-fluorophenyl)quinoxaline-6-carboxylate (60 mg, 0.18 mmol) in methanol (20 mL) was added sodium hydroxide (50 mg, 1.25 mmol) and water (1 mL). After stirring overnight at room temperature, the reaction mixture was concentrated under reduced pressure to afford a residue, which was dissolved in water (10 mL), adjusted to pH 6 with hydrochloric acid (3N), and the product was precipitated and filtered to give 3-(azetidin-1-yl)-2-(4-fluorophenyl)quinoxaline-6-carboxylic acid as a light yellow solid (35.3 mg, 61%).

LC/MS (ES, m/z): [M+H]$^+$ 324.0

$^1$H-NMR (300 MHz, DMSO) δ 8.24 (s, 1H), 7.88-7.95 (m, 2H), 7.75-7.80 (m, 2H), 7.34-7.50 (t, J=8.7 Hz, 2H), 3.70-3.85 (t, J=7.5 Hz, 4H), 2.13-2.23 (m, 2H)

Example 146

3-(Cyclobutyl(methyl)amino)-2-(4-fluorophenyl)quinoxaline-6-carboxylic acid

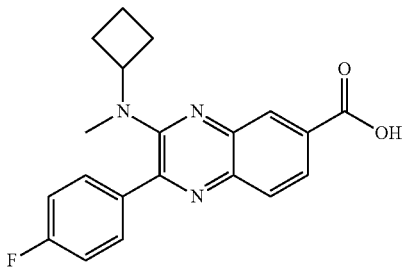

Step 1. Methyl 3-(cyclobutylamino)-2-(4-fluorophenyl)quinoxaline-6-carboxylate

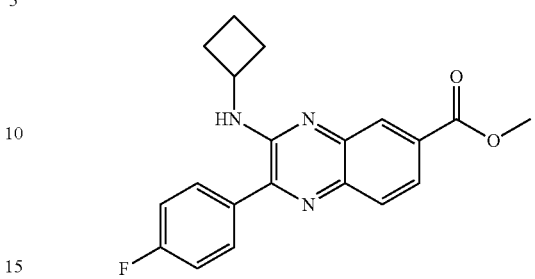

To a solution of methyl 3-chloro-2-(4-fluorophenyl)quinoxaline-6-carboxylate (100 mg, 0.32 mmol) in DMSO (1 mL) in was added cyclobutanamine (100 mg, 1.41 mmol) and DIEA (110 mg, 0.85 mmol). The resulting solution was stirred for 2 hours at 70° C., and then quenched by the addition of water (50 mL) and extracted with dichloromethane (4×20 mL). The organic layers were combined, dried over anhydrous magnesium sulfate, and concentrated in vacuo to give a residue, which was purified via silica gel column chromatography (2%-10% ethyl acetate in petroleum ether) to afford methyl 3-(cyclobutylamino)-2-(4-fluorophenyl)quinoxaline-6-carboxylate as a yellow solid (67 mg, 58%)

LC/MS (ES, m/z): [M+H]$^+$ 352.0

$^1$H-NMR (300 MHz, CDCl$_3$) δ 8.59 (s, 1H), 8.02-8.05 (m, 1H), 7.92 (d, J=8.4 Hz, 1H), 7.28-7.33 (m, 2H), 4.81-4.83 (m, 1H), 4.00 (s, 3H), 2.55-2.57 (m, 2H), 1.84-1.92 (m, 4H)

Step 2. Methyl 3-[cyclobutyl(methyl)amino]-2-(4-fluorophenyl)quinoxaline-6-carboxylate

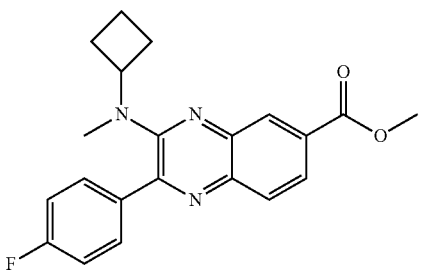 [SMILES: COC(=O)c1ccc2nc(-c3ccc(F)cc3)c(N(C)C3CCC3)nc2c1]

To a solution of methyl 3-(cyclobutylamino)-2-(4-fluorophenyl)quinoxaline-6-carboxylate (67 mg, 0.19 mmol) in tetrahydrofuran (20 mL) was added sodium hydride (30 mg, 60%) and CH$_3$I (135 mg, 0.95 mmol). The resulting solution was stirred overnight at 10° C. The reaction was then quenched by the addition of NH$_4$Cl solution (50 mL), extracted with ethyl acetate (4×20 mL), and the organic layers combined, dried over anhydrous magnesium sulfate, and concentrated in vacuo to give a residue, which was purified via silica gel column chromatography (2%-10% ethyl acetate in petroleum ether) to afford methyl 3-[cyclobutyl(methyl)amino]-2-(4-fluorophenyl)quinoxaline-6-carboxylate as a yellow solid (70 mg, crude).

LC/MS (ES, m/z): [M+H]$^+$ 366.0

Step 3. 3-(Cyclobutyl(methyl)amino)-2-(4-fluorophenyl)quinoxaline-6-carboxylic acid

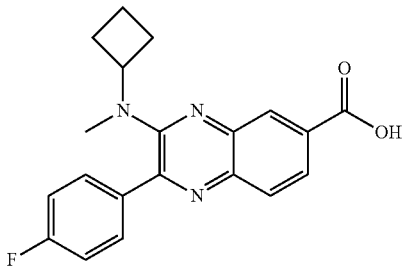 [SMILES: CN(c1nc2cc(C(=O)O)ccc2nc1-c1ccc(F)cc1)C1CCC1]

To a solution of methyl 3-(cyclobutyl(methyl)amino)-2-(4-fluorophenyl)quinoxaline-6-carboxylate (70.0 mg, crude) in MeOH (15 mL) was added sodium hydroxide (18.0 mg, 0.45 mmol) and water (0.5 mL). The resulting solution was stirred overnight at room temperature and concentrated in vacuo. The residue was dissolved in water (10 mL) and adjusted to pH 3 with hydrochloric acid (1N). The solids were collected by filtration to afford 3-(cyclobutyl(methyl)amino)-2-(4-fluorophenyl)quinoxaline-6-carboxylic acid as a yellow solid (30 mg).

LC/MS (ES, m/z): [M+H]$^+$ 352.0

$^1$H-NMR (300 MHz, DMSO) δ 8.24 (d, J=1.8 Hz, 1H), 7.99-7.89 (m, 4H), 7.41-7.39 (t, J=9.0 Hz, 2H), 4.19-4.08 (m, 1H), 2.68 (s, 3H), 2.14-2.04 (m, 4H), 1.62-1.56 (m, 2H)

Example 147

2-(2,4-Difluorophenyl)-3-[methyl(propan-2-yl)amino]quinoxaline-6-carboxylic acid

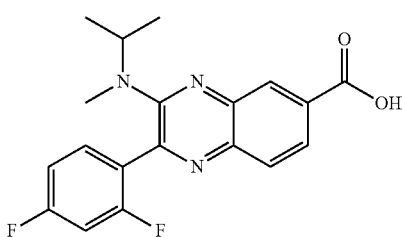 [SMILES: CC(C)N(C)c1nc2cc(C(=O)O)ccc2nc1-c1ccc(F)cc1F]

Step 1. Methyl 2-(2,4-difluorophenyl)-3-[methyl(propan-2-yl)amino]quinoxaline-6-carboxylate

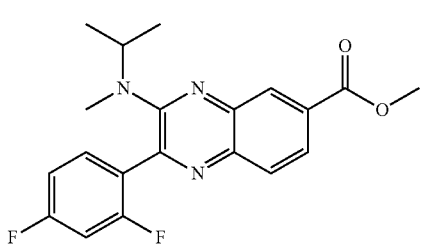 [SMILES: COC(=O)c1ccc2nc(-c3ccc(F)cc3F)c(N(C)C(C)C)nc2c1]

To a solution of methyl 3-[methyl(propan-2-yl)amino]-2-[(trifluoromethane)sulfonyloxy]quinoxaline-6-carboxylate (200 mg, 0.49 mmol) in dioxane (5.0 mL) and water (3 drops) was added (2,4-difluorophenyl)boronic acid (233 mg, 1.48 mmol), Pd(PPh$_3$)$_4$ (28.3 mg, 0.02 mmol), and K$_3$PO$_4$ (310 mg, 1.46 mmol), and the reaction mixture was stirred for 40 min at 90° C. under an atmosphere of nitrogen. The reaction mixture was concentrated in vacuo to give a residue, which was purified via silica gel column chromatography (2% ethyl acetate in petroleum ether) to afford methyl 2-(2,4-difluorophenyl)-3-[methyl(propan-2-yl)amino]quinoxaline-6-carboxylate as a light yellow solid (150 mg, 82%).

LC/MS (ES, m/z): [M+H]$^+$ 372.0

$^1$H-NMR (300 MHz, CDCl$_3$) δ 8.54 (d, J=1.5 Hz, 1H), 8.04-8.07 (m, 1H), 7.95 (d, J=8.4 Hz, 1H), 7.66-7.73 (m, 1H), 7.04-7.11 (m, 1H), 6.93-7.00 (m, 1H), 4.29-4.36 (m, 1H), 4.01 (s, 3H), 2.72 (s, 3H), 1.09 (d, J=6.6 Hz, 6H)

Step 2. 2-(2,4-Difluorophenyl)-3-[methyl(propan-2-yl)amino]quinoxaline-6-carboxylic acid

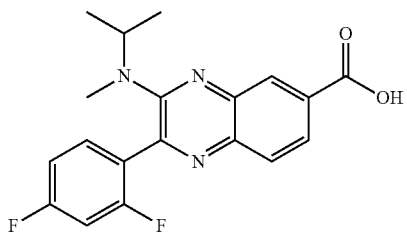

To a solution of methyl 2-(2,4-difluorophenyl)-3-[methyl(propan-2-yl)amino]quinoxaline-6-carboxylate (150 mg, 0.40 mmol) in methanol (25 mL) and water (1 mL) was added sodium hydroxide (64.7 mg, 1.62 mmol), and the reaction mixture was stirred overnight at room temperature. The reaction mixture was concentrated in vacuo, and then dissolved in water (30 mL), and adjusted to pH 4 with hydrochloric acid (3N) to give the precipitate, which was collected by filtration to afford 2-(2,4-difluorophenyl)-3-[methyl(propan-2-yl)amino]quinoxaline-6-carboxylic acid as a light yellow solid (100 mg, 69%).

LC/MS (ES, m/z): [M+H]$^+$ 358.0

$^1$H-NMR (300 MHz, DMSO) δ 13.25 (s, 1H), 8.27 (s, 1H), 7.92-7.97 (m, 2H), 7.79-7.87 (m, 1H), 7.41-7.48 (m, 1H), 7.28-7.34 (m, 1H), 4.19-4.28 (m, 1H), 2.64 (s, 3H), 1.01 (d, J=6.6 Hz, 6H)

Example 148

(S)-2-(3,4-Difluorophenyl)-3-(2-methylpyrrolidin-1-yl)quinoxaline-6-carboxylic acid

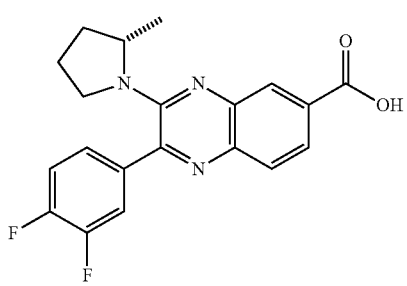 [SMILES: C[C@H]1CCCN1c1nc2cc(C(=O)O)ccc2nc1-c1ccc(F)c(F)c1]

Step 1. (S)-Methyl 3-(2-methylpyrrolidin-1-yl)-2-(trifluoromethylsulfonyloxy)quinoxaline-6-carboxylate

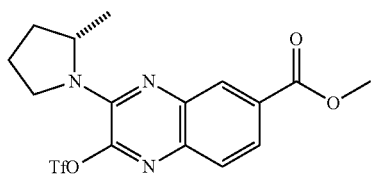 [SMILES: COC(=O)c1ccc2nc(OS(=O)(=O)C(F)(F)F)c(N3CCC[C@@H]3C)nc2c1]

To a solution of methyl 3-((S)-2-methylpyrrolidin-1-yl)-2-oxo-1,2,4a,8a-tetrahydroquinoxaline-6-carboxylate (140.0 mg, 0.48 mmol) in dichloromethane (50 mL) was added pyridine (152 mg, 1.92 mmol) and Tf$_2$O (271 mg, 0.96 mmol), and the reaction mixture was stirred overnight under an atmosphere of nitrogen at room temperature. The reaction mixture was then quenched with water (50 mL), extracted with dichloromethane (3×15 mL), and the organic layers combined, dried over anhydrous magnesium sulfate, and concentrated in vacuo to afford (S)-methyl 3-(2-methylpyrrolidin-1-yl)-2-(trifluoromethylsulfonyloxy)quinoxaline-6-carboxylate as red oil (195 mg, crude), which was used in the next step directly.

Step 2. (S)-Methyl 2-(3,4-difluorophenyl)-3-(2-methylpyrrolidin-1-yl)quinoxaline-6-carboxylate

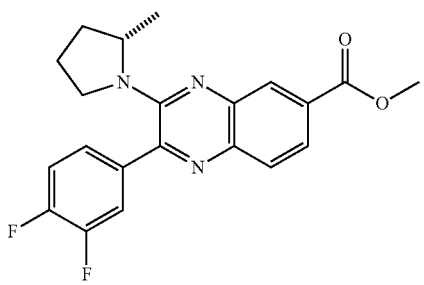 [SMILES: COC(=O)c1ccc2nc(-c3ccc(F)c(F)c3)c(N3CCC[C@@H]3C)nc2c1]

To a solution of (S)-methyl 3-(2-methylpyrrolidin-1-yl)-2-(trifluoromethylsulfonyloxy)quinoxaline-6-carboxylate (195 mg, crude) in dioxane (3 mL) was added 3,4-difluorophenylboronic acid (130 mg, 0.80 mmol), K$_3$PO$_4$ (180 mg, 0.8 mmol), Pd(PPh$_3$)$_4$ (28 mg, 0.024 mmol) and water (5 drops) under a nitrogen atmosphere. After stirring 1 h at 90° C., the reaction mixture was dissolved in water (100 mL), extracted with dichloromethane (3×30 mL), dried over anhydrous magnesium sulfate, and concentrated under reduced pressure to afford a residue, which was purified via silica gel column chromatography (2% ethyl acetate in petroleum ether) to afford (S)-methyl 2-(3,4-difluorophenyl)-3-(2-methylpyrrolidin-1-yl)quinoxaline-6-carboxylate as a light yellow solid (86.0 mg).

LC/MS (ES, m/z): [M+H]$^+$ 384.0

$^1$H-NMR (300 MHz, CDCl$_3$) δ 8.27 (d, J=1.5 Hz, 1H), 7.92-8.28 (m, 2H), 7.76-7.82 (m, 1H), 7.56-7.62 (m, 2H), 4.21-4.28 (m, 1H), 3.90 (s, 3H), 2.96-3.01 (m, 2H), 2.10-2.20 (m, 1H), 1.70-1.79 (m, 1H), 1.55-1.60 (m, 2H), 1.33 (d, J=6.0 Hz, 3H)

Step 3. (S)-2-(3,4-Difluorophenyl)-3-(2-methylpyrrolidin-1-yl)quinoxaline-6-carboxylic acid

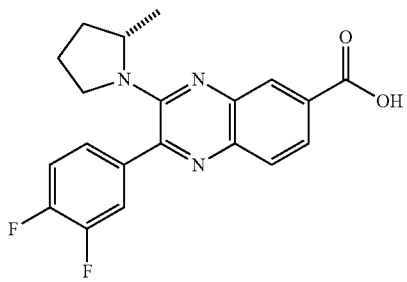 [SMILES: C[C@H]1CCCN1c1nc2cc(C(=O)O)ccc2nc1-c1ccc(F)c(F)c1]

To a solution of (S)-methyl 2-(3,4-difluorophenyl)-3-(2-methylpyrrolidin-1-yl)quinoxaline-6-carboxylate (80 mg, 0.23 mmol) in methanol (10 mL) was added sodium hydroxide (40 mg, 1 mmol). After stirring overnight at room temperature, the reaction mixture was concentrated under reduced pressure to afford a residue, which was dissolved in water (10 mL), adjusted the pH to 6 with 3N HCl, and filtered to give (S)-2-(3,4-difluorophenyl)-3-(2-methylpyrrolidin-1-yl)quinoxaline-6-carboxylic acid as a light yellow solid (44.5 mg, 58%).

LC/MS (ES, m/z): [M+H]$^+$ 370.0

$^1$H-NMR (300 MHz, DMSO) δ 8.25 (d, J=1.5 Hz, 1H), 7.91-7.95 (m, 2H), 7.80-7.90 (m, 1H), 7.58-7.61 (m, 2H), 4.21-4.28 (m, 1H), 2.93-3.04 (m, 2H), 2.05-2.13 (m, 1H), 1.70-1.79 (m, 1H), 1.55-1.60 (m, 2H), 1.32 (d, J=6.0 Hz, 3H)

Example 149

2-(4-Acetamidophenyl)-3-[methyl(propan-2-yl)amino]quinoxaline-6-carboxylic acid

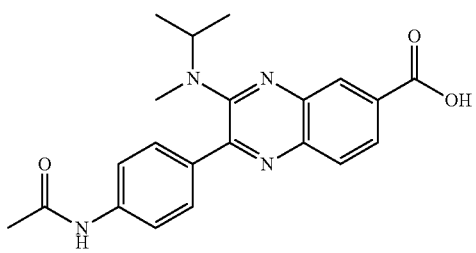 [SMILES: CC(=O)Nc1ccc(-c2nc3ccc(C(=O)O)cc3nc2N(C)C(C)C)cc1]

Step 1. N-(4-Bromophenyl)acetamide

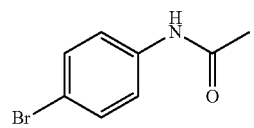

A solution of 4-bromoaniline (10 g, 58.13 mmol) in acetic anhydride (50 mL) was stirred for 20 minutes at room temperature, and then collected by filtration to give N-(4-bromophenyl)acetamide (12 g, 96%) as a white solid.

¹H-NMR (300 MHz, CDCl₃) δ 7.42-7.48 (m, 4H), 2.20 (s, 3H)

Step 2. N-(4-(4,4,5,5-Tetramethyl-1,3,2-dioxaborolan-2-yl)phenyl)acetamide

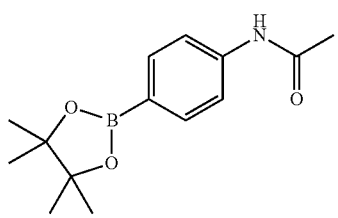 [SMILES: CC(=O)Nc1ccc(B2OC(C)(C)C(C)(C)O2)cc1]

To a solution of N-(4-bromophenyl)acetamide (5 g, 23.36 mmol) in dioxane (50 mL) was added 4,4,4',4',5,5,5',5'-octamethyl-2,2'-bi(1,3,2-dioxaborolane) (7.13 g, 28.08 mmol), KOAc (4.6 g, 46.87 mmol) and Pd(dppf)Cl₂ (1.5 g, 2.05 mmol), and the reaction mixture was stirred overnight under an atmosphere of nitrogen at 100° C. in an oil bath. The resulting mixture was concentrated in vacuo, diluted with water (300 mL), and extracted with dichloromethane (3×50 mL), and the organic layers combined, dried over anhydrous sodium sulfate, and concentrated in vacuo to give a residue, which was purified via silica gel column chromatography (14% ethyl acetate in petroleum ether) to give N-(4-(4,4,5,5-tetramethyl-1,3,2-dioxaborolan-2-yl)phenyl)acetamide (6 g, 98%) as a white solid.

LC/MS (ES, m/z): [M+H]⁺ 262.0

¹H-NMR (300 MHz, CDCl₃) δ 7.77 (d, J=8.4 Hz, 2H), 7.52 (d, J=8.1 Hz, 2H), 7.23 (d, J=15.6 Hz, 1H), 2.20 (s, 3H), 1.35 (s, 12H)

Step 3. Methyl 2-(4-acetamidophenyl)-3-[methyl(propan-2-yl)amino]quinoxaline-6-carboxylate

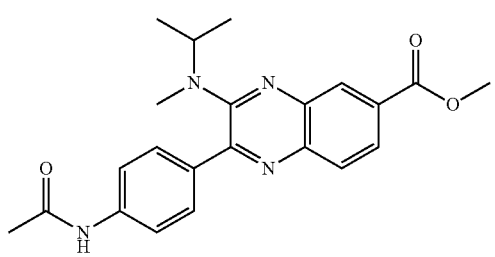 [SMILES: COC(=O)c1ccc2nc(-c3ccc(NC(C)=O)cc3)c(N(C)C(C)C)nc2c1]

To a solution of methyl 3-[methyl(propan-2-yl)amino]-2-[(trifluoromethane)sulfonyloxy]quinoxaline-6-carboxylate (150 mg, 0.37 mmol) in dioxane (5.0 mL) and water (3 drops) was added N-(4-(4,4,5,5-tetramethyl-1,3,2-dioxaborolan-2-yl)phenyl)acetamide (293 mg, 1.12 mmol), Pd(PPh₃)₄ (21 mg, 0.02 mmol), and K₃PO₄ (165 mg, 0.78 mmol), and the reaction mixture was stirred for 1 hour at 90° C. under an atmosphere of nitrogen. The resulting mixture was concentrated in vacuo to give a residue, which was purified via silica gel column chromatography (9% ethyl acetate in petroleum ether) to give methyl 2-(4-acetamidophenyl)-3-[methyl(propan-2-yl)amino]quinoxaline-6-carboxylate as a yellow solid (110 mg, 76%).

LC/MS (ES, m/z): [M+H]⁺ 393.0

¹H-NMR (300 MHz, DMSO) δ 10.20 (s, 1H), 8.25 (d, J=1.2 Hz, 1H), 7.94 (s, 2H), 7.81 (d, J=8.7 Hz, 2H), 7.72 (d, J=8.7 Hz, 2H), 4.21-4.26 (m, 1H), 3.92 (s, 3H), 2.68 (s, 3H), 2.09 (s, 3H), 1.04 (d, J=6.0 Hz, 6H)

Step 4. 2-(4-Acetamidophenyl)-3-[methyl(propan-2-yl)amino]quinoxaline-6-carboxylic acid

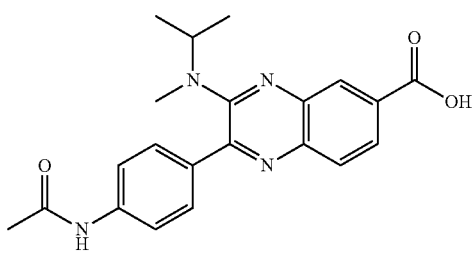 [SMILES: CC(=O)Nc1ccc(-c2nc3ccc(C(=O)O)cc3nc2N(C)C(C)C)cc1]

To a solution of methyl 2-(4-acetamidophenyl)-3-[methyl(propan-2-yl)amino]quinoxaline-6-carboxylate (110 mg, 0.28 mmol) in methanol (30 mL) and water (1 mL) was added sodium hydroxide (45 mg, 1.12 mmol), and the reaction mixture was stirred overnight at room temperature. The resulting mixture was concentrated in vacuo, dissolved in water (50 ml), adjusted to pH 6 with HCl (1N), and collected by filtration to give 2-(4-acetamidophenyl)-3-[methyl(propan-2-yl)amino]quinoxaline-6-carboxylic acid as a yellow solid (70 mg, 66%).

LC/MS (ES, m/z): [M+H]⁺ 379.0

¹H-NMR (300 MHz, DMSO) δ 10.18 (s, 1H), 8.24 (s, 1H), 7.96 (s, 2H), 7.92 (d, J=8.1 Hz, 2H), 7.81 (d, J=8.7 Hz, 2H), 7.73 (d, J=8.7 Hz, 2H), 4.16-4.25 (m, 1H), 2.68 (d, J=6.0 Hz, 3H), 2.09 (s, 3H), 1.03 (d, J=6.6 Hz, 6H)

Example 150

(R)-2-(4-Fluorophenyl)-3-(2-methylpyrrolidin-1-yl)quinoxaline-6-carboxylic acid

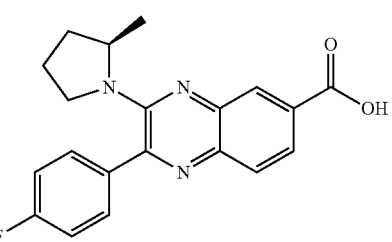

Step 1. (R)-Methyl 2-(4-fluorophenyl)-3-(2-methylpyrrolidin-1-yl)quinoxaline-6-carboxylate

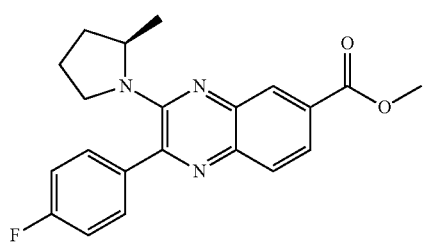 [SMILES: COC(=O)c1ccc2nc(-c3ccc(F)cc3)c(N3CCC[C@H]3C)nc2c1]

To a solution of methyl 3-chloro-2-(4-fluorophenyl)quinoxaline-6-carboxylate (150 mg, 0.47 mmol) in DMSO (2 mL), was added (R)-2-methylpyrrolidine hydrochloride (61 mg, 0.50 mmol) and DIEA (92 mg, 0.71 mmol). After stirring overnight at 70° C., the reaction mixture was dissolved in water (100 mL), extracted with dichloromethane (3×30 mL), dried over anhydrous magnesium sulfate, and concentrated under reduced pressure to afford a residue, which was purified via silica gel column chromatography (2% ethyl acetate in petroleum ether) to afford (R)-methyl 2-(4-fluorophenyl)-3-(2-methylpyrrolidin-1-yl)quinoxaline-6-carboxylate as a light yellow solid (95 mg, 55%).

LC/MS (ES, m/z): [M+H]⁺ 366.0

¹H-NMR (300 MHz, CDCl₃) δ 8.61 (s, 1H), 7.95-8.06 (m, 2H), 7.77-7.82 (m, 2H), 7.18-7.24 (t, J=8.4 Hz, 2H), 4.04-4.47 (m, 1H), 4.00 (s, 3H), 3.11-3.20 (m, 1H), 2.93-2.99 (m, 1H), 2.19-2.23 (m, 1H), 1.79-1.85 (m, 1H), 1.55-1.69 (m, 2H), 1.38 (d, J=6.0 Hz, 3H)

Step 2. (R)-2-(4-Fluorophenyl)-3-(2-methylpyrrolidin-1-yl)quinoxaline-6-carboxylic acid

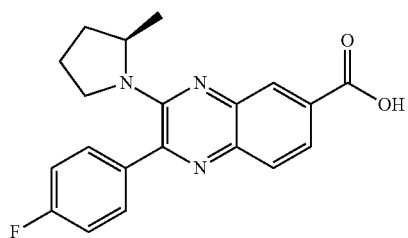 [SMILES: C[C@@H]1CCCN1c1nc2cc(C(=O)O)ccc2nc1-c1ccc(F)cc1]

To a solution of (R)-methyl 2-(4-fluorophenyl)-3-(2-methylpyrrolidin-1-yl)quinoxaline-6-carboxylate (95 mg, 0.26 mmol) in methanol (50 mL) was added sodium hydroxide (95 mg, 2.38 mmol) and water (2 mL). After stirring overnight at room temperature, the reaction mixture was concentrated under reduced pressure to afford a residue, which was dissolved in water (10 mL), adjusted to pH 6 with HCl (3N), and filtered to give (R)-2-(4-fluorophenyl)-3-(2-methylpyrrolidin-1-yl)quinoxaline-6-carboxylic acid as a light yellow solid (29.2 mg, 32%).

LC/MS (ES, m/z): [M+H]⁺ 352.0

¹H-NMR (300 MHz, DMSO) δ 8.24 (s, 1H), 7.90 (s, 2H), 7.77-7.82 (m, 2H), 7.34-7.39 (t, J=9.0 Hz, 2H), 4.20-4.25 (m, 1H), 2.94-3.03 (m, 2H), 2.13-2.20 (m, 1H), 1.70-1.80 (m, 1H), 1.49-1.54 (m, 2H), 1.31 (d, J=6.0 Hz, 3H)

The following compounds can generally be made using the methods known in the art and described above. It is expected that these compounds when made will have activity similar to those that have been made in the examples above.

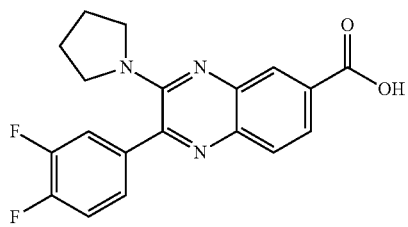

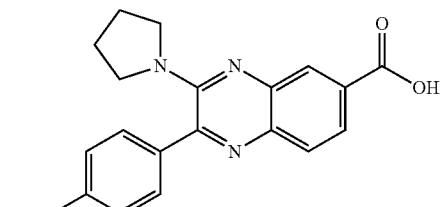

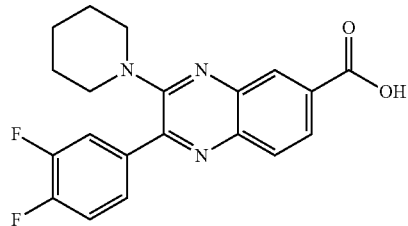

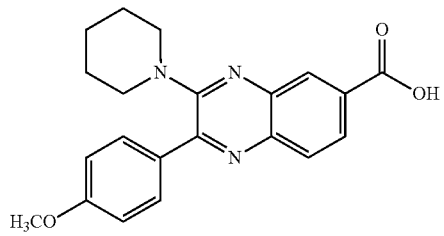

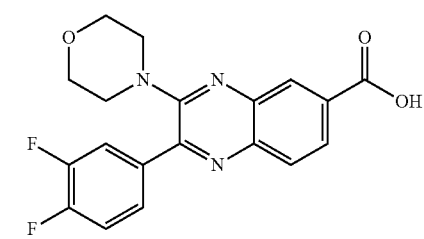

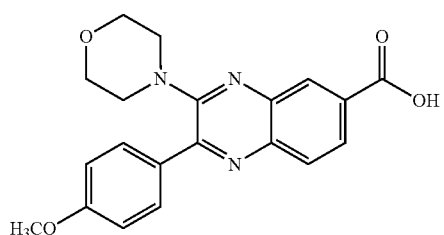

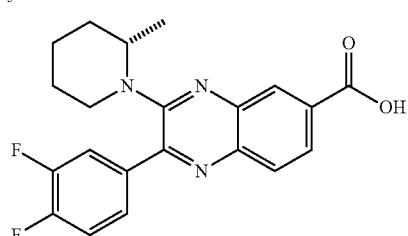

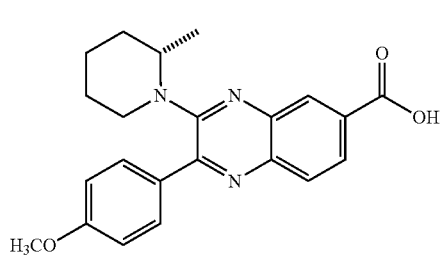

283
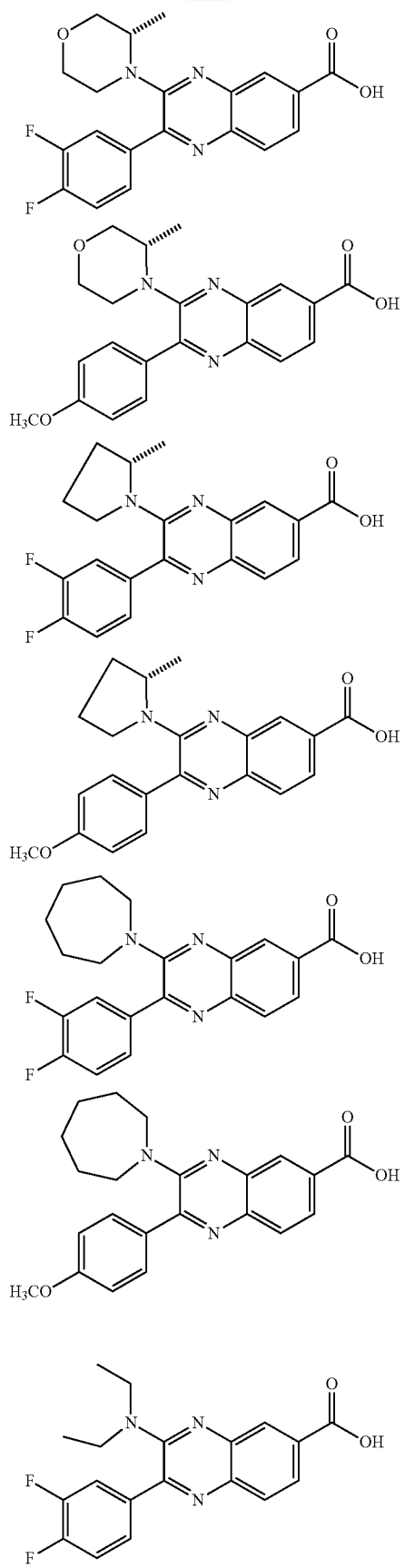
284
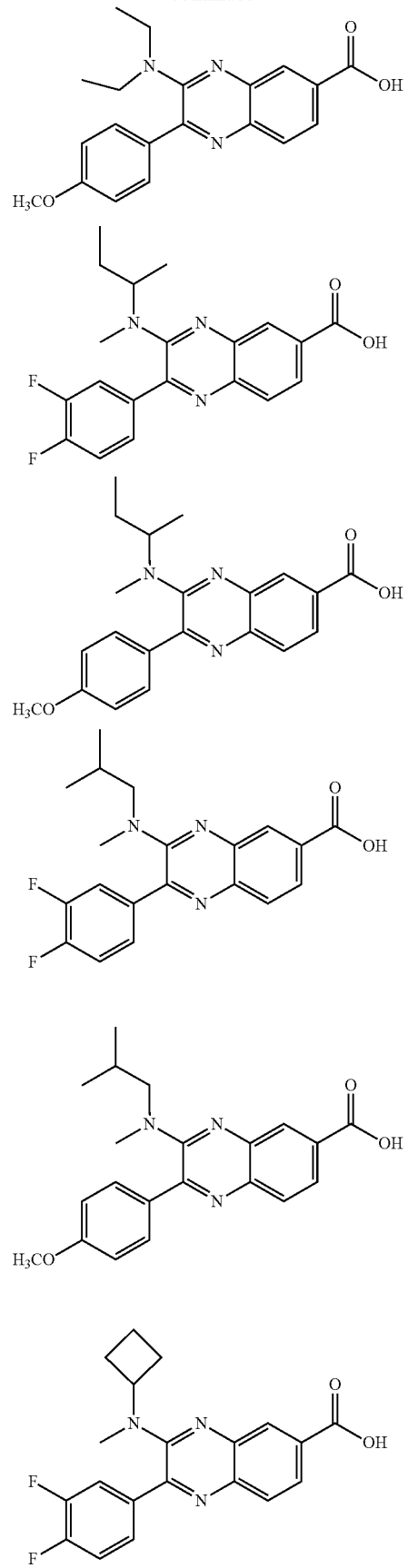

285
-continued
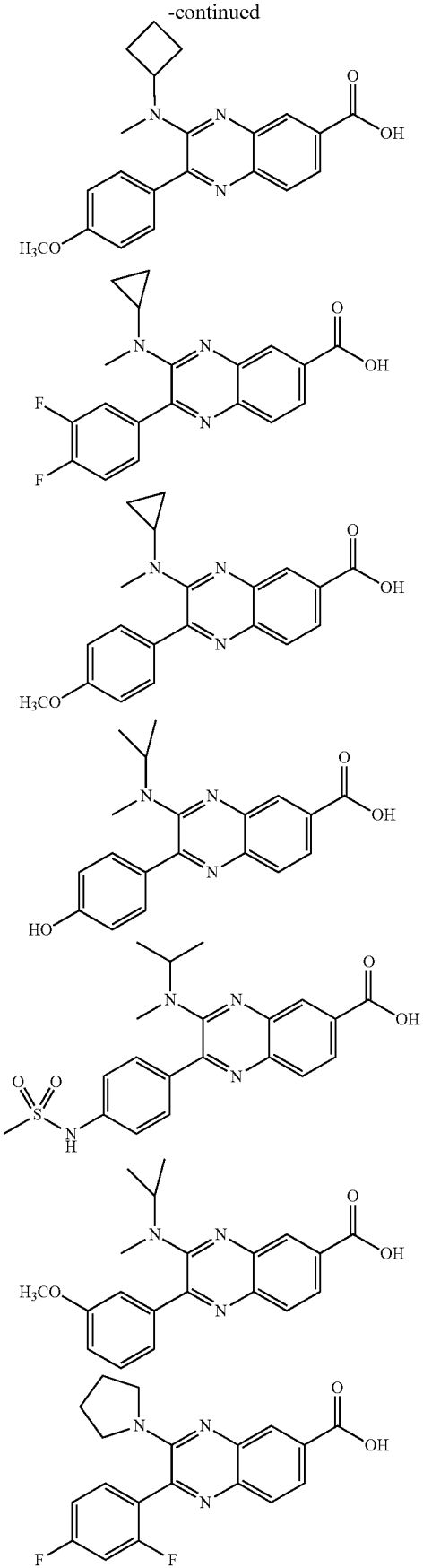
286
-continued
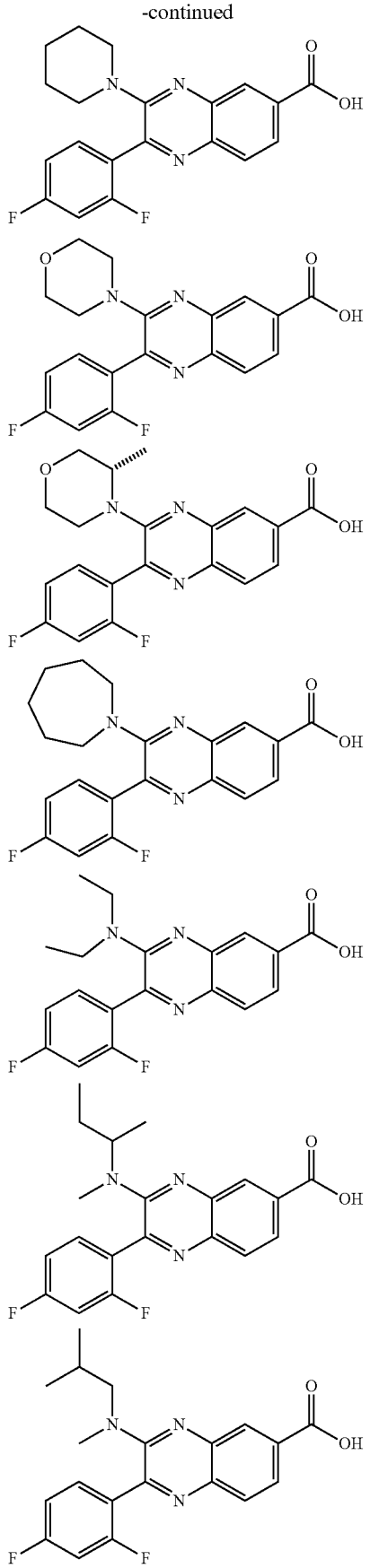

287
-continued
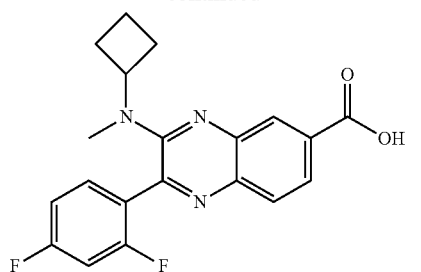
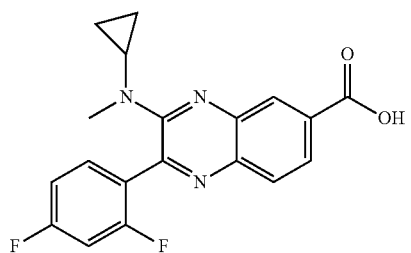
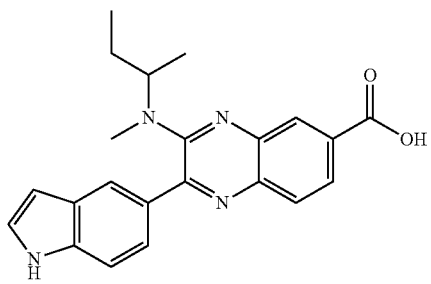
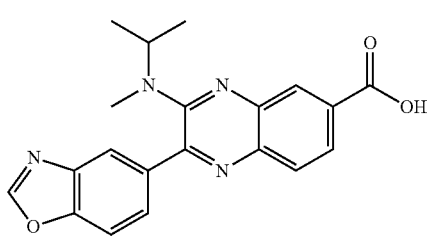
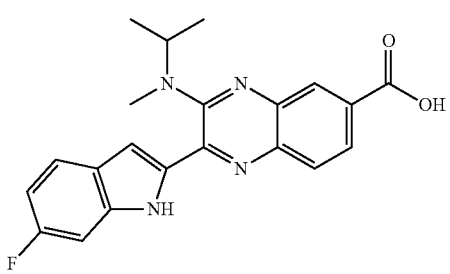
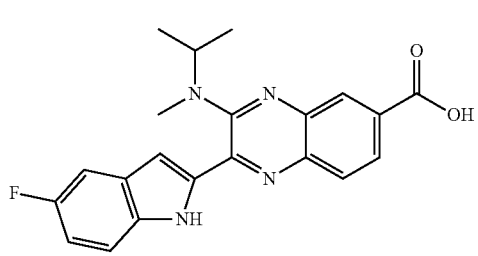
288
-continued
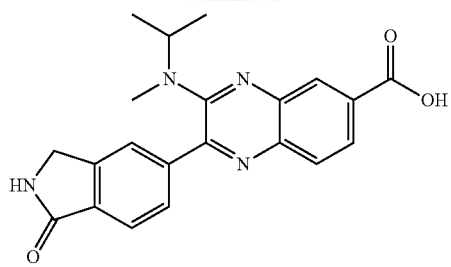
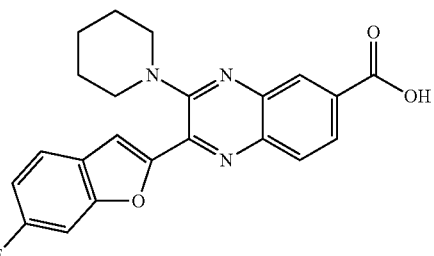
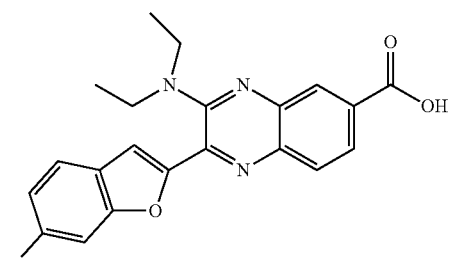
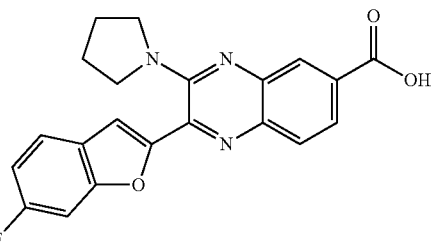
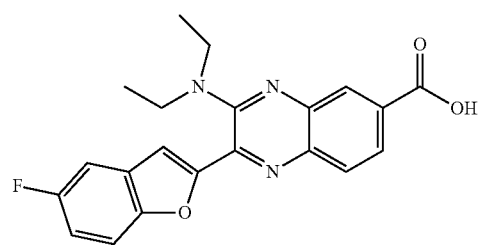
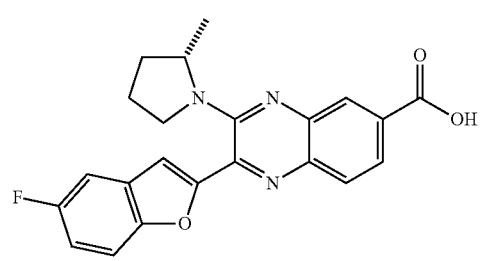

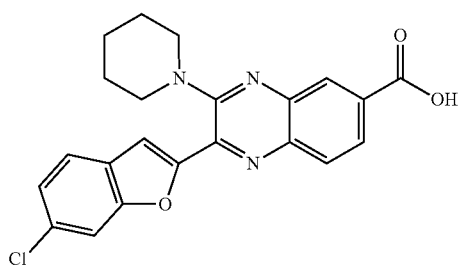
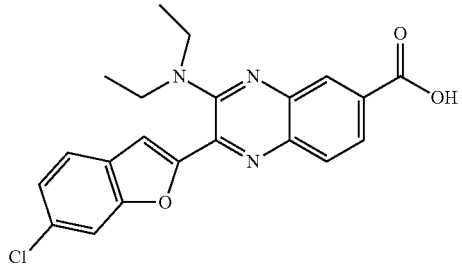
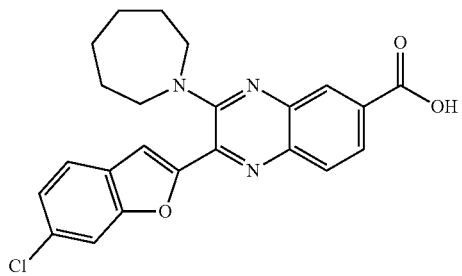
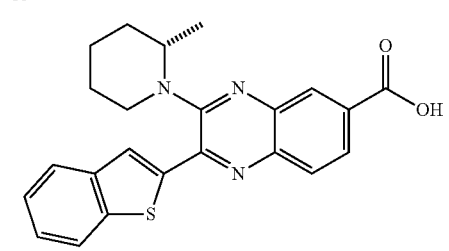
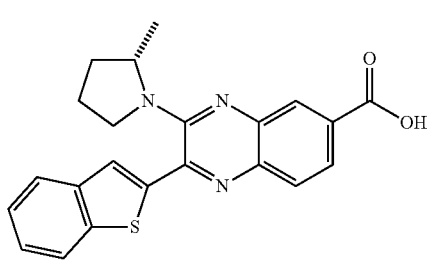
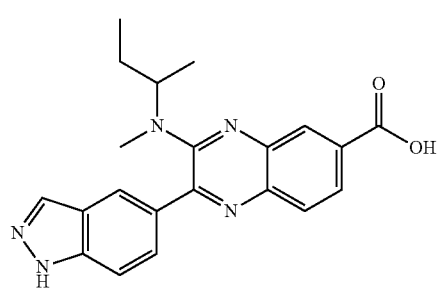
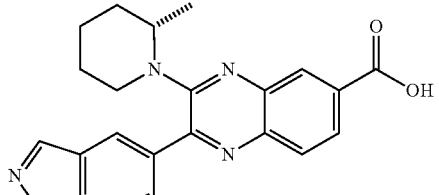
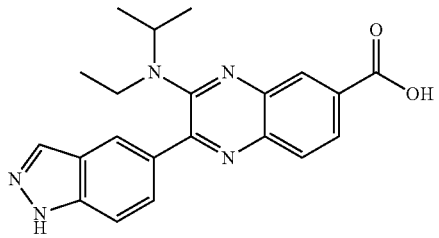
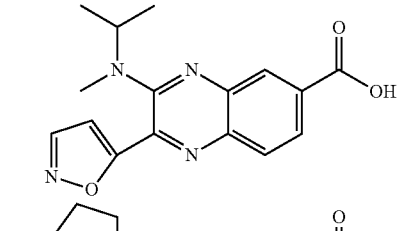
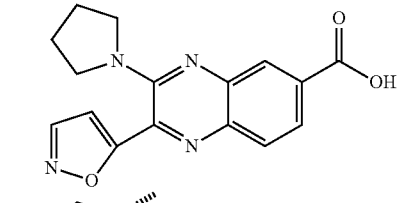
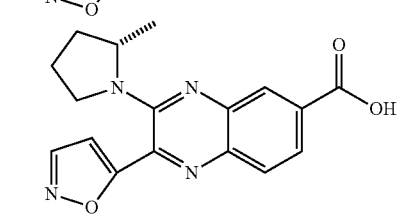
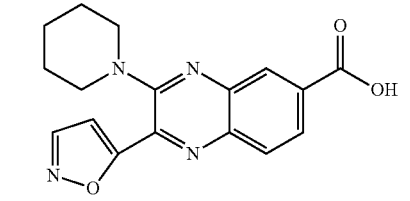
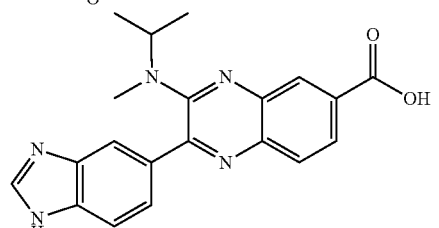
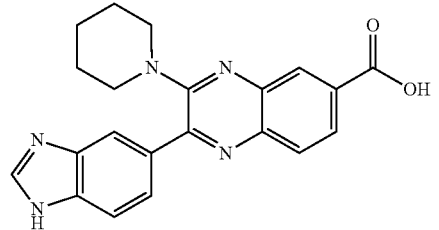

291
-continued
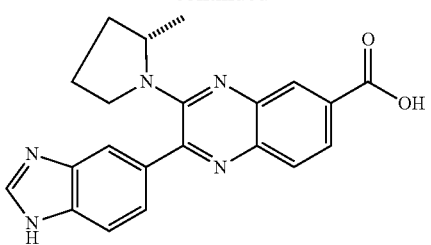
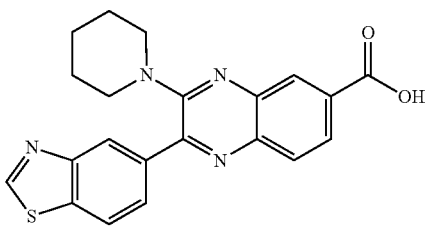
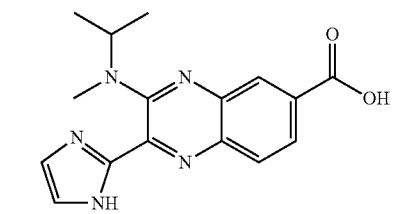
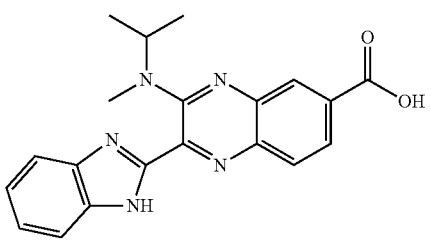
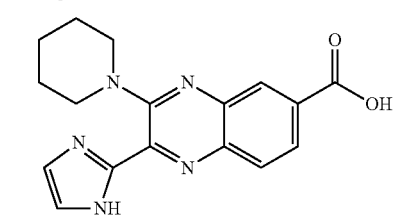
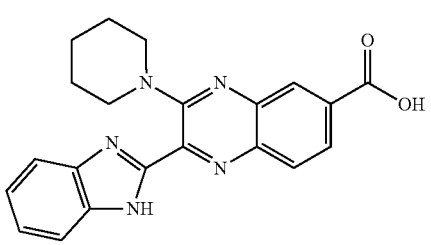
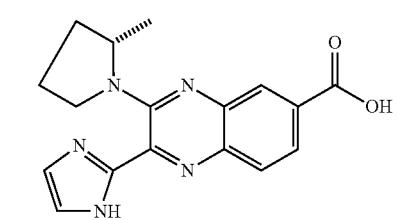
292
-continued
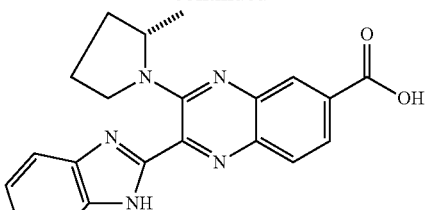
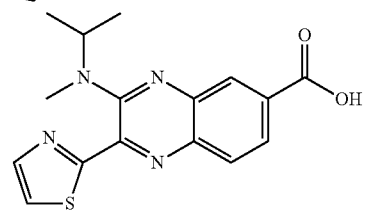
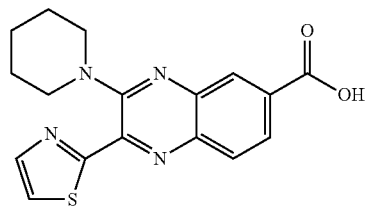
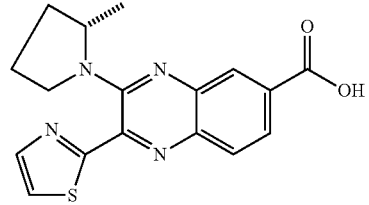
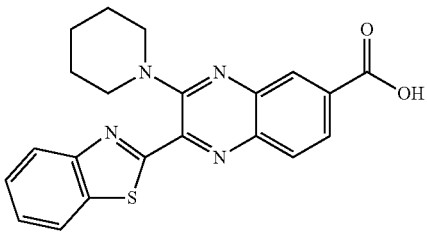
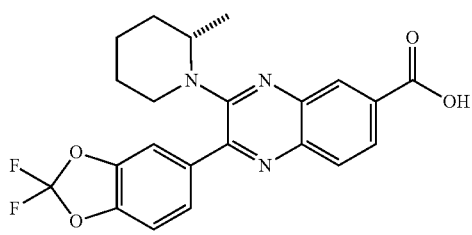
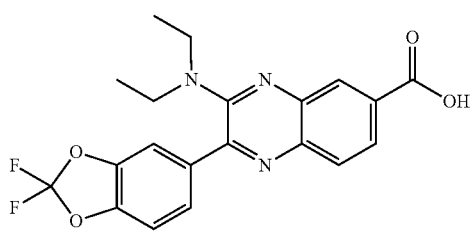

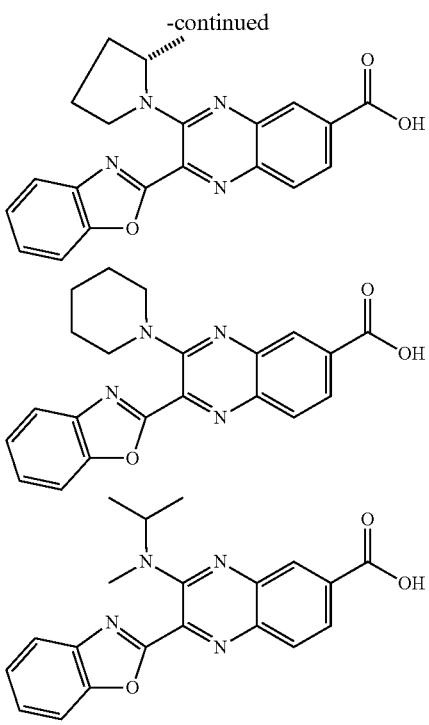

The activity of the compounds in Examples 1-150 as PASK modulators is illustrated in the following assays. The other compounds listed above, which have not yet been made and/or tested, are predicted to have activity in these assays as well.

Biochemical Assay for hPASK Activity

PASK ATP Radiochemical Assay

Purified PASK (UniProt #Q96RG2; human recombinant N-terminal GST tagged construct, residues 879-1323) from insect cells (final concentration 5 nM) is added to freshly prepared Base Reaction Buffer containing 20 mM HEPES (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO and Myelin Basic Protein (20 µM final). Test compounds in DMSO are then added and the mixture, followed by delivery of $^{33}$P-ATP (specific activity 0.01 µCi/µl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results for this assay are shown below in Table 1.

TABLE 1

| Example # | $IC_{50}$ Kinase Domain<br>+ indicates ≤10 µm<br>− indicates >10 µm |
|---|---|
| 14 | + |
| 15 | + |
| 18 | + |
| 19 | + |
| 21 | + |
| 23 | + |
| 44 | + |
| 45 | + |
| 48 | + |
| 51 | + |
| 52 | + |
| 55 | + |
| 57 | + |
| 61 | + |
| 63 | + |
| 64 | + |
| 66 | + |
| 68 | + |
| 69 | + |
| 73 | + |
| 74 | + |
| 75 | + |
| 76 | + |
| 77 | + |
| 81 | + |
| 85 | + |
| 86 | + |
| 87 | + |
| 88 | + |
| 89 | + |
| 93 | + |
| 104 | + |
| 105 | + |
| 106 | + |
| 107 | + |
| 108 | + |
| 111 | + |
| 112 | + |
| 113 | + |
| 115 | + |
| 116 | + |
| 120 | + |
| 121 | + |
| 135 | + |
| 140 | + |
| 146 | + |
| 147 | + |
| 148 | + |
| 149 | + |
| 150 | + |

PAS Kinase FRET Assay

The aim of the FRET assay is to determine the inhibition potential of test compounds on targeted kinase. This assay platform provides a homogenous screening method for measuring kinase activity by quantitating the amount of phospho-substrate in solution following a kinase reaction.

In the presence of kinase and ATP, the Ulight-peptide is phosphorylated and captured by an anti-phospho-substrate antibody, which brings the Eu chelate donor and Ulight acceptor dyes into close proximity. Upon excitation at 340 nm, the Eu chelate transfers its energy to the Ulight dye, resulting in a fluorescent light emission at 665 nm.

Titration of kinase at 1 mM ATP was achieved via the following protocol. After making serial three-fold dilutions of PASK (Invitrogen) in reaction buffer across the plate; 5 µl of kinase dilution and 5 µl substrate/ATP mix were added to the wells of the white Optiplate-384 (PerkinElmer). The contents of the plate were incubated at RT for 1 h. The reaction was stopped by adding 5 µl of stop solution to each test well followed by mixing and incubation at RT for 10 minutes. 5 µl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$.

Titration of ATP at the $EC_{50}$ concentration of kinase to determine ATP Km,app. was performed using the following method. After making serial dilutions of ATP (Invitrogen), 5

µl of ATP dilution and 5 µl substrate/kinase mix were added to the wells of the white Optiplate-384 (PerkinElmer). The contents of the plate were and incubated at RT for 1 h. The reaction was stopped by adding 5 µl of stop solution to each test well followed by mixing and incubation at RT for 10 minutes. 5 of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$ as the ATP Km,app.

Compound screening was done via the following method. 10 mM stock solution of test compound in DMSO was prepared by dissolving test compound in DMSO at RT for 1 hour, and then sonicating at 100% output for 8 minutes. If compound is not soluble under this condition, it was diluted to 3 mM. Kinase reaction buffer was prepared containing 10 mM $MgCl_2$, 50 mM HEPES, 1 mM EGTA, 0.01% TWEEN-20, 2 mM DTT. Serial dilutions of the test compounds were prepared at 4× final assay concentrations using Freedom EVO200® dispensing system as follows; $12 \times 10^{-5}$ M, $4 \times 10^{-5}$ M, $1.33 \times 10^{-5}$ M, $4.44 \times 10^{-6}$ M, $1.48 \times 10^{-6}$ M, $4.92 \times 10^{-7}$ M, $1.65 \times 10^{-7}$ M, $5.48 \times 10^{-7}$ M, $1.82 \times 10^{-8}$ M, $6.09 \times 10^{-9}$ M, $2.03 \times 10^{-9}$ M. Test compounds (2.5 µl at 4× the final assay concentration) was added to wells using Freedom EVO200® dispensing system. As a positive control, 2.5 µl of positive compound was added to assay wells, and 2.5 µl of DMSO to assay wells as vehicle control. Kinase solution was prepared in reaction buffer at 2× final assay concentration. Kinase solution (5 µl) was added to each well of the assay plate. The substrate and ATP solution was prepared in kinase reaction buffer at 4× final assay concentration. The kinase reaction was started by adding 2.5 µl of substrate+ATP mix solution to each well of the assay plate. The plate is mixed on a plate shaker; then covered and allowed to react for 2 hours in the dark at 25° C. without shaking. The reaction was stopped by adding 5 µl of stop solution to each test well followed by mixing and incubation at RT for 10 minutes in the dark. 5 µl of detection mix (detection antibody diluted in detection buffer) was added; the contents of the plate were mixed and then incubated in the dark for 1 hour at RT. The signal was recorded at TR-FRET mode (665 nm/615 nm).

Results are shown below in Table 2.

TABLE 2

| Example # | $IC_{50}$ Kinase Domain<br>+ indicates ≤10 µm<br>− indicates >10 µm |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | − |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 29 | + |
| 30 | + |
| 31 | + |
| 27 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | − |
| 96 | + |
| 97 | + |
| 98 | + |
| 99 | + |

TABLE 2-continued

| Example # | IC₅₀ Kinase Domain<br>+ indicates ≤10 μm<br>− indicates >10 μm |
|---|---|
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | + |
| 122 | − |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | + |
| 150 | + |

Pharmacokinetics of a PASK Inhibitor

The in vivo pharmacokinetics of Examples 14, 15, 18, 105 were evaluated in the Sprague Dawley rat. The test compounds were formulated in polyethylene glycol and beta cyclodextrin in water for administration at 1 mg/kg for Example 105, and at 3 mg/kg for Example 14, 15, and 18 for intravenous administration via the tail vein and 10 mg/kg for oral administration by gavage. Blood samples were collected at 0.083, 0.25, 0.5, 1, 2, 4, 6, 8, and 24 hours and the samples were analyzed for test compounds content using LC/MS/MS. The data was submitted to pharmacokinetic analysis using WinNonLin software and the observed and calculated pharmacokinetic parameters are shown in Table 3 for each compound.

TABLE 3

| Example # | Cl (ml/min/kg) | $t_{1/2}$ (hr) | $V_{ss}$ (L/kg) | F (%) | $T_{max}$ (hr) |
|---|---|---|---|---|---|
| 14 | 1.72 | 3.68 | 0.362 | 63.4 | 6 |
| 15 | 1.4 | 3.39 | 0.347 | 79 | 6 |
| 18 | 1.33 | 7.72 | 0.366 | 74.8 | 8 |
| 105 | 0.712 | 7.72 | 0.407 | 74.8 | 1 |

Cl = clearance;
$t_{1/2}$ = half-life;
$V_{ss}$ = volume of distribution;
F = oral bioavailability;
$T_{max}$ = Time to maximum blood concentration after an oral dose The data in Table 3 indicate that Example 105 has a low volume of distribution and good half-life of more than 7 hours. The compound also exhibits high oral bioavailability of more than 74%. Examples 14, 15, and 18 have a low volume of distribution and reasonable half-life of 3 hours or more, and exhibit high oral bioavailability of 63% or more. Thus, the pharmacokinetic parameters of these compounds suggest that they will display suitable drug properties to support efficacy in human clinical trials.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound chosen from
   2-(Benzofuran-3-yl)-3-(isopropyl(methyl)amino)quinoxaline-6-carboxylic acid,
   3-(Isopropyl(methyl)amino)-2-(1H-pyrazol-4-yl)quinoxaline-6-carboxylic acid,
   3-(Isopropyl(methyl)amino)-2-(6-methoxypyridin-3-yl)quinoxaline-6-carboxylic acid,
   2-(1H-Indazol-6-yl)-3-(isopropyl(methyl)amino)quinoxaline-6-carboxylic acid,
   3-(Isopropyl(methyl)amino)-2-(1-methyl-1H-indazol-6-yl)quinoxaline-6-carboxylic acid,
   3-(Isopropyl(methyl)amino)-2-(5-methoxy-1H-indol-2-yl)quinoxaline-6-carboxylic acid,
   2-(5-Bromopyridin-3-yl)-3-(isopropyl(methyl)amino)quinoxaline-6-carboxylic acid,
   2-(1H-Indazol-5-yl)-3-(isopropyl(methyl)amino)quinoxaline-6-carboxylic acid,
   3-(Isopropyl(methyl)amino)-2-(3-(trifluoromethyl)-1H-pyrazol-4-yl)quinoxaline-6-carboxylic acid,
   2-(6-(tent-Butoxycarbonylamino)pyridin-3-yl)-3-(isopropyl(methyl)amino)quinoxaline-6-carboxylic acid,
   2-(2-Fluoropyridin-4-yl)-3-(isopropyl(methyl)amino)quinoxaline-6-carboxylic acid,
   3-(Isopropyl(methyl)amino)-2-(6-(pyrrolidin-1-yl)pyridin-3-yl)quinoxaline-6-carboxylic acid,
   2-(6-Fluoropyridin-3-yl)-3-(isopropyl(methyl)amino)quinoxaline-6-carboxylic acid,
   (S)-2-(Benzofuran-2-yl)-3-(2-methylpyrrolidin-1-yl)quinoxaline-6-carboxylic acid,
   2-(Benzofuran-2-yl)-3-(cyclopropyl(methyl)amino)quinoxaline-6-carboxylic acid,
   2-(6-Aminopyridin-3-yl)-3-(isopropyl(methyl)amino)quinoxaline-6-carboxylic acid,
   3-(Isopropyl(methyl)amino)-2-(5-methoxybenzofuran-2-yl)quinoxaline-6-carboxylic acid,
   2-(5-Fluorobenzofuran-2-yl)-3-(isopropyl(methyl)amino)quinoxaline-6-carboxylic acid,
   2-(5-Chlorobenzofuran-2-yl)-3-(isopropyl(methyl)amino)quinoxaline-6-carboxylic acid, 2-(3,4-Dihydro-2H-benzo[b][1,4]dioxepin-7-yl)-3-(isopropyl(methyl)amino)quinoxaline-6-carboxylic acid,
2-(Chroman-6-yl)-3-(isopropyl(methyl)amino)quinoxaline-6-carboxylic acid,
2-(Benzo[d]oxazol-2-yl)-3-(isopropyl(methyl)amino)quinoxaline-6-carboxylic acid,
2-(Benzo[b]thiophen-2-yl)-3-(isopropyl(methyl)amino)quinoxaline-6-carboxylic acid,
2-(5-Fluorobenzo[b]thiophen-2-yl)-3-(isopropyl(methyl)amino)quinoxaline-6-carboxylic acid,
3-(Isopropyl(methyl)amino)-2-(1-methyl-1H-indazol-5-yl)quinoxaline-6-carboxylic acid,
2-(1-Ethyl-1H-indazol-5-yl)-3-(isopropyl(methyl)amino)quinoxaline-6-carboxylic acid,
2-(1-Benzofuran-2-yl)-3-(diethylamino)quinoxaline-6-carboxylic acid,
2-(6-Fluoro-1-benzofuran-2-yl)-3-[(2S)-2-methylpiperidin-1-yl]quinoxaline-6-carboxylic acid,
3-(Cyclopropyl(methyl)amino)-2-(1H-indazol-5-yl)quinoxaline-6-carboxylic acid,
2-(1-Benzofuran-5-yl)-3-[methyl(propan-2-yl)amino]quinoxaline-6-carboxylic acid,
2-(6-Chloro-1-benzofuran-2-yl)-3-[methyl(propan-2-yl)amino]quinoxaline-6-carboxylic acid,
(S)-2-(6-Fluorobenzofuran-2-yl)-3-(2-methylpyrrolidin-1-yl)quinoxaline-6-carboxylic acid,
2-(5,6-Difluorobenzofuran-2-yl)-3-(isopropyl(methyl)amino)quinoxaline-6-carboxylic acid,
(S)-2-(2,2-Difluorobenzo[d][1,3]dioxol-5-yl)-3-(2-methylpyrrolidin-1-yl)quinoxaline-6-carboxylic acid,
2-(1H-Indazol-5-yl)-3-(piperidin-1-yl)quinoxaline-6-carboxylic acid,
3-(Azepan-1-yl)-2-(1H-indazol-5-yl)quinoxaline-6-carboxylic acid,
3-(Azepan-1-yl)-2-(1H-indol-5-yl)quinoxaline-6-carboxylic acid,
3-(Diethylamino)-2-(1H-indol-5-yl)quinoxaline-6-carboxylic acid,
3-(Azepan-1-yl)-2-(5-fluorobenzofuran-2-yl)quinoxaline-6-carboxylic acid,
(S)-2-(1H-Indol-5-yl)-3-(2-methylpyrrolidin-1-yl)quinoxaline-6-carboxylic acid,
(S)-2-(5-Fluorobenzo[b]thiophen-2-yl)-3-(2-methylpyrrolidin-1-yl)quinoxaline-6-carboxylic acid,
2-(2,2-Difluorobenzo[d][1,3]dioxol-5-yl)-3-(isopropyl(methyl)amino)quinoxaline-6-carboxylic acid,
3-(Isopropyl(methyl)amino)-2-(1H-pyrazol-5-yl)quinoxaline-6-carboxylic acid,
2-(3-Methyl-1H-indazol-5-yl)-3-(isopropyl(methyl)amino)quinoxaline-6-carboxylic acid,
2-(6-Fluoro-1-benzofuran-2-yl)-3-[methyl(propan-2-yl)amino]quinoxaline-6-carboxylic acid,
3-(Isopropyl(methyl)amino)-2-(quinolin-6-yl)quinoxaline-6-carboxylic acid,
2-(1H-Indazol-5-yl)-3-[(2S)-2-methylpyrrolidin-1-yl]quinoxaline-6-carboxylic acid,
3-(Azepan-1-yl)-2-(6-fluoro-1-benzofuran-2-yl)quinoxaline-6-carboxylic acid,
3-(Cyclopropyl(methyl)amino)-2-(6-fluorobenzofuran-2-yl)quinoxaline-6-carboxylic acid,
2-(1,2-Benzoxazol-5-yl)-3-[methyl(propan-2-yl)amino]quinoxaline-6-carboxylic acid,
3-(Azepan-1-yl)-2-(2,2-difluoro-2H-1,3-benzodioxol-5-yl)quinoxaline-6-carboxylic acid,
3-[Methyl(propan-2-yl)amino]-2-(4-phenylfuran-2-yl)quinoxaline-6-carboxylic acid,
2-(Benzo[b]thiophen-2-yl)-3-(piperidin-1-yl)quinoxaline-6-carboxylic acid,
3-(Azepan-1-yl)-2-(benzo[b]thiophen-2-yl)quinoxaline-6-carboxylic acid,
(S)-2-(5-Fluorobenzo[b]thiophen-2-yl)-3-(2-methylpyrrolidin-1-yl)quinoxaline-6-carboxylic acid,
2-(Benzo[d]thiazol-5-yl)-3-(isopropyl(methyl)amino)quinoxaline-6-carboxylic acid,
2-(1,3-Benzothiazol-5-yl)-3-[(2S)-2-methylpyrrolidin-1-yl]quinoxaline-6-carboxylic acid,
2-(1,3-Benzothiazol-2-yl)-3-[methyl(propan-2-yl)amino]quinoxaline-6-carboxylic acid,
2-(1,3-Benzothiazol-2-yl)-3-[(2S)-2-methylpyrrolidin-1-yl]quinoxaline-6-carboxylic acid,
3-(Isopropyl(methyl)amino)-2,7'-biquinoxaline-6-carboxylic acid,
3-[Cyclopropyl(methyl)amino]-2-(5-fluoro-1-benzofuran-2-yl)quinoxaline-6-carboxylic acid,
2-(5-Fluoro-1-benzofuran-2-yl)-3-(pyrrolidin-1-yl)quinoxaline-6-carboxylic acid,
2-(1H-Benzo[d]imidazol-1-yl)-3-(isopropyl(methyl)amino)quinoxaline-6-carboxylic acid,
3-[Cyclopropyl(methyl)amino]-2-(1H-indol-5-yl)quinoxaline-6-carboxylic acid,
2-(1H-Indol-5-yl)-3-(piperidin-1-yl)quinoxaline-6-carboxylic acid,
(S)-2-(1H-Indol-5-yl)-3-(3-methylmorpholino)quinoxaline-6-carboxylic acid,
2-(1H-Indol-5-yl)-3-[(2R)-2-(methoxymethyl)pyrrolidin-1-yl]quinoxaline-6-carboxylic acid,
2-(5-Fluoro-1-benzofuran-2-yl)-3-[(2R)-2-(methoxymethyl)pyrrolidin-1-yl]quinoxaline-6-carboxylic acid,
(S)-3-(sec-Butyl(methyl)amino)-2-(5-fluorobenzofuran-2-yl)quinoxaline-6-carboxylic acid,
2-(1-Benzofuran-2-yl)-3-[(propan-2-yl)amino]quinoxaline-6-carboxylic acid,
3-[Methyl(propan-2-yl)amino]-2-[5-(trifluoromethyl)-1-benzofuran-3-yl]quinoxaline-6-carboxylic acid,
2-(1-Benzofuran-3-yl)-3-[(2S)-2-methylpyrrolidin-1-yl]quinoxaline-6-carboxylic acid,
(S)-2-(1H-Indol-5-yl)-3-(2-methylpiperidin-1-yl)quinoxaline-6-carboxylic acid,
(R)-3-(sec-Butyl(methyl)amino)-2-(5-fluorobenzofuran-2-yl)quinoxaline-6-carboxylic acid,
2-(2-Methyl-1H-indol-5-yl)-3-[(2S)-2-methylpyrrolidin-1-yl]quinoxaline-6-carboxylic acid,
3-[Methyl(propan-2-yl)amino]-2-(2-methyl-1H-indol-5-yl)quinoxaline-6-carboxylic acid,
3-[Methyl(propan-2-yl)amino]-2-(5-phenylfuran-2-yl)quinoxaline-6-carboxylic acid,
2-(Furan-3-yl)-3-[(2S)-2-methylpyrrolidin-1-yl]quinoxaline-6-carboxylic acid,
3-(Isopropyl(methyl)amino)-2-(4-phenylfuran-2-yl)quinoxaline-6-carboxylic acid,3-[(2S)-2-methylpyrrolidin-1-yl]-2-(1H-pyrrol-3-yl)quinoxaline-6-carboxylic acid,
3-[Methyl(propan-2-yl)amino]-2-(1H-pyrrol-3-yl)quinoxaline-6-carboxylic acid,
2-(1-Benzofuran-3-yl)-3-[(2S)-2-methylpyrrolidin-1-yl]quinoxaline-6-carboxylic acid,
3-[Methyl(propan-2-yl)amino]-2-(3-phenylfuran-2-yl)quinoxaline-6-carboxylic acid,
2-[5-(4-Fluorophenyl)furan-2-yl]-3-[methyl(propan-2-yl)amino]quinoxaline-6-carboxylic acid,
3-[Methyl(propan-2-yl)amino]-2-(3-methyl-1-benzofuran-5-yl)quinoxaline-6-carboxylic acid, 3-(Isopropyl(methyl)amino)-2-(3-methyl-1H-indol-5-yl)quinoxaline-6-carboxylic acid,
(R)-2-(Benzo[d][1,3]dioxol-5-yl)-3-(2-methylpyrrolidin-1-yl)quinoxaline-6-carboxylic acid,
(S)-2-(2-Methyl-1H-indol-5-yl)-3-(2-methylpiperidin-1-yl)quinoxaline-6-carboxylic acid,
3-[Cyclopropyl(methyl)amino]-2-(2-methyl-1H-indol-5-yl)quinoxaline-6-carboxylic acid,
3-[Methyl(propan-2-yl)amino]-2-(1-methyl-1H-pyrazol-4-yl)quinoxaline-6-carboxylic acid,
3-[Methyl(propan-2-yl)amino]-2-(1-phenyl-1H-pyrazol-4-yl)quinoxaline-6-carboxylic acid,
(S)-2-(1H-indazol-5-yl)-3-(2-methyl-4-(pyridin-2-yl)piperazin-1-yl)quinoxaline-6-carboxylic acid,
(S)-7-Hydroxy-2-(1H-indazol-5-yl)-3-(2-methylpyrrolidin-1-yl)quinoxaline-6-carboxylic acid,
2-(1H-Benzo[d][1,2,3]triazol-5-yl)-3-(isopropyl(methyl)amino)quinoxaline-6-carboxylic acid,
3-(Isopropyl(methyl)amino)-2-(1-methyl-1H-benzo[d][1,2,3]triazol-5-yl)quinoxaline-6-carboxylic acid,
(S)-2-(1H-Benzo[d][1,2,3]triazol-5-yl)-3-(2-methylpyrrolidin-1-yl)quinoxaline-6-carboxylic acid,
3-(Benzyl(methyl)amino)-2-(1H-indazol-5-yl)quinoxaline-6-carboxylic acid,
(S)-2-(1H-Indazol-5-yl)-3-(methyl(1-phenylethyl)amino)quinoxaline-6-carboxylic acid,
(S)-2-(2-Methyl-1H-indol-5-yl)-3-(2-methyl-4-(pyridin-2-yl)piperazin-1-yl)quinoxaline-6-carboxylic acid,
(S)-2-(5-Fluorobenzofuran-2-yl)-3-(2-methylpiperidin-1-yl)quinoxaline-6-carboxylic acid,
(R)-2-(4-Fluorophenyl)-3-(2-(trifluoromethyl)pyrrolidin-1-yl)quinoxaline-6-carboxylic acid,
2-(4-Fluorophenyl)-3-(methyl(tetrahydro-2H-pyran-4-yl)amino)quinoxaline-6-carboxylic acid,
2-(4-Fluorophenyl)-3-(methyl(piperidin-4-yl)amino)quinoxaline-6-carboxylic acid,
(S)-3-(sec-Butyl(methyl)amino)-2-(4-fluorophenyl)quinoxaline-6-carboxylic acid,
(S)-2-(4-Fluorophenyl)-3-(3-methylmorpholino)quinoxaline-6-carboxylic acid,
2-(4-Fluorophenyl)-3-[(2R)-2-(trifluoromethyl)piperidin-1-yl]quinoxaline-6-carboxylic acid,
3-(tert-Butyl(methyl)amino)-2-(4-fluorophenyl)quinoxaline-6-carboxylic acid,
3-(Cyclohexyl(methyl)amino)-2-(4-fluorophenyl)quinoxaline-6-carboxylic acid,
2-(4-Fluorophenyl)-3-(methyl(o-tolyl)amino)quinoxaline-6-carboxylic acid,
3-(tert-Butylamino)-2-(4-fluorophenyl)quinoxaline-6-carboxylic acid,
3-(Ethyl(isopropyl)amino)-2-(4-fluorophenyl)quinoxaline-6-carboxylic acid,
3-[Cyclohexyl(ethyl)amino]-2-(4-fluorophenyl)quinoxaline-6-carboxylic acid,
3-(Diethylamino)-2-(4-fluorophenyl)quinoxaline-6-carboxylic acid,
2-(4-Fluorophenyl)-3-[(2S)-2-methylpiperazin-1-yl]quinoxaline-6-carboxylic acid,
(S)-2-(2,4-Difluorophenyl)-3-(2-methylpyrrolidin-1-yl)quinoxaline-6-carboxylic acid,
(S)-2-(2,4-Difluorophenyl)-3-(2-methylpiperidin-1-yl)quinoxaline-6-carboxylic acid,
(S)-2-(4-Fluoro-2-methylphenyl)-3-(2-methylpyrrolidin-1-yl)quinoxaline-6-carboxylic acid,
2-(4-Fluoro-2-methylphenyl)-3-(isopropyl(methyl)amino)quinoxaline-6-carboxylic acid,
2-(4-Carbamoylphenyl)-3-(isopropyl(methyl)amino)quinoxaline-6-carboxylic acid,
2-(4-Fluorophenyl)-7-hydroxy-3-(isopropyl(methyl)amino)quinoxaline-6-carboxylic acid,
(R)-2-(4-Fluorophenyl)-3-(2-methylpiperidin-1-yl)quinoxaline-6-carboxylic acid,
2-(4-Fluorophenyl)-7-methoxy-3-[methyl(propan-2-yl)amino]quinoxaline-6-carboxylic acid,
7-Fluoro-2-(4-fluorophenyl)-3-[methyl(propan-2-yl)amino]quinoxaline-6-carboxylic acid,
2-(4-Fluorophenyl)-3-[methyl(2,2,2-trifluoroethyl)amino]quinoxaline-6-carboxylic acid,
2-(4-Fluorophenyl)-3-(((1r,4r)-4-hydroxycyclohexyl)(methyl)amino)quinoxaline-6-carboxylic acid,
2-(4-Fluorophenyl)-3-(methyl((1r,4r)-4-(methylamino)cyclohexyl)amino)quinoxaline-6-carboxylic acid,
3-(((1r,4r)-4-Acetamidocyclohexyl)(methyl)amino)-2-(4-fluorophenyl)quinoxaline-6-carboxylic acid,
3-(4-Acetylpiperazin-1-yl)-2-(4-fluorophenyl)quinoxaline-6-carboxylic acid,
3-(4-Benzoylpiperazin-1-yl)-2-(4-fluorophenyl)quinoxaline-6-carboxylic acid,
2-(4-Fluorophenyl)-3-(4-(methylsulfonyl)piperazin-1-yl)quinoxaline-6-carboxylic acid,
2-(4-Fluorophenyl)-3-[4-(pyridin-2-yl)piperidin-1-yl]quinoxaline-6-carboxylic acid,
(S)-2-(4-Fluorophenyl)-7-hydroxy-3-(2-methylpyrrolidin-1-yl)quinoxaline-6-carboxylic acid,
3-[Benzyl(methyl)amino]-2-(4-fluorophenyl)quinoxaline-6-carboxylic acid,
2-(4-Fluorophenyl)-3-[methyl(pyridin-2-ylmethyl)amino]quinoxaline-6-carboxylic acid,
3-(Cyclopentyl(methyl)amino)-2-(4-fluorophenyl)quinoxaline-6-carboxylic acid,
3-(Isopropyl(methyl)amino)-2-(4-(trifluoromethyl)phenyl)quinoxaline-6-carboxylic acid,
3-[(1-Ethylpiperidin-4-yl)(methyl)amino]-2-(4-fluorophenyl)quinoxaline-6-carboxylic acid,
(S)-3-(4-Ethyl-2-methylpiperazin-1-yl)-2-(4-fluorophenyl)quinoxaline-6-carboxylic acid,
3-[Ethyl(propyl)amino]-2-(4-fluorophenyl)quinoxaline-6-carboxylic acid,
3-(Dipropylamino)-2-(4-fluorophenyl)quinoxaline-6-carboxylic acid,
2-(4-Fluorophenyl)-3-(isobutyl(methyl)amino)quinoxaline-6-carboxylic acid,
3-(2-Ethylpiperidin-1-yl)-2-(4-fluorophenyl)quinoxaline-6-carboxylic acid,
(S)-2-(4-Fluorophenyl)-3-(methyl(1-phenylethyl)amino)quinoxaline-6-carboxylic acid,
2-(4-Fluorophenyl)-3-(pyrrolidin-1-yl)quinoxaline-6-carboxylic acid,
3-(Azetidin-1-yl)-2-(4-fluorophenyl)quinoxaline-6-carboxylic acid,
3-(Cyclobutyl(methyl)amino)-2-(4-fluorophenyl)quinoxaline-6-carboxylic acid,
2-(2,4-Difluorophenyl)-3-[methyl(propan-2-yl)amino]quinoxaline-6-carboxylic acid,
(S)-2-(3,4-Difluorophenyl)-3-(2-methylpyrrolidin-1-yl)quinoxaline-6-carboxylic acid,
2-(4-Acetamidophenyl)-3-[methyl(propan-2-yl)amino]quinoxaline-6-carboxylic acid, and
(R)-2-(4-Fluorophenyl)-3-(2-methylpyrrolidin-1-yl)quinoxaline-6-carboxylic acid.

2. A compound as recited in claim 1, wherein said compound is chosen from 2-(Benzofuran-2-yl)-3-(cyclopropyl(methyl)amino)quinoxaline-6-carboxylic acid, and (S)-2-(4-Fluorophenyl)-3-(3-methylmorpholino)quinoxaline-6-carboxylic acid.

3. A pharmaceutical composition comprising a compound as recited in claim 1 together with a pharmaceutically acceptable carrier.

4. A pharmaceutical kit comprising a compound as recited in claim 1.

5. A method for achieving an effect in a patient comprising the administration of a therapeutically effective amount of a compound as recited in claim 1 to a patient, wherein the effect is selected from the group consisting of reduction of triglycerides, reduction of cholesterol, and reduction of hemoglobin A1c.

6. The method of claim 5 wherein said cholesterol is chosen from low-density lipoprotein and very low-density lipoprotein cholesterol.

7. The method of claim 5 wherein said triglycerides are chosen from plasma triglycerides and liver triglycerides.

8. A method of inhibiting purine-analog sensitive kinase comprising contacting purine-analog sensitive kinase with a compound as recited in claim 1.

* * * * *